US007919523B2

(12) United States Patent
Hale et al.

(10) Patent No.: US 7,919,523 B2
(45) Date of Patent: *Apr. 5, 2011

(54) INHIBITORS OF ASPARTYL PROTEASE

(75) Inventors: Michael R. Hale, Bedford, MA (US);
Christopher T. Baker, Waltham, MA (US); Timothy A. Stammers, Etobicoke (CA); Ronald George Sherrill, Cary, NC (US); Andrew Spaltenstein, Raleigh, NC (US); Eric Steven Furfine, Durham, NC (US); Francois Maltais, Somerville, MA (US); Clarence Webster Andrews, III, Durham, NC (US); John Franklin Miller, Durham, NC (US); Vicente Samano, Chapel Hill, NC (US)

(73) Assignee: Vertex Pharmaceuticals, Inc., Cambridge, MA (US)

( * ) Notice: Subject to any disclaimer, the term of this patent is extended or adjusted under 35 U.S.C. 154(b) by 14 days.

This patent is subject to a terminal disclaimer.

(21) Appl. No.: 12/217,517

(22) Filed: Jul. 2, 2008

(65) Prior Publication Data

US 2009/0042973 A1  Feb. 12, 2009

Related U.S. Application Data

(62) Division of application No. 10/613,650, filed on Jul. 2, 2003, now Pat. No. 7,442,718, which is a division of application No. 09/927,271, filed on Aug. 9, 2001, now Pat. No. 6,617,350, which is a division of application No. 09/500,781, filed on Feb. 9, 2000, now Pat. No. 6,319,946.

(60) Provisional application No. 60/120,047, filed on Feb. 12, 1999.

(51) Int. Cl.
*A61K 31/357* (2006.01)
*C07D 319/06* (2006.01)
(52) U.S. Cl. .................... 514/452; 549/372; 549/370
(58) Field of Classification Search .................. 514/452; 549/372, 370
See application file for complete search history.

(56) References Cited

U.S. PATENT DOCUMENTS

| 4,629,724 | A | 12/1986 | Ryono et al. | |
| 5,723,490 | A | 3/1998 | Tung et al. | |
| 5,843,946 | A | 12/1998 | Vasquez et al. | |
| 6,143,747 | A | 11/2000 | Freskos et al. | |
| 6,617,350 | B2 * | 9/2003 | Hale et al. | 514/470 |

FOREIGN PATENT DOCUMENTS

| EP | 0159156 A1 | 10/1985 |
| EP | 0594540 A1 | 4/1994 |
| WO | WO 94/04492 | 3/1994 |
| WO | WO 94/05639 | 3/1994 |
| WO | WO 94/10136 | 5/1994 |
| WO | WO 95/06030 | 3/1995 |
| WO | WO 95/07269 | 3/1995 |
| WO | WO 95/09843 | 4/1995 |
| WO | WO 95/14016 | 5/1995 |
| WO | WO 95/32185 | 11/1995 |
| WO | WO 96/22287 | 7/1996 |
| WO | WO 96/33184 | 10/1996 |
| WO | WO 96/33187 | 10/1996 |

OTHER PUBLICATIONS

A.K. Ghosh et al., "Potent HIV Protease Inhibitors Incorporating High-Affinity P2-Ligands and (R)-(Hydroxyethylamino)sulfonamide Isostere," *Bioorg. Med. Chem. Lett.*, 8, pp. 687-690 (1998).
S. J. Hays et al., "Synthesis of cis-4-(Phosphonooxy)-2-piperidinecarboxylic Acid, an N-Methyl-D-aspartate Antagonist," *J. Org. Chem.*, 56, pp. 4084-4086 (1991).
Y. Kiso et al., "'O☐N Intramolecular Acyl Migration'-type Prodrugs of Tripeptide Inhibitors of HIV Protease," *Peptides: Chemistry, Structure and Biology*, 61, pp. 157-159 (1996).
A.C. Nair et al., "A Computational Study of the Resistance of HIV-1 Aspartic Protease to the Inhibitors ABT-538 and VX-478 and Design of New Analogues," *Biochem. Biophys. Res. Commun.*, 242, pp. 545-551 (1998).
J.W. Perich et al., "The Synthesis of Multiple O-Phosphoseryl-Containing Peptides via Phenyl Phosphate Protection," *J. Org. Chem.*, 53, pp. 4103-4105 (1988).
M.S. Plummer et al., "Design of Peptidomimetic Ligands for the pp60src SH2 Domain," *Bioorganic & Medicinal Chemistry*, 5, pp. 41-47 (1997).
S. Yamaguchi et al., "Synthesis of HIV Protease Dipeptide Inhibitors and Prodrugs," *Peptide Chemistry 1996*, pp. 297-300 (1997).
Banker et al., *Modern Pharmaceutics*, pp. 627-629 (1996).
C.T. Baker et al., "Design, Synthesis and Conformational Analysis of A Novel Series of HIV Protease Inhibitors," *Bioorg. & Med. Chem. Lett.*, vol. 8, pp. 3631-3636 (1998).

* cited by examiner

*Primary Examiner* — Charanjit S Aulakh
(74) *Attorney, Agent, or Firm* — Ropes & Gray LLP; James F. Haley, Jr.; Karen Mangasarian

(57) ABSTRACT

The present invention relates to a novel class of sulfonamides which are aspartyl protease inhibitors. In one embodiment, this invention relates to a novel class of HIV aspartyl protease inhibitors characterized by specific structural and physicochemical features. This invention also relates to pharmaceutical compositions comprising these compounds. The compounds and pharmaceutical compositions of this invention are particularly well suited for inhibiting HIV-1 and HIV-2 protease activity and consequently, may be advantageously used as anti-viral agents against the HIV-1 and HIV-2 viruses. This invention also relates to methods for inhibiting the activity of HIV aspartyl protease using the compounds of this invention and methods for screening compounds for anti-HIV activity.

20 Claims, No Drawings

INHIBITORS OF ASPARTYL PROTEASE

CROSS-REFERENCE TO RELATED APPLICATIONS

This application is a division of U.S. application Ser. No. 10/613,650, filed Jul. 2, 2003, now pending, which is a division of U.S. application Ser. No. 09/927,271, filed Aug. 9, 2001, now issued as U.S. Pat. No. 6,617,350, which is a division of U.S. application Ser. No. 09/500,781, filed Feb. 9, 2000, now issued as U.S. Pat. No. 6,319,946, which claims priority under 35 U.S.C. §119(e) from U.S. provisional application 60/120,047, filed Feb. 12, 1999. The entire disclosure of each of these prior applications is incorporated by reference herein.

TECHNICAL FIELD OF THE INVENTION

The present invention relates to a novel class of sulfonamides which are aspartyl protease inhibitors. In one embodiment, this invention relates to a novel class of HIV aspartyl protease inhibitors characterize d by specific structural and physicochemical features. This invention also relates to pharmaceutical compositions comprising these compounds. The compounds and pharmaceutical compositions of this invention are particularly well suited for inhibiting HIV-1 and HIV-2 protease activity and consequently, may be advantageously used as anti-viral agents against the HIV-1 and HIV-2 viruses. This invention also relates to methods for inhibiting the activity of HIV aspartyl protease using the compounds of this invention and methods for screening compounds for anti-HIV activity.

BACKGROUND OF THE INVENTION

The human immunodeficiency virus ("HIV") is the causative agent for acquired immunodeficiency syndrome ("AIDS")—a disease characterized by the destruction of the immune system, particularly of CD4$^+$ T-cells, with attendant susceptibility to opportunistic infections—and its precursor AIDS-related complex ("ARC")—a syndrome characterized by symptoms such as persistent generalized lymphadenopathy, fever and weight loss.

As in the case of several other retroviruses, HIV encodes the production of a protease which carries out post-translational cleavage of precursor polypeptides in a process necessary for the formation of infectious virions (S. Crawford et al., "A Deletion Mutation in the 5' Part of the pol Gene of Moloney Murine Leukemia Virus Blocks Proteolytic Processing of the gag and pol Polyproteins", *J. Virol.*, 53, p. 899 (1985)). These gene products include pol, which encodes the virion RNA-dependent DNA polymerase (reverse transcriptase), an endonuclease, HIV protease, and gag, which encodes the core-proteins of the virion (H. Toh et al., "Close Structural Resemblance Between Putative Polymerase of a Drosophila Transposable Genetic Element 17.6 and pol gene product of Moloney Murine Leukemia Virus", *EMBO J.*, 4, p. 1267 (1985); L. H. Pearl et al., "A Structural Model for the Retroviral Proteases", *Nature*, pp. 329-351 (1987); M.D. Power-et al., "Nucleotide Sequence of SRV-1, a Type D Simian Acquired Immune Deficiency Syndrome Retrovirus", *Science*, 231, p. 1567 (1986)).

A number of synthetic anti-viral agents have been designed to target various stages in the replication cycle of HIV. These agents include compounds which block viral binding to CD4$^+$ T-lymphocytes (for example, soluble CD4), and compounds which interfere with viral replication by inhibiting viral reverse transcriptase (for example, didanosine and zidovudine (AZT)) and inhibit integration of viral DNA into cellular DNA (M. S. Hirsh and R. T. D'Aqulia, "Therapy for Human Immunodeficiency Virus Infection", *N. Eng. J. Med.*, 328, p. 1686 (1993)). However, such agents, which are directed primarily to early stages of viral replication, do not prevent the production of infectious virions in chronically infected cells. Furthermore, administration of some of these agents in effective amounts has led to cell-toxicity and unwanted side effects, such as anemia and bone marrow suppression.

More recently, the focus of anti-viral drug design has been to create compounds which inhibit the formation of infectious virions by interfering with the processing of viral polyprotein precursors. Processing of these precursor proteins requires the action of virus-encoded proteases which are essential for replication (Kohl, N. E. et al. "Active HIV Protease is Required for Viral Infectivity" *Proc. Natl. Acad. Sci. USA*, 85, p. 4686 (1988)). The anti-viral potential of HIV protease inhibition has been demonstrated using peptidyl inhibitors. Such peptidyl compounds, however, are typically large and complex molecules that tend to exhibit poor bioavailability and are not generally consistent with oral administration. Accordingly, the need still exists for compounds that can effectively inhibit the action of viral proteases, for use as agents for preventing and treating chronic and acute viral infections.

SUMMARY OF THE INVENTION

The present invention provides a novel class of compounds, and pharmaceutically acceptable derivatives thereof, that are useful as inhibitors of aspartyl proteases, in particular, HIV aspartyl protease. These compounds can be used alone or in combination with other therapeutic or prophylactic agents, such as anti-virals, antibiotics, immunomodulators or vaccines, for the treatment or prophylaxis of viral infection.

According to a preferred embodiment, the compounds of this invention are capable of inhibiting HIV viral replication in human CD$_4$$^+$T-cells. These compounds are useful as therapeutic and prophylactic agents to treat or prevent infection by HIV-1 and related viruses which may result in asymptomatic infection, AIDS-related complex ("ARC"), acquired immunodeficiency syndrome ("AIDS"), or similar disease of the immune system.

It is a principal object of this invention to provide a novel class of sulfonamides which are aspartyl protease inhibitors, and particularly, HIV aspartyl protease inhibitors. The novel sulfonamides of this invention are those of formula I:

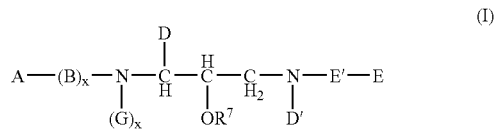

wherein:
E' is —CO— or —SO$_2$—;
A is selected from H; Ht; —R$^1$—Ht; —R$^1$—C$_1$-C$_6$ alkyl, which is optionally substituted with one or more groups independently selected from hydroxy, C$_1$-C$_4$ alkoxy, Ht, —O-Ht, —NR$^2$—CO—N(R$^2$)$_2$; —SO$_2$—R$^2$ or —CO—N(R$^2$)$_2$; —R$^1$—C$_2$-C$_6$ alkenyl, which is optionally substituted with one or more groups independently selected from hydroxy, C$_1$-C$_4$ alkoxy, Ht, —O-Ht, —NR$^2$—CO—N(R$^2$)$_2$ or —CO—N(R$^2$)$_2$; or R$^7$;

each $R^1$ is independently selected from —C(O)—, —S(O)$_2$—, —C(O)—C(O)—, —O—C(O)—, —O—S(O)$_2$, —NR$^2$—S(O)$_2$—, —NR$^2$—C(O)— or —NR$^2$—C(O)—C(O)—;

each Ht is independently selected from $C_3$-$C_7$ cycloalkyl; $C_5$-$C_7$ cycloalkenyl; $C_6$-$C_{14}$ aryl; or a 5-7 membered saturated or unsaturated heterocycle, containing one or more heteroatoms selected from N, O, or S; wherein said aryl or said heterocycle is optionally fused to Q; and wherein any member of said Ht is optionally substituted with one or more substituents independently selected from oxo, —OR$^2$, SR$^2$, —R$^2$, —N(R$^2$)(R$^2$), —R$^2$—OH, —CN, —CO$_2$R$^2$, —C(O)—N(R$^2$)$_2$—S(O)$_2$—N(R$^2$)$_2$, —N(R$^2$)—C(O)—R$^2$, —N(R$^2$)—C(O)O—R$^2$, —C(O)—R$^2$, —S(O)$_n$—R$^2$, —OCF$_3$, —S(O)$_n$-Q, methylenedioxy, —N(R$^2$)—S(O)$_2$(R$^2$), halo, —CF$_3$, —NO$_2$, Q, —OQ, —OR$^7$, —SR$^7$, —R$^7$, —N(R$^2$)(R$^7$) or —N(R$^7$)$_2$;

each Q is independently selected from a 3-7 membered saturated, partially saturated or unsaturated carbocyclic ring system; or a 5-7 membered saturated, partially saturated or unsaturated heterocyclic ring containing one or more heteroatoms selected from O, N, or S; wherein Q is optionally substituted with one or more groups selected from oxo, —OR$^2$, —R$^2$, —SO$_2$R$^2$, —SO$_2$—N(R$^2$)$_2$, —N(R$^2$)$_2$, —N(R$^2$)—C(O)—R$^2$, —R$^2$—OH, —CN, —CO$_2$R$^2$, —C(O)—N(R$^2$)$_2$, halo, —CF$_3$;

each $R^2$ is independently selected from H, or $C_1$-$C_4$ alkyl, and wherein said alkyl, when not a substituent of Q, is optionally substituted with Q or —OR$^3$; wherein when said R$^2$ is an —OR$^3$ substituted moiety, said R$^3$ in —OR$^3$ may not be —OR$^2$ substituted;

B, when present, is —N(R$^2$)—C(R$^3$)$_2$—C(O)—;

each x is independently 0 or 1;

each $R^3$ is independently selected from H, Ht, $C_1$-$C_6$ alkyl, $C_2$-$C_6$ alkenyl, $C_2$-$C_6$ alkynyl, $C_3$-$C_6$ cycloalkyl or $C_5$-$C_6$ cycloalkenyl; wherein any member of said R$^3$, except H, is optionally substituted with one or more substituents selected from —OR$^2$, —C(O)—NH—R$^2$, —S(O)$_n$—N(R$^2$)(R$^2$), —N(R$^2$)$_2$, —N(R$^2$)—C(O)—O(R$^2$), —N(R$^2$)—C(O)—N(R$^2$), —N(R$^2$)—C(O)—(R$^2$), Ht, —CN, —SR$^2$, —CO$_2$R$^2$, or NR$^2$—C(O)—R$^2$;

each n is independently 1 or 2;

G, when present, is selected from H, R$^7$ or $C_1$-$C_4$ alkyl, or, when G is $C_1$-$C_4$ alkyl, G and R$^7$ are optionally bound to one another either directly or through a $C_1$-$C_3$ linker to form a heterocyclic ring; or when G is not present, the nitrogen to which G is attached is bound directly to the R$^7$ group in —OR$^7$ with the concomitant displacement of one -ZM group from R$^7$;

D is selected from Q; $C_1$-$C_6$ alkyl optionally substituted with one or more groups selected from $C_3$-$C_6$ cycloalkyl, —OR$^2$, —S-Ht, —R$^3$, —O-Q or Q; $C_2$-$C_4$ alkenyl optionally substituted with one or more groups selected from —OR$^2$, —S-Ht, —R$^3$, —O-Q or Q; $C_3$-$C_6$ cycloalkyl optionally substituted with or fused to Q; or $C_5$-$C_6$ cycloalkenyl optionally substituted with or fused to Q;

D' is selected from $C_1$-$C_{15}$ alkyl, $C_2$-$C_{15}$ alkenyl or $C_2$-$C_{15}$ alkynyl, each of which contains one or more substituents selected from oxo, halo, —CF$_3$, —OCF$_3$, —NO$_2$, azido, —SH, —SR$^3$, —N(R$^3$)—N(R$^3$)$_2$, —O—N(R$^3$)$_2$, —(R$^3$)N—O—(R$^3$), —N(R$^3$)$_2$, —CN, —CO$_2$R$^3$, —C(O)—N(R$^3$)$_2$, —S(O)$_n$—N(R$^3$)$_2$, —N(R$^3$)—C(O)—R$^3$, —N(R$^3$)—C(O)—N(R$^3$)$_2$, —N(R$^3$)—S(O)—S(R$^3$), —C(O)—R$^3$, —S(O)$_n$—R$^3$, —N(R$^3$)—S(O)$_n$(R$^3$), —N(R$^3$)—S(O)$_n$—N(R$^3$)$_2$, —S—NR$^3$—C(O)R$^3$, —C(S)N(R$^3$)$_2$, —C(S)R$^3$, —NR$^3$—C(O)OR$^3$, —O—C(O)OR$^3$, —O—C(O)N(R$^3$)$_2$, —NR$^3$—C(S)R$^3$, =N—OH, =N—OR$^3$, =N—N(R$^3$)$_2$, =NR$^3$, =NNR$^3$C(O)N(R$^3$)$_2$, =NNR$^3$C(O)OR$^3$, =NNR$^3$S(O)$_n$, —N(R$^3$)$_2$, —NR$^3$—C(S)OR$^3$, —NR$^3$—C(S)N(R$^3$)$_2$, —NR$^3$—C[=N(R$^3$)]—N(R$^3$)$_2$, —N(R$^3$)—C[=N—NO$_2$]—N(R$^3$)$_2$, —N(R$^3$)—C[=N—NO$_2$]—OR$^3$, —N(R$^3$)—C[=N—CN]—OR$^3$, —N(R$^3$)—C[=N—CN]—(R$^3$)$_2$, —OC(O)R$^3$, —OC(S)R$^3$, —OC(O)N(R$^3$)$_2$, —C(O)N(R$^3$)—N(R$^3$)$_2$, —O—C(O)N(R$^3$)—N(R$^3$)$_2$, —O—C(O)N(OR$^3$)(R$^3$)N(R$^3$)—N(R$^3$)C(O)R$^3$, N(R$^3$)—OC(O)R$^3$, N(R$^3$)—OC(O)R$^3$, N(R$^3$)—OC(O)R$^3$, —OC(S)N(R$^3$)$_2$, —OC(S)N(R$^3$)(R$^3$) or PO$_3$—R$^3$; with the proviso that when R$^7$ is H, E' is —SO$_2$—, G is H or alkyl, and when B is present or when B is not present and R$^1$ is —C(O)—, D' may not be $C_1$-$C_{15}$ alkyl substituted with one substituent selected from —N(R$^3$)$_2$, —SR$^3$ or —S(O)$_n$—R$^3$, or substituted with two —N(R$^3$)$_2$ substituents;

E is selected from Ht; O-Ht; Ht-Ht; Ht fused with Ht; —O—R$^3$; —N(R$^2$)(R$^3$); $C_1$-$C_6$ alkyl optionally substituted with one or more groups selected from R$^4$ or Ht; $C_2$-$C_6$ alkenyl optionally substituted with one or more groups selected from R$^4$ or Ht; $C_3$-$C_6$ saturated carbocycle optionally substituted with one or more groups selected from R$^4$ or Ht; or $C_5$-$C_6$ unsaturated carbocycle optionally substituted with one or more groups selected from R$^4$ or Ht;

each $R^4$ is independently selected from —OR$^2$, —OR$^3$, —SR$^2$, —SOR$^2$, —SO$_2$R$^2$, —CO$_2$R$^2$, —C(O)—NHR$^2$, —C(O)—N(R$^2$)$_2$, —C(O)—NR$^2$(OR$^2$), —S(O)$_2$—NHR$^2$, halo, —NR$^2$—C(O)—R$^2$, —N(R$^2$)$_2$ or —CN;

each $R^7$ is independently selected from hydrogen,

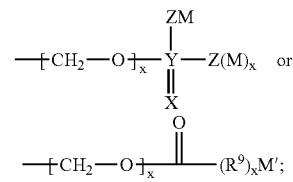

wherein each M is independently selected from H, Li, Na, K, Mg, Ca, Ba, —N(R$^2$)$_4$, $C_1$-$C_{12}$-alkyl, $C_2$-$C_{12}$-alkenyl, or —R$^6$; wherein 1 to 4 —CH$_2$ radicals of the alkyl or alkenyl group, other than the —CH$_2$ that is bound to Z, is optionally replaced by a heteroatom group selected from O, S(O), S(O)$_2$, or N(R$^2$); and wherein any hydrogen in said alkyl, alkenyl or R$^6$ is optionally replaced with a substituent selected from oxo, —OR$^2$, —R$^2$, N(R$^2$)$_2$, N(R$^2$)$_3$, R$^2$OH, —CN, —CO$_2$R$^2$, —C(O)—N(R$^2$)$_2$, S(O)$_2$—N(R$^2$)$_2$, N(R$^2$)—C(O)—R$^2$, C(O) R$^2$, —S(O)$_n$—R$^2$, OCF$_3$, —S(O)$_n$—R$^6$, N(R$^2$)—S(O)$_2$(R$^2$), halo, —CF$_3$, or —NO$_2$;

M' is H, $C_1$-$C_{12}$-alkyl, $C_2$-$C_{12}$-alkenyl, or —R$^6$; wherein 1 to 4 —CH$_2$ radicals of the alkyl or alkenyl group is optionally replaced by a heteroatom group selected from O, S, S(O), S(O)$_2$, or N(R$^2$); and wherein any hydrogen in said alkyl, alkenyl or R$^6$ is optionally replaced with a substituent selected from oxo, —OR$^2$, —R$^2$, —N(R$^2$)$_2$, N(R$^2$)$_3$, —R$^2$OH, —CN, —CO$_2$R$^2$, —C(O)—N(R$^2$)$_2$, —S(O)$_2$—N(R$^2$)$_2$, —N(R$^2$)—C(O)—R$_2$, —C(O)R$^2$, —S(O)$_n$—R$^2$, —OCF$_3$, —S(O)$_n$—R$^6$, —N(R$^2$)—S(O)$_2$ (R$^2$), halo, —CF$_3$, or —NO$_2$;

Z is O, S, N(R$^2$)$_2$, or, when M is not present, H.

Y is P or S;

X is O or S;

$R^9$ is $C(R^2)_2$, O or $N(R^2)$; and wherein when Y is S, Z is not S;

$R^6$ is a 5-6 membered saturated, partially saturated or unsaturated carbocyclic or heterocyclic ring system, or an 8-10 membered saturated, partially saturated or unsaturated bicyclic ring system; wherein any of said heterocyclic ring systems contains one or more heteroatoms selected from O, N, S, $S(O)_n$ or $N(R^2)$; and wherein any of said ring systems optionally contains 1 to 4 substituents independently selected from OH, $C_1$-$C_4$ alkyl, —O—$C_1$-$C_4$ alkyl or —O—C(O)—$C_1$-$C_4$ alkyl; and each $R^5$ is independently selected from hydrogen, $C_1$-$C_8$ alkyl, $C_2$-$C_8$ alkenyl, $C_2$-$C_8$ alkynyl or Ht, wherein any $R^5$, except for hydrogen, is optionally substituted with —$CF_3$, —$PO_3R^3$, azido or halo.

It is also an object of this invention to provide pharmaceutical compositions comprising the sulfonamides of formula (I) and methods for their use as inhibitors of HIV aspartyl protease.

DETAILED DESCRIPTION OF THE INVENTION

In order that the invention herein described may be more fully understood, the following detailed description is set forth. In the description, the following terms are employed herein:

Unless expressly stated to the contrary, the terms "—$SO_2$—" and "—$S(O)_2$—" as used herein refer to a sulfone or sulfone derivative (i.e., both appended groups linked to the S), and not a sulfinate ester.

For the compounds of formula I, and intermediates thereof, the stereochemistry of $OR^7$ is defined relative to D on the adjacent carbon atom, when the molecule is drawn in an extended zigzag representation (such as that drawn for compound of formula I). If both $OR^7$ and D reside on the same side of the plane defined by the extended backbone of the compound, the stereochemistry of $OR^7$ will be referred to as "syn". If $OR^7$ and D reside on opposite sides of that plane, the stereochemistry of $OR^7$ will be referred to as "anti".

The term "alkyl", alone or in combination with any other term, refers to a straight-chain or branch-chain saturated aliphatic hydrocarbon radical containing the specified number of carbon atoms, or where no number is specified, preferably from 1 to about 15 and more preferably from 1 to about 10 carbon atoms. Examples of alkyl radicals include, but are not limited to, methyl, ethyl, n-propyl, isopropyl, n-butyl, isobutyl, sec-butyl, tert-butyl, pentyl, isoamyl, n-hexyl and the like.

The term "alkenyl," alone or in combination with any other term, refers to a straight-chain or branched-chain mono- or poly-unsaturated aliphatic hydrocarbon radical containing the specified number of carbon atoms, or where no number is specified, preferably from 2 to about 18 carbon atoms and more preferably, from 2 to about 8 carbon atoms. Examples of alkenyl radicals include, but are not limited to, ethenyl, propenyl, isopropenyl, 1,4-butadienyl, pentenyl and the like.

The term "alkynyl," alone or in combination with any other term, refers to a straight-chain or branched-chain hydrocarbon radical having one or more triple bonds containing the specified number of carbon atoms, or where no number is specified, preferably from 2 to about 18 carbon atoms and more preferably, from 2 to about 8 carbon atoms. Examples of alkynyl radicals include, but are not limited to, ethynyl, propynyl, isopropynyl, butynyl, pentynyl and the like.

The term "alkoxy" refers to an alkyl ether radical, wherein the term "alkyl" is defined above. Examples of suitable alkyl ether radicals include, but are not limited to, methoxy, ethoxy, n-propoxy, isopropoxy, n-butoxy, isobutoxy, sec-butoxy, tert-butoxy and the like.

The term "aryl," alone or in combination with any other term, refers to a carbocyclic aromatic radical (such as phenyl or naphthyl) containing the specified number of carbon atoms, preferably from 6-15 carbon atoms, and more preferably from 6-10 carbon atoms, optionally substituted with one or more substituents selected from C1-6 alkoxy, (for example methoxy), nitro, halogen, (for example chloro), amino, carboxylate and hydroxy. Examples of aryl radicals include, but are not limited to phenyl, naphthyl, indenyl, indanyl, azulenyl, fluorenyl, anthracenyl and the like.

The term "heterocyclyl" or "heterocycle" refers to a stable 3-7 membered monocyclic heterocyclic ring or 8-11 membered bicyclic heterocyclic ring which is either saturated or unsaturated, and which may be optionally benzofused if monocyclic. Each heterocycle consists of one or more carbon atoms and from one to four heteroatoms selected from the group consisting of nitrogen, oxygen and sulfur. As used herein, the terms "nitrogen and sulfur heteroatoms" include any oxidized form of nitrogen and sulfur, and the quaternized form of any basic nitrogen. A heterocyclyl radical may be attached at any endocyclic carbon or heteroatom which results in the creation of a stable structure. Preferred heterocycles include 5-7 membered monocyclic heterocycles and 8-10 membered bicyclic heterocycles. Examples of such groups include imidazolyl, imidazolinoyl, imidazolidinyl, quinolyl, isoqinolyl, indolyl, indazolyl, indazolinolyl, perhydropyridazyl, pyridazyl, pyridyl, pyrrolyl, pyrrolinyl, pyrrolidinyl, pyrazolyl, pyrazinyl, quinoxolyl, piperidinyl, pyranyl, pyrazolinyl, piperazinyl, pyrimidinyl, pyridazinyl, morpholinyl, thiamorpholinyl, furyl, thienyl, triazolyl, thiazolyl, carbolinyl, tetrazolyl, thiazolidinyl, benzofuranoyl, thiamorpholinyl sulfone, oxazolyl, benzoxazolyl, oxopiperidinyl, oxopyrrolidinyl, oxoazepinyl, azepinyl, isoxozolyl, isothiazolyl, furazanyl, tetrahydropyranyl, tetrahydrofuranyl, thiazolyl, thiadiazoyl, dioxolyl, dioxinyl, oxathiolyl, benzodioxolyl, dithiolyl, thiophenyl, tetrahydrothiophenyl, sulfolanyl, dioxanyl, dioxolanyl, tetahydrofurodihydrofuranyl, tetrahydropyranodihydrofuranyl, dihydropyranyl, tetradyrofurofuranyl and tetrahydropyranofuranyl.

The term "pharmaceutically effective amount" refers to an amount effective in treating a virus infection, for example an HIV infection, in a patient either as monotherapy or in combination with other agents. The term "treating" as used herein refers to the alleviation of symptoms of a particular disorder in a patient or the improvement of an ascertainable measurement associated with a particular disorder. The term "prophylactically effective amount" refers to an amount effective in preventing a virus infection, for example an HIV infection, in a patient. As used herein, the term "patient" refers to a mammal, including a human.

The terms "HIV protease" and "HIV aspartyl protease" are used interchangeably and refer to the aspartyl protease encoded by the human immunodeficiency virus type 1 or 2. In a preferred embodiment of this invention, these terms refer to the human immunodeficiency virus type 1 aspartyl protease.

The term "thiocarbamates" refers to compounds containing the functional group N—$SO_2$—O.

Combinations of substituents and variables envisioned by this invention are only those that result in the formation of stable compounds. The term "stable", as used herein, refers to compounds which possess stability sufficient to allow manufacture and administration to a mammal by methods known in the art. Typically, such compounds are stable at a temperature of 40° C. or less, in the absence of moisture or other chemically reactive conditions, for at least a week.

This invention also envisions the quaternization of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

The novel sulfonamides of this invention are those of formula I:

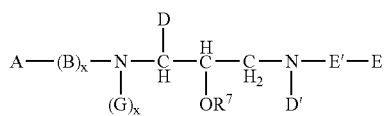

(I)

wherein:

E' is —CO— or —SO$_2$—;

A is selected from H; Ht; —R$^1$-Ht; —R$^1$—C$_1$-C$_6$ alkyl, which is optionally substituted with one or more groups independently selected from hydroxy, C$_1$-C$_4$ alkoxy, Ht, —O-Ht, —NR$^2$—CO—N(R$^2$)$_2$; —SO$_2$—R$^2$ or —CO—N(R$^2$)$_2$; —R$^1$—C$_2$-C$_6$ alkenyl, which is optionally substituted with one or more groups independently selected from hydroxy, C$_1$-C$_4$ alkoxy, Ht, —O-Ht, —NR$^2$—CO—N(R$^2$)$_2$ or —CO—N(R$^2$)$_2$; or R$^7$;

each R$^1$ is independently selected from —C(O)—, —S(O)$_2$—, —C(O)—C(O)—, —O—C(O)—, —O—S(O)$_2$, —NR$^2$—S(O)$_2$—, —NR$^2$—C(O)— or —NR$^2$—C(O)—C(O)—;

each Ht is independently selected from C$_3$-C$_7$ cycloalkyl; C$_5$-C$_7$ cycloalkenyl; C$_6$-C$_{14}$ aryl; or a 5-7 membered saturated or unsaturated heterocycle, containing one or more heteroatoms selected from N, O, or S; wherein said aryl or said heterocycle is optionally fused to Q; and wherein any member of said Ht is optionally substituted with one or more substituents independently selected from oxo, —OR$^2$, SR$^2$, —R$^2$, —N(R$^2$)(R$^2$), —R$^2$—OH, —CN, —CO$_2$R$^2$, —C(O)—N(R$^2$)$_2$, —S(O)$_2$—N(R$^2$)$_2$, —N(R$^2$)—C(O)—R$^2$, —N(R$^2$)—C(O)O—R$^2$, —C(O)—R$^2$, —S(O)$_n$—R$^2$, —OCF$_3$, —S(O)$_n$-Q, methylenedioxy, —N(R$^2$)—S(O)$_2$(R$^2$), halo, —CF$_3$, —NO$_2$, Q, —OQ, —OR$^7$, —SR$^7$, —R$^7$, —N(R$^2$)(R$^7$) or —N(R$^7$)$_2$;

each Q is independently selected from a 3-7 membered saturated, partially saturated or unsaturated carbocyclic ring system; or a 5-7 membered saturated, partially saturated or unsaturated heterocyclic ring containing one or more heteroatoms selected from O, N, or S; wherein Q is optionally substituted with one or more groups selected from oxo, —OR$^2$, —R$^2$, —SO$_2$R$^2$, —SO$_2$—N(R$^2$)$_2$, —N(R$^2$)$_2$, —N(R$^2$)—C(O)—R$^2$, —R$^2$—OH, —CN, —CO$_2$R$^2$, —C(O)—N(R$^2$)$_2$, halo, —CF$_3$;

each R$^2$ is independently selected from H, or C$_1$-C$_4$ alkyl, and wherein said alkyl, when not a substituent of Q, is optionally substituted with Q or —OR$^3$; wherein when said R$^2$ is an —OR$^3$ substituted moiety, said R$^3$ in —OR$^3$ may not be —OR$^2$ substituted;

B, when present, is —N(R$^2$)—C(R$^3$)$_2$—C(O)—;

each x is independently 0 or 1;

each R$^3$ is independently selected from H, Ht, C$_1$-C$_6$ alkyl, C$_2$-C$_6$ alkenyl, C$_2$-C$_6$ alkynyl, C$_3$-C$_6$ cycloalkyl or C$_5$-C$_6$ cycloalkenyl; wherein any member of said R$^3$, except H, is optionally substituted with one or more substituents selected from —OR$^2$, —C(O)—NH—R$^2$, —S(O)$_n$—N(R$^2$)(R$^2$), —N(R$^2$)$_2$, —N(R$^2$)—C(O)—O(R$^2$), —N(R$^2$)—C(O)—N(R$^2$), —N(R$^2$)—C(O)—(R$^2$), Ht, —CN, —SR$^2$, —CO$_2$R$^2$, or NR$^2$—C(O)—R$^2$;

each n is independently 1 or 2;

G, when present, is selected from H, R$^7$ or C$_1$-C$_4$ alkyl, or, when G is C$_1$-C$_4$ alkyl, G and R$^7$ are optionally bound to one another either directly or through a C$_1$-C$_3$ linker to form a heterocyclic ring; or when G is not present, the nitrogen to which G is attached is bound directly to the R$^7$ group in —OR$^7$ with the concomitant displacement of one -ZM group from R$^7$;

D is selected from Q; C$_1$-C$_6$ alkyl optionally substituted with one or more groups selected from C$_3$-C$_6$ cycloalkyl, —OR$^2$, —S-Ht, —R$^3$, —O-Q or Q; C$_2$-C$_4$ alkenyl optionally substituted with one or more groups selected from —OR$^2$, —S-Ht, —R$^3$, —O-Q or Q; C$_3$-C$_6$ cycloalkyl optionally substituted with or fused to Q; or C$_5$-C$_6$ cycloalkenyl optionally substituted with or fused to Q;

D' is selected from C$_1$-C$_{15}$ alkyl, C$_2$-C$_{15}$ alkenyl or C$_2$-C$_{15}$ alkynyl, each of which contains one or more substituents selected from oxo, halo, —CF$_3$, —OCF$_3$, —NO$_2$, azido, —SH, —SR$^3$, —N(R$^3$)—N(R$^3$)$_2$, —O—N(R$^3$)$_2$, —(R$^3$)N—O—(R$^3$), —N(R$^3$)$_2$, —CN, —CO$_2$R$^3$, —C(O)—N(R$^3$)$_2$, —S(O)$_n$—N(R$^3$)$_2$, —N(R$^3$)—C(O)—R$^3$, —N(R$^3$)—C(O)—N(R$^3$)$_2$, —N(R$^3$)—C(O)—S(R$^3$), —C(O)—R$^3$, —S(O)$_n$—R$^3$, —N(R$^3$)—S(O)$_n$(R$^3$), —N(R$^3$)—S(O)$_n$—N(R$^3$)$_2$, —S—NR$^3$—C(O)R$^3$, —C(S)N(R$^3$)$_2$, —C(S)R$^3$, —NR$^3$—C(O)OR$^3$, —O—C(O)OR$^3$, —O—C(O)N(R$^3$)$_2$, —NR$^3$—C(S)R$^3$, =N—OH, =N—OR$^3$, =N—N(R$^3$)$_2$, =NR$^3$, =NNR$^3$C(O)N(R$^3$)$_2$, =NNR$^3$C(O)OR$^3$, =NNR$^3$S(O)$_n$—N(R$^3$)$_2$, —NR$^3$—C(S)OR$^3$, —NR$^3$—C(S)N(R$^3$)$_2$, —NR$^3$—C[=N(R$^3$)]—N(R$^3$)$_2$, —N(R$^3$)—C[=N—NO$_2$]—N(R$^3$)$_2$, —N(R$^3$)—C[=N—NO$_2$]—OR$^3$, —N(R$^3$)—C[=N—CN]—OR$^3$, —N(R$^3$)—C[=N—CN]—(R$^3$)$_2$, —OC(O)R$^3$, —OC(S)R$^3$, —OC(O)N(R$^3$)$_2$, —C(O)N(R$^3$)—N(R$^3$)$_2$, —O—C(O)N(R$^3$)—N(R$^3$)$_2$, O—C(O)N(OR$^3$)(R$^3$), N(R$^3$)—N(R$^3$)C(O)R$^3$, N(R$^3$)—OC(O)R$^3$, N(R$^3$)—OC(O)R$^3$, N(R$^3$)—OC(O)R$^3$, —OC(S)N(R$^3$)$_2$, —OC(S)N(R$^3$)(R$^3$), or PO$_3$—R$^3$; with the proviso that when R$^7$ is H, E' is —SO$_2$—, G is H or alkyl, and when B is present or when B is not present and R$^1$ is —C(O)—, D' may not be C$_1$-C$_{15}$alkyl substituted with one substituent selected from —N(R$^3$)$_2$, —SR$^3$ or —S(O)$_n$—R$^3$, or substituted with two —N(R$^3$)$_2$ substituents;

E is selected from Ht; O-Ht; Ht-Ht; Ht fused with Ht; —O—R$^3$; —N(R$^2$)(R$^3$); C$_1$-C$_6$ alkyl optionally substituted with one or more groups selected from R$^4$ or Ht; C$_2$-C$_6$ alkenyl optionally substituted with one or more groups selected from R$^4$ or Ht; C$_3$-C$_6$ saturated carbocycle optionally substituted with one or more groups selected from R$^4$ or Ht; or C$_5$-C$_6$ unsaturated carbocycle optionally substituted with one or more groups selected from R$^4$ or Ht;

each R$^4$ is independently selected from —OR$^2$, —OR$^3$, —SR$^2$, —SOR$^2$, —SO$_2$R$^2$, —CO$_2$R$^2$, —C(O)—NHR$^2$, —C(O)—N(R$^2$)$_2$, —C(O)—NR$^2$(OR$^2$), —S(O)$_2$—NHR$^2$, halo, —NR$^2$—C(O)—R$^2$, —N(R$^2$)$_2$ or —CN;

each R⁷ is independently selected from hydrogen,

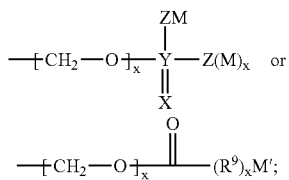

wherein each M is independently selected from H, Li, Na, K, Mg, Ca, Ba, —N(R²)₄, C₁-C₁₂-alkyl, C₂-C₁₂-alkenyl, or —R⁶; wherein 1 to 4 —CH₂ radicals of the alkyl or alkenyl group, other than the —CH₂ that is bound to Z, is optionally replaced by a heteroatom group selected from O, S(O), S(O)₂, or N(R²); and wherein any hydrogen in said alkyl, alkenyl or R⁶ is optionally replaced with a substituent selected from oxo, —OR², —R², N(R²)₂, N(R²)₃, R²OH, —CN, —CO₂R², —C(O)—N(R²)₂, S(O)₂—N(R²)₂, N(R²)—C(O)—R², C(O) R², —S(O)ₙ—R², OCF₃, —S(O)ₙ—R⁶, N(R²)—S(O)₂(R²), halo, —CF₃, or —NO₂;

M' is H, C₁-C₁₂-alkyl, C₂-C₁₂-alkenyl, or —R⁶; wherein 1 to 4 —CH₂ radicals of the alkyl or alkenyl group is optionally replaced by a heteroatom group selected from O, S, S(O), S(O)₂, or N(R²); and wherein any hydrogen in said alkyl, alkenyl or R⁶ is optionally replaced with a substituent selected from oxo, —OR², —R², —N(R²)₂, N(R²)₃, —R²OH, —CN, —CO₂R², —C(O)—N(R²)₂, —S(O)₂—N(R²)₂, —N(R²)—C(O)—R₂, —C(O)R², —S(O)ₙ—R², —OCF₃, —S(O)ₙ—R⁶, —N(R²)—S (O)₂ (R²), halo, —CF₃, or —NO₂;

Z is O, S, N(R²)₂, or, when M is not present, H.

Y is P or S;

X is O or S;

R⁹ is C(R²)₂, O or N(R²); and wherein when Y is S, Z is not S;

R⁶ is a 5-6 membered saturated, partially saturated or unsaturated carbocyclic or heterocyclic ring system, or an 8-10 membered saturated, partially saturated or unsaturated bicyclic ring system; wherein any of said heterocyclic ring systems contains one or more heteroatoms selected from O, N, S, S(O)ₙ or N(R²); and wherein any of said ring systems optionally contains 1 to 4 substituents independently selected from OH, C₁-C₄ alkyl, —O—C₁-C₄ alkyl or —O—C(O)—C₁-C₄ alkyl; and each R⁵ is independently selected from hydrogen, C₁-C₈ alkyl, C₂-C₈ alkenyl, C₂-C₈ alkynyl or Ht, wherein any R⁵, except for hydrogen, is optionally substituted with —CF₃, —PO₃R³, azido or halo.

Preferably, at least one R⁷ is selected from:

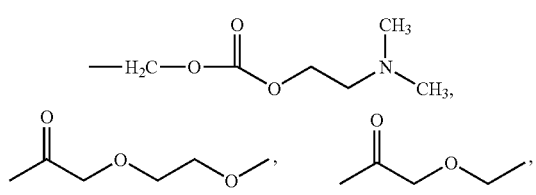

-(L)-lysine, —PO₃Na₂,

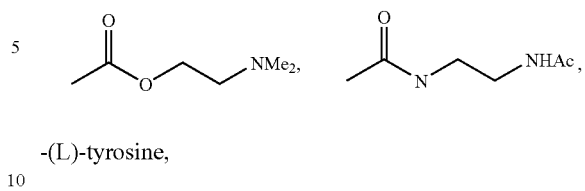

-(L)-tyrosine,

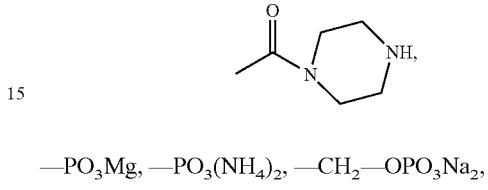

—PO₃Mg, —PO₃(NH₄)₂, —CH₂—OPO₃Na₂,

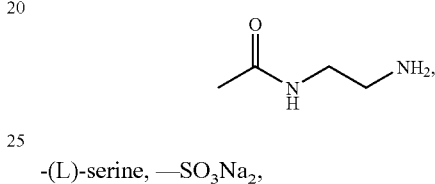

-(L)-serine, —SO₃Na₂,

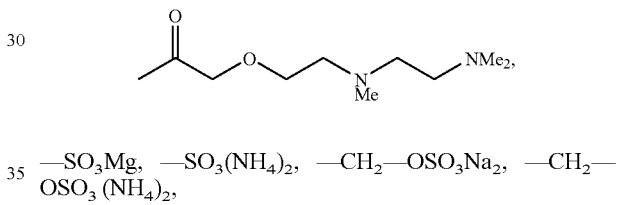

—SO₃Mg, —SO₃(NH₄)₂, —CH₂—OSO₃Na₂, —CH₂—OSO₃(NH₄)₂,

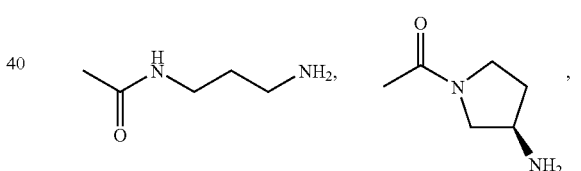

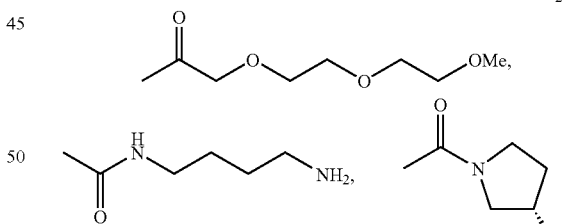

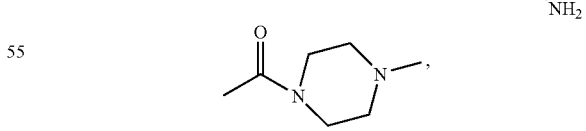

acetyl,

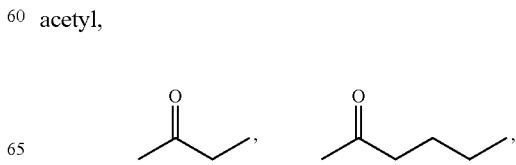

-(L)-valine, -(L)-glutamic acid, -(L)-aspartic acid, -(L)-γ-t-butyl-aspartic acid,

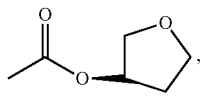

-(L)-(L)-3-pyridylalanine, -(L)-histidine, —CHO,

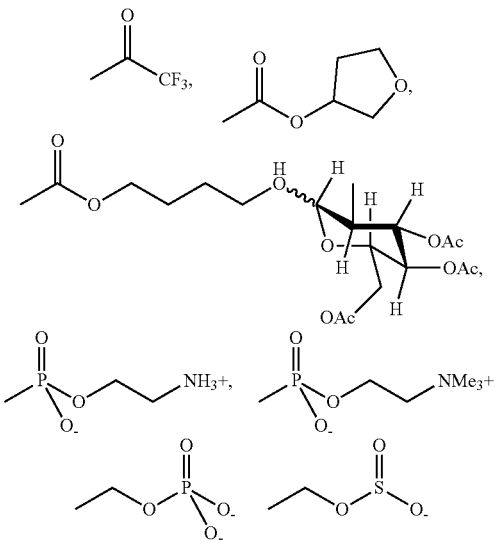

$PO_3K_2$, $PO_3Ca$, $PO_3$-spermine, $PO_3$— (spermidine)$_2$ or $PO_3$— (meglamine)$_2$.

It will be understood by those of skill in the art that component M or M' in the formulae set forth herein will have either a covalent, a covalent/zwitterionic, or an ionic association with either Z or $R^9$ depending upon the actual choice for M or M'. When M or M' is hydrogen, alkyl, alkenyl, or $R^6$, M or M' is covalently bound to $R^9$ or Z. If M is a mono- or bivalent metal or other charged species (i.e., $NH_4^+$), there is an ionic interaction between M and Z and the resulting compound is a salt.

When x is 0 in $(M)_x$, Z may be a charged species. When that occurs, the other M may be oppositely charged to produce a 0 net charge on the molecule. Alternatively, the counter ion may located elsewhere in the molecule.

According to another preferred embodiment, E' is $SO_2$.

According to yet another preferred embodiment, A-$(B)_x$ is R'—C(O), wherein R' is selected from any of the R' groups indicated in Tables 1 and 2, below. More preferably, R' is selected from:

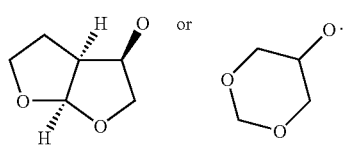

In another preferred embodiment, D' is —CH$_2$—R", wherein R" is selected from any of the R" groups indicated in Tables 1 and 2, below. More preferably, R" is selected from:

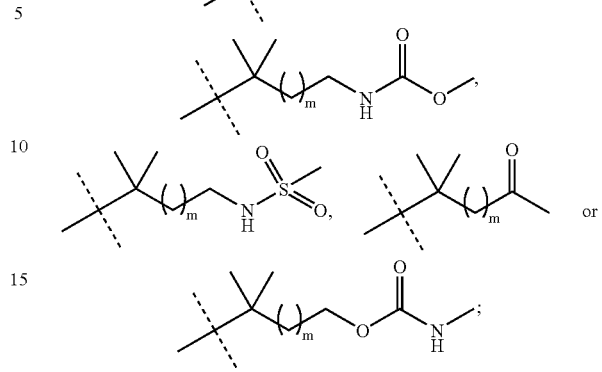

wherein m is 0 to 3.

According to another preferred embodiment, E is selected from any of the E groups indicated in Tables 1 and 2, below. More preferably, E is selected from:

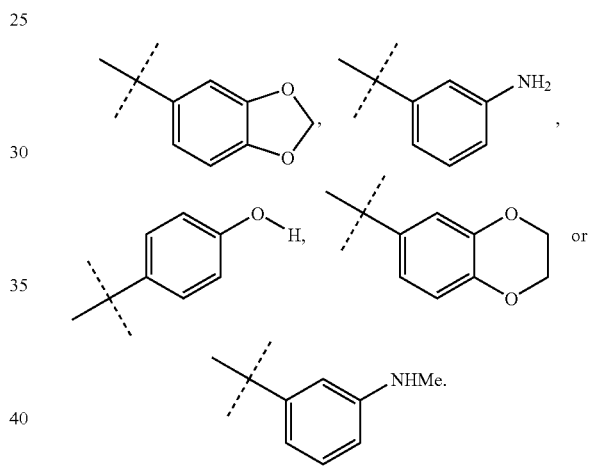

A more preferred compound of this invention is formula IA:

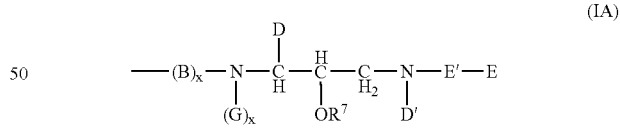

(IA)

wherein:
E' is —CO— or —SO$_2$—;
D' is selected from $C_{1-15}$ alkyl, $C_{2-15}$ alkenyl or $C_2$-$C_{15}$ alkynyl, wherein D' is substituted with one to two —CN groups and is optionally substituted with $C_3$-$C_8$ cycloalkyl; and
A, B, D, E, G, $R^7$, and x are defined as above for formula I.

In one embodiment of the more preferred compound of this invention represented by formula IA, D' is selected from $C_{1-15}$ alkyl or $C_{2-15}$ alkenyl; each of which is substituted with one to two —CN groups and each of which is optionally substituted with $C_3$-$C_8$ cycloalkyl.

In another embodiment of the more preferred compound of this invention represented by formula IA, D' is $C_2$-$C_{15}$ alkynyl which is substituted with one to two —CN groups and each of which is optionally substituted with $C_3$-$C_8$ cycloalkyl.

Another preferred compound of this invention is represented by formula IB:

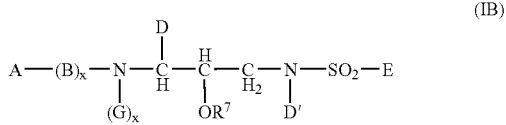

(IB)

wherein:

D' is selected from $C_1$-$C_{15}$ alkyl, $C_2$-$C_{15}$ alkenyl or $C_2$-$C_{15}$ alkynyl, each of which contains one or more substituents selected from oxo, halo, —$CF_3$, —$OCF_3$, —$NO_2$, azido, —SH, —$SR^3$, —N($R^3$)—N($R^3$)$_2$, —O—N($R^3$)$_2$, —($R^3$)N—O—($R^3$), —N($R^3$)$_2$, —$CO_2R^3$, —C(O)—N($R^3$)$_2$, —S(O)$_n$—N($R^3$)$_2$, —N($R^3$)—C(O)—$R^3$, —N($R^3$)—C(O)—N($R^3$)$_2$, —N($R^3$)—C(O)—S($R^3$), —C(O)—$R^3$, —S(O)$_n$—$R^3$, —N($R^3$)—S(O)$_n$($R^3$), —N($R^3$)—S(O)$_n$—N($R^3$)$_2$, —S—$NR^3$—C(O)$R^3$, —C(S)N($R^3$)$_2$, —C(S)$R^3$, —$NR^3$—C(O)$OR^3$, —O—C(O)$OR^3$, —O—C(O)N($R^3$)$_2$, —$NR^3$—C(S)$R^3$, =N—OH, =N—$OR^3$, =N—N($R^3$)$_2$, =$NR^3$, =$NNR^3$C(O)N($R^3$)$_2$, =$NNR^3$C(O)$OR^3$, =$NNR^3$S(O)$_n$—N($R^3$)$_2$, —$NR^3$—C(S)$OR^3$, —$NR^3$—C(S)N($R^3$)$_2$, —$NR^3$—C[=N($R^3$)]—N($R^3$)$_2$, —N($R^3$)—C[=N—$NO_2$]—N($R^3$)$_2$, —N($R^3$)—C[=N—$NO_2$]—$OR^3$, —N($R^3$)—C[=N—CN]—$OR^3$, —N($R^3$)—C[=N—CN]—($R^3$)$_2$, —OC(O)$R^3$, —OC(S)$R^3$, —OC(O)N($R^3$)$_2$, —C(O)N($R^3$)—N($R^3$)$_2$, —O—C(O)N($R^3$)—N($R^3$)$_2$, O—C(O)N($OR^3$)($R^3$), N($R^3$)—N($R^3$)C(O)$R^3$, N($R^3$)—OC(O)$R^3$, N($R^3$)—OC(O)$R^3$, N($R^3$)—OC(O)$R^3$, —OC(S)N($R^3$)$_2$, —OC(S)N($R^3$)($R^3$) or $PO_3$—$R^3$; with the proviso that when $R^7$ is H, E' is —$SO_2$, G is H or alkyl, and when B is present or when B is not present and $R^1$ is —C(O)—, D' may not be $C_1$-$C_{15}$alkyl substituted with one substituent selected from —N($R^3$)$_2$, —$SR^3$ or —S(O)$_n$—$R^3$, or substituted with two —N($R^3$)$_2$ substituents; and A, B, D, E, G, $R^7$ and x are defined as above for formula I.

In one embodiment of the more preferred compound of this invention represented by formula IB, D' is selected from $C_1$-$C_{15}$ alkyl or $C_2$-$C_{15}$ alkenyl, each of which contains one or more substituents selected from oxo, halo, —$CF_3$, —$OCF_3$, —$NO_2$, azido, —N($R^3$)—N($R^3$)$_2$, —O—N($R^3$)$_2$, —($R^3$)N—O—($R^3$), —N($R^3$)$_2$, —N($R^3$)—C(O)—N($R^3$)$_2$, —N($R^3$)—C(O)—S($R^3$), —C(O)—$R^3$, —S(O)$_n$—$R^3$, —N($R^3$)—S(O)$_n$($R^3$), —N($R^3$)—S(O)$_n$—N($R^3$)$_2$, —S—$NR^3$—C(O)$R^3$, —C(S)N($R^3$)$_2$, —C(S)$R^3$, —$NR^3$—C(O)$OR^3$, —O—C(O)$OR^3$, —O—C(O)N($R^3$)$_2$, —$NR^3$—C(S)$R^3$, =N—OH, =N—$OR^3$, =N—N($R^3$)$_2$, =$NR^3$, =$NNR^3$C(O)N($R^3$)$_2$, =$NNR^3$C(O)$OR^3$, =$NNR^3$S(O)$_n$—N($R^3$)$_2$, —$NR^3$—C(S)$OR^3$, —$NR^3$—C(S)N($R^3$)$_2$, —$NR^3$—C[=N($R^3$)]—N($R^3$)$_2$, —N($R^3$)—C[=N—$NO_2$]—N($R^3$)$_2$, —N($R^3$)—C[=N—$NO_2$]—$OR^3$, —N($R^3$)—C[=N—CN]—$OR^3$, —N($R^3$)—C[=N—CN]—($R^3$)$_2$, —OC(O)$R^3$, —OC(S)$R^3$, —OC(O)N($R^3$)$_2$, —C(O)N($R^3$)—N($R^3$)$_2$, —O—C(O)N($R^3$)—N($R^3$)$_2$, O—C(O)N($OR^3$)($R^3$), N($R^3$)—N($R^3$)C(O)$R^3$, N($R^3$)—OC(O)$R^3$, N($R^3$)—OC(O)$R^3$, N($R^3$)—OC(O)$R^3$, —OC(S)N($R^3$)$_2$, —OC(S)N($R^3$)($R^3$), or $PO_3$—$R^3$; $C_2$-$C_{15}$ alkynyl which contains one or more substituents selected from oxo, halo, —$CF_3$, —$OCF_3$, —$NO_2$, azido, —SH, —$SR^3$, —N($R^3$)—N($R^3$)$_2$, —O—N($R^3$)$_2$, —($R^3$)N—O—($R^3$), —N($R^3$)$_2$, —$CO_2R^3$, —C(O)—N($R^3$)$_2$, —S(O)$_n$—N($R^3$)$_2$, —N($R^3$)—C(O)—$R^3$, —N($R^3$)—C(O)—N($R^3$)$_2$, —N($R^3$)—C(O)—S($R^3$), —C(O)—$R^3$, —S(O)$_n$—$R^3$, —N($R^3$)—S(O)$_n$($R^3$), —N($R^3$)—S(O)$_n$—N($R^3$)$_2$, —S—$NR^3$—C(O)$R^3$, —C(S)N($R^3$)$_2$, —C(S)$R^3$, —$NR^3$—C(O)$OR^3$, —O—C(O)$OR^3$, —O—C(O)N($R^3$)$_2$, —$NR^3$—C(S)$R^3$, =N—OH, =N—$OR^3$, =N—N($R^3$)$_2$, =$NR^3$, =$NNR^3$C(O)N($R^3$)$_2$, =$NNR^3$C(O)$OR^3$, $NNR^3$S(O)$_n$—N($R^3$)$_2$, —$NR^3$—C(S)$OR^3$, —$NR^3$—C(S)N($R^3$)$_2$, —$NR^3$—C[=N($R^3$)]—N($R^3$)$_2$, —N($R^3$)—C[=N—$NO_2$]—N($R^3$)$_2$, —N($R^3$)—C[=N—$NO_2$]—$OR^3$, —N($R^3$)—C[=N—CN]—$OR^3$, —N($R^3$)—C[=N—CN]—($R^3$)$_2$, —OC(O)$R^3$, —OC(S)$R^3$, —OC(O)N($R^3$)$_2$, —C(O)N($R^3$)—N($R^3$)$_2$, —O—C(O)N($R^3$)—N($R^3$)$_2$, O—C(O)N($OR^3$)($R^3$), N($R^3$)—N($R^3$)C(O)$R^3$, N($R^3$)—OC(O)$R^3$, N($R^3$)—OC(O)$R^3$, N($R^3$)—OC(O)$R^3$, —OC(S)N($R^3$)$_2$, —OC(S)N($R^3$)($R^3$), or $PO_3$—$R^3$; with the proviso that when $R^7$ is H, E' is —$SO_2$—, G is H or alkyl, and when B is present or when B is not present and $R^1$ is —C(O)—, D' may not be $C_1$-$C_{15}$ alkyl substituted with one substituent selected from —N($R^3$)$_2$ or —S(O)$_n$—$R^3$, or substituted with two —N($R^3$)$_2$ substituents.

In another embodiment of the more preferred compound of this invention represented by formula IB, D' is selected from $C_1$-$C_{15}$ alkyl or $C_2$-$C_{15}$ alkenyl, each of which contains one or more substituents selected from —SH, —$SR^3$, —$CO_2R^3$, —C(O)—N($R^3$)$_2$, —S(O)$_n$—N($R^3$)$_2$ or —N($R^3$)—C(O)—$R^3$; with the proviso that when $R^7$ is H, E' is —$SO_2$—, G is H or alkyl, and when B is present or when B is not present and $R^1$ is —C(O)—, D' may not be $C_1$-$C_{15}$ alkyl substituted with one substituent selected from —$SR^3$.

More preferred compounds of formula I are those represented by formula II, formula III or formula IV:

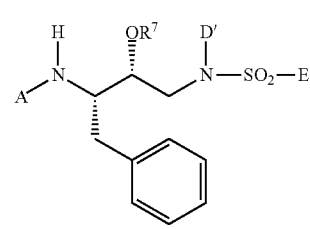

(II)

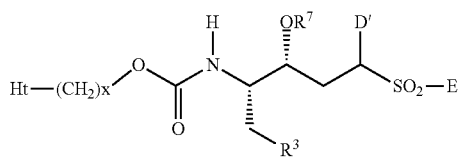

(III)

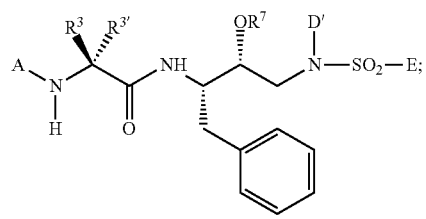

(IV)

wherein A, D', E, $R^3$, $R^7$, Ht and x are as defined for compounds of Formula I, above. For ease of reference, the two $R^3$ moieties present in formula IV have been labeled $R^3$ and $R^{3'}$ and wherein $R^{3'}$ is selected from H, Ht, $C_1$-$C_6$ alkyl, $C_2$-$C_6$ alkenyl, $C_3$-$C_6$ cycloalkyl or $C_5$-$C_6$ cycloalkenyl; wherein any member of said $R^3$, except H, is optionally substituted with one or more substituents selected from —$OR^2$, —C(O)—NH—$R^2$, —S(O)$_n$—N($R^2$)($R^2$), —N($R^2$)$_2$, —N(R²)—C(O)—O(R²), —N(R²)—C(O)—N(R²), —N(R²)—C(O)—(R²), —N(R²—OR²)₂, —C(O)-Ht, Ht, —CN, —SR², —CO₂R², or NR²—C(O)—R².

For compounds of formula II, more preferred compounds are those wherein:

A is —C(O)Ht;

E is $C_6$-$C_{10}$ aryl optionally substituted with one or more substituents selected from oxo, —OR², SR², —R², —N(R²)₂, —R²—OH, —CN, —CO₂R², —C(O)—N(R²)₂, —S(O)₂₋ₙ₍ᵣ²₎₂, —N(R²)—C(O)—R², —C(O)—R², —S(O)ₙ—R², —OCF₃, —S(O)ₙ-Q, methylenedioxy, —N(R²)—S(O)₂(R²), halo, —CF₃, —NO₂, Q, —OQ, —OR⁷, —SR⁷, —R⁷, —N(R²)(R⁷) or —N(R⁷)₂; or a 5-membered heterocyclic ring containing one S and optionally containing N as an additional heteroatom, wherein said heterocyclic ring is optionally substituted with one to two groups independently selected from —CH₃, R⁴, or Ht.

Another preferred embodiment of compounds of formula II are those wherein:

E is a 5-membered heterocyclic ring containing one S and optionally containing N as an additional heteroatom, wherein said heterocyclic ring is optionally substituted with one to two groups independently selected from —CH₃, R⁴, or Ht.

More preferred are compounds of formula II set forth above, wherein R⁷ in —OR⁷ is —PO(OM)₂ or C(O)CH₂OCH₂CH₂OCH₂CH₂OCH₃ and both R⁷ in —N(R⁷)₂ are H, wherein M is H, Li, Na, K or $C_1$-$C_4$ alkyl; or wherein R⁷ in —OR⁷ is C(O)CH₂OCH₂CH₂OCH₃, one R⁷ in —N(R⁷)₂ is C(O)CH₂OCH₂CH₂OCH₃ and the other is H.

The compounds according to the invention contain one or more asymmetric carbon atoms and thus occur as racemates and racemic mixtures, single enantiomers, diastereomeric mixtures and individual diastereomers. All such isomeric forms of these compounds are expressly included in the present invention. Each stereogenic carbon may be of the R or S configuration. Although the specific compounds exemplified in this application may be depicted in a particular stereochemical configuration, compounds having either the opposite stereochemistry at any given chiral center or mixtures thereof are also envisioned.

Specific preferred compounds of the present 7invention are set forth below in Table 1.

TABLE 1

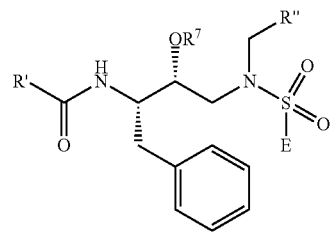

wherein R⁷ is H; and

| Compound | R' | R'' | E |
|---|---|---|---|
| 1 | tBu-O- | neopentyl-CN | 4-methoxyphenyl |
| 2 | tBu-O- | isopentyl-CN | 4-methoxyphenyl |
| 3 | tBu-O- | 3-ethylbutyl-CN | 4-methoxyphenyl |
| 4 | tBu-O- | butyl-CN | 4-methoxyphenyl |
| 5 | tBu-O- | neopentyl-CN | 3-aminophenyl |

TABLE 1-continued
wherein R⁷ is H; and
| Compound | R' | R" | E |
|---|---|---|---|
| 6 | 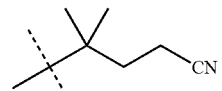 | 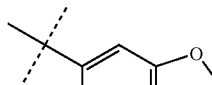 | 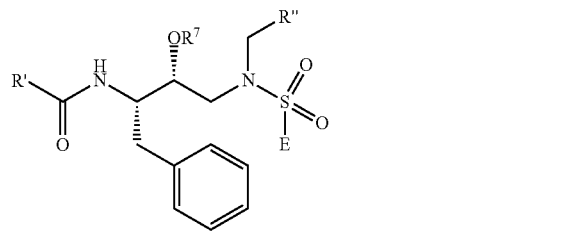 |
| 7 | 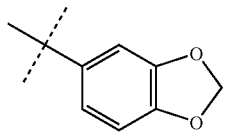 | 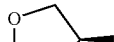 | 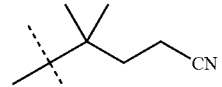 |
| 8 | 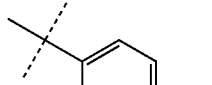 | 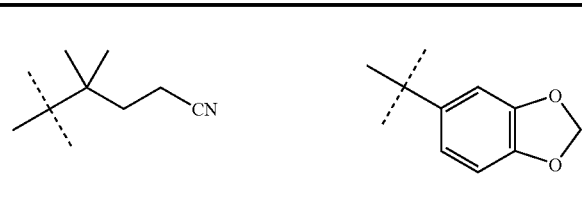 | 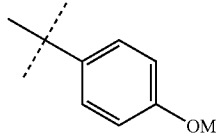 |
| 9 | 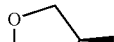 | 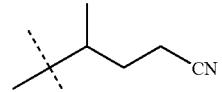 | 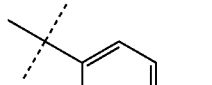 |
| 10 | 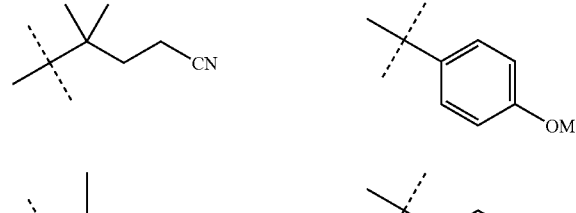 | 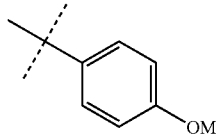 | 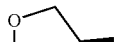 |
| 11 | 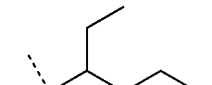 | 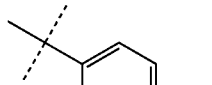 | 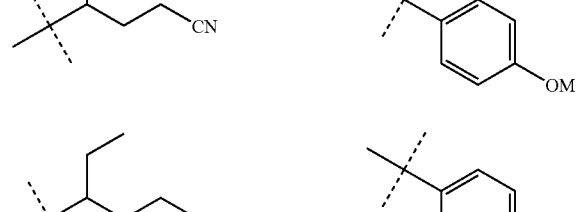 |
| 12 | 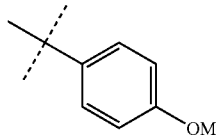 | 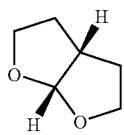 | 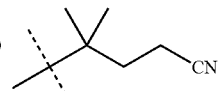 |
| 13 | 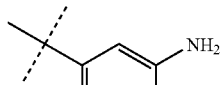 | 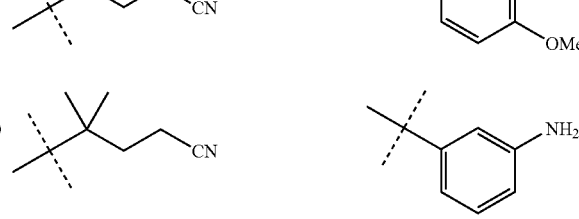 | 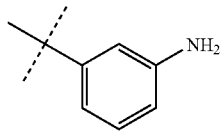 |

TABLE 1-continued

Structure: R'-C(=O)-NH-CH(CH2-Ph)-CH(OR7)-CH2-N(CH2-R")-SO2-E wherein R⁷ is H; and

| Compound | R' | R" | E |
|---|---|---|---|
| 14 | (S)-tetrahydrofuran-3-yloxy | 1-(cyanoethyl)cyclopentyl | 4-methoxyphenyl |
| 15 | (S)-tetrahydrofuran-3-yloxy | 1-(cyanoethyl)cyclohexyl | 4-methoxyphenyl |
| 16 | hexahydrofuro[3,2-b]furan-3-yloxy | 2,2-dimethyl-4-cyanobutyl | 3-aminophenyl |
| 17 | (S)-tetrahydrofuran-3-yloxy | 3-ethyl-3-(cyanoethyl)pentyl | 4-methoxyphenyl |
| 18 | (S)-tetrahydrofuran-3-yloxy | 2,2-dimethyl-5-cyanopentyl | 4-methoxyphenyl |
| 19 | 1,3-dioxan-5-yloxy | 2,2-dimethyl-4-cyanobutyl | 4-methoxyphenyl |
| 20 | hexahydrofuro[3,2-b]furan-3-yloxy | 2,2-dimethyl-4-cyanobutyl | 4-methoxyphenyl |
| 21 | hexahydrofuro[3,2-b]furan-3-yloxy | 2,2-dimethyl-4-cyanobutyl | 4-methoxyphenyl |

TABLE 1-continued wherein R⁷ is H; and

| Compound | R' | R" | E |
|---|---|---|---|
| 22 | methylsulfonyl-ethoxy | neopentyl-CH₂CN | 4-OMe-phenyl |
| 23 | hexahydrofuro[2,3-b]furan-3-yl | neopentyl-CH₂CN | 3-(N,N-dimethylamino)phenyl |
| 24 | 1,3-dioxan-5-yl | neopentyl-CH₂CN | 3-(NHMe)phenyl |
| 25 | hexahydrofuro[2,3-b]furan-3-yl | neopentyl-CH₂CN | benzo[1,3]dioxol-5-yl |
| 26 | (S)-tetrahydrofuran-3-yl | neopentyl-CH₂CH₂CN | 4-OMe-phenyl |
| 29 | hexahydrofuro[2,3-b]furan-3-yl | neopentyl-CH₂CN | 4-NHAc-phenyl |
| 30 | hexahydrofuro[2,3-b]furan-3-yl | neopentyl-CH₂CN | 3-NHAc-4-F-phenyl |
| 31 | hexahydrofuro[2,3-b]furan-3-yl | neopentyl-CH₂CN | 3-NHAc-phenyl |

TABLE 1-continued wherein R[7] is H; and

| Compound | R' | R" | E |
|---|---|---|---|
| 32 | hexahydrofuro[3,2-b]furan-3-yloxy | neopentyl-CN | 4-OBn-phenyl |
| 33 | 1,3-dioxan-5-yloxy | neopentyl-CN | 4-OBn-phenyl |
| 35 | hexahydrofuro[3,2-b]furan-3-yloxy | neopentyl-CN | 4-OH-phenyl |
| 36 | 1,3-dioxan-5-yloxy | neopentyl-CN | benzo[1,3]dioxol-5-yl |
| 37 | hexahydrofuro[3,2-b]furan-3-yloxy | neopentyl-CN | 2,3-dihydrobenzo[1,4]dioxin-6-yl |
| 38 | hexahydrofuro[3,2-b]furan-3-yloxy | gem-dimethyl-(CH$_2$)$_3$-CN | 3-(NHMe)-phenyl |
| 39 | hexahydrofuro[3,2-b]furan-3-yloxy | gem-dimethyl-(CH$_2$)$_3$-CN | benzo[1,3]dioxol-5-yl |

TABLE 1-continued wherein R⁷ is H; and

| Compound | R' | R" | E |
|---|---|---|---|
| 40 | (cis-hexahydrofuro[2,3-b]furan-3-yl)oxy | -C(CH₃)₂CH₂CH₂CN | 2,3-dihydrobenzo[1,4]dioxin-6-yl |
| 41 | (cis-hexahydrofuro[2,3-b]furan-3-yl)oxy | -C(CH₃)₂CH₂CH₂CN | 2,3-dihydrobenzo[1,4]dioxin-6-yl |
| 42 | 1,3-dioxan-5-yloxy | -C(CH₃)₂CH₂CH₂CN | 4-hydroxyphenyl |
| 43 | (cis-hexahydrofuro[2,3-b]furan-3-yl)oxy | -C(CH₃)₂CH₂CH₂CN | 3-(N-Boc-N-ethylamino)phenyl |
| 44 | (cis-hexahydrofuro[2,3-b]furan-3-yl)oxy | -C(CH₃)₂CH₂CH₂CN | 3-(ethylamino)phenyl |
| 124 | (cis-hexahydrofuro[2,3-b]furan-3-yl)oxy | -C(CH₃)₂CN | 4-methoxyphenyl |
| 125 | 1,3-dioxan-5-yloxy | -C(CH₃)₂CN | 4-methoxyphenyl |
| 127 | tert-butoxy | -C(CH₃)₂CN | 3-aminophenyl |

TABLE 1-continued wherein R⁷ is H; and

| Compound | R' | R'' | E |
|---|---|---|---|
| 203 | tert-butoxy | gem-dimethyl CH₂CH₂CH₂N₃ | 4-methoxyphenyl |
| 205 | (S)-tetrahydrofuran-3-yloxy | gem-dimethyl CH₂CH₂C(O)CH₃ | 4-methoxyphenyl |
| 206 | (S)-tetrahydrofuran-3-yloxy | CH(Et)CH₂CH₂C(O)CH₃ | 4-methoxyphenyl |
| 207 | (S)-tetrahydrofuran-3-yloxy | CH(CH₃)CH₂CH₂C(O)CH₃ | 4-methoxyphenyl |
| 208 | (S)-tetrahydrofuran-3-yloxy | C(CH₃)₂CH₂CH₂C(O)CH₃ | 4-methoxyphenyl |
| 209 | (S)-tetrahydrofuran-3-yloxy | gem-dimethyl CH₂CH₂CH₂C(O)CH₃ | 4-methoxyphenyl |
| 210 | hexahydrofuro[2,3-b]furan-3-yloxy | gem-dimethyl CH₂CH₂C(O)CH₃ | 4-methoxyphenyl |

TABLE 1-continued
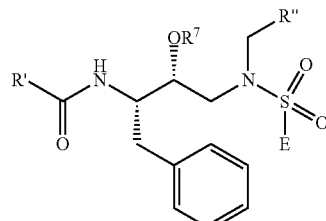
wherein R⁷ is H; and
| Compound | R' | R" | E |
|---|---|---|---|
| 211 | 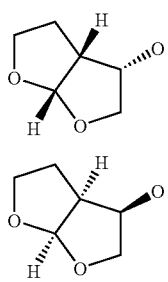 | 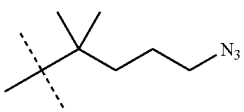 | 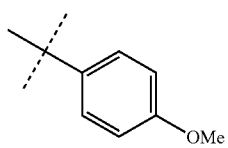 |
| 212 | 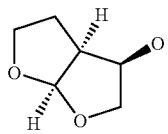 | 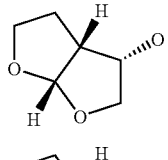 | 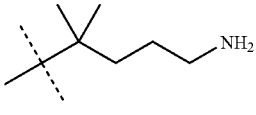 |
| 213 | 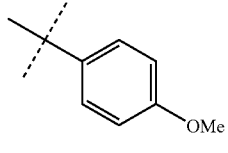 | 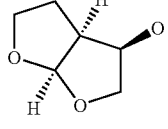 | 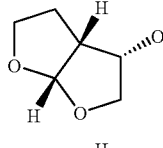 |
| 214 | 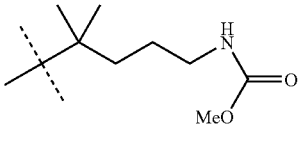 | 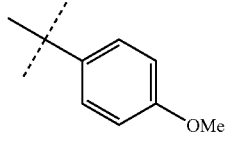 | 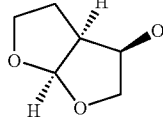 |

TABLE 1-continued wherein R⁷ is H; and

| Compound | R' | R" | E |
|---|---|---|---|
| 215 | hexahydrofuro[2,3-b]furan-3-yl | -C(CH₃)₂CH₂CH₂NHSO₂CH₃ | 4-methoxyphenyl |
| 216 | hexahydrofuro[2,3-b]furan-3-yl | -C(CH₃)₂CH₂CH₂NHC(O)NHCH₂COOEt | 4-methoxyphenyl |
| 217 | hexahydrofuro[2,3-b]furan-3-yl | -C(CH₃)₂CH₂CH₂NH₂ | 4-methoxyphenyl |
| 218 | hexahydrofuro[2,3-b]furan-3-yl | -C(CH₃)₂CH₂CH₂NHC(O)OMe | 4-methoxyphenyl |

TABLE 1-continued
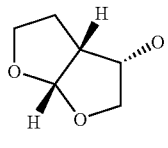
wherein R⁷ is H; and
| Compound | R' | R" | E |
|---|---|---|---|
| 219 | 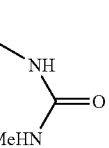 | 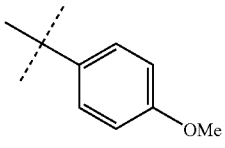 | 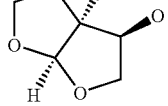 |
| 220 | 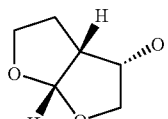 | 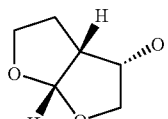 | 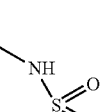 |
| 221 | 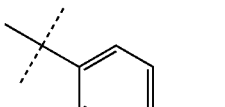 | 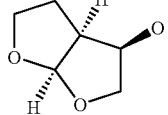 | 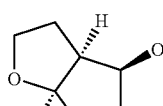 |
| 222 | 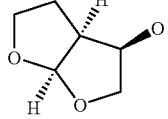 | 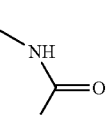 | 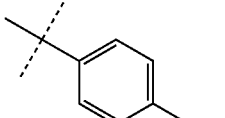 |
| 223 | 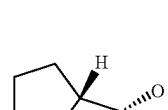 | 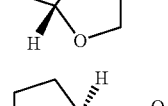 | 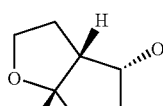 |

TABLE 1-continued
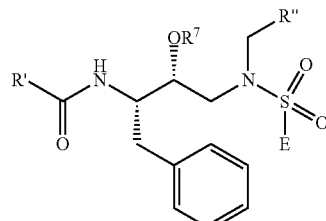
wherein R⁷ is H; and
| Compound | R' | R'' | E |
|---|---|---|---|
| 224 | 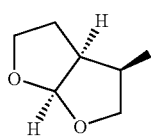 | 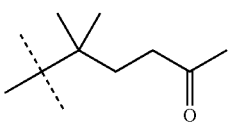 | 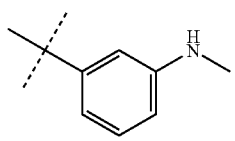 |
| 225 | 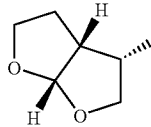 | 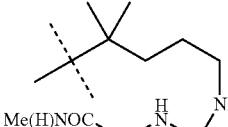 | 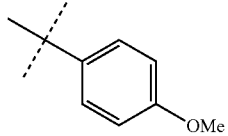 |
| 226 | 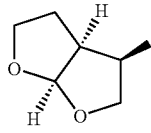 | 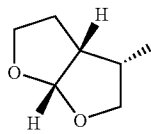 | 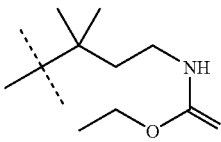 |
| 227 | 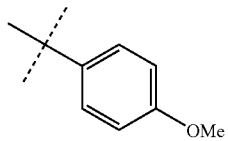 | 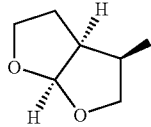 | 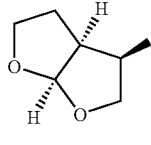 |
| 228 | 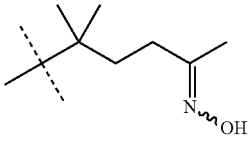 | 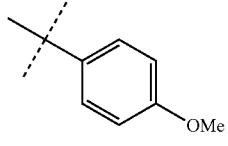 | 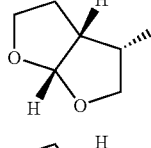 |

TABLE 1-continued
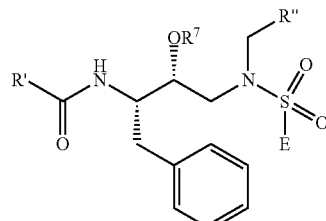
wherein R⁷ is H; and
| Compound | R' | R'' | E |
|---|---|---|---|
| 229 | 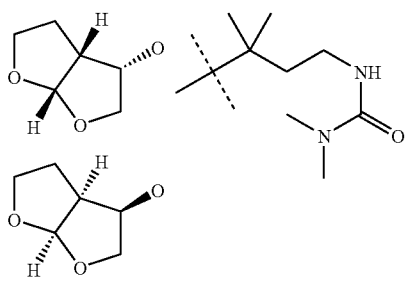 | 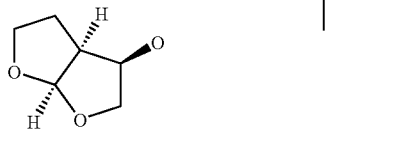 | 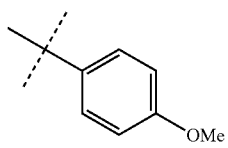 |
| 230 |  | 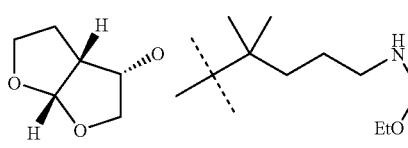 | 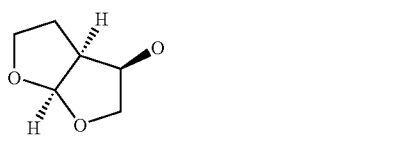 |
| 231 | 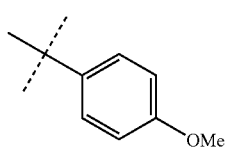 |  | 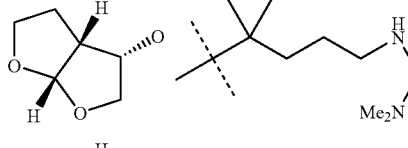 |
| 232 | 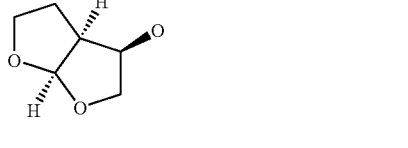 | 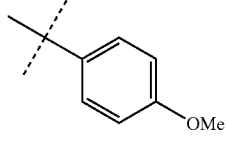 |  |

TABLE 1-continued
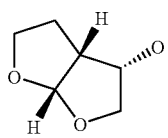
wherein R⁷ is H; and
| Compound | R' | R'' | E |
|---|---|---|---|
| 233 | 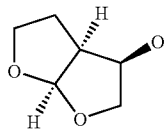 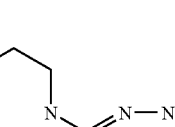 | 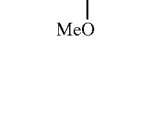 | 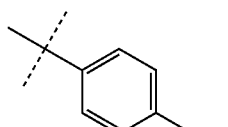 |
| 234 |  | 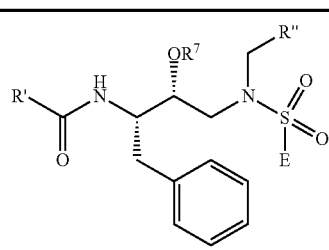 | 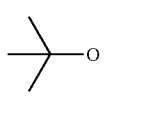 |
| 235 | 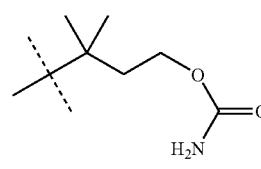 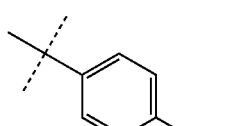 | 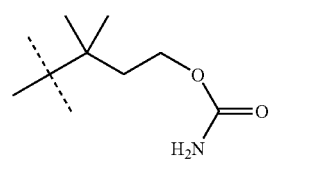 | 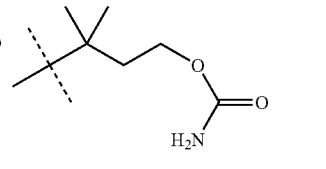 |
| 236 | 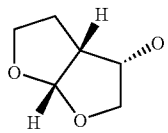 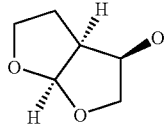 | 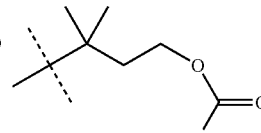 | 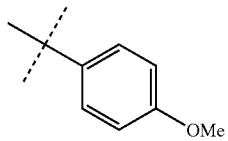 |
| 237 |  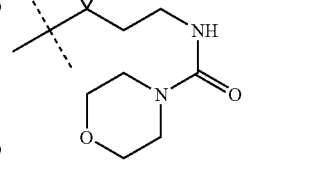 | 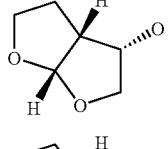 | 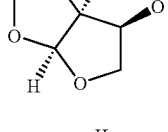 |

TABLE 1-continued
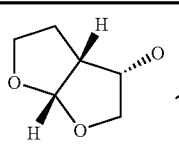
wherein R⁷ is H; and
| Compound | R' | R" | E |
|---|---|---|---|
| 238 | 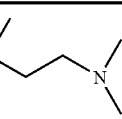 | 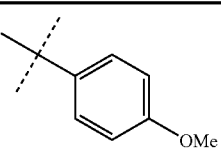 | 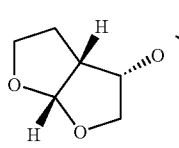 |
| 239 | 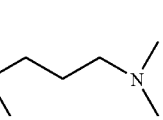 | 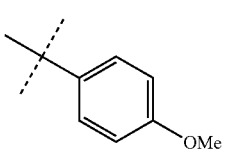 | 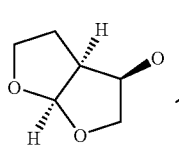 |
| 240 | 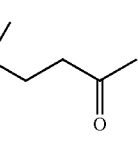 | 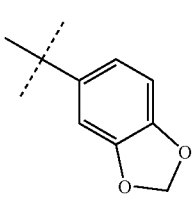 | 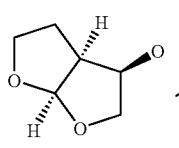 |
| 241 | 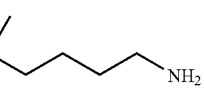 | 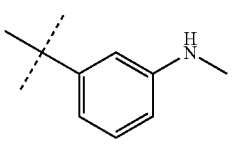 | 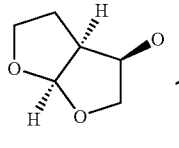 |
| 242 | 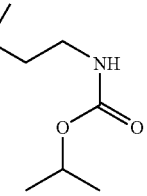 | 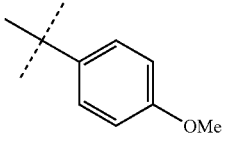 | 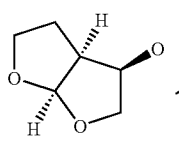 |
| 243 | 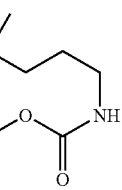 | 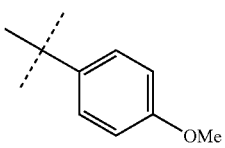 | |

TABLE 1-continued
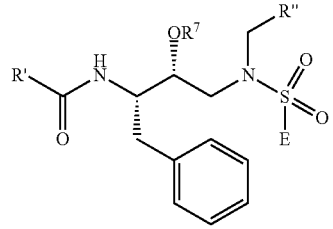
wherein R⁷ is H; and
| Compound | R' | R" | E |
|---|---|---|---|
| 244 | 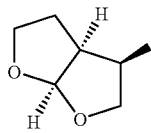 | 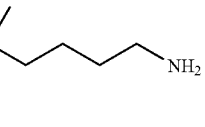 | 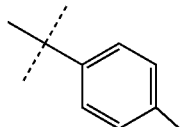 |
| 245 | 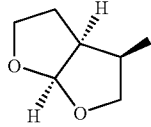 | 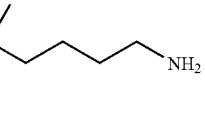 | 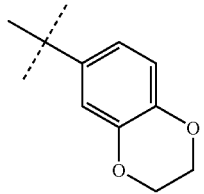 |
| 246 | 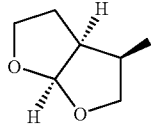 | 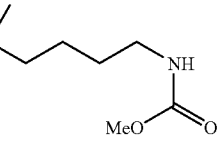 | 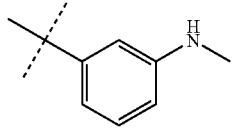 |
| 247 | 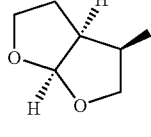 | 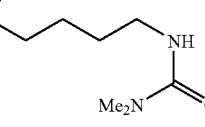 | 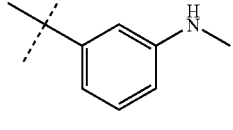 |
| 248 | 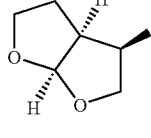 | 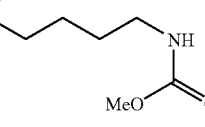 | 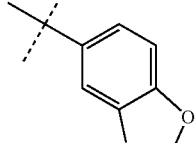 |
| 249 | 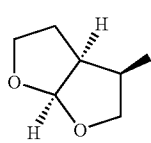 | 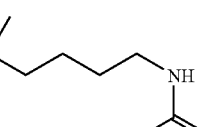 | 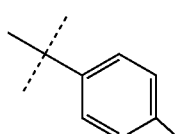 |
| 250 | 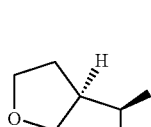 | 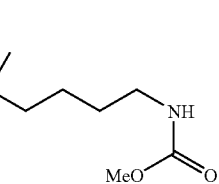 | 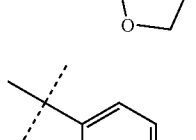 |

TABLE 1-continued wherein R⁷ is H; and

| Compound | R' | R" | E |
|---|---|---|---|
| 251 | hexahydrofuro[2,3-b]furan-3-yl | -C(CH₃)₂-CH₂CH₂CH₂-NH-C(O)-NMe₂ | 2,3-dihydro-1,4-benzodioxin-6-yl |
| 252 | hexahydrofuro[2,3-b]furan-3-yl | -C(CH₃)₂-CH₂CH₂-C(O)-CH₃ | 2,3-dihydro-1,4-benzodioxin-6-yl |
| 253 | hexahydrofuro[2,3-b]furan-3-yl | -C(CH₃)₂-CH₂CH₂-C(O)-CH₃ | 3-aminophenyl |
| 254 | hexahydrofuro[2,3-b]furan-3-yl | -C(CH₃)₂-CH₂CH₂-C(O)-CH₃ | 3-(dimethylamino)phenyl |
| 255 | hexahydrofuro[2,3-b]furan-3-yl | -C(CH₃)₂-CH₂CH₂CH₂-NH-SO₂Me | 1,3-benzodioxol-5-yl |
| 256 | hexahydrofuro[2,3-b]furan-3-yl | -C(CH₃)₂-CH₂CH₂CH₂-NH-SO₂Me | 2,3-dihydro-1,4-benzodioxin-6-yl |
| 257 | hexahydrofuro[2,3-b]furan-3-yl | -C(CH₃)₂-CH₂CH₂-NH₂ | 1,3-benzodioxol-5-yl |

TABLE 1-continued wherein R⁷ is H; and

| Compound | R' | R" | E |
|---|---|---|---|
| 258 | hexahydrofuro[2,3-b]furan-3-yl | neopentyl-CH₂CH₂NH₂ | 3-(NMe)-phenyl |
| 259 | hexahydrofuro[2,3-b]furan-3-yl | neopentyl-CH₂CH₂C(O)CH₃ | 4-OMe-phenyl |
| 260 | hexahydrofuro[2,3-b]furan-3-yl | neopentyl-CH₂CH₂C(=NOH)CH₃ | benzo[1,3]dioxol-5-yl |
| 261 | hexahydrofuro[2,3-b]furan-3-yl | neopentyl-CH₂CH₂C(=NOMe)CH₃ | benzo[1,3]dioxol-5-yl |
| 262 | hexahydrofuro[2,3-b]furan-3-yl | neopentyl-CH₂CH₂CH₂NH₂ | 2,3-dihydrobenzo[1,4]dioxin-6-yl |
| 263 | hexahydrofuro[2,3-b]furan-3-yl | neopentyl-CH₂CH₂CH₂NHC(O)OMe | benzo[1,3]dioxol-5-yl |
| 264 | hexahydrofuro[2,3-b]furan-3-yl | neopentyl-CH₂CH₂CH₂NHC(O)OMe | 3-(NMe)-phenyl |

TABLE 1-continued wherein R⁷ is H; and

| Compound | R' | R" | E |
|---|---|---|---|
| 265 | hexahydrofuro[3,2-b]furan-3-yl | -C(CH₃)₂CH₂CH₂CH₂-NHC(O)OMe | 2,3-dihydro-1,4-benzodioxin-6-yl |
| 266 | hexahydrofuro[3,2-b]furan-3-yl | -C(CH₃)₂CH₂CH₂CH₂-NHC(O)NMe₂ | benzo[1,3]dioxol-5-yl |
| 267 | hexahydrofuro[3,2-b]furan-3-yl | -C(CH₃)₂CH₂CH₂CH₂-NHC(O)NMe₂ | 3-(NMe)phenyl |
| 268 | hexahydrofuro[3,2-b]furan-3-yl | -C(CH₃)₂CH₂CH₂CH₂-NHC(O)NMe₂ | 2,3-dihydro-1,4-benzodioxin-6-yl |
| 269 | hexahydrofuro[3,2-b]furan-3-yl | -C(CH₃)₂CH₂CH₂CH₂-NHSO₂Me | benzo[1,3]dioxol-5-yl |
| 270 | hexahydrofuro[3,2-b]furan-3-yl | -C(CH₃)₂CH₂CH₂CH₂-NHSO₂Me | 3-(NHMe)phenyl |
| 271 | hexahydrofuro[3,2-b]furan-3-yl | -C(CH₃)₂CH₂CH₂CH₂-NHSO₂Me | 2,3-dihydro-1,4-benzodioxin-6-yl |

TABLE 1-continued wherein R⁷ is H; and

| Compound | R' | R'' | E |
|---|---|---|---|
| 272 | hexahydrofuro[2,3-b]furan-3-yl-O- | -C(CH₃)₂CH₂CH₂-O-C(O)-NHMe | benzo[1,3]dioxol-5-yl |
| 273 | 1,3-dioxan-5-yl-O- | -C(CH₃)₂CH₂CH₂-CONH₂ | 4-methoxyphenyl |
| 274 | 1,3-dioxan-5-yl-O- | -C(CH₃)₂CH₂CH₂-COOM | 4-methoxyphenyl |
| 277 | t-BuO- | -C(CH₃)₂CH₂CH(CH₃)CH₂CHO | 4-methoxyphenyl |
| 278 | t-BuO- | -C(CH₃)₂CH₂CH(CH₃)CH₂CHO | benzo[1,3]dioxol-5-yl |
| 279 | t-BuO- | -C(CH₃)₂CH₂C(O)CH₃ | 4-methoxyphenyl |
| 280 | hexahydrofuro[2,3-b]furan-3-yl-O- | -C(CH₃)₂CH₂C(O)CH₃ | 4-methoxyphenyl |
| 281 | 1,3-dioxan-5-yl-O- | -C(CH₃)₂CH₂C(O)CH₃ | 4-methoxyphenyl |

TABLE 2

| Compound | R' | R'' | E |
|---|---|---|---|
| 100 | hexahydrofuro[2,3-b]furan-3-yl | -C(CH₃)₂CH₂CH₂CN | 3-(NHMe)phenyl |
| 101 | hexahydrofuro[2,3-b]furan-3-yl | -C(CH₃)₂CH₂CH₂CN | 4-(OMe)phenyl |
| 47 | hexahydrofuro[2,3-b]furan-3-yl | -C(CH₃)₂CH₂CH₂CN | benzo[1,3]dioxol-5-yl |

TABLE 3

| Compound | R' | n | E |
|---|---|---|---|
| 282 | hexahydrofuro[2,3-b]furan-3-yloxy | 2 | methyl-benzo[1,3]dioxol-yl |
| 283 | hexahydrofuro[2,3-b]furan-3-yloxy | 5 | methyl-benzo[1,3]dioxol-yl |
| 284 | hexahydrofuro[2,3-b]furan-3-yloxy | 2 | 3-(NHMe)phenyl |
| 285 | hexahydrofuro[2,3-b]furan-3-yloxy | 2 | 3-(NH₂)phenyl |
| 286 | hexahydrofuro[2,3-b]furan-3-yloxy | 2 | 4-(NH₂)phenyl |

TABLE 3-continued

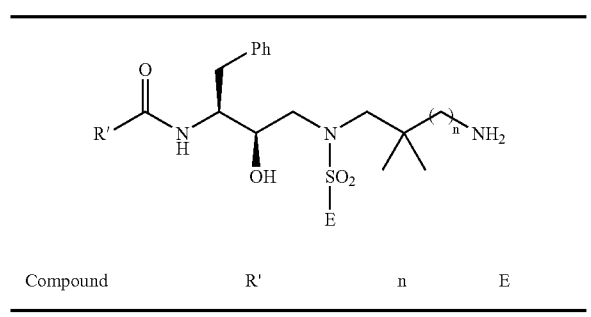

| Compound | R' | n | E |
|---|---|---|---|
| 287 | hexahydrofuro[2,3-b]furan-3-yloxy | 3 | 4-aminophenyl |
| 288 | hexahydrofuro[2,3-b]furan-3-yloxy | 3 | 3-aminophenyl |
| 289 | hexahydrofuro[2,3-b]furan-3-yloxy | 4 | 3-(NHMe)phenyl |
| 290 | hexahydrofuro[2,3-b]furan-3-yloxy | 4 | 4-aminophenyl |
| 291 | hexahydrofuro[2,3-b]furan-3-yloxy | 4 | 3-aminophenyl |
| 292 | hexahydrofuro[2,3-b]furan-3-yloxy | 4 | 4-aminophenyl |

TABLE 3-continued

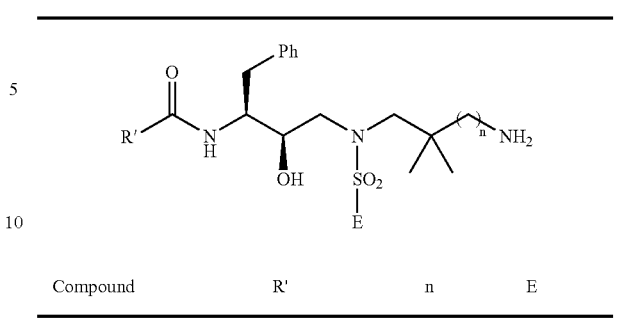

| Compound | R' | n | E |
|---|---|---|---|
| 293 | hexahydrofuro[2,3-b]furan-3-yloxy | 4 | benzo[1,3]dioxol-5-yl |
| 295 | tetrahydrofuran-3-yloxy | 4 | benzo[1,3]dioxol-5-yl |
| 296 | tetrahydrofuran-3-yloxy | 4 | 4-aminophenyl |
| 297 | 1,3-dioxan-5-yloxy | 4 | benzo[1,3]dioxol-5-yl |
| 298 | 1,3-dioxan-5-yloxy | 4 | 4-aminophenyl |

TABLE 4

| Compound | R' | E | n | R |
|---|---|---|---|---|
| 299 | hexahydrofuro[3,2-b]furan-3-yloxy | benzo[1,3]dioxol-5-yl | 3 | C(=O)OEt |
| 300 | hexahydrofuro[3,2-b]furan-3-yloxy | benzo[1,3]dioxol-5-yl | 3 | C(=O)OiPr |
| 301 | hexahydrofuro[3,2-b]furan-3-yloxy | benzo[1,3]dioxol-5-yl | 3 | C(=O)NHMe |
| 302 | hexahydrofuro[3,2-b]furan-3-yloxy | benzo[1,3]dioxol-5-yl | 2 | C(=O)OEt |
| 303 | hexahydrofuro[3,2-b]furan-3-yloxy | benzo[1,3]dioxol-5-yl | 2 | C(=O)OiPr |
| 304 | hexahydrofuro[3,2-b]furan-3-yloxy | benzo[1,3]dioxol-5-yl | 2 | C(=O)SMe |
| 305 | hexahydrofuro[3,2-b]furan-3-yloxy | benzo[1,3]dioxol-5-yl | 2 | C(=O)SEt |
| 306 | hexahydrofuro[3,2-b]furan-3-yloxy | benzo[1,3]dioxol-5-yl | 2 | C(=O)NHMe |
| 307 | hexahydrofuro[3,2-b]furan-3-yloxy | benzo[1,3]dioxol-5-yl | 1 | C(=O)OMe |

TABLE 4-continued

| Compound | R' | E | n | R |
|---|---|---|---|---|
| 308 | hexahydrofuro[2,3-b]furan-3-yl | benzo[1,3]dioxol-5-yl | 1 | –C(O)O-iPr |
| 309 | hexahydrofuro[2,3-b]furan-3-yl | benzo[1,3]dioxol-5-yl | 1 | –C(O)OEt |
| 310 | hexahydrofuro[2,3-b]furan-3-yl | benzo[1,3]dioxol-5-yl | 1 | –SO$_2$Me |
| 311 | hexahydrofuro[2,3-b]furan-3-yl | benzo[1,3]dioxol-5-yl | 1 | –C(O)NMe$_2$ |
| 312 | hexahydrofuro[2,3-b]furan-3-yl | benzo[1,3]dioxol-5-yl | 1 | –C(O)NHMe |
| 313 | hexahydrofuro[2,3-b]furan-3-yl | benzo[1,3]dioxol-5-yl | 4 | –C(O)OMe |
| 314 | hexahydrofuro[2,3-b]furan-3-yl | benzo[1,3]dioxol-5-yl | 4 | –C(O)OEt |
| 315 | hexahydrofuro[2,3-b]furan-3-yl | benzo[1,3]dioxol-5-yl | 4 | –C(O)O-iPr |
| 316 | hexahydrofuro[2,3-b]furan-3-yl | benzo[1,3]dioxol-5-yl | 4 | –SO$_2$Me |

TABLE 4-continued

| Compound | R' | E | n | R |
|---|---|---|---|---|
| 317 | hexahydrofuro[3,2-b]furan-3-yloxy | 3-(NHMe)phenyl | 1 | C(O)OMe |
| 318 | hexahydrofuro[3,2-b]furan-3-yloxy | 3-(NHMe)phenyl | 1 | SO₂Me |
| 319 | hexahydrofuro[3,2-b]furan-3-yloxy | 3-(NHMe)phenyl | 1 | C(O)NMe₂ |
| 320 | hexahydrofuro[3,2-b]furan-3-yloxy | 3-(NH₂)phenyl | 1 | C(O)OMe |
| 321 | hexahydrofuro[3,2-b]furan-3-yloxy | 3-(NH₂)phenyl | 1 | C(O)OEt |
| 322 | hexahydrofuro[3,2-b]furan-3-yloxy | 3-(NH₂)phenyl | 1 | C(O)OiPr |
| 323 | hexahydrofuro[3,2-b]furan-3-yloxy | 3-(NH₂)phenyl | 1 | C(O)NMe₂ |
| 324 | hexahydrofuro[3,2-b]furan-3-yloxy | 3-(NH₂)phenyl | 1 | SO₂Me |
| 325 | hexahydrofuro[3,2-b]furan-3-yloxy | 4-(NH₂)phenyl | 1 | C(O)OMe |

TABLE 4-continued

| Compound | R' | E | n | R |
|---|---|---|---|---|
| 326 | hexahydrofuro[3,2-b]furan-3-yloxy | 4-aminophenyl | 1 | C(=O)OEt |
| 327 | hexahydrofuro[3,2-b]furan-3-yloxy | 4-aminophenyl | 1 | SO₂Me |
| 328 | hexahydrofuro[3,2-b]furan-3-yloxy | 4-aminophenyl | 1 | C(=O)NMe₂ |
| 329 | hexahydrofuro[3,2-b]furan-3-yloxy | 4-aminophenyl | 1 | C(=O)OiPr |
| 330 | hexahydrofuro[3,2-b]furan-3-yloxy | 4-aminophenyl | 2 | C(=O)NMe₂ |
| 331 | hexahydrofuro[3,2-b]furan-3-yloxy | 4-aminophenyl | 2 | SO₂Me |
| 332 | hexahydrofuro[3,2-b]furan-3-yloxy | 4-aminophenyl | 2 | C(=O)OMe |
| 333 | hexahydrofuro[3,2-b]furan-3-yloxy | 4-aminophenyl | 2 | C(=O)OEt |

TABLE 4-continued

| Compound | R' | E | n | R |
|---|---|---|---|---|
| 334 | hexahydrofuro[2,3-b]furan-3-yl ether | 4-aminophenyl | 2 | –C(O)O-iPr |
| 335 | hexahydrofuro[2,3-b]furan-3-yl ether | 3-aminophenyl | 2 | –C(O)OMe |
| 336 | hexahydrofuro[2,3-b]furan-3-yl ether | 3-aminophenyl | 2 | –C(O)NMe₂ |
| 337 | hexahydrofuro[2,3-b]furan-3-yl ether | 3-aminophenyl | 2 | –SO₂Me |
| 338 | hexahydrofuro[2,3-b]furan-3-yl ether | 3-aminophenyl | 2 | –C(O)OEt |
| 339 | hexahydrofuro[2,3-b]furan-3-yl ether | 3-aminophenyl | 2 | –C(O)O-iPr |
| 340 | hexahydrofuro[2,3-b]furan-3-yl ether | 3-(NHMe)phenyl | 3 | –SO₂Me |
| 341 | hexahydrofuro[2,3-b]furan-3-yl ether | 3-(NHMe)phenyl | 3 | –C(O)OEt |
| 342 | hexahydrofuro[2,3-b]furan-3-yl ether | 3-(NHMe)phenyl | 3 | –C(O)O-iPr |

TABLE 4-continued

| Compound | R' | E | n | R |
|---|---|---|---|---|
| 343 | hexahydrofuro[2,3-b]furan-3-yloxy | 4-aminophenyl | 3 | C(O)OMe |
| 344 | hexahydrofuro[2,3-b]furan-3-yloxy | 4-aminophenyl | 3 | C(O)OEt |
| 345 | hexahydrofuro[2,3-b]furan-3-yloxy | 4-aminophenyl | 3 | C(O)OiPr |
| 346 | hexahydrofuro[2,3-b]furan-3-yloxy | 4-aminophenyl | 3 | C(O)NMe$_2$ |
| 347 | hexahydrofuro[2,3-b]furan-3-yloxy | 4-aminophenyl | 3 | SO$_2$Me |
| 348 | hexahydrofuro[2,3-b]furan-3-yloxy | 3-aminophenyl | 3 | C(O)OMe |
| 349 | hexahydrofuro[2,3-b]furan-3-yloxy | 3-aminophenyl | 3 | C(O)OEt |
| 350 | hexahydrofuro[2,3-b]furan-3-yloxy | 3-aminophenyl | 3 | C(O)OiPr |

TABLE 4-continued

| Compound | R' | E | n | R |
|---|---|---|---|---|
| 351 | hexahydrofuro[3,2-b]furan-3-yloxy | 3-aminophenyl | 3 | C(O)NMe₂ |
| 352 | hexahydrofuro[3,2-b]furan-3-yloxy | 3-aminophenyl | 3 | SO₂Me |
| 353 | hexahydrofuro[3,2-b]furan-3-yloxy | 3-aminophenyl | 3 | C(O)SMe |
| 354 | hexahydrofuro[3,2-b]furan-3-yloxy | 3-aminophenyl | 3 | C(O)SEt |
| 355 | hexahydrofuro[3,2-b]furan-3-yloxy | 4-aminophenyl | 3 | C(O)OMe |
| 356 | hexahydrofuro[3,2-b]furan-3-yloxy | 4-aminophenyl | 3 | C(O)OEt |
| 357 | hexahydrofuro[3,2-b]furan-3-yloxy | 4-aminophenyl | 3 | C(O)OiPr |
| 358 | hexahydrofuro[3,2-b]furan-3-yloxy | 4-aminophenyl | 3 | SO₂Me |

TABLE 4-continued
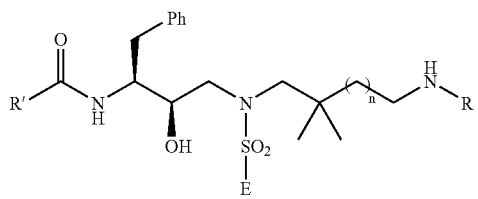
| Compound | R' | E | n | R |
|---|---|---|---|---|
| 359 |  |  | 3 | 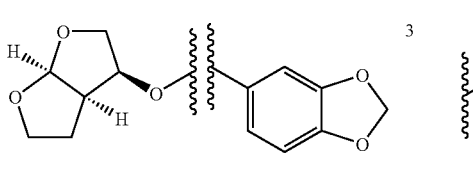 |
| 360 | 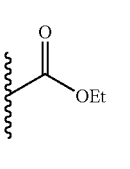 |  | 3 | 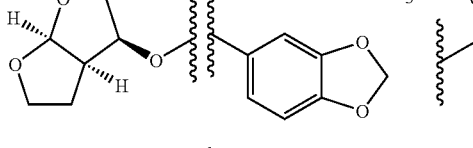 |
| 361 | 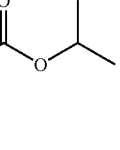 |  | 3 | 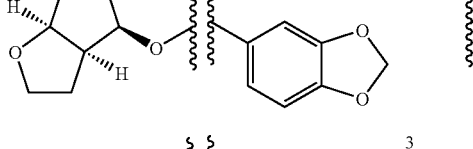 |
| 362 |  |  | 3 | 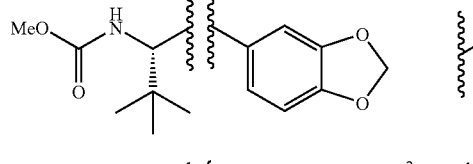 |
| 363 | 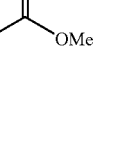 |  | 3 | 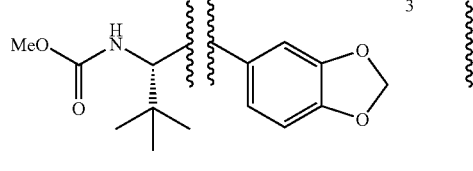 |
| 364 |  |  | 3 | 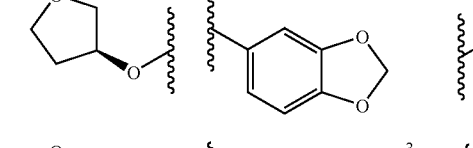 |
| 365 | 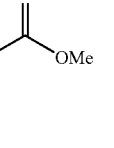 |  | 3 | 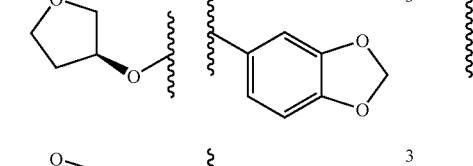 |
| 366 |  |  | 3 | 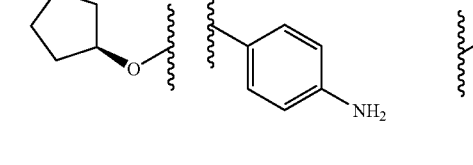 |
| 367 | 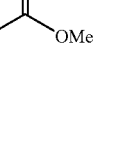 |  | 3 |  |

TABLE 4-continued

| Compound | R' | E | n | R |
|---|---|---|---|---|
| 368 | (S)-tetrahydrofuran-3-yloxy | 4-aminophenyl | 3 | SO₂Me |
| 369 | 1,3-dioxan-5-yloxy | benzo[1,3]dioxol-5-yl | 3 | C(O)OMe |
| 370 | 1,3-dioxan-5-yloxy | benzo[1,3]dioxol-5-yl | 3 | SO₂Me |
| 371 | 1,3-dioxan-5-yloxy | 4-aminophenyl | 3 | C(O)OMe |
| 372 | 1,3-dioxan-5-yloxy | 4-aminophenyl | 3 | SO₂Me |

TABLE 5

| Compound | n | R |
|---|---|---|
| 373 | 1 | C(O)CH₃ |
| 374 | 1 | C(O)C(CH₃)₃ |

TABLE 5-continued
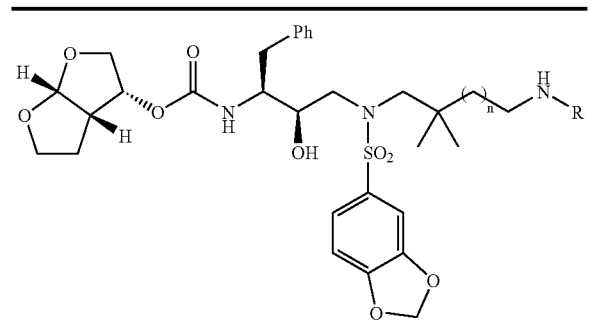
| Compound | n | R |
|---|---|---|
| 375 | 1 | cyclobutyl ketone |
| 376 | 1 | isobutyl ketone |
| 377 | 1 | phenyl ketone |
| 378 | 1 | 2-furyl ketone |
| 379 | 1 | 2-thienyl ketone |
| 380 | 1 | propyl ester |
| 381 | 1 | butyl ester |
| 382 | 1 | propargyl ester |
| 383 | 1 | isopropenyl ester |
TABLE 5-continued
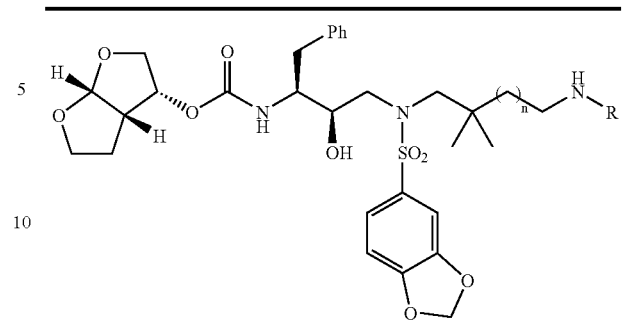
| Compound | n | R |
|---|---|---|
| 384 | 1 | but-3-enyl ester |
| 385 | 1 | 4-fluorophenyl ester |
| 386 | 1 | C(O)NEt$_2$ |
| 387 | 1 | C(O)N(iPr)$_2$ |
| 388 | 1 | morpholine amide |
| 389 | 1 | pyrrolidine amide |
| 390 | 1 | SO$_2$Et |
| 391 | 1 | propylsulfonyl |
| 392 | 1 | butylsulfonyl |

TABLE 5-continued

| Compound | n | R |
|---|---|---|
| 393 | 1 | -SO₂Ph |
| 394 | 1 | -C(O)OCH₂CH₂OMe |
| 395 | 1 | -C(O)-(4-F-C₆H₄) |
| 396 | 1 | -C(O)O-(4-OMe-C₆H₄) |
| 397 | 1 | -C(O)CH₂OMe |
| 398 | 1 | -C(O)CH(CH₃)₂ |
| 399 | 1 | -C(O)CH₂C(CH₃)₃ |
| 400 | 1 | -C(O)-cyclopropyl |
| 401 | 1 | -C(O)-cyclopentyl |

TABLE 5-continued

| Compound | n | R |
|---|---|---|
| 402 | 1 | -C(O)CH₂CH₂-cyclopentyl |
| 403 | 1 | -C(O)CH₂CH₂C(O)OMe |
| 404 | 1 | -C(O)-(3,5-F₂-C₆H₃) |
| 405 | 1 | -C(O)-(benzo[1,3]dioxol-5-yl) |
| 406 | 1 | -SO₂-(4-F-C₆H₄) |
| 407 | 1 | -SO₂-(4-OMe-C₆H₄) |
| 408 | 1 | -C(S)NHMe |
| 409 | 1 | -C(S)NH-n-Pr |
| 410 | 1 | -C(S)NH-i-Pr |

TABLE 5-continued
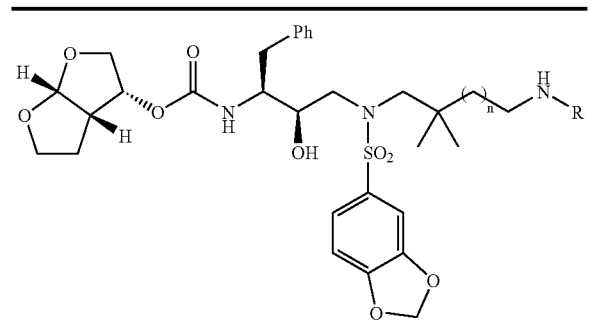
| Compound | n | R |
|---|---|---|
| 411 | 1 | ⁂C(=S)NHC(CH₃)₃ |
| 412 | 1 | ⁂C(=S)NHCH₂-(2-furyl) |
| 413 | 1 | ⁂C(=O)NHCH₂CH₂CH₃ |
| 414 | 1 | ⁂C(=O)NHC(CH₃)₃ |
| 415 | 1 | ⁂C(=O)NHCH₂Ph |
| 416 | 2 | ⁂C(=O)CH₃ |
| 417 | 2 | ⁂C(=O)C(CH₃)₃ |
| 418 | 2 | ⁂C(=O)-cyclobutyl |
| 419 | 2 | ⁂C(=O)CH₂CH(CH₃)₂ |
TABLE 5-continued
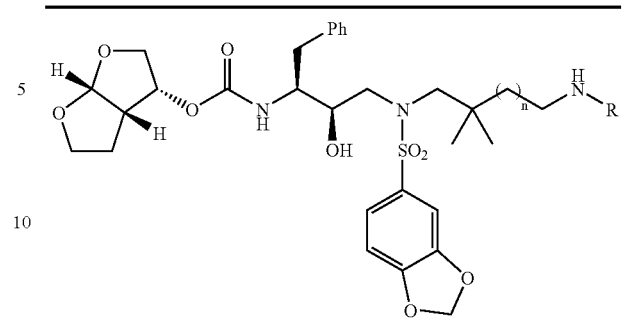
| Compound | n | R |
|---|---|---|
| 420 | 2 | ⁂C(=O)Ph |
| 421 | 2 | ⁂C(=O)-(2-furyl) |
| 422 | 2 | ⁂C(=O)-(2-thienyl) |
| 423 | 2 | ⁂C(=O)O-n-propyl |
| 424 | 2 | ⁂C(=O)O-n-butyl |
| 425 | 2 | ⁂C(=O)OCH₂C≡CH |
| 426 | 2 | ⁂C(=O)OC(CH₃)=CH₂ |
| 427 | 2 | ⁂C(=O)OCH₂CH₂CH=CH₂ |
| 428 | 2 | ⁂C(=O)O-(4-fluorophenyl) |

81
TABLE 5-continued
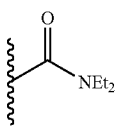
| Compound | n | R |
|---|---|---|
| 429 | 2 | 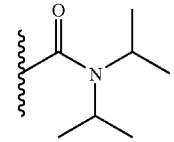 |
| 430 | 2 | 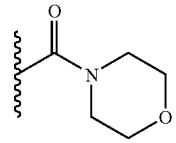 |
| 431 | 2 | 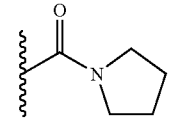 |
| 432 | 2 |  |
| 433 | 2 | 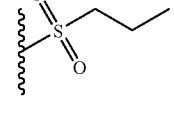 |
| 434 | 2 | 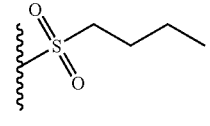 |
| 435 | 2 |  |
| 436 | 2 | 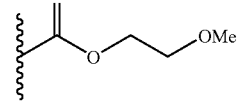 |
| 437 | 2 | 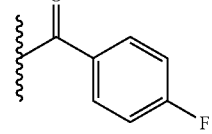 |
82
TABLE 5-continued
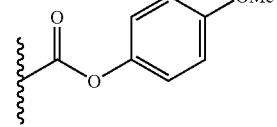
| Compound | n | R |
|---|---|---|
| 438 | 2 | 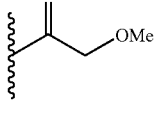 |
| 439 | 2 | 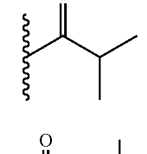 |
| 440 | 2 | 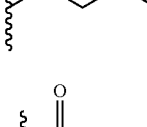 |
| 441 | 2 | 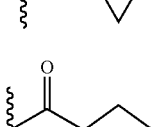 |
| 442 | 2 | 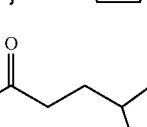 |
| 443 | 2 | 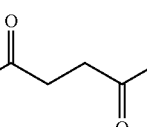 |
| 444 | 2 | 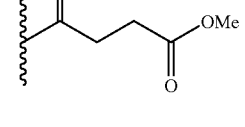 |
| 445 | 2 | |
| 446 | 2 | |

TABLE 5-continued
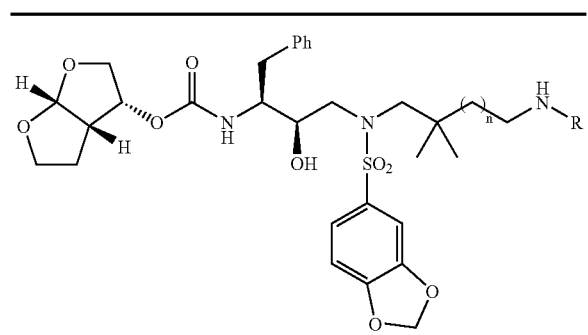
| Compound | n | R |
|---|---|---|
| 447 | 2 | 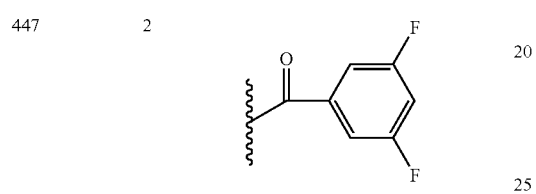 |
| 448 | 2 | 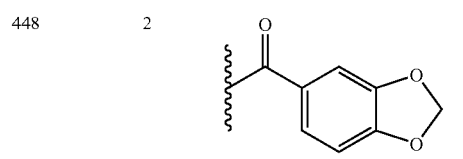 |
| 449 | 2 | 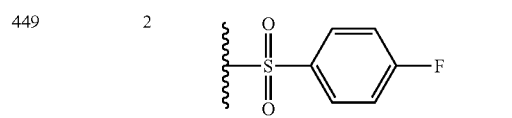 |
| 450 | 2 | 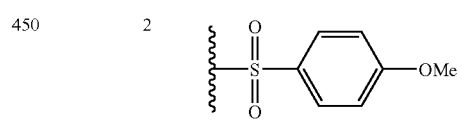 |
| 451 | 2 |  |
| 452 | 2 | 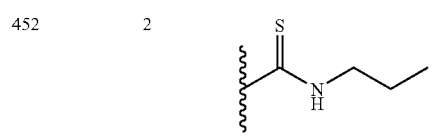 |
| 453 | 2 | 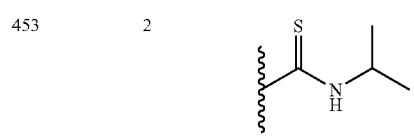 |
| 454 | 2 |  |
TABLE 5-continued
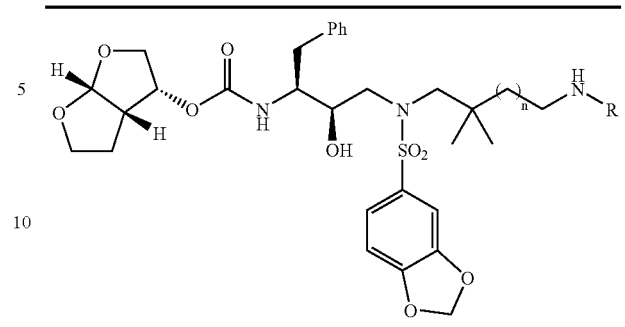
| Compound | n | R |
|---|---|---|
| 455 | 2 |  |
| 456 | 2 | 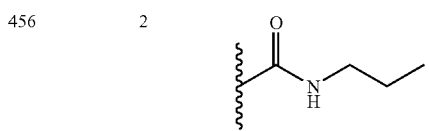 |
| 457 | 2 | 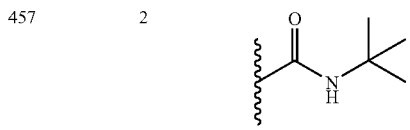 |
| 458 | 2 | 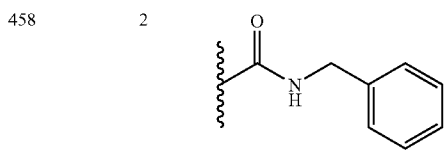 |
| 459 | 3 |  |
| 460 | 3 |  |
| 461 | 3 | 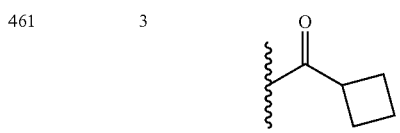 |
| 462 | 3 | 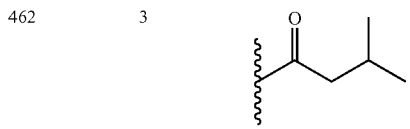 |
| 463 | 3 | 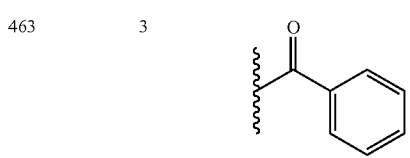 |

TABLE 5-continued
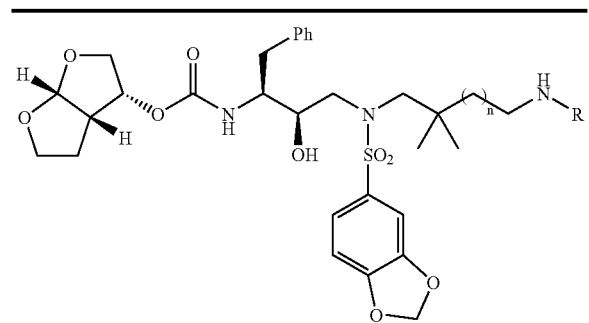
| Compound | n | R |
|---|---|---|
| 464 | 3 | 2-furoyl |
| 465 | 3 | 2-thienoyl |
| 466 | 3 | -C(O)O-propyl |
| 467 | 3 | -C(O)O-butyl |
| 468 | 3 | -C(O)O-CH2-C≡CH |
| 469 | 3 | -C(O)O-C(CH3)=CH2 |
| 470 | 3 | -C(O)O-CH2CH2CH=CH2 |
| 471 | 3 | -C(O)O-(4-F-C6H4) |
| 472 | 3 | -C(O)NEt2 |
TABLE 5-continued
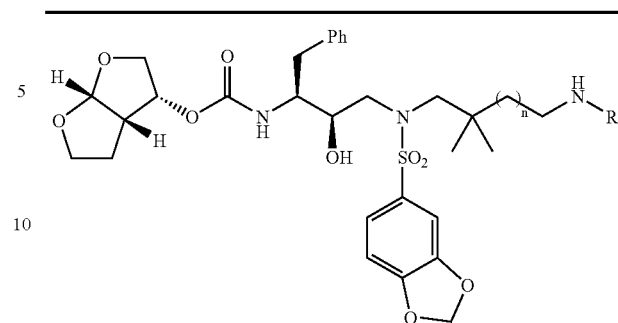
| Compound | n | R |
|---|---|---|
| 473 | 3 | -C(O)N(iPr)2 |
| 474 | 3 | -C(O)-morpholinyl |
| 475 | 3 | -C(O)-pyrrolidinyl |
| 476 | 3 | -SO2Et |
| 477 | 3 | -SO2-propyl |
| 478 | 3 | -SO2-butyl |
| 479 | 3 | -SO2Ph |
| 480 | 3 | -C(O)O-CH2CH2-OMe |
| 481 | 3 | -C(O)-(4-F-C6H4) |

TABLE 5-continued
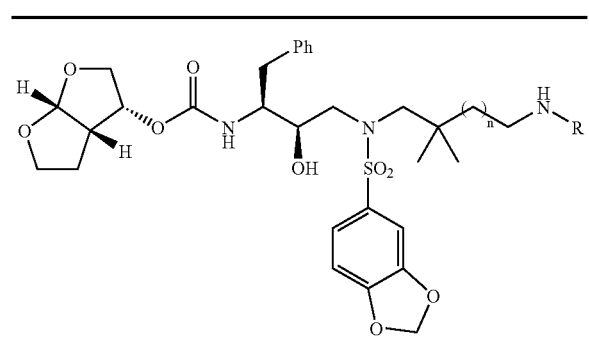
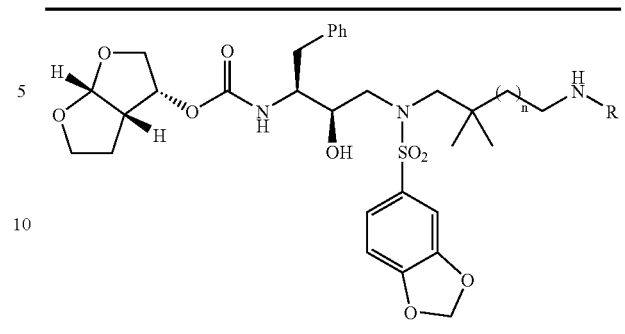
| Compound | n | R |
|---|---|---|
| 482 | 3 | 4-methoxyphenyl ester (C(=O)O-C6H4-OMe) |
| 483 | 3 | C(=O)CH2OMe |
| 484 | 3 | C(=O)CH(CH3)2 |
| 485 | 3 | C(=O)CH2C(CH3)3 |
| 486 | 3 | C(=O)-cyclopropyl |
| 487 | 3 | C(=O)-cyclopentyl |
| 488 | 3 | C(=O)CH2CH2-cyclopentyl |
| 489 | 3 | C(=O)CH2C(=O)OMe |
| 490 | 3 | C(=O)-(3,5-difluorophenyl) |
| 491 | 3 | C(=O)-(benzo[1,3]dioxol-5-yl) |
| 492 | 3 | SO2-(4-fluorophenyl) |
| 493 | 3 | SO2-(4-methoxyphenyl) |
| 494 | 3 | C(=S)NHMe |
| 495 | 3 | C(=S)NH-propyl |
| 496 | 3 | C(=S)NH-isopropyl |
| 497 | 3 | C(=S)NH-tert-butyl |
| 498 | 3 | C(=S)NH-CH2-(2-furyl) |

TABLE 5-continued
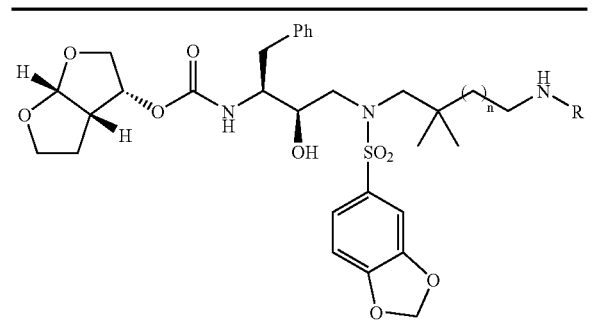
| Compound | n | R |
|---|---|---|
| 499 | 3 | -C(O)NH-propyl |
| 500 | 3 | -C(O)NH-tBu |
| 501 | 3 | -C(O)NH-benzyl |
| 502 | 4 | -C(O)CH₃ |
| 503 | 4 | -C(O)CH₂CH(CH₃)₂ |
| 504 | 4 | -C(O)-cyclobutyl |
| 505 | 4 | -C(O)-cyclopropyl |
| 506 | 4 | -C(O)-phenyl |
| 507 | 4 | -C(O)CH₂OMe |
TABLE 5-continued
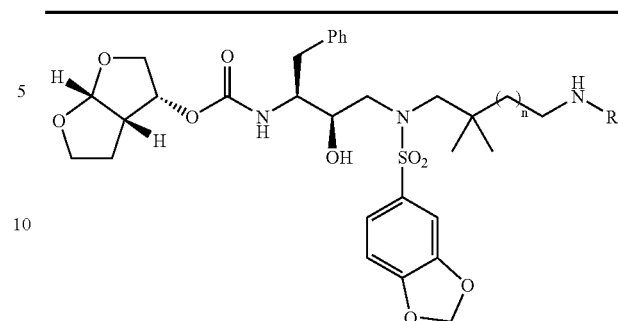
| Compound | n | R |
|---|---|---|
| 508 | 4 | -C(O)-2-furyl |
| 509 | 4 | -C(O)-2-thienyl |
| 510 | 4 | -C(O)O-propyl |
| 511 | 4 | -C(O)O-butyl |
| 512 | 4 | -C(O)O-isopropenyl |
| 513 | 4 | -C(O)O-CH₂CH₂CH=CH₂ |
| 514 | 4 | -C(O)O-CH₂C≡CH |
| 515 | 4 | -C(O)O-CH₂CH₂OMe |
| 516 | 4 | -C(O)NMe₂ |

TABLE 5-continued
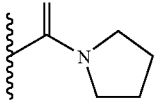
| Compound | n | R |
|---|---|---|
| 517 | 4 | 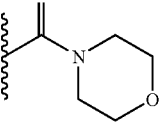 |
| 518 | 4 |  |
| 519 | 4 | 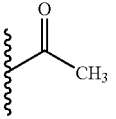 |
TABLE 6
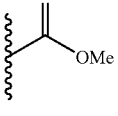
| Compound | n | R$^z$ |
|---|---|---|
| 520 | 1 | H |
| 521 | 2 | H |
| 522 | 3 | H |
| 523 | 1 | 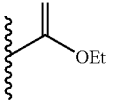 |
| 524 | 1 | 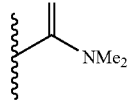 |
| 525 | 1 | 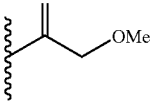 |
TABLE 6-continued
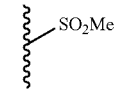
| Compound | n | R$^z$ |
|---|---|---|
| 526 | 1 | 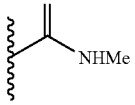 |
| 527 | 1 | 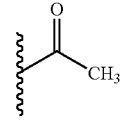 |
| 528 | 1 | 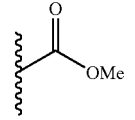 |
| 529 | 1 | 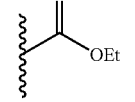 |
| 530 | 2 | 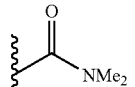 |
| 531 | 2 | 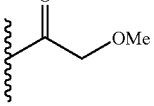 |
| 532 | 2 | 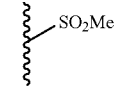 |
| 533 | 2 | NMe$_2$ (amide) |
| 534 | 2 | OMe (ketone) |
| 535 | 2 | SO$_2$Me |

TABLE 6-continued
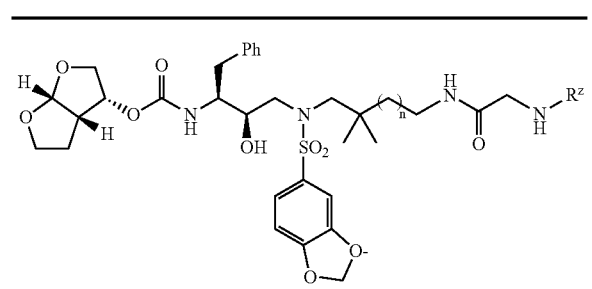
| Compound | n | R$^z$ |
|---|---|---|
| 536 | 2 | ~C(O)NHMe |
| 537 | 3 | ~C(O)CH$_3$ |
| 538 | 3 | ~C(O)OMe |
| 539 | 3 | ~C(O)OEt |
| 540 | 3 | ~C(O)NMe$_2$ |
| 541 | 3 | ~C(O)CH$_2$OMe |
| 542 | 3 | ~SO$_2$Me |
| 543 | 3 | ~C(O)NHMe |
TABLE 7
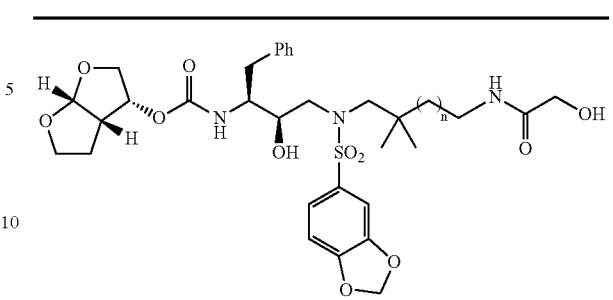
| Compound | N |
|---|---|
| 544 | 1 |
| 545 | 2 |
| 546 | 3 |
| 547 | 4 |
TABLE 8
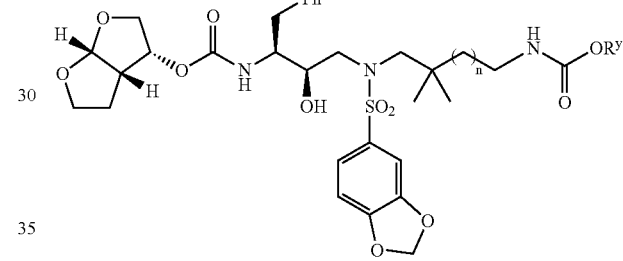
| Compound | n | R$^y$ |
|---|---|---|
| 548 | 1 | tetrahydrofuran-3-yl |
| 549 | 1 | 1,3-dioxan-5-yl |
| 550 | 2 | tetrahydrofuran-3-yl |
| 551 | 2 | 1,3-dioxan-5-yl |
| 552 | 3 | tetrahydrofuran-3-yl |

TABLE 8-continued
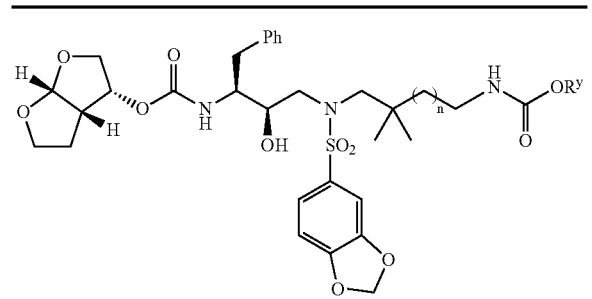
| Compound | n | R$^y$ |
|---|---|---|
| 553 | 3 | (1,3-dioxan-5-yl) |
| 554 | 4 | (tetrahydrofuran-3-yl) |
| 555 | 4 | (1,3-dioxan-5-yl) |
TABLE 9
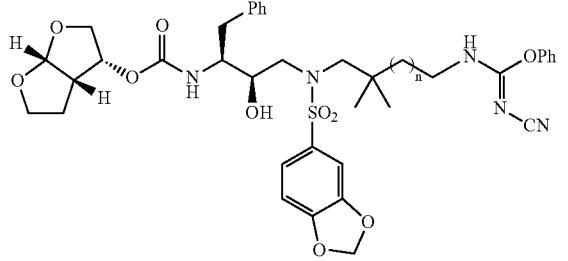
| Compound | n |
|---|---|
| 556 | 1 |
| 557 | 2 |
| 558 | 3 |
| 559 | 4 |
TABLE 10
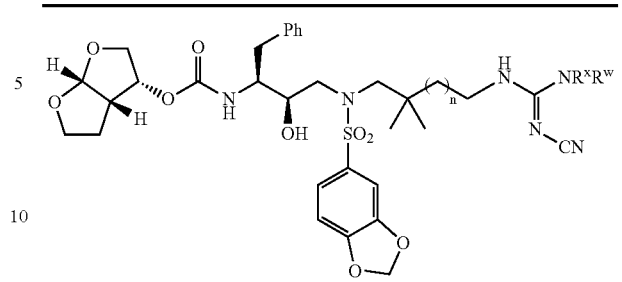
| Compound | n | R$^x$ | R$^w$ |
|---|---|---|---|
| 560 | 1 | H | H |
| 561 | 1 | Me | H |
| 562 | 1 | n-Pr | H |
| 563 | 1 | Me | Me |
| 564 | 2 | H | H |
| 565 | 2 | Me | H |
| 566 | 2 | n-Pr | H |
| 567 | 2 | Me | Me |
| 568 | 3 | H | H |
| 569 | 3 | Me | H |
| 570 | 3 | n-Pr | H |
| 571 | 3 | Me | Me |
| 572 | 4 | H | H |
| 573 | 4 | Me | H |
| 574 | 4 | n-Pr | H |
| 575 | 4 | Me | Me |
TABLE 11
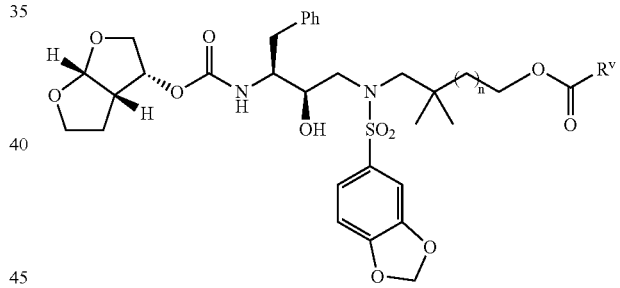
| Compound | n | R$^v$ |
|---|---|---|
| 576 | 1 | 4-nitrophenoxy |
| 577 | 2 | 4-nitrophenoxy |
| 578 | 3 | 4-nitrophenoxy |
| 579 | 1 | NMe$_2$ |

TABLE 11-continued
| Compound | n | R^v |
|---|---|---|
| 580 | 1 | —NH$_2$ |
| 581 | 1 | —NHEt |
| 582 | 1 | —NHn-Pr |
| 583 | 1 | —NHi-Pr |
| 584 | 1 | —NHn-Bu |
| 585 | 1 | —NH-cyclopropyl |
| 586 | 1 | —N(pyrrolidinyl) |
| 587 | 1 | —N(morpholinyl) |
| 588 | 1 | —NHNH$_2$ |
| 589 | 2 | —NHn-Pr |
| 590 | 2 | —NHn-Bu |
| 591 | 2 | —NH-cyclopropyl |
TABLE 11-continued
| Compound | n | R^v |
|---|---|---|
| 592 | 2 | —N(pyrrolidinyl) |
| 593 | 2 | —N(morpholinyl) |
| 594 | 2 | —NHNH$_2$ |
| 595 | 3 | —NMe$_2$ |
| 596 | 3 | —NH$_2$ |
| 597 | 3 | —NHEt |
| 598 | 3 | —NHn-Pr |
| 599 | 3 | —NHi-Pr |
| 600 | 3 | —NHn-Bu |
| 601 | 3 | —NH-cyclopropyl |
| 602 | 3 | —N(pyrrolidinyl) |
| 603 | 3 | —N(morpholinyl) |

TABLE 11-continued

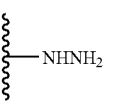

| Compound | n | R$^v$ |
|---|---|---|
| 604 | 3 | 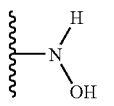 —NHNH$_2$ |
| 605 | 1 | 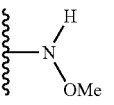 |
| 606 | 1 | 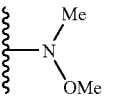 |
| 607 | 1 | 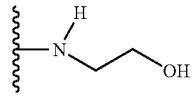 |
| 608 | 1 | 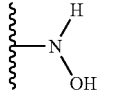 |
| 609 | 2 | 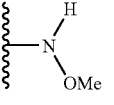 |
| 610 | 2 | 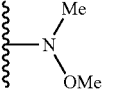 |
| 611 | 2 | 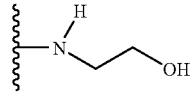 |
| 612 | 2 | 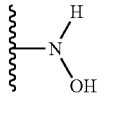 |
| 613 | 3 | 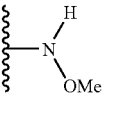 |
| 614 | 3 | 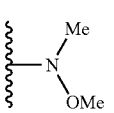 |

TABLE 11-continued

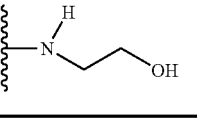

| Compound | n | R$^v$ |
|---|---|---|
| 615 | 3 | —N(Me)OMe |
| 616 | 3 | —NH-CH$_2$CH$_2$-OH |

Preferred compounds are compound numbers: 12, 16, 25, 29, 30, 31, 35, 39, 41, 42, 47, 100, 124, 210, 224, 240, 248, 250, 255, 263, 270, 272, 280, 299, 300, 307, 309, 313, 314, 315, 316, 359, 360, 375, 378, 384, 421, 459, 464, 483, 494, 496, 523, 524, 531, 542, 548, 553, 558, 563, 570, 571, 575, 579, 589, 596, 606, 609, 616.

In one embodiment of preferred compounds, the compounds are numbers: 210, 224, 240, 248, 250, 255, 263, 270, 272, 280, 299, 300, 307, 309, 313, 314, 315, 316, 359, 360, 384, 483, 494, 496, 523, 524, 531, 542, 548, 553, 558, 563, 570, 571, 575, 579, 589, 596, 606, 609, 616.

In another embodiment of preferred compounds, the compounds are numbers: 12, 16, 25, 29, 30, 31, 35, 39, 41, 42, 47, 100, 124, 375, 378, 421, 459, 464.

More preferred are compound numbers 12, 16, 25, 35, 39, 42, 47, 100, 224, 240, 263, 270, 272, 280, 299, 300, 307, 309, 313, 314, 315, 316, 359, 360, 375, 378, 384, 421, 459, 464, 483, 494, 496, 548, 553, 558, 563, 570, 571, 575, 579, 589, 596, 606, 609, 616.

In one embodiment of more preferred compounds, the compounds are numbers: 224, 240, 263, 270, 272, 280, 299, 300, 307, 309, 313, 314, 315, 316, 359, 360, 384, 483, 494, 496, 548, 553, 558, 563, 570, 571, 575, 579, 589, 596, 606, 609, 616.

In another embodiment of more preferred compounds, the compounds are numbers: 12, 16, 25, 35, 39, 42, 47, 100, 375, 378, 421, 459, 464.

The most preferred compounds are compound numbers 16, 25, 42, 47, 100, 224, 240, 272, 299, 314.

In one embodiment of most preferred compounds, the compounds are numbers: 224, 240, 272, 299, 314.

In another embodiment of most preferred compounds, the compounds are numbers: 16, 25, 42, 47, 100.

The compounds of the present invention can be readily prepared by techniques known in the art. Scheme I illustrates a general synthetic route to compounds of formula (I).

SCHEME I

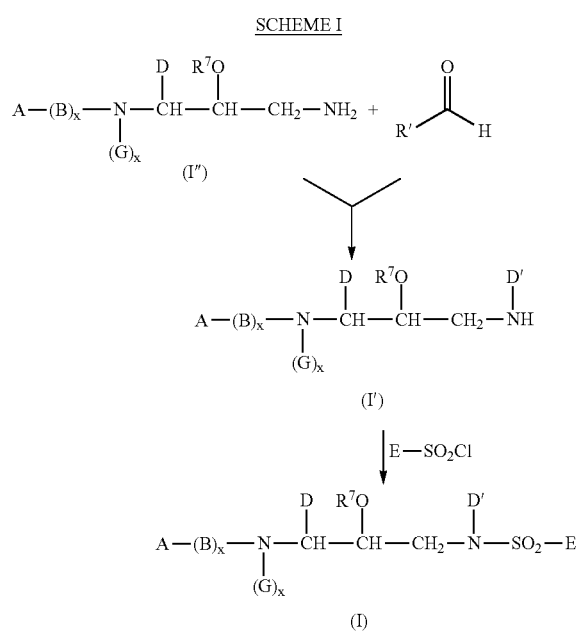

In Step 1 of Scheme I, radical R' is selected such that R'—CH₂— is D'.

The synthetic approach illustrated in Scheme I can be readily extended to produce other compounds of the present invention. The above synthetic scheme is not intended to comprise a comprehensive list of all means by which compounds described and claimed in this application may be synthesized. Further methods will be evident to those of ordinary skill in the art.

As discussed above, the novel compounds of the present invention are excellent ligands for aspartyl proteases, particularly HIV-1 and HIV-2 proteases. Accordingly, these compounds are capable of targeting and inhibiting late stage events in HIV replication, i.e., the processing of the viral polyproteins by HIV encoded proteases. Such compounds inhibit the proteolytic processing of viral polyprotein precursors by inhibiting aspartyl protease. Because aspartyl protease is essential for the production of mature virions, inhibition of that processing effectively blocks the spread of virus by inhibiting the production of infectious virions, particularly from chronically infected cells. Compounds according to this invention advantageously inhibit the ability of the HIV-1 virus to infect immortalized human T cells over a period of days, as determined by an assay of extracellular p24 antigen—a specific marker of viral replication. Other anti-viral assays have confirmed the potency of these compounds.

The compounds of this invention may be employed in a conventional manner for the treatment of viruses, such as HIV and HTLV, which depend on aspartyl proteases for obligatory events in their life cycle. Such methods of treatment, their dosage levels and requirements may be selected by those of ordinary skill in the art from available methods and techniques. For example, a compound of this invention may be combined with a pharmaceutically acceptable adjuvant for administration to a virally-infected patient in a pharmaceutically acceptable manner and in an amount effective to lessen the severity of the viral infection.

Alternatively, the compounds of this invention may be used in vaccines and methods for protecting individuals against viral infection over an extended period of time. The compounds may be employed in such vaccines either alone or together with other compounds of this invention in a manner consistent with the conventional utilization of protease inhibitors in vaccines. For example, a compound of this invention may be combined with pharmaceutically acceptable adjuvants conventionally employed in vaccines and administered in prophylactically effective amounts to protect individuals over an extended period time against HIV infection. As such, the novel protease inhibitors of this invention can be administered as agents for treating or preventing HIV infection in a mammal.

The compounds of formula I, especially those having a molecular weight of less than about 700 g/mole, may be readily absorbed by the bloodstream of mammals upon oral administration. Compounds of formula I having a molecular weight of less than about 600 g/mole are most likely to demonstrate oral availability. This surprisingly impressive oral availability makes such compounds excellent agents for orally-administered treatment and prevention regimens against HIV infection.

The compounds of this invention may be administered to a healthy or HIV-infected patient either as a single agent or in combination with other anti-viral agents which interfere with the replication cycle of HIV. By administering the compounds of this invention with other anti-viral agents which target different events in the viral life cycle, the therapeutic effect of these compounds is potentiated. For instance, the co-administered anti-viral agent can be one which targets early events in the life cycle of the virus, such as cell entry, reverse transcription and viral DNA integration into cellular DNA. Anti-HIV agents targeting such early life cycle events include, didanosine (ddI), alcitabine (ddC), d4T, zidovudine (AZT), polysulfated polysaccharides, sT4 (soluble CD4), ganiclovir, dideoxycytidine, trisodium phosphonoformate, eflornithine, ribavirin, acyclovir, alpha interferon and trimenotrexate. Additionally, non-nucleoside inhibitors of reverse transcriptase, such as TIBO or nevirapine, may be used to potentiate the effect of the compounds of this invention, as may viral uncoating inhibitors, inhibitors of trans-activating proteins such as tat or rev, or inhibitors of the viral integrase.

Combination therapies according to this invention exert a synergistic effect in inhibiting HIV replication because each component agent of the combination acts on a different site of HIV replication. The use of such combinations also advantageously reduces the dosage of a given conventional anti-retroviral agent which would be required for a desired therapeutic or prophylactic effect as compared to when that agent is administered as a monotherapy. These combinations may reduce or eliminate the side effects of conventional single anti-retroviral agent therapies while not interfering with the anti-retroviral activity of those agents. These combinations reduce potential of resistance to single agent therapies, while minimizing any associated toxicity. These combinations may also increase the efficacy of the conventional agent without increasing the associated toxicity. In particular, we have discovered that these compounds act synergistically in preventing the replication of HIV in human T cells. Preferred combination therapies include the administration of a compound of this invention with AZT, ddI, ddC or d4T.

Alternatively, the compounds of this invention may also be co-administered with other HIV protease inhibitors such as Ro 31-8959 (Roche), L-735,524 (Merck), XM 323 (Du-Pont Merck) and A-80,987 (Abbott) to increase the effect of therapy or prophylaxis against various viral mutants or members of other HIV quasi species.

We prefer administering the compounds of this invention as single agents or in combination with retroviral reverse transcriptase inhibitors, such as derivatives of AZT, or other HIV aspartyl protease inhibitors. We believe that the co-administration of the compounds of this invention with retroviral reverse transcriptase inhibitors or HIV aspartyl protease inhibitors may exert a substantial synergistic effect, thereby preventing, substantially reducing, or completely eliminating viral infectivity and its associated symptoms.

The compounds of this invention can also be administered in combination with immunomodulators (e.g., bropirimine, anti-human alpha interferon antibody, IL-2, GM-CSF, methionine enkephalin, interferon alpha, diethyldithiocarbamate, tumor necrosis factor, naltrexone and rEPO); and antibiotics (e.g., pentamidine isethiorate) to prevent or combat infection and disease associated with HIV infections, such as AIDS and ARC.

When the compounds of this invention are administered in combination therapies with other agents, they may be administered sequentially or concurrently to the patient. Alternatively, pharmaceutical or prophylactic compositions according to this invention may be comprised of a combination of an aspartyl protease inhibitor of this invention and another therapeutic or prophylactic agent.

Although this invention focuses on the use of the compounds disclosed herein for preventing and treating HIV infection, the compounds of this invention can also be used as inhibitory agents for other viruses which depend on similar aspartyl proteases for obligatory events in their life cycle. These viruses include, as well as other AIDS-like diseases caused by retroviruses, such as simian immunodeficiency viruses, but are not limited to, HTLV-I and HTLV-II. In addition, the compounds of this invention may also be used to inhibit other aspartyl proteases, and in particular, other human aspartyl proteases, including renin and aspartyl proteases that process endothelin precursors. Pharmaceutical compositions of this invention comprise any of the compounds of the present invention, and pharmaceutically acceptable salts thereof, with any pharmaceutically-acceptable carrier, adjuvant or vehicle. Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of this invention may be administered orally, parenterally, by inhalation spray, topically, rectally, nasally, buccally, vaginally or via an implanted reservoir. We prefer oral administration or administration by injection. The pharmaceutical compositions of this invention may contain any conventional non-toxic pharmaceutically-acceptable carriers, adjuvants or vehicles. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as Ph. Helv or a similar alcohol.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Dosage levels of between about 0.01 and about 100 mg/kg body weight per day, preferably between about 0.5 and about 50 mg/kg body weight per day of the active ingredient compound are useful in the prevention and treatment of viral infection, including HIV infection. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician.

The compounds of this invention are also useful as commercial reagents which effectively bind to aspartyl proteases, particularly HIV aspartyl protease. As commercial reagents, the compounds of this invention, and their derivatives, may be used to block proteolysis of a target peptide or may be derivatized to bind to a stable resin as a tethered substrate for affinity chromatography applications. These and other uses which characterize commercial aspartyl protease inhibitors will be evident to those of ordinary skill in the art.

As used herein, the compounds according to the invention are defined to include pharmaceutically acceptable derivatives or prodrugs thereof. A "pharmaceutically acceptable derivative" or "pharmaceutically acceptable prodrug" means any pharmaceutically acceptable salt, ester, salt of an ester, or other derivative of a compound of this invention which, upon administration to a recipient, is capable of providing (directly or indirectly) a compound of this invention or an active metabolite or residue thereof. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species.

The compounds according to the invention may be used in the form of salts derived from inorganic or organic acids. Included among such acid salts, for example, are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxy-ethanesulfonate, lactate, maleate, methanesulfonate, 2-naphthalenesulfonate, nicotinate, oxalate, pamoate, pectianate, persulfate, phenylproprionate, picrate, pivalate, propionate, succinate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g. sodium), alkaline earth metal (e.g., magnesium), ammonium and $^+NW4$ (wherein W is $C_{1-4}$ alkyl). Physiologically acceptable salts of a hydrogen atom or an amino group include salts or organic carboxylic acids such as acetic, lactic, tartaric, malic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids.

Physiologically acceptable salts of a compound with a hydroxy group include the anion of said compound in combination with a suitable cation such as $Na^+$, $NH_4^+$, and $NW_4^+$ (wherein W is a $C_{1-4}$ alkyl group).

Pharmaceutically acceptable salts include salts of organic carboxylic acids such as ascorbic, acetic, citric, lactic, tartaric, malic, maleic, isothionic, lactobionic, p-aminobenzoic and succinic acids; organic sulphonic acids such as methanesulphonic, ethanesulphonic, benzenesulphonic and p-toluenesulphonic acids and inorganic acids such as hydrochloric, sulphuric, phosphoric, sulphamic and pyrophosphoric acids.

For therapeutic use, salts of the compounds according to the invention will be pharmaceutically acceptable. However, salts of acids and bases which are non-pharmaceutically acceptable may also find use, for example, in the preparation or purification of a pharmaceutically acceptable compound.

Preferred salts include salts formed from hydrochloric, sulfuric, acetic, succinic, citric and ascorbic acids.

Preferred esters of the compounds according to the invention are independently selected from the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted by, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

In such esters, unless otherwise specified, any alkyl moiety present advantageously contains from 1 to 18 carbon atoms, particularly from 1 to 6 carbon atoms, more particularly from 1 to 4 carbon atoms, Any cycloalkyl moiety present in such esters advantageously contains from 3 to 6 carbon atoms. Any aryl moiety present in such esters advantageously comprises a phenyl group.

Any reference to any of the above compounds also includes a reference to a pharmaceutically acceptable salts thereof.

The compounds according to the invention are especially useful for the treatment of AIDS and related clinical conditions such as AIDS related complex (ARC), progressive generalized lymphadenopathy (PGL), Kaposi's sarcoma, thrombocytopenic purpura, AIDS-related neurological conditions such as AIDS dementia complex, multiple sclerosis or tropical paraperesis, and also anti-HIV antibody-positive and HIV-positive conditions, including such conditions in asymptomatic patients.

In a further aspect of the invention there are provided the compounds according to the invention for use in medical therapy particularly for the treatment or prophylaxis of viral infections such as HIV infections.

According to another aspect, the present invention provides a method for the treatment or prevention of the symptoms or effects of a viral infection in an infected animal, for example, a mammal including a human, which comprises treating said animal with a therapeutically effective amount of a compound according to the invention. According to a particular embodiment of this aspect of the invention, the viral infection is an HIV infection. A further aspect of the invention includes a method for the treatment or prevention of the symptoms or effects of an HBV infection.

The compounds according to the invention may also be used in adjuvant therapy in the treatment of HIV infections or HIV-associated symptoms or effects, for example Kaposi's sarcoma.

The present invention further provides a method for the treatment of a clinical condition in an animal, for example, a mammal including a human which clinical condition includes those which have been discussed in the introduction hereinbefore, which comprises treating said animal with a therapeutically effective amount of a compound according to the invention. The present invention also includes a method for the treatment or prophylaxis of any of the aforementioned infections or conditions.

In yet a further aspect, the present invention provides the use of a compound according to the invention in the manufacture of a medicament for the treatment or prophylaxis of any of the above mentioned viral infections or conditions. It will be appreciated that of compounds of Formula (I), (IA), (IB), (II), (III), (IV), and (V) and one or more other HIV protease inhibitors, reverse transcriptase inhibitors, or non-nucleoside reverse transcriptase inhibitors may be used in the manufacture of the above medicament.

Reference herein to treatment extends to prophylaxis as well as the treatment of established infections or symptoms.

The above compounds according to the invention and their pharmaceutically acceptable derivatives may be employed in combination with other therapeutic agents for the treatment of the above infections or conditions. Combination therapies according to the present invention comprise the administration of at least one compound of the formula (I) or a pharmaceutically acceptable derivative thereof and at least one other pharmaceutically active ingredient. The active ingredient(s) and pharmaceutically active agents may be administered simultaneously in either the same or different pharmaceutical formulations or sequentially in any order. The amounts of the active ingredient(s) and pharmaceutically active agent(s) and the relative timings of administration will be selected in order to achieve the desired combined therapeutic effect. Preferably the combination therapy involves the administration of one compound according to the invention and one of the agents mentioned herein below.

Examples of such further therapeutic agents include agents that are effective for the treatment of viral infections or associated conditions such as (1 alpha, 2 beta, 3 alpha)-9-[2,3-bis (hydroxymethyl) cyclobutyl]guanine [(−)BHCG, SQ-34514], oxetanocin-G (3,4-bis-(hydroxymethyl)-2-oxetanosyl]guanine), acyclic nucleosides (e.g. acyclovir, valaciclovir, famciclovir, ganciclovir, penciclovir), acyclic nucleoside phosphonates (e.g. (S)-1-(3-hydroxy-2-phosphonylmethoxypropyl)cytosine (HPMPC), ribonucleotide reductase inhibitors such as 2-acetylpyridine 5-[(2-chloroanilino)thiocarbonyl)thiocarbonohydrazone, 3'azido-3'-deoxythymidine, other 2',3'-dideoxynucleosides such as 2',3'-dideoxycytidine, 2',3'-dideoxyadenosine, 2',3'-dideoxyinosine, 2',3'-didehydrothymidine, protease inhibitors such as indinavir, ritonavir, nelfinavir, [3S-[3R*(1R*,2S*)]]-[3-[[(4-aminophenyl)sulfonyl](2-methylpropyl)amino]-2-hydroxy-1-(phenylmethyl)propyl]-tetrahydro-3-furanyl ester (141W94), oxathiolane nucleoside analogues such as (−)-cis-1-(2-hydroxymethyl)-1,3-oxathiolane 5-yl)-cytosine (lamivudine) or cis-1-(2-(hydroxymethyl)-1,3-oxathiolan-5-yl)-5-fluorocytosine (FTC), 3'-deoxy-3'-fluorothymidine, 5-chloro-2',3'-dideoxy-3'-fluorouridine, (−)-cis-4-[2-amino-6-(cyclopropylamino)-9
H-purin-9-yl]-2-cyclopentene-1-methanol, ribavirin, 9-[4-hydroxy-2-(hydroxymethyl)but-1-yl]-guanine (H2G), tat inhibitors such as 7-chloro-5-(2-pyrryl)-3H-1,4-benzodiazepin-2-(H)one (Ro5-3335), 7-chloro-1,3-dihydro-5-(1H-pyrrol-2yl)-3H-1,4-benzodiazepin-2-amine (Ro24-7429), interferons such as α-interferon, renal excretion inhibitors such as probenecid, nucleoside transport inhibitors such as dipyridamole; pentoxifylline, N-acetylcysteine (NAC), Procysteine, α-trichosanthin, phosphonoformic acid, as well as immunomodulators such as interleukin II or thymosin, granulocyte macrophage colony stimulating factors, erythropoetin, soluble $CD_4$ and genetically engineered derivatives thereof, or non-nucleoside reverse transcriptase inhibitors (NNRTIs) such as nevirapine (BI-RG-587), loviride (α-APA) and delavuridine (BHAP), and phosphonoformic acid, and 1,4-dihydro-2H-3,1-benzoxazin-2-ones NNRTIs such as (−)-6-chloro-4-cyclopropylethynyl-4-trifluoromethyl-1,4-dihydro-2H-3,1-benzoxazin-2-one (L-743,726 or DMP-266), and quinoxaline NNRTIs such as isopropyl (2S)-7-fluoro-3,4-dihydro-2-ethyl-3-oxo-1(2H)-quinoxalinecarboxylate (HBY1293).

More preferably the combination therapy involves the administration of one of the above mentioned agents and a compound within one of the preferred or particularly preferred sub-groups within formula (I) as described above. Most preferably the combination therapy involves the joint use of one of the above named agents together with one of the compounds of formula (I) specifically named herein.

The present invention further includes the use of a compound according to the invention in the manufacture of a medicament for simultaneous or sequential administration with at least one other therapeutic agent, such as those defined hereinbefore.

In order that this invention may be more fully understood, the following examples are set forth. These examples are for the purpose of illustration only and are not to be construed as limiting the scope of the invention in any way.

EXAMPLE (COMPOUND 1)

Step 1:

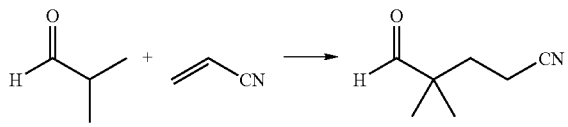

3,3-Dimethyl-4-oxobutyl cyanide

To a stirred solution of isobutyraldehyde (6.3 mL, 69.3 mmol), hydroquinone (25 mg) and acrylonitrile (5.7 mL, 86.7 mmol) in 1,4-dioxane (25 mL) was added 5% sodium hydroxide (4.6 mL). The reaction was heated at 65° C. for 2.5 hours and then stirred at ambient temperature for 16 hours. The dioxane was removed in vacuo and the residue was taken up in dichloromethane (80 mL). The dichloromethane was washed with water (3×80 mL), dried (magnesium sulfate), concentrated in vacuo and then distilled to afford the title compound (5.4 g, 63%) as a colorless liquid; bp 70° C. (0.8 mm);

$^1$H NMR (CDCl$_3$): δ 1.11 (6H, s), 1.87 (2H, t), 2.29 (2H, t), 9.40 (1H, s)

Step 2:

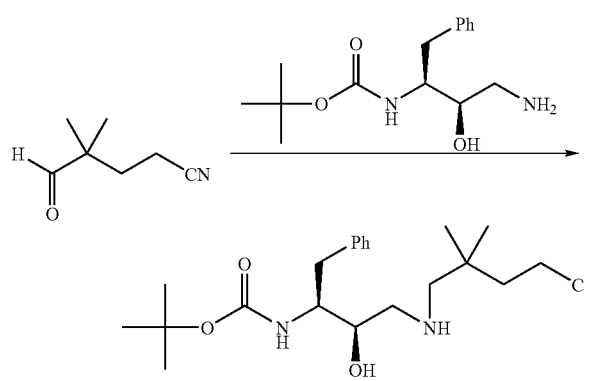

tert-Butyl N-(1S,2R)-1-benzyl-3-[(4-cyano-2,2-dimethyl butyl)amino]-2-hydroxypropylcarbamate To a suspension of the product of Step 1 (1.1 g, 8.7 mmol) and tert-butyl N-(1S,2R)-3-amino-1-benzyl-2-hydroxypropylcarbamate (3.1 g, 11.0 mmol) in 1,2-dichloroethane (30 mL), tetrahydrofuran (30 mL) and N,N-dimethylformamide (30 mL) was added sodium triacetoxy borohydride (3.2 g, 15.0 mmol) and the mixture was stirred under nitrogen atmosphere for 3.5 hours. The mixture was filtered and the filtrate was concentrated to 25 mL. The residue was partitioned between ethyl acetate and 2M sodium hydroxide/water. The organic phase was washed with water, brine, dried (sodium sulfate), and evaporated. The residue was chromatographed (silica gel, dichloromethane/methanol, 95:5) to provide the title compound as a white solid (2.8 g, 90%); mp 79-80 C;

$^1$H NMR (DMSO-d$_6$): δ 0.81 (6H, s), 1.24 (9H, s), 1.50 (3H, br dd), 2.22 (2H, s), 2.40 (2H, br dd), 2.45-2.60 (3H, m), 2.96 (1H, dd), 3.40 (1H, br s), 3.50-3.55 (1H, m), 4.87 (1H, br s), 6.70 (1H, d), 7.10-7.18 (3H, m), 7.20-7.25 (2H, m); MS: 390.2 (MH$^+$)

Step 3:

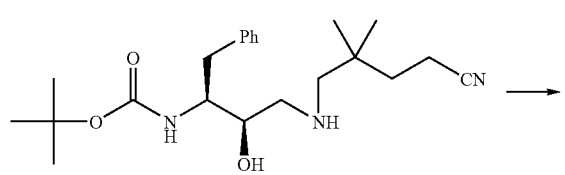

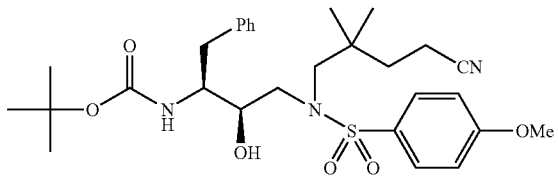

tert-Butyl N-((1S,2R)-1-benzyl-3-(4-cyano-2,2-dimethylbutyl)[(4-methoxyphenyl)sulfonyl]amino-2-hydroxypropyl)carbamate To a solution of the product of Step 2 (0.5 g, 1.3 mmol) in anhydrous dichloromethane (15 mL) at 0° C. was added N-ethyldiisopropylamine (0.48 mL, 0.36 g, 2.8 mmol) and a solution of 4-methoxybenzenesulfonyl chloride (0.27 g, 1.3 mmol) in anhydrous dichloromethane (2 mL) and the mixture was stirred at ambient temperature under nitrogen atmosphere for 18 hours. The mixture was washed sequentially with 1M hydrochloric acid, sodium bicarbonate/water, brine, dried (sodium sulfate) and concentrated. The residue was chromatographed (silica gel, dichloromethane/methanol, 97:3) to provide the title compound as a colorless foam (0.34 g, 48%);

$^1$H NMR (DMSO-d$_6$): δ 0.88 (3H, s), 0.92 (3H, s), 1.20 (9H, s), 1.67 (2H, t), 2.40-2.50 (2H, m), 2.70 (1H, d), 2.80-2.95 (2H, m), 3.12-3.2 (4H, m), 3.73 (1H, br s), 3.82 (3H, s), 5.10 (1H, d), 6.63 (1H, d), 7.08 (2H, d), 7.10-7.27 (5H, m), 7.78 (2H, d); MS: 560.2 (MH$^+$)

EXAMPLE (COMPOUND 2)

Step 1:

3-Methyl-4-oxobutyl cyanide

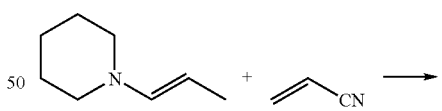

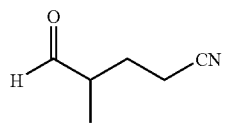

N-(1-propen-1-yl)piperidine [Mannich, D.; Ber. 1936, 69, 2106] was subjected to the procedure used in Step 1 of Example (Compound 3) to give the title compound as a pale yellow oil; bp 127-129 C (19 mm); $^1$H NMR (CDCl$_3$): δ 1.19 (3H, d), 1.62-1.72 (1H, m), 2.03-2.13 (1H, m), 2.43 (2H, t), 2.51-2.61 (1H, m), 9.62 (1H, s).

Step 2:

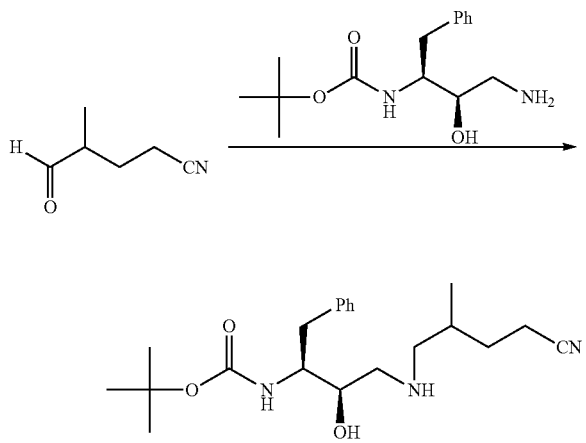

tert-Butyl N-(1S,2R)-1-benzyl-3-[(2RS)-(4-cyano-2-methylbutyl)amino]-2-hydroxypropylcarbamate The product from step 1 was subjected to the procedure used in Example (Compound 1), Step 2, to provide the title compound as a white solid;
$^1$H NMR (DMSO-$d_6$): δ 0.93 (3H, d), 1.32 (9H, s), 1.34-1.84 (4H, m), 2.36-2.68 (7H, m), 3.04 (1H, dd), 3.42-3.66 (2H, m), 4.82 (1H, br s), 6.75 (1H, d), 7.15-7.35 (5H, m); MS: 376 (MH$^+$)

Step 3:

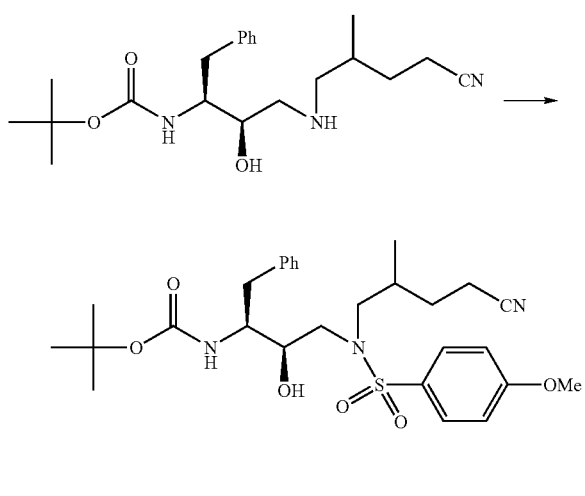

ter-Butyl N-((1S,2R)-1-benzyl-3-[(2RS)-(4-cyano-2-methylbutyl)][(4-methoxyphenyl)sulfonyl]amino-2-hydroxypropyl)carbamate The product from Step 2 was subjected to the procedure used above (Step 3, Example (Compound 1)) to give the title compound as a white foam (~1:1 mixture of diastereomers by $^1$H NMR spectroscopy);
$^1$H NMR (DMSO-$d_6$): δ 0.80 (3H, d), 1.21 (9H, s), 1.2-1.3 (1H, m), 1.8-1.9 (2H, m), 2.35-2.45 (3H, m), 2.60-2.65 (1H, m), 2.70-2.82 (1H, m), 2.9-3.0 (2H, m), 3.22-3.30 (1H, m), 3.4-3.6 (2H, m), 3.8 (3H, m), 5.05 (1H, br s), 6.70 (1H, d), 7.05 (2H, d), 7.10-7.23 (5H, m), 7.70 (2H, d); MS: 546.3 (MH$^+$)

EXAMPLE (COMPOUND 3)

Step 1:

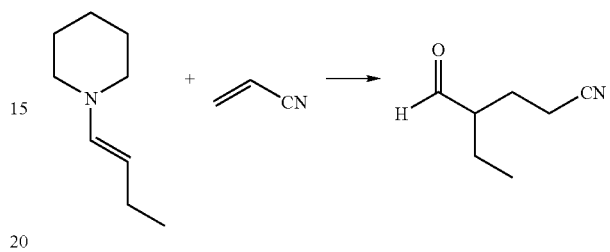

3-Ethyl-4-oxobutyl cyanide

A stirred solution of N-(1-buten-1-yl)piperidine [Mannich, D.; Ber. 1936, 69, 2106] (4.2 g, 29.9 mmol) and acrylonitrile (2.1 g, 38.8 mmol) in acetonitrile (25 mL) was heated at reflux for 18 hours. Acetic acid and water (10 mL, 1:1) was added and the reaction was heated an additional 4 hours. The acetonitrile was removed in vacuo and the residue was taken up in ether (60 mL). The ether was washed with water (2×40 mL), saturated sodium bicarbonate/water (40 mL), dried (magnesium sulfate), concentrated in vacuo and then distilled to afford the title compound (1.6 g, 42%) as a colorless liquid. bp 132° C. (18 mm);
$^1$H NMR (CDCl$_3$): δ 0.97 (3H, t), 1.55-1.82 (3H, m), 1.96-2.07 (1H, m), 2.40 (2H, q), 2.40-2.48 (1H, m), 9.62 (1H, s).

Step 2:

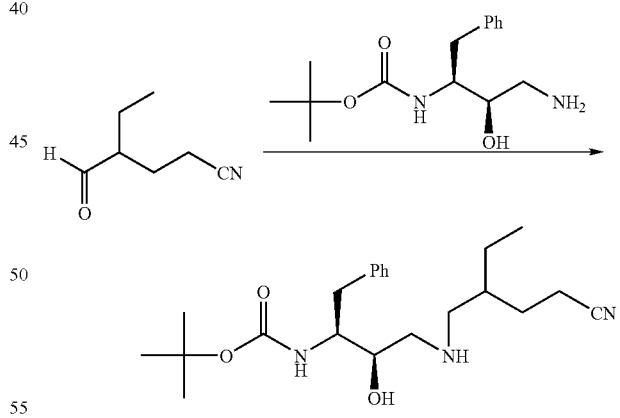

tert-Butyl N-(1S,2R)-1-benzyl-3-[(2RS)-(4-cyano-2-ethylbutyl)amino]-2-hydroxypropylcarbamate The product from step a was subjected to the general procedure (Step 2, Example (Compound 1)) to provide the title compound as a white solid; mp 67-68° C.;
$^1$H NMR (DMSO-$d_6$): δ 0.90 (3H, t), 1.22 (9H, s), 1.23-1.28 (1H, m), 1.35-1.42 (1H, m), 1.45-1.62 (3H, m), 2.35-2.60 (7H, m), 2.96 (1H, dd), 3.40 (1H, br s), 3.5 (1H, qd), 4.80 (1H, br s), 6.73 (1H, d), 7.10-7.25 (5H, m); MS: 390.2 (MH$^+$).

Step 3:

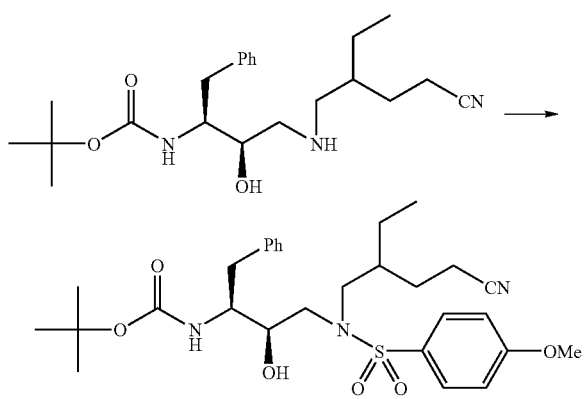

tert-Butyl N-((1S,2R)-1-benzyl-3-[(2RS)-(4-cyano-2-ethylbutyl)][(4-methoxyphenyl)sulfonyl]amino-2-hydroxypropyl)carbamate The product from step 2 was subjected to general procedure (Step 3, Example (Compound 1)) to give the title compound as a white glass (~1:1 mixture of diastereomers by $^1$H NMR spectroscopy);

$^1$H NMR (DMSO-d$_6$): δ 0.80 (3H, t), 1.22 (9H, s), 1.32-1.40 (1H, m), 1.45-1.60 (1H, m), 1.75-1.82 (1H, m), 2.40-2.50 (3H, m), 2.75-2.85 (2H, m), 2.90 (1H, dd), 3.20 (1H, dd), 3.25-3.30 (1H, m), 3.40-3.48 (1H, m), 3.50-3.58 (1H, m), 3.80 (3H, s), 5.0 (1H, br s), 6.70 (1H, d), 7.08 (2H, d), 7.10-7.24 (5H, m), 7.75 (2H, m); MS: 582.3 (MH$^+$)

EXAMPLE (COMPOUND 4)

Step 1:

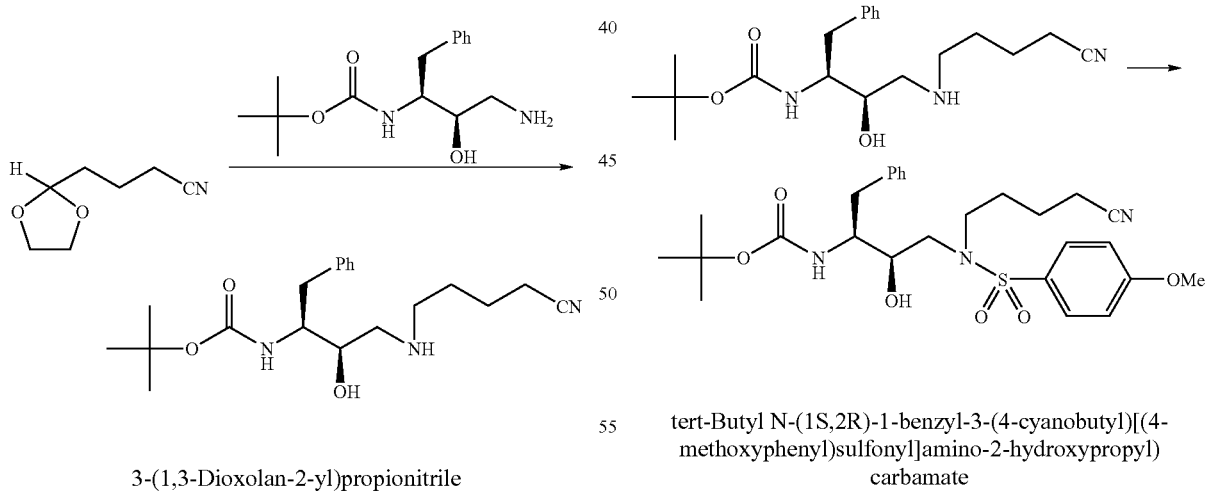

3-(1,3-Dioxolan-2-yl)propionitrile

A mixture of 2-(3-chloropropyl)-1,3-dioxolane (5.7 g, 37.8 mmol) and potassium cyanide (3.8 g, 58.4 mmol) in dimethylsulfoxide (12 mL) was heated at 100° C. for 48 hours. The reaction mixture was diluted with water (80 mL) and extracted with ether (3×60 mL). The combined ether layer was washed with water (3×60 mL), dried (magnesium sulfate), concentrated in vacuo and purified by silica gel chromatography (ethyl acetate in hexane, 1:2) to afford the title compound (2.1 g, 40%) as a pale yellow liquid;

$^1$H NMR (CDCl3): δ 1.76-1.84 (4H, m), 4.21 (2H, t), 3.78-4.01 (4H, m), 4.87 (1H, t).

Step 2:

tert-Butyl N-(1S,2R)-1-benzyl-3-[(4-cyanobutyl)amino]-2-hydroxypropylcarbamate

To a stirred solution of the product from step 1 (2.0 g, 14.2 mmol) in tetrahydrofuran (85 mL) was added 5% hydrochloric acid (17 mL). The reaction was heated at 70° C. for 5 hours and then cooled to ambient temperature. The mixture was poured into saturated sodium bicarbonate (80 mL) and extracted with ether (3×60 mL). The organic extracts were dried (magnesium sulfate), concentrated down in vacuo to ~30 mL and added to a stirred suspension of tert-butyl N-(1S, 2R)-3-amino-1-benzyl-2-hydroxypropylcarbamate (3.9 g, 14.1 mmol) in dichloroethane (30 mL) and dimethylformamide (20 mL). Sodium triacetoxyborohydride (4.5 g, 21.2 mmol) was added followed by glacial acetic acid (0.8 mL) and the reaction was stirred at ambient temperature for 16 hours. The mixture was filtered and the filtrate was concentrated in vacuo to ~25 mL, diluted with water (60 mL), adjusted to pH~12 with 1N sodium hydroxide and extracted with ethyl acetate (80 mL). The ethyl acetate was washed with water (2×60 mL), dried (magnesium sulfate), concentrated in vacuo and purified by silica gel chromatography (92:8:1; chloroform:methanol:ammonium hydroxide) to afford the title compound (1.8 g, 34%) as a white solid.

$^1$H NMR (d$_6$-DMSO): δ 1.32 (9H, s), 1.48-1.72 (4H, m), 2.02 (1H, br s), 2.44-2.70 (7H, m), 3.04 (1H, dd), 3.42-3.64 (2H, m), 4.82 (1H, br s), 6.72 (1H, d), 7.15-7.35 (5H, m); MS: 362 (MH$^+$).

Step 3:

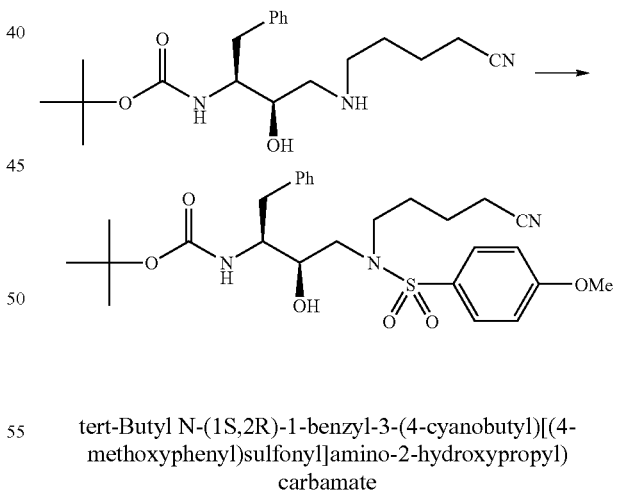

tert-Butyl N-(1S,2R)-1-benzyl-3-(4-cyanobutyl)[(4-methoxyphenyl)sulfonyl]amino-2-hydroxypropyl)carbamate The product from Step 2 was subjected to the general procedure Step 3, Example (Compound 1) to afford the title compound as a white foam;

$^1$H NMR (DMSO-d$_6$): δ 1.22 (9H, s), 1.4-1.6 (4H, m), 2.4-2.5 (3H, m), 2.75 (1H, dd), 2.95 (2H, br d), 3.2-3.3 (2H, m), 3.4-3.6 (2H, m), 3.8 (3H, s), 5.07 (1H, br s), 6.7 (1H, d), 7.09 (2H, d), 7.10-7.14 (5H, m), 7.7 (1H, m); MS: 532.2 (MH$^+$)

EXAMPLE (COMPOUND 5)

Step 1:

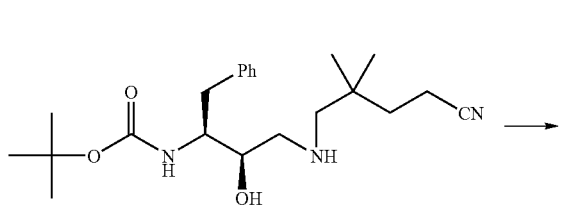

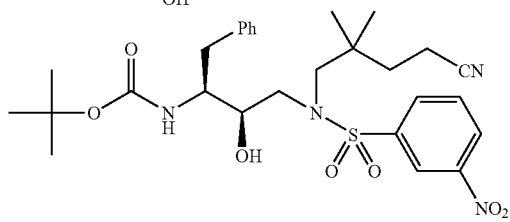

tert-Butyl N-((1S,2R)-1-benzyl-3-(4-cyano-2,2-dimethylbutyl)[(3-nitrophenyl)sulfonyl]amino-2-hydroxypropyl)carbamate To a solution of the product from step 2 (Example (Compound 1); 0.65 g, 1.6 mmol) in dichloromethane (5 mL) was added 3-nitrobenzenesulfonyl chloride (0.4 g, 1.8 mmol) and 1M sodium hydroxide/water (3 mL, 3 mmol) and the mixture was stirred at ambient temperature for 7 hours. Excess 3-nitrobenzenesulfonyl chloride (0.2 g, 0.9 mmol) and 1M sodium hydroxide/water (1.5 mL, 1.5 mmol) were added and stirring was continued for 18 hours. The organic phase was dried (sodium sulfate) and evaporated. The residue was chromatographed (silica gel, dichloromethane/methanol, 97:3) to provide the title compound (0.52 g, 55%) as a white foam;

$^1$H NMR (DMSO-d$_6$): δ 0.9 (3H, s), 0.95 (3H, s), 1.2 (9H, s), 1.65 (2H, t), 2.4 (1H, dd), 2.50-2.55 (1H, m), 2.8 (1H, d), 3.0 (1H, d), 3.2 (1H, dd), 3.3-3.5 (5H, m), 4.95 (1H, d), 6.6 (1H, d), 7.10-7.25 (5H, m), 7.85 (1H, t), 8.15 (1H, d), 8.45 (1H, d), 8.5 (1H, s).

Step 2:

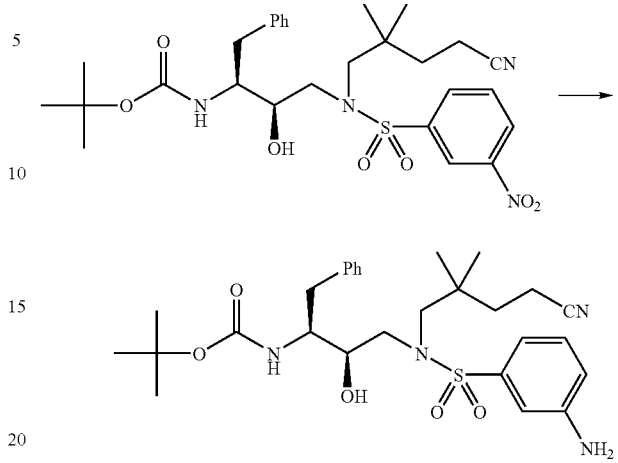

tert-ButylN-((1S,2R)-3-[(3-aminophenyl)sulfonyl](4-cyano-2,2-dimethylbutyl)amino-1-benzyl-2-hydroxypropyl)carbamate A mixture of the product form step 1 (0.19 g), 10% Pd/C (40 mg), and ethylacetate (4 mL) was hydrogenated at atmospheric pressure for 18 hours. Solvent was evaporated and the residue was chromatographed (silica gel, dichloromethane/methanol, 97:3) to give the title compound (0.16 g, 85%) as a foam;

$^1$H NMR (CDCl$_3$): δ 0.99 (6H, s), 1.25 (9H, s), 1.75 (2H, t), 2.4 (2H, t), 2.8 (1H, dd), 2.95-3.20 (5H, m), 3.6-3.8 (2H, br m), 3.9-4.1 (3H, br m), 4.58 (1H, br d), 6.85 (1H, d), 7.05 (1H, br s), 7.09 (1H, d), 7.18-7.31 (6H, m); MS: 545.2 (MH$^+$).

EXAMPLE (COMPOUND 6)

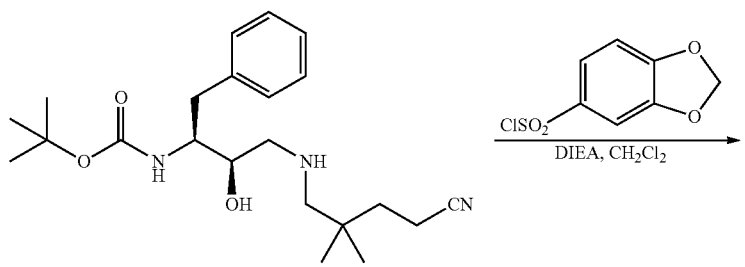

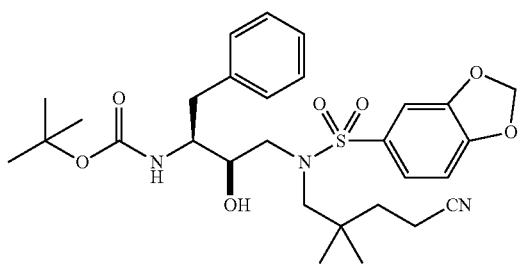

{(1S,2R)-3-[(Benzo[1,3]dioxole-5-sulfonyl)-(4-cyano-2,2-dimethyl-butyl)-amino]-1-benzyl-2-hydroxy-propyl}-carbamic acid tert-butyl ester

[(1S,2R)-1-Benzyl-3-(4-cyano-2,2-dimethyl-butylamino)-2-hydroxy-propyl]-carbamic acid tert-butyl ester (0.099 g, 0.25 mmol) was dissolved in CH$_2$Cl$_2$ and treated with diisopropylethylamine (0.066 ml, 0.38 mmol) and Benzo[1,3]dioxole-5-sulfonyl chloride (0.067 g, 0.31 mmol) at ambient temperature under argon with stirring. After 15 h the reaction mixture was concentrated in vacuo, taken up in EtOAc, washed with sat. aq. NaHCO$_3$, and brine. The organic phase was dried over MgSO$_4$, filtered and solvent removed in vacuo. Purification by column chromatography (1% MeOH in CH$_2$Cl$_2$) gave 0.083 g of a white solid. MS (ES): 574 (M+1).

EXAMPLE (COMPOUND 7)

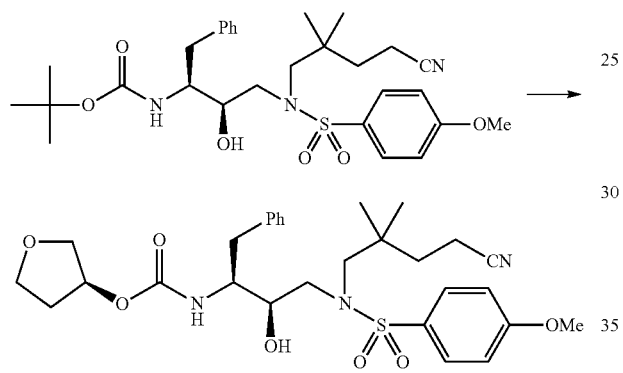

(3S)-Tetrahydro-3-furanyl N-((1S,2R)-1-benzyl-3-(4-cyano-2,2-dimethylbutyl)[(4-methoxyphenyl)sulfonyl]amino-2-hydroxypropyl)carbamate To a solution of the product of Step 3, Example (Compound 1) (0.22 g, 0.4 mmol) in dichloromethane (2.5 mL) at 0° C. was added trifluoroacetic acid (2.5 mL) and the mixture was stirred at ambient temperature for 1 hour. Solvent was evaporated and coevaporated with dichloromethane. The residue was dissolved in dichloromethane and washed with 0.1 M sodium hydroxide/water, water, brine, dried (sodium sulfate), concentrated and dried in vacuo. The resulting pale yellow foam was dissolved in acetonitrile (4 mL) and N-ethyldiisopropylamine (0.08 mL, 0.059 g, 0.46 mmol) and N-succinimidyl (3S)-tetrahydro-3-furanyl carbonate (0.098 g, 0.43 mmol) were added. The mixture was stirred at ambient temperature for 1 hour and the solvent was evaporated. The residue was chromatographed (silica gel, dichloromethane/methanol, 98:2) to give the title compound as a white foam (0.18 g, 82%);

$^1$H NMR (DMSO-d$_6$): δ 0.88 (3H, s), 0.92 (3H, s), 1.65 (2H, t), 1.75 (1H, dt), 2.05 (1H, sextuplet), 2.45-2.50 (2H, m), 2.70 (1H, s), 2.85 (1H, dd), 2.93 (1H, dd), 3.2-3.4 (5H, m), 3.57 (1H, dd), 3.63 (1H, td), 3.69 (1H, dd), 3.72-3.80 (1H, s), 3.84 (3H, s), 4.90 (1H, br s), 5.18 (1H, d), 7.08 (2H, d), 7.10-7.25 (6H, m), 7.75 (2H, d); MS: 574.2 (MH$^+$).

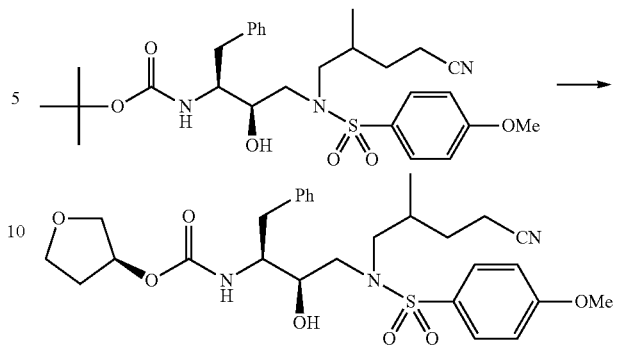

EXAMPLE (COMPOUND 8)

(3S)-Tetrahydro-3-furanyl N-((1S,2R)-1-benzyl-3-[(2RS)-4-cyano-2-methyl][(4-methoxyphenyl)sulfonyl]amino-2-hydroxypropyl)carbamate The product from step 3, Example (Compound 2) was subjected to general procedure in Example (Compound 7) to give the title compound as a white glass (~1:1 mixture of diastereomers by $^1$H NMR spectroscopy); $^1$H NMR (DMSO-d$_6$): δ 0.80 (3H, d), 1.2-1.3 (1H, m), 1.75 (1H, dd), 1.8-1.9 (2H, m), 2.0-2.1 (1H, m), 2.40 (1H, dd), 2.45-2.50 (2H, m), 2.6-2.7 (2H, m), 2.98 (1H, d), 3.10 (1H, dd), 3.3-3.4 (2H, m), 3.5-3.7 (5H, m), 3.82 (3H, s), 4.90 (1H, br s), 5.10 (1H, d), 7.08 (2H, d), 7.10-7.25 (6H, m), 7.72 (2H, d); MS: 560.2 (MH$^+$).

EXAMPLE (COMPOUND 9)

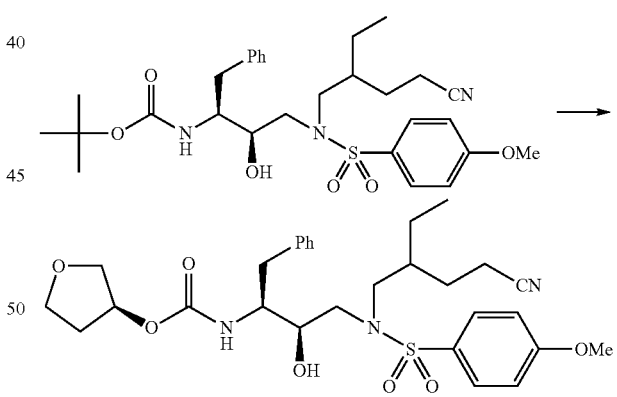

(3S)-Tetrahydro-3-furanyl N-((1S,2R)-1-benzyl-3-[(2RS)-4-cyano-2-ethyl][(4-methoxyphenyl)sulfonyl]amino-2-hydroxypropyl)carbamate The product from Step 3, Example (Compound 3) was subjected to general procedure in Example (Compound 7) to provide the title compound as a white glass (~1:1 mixture of diastereomers by $^1$H NMR spectroscopy);

$^1$H NMR (DMSO-d$_6$): δ 0.80 (3H, t), 1.2-1.4 (2H, m), 1.42-1.60 (2H, m), 1.70-1.80 (2H, m), 1.95-2.05 (1H, m), 2.4-2.5 (2H, m), 2.90-2.95 (3H, m), 2.98 (1H, dd), 3.10 (1H, dd), 3.2-3.3 (1H, m), 3.4-3.90 (6H, m), 3.94 (3H, s), 4.90 (1H, br s), 5.05 (1H, d), 7.05-7.30 (8H, m), 7.75 (2H, d); MS: 574.2 (MH+).

EXAMPLE (COMPOUND 10)

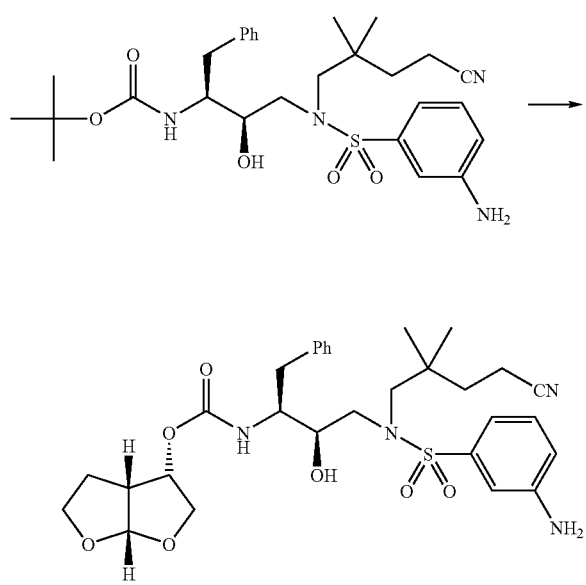

(3S,3aR,6aS)-Hexahydrofuro[2,3-b]furan-3-yl N-((1S,2R)-3-[(3-aminophenyl)sulfonyl](4-cyano-2,2-dimethylbutyl)-amino-1-benzyl-2-hydroxypropyl) carbamate To a solution of the product form Step 2, Example (Compound 5) (0.13 g) in dichloromethane (1.5 mL) at 0° C. was added trifluoroacetic acid (1 mL) and the mixture was stirred at ambient temperature for 1 hour. Solvent was evaporated and coevaporated with dichloromethane. The residue was dissolved in dichloromethane and washed with 0.1 M sodium hydroxide/water, dried (sodium sulfate), concentrated and dried in vacuo. The resulting pale yellow foam was dissolved in acetonitrile (3 mL) and N-ethyldiisopropylamine (0.09 mL, 0.067 g, 0.52 mmol) and [(3S,3aR,6aS)-hexahydrofuro[2,3-b]furan-3-yl][4-nitrophenyl]carbonate (0.08 g, 0.31 mmol) were added. The mixture was stirred at ambient temperature under nitrogen atmosphere for 18 hours. Solvent was evaporated and the residue was dissolved in dichloromethane, washed with saturated sodium bicarbonate/water, dried (sodium sulfate) and chromatographed (silica gel, dichloromethane/methanol, 97:3) to give the title compound (0.09 g, 65%) as a foam;
$^1$H NMR (DMSO-$d_6$): δ 0.9 (3H, s), 0.97 (3H, s), 1.6-1.7 (3H, m), 1.8 (1H, dd), 2.2-2.3 (3H, m), 2.7 (1H, d), 2.80-2.95 (3H, m), 3.3-3.4 (3H, m), 3.45 (1H br q), 3.6-3.8 (4H, m), 4.8 (1H, q), 5.15 (1H, d), 5.58 (1H, d), 5.6 (2H, br s), 6.8 (1H, d), 6.85 (1H, d), 6.98 (1H, br s), 7.10-7.25 (7H, m); MS: 601.2 (MH+).

EXAMPLE (COMPOUND 11)

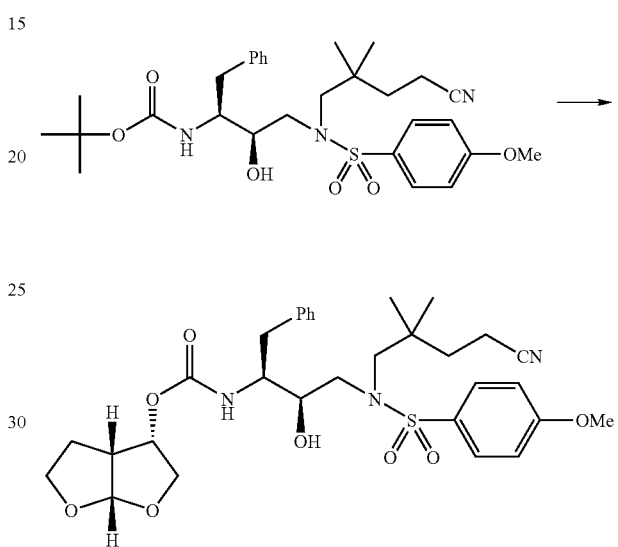

(3S,3aR,6aS)-Hexahydrofuro[2,3-b]furan-3-yl N-((1S,2R)-1-benzyl-3-(4-cyano-2,2-dimethylbutyl) [(4-methoxyphenyl)sulfonyl]amino-2-hydroxypropyl)carbamate The product from Step 3 of Example (Compound 1) was subjected to the procedure used in Example (Compound 10) to provide the title compound as a white foam;
$^1$H NMR (DMSO-$d_6$): δ 0.89 (3H, s), 0.92 (3H, s), 1.6-1.7 (3H, m), 1.5 (1H, dd), 2.4-2.5 (3H, m), 2.7 (1H, d), 2.85-2.95 (3H, m), 3.25-3.45 (4H, m), 3.6-3.8 (4H, m), 3.82 (3H, s), 4.79 (1H, q), 5.15 (1H, d), 5.53 (1H, d), 7.08 (2H, d), 7.12-7.28 (6H, m), 7.75 (2H, d); MS: 616.5 (MH+).

Alternative Synthesis

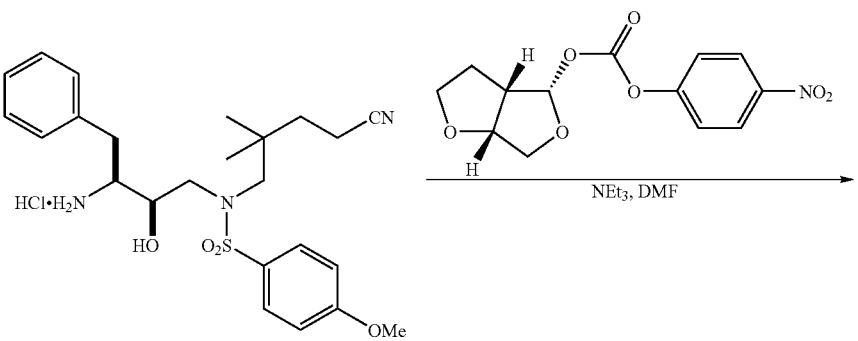

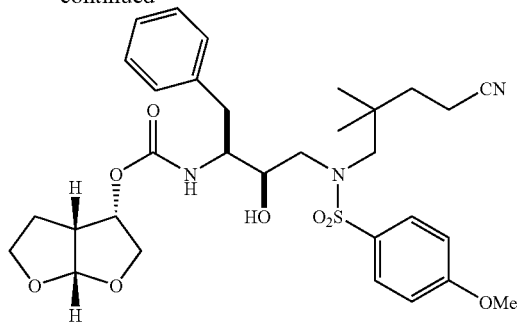

(3S,3aR,6aS)-Hexahydrofuro[2,3-b]furan-3-yl N-((1S,2R)-1-benzyl-3-(4-cyano-2,2-dimethylbutyl)[(4-methoxyphenyl)sulfonyl]amino-2-hydroxypropyl) carbamate N-(2R,3S)-(3-Amino-2-hydroxy-4-phenyl-butyl)-N-(4-cyano-2,2-dimethyl-butyl)-4-methoxy-benzenesulfonamide hydrochloride (0.086 mmol) was dissolved in 1 mL of DMF and treated with triethylamine (60 μL, 0.43 mmol) and (3S,3aR,6aS) hexahydrofuro[2,3-b]furan-2-yl 4-nitrophenyl carbonate (0.028 g, 0.095 mmol) at ambient temperature under argon with stirring. After 3 days the reaction mixture was dissolved in EtOAc, washed with water and brine. The organic phase was dried over MgSO₄, filtered and solvent removed in vacuo. Purification by column chromatography (EtOAc, 50% in Hexane) gave 0.028 g of a white solid. MS (ES): 616.3 (M+1), HPLC showed the material to be 98% pure; ret. time=11.80 min.

EXAMPLE (COMPOUND 12)

Step 1:

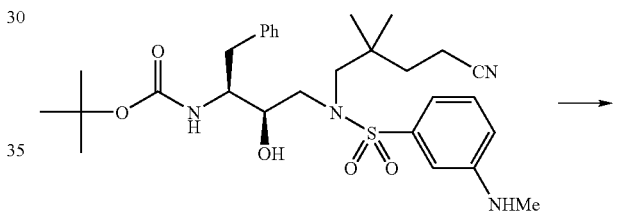

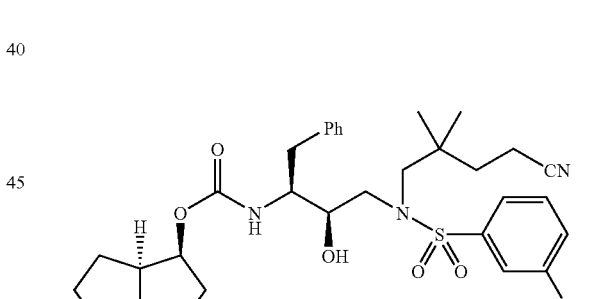

tert-Butyl N-[(1S,2R)-1-benzyl-3-((4-cyano-2,2-dimethylbutyl) [3-(methylamino)phenyl]sulfonylamino)-2-hydroxypropyl]carbamate A mixture of the product from Step 1 (Example (Compound 5), 0.21 g), 10% Pd/C (0.2 g), methanol (7 mL), and acetic acid (0.3 mL) was hydrogenated at atmospheric pressure for 48 hours. The mixture was filtered through a bed of celite and the solvent was evaporated. The residue was dissolved in dichloromethane and the solution was washed with saturated sodium bicarbonate/water, dried (sodium sulfate), evaporated, and the residue was chromatographed (silica gel, dichloromethane/methanol, 98:2) to afford the title compound (25 mg, 13%) as a glass;

$^1$H NMR (CDCl₃): δ 0.95 (6H, s), 1.29 (9H, s), 1.72 (2H, t), 2.37 (2H, t), 2.75-2.85 (1H, m), 2.87 (3H, s), 2.90-3.20 (5H, m), 3.75 (1H, brs), 3.95 (1H, brs), 4.02 (1H, brs), 4.18 (1H, brs), 4.55 (1H, d), 6.76 (1H, dd), 6.95 (1H, t), 7.02 (1H, d), 7.18-7.23 (3H, m), 7.25-7.32 (3H, m).

Step 2:

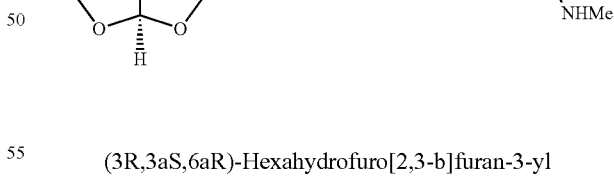

(3R,3aS,6aR)-Hexahydrofuro[2,3-b]furan-3-yl N-[(1S,2R)-1-benzyl-3-((4-cyano-2,2-dimethylbutyl)[3-(methylamino)-phenyl]sulfonylamino)-2-hydroxypropyl]carbamate The product from Step 1 was subjected to the procedure used in Example (Compound 10) to afford the title compound as a white foam;

$^1$H NMR (DMSO-d₆): δ 0.97 (3H, s), 1.02 (3H, s), 1.20-1.26 (1H, m), 1.30-1.35 (1H, m), 1.78 (2H, t), 2.50-2.62 (3H, m), 2.78 (3H, d), 2.80-2.97 (3H, m), 3.05 (1H, d), 3.38-3.42 (2H, m), 3.50-3.60 (1H, m), 3.65 (2H, dd), 3.78 (1H, td), 3.90

(2H, dd), 4.85 (1H, q), 5.26 (1H, d), 5.58 (1H, d), 6.24 (1H, brq), 6.85 (1H, d), 6.94-7.0 (2H, m), 7.2-7.4 (7H, m); MS: 615.5 (MH+).

EXAMPLE (COMPOUND 13)

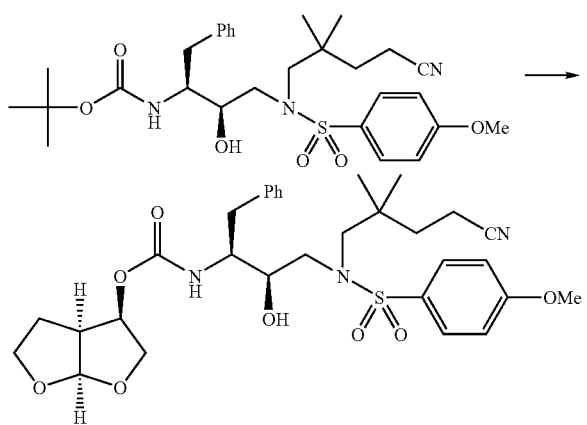

(3R,3aS,6aR)-Hexahydrofuro[2,3-b]furan-3-yl N-((1S,2R)-1-benzyl-3-(4-cyano-2,2-dimethylbutyl) [(4-methoxyphenyl)sulfonyl]amino-2-hydroxypropyl)carbamate The product from Step 3 (Example (Compound 1) was subjected to the procedure used in Example (Compound 11), except the enantiomeric activated ester was employed, to afford the title compound as a white foam;

$^1$H NMR (DMSO-d$_6$): δ 0.92 (3H, s), 1.0 (3H, s), 1.25 (1H, d), 1.38-1.48 (1H, m), 1.79 (2H, t), 2.43-2.60 (3H, m), 2.75 (1H, d), 2.8 (1H, dd), 2.9 (1H, dd), 3.05 (1H, dd), 3.3-3.5 (4H, m), 3.6-3.8 (4H, m), 3.92 (3H, s), 4.86 (1H, q), 5.25 (1H, d), 5.6 (1H, d), 7.18 (2H, d), 7.22-7.40 (6H, m), 7.8 (2H, d); MS: 616.4 (MH+).

EXAMPLE (COMPOUND 14)

Step 1:

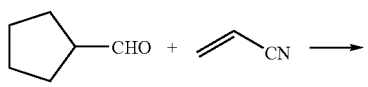

3-(1-Formylcyclopentyl)propanenitrile

Cyclopentanecarboxaldehyde was subjected to Step 1 of Example (Compound 1) to provide the title compound.

$^1$H NMR (CDCl$_3$): δ 1.44-1.58 (2H, m), 1.63-1.80 (4H, m), 1.89-2.01 (4H, m), 2.29 (2H, t), 9.40 (1H, s).

Step 2:

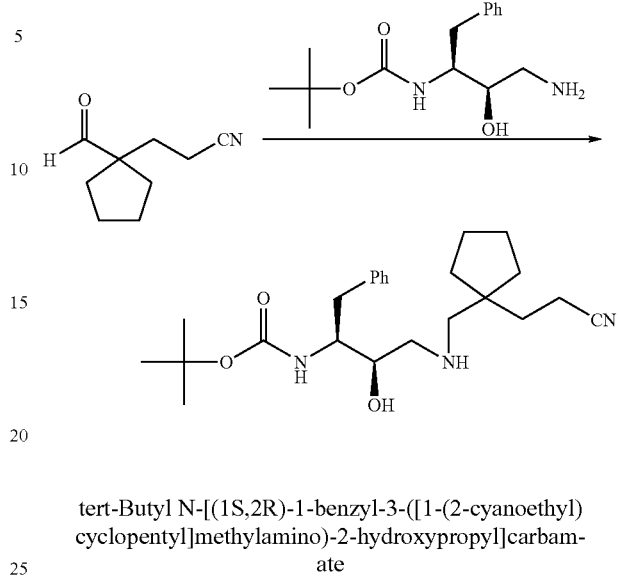

tert-Butyl N-[(1S,2R)-1-benzyl-3-([1-(2-cyanoethyl) cyclopentyl]methylamino)-2-hydroxypropyl]carbamate The product from Step 1 was subjected to procedure 2 (Example (Compound 1)) to give the title compound as a thick yellow oil.

$^1$H NMR (DMSO-d$_6$): δ 1.24 (9H, s), 1.28-1.60 (8H, m), 1.64 (2H, t), 2.29 (2H, s), 2.40 (2H, t), 2.46-2.62 (3H, m), 2.96 (1H, dd), 3.36-3.58 (2H, m), 4.75 (1H, br s), 6.70 (1H, d), 7.08-7.25 (5H, m); MS 416 (MH+).

Step 3:

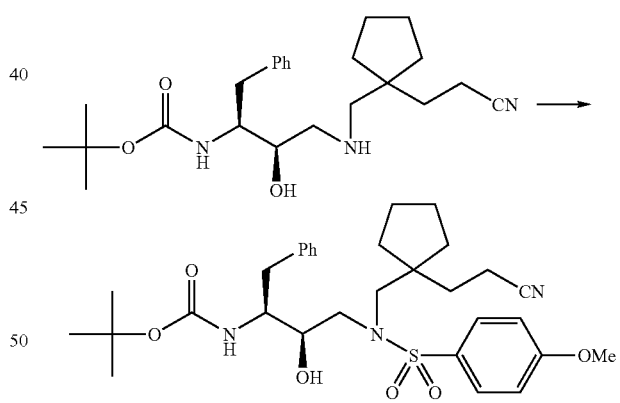

tert-Butyl N-((1S,2R)-1-benzyl-3-[1-(2-cyanoethyl) cyclopentyl]methyl[(4-methoxyphenyl)sulfonyl] amino-2-hydroxypropyl)carbamate The product from Step 2 was subjected to Step 3 (Example (Compound 1)) to afford the title compound as a white solid.

$^1$H NMR (DMSO-d$_6$): δ 1.22 (9H, s), 1.38-1.60 (8H, m), 1.66-1.76 (1H, m), 1.82-1.92 (1H, m), 2.44-2.56 (2H, m), 2.68-2.96 (3H, m), 3.24-3.44 (4H, m), 3.68-3.78 (1H, m), 3.82 (3H, s), 5.08 (1H, d), 6.64 (1H, d), 7.04-7.24 (7H, m), 7.74 (2H, d); MS: 586 (MH+).

Step 4:

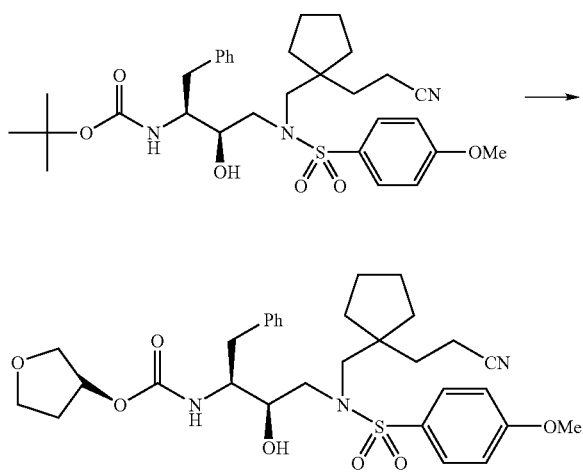

(3S)-Tetrahydro-3-furanyl-N-((1S,2R)-1-benzyl-3-[1-(2-cyanoethyl)cyclopentyl]methyl[(4-methoxyphenyl)sulfonyl]amino-2-hydroxypropyl)carbamate The product from Step 3 was subjected to the procedure used in Example (Compound 7) to give the title compound as a white foam.

$^1$H NMR (DMSO-d$_6$): δ 1.4-1.7 (8H, m), 1.75-2.00 (3H, m), 2.1 (1H, sextuplet), 2.5-2.6 (2H, m), 2.8 (1H, d), 2.9 (1H, dd), 3.0 (1H, d), 3.3-3.5 (5H, m), 3.65 (1H, dd), 3.7 (1H, dd), 3.8 (1H, dd), 3.82-3.87 (1H, m), 3.92 (3H, s), 5.0 1H, brs), 5.21 (1H, d), 7.18 (2H, d), 7.2-7.4 (6H, m), 7.82 (2H, d); MS: 600.4 (MH$^+$).

EXAMPLE (COMPOUND 15)

Step 1:

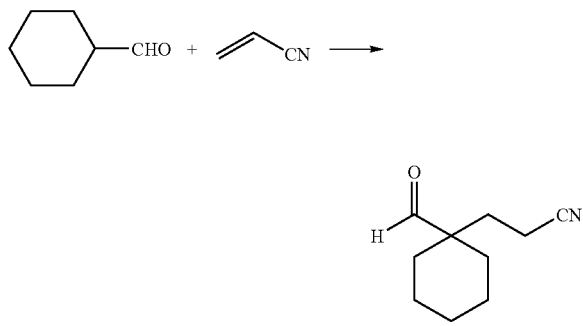

3-(1-Formylcyclohexyl)propanenitrile

Cyclohexylcarboxaldehyde was subjected to Step in Step 1 of Example (Compound 1) to give the title compound.

$^1$H NMR (CDCl$_3$): δ 1.22-1.43 (5H, m), 1.47-1.62 (3H, m), 1.81-1.91 (4H, m), 2.21 (2H, t), 9.40 (1H, s)

Step 2:

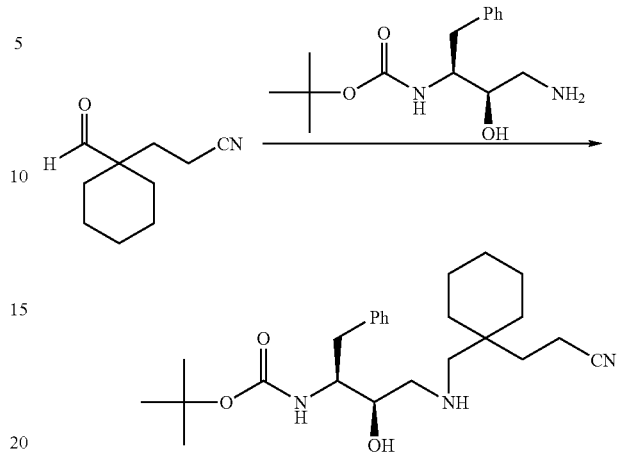

tert-Butyl N-[(1S,2R)-1-benzyl-3-([1-(2-cyanoethyl)cyclohexyl]methylamino)-2-hydroxypropyl]carbamate The product from step 1 was subjected to Step 2 (Example (Compound 1)) to afford the title compound as a thick yellow oil.

$^1$H NMR (DMSO-d$_6$): δ 1.24 (9H, s), 1.18-1.42 (10H, m), 1.60 (2H, t), 2.30 (2H, s), 2.39 (2H, t), 2.46-2.62 (3H, m), 2.96 (1H, dd), 3.36-3.58 (2H, m), 4.74 (1H, br s), 6.71 (1H, d), 7.08-7.26 (5H, m); MS: 430 (MH$^+$).

Step 3:

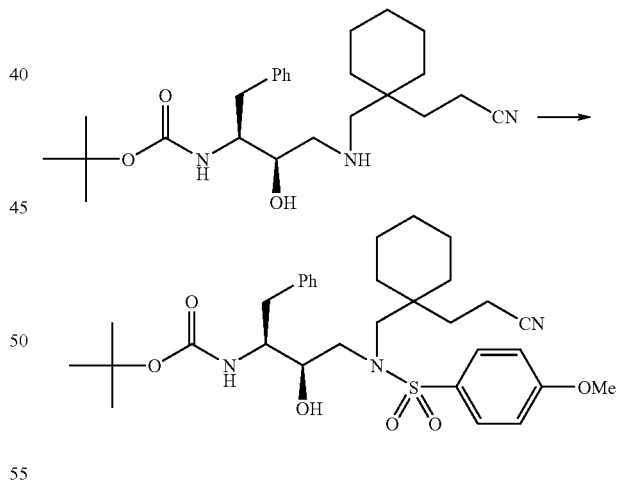

tert-Butyl N-((1S,2R)-1-benzyl-3-[1-(2-cyanoethyl)cyclohexyl]methyl[(4-methoxyphenyl)sulfonyl]amino-2-hydroxypropyl)carbamate The product from Step 2 was subjected to Step 3 (Example (Compound 1)) to provide the title compound as a white solid.

$^1$H NMR (DMSO-d$_6$): δ 1.20 (9H, s), 1.18-1.52 (10H, m), 1.75-1.90 (2H, m), 2.40-2.50 (2H, m), 2.64-2.94 (3H, m), 3.22-3.38 (4H, m), 3.70-3.78 (1H, m), 3.82 (3H, s), 5.11 (1H, d), 6.64 (1H, d), 7.04-7.24 (7H, r m), 7.76 (2H, d); MS: 600 (MH$^+$)

Step 4:

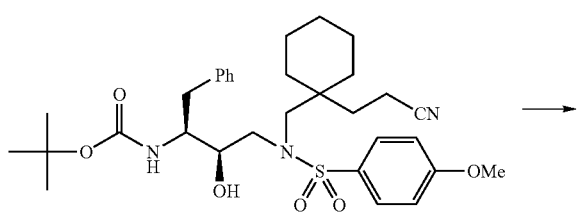

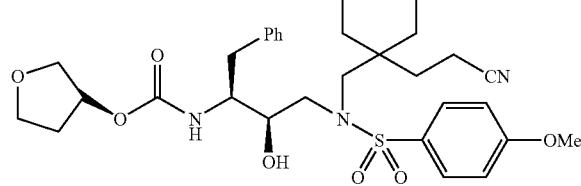

(3S)-Tetrahydro-3-furanyl-N-((1S,2R)-1-benzyl-3-
[1-(2-cyanoethyl)cyclohexyl]methyl[(4-methoxyphe-
nyl)sulfonyl]amino-2-hydroxypropyl)carbamate The product from Step 3 was subjected to conditions used in Example (Compound 7) to give the title compound as a white foam.

$^1$H NMR (DMSO-$d_6$): δ 1.2-1.6 (10H, m), 1.7-1.9 (3H, m), 2.05 (1H, sextuplet), 2.4-2.5 (2H, m), 2.65 (1H, d), 2.8 (1H, dd), 2.92 (1H, d), 3.2-3.4 (5H, m), 3.55 (1H, dd), 3.65 (1H, dd), 3.72 (1H, dd), 3.80 (1H, brs), 3.85 (3H, s), 4.9 (1H, brs), 5.10 (1H, d), 7.08 (2H, d), 7.1-7.3 (6H, m), 7.8 (2H, d); MS: 614.4 (MH$^+$).

EXAMPLE (COMPOUND 16)

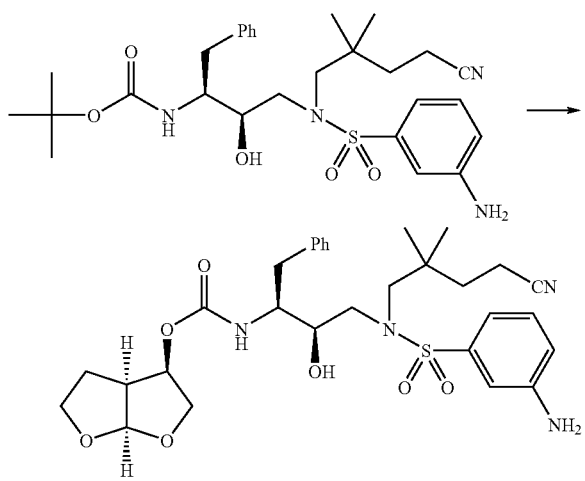

(3R,3aS,6aR)-Hexahydrofuro[2,3-b]furan-3-yl
N-((1S,2R)-3-[(3-aminophenyl)sulfonyl](4-cyano-2,
2-dimethylbutyl)amino-1-benzyl-2-hydroxypropyl)
carbamate The product from Example (Compound 5) was subjected to general procedure in Example (Compound 11) using [(3R,3aS,6aR) hexahydrofuro[2,3-b]furan-3-yl][4-nitrophenyl] carbonate to give the title compound as a white foam.

$^1$H NMR (DMSO-$d_6$): δ 0.95 (3H, s), 0.98 (3H, s), 1.15 (1H, dd), 1.3-1.4 (1H, m), 1.7 (2H, t), 2.4-2.5 (3H, m), 2.68 (1H, d), 2.72 (1H, dd), 2.8 (1H, dd), 3.25-3.35 (2H, m), 3.40-3.47 (1H, m), 3.57 (1H, dd), 3.7 (1H, td), 3.8 (1H, d), 3.83 (1H, d), 4.79 (1H, dd), 5.2 (1H, d), 5.48 (1H, d), 5.56 (2H, s), 6.78 (1H, dd), 6.86 (1H, d), 6.97 (1H, s), 7.10-7.25 (7H, m); MS: 601.1 (MH$^+$).

EXAMPLE (COMPOUND 17)

Step 1:

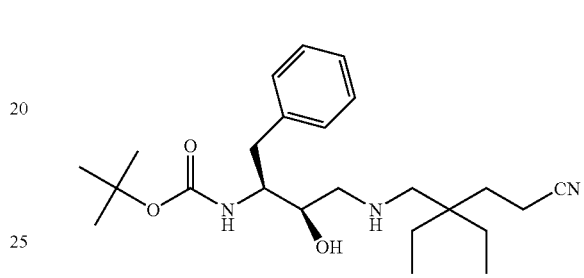

tert-Butyl N-(1S,2R)-1-benzyl-3-[(4-cyano-2,2-di-
ethylbutyl)amino]-2-hydroxypropylcarbamate 3,3-Diethyl-4-oxobutyl cyanide was subjected to Step 2, Example (Compound 1) to provide the title compound as a foam.

$^1$H NMR (DMSO-$d_6$): δ 0.90 (6H, t), 1.16 (4H, q), 1.24 (9H, s), 1.36 (1H, br), 1.50 (2H, t), 2.21 (2H, s), 2.36 (2H, t), 2.45-2.60 (3H, m), 2.95 (1H, dd), 3.36-3.58 (2H, m), 4.74 (1H, d), 6.71 (1H, d), 7.08-7.26 (5H, m); MS 418 (MH$^+$).

Step 2:

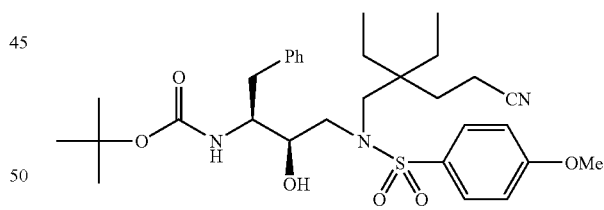

tert-Butyl N-((1S,2R)-1-benzyl-3-(4-cyano-2,2-di-
ethylbutyl)[(4-methoxyphenyl)sulfonyl]amino-2-
hydroxypropyl)carbamate The product from the previous step was subjected to Step 3 (Example (Compound 1)) to give the title compound as a foam.

$^1$H NMR (DMSO-$d_6$): δ 0.75 (6H, dt), 1.20 (9H, s), 1.15-1.50 (4H, m), 1.65-1.75 (2H, m), 2.40-2.50 (2H, m), 2.60-2.95 (3H, m), 3.22-3.42 (4H, m), 3.72-3.82 (1H, m), 3.85 (3H, s), 5.14 (1H, d), 6.62 (1H, d), 7.04-7.26 (7H, m), 7.75 (2H, d); MS 588 (MH$^+$).

Step 3:

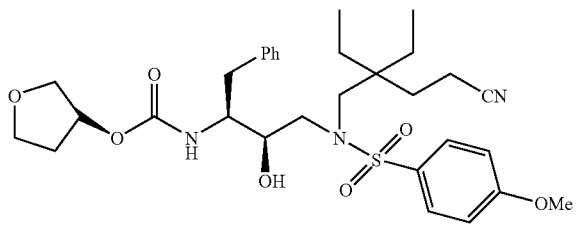

(3S)-Tetrahydro-3-furanyl N-((1S,2R)-1-benzyl-3-(4-cyano-2,2-diethylbutyl)[(4-methoxyphenyl)sulfonyl]amino-2-hydroxypropyl)carbamate The product from the previous step was subjected to the procedure used in Example (Compound 10) to give the title compound as white foam.

$^1$H NMR (DMSO-$d_6$): δ 0.70 (6H, s), 1.15-1.20 (3H, m), 1.35-1.40 (m, 1H), 1.60-1.80 (3H, m), 2.0-2.1 (1H, m), 2.25-2.35 (2H, m), 2.6-2.8 (2H, m), 2.90 (1H, d), 3.2-3.4 (5H, m), 3.5-3.8 (4H, m) 3.83 (3H, s), 4.90 (1H, br s), 5.2 (1H, d), 7.05 (2H, d), 7.2-7.3 (6H, m), 7.7 (2H, d); MS: 602 (MH$^+$).

EXAMPLE (COMPOUND 18)

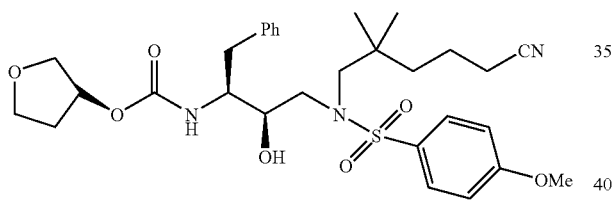

Step 1:

4-(1,3-Dioxolan-2-yl)-4-methylpentanenitrile

The product from Step 2 was subjected to Step 1 (Example (Compound 8) except sodium cyanide was used in place of sodium azide to provide the title compound.

$^1$H NMR (CDCl$_3$): δ 0.92 (6H, s), 1.41-1.48 (2H, m), 1.65-1.75 (2H, m), 2.32 (2H, t), 3.82-3.97 (4H, m), 4.53 (1H, s).

Step 2:

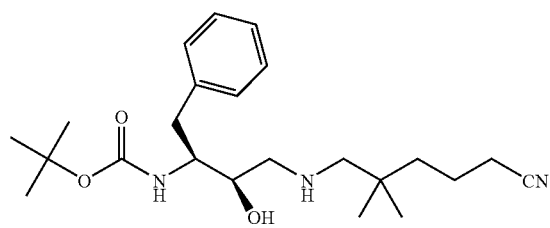

tert-Butyl N-(1S,2R)-1-benzyl-3-[(5-cyano-2,2-dimethylpentyl)amino]-2-hydroxypropylcarbamate The product from Step 1 was subjected to Step 2 (Example (Compound 8) to give the title compound as a foam.

$^1$H NMR (DMSO-$d_6$): δ 0.82 (6H, s), 1.18-1.30 (11H, m), 1.40-1.53 (2H, m), 2.24 (2H, s), 2.38-2.62 (5H, m), 2.96 (1H, dd), 3.36-3.56 (2H, m), 4.75 (1H, br), 6.71 (1H, d), 7.08-7.26 (5H, m); MS 404 (MH$^+$).

Step 3:

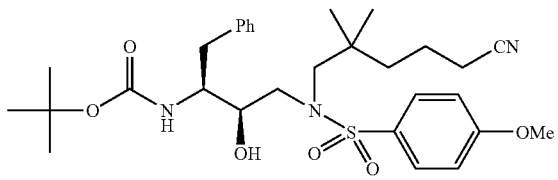

tert-Butyl N-((1S,2R)-1-benzyl-3-(5-cyano-2,2-dimethylpentyl)[(4-methoxyphenyl)sulfonyl]amino-2-hydroxypropyl)carbamate The product from the previous step was subjected to Step 3 (Example (Compound 1) to provide the title compound.

$^1$H NMR (DMSO-$d_6$): δ 0.88 (3H, s), 0.92 (3H, s), 1.21 (9H, s), 1.26-1.37 (2H, m), 1.45-1.58 (2H, m), 2.43 (2H, t), 2.77 (1H, d), 2.87-2.97 (2H, m), 3.26-3.43 (4H, m), 3.66-3.75 (1H, m), 3.82 (3H, s), 4.98 (1H, d), 6.62 (1H, d), 7.06 (2H, d), 7.08-7.24 (5H, m), 7.73 (2H, d); MS 574 (MH$^+$).

Step 4:

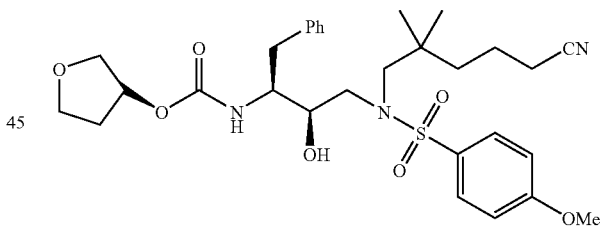

(3S)-Tetrahydro-3-furanyl N-((1S,2R)-1-benzyl-3-(5-cyano-2,2-dimethylpentyl)[(4-methoxyphenyl)sulfonyl]amino-2-hydroxypropyl)carbamate The product from the previous step was subjected to the procedure outlined in Example (Compound 7 to provide the title compound as a foam.

$^1$H NMR (DMSO-$d_6$): δ 0.84 (3H, s), 0.89 (3H, s), 1.3 (2H, t), 1.4-1.6 (2H, m), 1.7-1.8 (1H, m), 1.95-2.05 (1H, m), 2.4-2.5 (2H, m), 2.77 (1H, d), 2.90-2.98 (2H, br d), 3.3-3.4 (5H, m), 3.56 (1H, dd), 3.6-3.8 (3H, m), 3.82 (3H, s), 4.90 (1H, br s), 5.03 (1H, d), 7.06 (2H, d), 7.1-7.2 (6H, m), 7.7 (2H, d); MS: 588 (MH$^+$).

EXAMPLE (COMPOUND 19)

Step 1:

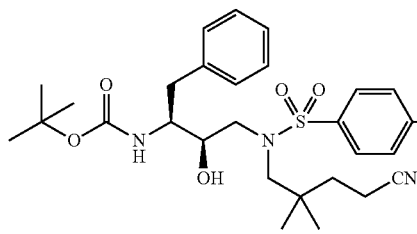

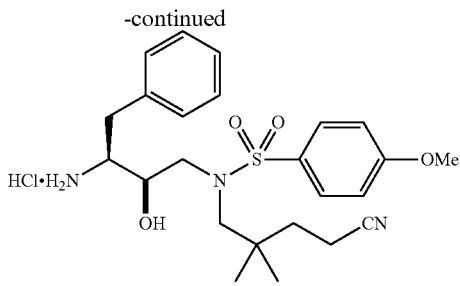

N-(2R,3S)-(3-Amino-2-hydroxy-4-phenyl-butyl)-N-(4-cyano-2,2-dimethyl-butyl)-4-methoxy-benzenesulfonamide; hydrochloride A solution of {(1S,2R)-1-Benzyl-3-[(4-cyano-2,2-dimethyl-butyl)-(4-methoxy-benzenesulfonyl)-amino]-2-hydroxy-propyl}-carbamic acid tert-butyl ester (0.600 g, 1.07 mmol) in EtOAc was cooled to −15° C. and dry HCl gas bubbled through for 30 min. The reaction was warmed to ambient temperature and solvent removed in vacuo to give desired product as a white solid which was used directly in the next step.

Step 2:

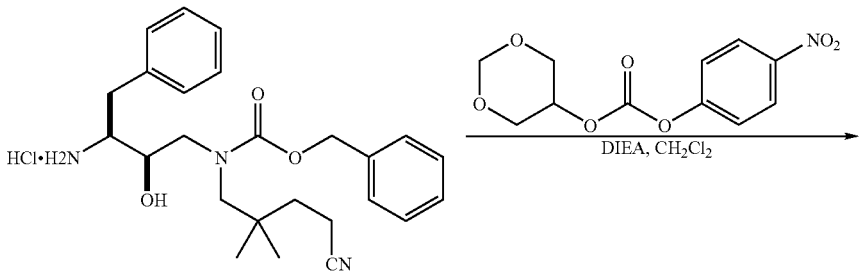

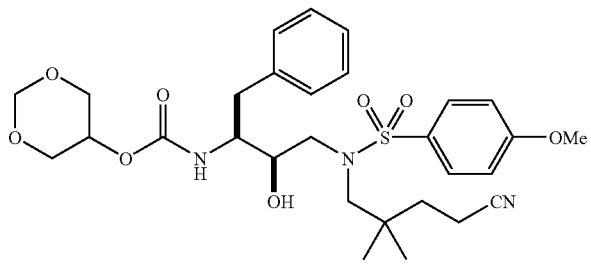

{(1S,2R)-1-Benzyl-3-[(4-cyano-2,2-dimethyl-butyl)-(4-methoxy-benzenesulfonyl)-amino]-2-hydroxy-propyl}-carbamic acid [1,3]dioxan-5-yl ester.

N-(2R,3S)-(3-Amino-2-hydroxy-4-phenyl-butyl)-N-(4-cyano-2,2-dimethyl-butyl)-4-methoxy-benzenesulfonamide hydrochloride (0.111 g, 0.22 mmol) was dissolved in CH$_2$Cl$_2$ and treated with diisopropylethylamine (0.120 ml, 0.67 mmol) and 1,3-dioxan-5-yl 4-nitrophenyl carbonate (0.066 g, 0.25 mmol) at ambient temperature under argon with stirring. After 15 h the reaction mixture was concentrated in vacuo, taken up in EtOAc, washed with sat. aq. NaHCO$_3$, and brine. The organic phase was dried over MgSO$_4$, filtered and solvent removed in vacuo. Purification by column chromatography (1% to 3% MeOH in CH$_2$Cl$_2$) gave 0.084 g of a white solid. MS (ES): 590 (M+1).

EXAMPLE (COMPOUND 20)

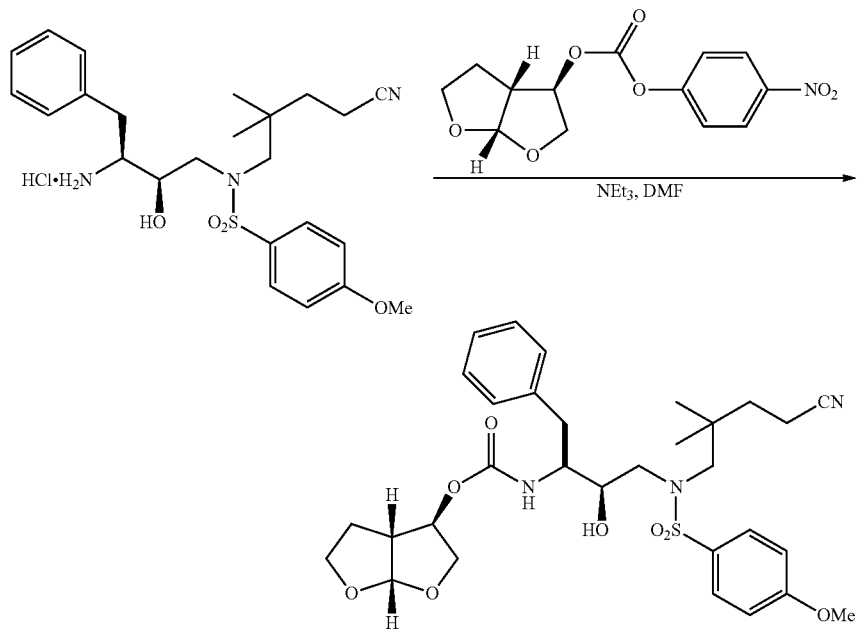

{(1S,2R)-3-[(3-Methoxybenzenesulfonyl)-(4-cyano-2,2-dimethyl-butyl)-amino]-1-benzyl-2-hydroxy-propyl}-carbamic acid (3R,3aR,6aS)hexahydro-furo[2,3-b]furan-3-yl ester N-(2R,3S)-(3-Amino-2-hydroxy-4-phenyl-butyl)-N-(4-cyano-2,2-dimethyl-butyl)-4-methoxy-benzenesulfonamide hydrochloride (0.11 mmol) was dissolved in 1 mL of DMF and treated with triethylamine (75 µL, 0.5 mmol) and (3R, 3aR,6aS) hexahydrofuro[2,3-b]furan-2-yl 4-nitrophenyl carbonate (0.034 g, 0.12 mmol) at ambient temperature under argon with stirring. After 2 days the reaction mixture was dissolved in EtOAc, washed with water and brine. The organic phase was dried over MgSO₄, filtered and solvent removed in vacuo. Purification by column chromatography (EtOAc 50% in Hexane) gave 0.037 g of a white solid. MS (ES): 616.3 (M+1), HPLC showed the material to be 98% pure; ret. time=11.55 min.

EXAMPLE (COMPOUND 21)

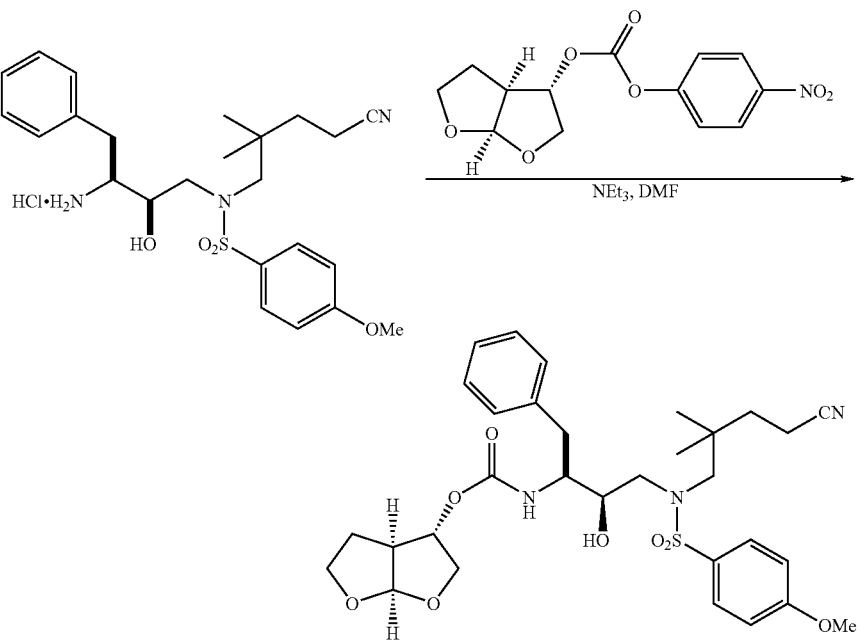

{(1S,2R)-3-[(3-Methoxybenzenesulfonyl)-(4-cyano-2,2-dimethyl-butyl)-amino]-1-benzyl-2-hydroxy-propyl}-carbamic acid (3S,3aS,6aR)hexahydro-furo[2,3-b]furan-3-yl ester N-(2R,3S)-(3-Amino-2-hydroxy-4-phenyl-butyl)-N-(4-cyano-2,2-dimethyl-butyl)-4-methoxy-benzenesulfonamide hydrochloride (0.11 mmol) was dissolved in 1 mL of DMF and treated with triethylamine (77 μL, 0.55 mmol) and (3S, 3aS,6aR) hexahydrofuro[2,3-b]furan-2-yl 4-nitrophenyl carbonate (0.036 g, 0.12 mmol) at ambient temperature under argon with stirring. After 2 days the reaction mixture was dissolved in EtOAc, washed with water and brine. The organic phase was dried over MgSO₄, filtered and solvent removed in vacuo. Purification by column chromatography (EtOAc 50% in Hexane) gave 0.044 g of a white solid. MS (ES): 616.3 (M+1), HPLC showed the material to be 98% pure; ret. time=11.46 min.

EXAMPLE (COMPOUND 22)

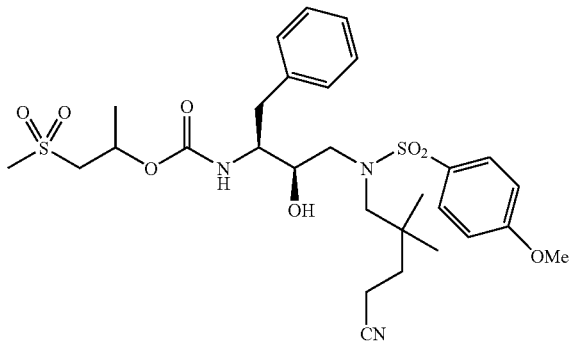

1N-(3-Methylsulfonylisobutyryl)-(1S,2R)-1-benzyl-3-(4-cyano-2,2-dimethylbutyl)[4-methoxyphenylsulfonyl]amino-2-hydroxypropylamine (1S,2R)-1-benzyl-3-(4-cyano-2,2-dimethylbutyl)[(4-methoxy phenyl)sulfonyl]amino-2-hydroxypropylamine (13.4, 0.027 mmol) was combined with 3-methyl sulfonyl-isobutyric acid (0.007 g, 0.032 mmol) and 1-hydroxybenzotriazole hydrate (0.004 g, 0.03 mmol) in anhydrous DMF (1 ml). Triethylamine (0.020 ml) was added followed by 1-(3-dimethylaminopropyl)-3-ethylcarbodiimide hydrochloride (0.007 g, 0.035 mmol). The reaction was stirred at room temperature for 2 hours, diluted in EtOAc and washed with sat. NaHCO₃, 0.5N KHSO₄ and brine. Organic phase was dried with MgSO₄ and the solvent was removed in vacuo. Purification by preparative TLC (3:1 EtOAc/Hex). Isolated 0.004 g of the product as a colorless residue. Rf=0.40 (3:1 EtOAc/Hex LRMS (M+H)⁺ 609 amu. HPLC analysis (C18); obs two peaks Tr=10.8 and 11.07 min., derived from mixture of epimers at alpha methyl proprionate linkage.

EXAMPLE (COMPOUND 23)

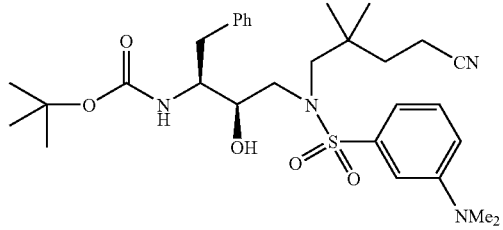

tert-Butyl N-((1S,2R)-3-(4-cyano-2,2-dimethylbutyl)[(3-dimethylaminophenyl)sulfonyl]amino-1-benzyl-2-hydroxypropyl)carbamate The product from Example (Compound 5) (0.10 g) in ethanol (3 mL) and 37% HCOH/water (0.4 mL) was hydrogenated at atmospheric pressure with 10% Pd/C (25 mg) for 18 hours. The mixture was filtered through a bed celite, evaporated, and dissolved in dichloromethane. The solution was washed with water, dried (sodium sulfate), evaporated, and dried in vacuo to provide the title compound (90 mg) as a foam.

¹H NMR (DMSO-d₆): δ 0.89 (3H, s), 0.93 (3H, s), 1.2 (9H, s), 1.7 (2H, t), 2.4-2.5 (3H, m), 2.7 (1H, d), 2.8-2.9 (2H, m), 2.96 (6H, s), 3.3-3.4 (3H, m), 3.8 (1H, br s), 5.1 (1H, d), 6.6 (1H, d), 6.9-7.0 (2H, m), 7.05 (1H, d), 7.15-7.22 (5H, m), 7.37 (1H, t); MS: 573 (MH⁺).

Step 2:

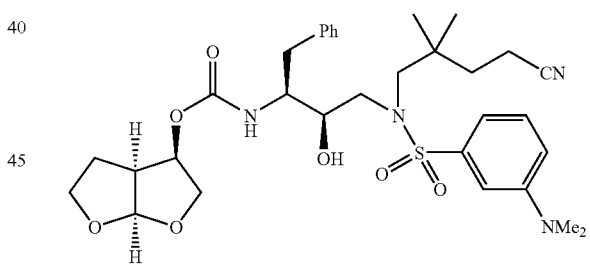

(3R,3aS,6aR)-Hexahydrofuro[2,3-b]furan-3-yl N-((1S,2R)-3-(4-cyano-2,2-dimethylbutyl)[(3-dimethylaminophenyl)sulfonyl]amino-1-benzyl-2-hydroxypropyl)carbamate The product from Step 1 was subjected to procedure similar to Example (Compound 16 to provide the title compound as a foam.

¹H NMR (DMSO-d₆): δ 0.9 (3H, s), 0.94 (3H, s), 1.1 (1H, br d), 1.3 (1H, br t), 1.7 (2H, t), 2.4-2.5 (3H, m), 2.6-2.9 (3H, m), 2.95 (6H, s), 3.2-3.4 (2H, m), 3.42-3.45 (1H, m), 3.5-3.6 (2H, m), 3.7 (1H, t), 3.8-3.9 (2H, m), 4.8 (1H, quartet), 5.2 (1H, d), 5.5 (1H, d), 6.9-7.4 (10H, m); MS: 629 (MH⁺).

EXAMPLE (COMPOUND 24)

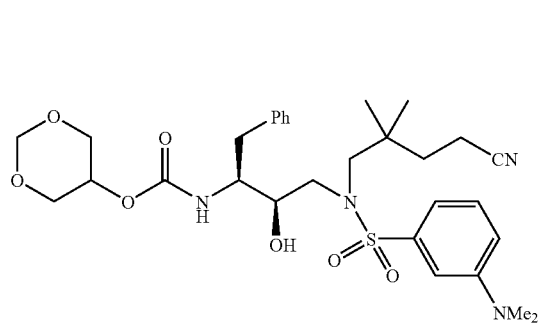

1,3-Dioxan-5-yl N-[(1S,2R)-1-benzyl-3-((4-cyano-2,2-dimethylbutyl)[3-(methylamino)phenyl]sulfonylamino)-2-hydroxypropyl]carbamate The product from step 1 (Example (Compound 12) was subjected to procedure used in Example (Compound 7) using 1,3-dioxan-5-yl 4-nitrophenylcarbonate to provide the title compound as a foam.
$^1$H NMR (DMSO-d$_6$): δ 0.9 (3H, s), 0.95 (3H, s), 1.7 (2H, t), 2.4-2.5 (2H, m), 2.7 (3H, d), 2.73 (1H, d), 2.85 (1H, dd), 2.9 (1H, dd), 3.2-3.3 (3H, m), 3.4 (2H, br d), 3.65 (1H dd), 3.77 (1H, dd), 3.8-3.9 (2H, m), 4.25 (1H, br s), 4.7 (1H, d), 4.8 (1H, d), 5.1 (1H, d), 6.15 (1H, quartet), 6.75 (1H, d), 6.88 (1H, s), 6.92 (1H, d), 7.1-7.3 (7H, m); MS: 589 (MH$^+$).

EXAMPLE (COMPOUND 25)

Step 1:

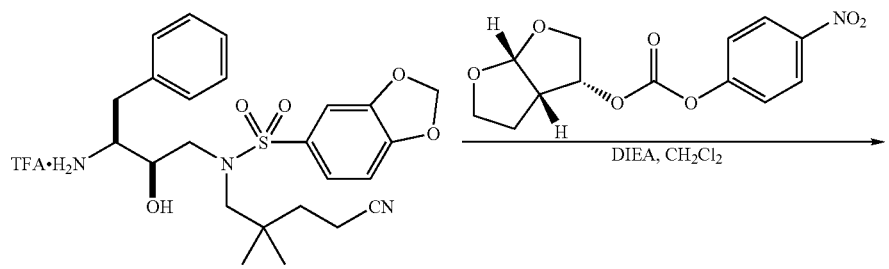

Benzo[1,3]dioxole-5-sulfonic acid [(2R,3S)-3-amino-2-hydroxy-4-phenyl-butyl]-(4-cyano-2,2-dimethyl-butyl)-amide trifluoroacetate A solution of {(1S,2R)-3-[(Benzo[1,3]dioxole-5-sulfonyl)-(4-cyano-2,2-dimethyl-butyl)-amino]-1-benzyl-2-hydroxy-propyl}-carbamic acid tert-butyl ester (0.075 g, 0.13 mmol) in CH$_2$Cl$_2$ at ambient temperature was treated with TFA. After stirring 30 min solvent was removed in vacuo to give desired product as a white solid which was used directly in the next step.

Step 2:

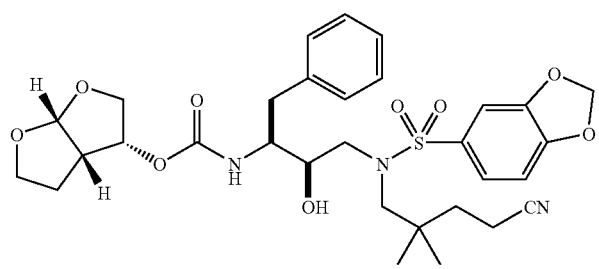

{(1S,2R)-3-[(Benzo[1,3]dioxole-5-sulfonyl)-(4-cyano-2,2-dimethyl-butyl)-amino]-1-benzyl-2-hydroxy-propyl}-carbamic acid (3R,3aS,6aR)hexahydro-furo[2,3-b]furan-3-yl ester Benzo[1,3]dioxole-5-sulfonic acid [(2R,3S)-3-amino-2-hydroxy-4-phenyl-butyl]-(4-cyano-2,2-dimethyl-butyl)-amide hydrochloride (0.13 mmol) was dissolved in $CH_2Cl_2$ and treated with diisopropylethylamine (0.114 ml, 0.65 mmol) and (3R,3aS,6aR)hexahydrofuro[2,3-b]furan-2-yl 4-nitrophenyl carbonate (0.046 g, 0.16 mmol) at ambient temperature under argon with stirring. After 15 h the reaction mixture was concentrated in vacuo, taken up in EtOAc, washed with sat. aq. $NaHCO_3$, and brine. The organic phase was dried over $MgSO_4$, filtered and solvent removed in vacuo. Purification by column chromatography (1% to 2% MeOH in $CH_2Cl_2$) gave 0.052 g of a white solid.
MS (ES): 630 (M+1).

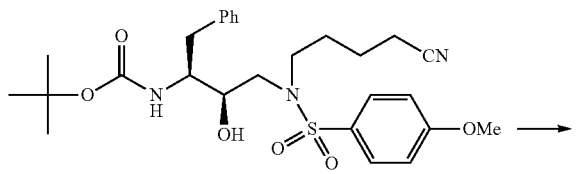

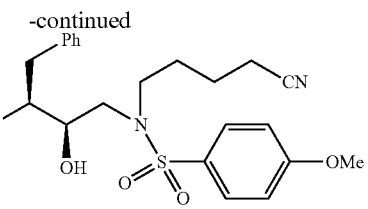

EXAMPLE (COMPOUND 26)

(3S)-Tetrahydro-3-furanyl N-((1S,2R)-1-benzyl-3-(4-cyanobutyl) [(4-methoxyphenyl)sulfonyl]amino-2-hydroxypropyl)carbamate The product from Example (Compound 4) was subjected to general procedure listed in Example (Compound 7 to give the title compound as a white glass.
$^1$H NMR (DMSO-$d_6$): δ 1.4-1.6 (4H, m), 1.7-1.8 (1H, m), 2.0-2.1 (1H, m), 2.4-2.5 (3H, m), 2.75 (1H, dd), 3.0 (2H, br d), 3.2-3.4 (3H, m), 3.5-3.7 (5H, m), 3.8 (3H, s), 4.95 (1H, br s), 5.1 (1H, br s), 7.1 (2H, d), 7.15-7.30 (6H, m), 7.75 (2H, d); MS: 546 (MH$^+$).

EXAMPLE (COMPOUND 28)

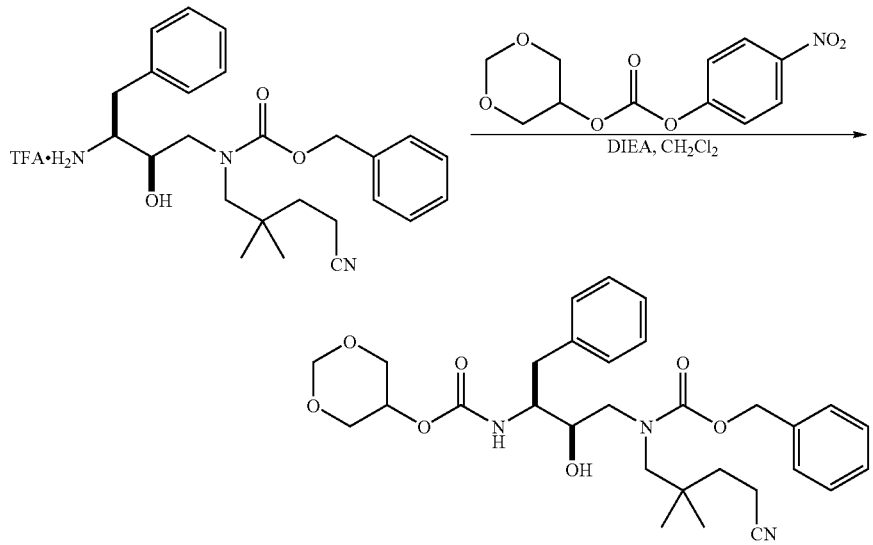

(4-Cyano-2,2-dimethyl-butyl)-[(2R,3S)-3-([1,3]dioxan-5-yloxycarbonylamino)-2-hydroxy-4-phenyl-butyl]-carbamic acid benzyl ester

[(2R,3S)-3-Amino-2-hydroxy-4-phenyl-butyl]-(4-cyano-2,2-dimethyl-butyl)-carbamic acid benzyl ester; hydrochloride (1.30 mmol) was dissolved in $CH_2Cl_2$ and treated with diisopropylethylamine (0.680 ml, 3.91 mmol) and 1,3-dioxan-5-yl 4-nitrophenyl carbonate (0.421 g, 1.56 mmol) at ambient temperature under argon with stirring. After 15 h the reaction mixture was concentrated in vacuo, taken up in EtOAc, washed with sat. aq. $NaHCO_3$, and brine. The organic phase was dried over $MgSO_4$, filtered and solvent removed in vacuo. Purification by column chromatography (3% MeOH in $CH_2Cl_2$) gave 0.430 g of a white solid. MS (ES): 554 (M+1).

EXAMPLE (COMPOUND 29)

Step 1:

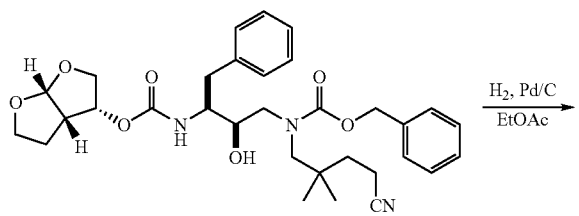 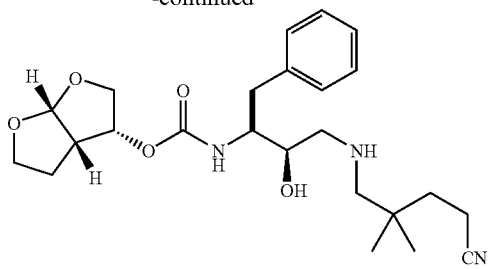

[(1S,2R)-1-Benzyl-3-(4-cyano-2,2-dimethyl-butylamino)-2-hydroxy-propyl]-carbamic acid (3R,3aS,6aR)hexahydro-furo[2,3-b]furan-3-yl ester A solution of (2S,3R)-(4-Cyano-2,2-dimethyl-butyl)-[3-((3R,3aS,6aR)hexahydro-furo[2,3-b]furan-3-yloxycarbonylamino)-2-hydroxy-4-phenyl-butyl]-carbamic acid benzyl ester (0.740 g, 1.28 mmol) in EtOAc at ambient temperature was treated with 10% palladium on carbon (0.075 g) and stirred under a balloon of hydrogen. After stirring 16 h the mixture was filtered and solvent was removed in vacuo to give desired product as a colorless oil.

Step 2:

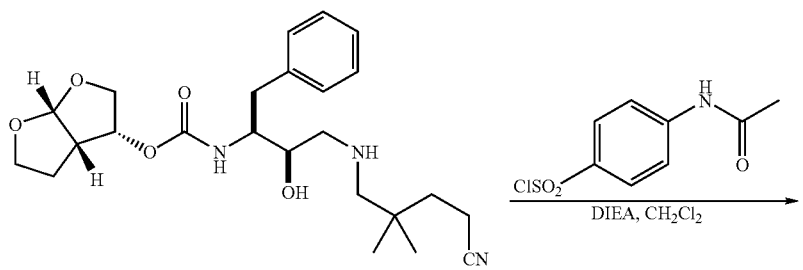

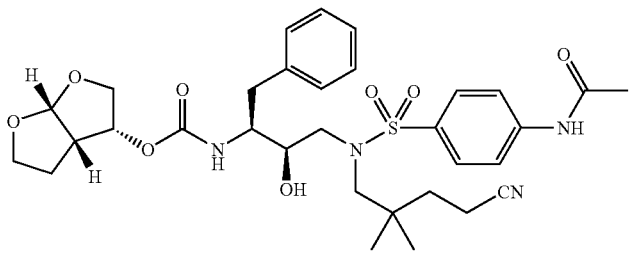

{(1S,2R)-3-[(4-Acetylamino-benzenesulfonyl)-(4-cyano-2,2-dimethyl-butyl)-amino]-1-benzyl-2-hydroxy-propyl}-carbamic acid (3R,3aS,6aR)hexahydro-furo[2,3-b]furan-3-yl ester

[(1S,2R)-1-Benzyl-3-(4-cyano-2,2-dimethyl-butylamino)-2-hydroxy-propyl]-carbamic acid (3R,3aS,6aR) hexahydro-furo[2,3-b]furan-3-yl ester (0.020 g, 0.05 mmol) was dissolved in $CH_2Cl_2$ and treated with diisopropylethylamine (0.016 ml, 0.09 mmol) and 4-acetamidobenzenesulfonyl chloride (0.011 g, 0.05 mmol) at ambient temperature under argon with stirring. After 15 h the reaction mixture was concentrated in vacuo, taken up in EtOAc, washed with sat. aq. $NaHCO_3$, and brine. The organic phase was dried over $MgSO_4$, filtered and solvent removed in vacuo. Purification by preparative thin layer chromatography (EtOAc) gave 0.006 g of a white solid. MS (ES): 643 (M+1).

EXAMPLE (COMPOUND 30)

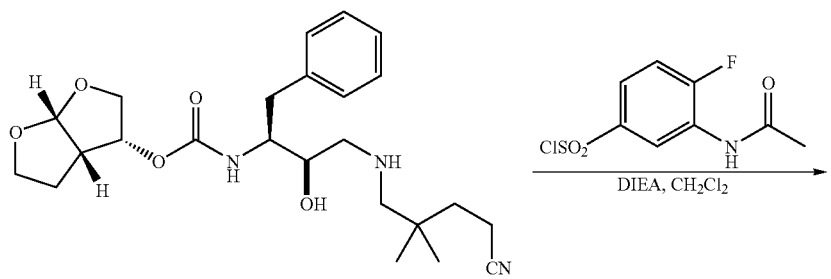

{(1S,2R)-3-[(3-Acetylamino-4-fluoro-benzenesulfonyl)-(4-cyano-2,2-dimethyl-butyl)-amino]-1-benzyl-2-hydroxy-propyl}-carbamic acid (3R,3aS,6aR) hexahydro-furo[2,3-b]furan-3-yl ester

[(1S,2R)-1-Benzyl-3-(4-cyano-2,2-dimethyl-butylamino)-2-hydroxy-propyl]-carbamic acid (3R,3aS,6aR) hexahydro-furo[2,3-b]furan-3-yl ester (0.020 g, 0.05 mmol) was dissolved in $CH_2Cl_2$ and treated with diisopropylethylamine (0.025 ml, 0.13 mmol) and 3-acetamido-4-fluorobenzenesulfonyl chloride (0.012 g, 0.05 mmol) at ambient temperature under argon with stirring. After 15 h the reaction mixture was concentrated in vacuo, taken up in EtOAc, washed with sat. aq. $NaHCO_3$, and brine. The organic phase was dried over $MgSO_4$, filtered and solvent removed in vacuo. Purification by preparative thin layer chromatography (3% MeOH in $CH_2Cl_2$) gave 0.013 g of a white solid. MS (ES): 661 (M+1).

EXAMPLE (COMPOUND 31)

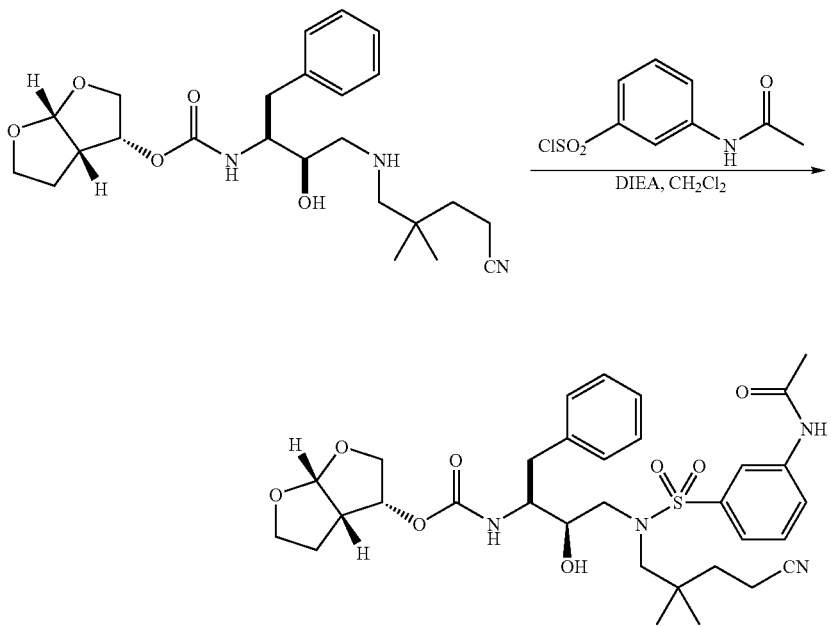

{(1S,2R)-3-[(3-Acetylamino-benzenesulfonyl)-(4-cyano-2,2-dimethyl-butyl)-amino]-1-benzyl-2-hydroxy-propyl}-carbamic acid (3R,3aS,6aR)hexahydro-furo[2,3-b]furan-3-yl ester

[(1S,2R)-1-Benzyl-3-(4-cyano-2,2-dimethyl-butylamino)-2-hydroxy-propyl]-carbamic acid (3R,3aS,6aR) hexahydro-furo[2,3-b]furan-3-yl ester (0.020 g, 0.05 mmol) was dissolved in CH$_2$Cl$_2$ and treated with diisopropylethylamine (0.025 ml, 0.13 mmol) and 3-acetamidobenzenesulfonyl chloride (0.012 g, 0.05 mmol) at ambient temperature under argon with stirring. After 15 h the reaction mixture was concentrated in vacuo, taken up in EtOAc, washed with sat. aq. NaHCO$_3$, and brine. The organic phase was dried over MgSO$_4$, filtered and solvent removed in vacuo. Purification by preparative thin layer chromatography (3% MeOH in CH$_2$Cl$_2$) gave 0.019 g of a white solid. MS (ES): 643. (M+1).

EXAMPLE (COMPOUND 32)

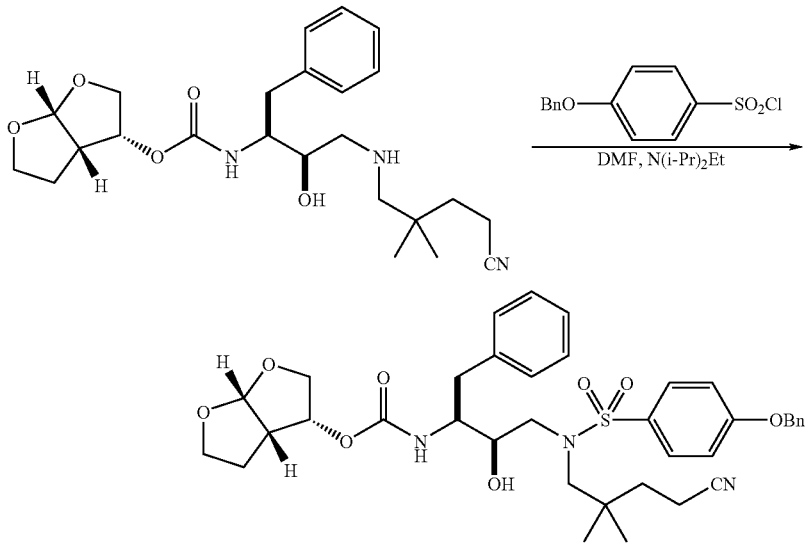

{(1S,2R)-3-[(4-benzyloxybenzenesulfonyl)-(4-cyano-2,2-dimethyl-butyl)-amino]-1-benzyl-2-hydroxy-propyl}-carbamic acid (2R,3aS,6aR)hexahydro-furo[2,3-b]furan-3-yl ester

[(1S,2R)-1-Benzyl-3-(4-cyano-2,2-dimethyl-butylamino)-2-hydroxy-propyl]-carbamic acid (3R,3aS,6aR) hexahydro-furo[2,3-b]furan-3-yl ester (9.5 mg, 0.02 mmol) was combined with 4-benzyloxybenzenesulfonyl chloride (7.2 mg, 1.2 eq.) in anhydrous DMF (1 mL). Solution was chilled to 0° C. and N(i-Pr)$_2$Et (13.4 µL, 3 eq.) was added. Reaction was allowed to warm to room temperature and stirred for 5 hours. Reaction mixture was diluted in EtOAc (10 mL) and washed with sat. NaHCO$_3$ (10 mL), 0.5N KHSO$_4$ (10 mL) and brine (10 mL). Organic phase was dried with MgSO$_4$ and solvent was removed in vacuo. Purification by preparative TLC (1:1, EtOAc:Hex). Recovered 6.1 mg (41%) of the product as a colorless residue. MS (ES): 692.2 (M+1), HPLC; t$_R$=13.19 min. (94%).

EXAMPLE (COMPOUND 33)

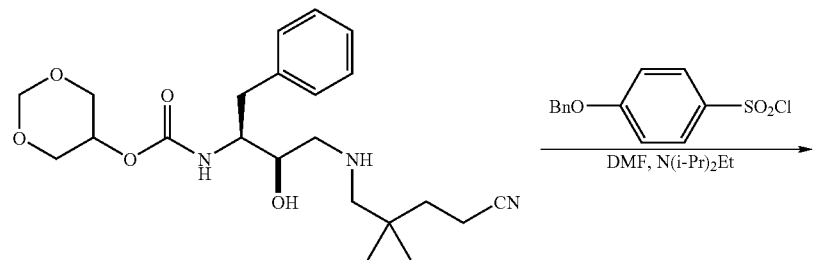

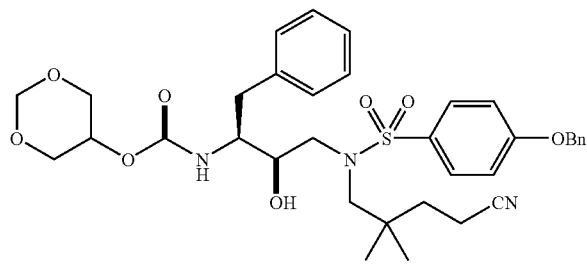

{(1S,2R)-1-Benzyl-3-[(4-cyano-2,2-dimethyl-butyl)-(4-benzyloxybenzenesulfonyl)-amino]-2-hydroxy-propyl}-carbamic acid [1,3]dioxan-5-yl ester {(1S,2R)-1-Benzyl-3-(4-cyano-2,2-dimethyl-butylamino)-2-hydroxy-propyl}-carbamic acid [1,3]dioxan-5-yl ester (14.8 mg, 0.04 mmol) was combined with 4-benzyloxybenzenesulfonyl chloride (12.0 mg, 1.2 eq.) in anhydrous DMF (1 mL). Solution was chilled to 0° C. and N(i-Pr)$_2$Et (18.4 µL, 3 eq.) was added. Reaction was allowed to warm to room temperature and stirred for 5 hours. Reaction mixture was diluted in EtOAc (10 mL) and washed with sat. NaHCO$_3$ (10 mL), 0.5 N KHSO$_4$ (10 mL) and brine (10 mL). Organic phase was dried with MgSO$_4$ and solvent was removed in vacuo. Purification by preparative TLC (1:1, EtOAc:Hex). Recovered 4.2 mg (18%) of the product as a colorless residue. MS (ES); 666.2 (M+1), HPLC; t$_R$=13.24 min. (98%).

EXAMPLE (COMPOUND 35)

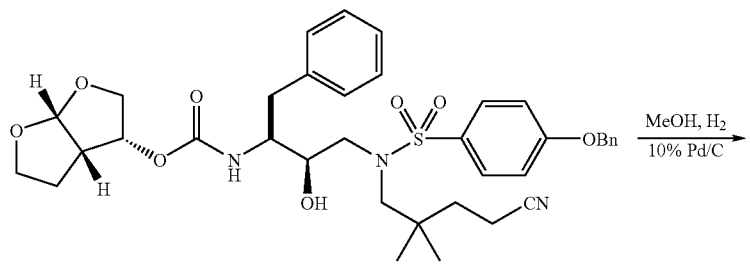

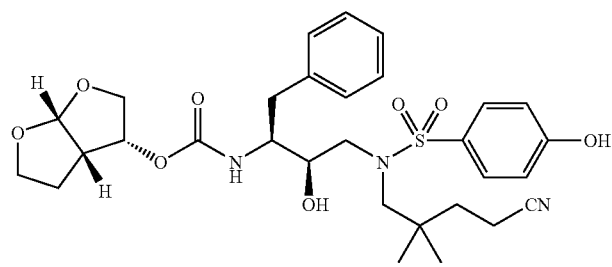

{(1S,2R)-3-[(4-hydroxybenzenesulfonyl)-(4-cyano-2,2-dimethyl-butyl)-amino]-1-benzyl-2-hydroxy-propyl}-carbamic acid (2R,3aS,6aR)hexahydro-furo[2,3-b]furan-3-yl ester {(1S,2R)-3-[(4-benzyloxybenzenesulfonyl)-(4-cyano-2,2-dimethyl-butyl)-amino]-1-benzyl-2-hydroxy-propyl}-carbamic acid (2R,3aS,6aR)hexahydro-furo[2,3-b]furan-3-yl ester (18.1 mg, 0.03 mmol) was dissolved in methanol (1 mL). Solution was degassed with nitrogen for 5 minutes the 10% Pd/C (2 mg) was added. Reaction was pressurized with H₂ (1 ATM) and stirred for 30 minutes. Catalyst removed by filtration and solvent was removed in vacuo leaving 15.2 mg (97%) of product as a colorless residue. MS (ES): 602 (M+1), HPLC; $t_R$=10.32 min. (100%).

EXAMPLE (COMPOUND 36)

Step 1:

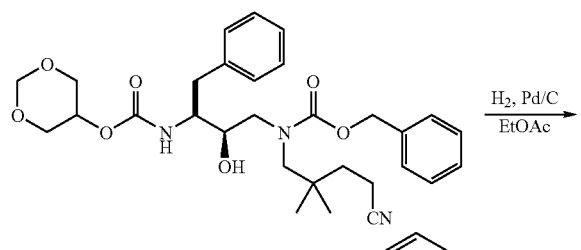

[(1S,2R)-1-Benzyl-3-(4-cyano-2,2-dimethyl-butylamino)-2-hydroxy-propyl]-carbamic acid [1,3]dioxan-5-yl ester A solution of (4-Cyano-2,2-dimethyl-butyl)-[(2R,3S)-3-([1,3]dioxan-5-yloxycarbonylamino)-2-hydroxy-4-phenylbutyl]-carbamic acid benzyl ester (0.420 g, 0.76 mmol) in EtOAc at ambient temperature was treated with palladium on carbon (0.050 g) and stirred under a balloon of hydrogen. After stirring 16 h the mixture was filtered and solvent was removed in vacuo to give desired product as a colorless oil.

Step 2:

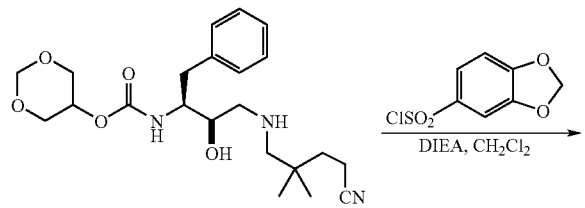

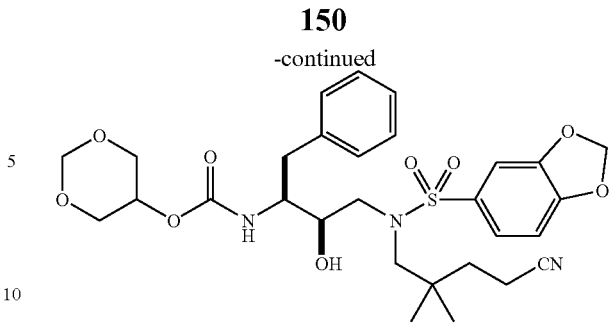

{(1S,2R)-3-[(Benzo[1,3]dioxole-5-sulfonyl)-(4-cyano-2,2-dimethyl-butyl)-amino]-1-benzyl-2-hydroxy-propyl}-carbamic acid [1,3]dioxan-5-yl ester

[(1S,2R)-1-Benzyl-3-(4-cyano-2,2-dimethyl-butylamino)-2-hydroxy-propyl]-carbamic acid [1,3]dioxan-5-yl ester (0.059 g, 0.14 mmol) was dissolved in CH₂Cl₂ and treated with diisopropylethylamine (0.075 ml, 0.42 mmol) and Benzo[1,3]dioxole-5-sulfonyl chloride (0.037 g, 0.17 mmol) at ambient temperature under argon with stirring. After 15 h the reaction mixture was concentrated in vacuo, taken up in EtOAc, washed with sat. aq. NaHCO₃, and brine. The organic phase was dried over MgSO₄, filtered and solvent removed in vacuo. Purification by column chromatography (1% to 3% MeOH in CH₂Cl₂) gave 0.062 g of a white solid. MS (ES): 604 (M+1).

EXAMPLE (COMPOUND 42)

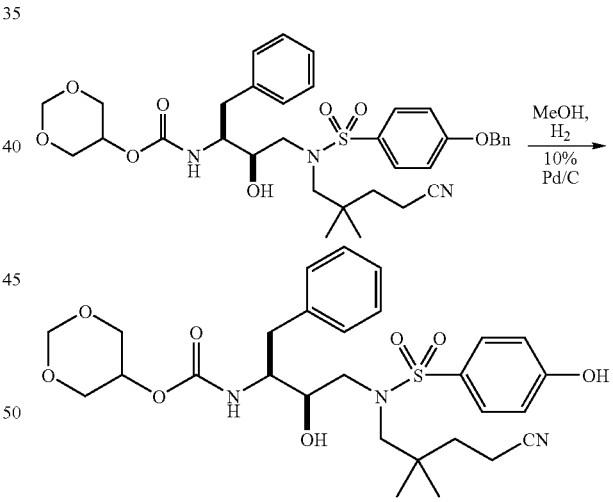

{(1S,2R)-1-Benzyl-3-[(4-cyano-2,2-dimethyl-butyl)-(4-hydroxybenzenesulfonyl)-amino]-2-hydroxy-propyl}-carbamic acid [1,3]dioxan-5-yl ester {(1S,2R)-1-Benzyl-3-[(4-cyano-2,2-dimethyl-butyl)-(4-benzyloxybenzenesulfonyl)-amino]-2-hydroxy-propyl}-carbamic acid [1,3]dioxan-5-yl ester (2.2 mg, 0.003 mmol) was dissolved in methanol (1 mL). Solution was degassed with nitrogen for 5 minutes the 10% Pd/C (2 mg) was added. Reaction was pressurized with H₂ (1 ATM) and stirred for 30 minutes. Catalyst removed by filtration and solvent was removed in vacuo leaving 2.0 mg (95%) of product as a colorless residue. MS (ES): 576.2 (M+1), HPLC; $t_R$=10.39 min. (84%).

EXAMPLE (COMPOUND 43)

Step 1:

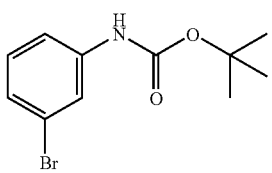

3-Bromo-N-tert-butoxycarbonyl aniline

3-Bromoaniline (0.50 ml, 4.6 mmol) di-tert-butyldicarbonate (1.20 g, 5.5 mmol) and 4-dimethylaminopyridine (0.003 g) were combined in anhydrous $CH_2Cl_2$ (10 ml). Solution chilled to 0° C. and triethylamine (1.28 ml, 9.2 mmol) was added. Reaction was allowed to warm to room temperature then was heated to reflux for 1 hour. Reaction mixture was diluted in EtOAc and washed with sat. $NaHCO_3$, 0.5 N $KHSO_4$ and brine. Organic phase was dried with $MgSO_4$ and the solvent was removed in vacuo. Purification by flash chromatography (1:4, EtOAc: Hex., gradient to 1:3 then 1:2). Recovered 1.01 g (81%) of the product as a light yellow solid. Rf=0.62 (1:4, EtOAc:Hex). $^1$H NMR ($CDCl_3$) 7.68 (1H, s), 7.22-7.10 (3H, m), 6.48 (1H, b), 1.51 (9H, s).

Step 2:

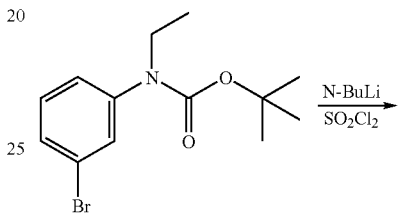

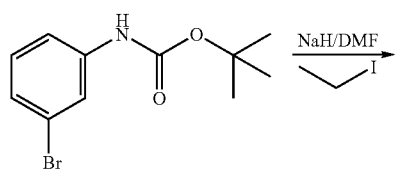

3-Bromo-N-tert-butoxycarbonyl-N-ethylaniline

3-Bromo-N-tert-butoxycarbonylaniline (0.82 g, 3.0 mmol) was dissolved in anhydrous DMF (15 ml) and cooled to 0° C. Sodium hydride (0.145 g, 3.6 mmol, 1.2 eq.) was added to the solution. The reaction stirred at 0° C. for 10 minutes then was warmed to room temperature. After 30 minutes at room temperature the reaction was cooled to 0° C. and Ethyl iodide (0.27 ml, 3.3 mmol, 1.1 eq.) was added over ~1 minute. The reaction was stirred at 0° C. for 5 minutes then was warmed to room temperature. The reaction stirred at room temperature for 22 hours and was then cooled to 0° C. and quenched with a saturated bicarbonate solution and extracted with EtOAc (2 times). The combined organic layers were washed with $H_2O$ (5 times) then brine. The organic phase was dried with $MgSO_4/Na_2SO_4$, filtered and the solvent was removed in vacuo to give 0.93 g of crude product which was used as is. HPLC ret time 11.83 min. (100%).

Step 3:

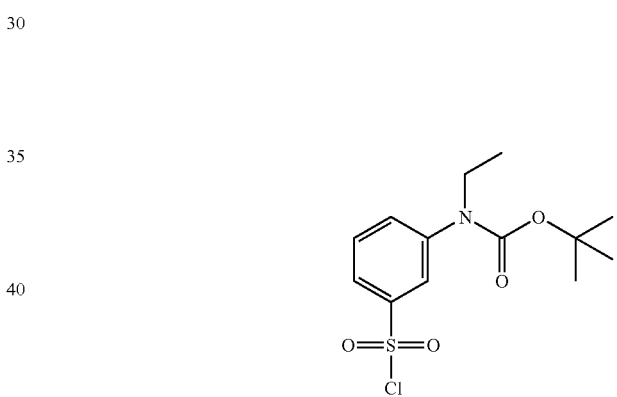

N-tert-Butoxycarbonyl-3-chlorosulfonyl-N-ethylaniline

3-Bromo-N-tert-butoxycarbonyl-N-ethylaniline (3.0 mmol) was dissolved in freshly distilled THF (25 ml) under a $N_2$ atmosphere. The solution was chilled to −78° C. and butyl lithium (1.8 ml, 2.0 M solution in cyclohexane, 3.6 mmol) was added. After 35 minutes, sulfuryl chloride (0.30 ml, 3.6 mmol) was added over ~2 minutes. The reaction was stirred for 5 minutes at −78° C. then was allowed to warm to room temperature. After 30 minutes at room temperature the reaction was cooled to −78° C. and quenched with a saturated ammonium chloride solution. The THF was removed by evaporation and the resulting residue was and partitioned between EtOAc and H2O. The aqueous phase was extracted with EtOAc and the combined organic phases were washed with H2O and brine before being dried with $Na_2SO_4$. The solvent was removed in vacuo to give 900 mg of crude product. HPLC showed the material to be ~80% pure and it was used as is. LC/MS (ES): 320.1 (M+1).

Step 4:

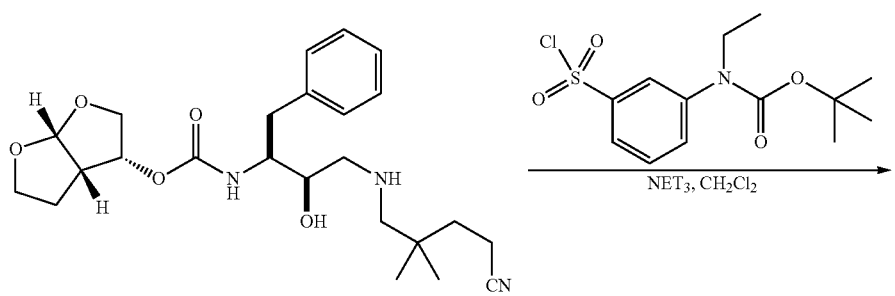

{(1S,2R)-3-[(3-N-tert-butoxycarbonyl-N-ethylaminophenyl)sulfonyl]-(4-cyano-2,2-dimethyl-butyl)-amino]-1-benzyl-2-hydroxy-propyl}-carbamic acid (3R,3aS,6aR)hexahydro-furo[2,3-b]furan-3-yl ester

[(1S,2R)-1-Benzyl-3-(4-cyano-2,2-dimethyl-butylamino)-2-hydroxy-propyl]-carbamic acid (3R,3aS,6aR) hexahydro-furo[2,3-b]furan-3-yl ester (0.025 g, 0.056 mmol) was dissolved in 1 mL of CH$_2$Cl$_2$ and treated with triethylamine (0.032 ml, 0.22 mmol). A solution N-tert-Butoxycarbonyl-3-chlorosulfonyl-N-ethylaniline (0.045 g, 0.14 mmol) in 1 mL of CH$_2$Cl$_2$ was added followed by 4-dimethylaminopyridine (0.005 g). The reaction was stirred at room temperature under N$_2$ for 23 hours, then quenched with a saturated bicarbonate solution and extracted with EtOAc (2 times). The combined organic layers were washed with H$_2$O, then brine. The organic phase was dried over MgSO$_4$, filtered and solvent removed in vacuo. Purification by preparative thin layer chromatography (70:30:2, EtOAc:Hexanes: MeOH) gave 0.0018 g of product. HPLC ret time=11.49 min. LC/MS (ES);=729.3 (M+1).

EXAMPLE (COMPOUND 44)

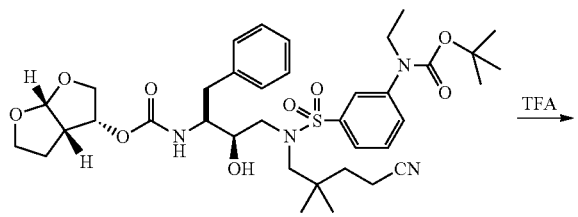

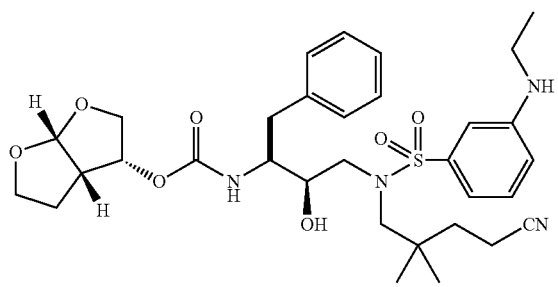

{(1S,2R)-3-[(3-N-ethylaminophenyl)sulfonyl]-(4-cyano-2,2-dimethyl-butyl)-amino]-1-benzyl-2-hydroxy-propyl}carbamic acid (3R,3aS,6aR)hexahydro-furo[2,3-b]furan-3-yl ester {(1S,2R)-3-[(3-N-tert-butoxycarbonyl-N-ethylaminophenyl)sulfonyl]-(4-cyano-2,2-dimethyl-butyl)-amino]-1-benzyl-2-hydroxy-propyl}-carbamic acid (3R,3aS,6aR)hexahydro-furo[2,3-b]furan-3-yl ester (0.007 g, 0.009 mmol) was dissolved in 0.5 mL of CH$_2$Cl$_2$. Trifluoroacetic acid (0.25 mL) was added and the reaction was stirred for 1 hour at room temperature under N$_2$. The solvent was removed in vacuo and the residue was partitioned between EtOAc and a saturated bicarbonate solution. The aqueous phase was extracted with EtOAc and the combined organic phases were washed with H$_2$O and brine before being dried with Na$_2$SO$_4$ and filtered. The solvent was removed in vacuo to give the 2.1 mg of product. HPLC ret. time=9.156 min. LC/MS (ES) =629.3 (M+1).

EXAMPLE (COMPOUND 47)

Step 1:

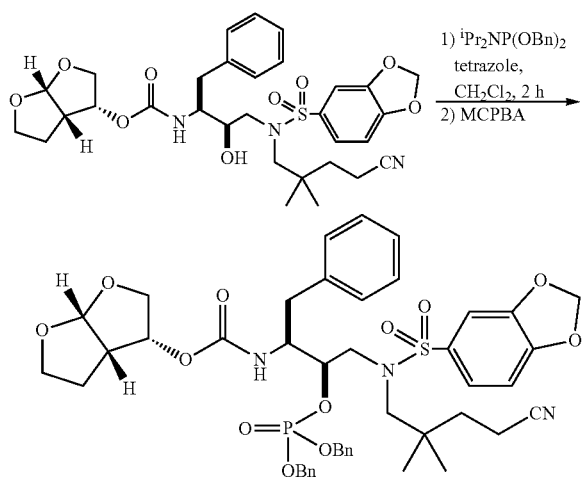

[(1S,2R)-3-[(Benzo[1,3]dioxole-5-sulfonyl)-(4-cyano-2,2-dimethyl-butyl)-amino]-1-benzyl-2-(dibenzyloxy-phosphoryloxy)-propyl]-carbamic acid (3R,3aS,6aR)hexahydro-furo[2,3-b]furan-3-yl ester A solution of {(1S,2R)-3-[(Benzo[1,3]dioxole-5-sulfonyl)-(4-cyano-2,2-dimethyl-butyl)-amino]-1-benzyl-2-hydroxy-propyl}-carbamic acid (3R,3aS,6aR)hexahydro-furo[2,3-b]furan-3-yl ester (0.077 g, 0.12 mmol) and 1H-tetrazole (0.012 g, 0.17 mmol) in CH$_2$Cl$_2$ was treated with dibenzyl diisopropylphosphoramidite (0.050 ml, 0.015 mmol) and stirred at ambient temperature under argon. After 2 h 3-chloroperoxybenzoic acid (0.072 g, 0.30 mmol) was added and the reaction mixture stirred an additional 1 h. Solvent was removed in vacuo, the residue taken up in EtOAc, washed with sat. aq. NaHCO$_3$, and brine. The organic phase was dried over MgSO$_4$, filtered and solvent removed in vacuo to give desired product, which was used directly in the next step.

Step 2:

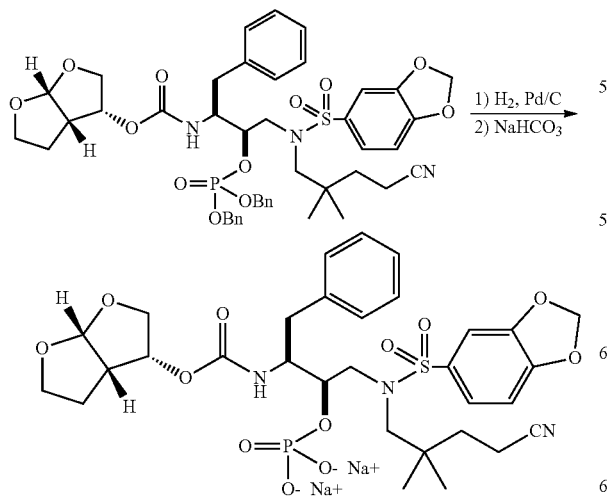

{(1S,2R)-3-[(Benzo[1,3]dioxole-5-sulfonyl)-(4-cyano-2,2-dimethyl-butyl)-amino]-1-benzyl-2-phosphonooxy-propyl}-carbamic acid (3R,3aS,6aR) hexahydro-furo[2,3-b]furan-3-yl ester; disodium salt

[(1S,2R)-3-[(Benzo[1,3]dioxole-5-sulfonyl)-(4-cyano-2,2-dimethyl-butyl)-amino]-1-benzyl-2-(dibenzyloxy-phosphoryloxy)-propyl]-carbamic acid (3R,3aS,6aR)hexahydro-furo[2,3-b]furan-3-yl ester (0.081 g, 0.09 mmol) was dissolved in EtOAc and treated with 10% palladium on carbon (0.020 g) and stirred under a balloon of hydrogen. After stirring 14 h the mixture was filtered and solvent was removed in vacuo. The crude residue was purified by preparative HPLC (15% to 80% CH$_3$CN in H$_2$O) and the pooled fractions concentrated in vacuo to give 0.029 g of product. This was taken up in 0.10 M sodium bicarbonate (2.0 equiv., 0.817 ml, 0.09 mmol) stirred 2 h at ambient temperature and lyophilized to give 0.029 g of the bis sodium salt as a white solid.

EXAMPLE (COMPOUND 100)

Step 1:

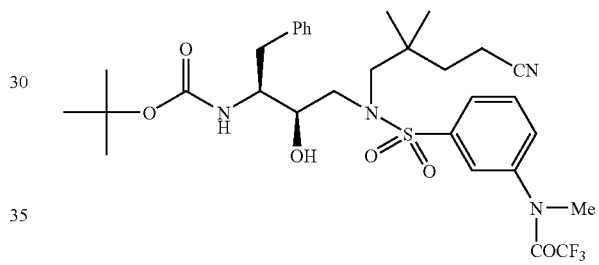

ter-Butyl N-((1S,2R)-1-benzyl-3-(4-cyano-2,2-dimethylbutyl)[(3-(N-methyl,N-trifluoroacetyl)aminophenyl)sulfonyl]amino-2-hydroxypropyl)carbamate To a solution of the product from Example (Compound 6), 0.44 g, 0.8 mmol), in dichloromethane (17 mL), and pyridine (1 mL, 0.97 g, 12.3 mmol) at 0° C. was added trifluoroacetic anhydride (0.45 mL, 0.67 g, 3.2 mmol) and the mixture was stirred at ambient temperature for 2 hours. The mixture was washed with saturated sodium bicarbonate, dried (sodium sulfate) and coevaporated with ethyl acetate (3×). The residue was dissolved in methanol (10 mL) and potassium carbonate (10 mg) was added. After stirring for 1 hour at ambient temperature, the solvent was evaporated and the residue was dissolved in acetone (15 mL) and potassium carbonate (0.26 g, 2 mmol) and methyl iodide (0.25 mL, 0.56 g, 4.0 mmol) were added. After 3 hours, the solvent was evaporated and the residue was partitioned between dichloromethane and water. The organic phase was dried (sodium sulfate), evaporated, dried in vacuo to provide the title compound (0.52 g) as a foam.

$^1$H NMR (CDCl$_3$): δ 1.0 (6H, s), 1.14 (9H, s), 1.75 (2H, t), 2.38 (2H, t), 2.7-2.8 (1H, m), 2.9 (1H, dd), 3.05-3.25 (3H, m), 3.4 (3H, s), 3.5-3.7 (3H, m), 3.9 (1H, br s), 4.5 (1H, br s), 7.1-7.3 (5H, m), 7.5 (1H, d), 7.6 (1H, t), 7.7-7.9 (2H, m); MS: 677 (M+23)

Step 2:

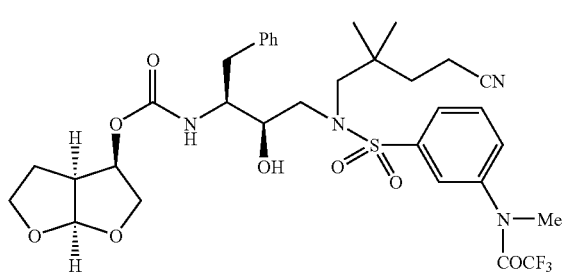

(3R,3aS,6aR)-Hexahydrofuro[2,3-b]furan-3-yl
N-[(1S,2R)-1-benzyl-3-((4-cyano-2,2-dimethylbutyl)
[3-(N-methyl,N-trifluoroacetylmethylamino)phenyl]
sulfonylamino)-2-hydroxypropyl]carbamate The product from step 1 was subjected to the procedure outlined in Example (Compound 10) to provide the title compound as a foam.

$^1$H NMR (DMSO-d$_6$): δ 0.93 (3H, s), 0.96 (3H, s), 1.14 (1H, dd), 1.33-1.36 (1H, m), 1.65 (2H, t), 2.4-2.5 (3H, m), 2.6-2.8 (2H, m), 2.9-3.1 (2H, m), 3.3 (3H, s), 3.32-3.60 (5H, m), 3.65-3.82 (3H, m), 4.8 (1H, quartet), 5.1 (1H, d), 5.5 (1H, d), 7.1-7.3 (6H, m), 7.7 (1H, t), 7.79 (1H, d), 7.88 (1H, d), 8.0 (1H, s); MS: 711 (MH$^+$)

Step 3:

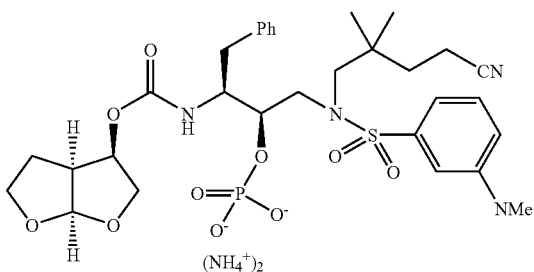

(3R,3aS,6aR)-Hexahydrofuro[2,3-b]furan-3-yl
N-((1S,2R)-1-benzyl-3-(4-cyano-2,2-dimethylbutyl)
[(3-methylaminophenyl)sulfonyl]amino-2-hydroxypropylcarbamate bis-ammonium phosphate The product from step 2 was subjected to procedures listed in Example (Compound 101) to provide the title compound as a tan solid.

$^1$H NMR (DMSO-d$_6$): δ 0.93 (3H, s), 0.96 (3H, s)., 1.15-1.40 (2H, m), 1.6 (2H, t), 2.43 (2H, t), 2.6-3.0 (8H, m), 3.2-3.6 (4H, m), 3.7 (1H, t), 3.8 (1H, t), 4.0 (1H, br s), 4.35 (1H, br s), 4.4-4.5 (1H, m), 4.8 (1H, quartet(, 5.5(1H, d), 6.7 (1H, d), 6.9 (1H, d), 7.0 (1H, s), 7.1-7.4 (7H, m); MS: 695 (MH$^+$);

EXAMPLE (COMPOUND 101)

Step 1:

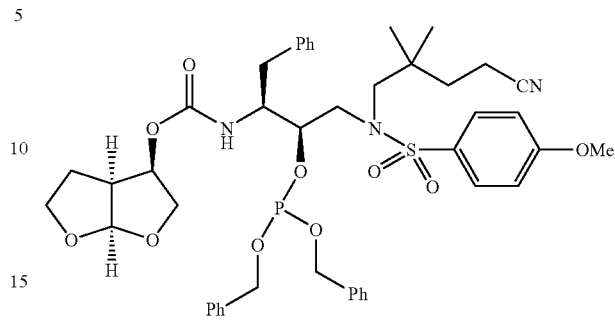

(3R,3aS,6aR)-Hexahydrofuro[2,3-b]furan-3-yl
N-((1S,2R)-1-benzyl-3-(4-cyano-2,2-dimethylbutyl)
[(4-methoxyphenyl)sulfonyl]-2-dibenzylphosphite-aminopropyl)carbamate To a solution of the product from Example (Compound 21), (0.22 g, 0.36 mmol) in dichloromethane (5 mL) was added tetrazole (32 mg, 0.47 mmol) and dibenzyl diisopropyl phosphoramidite (0.151 mL, 0.155 mg, 0.45 mmol) and the mixture was stirred at ambient temperature under nitrogen atmosphere for 18 hours. The mixture was washed with saturated sodium bicarbonate/water, dried (sodium sulfate) and evaporated. The residue was chromatographed (silica gel, hexane/acetone, 2:1) to provide the title compound as a solid (0.23 g);

$^1$H NMR (DMSO-d$_6$): δ 0.8 (3H, s), 0.86 (3H, s), 1.33 (1H, dd), 1.28-1.40 (1H, m), 1.55-1.70 (2H, m), 2.35 (2H, td), 2.4-2.5 (1H, m), 2.73 (1H, br quartet), 2.85 (1H, dd), 3.05 (1H, dd), 3.2-3.3 (3H, m), 3.5 (1H, dd), 3.55 (1H, dd), 3.66 (1H, dd), 3.74 (1H, dd), 3.8 (3H, s), 3.84-3.94 (1H, m), 4.6-4.7 (1H, m), 4.75 (1H, quartet), 4.8-4.9 (4H, m), 7.1-7.2 (8H, m), 7.23-7.33 (10H, m), 7.8 (2H, d); MS: 882 (M+23).

Step 2:

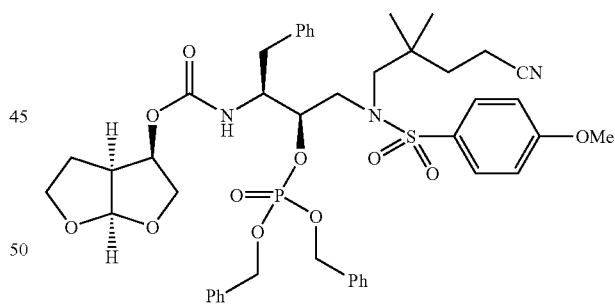

(3R,3aS,6aR)-Hexahydrofuro[2,3-b]furan-3-yl
N-((1S,2R)-1-benzyl-3-(4-cyano-2,2-dimethylbutyl)
[((4-methoxyphenyl)sulfonyl]-2-dibenzylphosphate-aminopropyl)carbamate To a solution of the product from step 1 (0.18 g, 0.21 mmol) in anhydrous acetonitrile (5 mL) was added iodobenzene diacetate (0.10 g, 0.31 mmol) and the mixture was stirred at ambient temperature for 1 hour. Solvent was evaporated and the residue was dissolved in dichloromethane, washed with saturated sodium bicarbonate/water, dried (sodium sulfate) and evaporated. The residue was chromatographed (silica gel, dichloromethane/methanol, 98.5:1.5) to give the title compound as a foam (85 mg);

¹H NMR (CDCl₃): δ 0.83 (3H, s), 0.89 (3H, s), 1.38 (1H, dd), 1.5-1.7 (3H, m), 2.2 (2H, t), 2.54 (1H, d), 2.66 (1H, dd), 2.82-2.94 (2H, m), 3.0 (1H, m), 3.22 (1H, d), 3.38 (1H, dt), 3.6-3.7 (2H, m), 3.8 (1H, td), 3.83 (3H, s), 3.9 (1H, dd), 4.15 (1H, td), 4.97 (1H, quartet), 5.0-5.2 (4H, m), 5.62 (1H, d), 6.0 (1H, d), 6.98 (2H, d), 7.10-7.25 (6H, m), 7.4 (10H, s), 7.7 (1H, d).

Step 3:

(a)

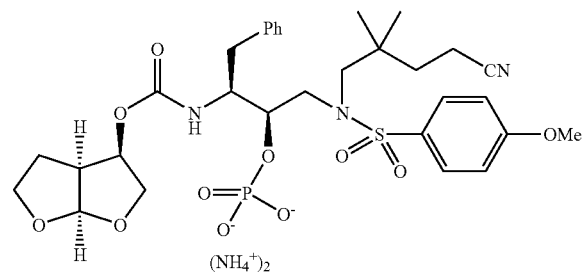

(3R,3aS,6aR)-Hexahydrofuro[2,3-b]furan-3-yl N-((1S,2R)-1-benzyl-3-(4-cyano-2,2-dimethylbutyl) [(4-methoxyphenyl)sulfonyl]amino-2-hydroxypropyl)carbamate-bis-ammonium phosphate To a solution of the product from step 2 (0.08 g) in 2M ammonia/methanol (5 mL) was added 10 Pd/C (0.02 g) and the mixture was hydrogenated at atmospheric pressure for 4 hours. The mixture was filtered through a bed of celite. Solvent was evaporated and the residue was dried in vacuo to provide the title compound as a solid.

¹H NMR (DMSO-d₆): δ 0.92 (3H, s), 0.95 (3H, s), 1.2-1.4 (2H, m), 1.6 (2H, t), 2.4-2.5 (3H, m), 2.6 (1H, dd), 2.7-2.9 (3H, m), 3.3-3.4 (3H, m), 3.5 (1H, dd), 3.55 (1H, dd), 3.7 (1H, td), 3.8 (3H, s), 3.9 (1H, br t), 4.2 (1H, br s), 4.8 (1H, quartet), 5.5 (1H, d), 7.05 (2H, d), 7.10-7.22 (6H, m), 7.75 (2H, d); MS: 694 (MH⁺).

EXAMPLE (COMPOUND 102)

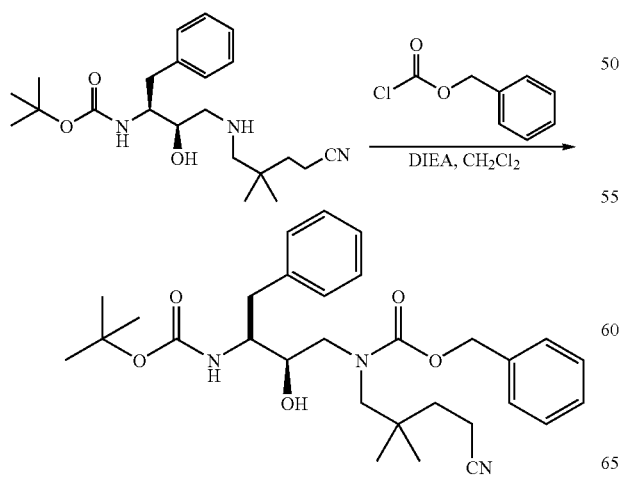

[(2R,3S)-3-tert-Butoxycarbonylamino-2-hydroxy-4-phenyl-butyl]-(4-cyano-2,2-dimethyl-butyl)-carbamic acid benzyl ester

[(1S,2R)-1-Benzyl-3-(4-cyano-2,2-dimethyl-butylamino)-2-hydroxy-propyl]-carbamic acid tert-butyl ester (1.300 g, 3.34 mmol) was dissolved in CH₂Cl₂ and treated with diisopropylethylamine (1.740 ml, 10.01 mmol) and benzyl chloroformate (0.683 g, 4.00 mmol) at ambient temperature under argon with stirring. After 15 h the reaction mixture was concentrated in vacuo, taken up in EtOAc, washed with sat. aq. NaHCO₃, and brine. The organic phase was dried over MgSO₄, filtered and solvent removed in vacuo. Purification by column chromatography (10% Et₂O in CH₂Cl₂) gave 0.083 g of a white solid. MS (ES): 524 (M+1).

EXAMPLE (COMPOUND 103)

Step 1:

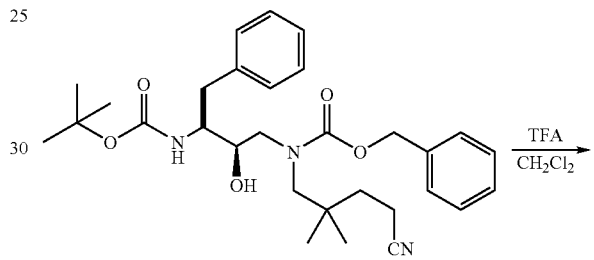

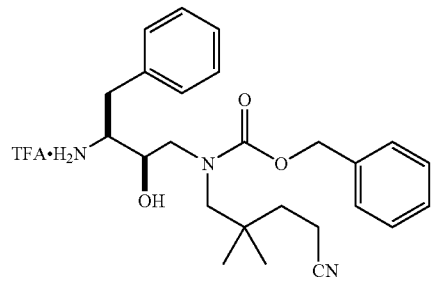

[(2R,3S)-3-Amino-2-hydroxy-4-phenyl-butyl]-(4-cyano-2,2-dimethyl-butyl)-carbamic acid benzyl ester; trifluoroacetate A solution of [(2R,3S)-3-tert-butoxycarbonylamino-2-hydroxy-4-phenyl-butyl]-(4-cyano-2,2-dimethyl-butyl)-carbamic acid benzyl ester (1.291 g, 2.47 mmol) in CH₂Cl₂ at ambient temperature was treated with TFA. After stirring 30 min solvent was removed in vacuo to give desired product as a white solid which was used directly in the next step.

Step 2:

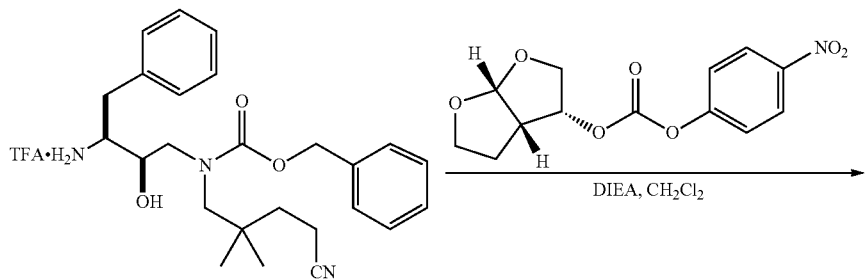

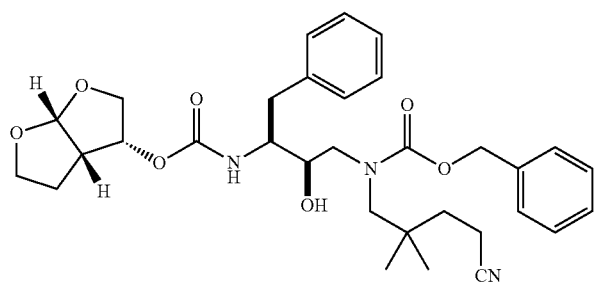

(2S,3R)-(4-Cyano-2,2-dimethyl-butyl)-[3-((3R,3aS,6aR)hexahydro-furo[2,3-b]furan-3-yloxycarbonylamino)-2-hydroxy-4-phenyl-butyl]-carbamic acid benzyl ester.

[(2R,3S)-3-Amino-2-hydroxy-4-phenyl-butyl]-(4-cyano-2,2-dimethyl-butyl)-carbamic acid benzyl ester; hydrochloride (2.47 mmol) was dissolved in CH$_2$Cl$_2$ and treated with diisopropylethylamine (1.300 ml, 7.40 mmol) and (3R,3aS,6aR)hexahydrofuro[2,3-b]furan-2-yl 4-nitrophenyl carbonate (0.801 g, 2.71 mmol) at ambient temperature under argon with stirring. After 15 h the reaction mixture was concentrated in vacuo, taken up in EtOAc, washed with sat. aq. NaHCO$_3$, and brine. The organic phase was dried over MgSO$_4$, filtered and solvent removed in vacuo. Purification by column chromatography (3% MeOH in CH$_2$Cl$_2$) gave 0.747 g of a white solid. MS (ES): 580 (M+1).

EXAMPLE (COMPOUND 113)

Step 1:

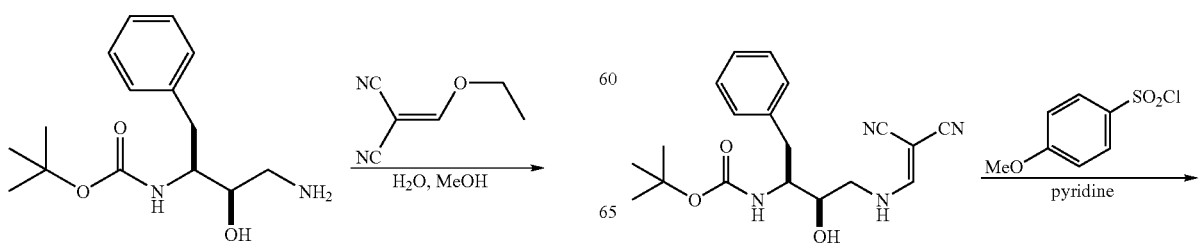

-continued

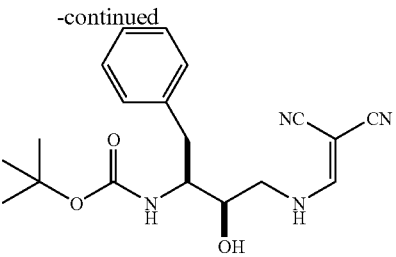

tert-Butyl-N-[(1S,2R)-1-benzyl-3-amino methylene malonitrile-2-hydroxypropyl]carbamate tert-Butyl-N-[(1S,2R)-1-benzyl-3-amino-2-hydroxy]carbamate (0.87 mmol) was dissolved in 10 mL of MeOH containing 1% of water and ethoxymethylene malonitrile (107 mg, 0.87 mmol) at ambient temperature with stirring. After 1 hr the reaction mixture was dissolved in EtOAc, washed with water and brine. The organic phase was dried over MgSO$_4$, filtered and solvent removed in vacuo. Purification by column chromatography (EtOAc 50% in Hexane) gave 0.282 g as an oil. MS (ES): 357.3 (M+1), HPLC showed the material to be 97% pure; ret. time 11.6 min.

Step 2:

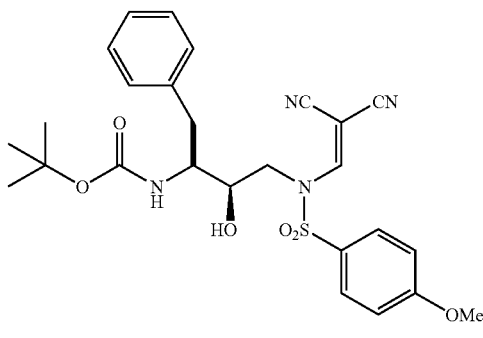

tert-Butyl-N-[(1S,2R)-1-benzyl-3-(methylene malonitrile)-2-hydroxypropyl][(4-methoxyphenyl)sulfonyl]amino]carbamate tert-Butyl-N-[(1S,2R)-1-benzyl-3-amino methylene malonitrile-2-hydroxypropyl]carbamate (0.36 mmol) was dissolved in 2 mL of pyridine. p-Methoxybenzene sulfonylchloride (0.09 g, 0.43 mmol) was added and the reaction was stirred at ambient temperature for 3 days. The reaction mixture was dissolved in dichloromethane, washed with HCl (1N) and brine. The organic phase was dried over MgSO$_4$, filtered and solvent removed in vacuo. Purification by column chromatography (EtOAc, 50% in Hexane) gave 0.017 g as a solid. MS (ES): 527.3 (M+1), HPLC showed the material to be 97% pure; ret. time 12.6 min.

EXAMPLE (COMPOUND 122)

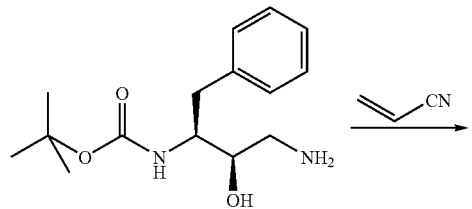

[(2R,3S)-3-tert-Butoxycarbonylamino-2-hydroxy-4-phenyl-(1-amino-2-cyanoethyl)butane]

[(2R,3S)-3-tert-Butoxycarbonylamino-2-hydroxy-4-phenyl-(1-amino)butane] (0.503 g, 1.8 mmol) was dissolved in EtOH (6 mL) and cooled to 0° C. This was followed by the addition of acrylonitrile (118 uL, 1.8 mmol). The reaction was stirred under N2 for 1.5 hrs and gradually warmed to room temperature as the ice bath melted. The reaction mixture was then concentrated in vacuo and purified by silica gel chromatography (gradient: 2% MeOH/CH$_2$Cl$_2$ to 4% MeOH/CH$_2$Cl$_2$). Isolated 339 mg of the mono-addition product (56% yield).

EXAMPLE (COMPOUND 123)

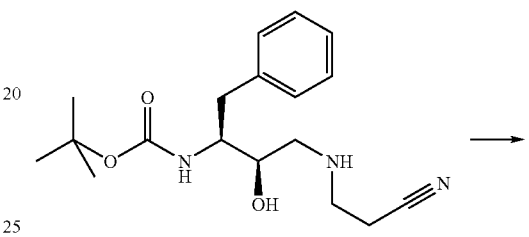

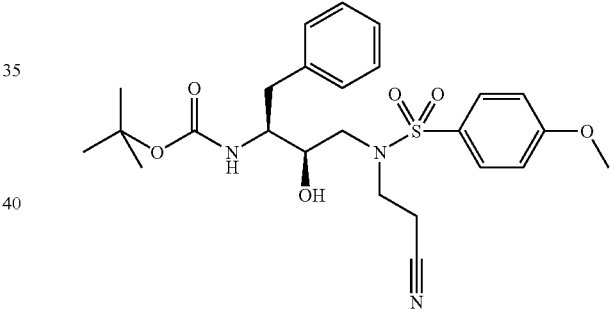

[(2R,3S)-3-tert-Butoxycarbonylamino-2-hydroxy-4-phenyl-(1-amino-(2-cyanoethyl(4-methoxyphenyl-sulfonyl))butane]

[(2R,3S)-3-tert-Butoxycarbonylamino-2-hydroxy-4-phenyl-(1-amino-2-cyanoethyl) butane]. (124 mg, 0.4 mmol) was combined with 4-methoxyphenylsulfonyl chloride (146 mg, 0.7 mmol) in DMF and cooled to 0° C. This was followed by the addition of diisopropyl ethyl amine (186 uL, 1.1 mmol). The reaction was then warmed to room temperature and stirred for 15 hours. The reaction was quenched by the addition of 3 mL of saturated NaHCO$_3$, followed by washing with sat. NaHCO$_3$, KHSO$_3$ and then brine. The organic phase was dried with MgSO$_4$ and the solvent was removed in vacuo. Purification by SiO$_2$ (1:3, EtOAc:Hex to 2:1 EtOAc:Hex). Isolated 0.038 g of the product as a colorless oil: 20.8% yield, Rf=0.27 (1:1 EtOAc:Hex/SiO2), MS (ES)=521 amu (M+1).

EXAMPLE (COMPOUND 124)

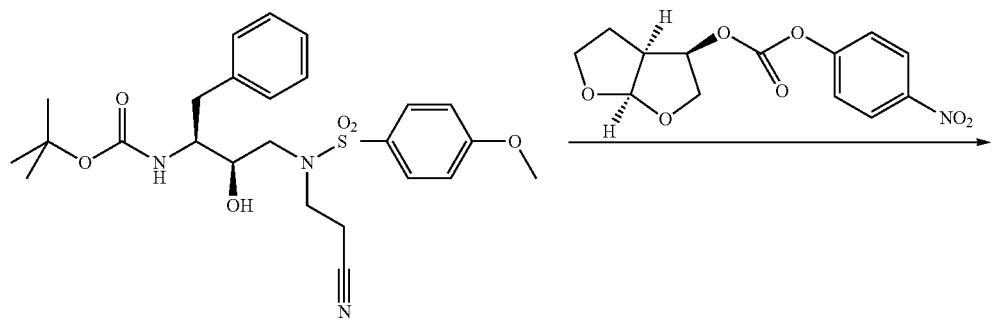

{(1S,2R)-3-[(4-methoxybenzenesulfonyl)-(2-cyano-ethyl)-amino]-1-benzyl-2-hydroxy-propyl}-carbamic acid (3R,3aS,6aR)hexahydro-furo[2,3-b]furan-3-yl ester Step 1:

[(2R,3S)-3-tert-Butoxycarbonylamino-2-hydroxy-4-phenyl-(1-amino-(2-cyanoethyl (4-methoxyphenylsulfonyl))butane] (521 mg, 0.1 mmol) was dissolved in 1 mL of $CH_2Cl_2$ followed by the addition of 1 mL of TFA. The reaction was stirred at room temperature for 15 minutes followed by concentration in vacuo to provide 655 mg of the desired deprotected amine. This material was used without further purification.

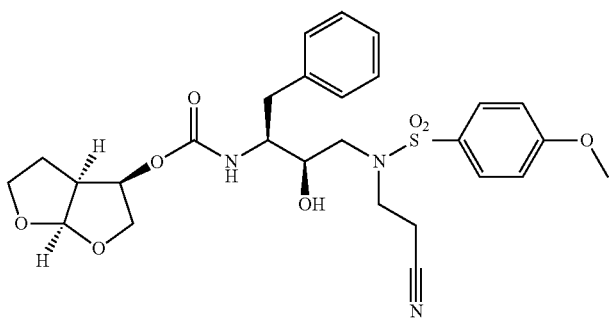

Step 2:

31.2 mg (0.1 mmol) of the material provided in the above deprotection step was then dissolved into DMF (1 mL) followed by the addition of the 3R,3aS,6aR)hexahydro-furo[2,3-b]furan-3-yl mixed carbonate (30.5 mg, 0.1 mmol). After cooling to 0° C. diisopropylethyl amine was added and the reaction was stirred for 3 hours while gradually warming to room temperature. The reaction mixture was then diluted with EtOAc washed with sat. $NaHCO_3$, $KHSO_3$ and then brine. The organic phase was dried with $MgSO_4$ and the solvent was removed in vacuo. Purification by Prep. TLC (SiO2 2:1, EtOAc:Hex). Isolated 0.0217 g of the product as a white solid: Rf=0.28 (2:1 EtOAc:Hex,/SiO2), MS (ES)=560 amu (M+1).

EXAMPLE (COMPOUND 125)

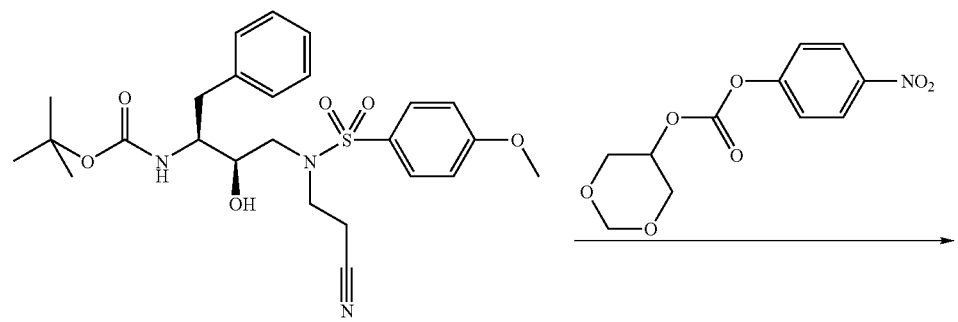

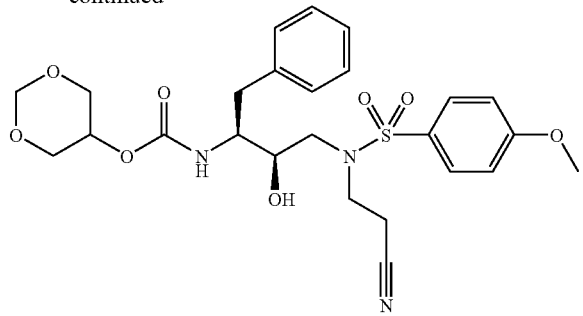

34.3 mg (0.1 mmol) of the material provided in the above-deprotection step (Step 1, Example (Compound 122)) was then dissolved into DMF (1 mL) followed by the 1,3-dioxan-5-yl derived mixed carbonate (127.9 mg, 0.1 mmol). After cooling to 0° C., diisopropylethylamine was added and the reaction was stirred for 15 hours (warmed to room temperature overnight). The reaction mixture was then diluted with EtOAc washed with sat. NaHCO₃, KHSO3 and then brine. The organic phase was dried with MgSO₄ and the solvent was removed in vacuo. Purification by Prep. TLC (SiO2 2:1, EtOAc:Hex). Isolated 0.0122 g of the product as a white solid: Rf=0.34 (2:1, EtOAc:Hex/SiO2), MS (ES)=534 amu (M+1).

EXAMPLE (COMPOUND 126)

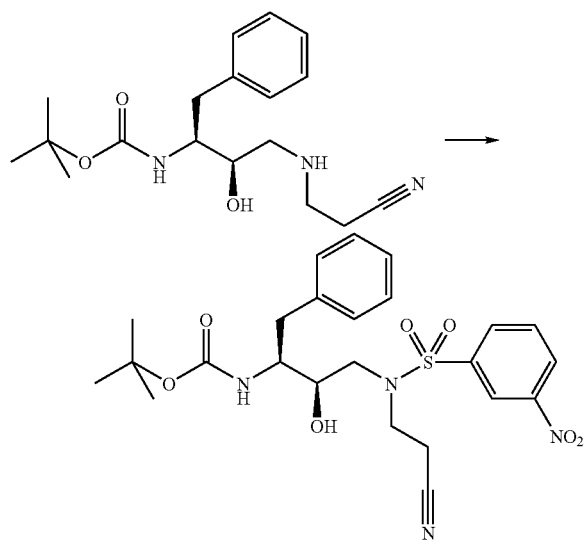

[(2R,3S)-3-tert-Butoxycarbonylamino-2-hydroxy-4-phenyl-(1-amino-(2-cyanoethyl (3-nitrophenylsulfonyl)) butane]

[(2R,3S)-3-tert-Butoxycarbonylamino-2-hydroxy-4-phenyl-(1-amino-2-cyanoethyl) butane]. (100.6 mg, 0.3 mmol) was combined with 3-nitrophenylsulfonyl chloride (134 mg, 0.6 mmol) in DMF and cooled to 0° C. This was followed by the addition of diisopropyl ethyl amine (160 uL, 0.9 mmol). The reaction was then warmed to room temperature and stirred for 15 hours. The reaction was quenched by the addition of 3 mLs of saturated NaHCO₃, followed by washing with sat. NaHCO₃, KHSO₃ and then brine. The organic phase was dried with MgSO₄ filtered and the solvent was removed in vacuo. Purification by SiO₂ (1:3, EtOAc:Hex to 2:1 EtOAc:Hex). Isolated 0.0389 g of the product as a colorless oil: 24.9% yield, Rf=0.39 (1:1 EtOAc:Hex/SiO₂.

EXAMPLE (COMPOUND 127)

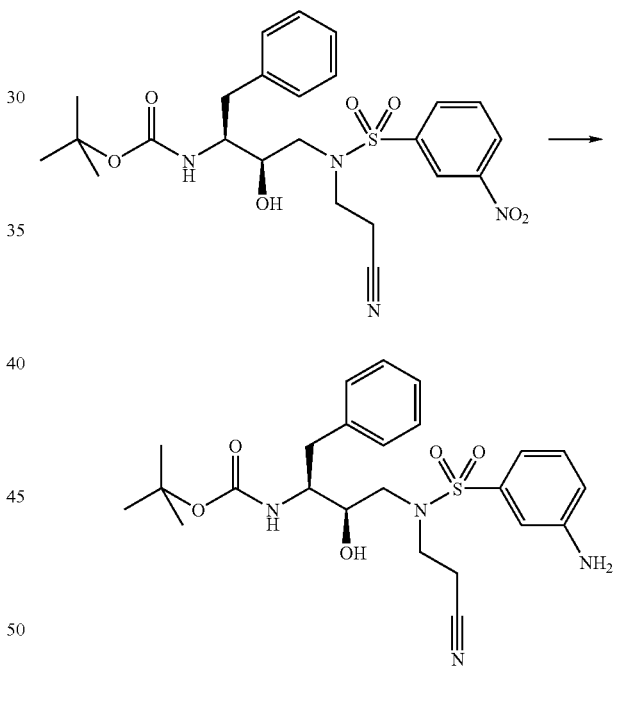

[(2R,3S)-3-tert-Butoxycarbonylamino-2-hydroxy-4-phenyl-(1-amino-(2-cyanoethyl (3-aminophenylsulfonyl))butane]

[(2R,3S)-3-tert-Butoxycarbonylamino-2-hydroxy-4-phenyl-(1-amino-(2-cyanoethyl (3-nitrophenylsulfonyl)butane] (4.0 mg) was dissolved in methanol (1 mL) followed by catalytic 10% Pd/C. The reaction vessel was purged of air and pressurized with H2 at ~1 ATM and stirred for 3 hours. The reaction was then filtered and concentrated in vacuo to provide 2.1 mg of a colorless film: Rf=0.22 (1:1 EtOAc:Hex,/SiO2), MS (ES)=489 amu (M+1).

EXAMPLE (COMPOUND 201)

Step 1:

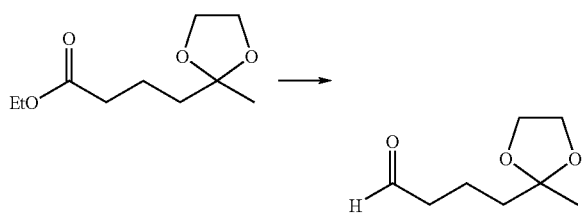

4-(2-Methyl-1,3-dioxolan-2-yl)butanal

A stirred slurry of lithium aluminum hydride (940 mg, 24.7 mmol) in anhydrous ether (25 mL) was cooled in an ice bath. Ethyl 4-(2-methyl-1,3-dioxolan-2-yl)butanoate [Benchikhle-Hocine, M.; Do Khac, D.; Fetizon, M.; Prange, T. *Synthetic Communications* 1992, 22, 1871-1882] (5.0 g, 24.7 mmol) in ether (25 mL) was added dropwise over 20 minutes. The reaction was stirred at 5° C. for 2 hours and then quenched by the slow addition of water (1 mL), followed by 15% sodium hydroxide (1 mL) and water (3 mL). After stirring for 30 minutes, the resulting precipitate was filtered and rinsed with ether. The ether was dried (magnesium sulfate) and concentrated in vacuo to afford the desired alcohol (3.6 g, 90%) as a colorless liquid.

$^1$H NMR (CDCl$_3$): δ 1.30 (3H, s), 1.42-1.72 (7H, m), 3.64 (2H, t), 3.88-3.98 (4H, m).

To a stirred suspension of pyridinium chlorochromate (7.1 g, 32.8 mmol) in dichloromethane (35 mL) was added a solution of the above alcohol (3.5 g, 21.8 mmol) in dichloromethane (15 mL). After stirring at ambient temperature for 2 hours, the reaction was diluted with ether (50 mL) and filtered through celite. The filtrate was concentrated in vacuo and chromatographed (silica gel, ethyl acetate/hexane, 1:4) to afford the title compound (1.8 g, 50%) as a clear liquid; $^1$H NMR (CDCl$_3$): δ 1.30 (3H, s), 1.62-1.78 (4H, m), 2.46 (2H, t), 3.88-3.98 (4H, m), 9.78 (1H, s).

Step 2:

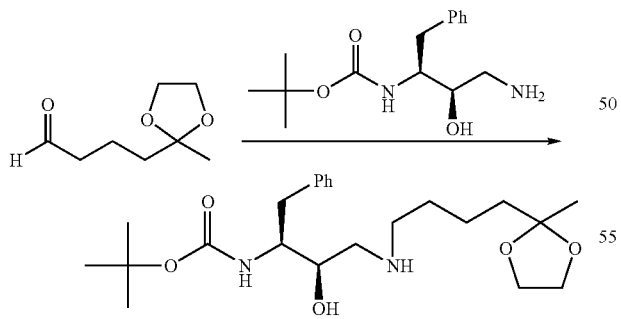

tert-Butyl N-((1S,2R)-1-benzyl-2-hydroxy-3-[4-(2-methyl-1,3-dioxolan-2-yl)butyl]aminopropyl)carbamate To a suspension of the product of Step 1 (1.8 g, 11.4 mmol) and tert-butyl N-(1S,2R)-3-amino-1-benzyl-2-hydroxypropylcarbamate (3.2 g, 11.4 mmol) in 1,2-dichloroethane (30 mL), tetrahydrofuran (30 mL) and N,N-dimethylformamide (20 mL) was added sodium triacetoxy borohydride (3.6 g, 17.0 mmol) and the mixture was stirred under nitrogen atmosphere for 3.5 hours. The mixture was filtered and the filtrate was concentrated to 25 mL. The residue was partitioned between ethyl acetate and 2M sodium hydroxide/water. The organic phase was washed with water, brine, dried (sodium sulfate), and evaporated. The residue was chromatographed (silica gel, dichloromethane/methanol, 95:5) to provide the title compound as a white solid.

Step 3:

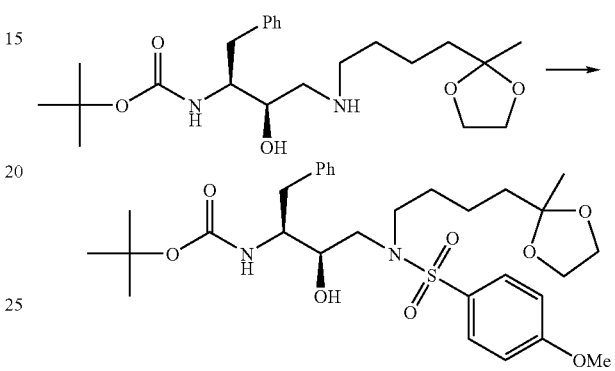

tert-Butyl N-((1S,2R)-1-benzyl-2-hydroxy-3-[(4-methoxyphenyl)sulfonyl][4-(2-methyl-1,3-dioxolan-2-yl)butyl]aminopropyl)carbamate To a solution of the product of Step 2 (0.63 g, 1.49 mmol) in anhydrous dichloromethane (7 mL) at 0° C. was added N-ethyldiisopropylamine (0.38 g, 0.51 mL, 2.98 mmol) and a solution of 4-methoxybenzenesulfonyl chloride (0.32 g, 1.56 mmol) in anhydrous dichloromethane (2 mL) and the mixture was stirred at ambient temperature under nitrogen atmosphere for 18 hours. The mixture was washed sequentially with 1M hydrochloric acid, sodium bicarbonate/water, brine, dried (sodium sulfate) and concentrated. The residue was chromatographed (silica gel, dichloromethane/methanol, 97:3) to provide the title compound as a thick oil.

$^1$H NMR (DMSO-d$_6$): δ 1.18 (3H, s), 1.21 (9H, s), 1.4-1.5 (4H, m), 2.45 (2H, brs), 2.82 (1H, dd), 2.94-3.00 (2H, m), 3.18 (1H, dt), 3.28-3.34 (2H, m), 3.45-3.60 (2H, m), 3.75-3.84 (7H, m), 5.0 (1H, brs), 6.7 (1H, d), 7.08 (2H, d), 7.10-7.25 (5H, m), 7.7 (2H, d); MS: 615.1 (MH$^+$)

EXAMPLE (COMPOUND 202)

Step 1:

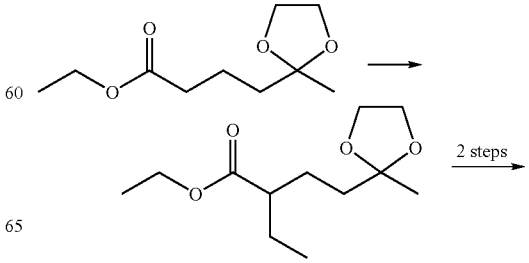

2 steps

-continued

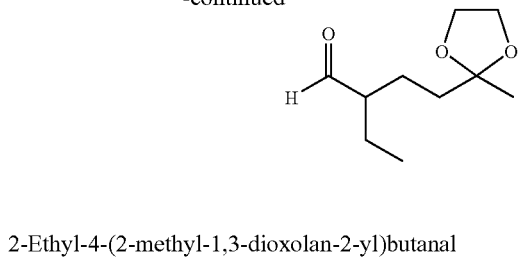

2-Ethyl-4-(2-methyl-1,3-dioxolan-2-yl)butanal

To a freshly prepared solution of lithium diisopropylamide (40.0 mmol in tetrahydrofuran/hexane; 50 mL, 1:1) at −78° C. was added a solution of ethyl-4-(2-methyl-1,3-dioxolan-2-yl) butanoate (6.7 g, 33.3 mmol) in tetrahydrofuran (15 mL) over 15 minutes. After stirring for 15 minutes, ethyl iodide (4.0 mL, 50.0 mmol) was added rapidly via syringe. The reaction was stirred at −78° C. for 6 hours and then allowed to warm slowly to ambient temperature and stir for 16 hours. The reaction was quenched by the addition of water (50 mL) and extracted with ether (3×50 mL). The combined organics were washed with brine (50 mL), dried (magnesium sulfate), concentrated in vacuo and chromatographed (silica gel, ethyl acetate/hexane, 1:4) to afford ethyl 2-ethyl-4-(2-methyl-1,3-dioxolan-2-yl) butanoate (2.6 g, 33%) as a colorless liquid.

$^1$H NMR (CDCl$_3$): δ 0.88 (3H, t), 1.23 (3H, t), 1.30 (3H, s), 1.45-1.75 (6H, m), 2.20-2.28 (1H, m), 3.85-3.95 (4H, m), 4.12 (2H, q).

The above ester (2.5 g, 10.9 mmol) was subjected to the conditions used in Step 1 (Example (Compound 201)) to afford the title compound (1.2 g, 60%) as a clear liquid.

$^1$H NMR (CDCl$_3$): δ 0.90 (3H, t), 1.30 (3H, s), 1.45-1.78 (6H, m), 2.14-2.22 (1H, m), 3.87-3.97 (4H, m), 9.58 (1H, s).

Step 2:

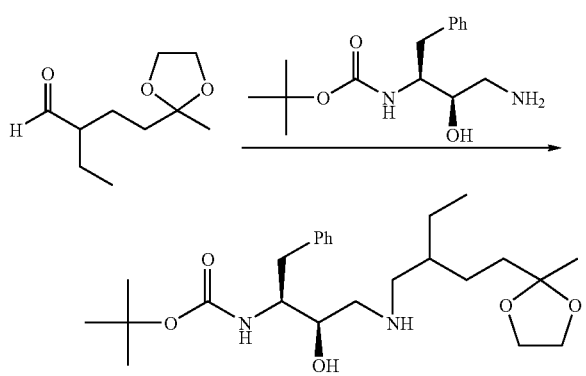

tert-Butyl N-((1S,2R)-1-benzyl-3-[2-ethyl-4-(2-methyl-1,3-dioxolan-2-yl)butyl]amino-2-hydroxypropyl)carbamate The product from Step 1 was subjected to procedure Step 2, Example (Compound 201) to afford the title compound as a white solid (mixture of diastereomers by $^1$H NMR spectroscopy);

$^1$H NMR (DMSO-d$_6$): δ 0.78 (3H, t), 1.17 (3H, s), 1.20-1.35 (5H, m), 1.22 (9H, s), 1.48 (2H, t), 2.33-2.58 (5H, m), 2.92-2.98 (1H, m), 3.34-3.55 (2H, m), 3.75-3.84 (4H, m), 4.78 (1H, br s), 6.68 (1H, dd), 7.05-7.25 (5H, m); MS: 451 (MH$^+$).

Step 3:

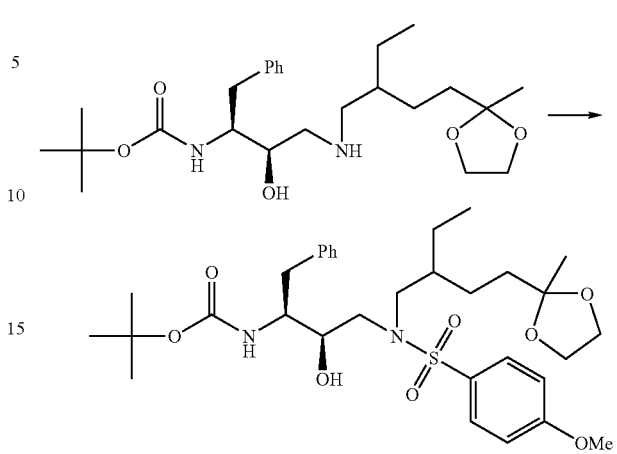

tert-ButylN-((1S,2R)-1-benzyl-3-[2-ethyl-4-(2-methyl-1,3-dioxolan-2-yl)butyl][(4-methoxyphenyl) sulfonyl]amino-2-hydroxypropyl)carbamate The product from above Step 2 was subjected to the procedure outlined in Step 3 of Example (Compound 201) to give the title compound as a pale yellow glass (mixture of diastereomers by $^1$H NMR spectroscopy);

$^1$H NMR (DMSO-d$_6$): δ 0.79 (3H, td), 1.2 (3H, s), 1.24 (9H, s), 1.3-1.6 (3H, m), 1.7 (1H, brs), 2.45-2.55 (2H, m), 2.73 (1H, dd), 2.85 (1H, dd), 2.9 (1H, d), 3.1 (1H, td), 3.40-3.65 (4H, m), 3.75-3.90 (7H, m), 4.96 (1H, brs), 6.7 (1H, d), 7.05 (2H, d), 7.1-7.3 (5H, m), 7.78 (2H, d); MS: 643.1 (M+23)

EXAMPLE (COMPOUND 203)

Step 1:

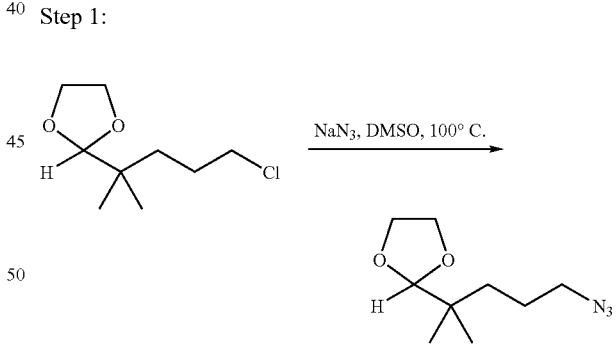

4-(1,3-dioxolan-2-yl)-4-methylpentyl azide

A solution of 0.74 g (3.8 mmol) of 2-(4-chloro-1,1-dimethylbutyl)-1,3-dioxolane and 0.50 g (7.7 mmol) of sodium azide in 5 mL of DMSO was heated to 100° C. with stirring. After 18 hours the solution was cooled to RT, diluted with water, and the mixture extracted with ether (3×). The combined ether extracts were washed with water (3×), dried over MgSO$_4$, and concentrated in vacuo to afford 0.69 g (90%) of the desired compound as a light yellow liquid.

$^1$H NMR (CDCl$_3$): δ 4.60 (1H), 3.91 (4H), 3.29 (2H), 1.67 (2H), 1.41 (2H), 0.96 (6H).

Step 2:

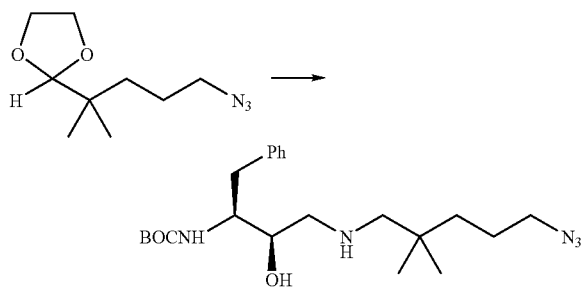

tert-butyl N-(1S,2R)-3-[(5-azido-2,2-dimethylpentyl)amino]-1-benzyl-2-hydroxypropylcarbamate A solution of 0.44 g (2.2 mmol) of 4-(1,3-dioxolan-2-yl)-4-methylpentyl azide in 15 mL of THF was treated with 3 mL of 1M aqueous HCl and the solution stirred at reflux. After 4 hours the solution was cooled to RT and poured into 40 mL of rapidly stirred saturated aqueous NaHCO$_3$. The resulting mixture was extracted with ether (3×). The combined ether extracts were washed with water (2×), dried over MgSO$_4$ and concentrated to a volume of approximately 3 mL. This solution was added to a solution of 0.62 g (2.2 mmol) of tert-butyl N-(1S,2R)-3-amino-1-benzyl-2-hydroxypropylcarbamate in 20 mL of 1:1 THF/DMF. The solution was treated with 1 g of powdered 4A molecular sieves and the mixture heated at 50° C. After 2 hours the mixture was cooled in an ice water bath and treated with 0.47 g (2.2 mmol) of NaBH(OAc)$_3$. After stirring at RT for 18 hours the mixture was concentrated in vacuo. The residue was suspended in CH$_2$Cl$_2$ and stirred vigorously with 0.5M aqueous NaOH for 5 minutes. The layers were separated and the aqueous phase extracted with two additional portions of CH$_2$Cl$_2$. The combined CH$_2$Cl$_2$ solutions were washed with water (2×), dried over MgSO$_4$, and concentrated to give a clear viscous oil. This material was subjected to flash chromatography (SiO$_2$, 95:5 CH$_2$Cl$_2$/2M NH$_3$ in MeOH) to afford 0.45 g (49%) of the desired product as a white foam.

$^1$H-NMR (DMSO-d$_6$): δ 7.27-7.05 (5H), 6.70 (1H), 4.73 (1H), 3.49 (1H), 3.39 (1H), 3.25 (2H), 2.92 (1H), 2.60-2.42 (4H), 2.22 (2H), 1.41 (3H), 1.21 (10H), 0.80 (6H). MS (ESI): 420 (M+H).

Step 3:

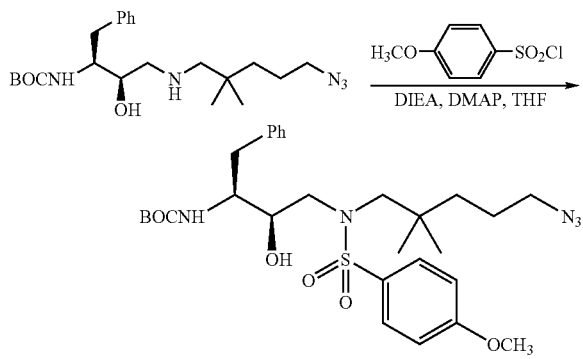

tert-butyl N-((1S,2R)-3-(5-azido-2,2-dimethylpentyl)[(4-methoxyphenyl)sulfonyl]amino-1-benzyl-2-hydroxypropyl)carbamate A solution of 0.40 g (0.95 mmol) of tert-butyl N-(1S,2R)-3-[(5-azido-2,2-dimethylpentyl)amino]-1-benzyl-2-hydroxypropylcarbamate in 10 mL of anhydrous THF was treated with 0.20 g (0.95 mmol) of 4-methoxybenzene-sulfonyl chloride, 0.17 mL (0.95 mmol) of N,N-diisopropylethylamine, and 35 mg (0.29 mmol) of DMAP. The resulting solution was stirred at RT. After 2 hours thin layer chromatography ("tlc") (SiO$_2$, hexane/EtOAc) indicated reaction to be complete. The solution was concentrated in the presence of silica gel and the material, subjected to flash chromatography (SiO$_2$, 8:2 to 7:3 hexane/EtOAc) to afford 0.50 g (89%) of the desired compound as a viscous oil.

$^1$H-NMR (DMSO-d$_6$): δ 7.76 (2H), 7.30-7.03 (7H), 6.65 (1H), 5.01 (1H), 3.85 (3H), 3.74 (1H), 3.48-3.23 (4H), 2.95 (2H), 2.81 (1H), 2.50 (2H), 1.52 (2H), 1.40-1.20 (1H), 0.94 (6H); MS (ESI): 590 (M+H).

EXAMPLE (COMPOUND 204)

Step 1:

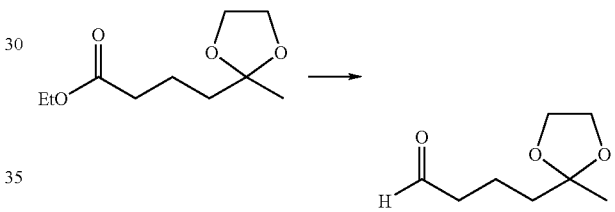

4-(2-Methyl-1,3-dioxolan-2-yl)butanal

A stirred slurry of lithium aluminum hydride (940 mg, 24.7 mmol) in anhydrous ether (25 mL) was cooled in an ice bath. Ethyl 4-(2-methyl-1,3-dioxolan-2-yl) butanoate [Benchikhle-Hocine, M.; Do Khac, D.; Fetizon, M.; Prange, T. *Synthetic Communications* 1992, 22, 1871-1882] (5.0 g, 24.7 mmol) in ether (25 mL) was added dropwise over 20 minutes. The reaction was stirred at 5° C. for 2 hours and then quenched by the slow addition of water (1 mL), followed by 15% sodium hydroxide (1 mL) and water (3 mL). After stirring for 30 minutes, the resulting precipitate was filtered and rinsed with ether. The ether was dried (magnesium sulfate) and concentrated in vacuo to afford the desired alcohol (3.6 g, 90%) as a colorless liquid;

$^1$H NMR (CDCl$_3$): δ 1.30 (3H, s), 1.42-1.72 (7H, m), 3.64 (2H, t), 3.88-3.98 (4H, m);

To a stirred suspension of pyridinium chlorochromate (7.1 g, 32.8 mmol) in dichloromethane (35 mL) was added a solution of the above alcohol (3.5 g, 21.8 mmol) in dichloromethane (15 mL). After stirring at ambient temperature for 2 hours, the reaction was diluted with ether (50 mL) and filtered through celite. The filtrate was concentrated in vacuo and chromatographed (silica gel, ethyl acetate/hexane, 1:4) to afford the title compound (1.8 g, 50%) as a clear liquid;

$^1$H NMR (CDCl$_3$): δ 1.30 (3H, s), 1.62-1.78 (4H, m), 2.46 (2H, t), 3.88-3.98 (4H, m), 9.78 (1H, s).

Step 2:

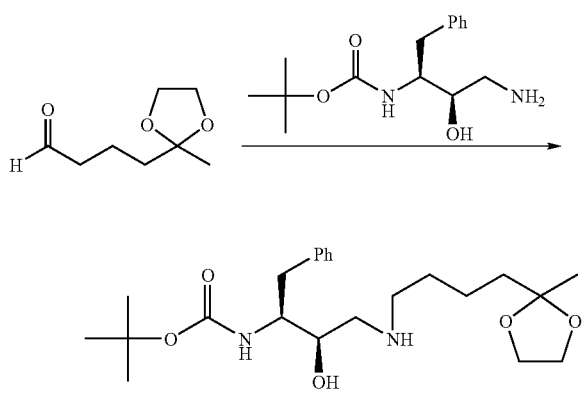

tert-Butyl N-((1S,2R)-1-benzyl-2-hydroxy-3-[4-(2-methyl-1,3-dioxolan-2-yl)butyl]aminopropyl)carbamate The product from step a was subjected to the procedure used in Step 2 of Example (Compound 201) to afford the title compound as a white solid;

$^1$H NMR (DMSO-d$_6$): δ 1.18 (3H, s), 1.23 (9H, s), 1.26-1.41 (4H, m), 1.48-1.55 (2H, m), 1.98 (1H, brs), 2.39-2.59 (5H, m), 2.95 (1H, dd), 3.34-3.54 (2H, m), 3.75-3.84 (4H, m), 4.78 (1H, brs), 6.65 (1H, d), 7.08-7.27 (5H, m); MS: 423 (MH$^+$).

Step 3:

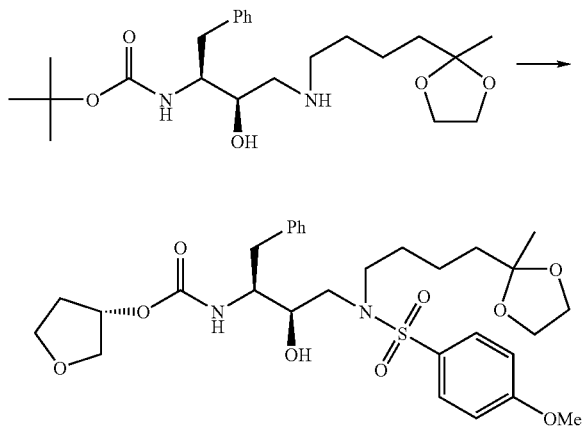

tert-Butyl N-((1S,2R)-1-benzyl-2-hydroxy-3-[(4-methoxyphenyl)sulfonyl][4-(2-methyl-1,3-dioxolan-2-yl)butyl]aminopropyl)carbamate The product from Step 2 was subjected to the procedure used in step 3 of Example (Compound 201) to give the title compound as a thick oil;

$^1$H NMR (DMSO-d$_6$): δ 1.18 (3H, s), 1.21 (9H, s), 1.4-1.5 (4H, m), 2.45 (2H, brs), 2.82 (1H, dd), 2.94-3.00 (2H, m), 3.18 (1H, dt), 3.28-3.34 (2H, m), 3.45-3.60 (2H, m), 3.75-3.84 (7H, m), 5.0 (1H, brs), 6.7 (1H, d), 7.08 (2H, d), 7.10-7.25 (5H, m), 7.7 (2H, d); MS: 615.1 (MH$^+$).

EXAMPLE (COMPOUND 205)

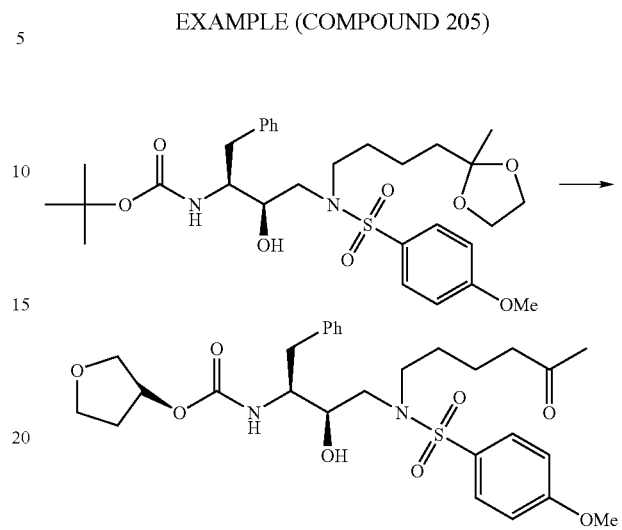

(3S)-Tetrahydro-3-furanyl N-(1S,2R)-1-benzyl-2-hydroxy-3-[[(4-methoxyphenyl)sulfonyl](5-oxo-hexyl)amino]-propylcarbamate The product from Step 3 of Example (Compound 204) (0.22 g, 0.4 mmol) was dissolved in dichloromethane (2.5 mL) at 0° C. was added trifluoroacetic acid (2.5 mL) and a drop of water, and the mixture was stirred at ambient temperature for 1 hour. Solvent was evaporated and coevaporated with dichloromethane. The residue was dissolved in dichloromethane and washed with 0.1 M sodium hydroxide/water, water, brine, dried (sodium sulfate), concentrated and dried in vacuo. The resulting pale yellow foam was dissolved in acetonitrile (4 mL) and N-ethyldiisopropylamine (0.08 mL, 0.059 g, 0.46 mmol) and N-succinimidyl (3S)-tetrahydro-3-furanyl carbonate (0.098 g, 0.43 mmol) were added. The mixture was stirred at ambient temperature for 1 hour and the solvent was evaporated. The residue was chromatographed (silica gel, dichloromethane/methanol, 98:2) to give the title compound as a white foam;

$^1$H NMR (DMSO-d$_6$): δ 1.3-1.5 (4H, m), 1.73 (1H, brs), 2.05 (4H, brs), 2.35 (2H, brs), 2.5 (1H, brs), 2.8 (1H, dd), 2.95 (2H, brd), 3.15-3.20 (1H, m), 3.35 (H, t), 3.45-3.75 (5H, m), 3.8 (3H, s), 4.93 (1H, s), 5.1 (1H, brs), 7.1-7.3 (8H, m), 7.7 (2H, d); MS: 563.1 (MH$^+$).

EXAMPLE (COMPOUND 206)

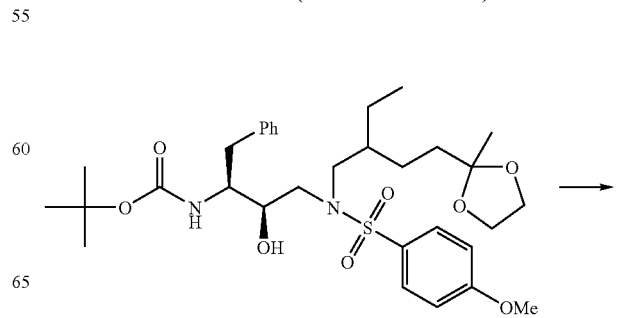

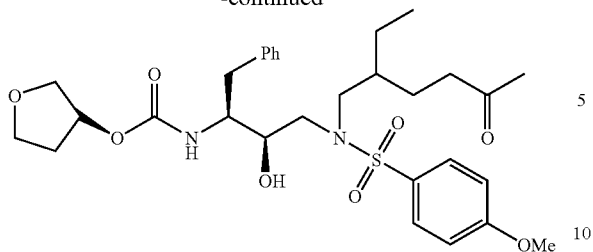

(3S)-Tetrahydro-3-furanyl N-((1S,2R)-1-benzyl-3-(2-ethyl-5-oxohexyl)[(4-methoxyphenyl)sulfonyl]amino-2-hydroxypropyl)carbamate The product from Step 3 of Example (Compound 202) was subjected to the procedure used in Example (Compound 205) to provide the title compound as a thick oil (mixture of diastereomers by $^1$H NMR spectroscopy);

$^1$H NMR (DMSO-$d_6$): δ 0.85 (3H, td), 1.2-1.3 (2H, m), 1.4-1.6 (3H, m), 1.7-1.9 (2H, m), 2.10-2.15 (1H, m), 2.18 (3H, s), 2.2-2.3 (2H, m), 2.85 (1H, d), 2.90 (1H, d), 3.05 (1H, d), 3.15 (1H, dd), 3.38-3.42 (1H, m), 3.45-3.80 (6H, m), 3.9 (3H, s), 5.0 (1H, brt), 5.1 (1H, t), 7.1 (2H, d), 7.2-7.4 (6H, m), 7.8 (2H, m): MS: 591.1 (MH$^+$).

EXAMPLE (COMPOUND 207)

Step 1:

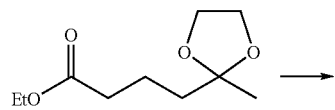

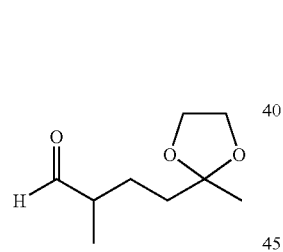

2-Methyl-4-(2-methyl-1,3-dioxolan-2-yl)butanal

The title compound was prepared by the procedure used in Example (Compound 202) using methyl iodide in the alkylation step.

$^1$H NMR (CDCl$_3$): δ 1.10 (3H, d), 1.31 (3H, s), 1.40-1.88 (4H, m), 2.26-2.40 (1H, m), 3.86-3.98 (4H, m), 9.61 (1H,

Step 2:

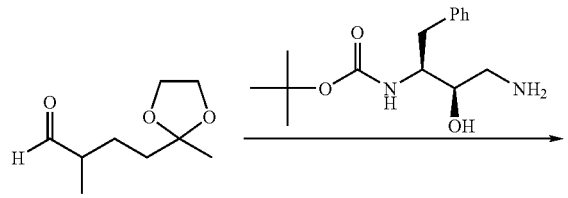

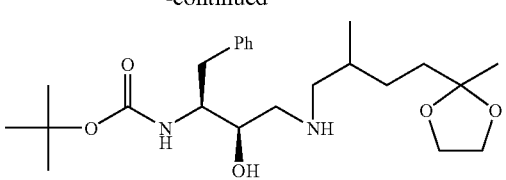

tert-Butyl N-((1S,2R)-1-benzyl-2-hydroxy-3-[2-methyl-4-(2-methyl-1,3-dioxolan-2-yl)butyl]aminopropyl)carbamate The product from Step 1 was subjected to procedure used in Step 2 of Example (Compound 201) to provide the title compound as a white solid (mixture of diastereomers by $^1$H NMR spectroscopy);

$^1$H NMR (DMSO-$d_6$): δ 0.82 (3H, d), 1.18 (3H, s), 1.23 (9H, s), 1.33-1.62 (5H, m), 1.84 (1H, br), 2.23-2.58 (5H, m), 2.96 (1H, d), 3.36-3.55 (2H, m), 3.75-3.85 (4H, m), 4.78 (1H, br s), 6.67 (1H, dd), 7.07-7.25 (5H, m); MS: 437 (MH$^+$).

Step 3:

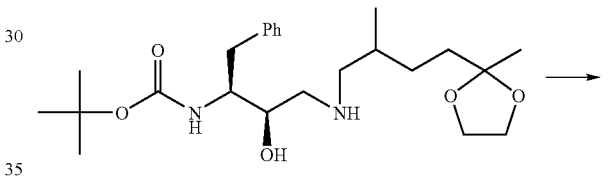

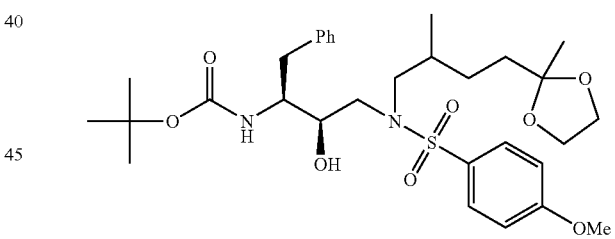

tert-Butyl N-((1S,2R)-1-benzyl-2-hydroxy-3-[2-methyl-4-(2-methyl-1,3-dioxolan-2-yl)butyl][(4-methoxyphenyl)sulfonyl]aminopropyl)carbamate The product from Step 2 was subjected to Step 3 of Example (Compound 201) to afford the title compound as a yellow foam (mixture of diastereomers by $^1$H NMR spectroscopy);

$^1$H NMR (DMSO-$d_6$): δ 0.8 (3H, d), 1.00-1.05 (1H, m), 1.1 (1H, brs), 1.2 (9H, s), 1.2-1.3 (1H, m), 1.35-1.50 (2H, m), 1.6 (1H, td), 1.75-1.83 (1H, m), 2.5 (1H, dd), 2.8 (1H, dd), 2.85 (1H, dd), 2.93 (1H, dd), 3.05 (1H, dd), 3.15-3.2 (2H, m), 3.37-3.46 (1H, m), 3.59 (1H, brs), 3.80-3.95 (7H, m), 4.95 (1H, brs), 6.7 (1H, d), 7.1 (2H, d), 7.15-7.24 (5H, m), 7.75 (2H, d); MS: 629.1 (M+23).

Step 4:

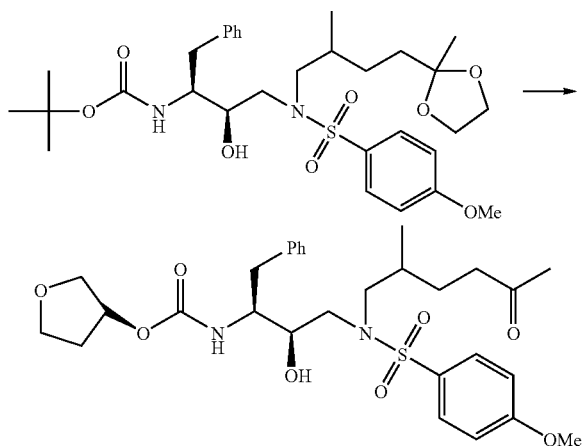

(3S)-Tetrahydro-3-furanyl N-(1S,2R)-1-benzyl-2-hydroxy-3-[[(4-methoxyphenyl)sulfonyl](2-methyl-5-oxohexyl)amino]propylcarbamate The product from Step 3 was subjected to the procedure in Example (Compound 205) to give the title compound as a white foam (mixture of diastereomers by $^1$H NMR spectroscopy);

$^1$H NMR (DMSO-d$_6$): δ 0.83 (3H, d), 1.2-1.3 (2H, m), 1.5-1.6 (1H, m), 1.8-1.9 (2H, m), 2.05-2.10 (1H, m), 2.2 (3H, s), 2.3-2.5 (2H, m), 2.8 (1H, dd), 2.9 (1H, brs), 3.05 (1H, brd), 3.15 (1H, dd), 3.30-3.45 (2H, m), 3.5-3.8 (6H, m), 3.9 (3H, s), 5.0 (1H, brt), 5.1 (1H, brdd), 6.2 (2H, d), 6.25-6.40 (6H, m), 7.8 (2H, m); MS: 577.5 (MH$^+$).

EXAMPLE (COMPOUND 208)

Step 1:

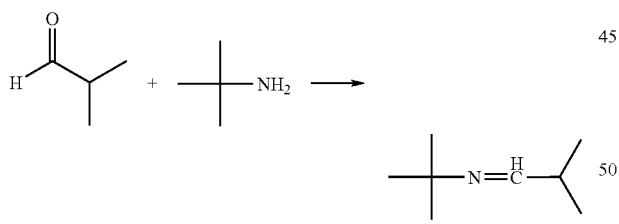

N-(2-methylpropylidene)-2-methyl-2-propanamine

To a stirred solution of t-butylamine (20.0 mL, 190 mmol) in anhydrous ether (200 mL) was added magnesium sulfate (20 g). A solution of isobutyraldehyde (17.3 mL, 190 mmol) in ether (50 mL) was then added dropwise over 30 minutes. After stirring at ambient temperature for 3 days, the reaction was filtered and the ether removed in vacuo (300 mm). The residual liquid was distilled to afford the title compound (14.0 g, 58%) as a colorless liquid; bp 52° C. (75 mm);

$^1$H NMR (CDCl$_3$): δ 1.01 (6H, d), 1.13 (9H, s), 2.37 (1H, m), 7.36 (1H, d).

2,2-Dimethyl-4-(2-methyl-1,3-dioxolan-2-yl)butanal

A freshly prepared solution of lithium diisopropylamide, was generated by the addition of n-butyllithium (16.2 mL, 25.9 mmol, 1.6 M in hexane) to a solution of diisopropylamine (6.6 mL, 47.0 mmol) in tetrahydrofuran (20 mL) at −20° C., and allowed to warm to 0° C. and stir for 30 minutes. N-(2-methylpropylidene)-2-methyl-2-propanamine (3.0 g, 23.5 mmol) in tetrahydrofuran (10 mL) was added dropwise over 10 minutes. After stirring at 0° C. for 2 hours, 2-bromoethyl-2-methyl-1,3-dioxolane (5.0 g, 25.9 mmol) in tetrahydrofuran (10 mL) was added over 15 minutes. The reaction was allowed to warm to ambient temperature and stirring was continued for 16 hours. After cooling in an ice bath, an aqueous solution of oxalic acid (100 mL, 10 wgt %) was added and reaction stirred for 1 hour. The layers were separated and the aqueous was extracted with ether (100 mL). The combined organic layers were washed with brine (50.mL), saturated sodium bicarbonate/water (50 mL), brine (50 mL), dried (magnesium sulfate), concentrated in vacuo and chromatographed (silica gel, ethyl acetate/hexane, 1:9) to afford the title compound (1.0 g, 23%) as a clear liquid;

$^1$H NMR (CDCl$_3$): δ 1.05 (6H, s), 1.31 (3H, s), 1.52-1.62 (4H, m), 3.88-3.98 (4H, m), 9.45 (1H, s).

Step 2:

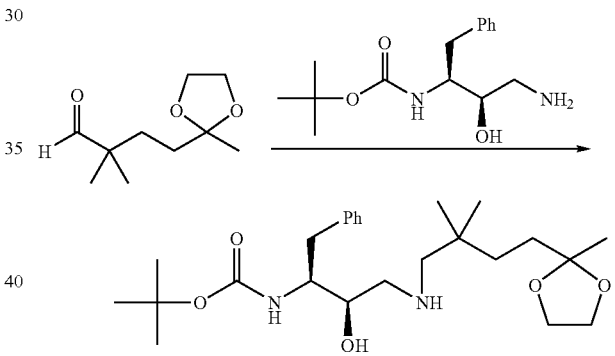

tert-Butyl N-((1S,2R)-1-benzyl-3-[2,2-dimethyl-4-(2-methyl-1,3-dioxolan-2-yl)butyl]amino-2-hydroxypropyl)carbamate The product from Step 1 was subjected to Step 2 (Example (Compound 201)) to afford the title compound as a thick oil;
$^1$H NMR (DMSO-d$_6$): δ 0.80 (6H, s), 1.17-1.27 (14H, m), 1.38 (1H, br), 1.42-1.50 (2H, m), 2.22 (2H, s), 2.45-2.59 (3H, m), 2.96 (1H, dd), 3.36-3.55 (2H, m), 3.75-3.85 (4H, m), 4.76 (1H, br s), 6.71 (1H, d), 7.08-7.24 (5H, m); MS 451 (MH$^+$)

Step 3:

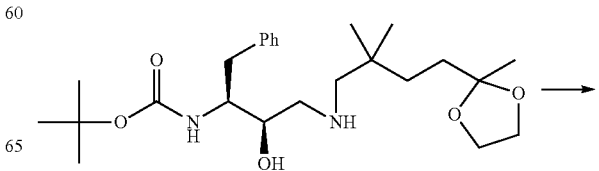

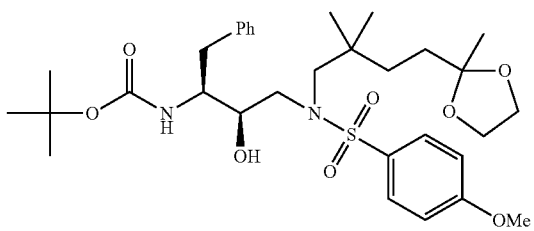

tert-Butyl N-((1S,2R)-1-benzyl-3-[2,2-dimethyl-4-(2-methyl-1,3-dioxolan-2-yl)butyl][(4-methoxyphenyl)sulfonyl]amino-2-hydroxypropyl)carbamate The product from Step 2 was subjected to Step 3 (Example (Compound 201)) to give the title compound as a white solid; $^1$H NMR (DMSO-d$_6$): δ 0.88 (6H, s), 1.19 (3H, s), 1.22 (9H, s), 1.28 (2H, t), 1.44-1.56 (2H, m), 2.42-2.49 (1H, m), 2.77 (1H, d), 2.87-2.98 (2H, m), 3.25-3.40 (3H, m), 3.65-3.73 (1H, m), 3.82 (7H, s), 4.95 (1H, d), 6.60 (1H, d), 7.03-7.23 (7H, m), 7.77 (2H, d); MS 621 (MH+).

Step 4:

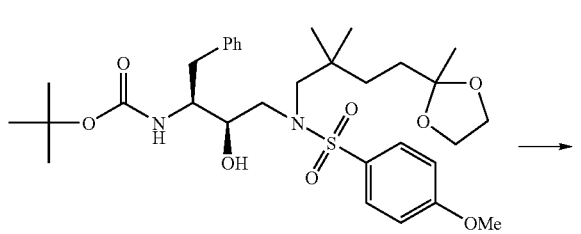

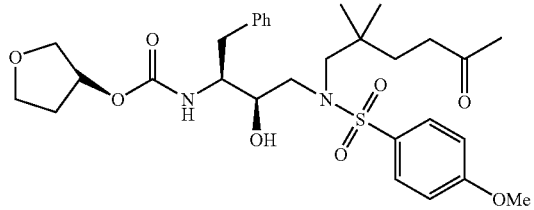

(3S)-Tetrahydro-3-furanylN-((1S,2R)-1-benzyl-3-(2-,2-dimethyl-5-oxohexyl)[(4-methoxyphenyl)sulfonyl]amino-2-hydroxypropyl)carbamate The product from Step 3 was subjected to the procedure used in Example (Compound 205) to provide the title compound as a white foam;

$^1$H NMR (DMSO-d$_6$): δ 0.87 (3H, s), 0.9 (3H, s), 1.47 (2H, t), 1.75 (1H, dt), 2.03-2.08 (1H, m), 2.1 (3H, s), 2.35-2.45 (3H, m), 2.75 (1H, dd), 2.85-2.95 (2H, m), 3.3-3.5 (3H, m), 3.57 (1H, dd), 3.64 (1H, dd), 3.66 (1H, dd), 3.70 (1H, dd), 3.75 (1H, dd), 3.82 (3H, s), 4.9 (1H, brt), 5.1 (1H, d), 7.08 (2H, d), 7.10-7.25 (6H, m), 7.7 (2H, d); MS: 591.1 (MH$^+$).

EXAMPLE (COMPOUND 209)

Step 1:

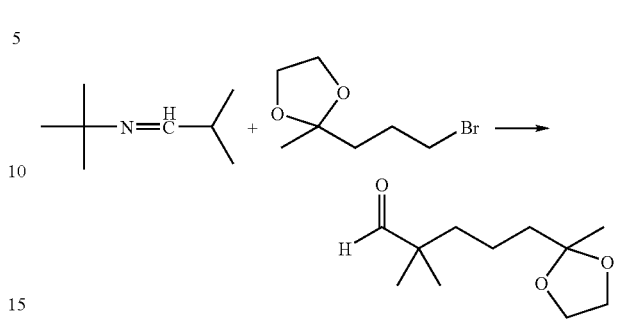

2,2-Dimethyl-5-(2-methyl-1,3-dioxolan-2-yl)pentanal

The title compound was prepared by procedure used in Example (Compound 202) using 2-(3-chloropropyl)-2-methyl-1,3-dioxolane as alkylating agent.

$^1$H NMR (CDCl$_3$): δ 1.05 (6H, s), 1.24-1.36 (5H, m), 1.44-1.50 (2H, m), 1.60-1.65 (2H, m), 3.88-3.98 (4H, m), 9.45 (1H, s)

Step 2:

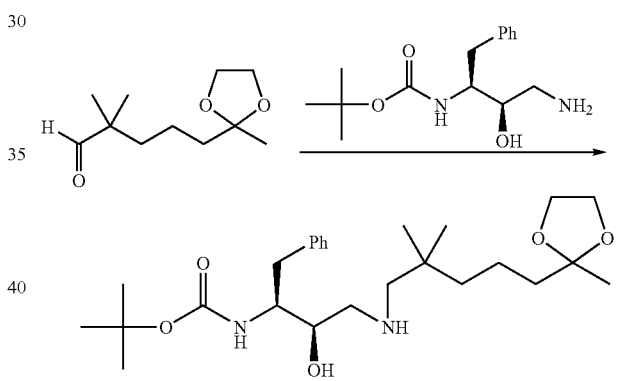

tert-Butyl N-((1S,2R)-1-benzyl-3-[2,2-dimethyl-5-(2-methyl-1,3-dioxolan-2-yl)pentyl]amino-2-hydroxypropyl) carbamate The product from step 1 was subjected to Step 2 (Example (Compound 201)) to provide the title compound as a thick oil; $^1$H NMR (DMSO-d$_6$): δ 0.80 (6H, s), 1.10-1.30 (16H, m), 1.42 (1H, brs), 1.45-1.52 (2H, m), 2.22 (2H, s), 2.47-2.60 (3H, m), 2.95 (1H, dd), 3.37-3.57 (2H, m), 3.75-3.85 (4H, m), 4.76 (1H, br s), 6.75 (1H, dd), 7.08-7.26 (5H, m); MS: 465 (MH$^+$)

Step 3:

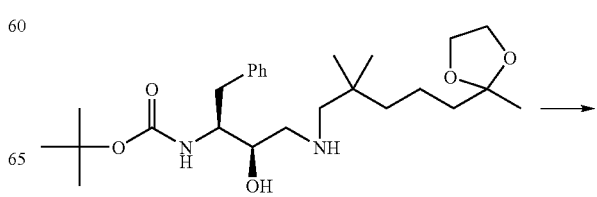

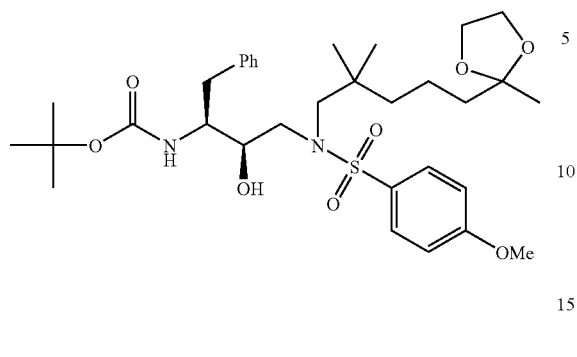

The product from the previous step was subjected to Step 3 (Example (Compound 201)) to afford the title compound as a white solid;

$^1$H NMR (DMSO-d$_6$): δ 0.88 (6H, s), 1.14-1.30 (16H, m), 1.44-1.51 (2H, m), 2.42-2.48 (1H, m), 2.77 (1H, d), 2.87-2.98 (2H, m), 3.25-3.40 (3H, m), 3.65-3.75 (1H, m), 3.75-3.85 (7H, m), 4.96 (1H, d), 6.60 (1H, dd), 7.04-7.24 (7H, m), 7.72 (2H, d); MS: 635 (MH$^+$).

Step 4:

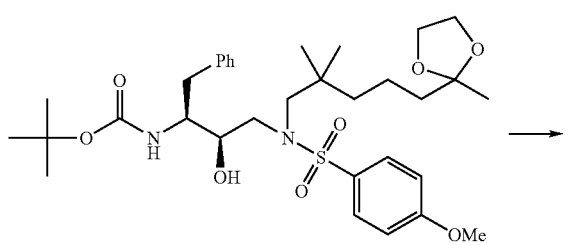

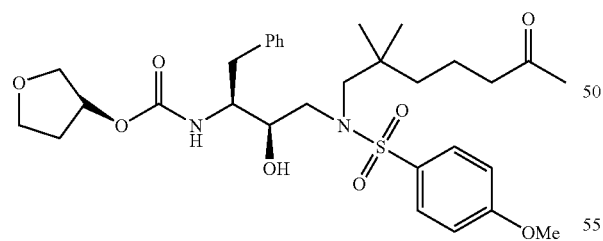

The product from the previous step was subjected to the Step used in Example (Compound 205) to give the title compound as a thick oil;

$^1$H NMR (DMSO-d$_6$): δ 0.89 (3H, s), 1.15 (2H, dd), 1.3-1.5 (2H, m), 1.75 (1H, dd), 1.95-2.05 (1H, m), 2.08 (3H, s), 2.35 (2H, t), 2.4-2.5 (1H, m), 2.75 (1H, d), 2.93 (2H, brd), 3.30-3.45 (4H, m), 3.6 (1H, dd), 3.63 (1H, dd), 3.7 (1H, d), 3.72-3.77 (1H, m), 3.81 (3H, s), 4.9 (1H, brt), 5.0 (1H, d), 7.08 (2H, d), 7.10-7.25 (6H, m), 7.7 (2H, d); MS: 604.9 (MH$^+$)

EXAMPLE (COMPOUND 210)

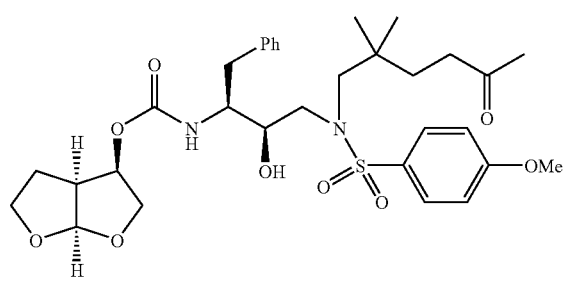

(3R,3aS,6aR)-Hexahydrofuro[2,3-b]furan-3-yl N-((1S,2R)-1-benzyl-3-(2,2-dimethyl-5-oxohexyl) [(4-methoxyphenyl) sulfonyl]amino-2-hydroxypropyl)carbamate The product from Step 3 (Example (Compound 208)) was subjected to a procedure similar to that of Example (Compound 205) (except for the use of (3R,3aS,6aR)-Hexahydrofuro[2,3-b]furan-3-yl-p-nitrophenyl carbonate in the acylation step) to give the title compound as a foam;

$^1$H NMR (DMSO-d$_6$): δ 0.82 (3H, s), 0.86 (3H, s), 1.2 (1H, dd), 1.3-1.4 (1H, m), 1.43 (2H, t), 2.04 (3H, s), 2.3-2.5 (3H, m), 2.65-2.80 (2H, m), 2.89 (1H, dd), 2.92 (1H, dd), 3.3-3.4 (3H, m), 3.42-3.50 (1H, m), 3.57 (2H, dd), 3.73 (2H, dd), 3.9 (3H, s), 4.8 (1H, quartet), 5.1 (1H, d), 5.48 (1H, d), 7.05 (2H, d), 7.10-7.25 (6H, m), 7.7 (2H, d); MS: 633 (MH$^+$)

EXAMPLE (COMPOUND 211)

Step 1:

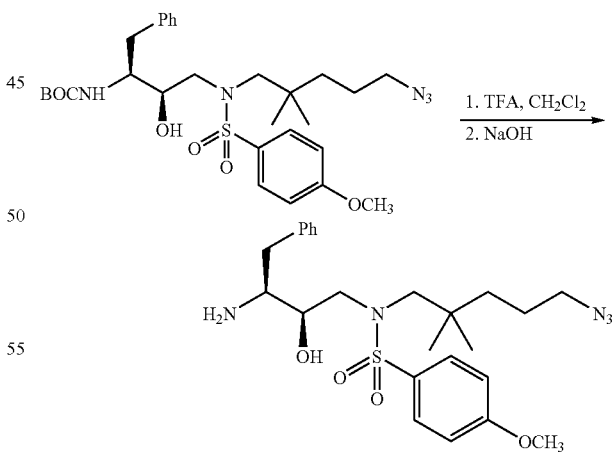

N-[(2R,3S)-3-amino-2-hydroxy-4-phenylbutyl]-N-(5-azido-2,2-dimethylpentyl)-4-methoxybenzene-sulfonamide A solution of 0.49 g (1.7 mmol) of tert-butyl N-((1S,2R)-3-(5-azido-2,2-dimethylpentyl)[(4-methoxyphenyl)sulfonyl]amino-1-benzyl-2-hydroxypropyl)carbamate (Example (Compound 203)) in 10 mL of CH$_2$Cl$_2$ was treated with 10 mL of TFA and the solution was stirred at RT. After 3 hours the solution was concentrated in vacuo. The residue was dissolved in CH$_2$Cl$_2$. The solution was washed with 1M aqueous NaOH (1×), water (2×), dried over MgSO$_4$, and concentrated in vacuo. The crude material was subjected to flash chromatography (SiO$_2$, 97:3 CH$_2$Cl$_2$/2M NH$_3$ in MeOH) to afford 0.32 g of the desired compound as white foam.

$^1$H NMR (DMSO-d$_6$): δ 7.66 (2H), 7.22 (2H), 7.15 (3H), 7.03 (2H), 4.64 (1H), 3.79 (3H), 3.62-3.20 (5H), 3.03 (1H), 2.85 (1H), 2.74-2.60 (2H), 2.27 (1H), 1.48 (2H), 1.23 (2H), 1.10 (2H), 0.84 (6H). MS (ESI): 490 (M+H).

Step 2:

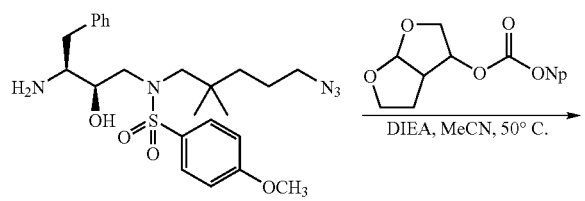

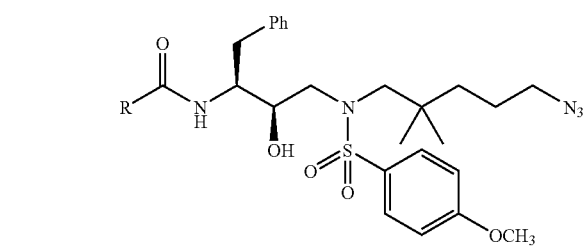

(3R,3aS,6aR)hexahydrofuro[2,3-b]furan-3-yl N-((1S,2R)-3-(5-azido-2,2-dimethylpentyl)[(4-methoxyphenyl)sulfonyl]amino-1-benzyl-2-hydroxypropyl)carbamate and (3S,3aR,6aS)hexahydrofuro[2,3-b]furan-3-yl N-((1S,2R)-3-(5-azido-2,2-dimethylpentyl)[(4-methoxyphenyl)sulfonyl]amino-1-benzyl-2-hydroxypropyl)carbamate A solution of 0.31 g (0.63 mmol) of N-[(2R,3S)-3-amino-2-hydroxy-4-phenylbutyl]-N-(5-azido-2,2-dimethylpentyl)-4-methoxybenzenesulfonamide (step 1), 0.20 g (0.67 mmol) of a 1:1 mixture of (3R,3aS,6aR) hexahydrofuro[2,3-b]furan-3-yl (4-nitrophenyl)carbonate and (3S,3aR,6aS)hexahydrofuro[2,3-b]furan-3-yl (4-nitrophenyl)carbonate, and 0.18 mL of N,N-diisopropylethylamine in 10 mL of acetonitrile was stirred at 50° C. under nitrogen. After 24 hours the solution was cooled to RT and concentrated in vacuo. The residue was dissolved in CH$_2$Cl$_2$. The solution was washed with 0.2M aqueous NaOH (4×), water (2×), dried over MgSO$_4$, and concentrated to dryness. The crude product was subjected to flash chromatography (SiO$_2$, 1:1 hexane/EtOAc) to afford 0.27 g (66%) of the desired product as a white foam.

$^1$H NMR (CDCl$_3$): δ 7.70 (2H), 7.32-7.11 (5H), 7.00 (2H), 5.62 (1H), 4.97 (2H), 4.18-3.97 (2H), 3.96-3.72 (6H), 3.70-3.42 (2H), 3.30-3.01 (4H), 3.00-2.63 (4H), 1.99-1.72 (1H), 1.53 (2H), 1.41-1.15 (3H), 0.90 (6H). LCMS (ESI): 646 (M+H).

EXAMPLE (COMPOUND 212)

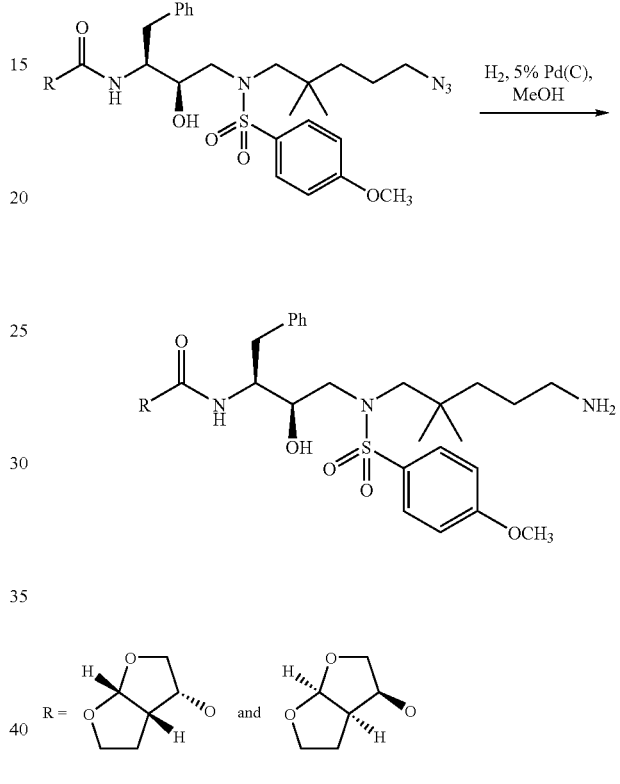

(3R,3aS,6aR)hexahydrofuro[2,3-b]furan-3-yl N-((1S,2R)-3-(5-amino-2,2-dimethylpentyl)[(4-methoxyphenyl)sulfonyl]amino-1-benzyl-2-hydroxypropyl)carbamate and (3S,3aR,6aS)hexahydrofuro [2,3-b]furan-3-yl N-((1S,2R)-3-(5-amino-2,2-dimethylpentyl) [(4-methoxyphenyl)sulfonyl]amino-1-benzyl-2-hydroxypropyl)carbamate A solution of 0.25 g (0.39 mmol) of a 1:1 mixture of (3R,3aS,6aR)hexahydrofuro[2,3-b]furan-3-yl N-((1S,2R)-3-(5-azido-2,2-dimethylpentyl)[(4-methoxyphenyl)sulfonyl] amino-1-benzyl-2-hydroxypropyl)carbamate and (3S,3aR,6aS)hexahydrofuro[2,3-b]furan-3-yl N-((1S,2R)-3-(5-azido-2,2-dimethylpentyl) [(4-methoxyphenyl)sulfonyl] amino-1-benzyl-2-hydroxypropyl)carbamate (Example (Compound 211)) in 40 mL of MeOH under nitrogen was treated with 50 mg of 5% Pd(C). The resulting mixture was subjected to hydrogenation at 30 psi. After 2 hours the vessel was purged with nitrogen, catalyst removed by filtration through celite and the filtrate concentrated in vacuo to afford 0.23 g (96%) of the desired product as a light yellow foam.

¹H NMR (CDCl₃): δ 7.75 (2H), 7.38-7.12 (5H), 7.03 (2H), 5.65 (1H), 5.02 (1H), 4.13-3.44 (8H), 3.38-2.55 (10H), 2.02-1.08 (6H), 1.07-0.83 (6H). LCMS (ESI): 620 (M+H).

EXAMPLE (COMPOUND 213)

¹H NMR (CDCl₃): δ 7.70 (2H), 7.29-7.12 (5H), 6.99 (2H), 5.61 (1H), 5.46-5.21 (1H), 5.10-4.88 (2H), 4.20-3.42 (12H), 3.23-2.61 (9H), 1.99-1.13 (6H), 0.91 (3H), 0.83 (3H). LCMS (ESI): 678 (M+H).

EXAMPLE (COMPOUND 214)

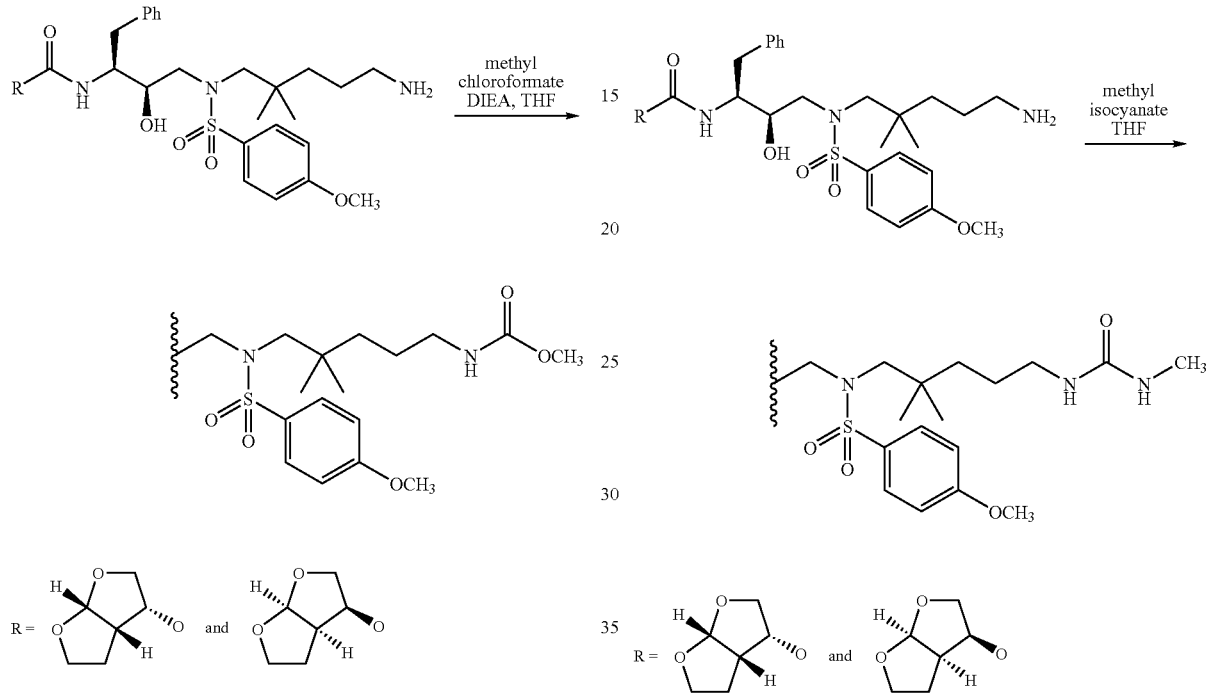

(3R,3aS,6aR)hexahydrofuro[2,3-b]furan-3-yl N-((1S,2R)-1-benzyl-2-hydroxy-3-5-[(methoxycarbonyl)amino]-2,2-dimethylpentyl[(4-methoxyphenyl)sulfonyl]aminopropyl)carbamate and (3S,3aR,6aS)hexahydrofuro[2,3-b]furan-3-yl N-((1S,2R)-1-benzyl-2-hydroxy-3-5-[(methoxycarbonyl)amino]-2,2-dimethylpentyl[(4-methoxyphenyl)sulfonyl]aminopropyl)carbamate A solution of 20 mg (0.032 mmol) of a 1:1 mixture of (3R,3aS,6aR)hexahydrofuro[2,3-b]furan-3-yl N-((1S,2R)-3-(5-amino-2,2-dimethylpentyl) [(4-methoxyphenyl)sulfonyl]amino-1-benzyl-2-hydroxypropyl)carbamate and (3S,3aR,6aS)hexahydrofuro[2,3-b]furan-3-yl N-((1S,2R)-3-(5-amino-2,2-dimethylpentyl) [(4-methoxyphenyl)sulfonyl]amino-1-benzyl-2-hydroxypropyl)carbamate (Example (Compound 212)) in 1.5 mL of anhydrous THF at 0° C. was treated with 6.3 μL (0.036 mmol) of N,N-diisopropylethylamine followed by 2.8 μL (0.036 mmol) of methyl chloroformate. The resulting solution was allowed to warm to RT with stirring. After 2.5 hours the solution was concentrated in vacuo and the residue subjected to flash chromatography (SiO₂, 97:3 CH₂Cl₂/MeOH) to afford 16 mg (74%) of the desired product as a white foam.

(3R,3aS,6aR)hexahydrofuro[2,3-b]furan-3-yl N-((1S,2R)-1-benzyl-3-(2,2-dimethyl-5-[(methylamino)carbonyl]aminopentyl)[(4-methoxyphenyl)sulfonyl]amino-2-hydroxypropyl)carbamate and (3S,3aR,6aS)hexahydrofuro[2,3-b]furan-3-yl N-((1S,2R)-1-benzyl-3-(2,2-dimethyl-5-[(methylamino)carbonyl]aminopentyl)[(4-methoxyphenyl)sulfonyl]amino-2-hydroxypropyl)carbamate A solution of 20 mg (0.032 mmol) of a 1:1 mixture of (3R,3aS,6aR)hexahydrofuro[2,3-b]furan-3-yl N-((1S,2R)-3-(5-amino-2,2-dimethylpentyl)[(4-methoxyphenyl)sulfonyl]amino-1-benzyl-2-hydroxypropyl)carbamate and (3S,3aR,6aS)hexahydrofuro[2,3-b]furan-3-yl N-((1S,2R)-3-(5-amino-2,2-dimethylpentyl) [(4-methoxyphenyl)sulfonyl]amino-1-benzyl-2-hydroxypropyl)carbamate (Example (Compound 212)) in 1.5 mL of anhydrous THF at 0° C. was treated with 2.0 μL (0.032 mmol) of methyl isocyanate. The resulting solution was allowed to warm to RT with stirring. After 2.5 hours the solution was concentrated in vacuo and the residue subjected to flash chromatography (SiO₂, 95:5 CH₂Cl₂/MeOH) to afford 15 mg (69%) of the desired product as a white foam.

¹H NMR (CDCl₃): δ 7.70 (2H), 7.30-7.10 (5H), 7.00 (2H), 5.83-5.48 (2H), 5.10-4.50 (2H), 4.30-3.43 (10H), 3.30-2.62 (12H), 2.10-1.18 (6H), 0.93 (3H), 0.84 (3H). LCMS(ESI): 677 (M+H).

EXAMPLE (COMPOUND 215)

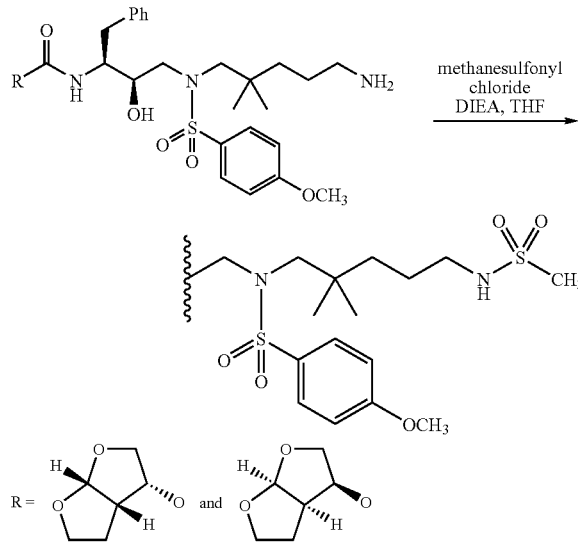

(3R,3aS,6aR)hexahydrofuro[2,3-b]furan-3-yl N-((1S,2R)-1-benzyl-3-2,2-dimethyl-5-[(methylsulfonyl)amino]pentyl[(4-methoxyphenyl)sulfonyl]amino-2-hydroxypropyl)carbamate and (3S,3aR,6aS)hexahydrofuro[2,3-b]furan-3-yl N-((1S,2R)-1-benzyl-3-2,2-dimethyl-5-[(methylsulfonyl) amino]pentyl[(4-methoxyphenyl)sulfonyl]amino-2-hydroxypropyl)carbamate A solution of 20 mg (0.032 mmol) of a 1:1 mixture of (3R,3aS,6aR)hexahydrofuro[2,3-b]furan-3-yl N-((1S,2R)-3-(5-amino-2,2-dimethylpentyl)[(4-methoxyphenyl)sulfonyl]amino-1-benzyl-2-hydroxypropyl)carbamate and (3S,3aR,6aS)hexahydrofuro[2,3-b]furan-3-yl N-((1S,2R)-3-(5-amino-2,2-dimethylpentyl)[(4-methoxyphenyl)sulfonyl]amino-1-benzyl-2-hydroxypropyl)carbamate (Example (Compound 212)) in 1.5 mL of anhydrous THF at 0° C. was treated with 6.0 μL (0.032 mmol) of N,N-diisopropylethylamine followed by 2.5 μL (0.032 mmol) of methanesulfonyl chloride. The resulting solution was allowed to warm to RT with stirring. After 2.5 hours the solution was concentrated in vacuo and the residue subjected to flash-chromatography (SiO₂, 97:3 CH₂Cl₂/MeOH) to afford 15 mg (68%) of the desired product as a white foam.

¹H NMR (CDCl₃): 7.69 (2H), 7.31-7.10 (5H), 7.00 (2H), 5.61 (1H), 5.18-5.02 (1H), 4.92 (2H), 4.07 (1H), 3.99-3.34 (8H), 3.21-2.63 (12H), 2.04-1.20 (6H), 0.93 (3H), 0.87 (3H). LCMS (ESI): 698 (M+H).

EXAMPLE (COMPOUND 216)

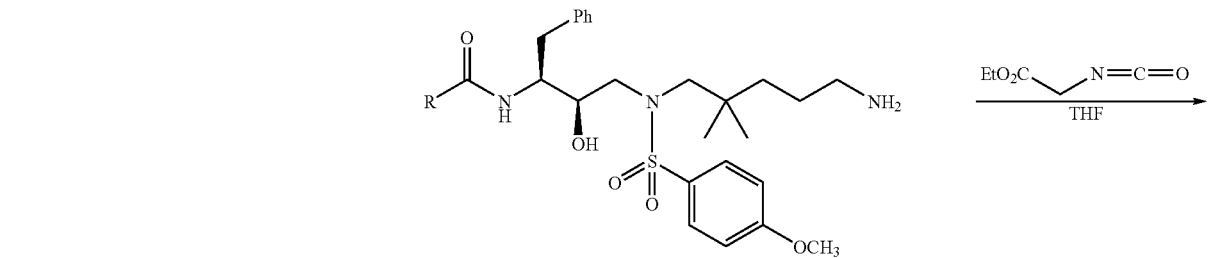

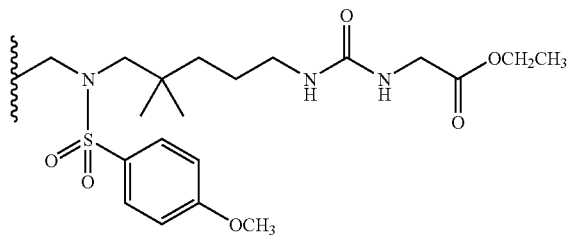

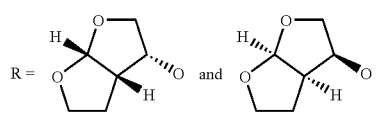

Ethyl (3S,4R)-1-[(3R,3aS,6aR)hexahydrofuro[2,3-b]furan-3-yloxy]-3-benzyl-4-hydroxy-6-[(4-methoxyphenyl)sulfonyl]-8,8-dimethyl-1,13-dioxo-2,6,12,14-tetraazahexadecan-16-oate and ethyl (3S,4R)-1-[(3S,3aR,6aS)hexahydrofuro[2,3-b]furan-3-yloxy]-3-benzyl-4-hydroxy-6-[(4-methoxyphenyl)sulfonyl]-8,8-dimethyl-1,13-dioxo-2,6,12,14-tetraazahexadecan-16-oate A solution of 33 mg (0.053 mmol) of a 1:1 mixture of (3R,3aS,6aR)hexahydrofuro[2,3-b]furan-3-yl N-((1S,2R)-3-(5-amino-2,2-dimethylpentyl)[(4-methoxyphenyl)sulfonyl]amino-1-benzyl-2-hydroxypropyl)carbamate and (3S,3aR,6aS)hexahydrofuro[2,3-b]furan-3-yl N-((1S,2R)-3-(5-amino-2,2-dimethylpentyl)[(4-methoxyphenyl)sulfonyl]amino-1-benzyl-2-hydroxypropyl)carbamate (Example (Compound 212)) in 1.5 mL of anhydrous THF was treated with 6.5 µL (0.058 mmol) of ethyl isocyanato acetate and the resulting solution was stirred at RT. After 18 hours the solution was concentrated in vacuo and the residue subjected to flash chromatography (SiO$_2$, 97:3 CH$_2$Cl$_2$/2M NH$_3$ in MeOH) to afford 31 mg (78%) of the desired compound as a white foam.

$^1$H NMR (CDCl$_3$): 7.76 (2H), 7.35-7.16 (5H), 7.04 (2H), 5.80-5.42 (2H), 5.02 (1H), 4.37-3.46 (13H), 3.40-2.63 (9H), 2.18-1.78 (2H), 1.70-1.22 (7H), 1.01 (3H), 0.92 (3H). LCMS (ESI): 749 (M+H).

EXAMPLE (COMPOUND 217)

Step 1:

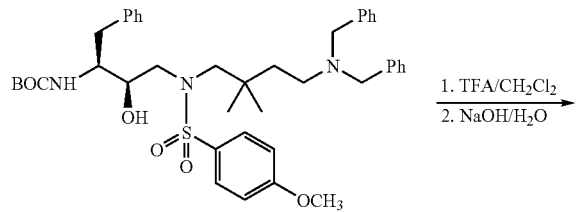

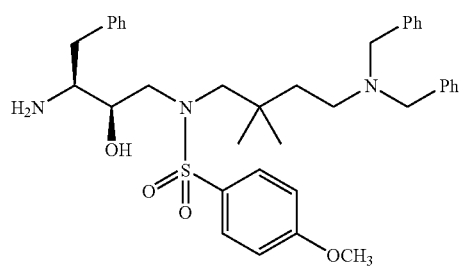

N-[(2R,3S)-3-amino-2-hydroxy-4-phenylbutyl]-N-[4-(dibenzylamino)-2,2-dimethylbutyl]-4-methoxy-benzenesulfonamide A solution of 1.00 g (1.37 mmol) of text-butyl N-((1S,2R)-1-benzyl-3-[4-(dibenzylamino)-2,2-dimethylbutyl][(4-methoxyphenyl)sulfonyl]amino-2-hydroxypropyl)carbamate in 40 mL of 1:1 CH$_2$Cl$_2$/TFA was stirred at RT for 2 hours. The solution was then concentrated to dryness and the residue dissolved in CH$_2$Cl$_2$. The resulting solution was washed with 1 M aqueous NaOH (1×), water (3×), dried over MgSO$_4$ and concentrated in vacuo to afford 0.81 g (94%) of the desired amine as a thick oil.

$^1$H NMR (CDCl$_3$): 7.76$^-$ (2H), 7.44-7.19 (15H), 7.01 (2H), 4.00 (1H), 3.92 (3H), 3.63 (4H), 3.34-2.88 (6H), 2.53 (3H), 1.64 (2H), 0.92 (6H).

Step 2:

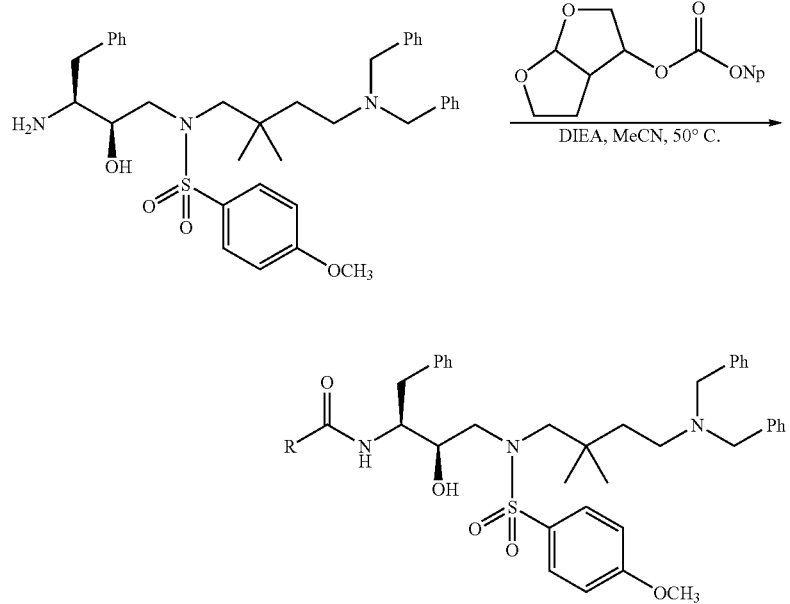

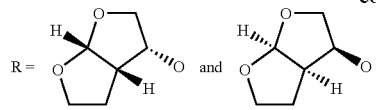
R =   and (3R,3aS,6aR)hexahydrofuro[2,3-b]furan-3-yl N-((1S,2R)-1-benzyl-3-[4-(dibenzylamino)-2,2-dimethylbutyl][(4-methoxyphenyl)sulfonyl]amino-2-hydroxypropyl)carbamate and (3S,3aR,6aS)hexahydrofuro[2,3-b]furan-3-yl N-((1S,2R)-1-benzyl-3-[4-(dibenzylamino)-2,2-dimethylbutyl][(4-methoxyphenyl)sulfonyl]amino-2-hydroxypropyl)carbamate A solution of 0.81 g (1.3 mmol) of N-[(2R,3S)-3-amino-2-hydroxy-4-phenylbutyl]-N-[4-(dibenzylamino)-2,2-dimethylbutyl]-4-methoxybenzenesulfonamide (step 1), 0.40 g (1.4 mmol) of a 1:1 mixture of (3R,3aS,6aR) hexahydrofuro [2,3-b]furan-3-yl (4-nitrophenyl)carbonate and (3S,3aR, 6aS)hexahydrofuro[2,3-b]furan-3-yl (4-nitrophenyl)carbonate, and 0.37 mL (2.1 mmol) of N,N-diisopropylethylamine in 20 mL of acetonitrile was stirred at 50° C. After 3.5 hours the solution was cooled to RT and concentrated to dryness. The residue was dissolved in CH$_2$Cl$_2$ and the solution washed with 1 M aqueous NaOH (4×), water (3×), dried over MgSO$_4$ and concentrated in vacuo. The crude product was subjected to flash chromatography (SiO$_2$, 1:1 hexane/EtOAc) to afford 0.85 g (84%) of the desired product as a white foam.

$^1$H NMR (CDCl$_3$): δ 7.71 (2H), 7.58-7.13 (15H), 7.01 (2H), 5.66 (1H), 5.07-4.60 (2H), 4.40-3.40 (12H), 3.27-2.63 (9H), 2.46 (1H), 2.20-1.45 (4H), 0.87 (6H). LCMS (ESI): 786 (M+H).

Step 3:

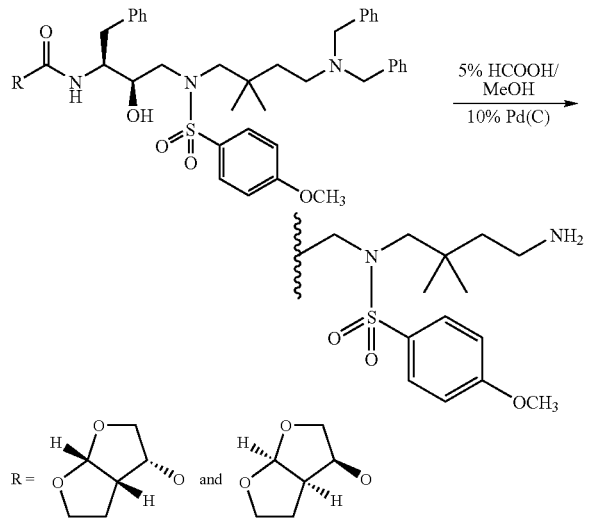

(3R,3aS,6aR)hexahydrofuro[2,3-b]furan-3-yl N-((1S,2R)-3-(4-amino-2,2-dimethylbutyl)[(4-methoxyphenyl)sulfonyl]amino-1-benzyl-2-hydroxypropyl)carbamate and (3S,3aR,6aS)hexahydrofuro[2,3-b]furan-3-yl N-((1S,2R)-3-(4-amino-2,2-dimethylbutyl)[(4-methoxyphenyl)sulfonyl]amino-1-benzyl-2-hydroxypropyl)carbamate A solution of 0.78 g (0.99 mmol) of a 1:1 mixture of (3R,3aS,6aR)hexahydrofuro[2,3-b]furan-3-yl N-((1S,2R)-1-benzyl-3-[4-(dibenzylamino)-2,2-dimethylbutyl][(4-methoxyphenyl)sulfonyl]amino-2-hydroxypropyl)carbamate and (3S,3aR,6aS)hexahydrofuro[2,3-b]furan-3-yl N-((1S,2R)-1-benzyl-3-[4-(dibenzylamino)-2,2-dimethylbutyl][(4-methoxyphenyl)sulfonyl]amino-2-hydroxypropyl)carbamate (Step 2) in 50 mL of 5% formic acid/MeOH under nitrogen was treated with 1.00 g of 10% Pd(C) and the resulting mixture was stirred at RT. After 18 hours the catalyst was removed by filtration through celite and the filtrate concentrated to dryness in vacuo. The residue was dissolved in CH$_2$Cl$_2$ and the solution was washed with 1M aqueous NaOH (1×), water (2×), dried over MgSO$_4$, and concentrated to dryness. The crude product was subjected to flash chromatography (SiO$_2$, 9:1 CH$_2$Cl$_2$/2M NH$_3$ in MeOH) to afford 0.45 g (75%) of the desired product as a white foam.

$^1$H NMR (CDCl$_3$): δ 7.70 (2H), 7.21 (5H), 6.99 (2H), 5.60 (1H), 5.00 (1H), 4.18-3.40 (8H), 3.30-2.63 (10H), 2.02-1.30 (4H), 1.01 (3H), 0.88 (3H). MS (ESI): 606 (M+H).

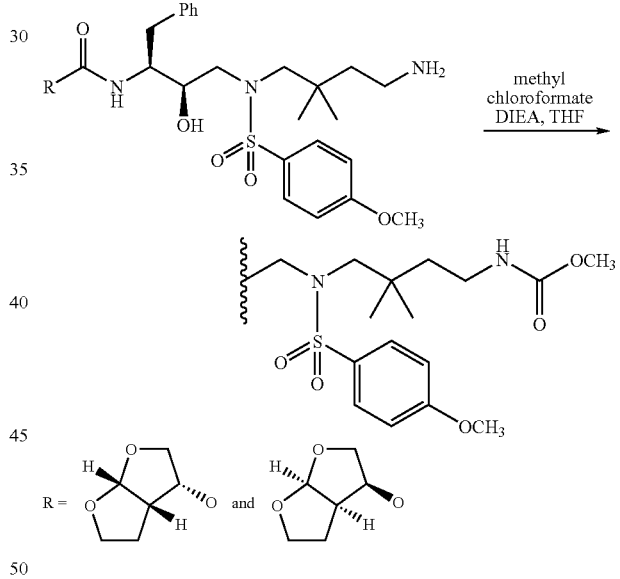

EXAMPLE (COMPOUND 218)

(3R,3aS,6aR)hexahydrofuro[2,3-b]furan-3-yl N-((1S,2R)-1-benzyl-2-hydroxy-3-4-[(methoxycarbonyl)amino]-2,2-dimethylbutyl[(4-methoxyphenyl)sulfonyl]aminopropyl)carbamate and (3S,3aR,6aS)hexahydrofuro[2,3-b]furan-3-yl N-((1S,2R)-1-benzyl-2-hydroxy-3-4-[(methoxycarbonyl)amino]-2,2-dimethylbutyl[(4-methoxyphenyl)sulfonyl]aminopropyl)carbamate A solution of 25 mg (0.041 mmol) of a 1:1 mixture of (3R,3aS,6aR)hexahydrofuro[2,3-b]furan-3-yl N-((1S,2R)-3-(4-amino-2,2-dimethylbutyl)[(4-methoxyphenyl)sulfonyl]amino-1-benzyl-2-hydroxypropyl)carbamate and (3S,3aR, 6aS)hexahydrofuro[2,3-b]furan-3-yl N-((1S,2R)-3-(4- amino-2,2-dimethylbutyl)  [(4-methoxyphenyl)sulfonyl] amino-1-benzyl-2-hydroxypropyl)carbamate (Example (Compound 217)) in 1.5 mL of anhydrous THF was cooled to 0° C. and was treated with 8.0 µL (0.045 mmol) of N,N-diisopropylethylamine followed by 3.5 µL (0.045 mmol) of methyl chloroformate. The solution was allowed to warm to RT with stirring. After 1.5 hours the solution was concentrated in vacuo and the residue was subjected to flash chromatography (SiO$_2$, 95:5 CH$_2$Cl$_2$/2M NH$_3$ in MeOH) to afford 18 mg (67%) of the desired product as a white foam.

$^1$H NMR (CDCl$_3$): 7.75 (2H), 7.37-7.18 (5H), 7.03 (2H), 5.65 (1H), 5.39-4.90 (3H), 4.20-3.50 (12H), 3.38-2.69 (9H), 2.18-1.39 (4H), 1.09 (3H), 0.95 (3H). MS (ESI): 664 (M+H).

EXAMPLE (COMPOUND 219)

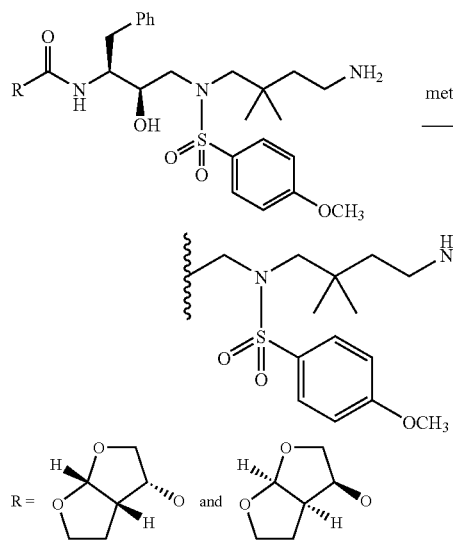

(3R,3aS,6aR)hexahydrofuro[2,3-b]furan-3-yl N-((1S,2R)-1-benzyl-3-(2,2-dimethyl-4-[(methylamino)carbonyl]aminobutyl)[(4-methoxyphenyl) sulfonyl]amino-2-hydroxypropyl)carbamate and (3S, 3aR,6aS)hexahydrofuro[2,3-b]furan-3-yl N-((1S, 2R)-1-benzyl-3-(2,2-dimethyl-4-[(methylamino) carbonyl]aminobutyl)[(4-methoxyphenyl)sulfonyl] amino-2-hydroxypropyl)carbamate A solution of 25 mg (0.041 mmol) of a 1:1 mixture of (3R,3aS,6aR)hexahydrofuro[2,3-b]furan-3-yl N-((1S,2R)-3-(4-amino-2,2-dimethylbutyl)[(4-methoxyphenyl)sulfonyl] amino-1-benzyl-2-hydroxypropyl)carbamate and (3S,3aR, 6aS)hexahydrofuro[2,3-b]furan-3-yl N-((1S,2R)-3-(4-amino-2,2-dimethylbutyl) [(4-methoxyphenyl)sulfonyl] amino-1-benzyl-2-hydroxypropyl)carbamate (Example (Compound 217)) in 1.5 mL of anhydrous THF was cooled to 0° C. and was treated with 2.5 µL (0.043 mmol) of methyl isocyanate. The resulting solution was allowed to warm to RT with stirring. After 2 hours the solution was concentrated in vacuo and the residue subjected to flash chromatography (SiO$_2$, 95:5 CH$_2$Cl$_2$/MeOH) to afford 16 mg (59%) of the desired product as a white foam.

$^1$H NMR (CDCl$_3$): δ 7.74 (2H), 7.37-7.14 (5H), 7.02 (2H), 5.75-5.50 (2H), 5.01 (1H), 4.19-3.49 (9H), 3.40-2.70 (12H), 2.18-1.23 (4H), 1.03 (3H), 0.97 (3H). MS (ESI): 663 (M+H).

EXAMPLE (COMPOUND 220)

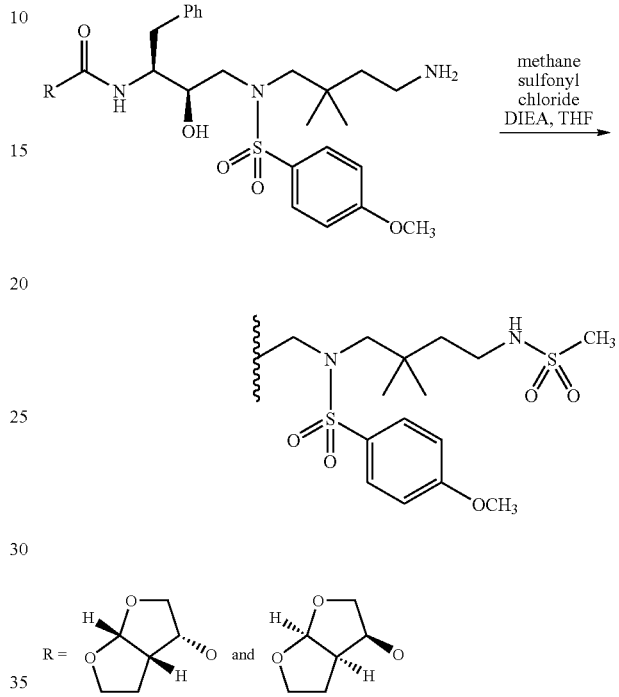

(3R,3aS,6aR)hexahydrofuro[2,3-b]furan-3-yl N-((1S,2R)-1-benzyl-3-2,2-dimethyl-4-[(methylsulfonyl)amino]butyl[(4-methoxyphenyl)sulfonyl] amino-2-hydroxypropyl)carbamate and (3S,3aR,6aS) hexahydrofuro[2,3-b]furan-3-yl N-((1S,2R)-1-benzyl-3-2,2-dimethyl-4-[(methylsulfonyl)amino] butyl[(4-methoxyphenyl)sulfonyl]amino-2-hydroxypropyl)carbamate A solution of 25 mg (0.041 mmol) of a 1:1 mixture of (3R,3aS,6aR)hexahydrofuro[2,3-b]furan-3-yl N-((1S,2R)-3-(4-amino-2,2-dimethylbutyl)[(4-methoxyphenyl)sulfonyl] amino-1-benzyl-2-hydroxypropyl)carbamate and (3S,3aR, 6aS)hexahydrofuro[2,3-b]furan-3-yl N-((1S,2R)-3-(4-amino-2,2-dimethylbutyl) [(4-methoxyphenyl)sulfonyl] amino-1-benzyl-2-hydroxypropyl)carbamate (Example (Compound 217)) in 1.5 mL of anhydrous THF was cooled to 0° C. and was treated with 7.0 µL (0.041 mmol) of N,N-diisopropylethylamine followed by 3.2 µL (0.041 mmol) of methane sulfonyl chloride. The solution was allowed to warm to RT with stirring. After 2 hours the solution was concentrated in vacuo and the residue was subjected to flash chromatography (SiO$_2$, 95:5 CH$_2$Cl$_2$/MeOH) to afford 20 mg (71%) of the desired product as a white foam.

$^1$H NMR (CDCl$_3$): δ 7.76 (2H), 7.38-7.19 (5H), 7.06 (2H), 5.67 (1H), 5.29-4.99 (3H), 4.31-3.54 (10H), 3.32-2.63 (11H), 2.10-1.37 (4H), 1.04 (3H), 0.99 (3H). MS (ESI): 684 (M+H).

EXAMPLE (COMPOUND 221)

Step 1:

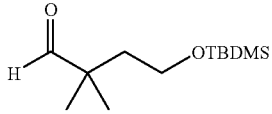

4-tert-Butyldimethylsilyloxy-2,2-dimethylbutanal

The title compound was prepared by a procedure similar to Example (Compound 202) using 2-tert-butyldimethyl silyloxybromoethane as alkylating agent.

$^1$H NMR (CDCl$_3$): δ −0.02 (6H, s), 0.84 (9H, s), 1.04 (6H, s), 1.74 (2H, t), 3.61 (2H, t), 9.43 (1H, s)

Step 2:

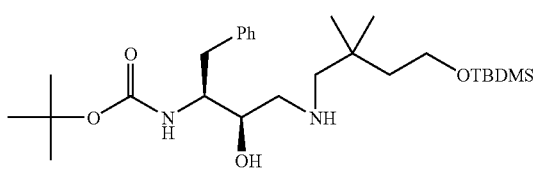

The product from Step 1 was subjected to Step 2 (Example (Compound 201)) to give the title compound as a foam;

$^1$H NMR (DMSO-d$_6$): δ 0.01 (6H, s), 0.82 (15H, s), 1.22 (9H, s), 1.42 (2H, t), 2.23 (2H, s), 2.43-2.60 (3H, m), 2.95 (1H, dd), 3.33-3.58 (2H, m), 3.60 (2H, t), 4.72 (1H, br s), 6.71 (1H, d), 7.07-7.25 (5H, m); MS: 495 (MH$^+$)

Step 3:

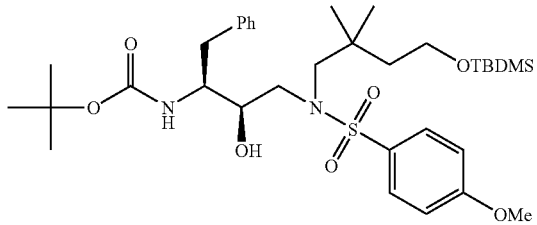

tert-Butyl N-((1S,2R)-1-benzyl-3-(4-tert-butyldimethylsilyloxy-2,2-dimethylbutyl) [(4-methoxyphenyl)sulfonyl]amino-2-hydroxypropyl)carbamate The product from Step 2 was subjected to Step 3 (Example (Compound 201)) to provide the title compound as a foam;

$^1$H NMR (DMSO-d$_6$): δ 0.00 (6H, s), 0.82 (9H, s), 0.93 (6H, s), 1.20 (9H, s), 1.48 (2H, t), 2.41-2.49 (1H, m), 2.74-2.96 (3H, m), 3.24-3.40 (3H, m), 3.63 (2H, t), 3.67-3.75 (1H, m), 3.81 (3H, s), 4.95 (1H, broad), 6.61 (1H, d), 7.04 (2H, d), 7.08-7.24 (2H, d), 7.71 (2H, d); MS: 665 (MH$^+$).

Step 4:

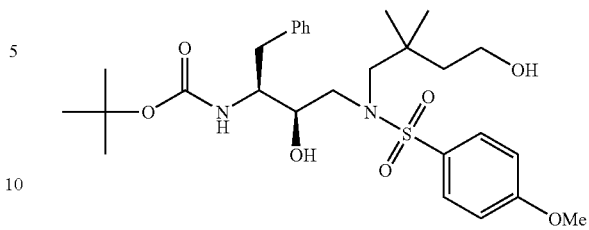

tert-Butyl N-((1S,2R)-1-benzyl-3-(2,2-dimethyl-4-hydroxybutyl)[(4-methoxyphenyl)sulfonyl]amino-2-hydroxypropyl)carbamate To a stirred solution of the product of Step 3 (3.47 g, 5.2 mmol) in tetrahydrofuran (25 mL) was added tetrabutylammonium fluoride (6.2 mL, 1M in tetrahydrofuran) over 15 minutes. After stirring at ambient temperature for 2 hours, the reaction was concentrated in vacuo and partitioned in ether/water (1:1; 200 mL). The layers were separated and the aqueous phase was extracted with ether (50 mL). The combined organic layers were washed with water (100 mL), dried (magnesium sulfate), concentrated in vacuo and purified by silica gel chromatography (4% methanol in chloroform) to afford the title compound (2.78 g, 97%) as a white foam.

$^1$H NMR (DMSO-d$_6$): δ 0.98 (6H, s), 1.27 (9H, s), 1.51 (2H, t), 2.46-2.57 (1H, m), 2.81-3.06 (3H, m), 3.32-3.55 (5H, m), 3.71-3.82 (1H, m), 3.87 (3H, s), 4.32 (1H, t), 5.01 (1H, d), 6.66 (1H, d), 7.12 (2H, d), 7.16-7.31 (5H, m), 7.77 (2H, d); MS: 551 (MH$^+$).

Step 5:

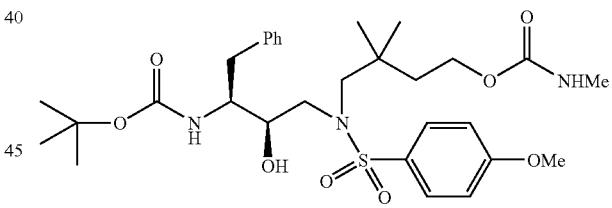

tert-Butyl N-((1S,2R)-1-benzyl-3-(2,2-dimethyl-4-N'-methylcarbamoyloxybutyl)[(4-methoxyphenyl)sulfonyl]amino-2-hydroxypropyl)carbamate To a solution of the product from Step 4 (500 mg, 0.9 mmol) in dichloromethane (4 mL) was added methylisocyanate (1.1 mL, 18.0 mmol). After stirring at ambient temperature for 48 hours, the reaction was concentrated in vacuo and purified by silica gel chromatography (40% ethyl acetate in hexane) to afford the title compound (460 mg, 83%) as a white foam.

$^1$H NMR (DMSO-d$_6$): δ 0.93 (3H, s), 0.96 (3H, s), 1.21 (9H, s), 1.58 (2H, t), 2.40-2.50 (1H, m), 2.54 (3H, d), 2.72-2.97 (3H, m), 3.24-3.42 (3H, m), 3.65-3.75 (1H, m), 3.82 (3H, s), 3.99 (2H, t), 4.99 (1H, d), 6.62 (1H, d), 6.88 (1H, q), 7.06 (2H, d), 7.10-7.24 (5H, m), 7.72 (2H, d); MS: 608 (MH$^+$).

Step 6:

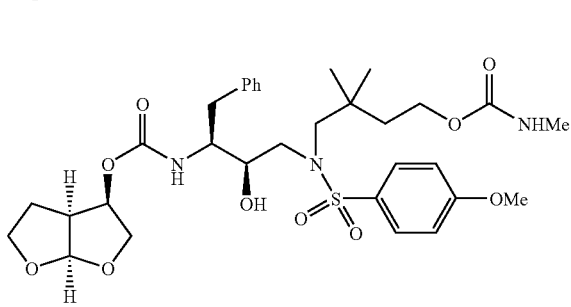

(3R,3aS,6aR)-Hexahydrofuro[2,3-b]furan-3-yl
N-((1S,2R)-benzyl-3-(2,2-dimethyl-4-N'-methylcar-
bamoyloxybutyl) [(4-methoxyphenyl)sulfonyl]
amino-2-hydroxypropyl)carbamate The product from step 5 was subjected to a protocol similar to that used in Example (Compound 210) to give the title compound as a foam.

$^1$H NMR (DMSO-d$_6$): δ 0.93 (1H, s), 0.94 (1H, s), 1.2 (1H, dd), 1.3-1.42 (1H, m), 1.6 (2H, t), 2.4 (1H, t), 2.55 (3H, d), 2.7-2.8 (2H, m), 2.83-3.00 (2H, m), 3.20-3.45 (3H, m), 3.55-3.62 (2H, m), 3.65-3.80 (3H, m), 3.82 (3H, s), 4.0 (2H, s), 4.8 (1H, quartet), 5.1 (1H, d), 5.5 (1H, d), 6.9 (1H, br s), 7.1 (2H, d), 7.15-7.25 (6H, m), 7.78 (2H, d); MS: 664 (MH$^+$)

EXAMPLE (COMPOUND 222)

Step 1:

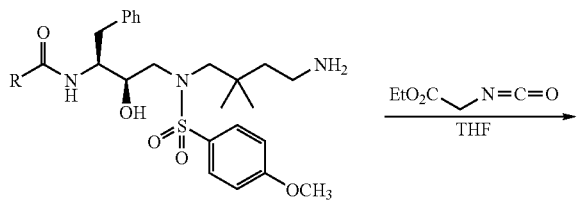

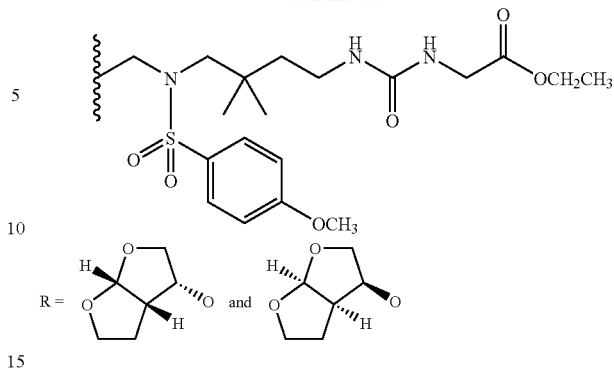

Ethyl (3S,4R)-1-[(3R,3aS,6aR)hexahydrofuro[2,3-b]
furan-3-yloxy]-3-benzyl-4-hydroxy-6-[(4-methox-
yphenyl)sulfonyl]-8,8-dimethyl-1,12-dioxo-2,6,11,
13-tetraazapentadecan-15-oate and ethyl (3S,4R)-1-
[(3S,3aR,6aS)hexahydrofuro[2,3-b]furan-3-yloxy]-3-
benzyl-4-hydroxy-6-[(4-methoxyphenyl)sulfonyl]-8,
8-dimethyl-1,12-dioxo-2,6,11,13-
tetraazapentadecan-15-oate A solution of 50 mg (0.083 mmol) of a 1:1 mixture of (3R,3aS,6aR)hexahydrofuro[2,3-b]furan-3-yl N-((1S,2R)-3-(4-amino-2,2-dimethylbutyl) [(4-methoxyphenyl)sulfonyl] amino-1-benzyl-2-hydroxypropyl)carbamate and (3S,3aR, 6aS)hexahydrofuro[2,3-b]furan-3-yl N-((1S,2R)-3-(4-amino-2,2-dimethylbutyl)[(4-methoxyphenyl)sulfonyl] amino-1-benzyl-2-hydroxypropyl)carbamate (Example (Compound 217)) in 3 mL of anhydrous THF was treated with 9.0 μL (0.087 mmol) of ethyl isocyanato acetate and the resulting solution stirred at RT. After 2.5 hours the solution was concentrated in vacuo and the residue subjected to flash chromatography (SiO$_2$, 95:5 CH$_2$Cl$_2$/2M NH$_3$ in MeOH) to afford 47 mg (77%) of the desired product as a white foam.

$^1$H NMR (CDCl$_3$): δ 7.70 (2H), 7.28-7.11 (5H), 7.00 (2H), 5.62 (1H), 5.47-5.30 (1H), 5.02 (1H), 4.24-3.46 (13H), 3.37-2.58 (9H), 2.04-1.39 (4H), 1.24 (3H), 1.03 (3H), 0.88 (3H). MS (ESI): 735 (M+H).

Step 2:

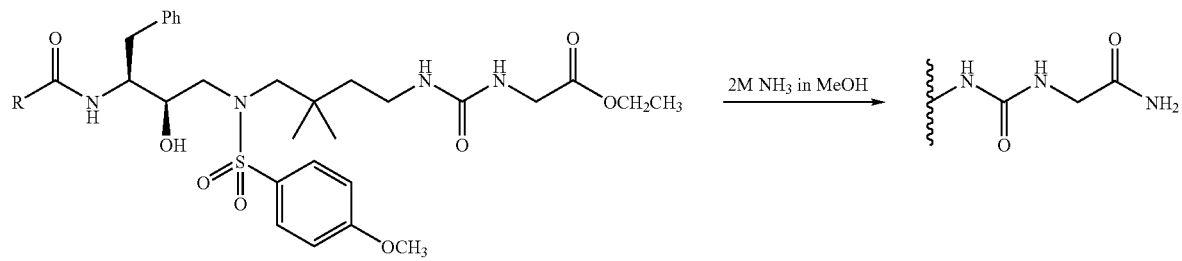

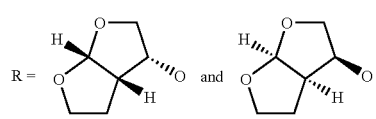

(3R,3aS,6aR)hexahydrofuro[2,3-b]furan-3-yl N-((1S,2R)-3-[4-([(2-amino-2-oxoethyl)amino]carbonylamino)-2,2-dimethylbutyl][(4-methoxyphenyl)sulfonyl]amino-1-benzyl-2-hydroxypropyl)carbamate and (3S,3aR,6aS)hexahydrofuro[2,3-b]furan-3-yl N-((1S,2R)-3-[4-([(2-amino-2-oxoethyl)amino]carbonylamino)-2,2-dimethylbutyl][(4-methoxyphenyl)sulfonyl]amino-1-benzyl-2-hydroxypropyl)carbamate A solution of 22 mg (0.030 mmol) of a 1:1 mixture of ethyl (3S,4R)-1-[(3R,3aS,6aR)hexahydrofuro[2,3-b]furan-3-yloxy]-3-benzyl-4-hydroxy-6-[(4-methoxyphenyl)sulfonyl]-8,8-dimethyl-1,12-dioxo-2,6,11,13-tetraazapentadecan-15-oate and ethyl (3S,4R)-1-[(3S,3aR,6aS)hexahydrofuro[2,3-b]furan-3-yloxy]-3-benzyl-4-hydroxy-6-[(4-methoxyphenyl)sulfonyl]-8,8-dimethyl-1,12-dioxo-2,6,11,13-tetraazapentadecan-15-oate in 3 mL of 2M $NH_3$ in MeOH in a sealed tube was stirred at RT. After 5 days the solution was concentrated in vacuo and the residue subjected to flash chromatography ($SiO_2$, 93:7 $CH_2Cl_2$/2M $NH_3$ in MeOH) to afford 11 mg (52%) of the desired product as a white foam.

$^1$H NMR ($CDCl_3$): δ 7.69 (2H), 7.28-7.10 (5H), 6.97 (2H), 6.82-6.50 (1H), 6.12-4.43 (6H), 4.05 (1H), 3.97-3.42 (10H), 3.33-2.61 (9H), 2.00-1.35 (4H), 1.00 (3H), 0.88 (3H). MS (ESI): 706 (M+H).

EXAMPLE (COMPOUND 224)

Step 1:

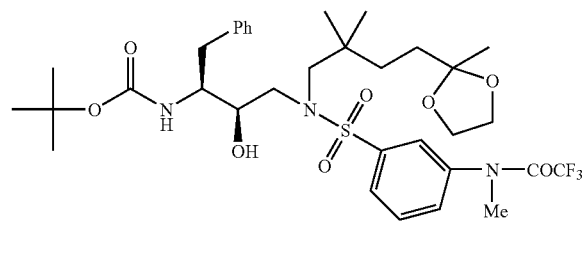

ter-Butyl N-((1S,2R)-1-benzyl-3-[2,2-dimethyl-4-(2-methyl-1,3-dioxolan-2-yl)butyl][(3-(N-methyl,N-trifluoroacetyl)aminophenyl)sulfonyl]amino-2-hydroxypropyl)carbamate The product from Step 3 (Example (Compound 208)) (0.44 g, 0.8 mmol), was dissolved, in dichloromethane (17 mL), and pyridine (1 mL, 0.97 g, 12.3 mmol) at 0° C. was added trifluoroacetic anhydride (0.45 mL, 0.67 g, 3.2 mmol) and the mixture was stirred at ambient temperature for 2 hours. The mixture was washed with saturated sodium bicarbonate, dried (sodium sulfate) and coevaporated with ethyl acetate (3×). The residue was dissolved in methanol (10 mL) and potassium carbonate (10 mg) was added. After stirring for 1 hour at ambient temperature, the solvent was evaporated and the residue was dissolved in acetone (15 mL) and potassium carbonate (0.26 g, 2 mmol) and methyl iodide (0.25 mL, 0.56 g, 4.0 mmol) were added. After 3 hours, the solvent was evaporated and the residue was partitioned between dichloromethane and water. The organic phase was dried (sodium sulfate), evaporated, dried.

$^1$H NMR (DMSO-$d_6$): δ 0.83 (6H, s), 1.2 (9H, s), 1.21-1.35 (2H, m), 1.5 (2H, br d), 2.40-2.48 (2H, m), 2.7-3.0 (3H, m), 3.05-3.15 (1H, m), 3.3-3.5 (8H, m), 3.65-3.75 (1H, m), 3.8 (3H, s), 4.9 (1H, d), 7.1-7.3 (6H, m), 7.6-7.8 (2H, m), 7.87 (1H, d), 7.95 (1H, s); MS: 738 (M+23).

Step 2:

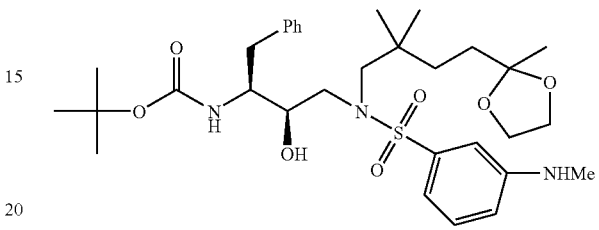

The product from Step 1 (0.16 g) was dissolved in 2M ammonia/ethanol (15 mL) and the mixture was stirred at ambient temperature for 2 hours. Solvent was evaporated ant the residue was partitioned between water and dichloromethane. The organic phase was dried (sodium sulfate) and evaporated to give the title compound as a foam.

$^1$H NMR ($CDCl_3$): δ 0.92 (3H, s), 0.96 (3H, s), 1.2-1.4 (11, m), 1.6 (2H, d), 2.7-2.9 (6H, m), 3.0-3.3 (4H, m), 3.7 (1H, br s), 3.9 (7H, br s), 4.2 (1H, br s), 4.83 (1H, d), 6.75 (1H, d), 6.95 (1H, s), 7.02 (1H, d), 7.1-7.3 (7H, m); MS: 620 (MH$^+$)

Step 3:

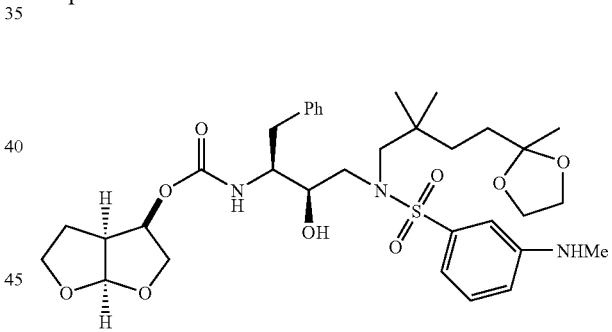

(3R,3aS,6aR)-Hexahydrofuro[2,3-b]furan-3-yl N-((1S,2R)-1-benzyl-3-(2,2-dimethyl-5-oxohexyl)[(3-methylaminophenyl)sulfonyl]amino-2-hydroxypropyl)carbamate The product from Step 2 was subjected to the procedure used in Example (Compound 210) to afford the title compound as a foam.

$^1$H NMR (DMSO-$d_6$): δ 0.9 (3H, s), 0.94 (3H, s), 1.17 (1H, dd), 1.3-1.4 (1H, m), 1.45 (2H, t), 2.06 (3H, s), 2.35-2.45 (3H, m), 2.7 (3H, d), 2.71-2.80 (2H, m)., 2.78 (1H, dd), 2.90 (1H, dd), 3.25-3.39 (3H, m), 3.4-3.5 (1H, m), 3.52-3.60 (2H, m), 3.7 (1H, t), 3.8 (2, dd), 4.8 (1H, quartet), 5.1 (1H, d), 5.5 (1H, d), 6.2 (1H, quartet), 6.75 (1H, d), 6.85 (1H, s), 6.86 (1H, d), 7.1-7.25 (6H, m); MS: 632 (MH$^+$).

EXAMPLE (COMPOUND 225)

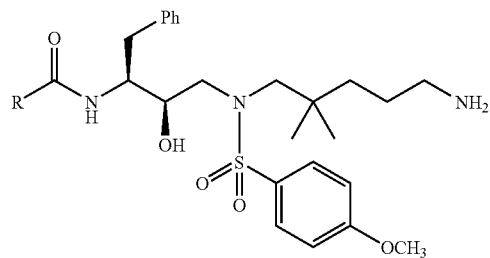 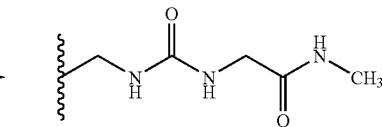

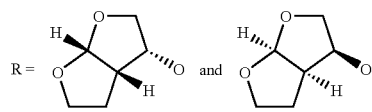

(3R,3aS,6aR)hexahydrofuro[2,3-b]furan-3-yl N-(1S, 2R)-1-benzyl-2-hydroxy-4-[(4-methoxyphenyl)sulfonyl]-6,6-dimethyl-11,14-dioxo-4,10,12,15-tetraazahexadec-1-ylcarbamate and (3S,3aR,6aS) hexahydrofuro[2,3-b]furan-3-yl N-(1S,2R)-1-benzyl-2-hydroxy-4-[(4-methoxyphenyl)sulfonyl]-6,6-dimethyl-11,14-dioxo-4,10,12,15-tetraazahexadec-1-ylcarbamate A solution of 39 mg (0.063 mmol) of a 1:1 mixture of (3R,3aS,6aR)hexahydrofuro[2,3-b]furan-3-yl N-((1S,2R)-3-(5-amino-2,2-dimethylpentyl)[(4-methoxyphenyl) sulfonyl] amino-1-benzyl-2-hydroxypropyl)carbamate and (3S,3aR, 6aS)hexahydrofuro[2,3-b]furan-3-yl N-((1S,2R)-3-(5-amino-2,2-dimethylpentyl)[(4-methoxyphenyl)sulfonyl] amino-1-benzyl-2-hydroxypropyl)carbamate (Example (Compound 212)) in 2 mL of anhydrous THF was treated with 7.4 μL (0.066 mmol) of ethyl isocyanato acetate and the resulting solution was stirred at RT. After 2.5 hours the solution was concentrated in vacuo. The residue was dissolved in 3 mL of 2M MeNH$_2$ in MeOH in a sealed tube and the solution was stirred at RT. After 18 hours the solution was concentrated in vacuo and the residue subjected to flash chromatography (SiO$_2$, 93:7 CH$_2$Cl$_2$/2M NH$_3$ in MeOH) to afford 25 mg (54%) of the desired product as a white foam.

$^1$H NMR (CDCl$_3$): δ 7.78 (2H), 7.33-7.15 (5H), 7.08-6.83 (3H), 6.30-4.80 (5H), 4.18-3.48 (11H), 3.38-2.62 (12H), 2.03-1.17 (6H), 0.98 (3H), 0.90 (3H). MS (ESI): 734 (M+H).

EXAMPLE (COMPOUND 226)

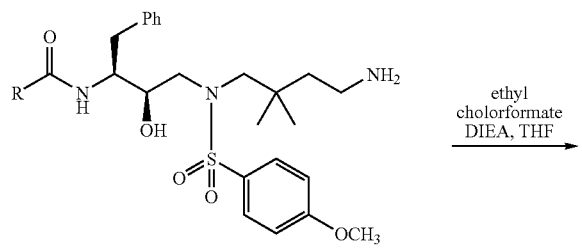 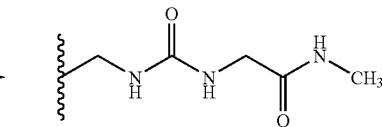

-continued

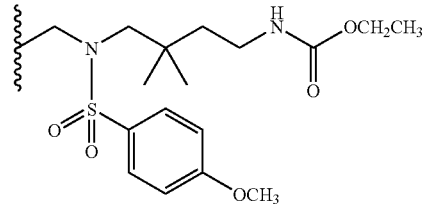

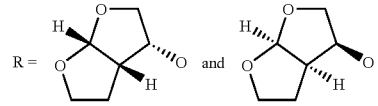

(3R,3aS,6aR)hexahydrofuro[2,3-b]furan-3-yl N-((1S,2R)-1-benzyl-3-4-[((ethoxycarbonyl)amino]-2,2-dimethylbutyl][(4-methoxyphenyl)sulfonyl] amino-2-hydroxypropyl)carbamate and (3S,3aR,6aS) hexahydrofuro[2,3-b]furan-3-yl N-((1S,2R)-1-benzyl-3-4-[(ethoxycarbonyl)amino]-2,2-dimethylbutyl [(4-methoxyphenyl)sulfonyl]amino-2-hydroxypropyl)carbamate A solution of 30 mg (0.050 mmol) of a 1:1 mixture of (3R,3aS,6aR)hexahydrofuro[2,3-b]furan-3-yl N-((1S,2R)-3-(4-amino-2,2-dimethylbutyl)[(4-methoxyphenyl)sulfonyl] amino-1-benzyl-2-hydroxypropyl)carbamate and (3S,3aR, 6aS)hexahydrofuro[2,3-b]furan-3-yl N-((1S,2R)-3-(4-amino-2,2-dimethylbutyl)[(4-methoxyphenyl)sulfonyl] amino-1-benzyl-2-hydroxypropyl)carbamate (Example (Compound 217)) in 2 mL of anhydrous THF was cooled to 0° C. and was treated with 9.6 μL (0.055 mmol) of N,N-diisopropylethylamine followed by 5.2 μL (0.055 mmol) of ethyl chloroformate. The solution was allowed to warm to RT with stirring. After 18 hours the solution was concentrated in vacuo and the residue was subjected to flash chromatography (SiO$_2$, 97:3 CH$_2$Cl$_2$/2M NH$_3$ in MeOH) to afford 31 mg (92%) of the desired product as a white foam.

¹H NMR (CDCl₃): 7.74 (2H), 7.35-7.16 (5H), 7.02 (2H), 5.68 (1H), 5.31 (1H), 5.18-4.90 (2H), 4.28-3.50 (11H), 3.35-2.70 (9H), 2.08-1.32 (4H), 1.27 (3H), 1.03 (3H), 0.98 (3H). MS (ESI): 678 (M+H).

EXAMPLE (COMPOUND 227)

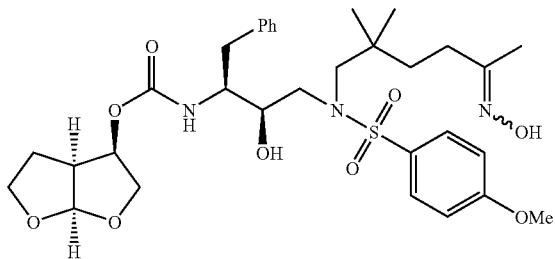

(3R,3aS,6aR)-Hexahydrofuro[2,3-b]furan-3-yl N-((1S,2R)-1-benzyl-3-(2,2-dimethyl-5-hydroxyiminohexyl)[(4-methoxyphenyl)sulfonyl]amino-2-hydroxypropyl)carbamate To a solution of the product from Example (Compound 210), (37 mg, 0.06 mmol) in pyridine (0.5 mL) and ethanol (0.5 mL) was added hydroxylamine hydrochloride (22 mg, 0.31 mmol) and the mixture was stirred at ambient temperature for 2 hours. Solvent was evaporated and the residue was dissolved in dichloromethane, washed with saturated sodium bicarbonate, dried (sodium sulfate), evaporated and chromatographed (silica gel, hexanes/ethyl acetate, 2:3) to provide the title compound as a foam; ¹H NMR (CDCl₃, signals for the major diastereomer): δ 0.85 (3H, s), 0.98 (3H, s), 1.3-1.7 (4H, m), 1.85 (3H, s), 2.1 (1H, dd), 2.58 (1H, d), 2.7-3.0 (4H, m), 3.1-3.3 (3H, m), 3.6-3.7 (3H, m), 3.8-4.0 (3H, m), 3.9 (3H, s), 4.05-4.15 (2H, m), 5.0 (1H, quartet), 5.6 (2H, d), 7.0 (2H, d), 7.15-7.25 (5H, m), 7.75 (2H, d); MS: 648 (MH⁺); C₃₂H₄₅N₃O₉S.

EXAMPLE (COMPOUND 228)

(3R,3aS,6aR)hexahydrofuro[2,3-b]furan-3-yl N-(1S,2R)-1-benzyl-2-hydroxy-4-[(4-methoxyphenyl)sulfonyl]-6,6-dimethyl-10,13-dioxo-4,9,11,14-tetraazapentadec-1-ylcarbamate and (3S,3aR,6aS) hexahydrofuro[2,3-b]furan-3-yl N-(1S,2R)-1-benzyl-2-hydroxy-4-[(4-methoxyphenyl)sulfonyl]-6,6-dimethyl-10,13-dioxo-4,9,11,14-tetraazapentadec-1-ylcarbamate A solution of 22 mg (0.030 mmol) of a 1:1 mixture of ethyl (3S,4R)-1-[(3R,3aS,6aR)hexahydrofuro[2,3-b]furan-3-yloxy]-3-benzyl-4-hydroxy-6-[(4-methoxyphenyl)sulfonyl]-8,8-dimethyl-1,12-dioxo-2,6,11,13-tetraazapentadecan-15-oate and ethyl (3S,4R)-1-[(3S,3aR,6aS) hexahydrofuro[2,3-b]furan-3-yloxy]-3-benzyl-4-hydroxy-6-[(4-methoxyphenyl)sulfonyl]-8,8-dimethyl-1,12-dioxo-2,6,11,13-tetraazapentadecan-15-oate in 3 mL of 2M methylamine in MeOH in a sealed tube was stirred at RT. After 18 hours the solution was concentrated in vacuo and the residue subjected to flash chromatography (SiO₂, 93:7 CH₂Cl₂/2M NH₃ in MeOH) to afford 13 mg (60%) of the desired product as a white foam.

¹H NMR (CDCl₃): 7.75 (2H), 7.37-7.13 (5H), 7.02 (2H), 6.90-6.61 (1H), 6.10-4.49 (5H), 4.15-3.50 (11H), 3.40-2.67 (12H), 2.10-1.20 (4H), 1.06 (3H), 0.93 (3H).

MS(ESI): 720(M+H)

EXAMPLE (COMPOUND 229)

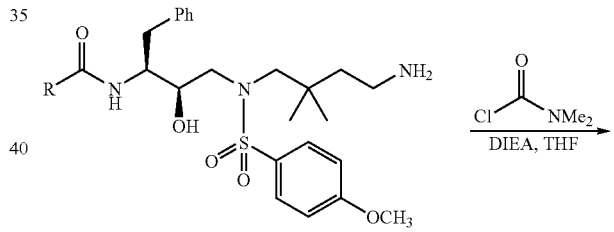

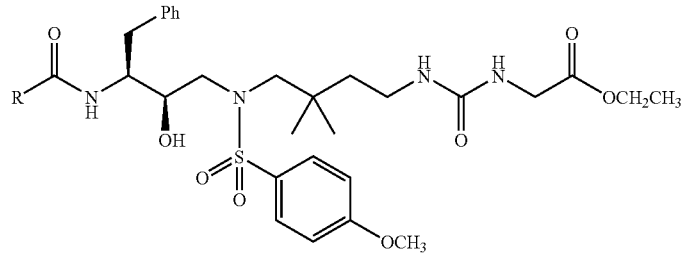

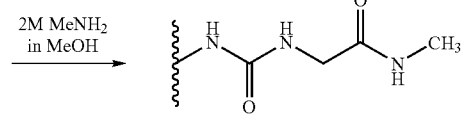

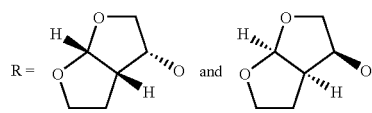

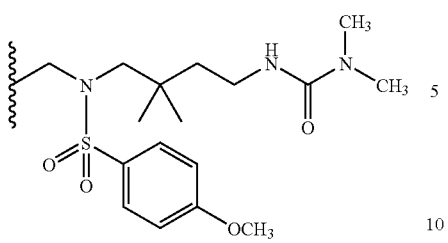

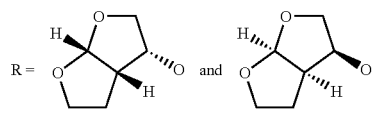

(3R,3aS,6aR)hexahydrofuro[2,3-b]furan-3-yl
N-((1S,2R)-1-benzyl-3-(4-[(dimethylamino)carbo-
nyl]amino-2,2-dimethylbutyl)[(4-methoxyphenyl)
sulfonyl]amino-2-hydroxypropyl)carbamate and (3S,
3aR,6aS)hexahydrofuro[2,3-b]furan-3-yl N-((1S,
2R)-1-benzyl-3-(4-[(dimethylamino)carbonyl]
amino-2,2-dimethylbutyl)[(4-methoxyphenyl)
sulfonyl]amino-2-hydroxypropyl)carbamate A solution of 30 mg (0.050 mmol) of a 1:1 mixture of (3R,3aS,6aR)hexahydrofuro[2,3-b]furan-3-yl N-((1S,2R)-3-(4-amino-2,2-dimethylbutyl)[(4-methoxyphenyl)sulfonyl]amino-1-benzyl-2-hydroxypropyl)carbamate and (3S,3aR,6aS)hexahydrofuro[2,3-b]furan-3-yl N-((1S,2R)-3-(4-amino-2,2-dimethylbutyl)[(4-methoxyphenyl)sulfonyl]amino-1-benzyl-2-hydroxypropyl)carbamate (Example (Compound 217)) in 2 mL of anhydrous THF was cooled to 0° C. and was treated with 9.6 µL (0.055 mmol) of N,N-diisopropylethylamine followed by 5.0 µL (0.053 mmol) of dimethylcarbamyl chloride. The solution was allowed to warm to RT with stirring. After 18 hours the solution was concentrated in vacuo and the residue was subjected to flash chromatography (SiO$_2$, 95:5 CH$_2$Cl$_2$/2M NH$_3$ in MeOH) to afford 30 mg (89%) of the desired product as a white foam.

$^1$H NMR (CDCl$_3$): 7.69 (2H), 7.29-7.10 (5H), 6.96 (2H), 5.80-5.52 (2H), 4.99-4.23 (2H), 3.99-3.43 (11H), 3.35-3.02 (5H), 3.01-2.62 (8H), 2.01-1.24 (4H), 1.01 (3H), 0.93 (3H). MS(ESI): 677(M+H).

EXAMPLE (COMPOUND 230)

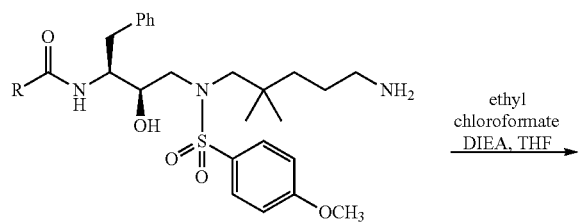

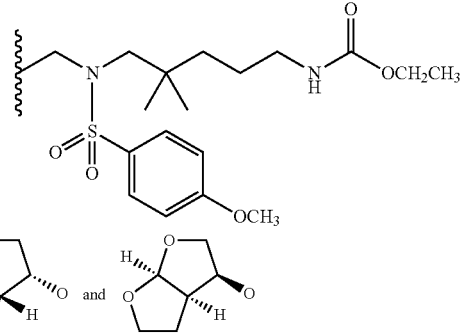

(3R,3aS,6aR)hexahydrofuro[2,3-b]furan-3-yl
N-((1S,2R)-1-benzyl-3-5-[(ethoxycarbonyl)amino]-
2,2-dimethylpentyl[(4-methoxyphenyl)sulfonyl]
amino-2-hydroxypropyl)carbamate and (3S,3aR,6aS)
hexahydrofuro[2,3-b]furan-3-yl N-((1S,2R)-1-
benzyl-3-5-[(ethoxycarbonyl)amino]-2,2-
dimethylpentyl[(4-methoxyphenyl)sulfonyl]amino-
2-hydroxypropyl)carbamate A solution of 30 mg (0.048 mmol) of a 1:1 mixture of (3R,3aS,6aR)hexahydrofuro[2,3-b]furan-3-yl N-((1S,2R)-3-(5-amino-2,2-dimethylpentyl)[(4-methoxyphenyl)sulfonyl]amino-1-benzyl-2-hydroxypropyl)carbamate and (3S,3aR,6aS)hexahydrofuro[2,3-b]furan-3-yl N-((1S,2R)-3-(5-amino-2,2-dimethylpentyl)[(4-methoxyphenyl)sulfonyl]amino-1-benzyl-2-hydroxypropyl)carbamate (Example (Compound 236)) in 2 mL of anhydrous THF at 0° C. was treated with 9.2 µL (0.053 mmol) of N,N-diisopropylethylamine followed by 5.0 µL (0.053 mmol) of ethyl chloroformate. The resulting solution was allowed to warm to RT with stirring. After 18 hours the solution was concentrated in vacuo and the residue subjected to flash chromatography (SiO$_2$, 97:3 CH$_2$Cl$_2$/2M NH$_3$ in MeOH) to afford 30 mg (94%) of the desired product as a white foam. H1-NMR (CDCl$_3$): 7.76 (2H), 7.37-7.18 (5H), 7.04 (2H), 5.67 (1H), 5.60-5.32 (1H), 5.01 (2H), 4.24-3.44 (11H), 3.30-2.70 (9H), 2.10-1.20 (9H), 0.96 (3H), 0.90 (3H). MS(ESI): 692(M+H).

EXAMPLE (COMPOUND 231)

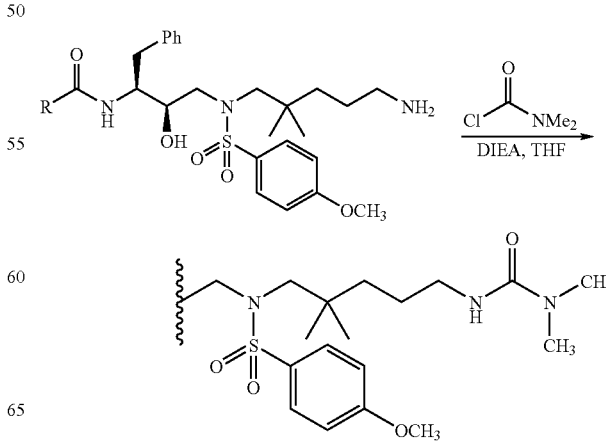

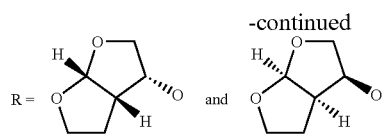

(3R,3aS,6aR)hexahydrofuro[2,3-b]furan-3-yl N-((1S,2R)-1-benzyl-3-(5-[(dimethylamino)carbonyl]amino-2,2-dimethylpentyl)[(4-methoxyphenyl)sulfonyl]amino-2-hydroxypropyl)carbamate and (3S,3aR,6aS)hexahydrofuro[2,3-b]furan-3-yl N-((1S,2R)-1-benzyl-3-(5-[(dimethylamino)carbonyl]amino-2,2-dimethylpentyl)[(4-methoxyphenyl)sulfonyl]amino-2-hydroxypropyl)carbamate A solution of 30 mg (0.048 mmol) of a 1:1 mixture of (3R,3aS,6aR)hexahydrofuro[2,3-b]furan-3-yl N-((1S,2R)-3-(5-amino-2,2-dimethylpentyl)[(4-methoxyphenyl)sulfonyl]amino-1-benzyl-2-hydroxypropyl)carbamate and (3S,3aR,6aS)hexahydrofuro[2,3-b]furan-3-yl N-((1S,2R)-3-(5-amino-2,2-dimethylpentyl)[(4-methoxyphenyl)sulfonyl]amino-1-benzyl-2-hydroxypropyl)carbamate (Example (Compound 212) in 2 mL of anhydrous THF at 0° C. was treated with 9.2 µL (0.053 mmol) of N,N-diisopropylethylamine followed by 4.6 µL (0.050 mmol) of dimethylcarbamyl chloride. The resulting solution was allowed to warm to RT with stirring. After 18 hours the solution was concentrated in vacuo and the residue subjected to flash chromatography (SiO$_2$, 95:5 CH$_2$Cl$_2$/2M NH$_3$ in MeOH) to afford 26 mg (79%) of the desired product as a white foam. H1-NMR (CDCl$_3$): 7.71 (2H), 7.29-7.09 (5H), 6.98 (2H), 6.08-5.72 (1H), 5.61 (1H), 4.92 (1H), 4.65 (1H), 4.24 (1H), 3.99-3.43 (8H), 3.28-2.63 (15H), 1.99-1.70 (1H), 1.54-1.18 (5H), 0.92 (3H), 0.84 (3H). MS(ESI): 691(M+H).

EXAMPLE (COMPOUND 232)

(3R,3aS,6aR)hexahydrofuro[2,3-b]furan-3-yl N-((1S,2R)-3-[5-([(2-amino-2-oxoethyl)amino]carbonylamino)-2,2-dimethylpentyl][(4-methoxyphenyl)sulfonyl]amino-1-benzyl-2-hydroxypropyl)carbamate and (3S,3aR,6aS)hexahydrofuro[2,3-b]furan-3-yl N-((1S,2R)-3-[5-([(2-amino-2-oxoethyl)amino]carbonylamino)-2,2-dimethylpentyl][(4-methoxyphenyl)sulfonyl]amino-1-benzyl-2-hydroxypropyl)carbamate A solution of 27 mg (0.036 mmol) of a 1:1 mixture of ethyl (3S,4R)-1-[(3R,3aS,6aR)hexahydrofuro[2,3-b]furan-3-yloxy]-3-benzyl-4-hydroxy-6-[(4-methoxyphenyl)sulfonyl]-8,8-dimethyl-1,13-dioxo-2,6,12,14-tetraazahexadecan-5.47 (2H), 5.00-4.74 (1H), 4.28-3.40 (12H), 3.28-2.42 (9H), 1.97-1.08 (6H), 0.89 (3H), 0.79 (3H). MS(ESI): 720(M+H) 16-oate and ethyl (3S,4R)-1-[(3S,3aR,6aS)hexahydrofuro[2,3-b]furan-3-yloxy]-3-benzyl-4-hydroxy-6-[(4-methoxyphenyl)sulfonyl]-8,8-dimethyl-1,13-dioxo-2,6,12,14-tetraazahexadecan-16-oate (Example (Compound 216)) in 6 mL of 2M NH$_3$ in MeOH in a sealed tube was stirred at RT. After 3 days the solution was concentrated in vacuo and the residue was subjected to flash chromatography (SiO$_2$, 93:7 CH$_2$Cl$_2$/2M NH$_3$ in MeOH) to afford 11 mg (43%) of the desired compound as a white foam. H1-NMR (CDCl$_3$): 7.64 (2H), 7.29-7.01 (5H), 6.99-6.63 (3H), 6.40-5.80 (2H), 5.74-

EXAMPLE (COMPOUND 233)

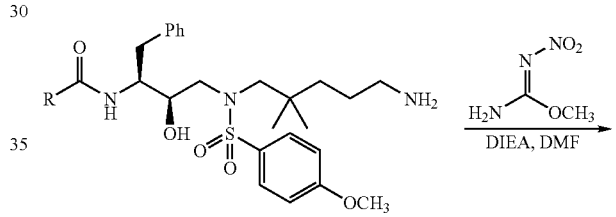

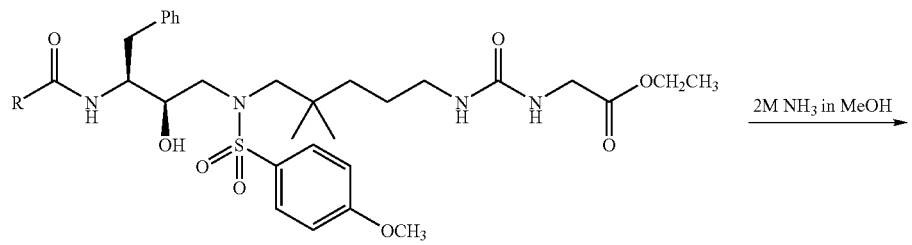

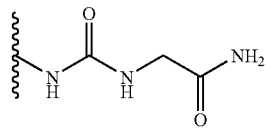

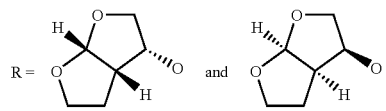

-continued

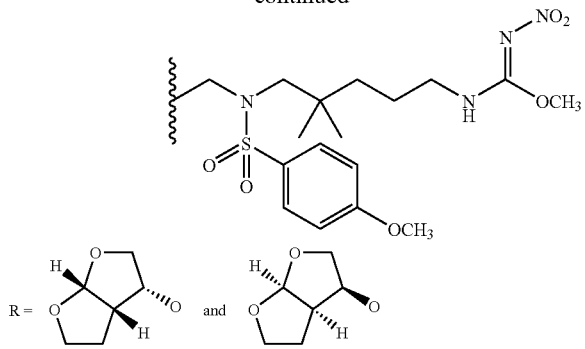

2-[(Z)-[(5-[(2R,3S)-3-([(3R,3aS,6aR)hexahydrofuro
[2,3-b]furan-3-yloxy]carbonylamino)-2-hydroxy-4-
phenylbutyl][(4-methoxyphenyl)sulfonyl]amino-4,4-
dimethylpentyl)amino](methoxy)methylidene]-1-
hydroxy-1-oxohydrazihium and 2-[(Z)-[(5-[(2R,3S)-
3-([(3S,3aR,6aS)hexahydrofuro[2,3-b]furan-3-yloxy]
carbonylamino)-2-hydroxy-4-phenylbutyl][(4-
methoxyphenyl)sulfonyl]amino-4,4-dimethylpentyl)
amino](methoxy)methylidene]-1-hydroxy-1-
oxohydrazinium A solution of 30 mg (0.048 mmol) of a 1:1 mixture of (3R,3aS,6aR)hexahydrofuro[2,3-b]furan-3-yl N-((1S,2R)-3-(5-amino-2,2-dimethylpentyl)[(4-methoxyphenyl)sulfonyl]amino-1-benzyl-2-hydroxypropyl)carbamate and (3S,3aR, 6aS)hexahydrofuro[2,3-b]furan-3-yl N-((1S,2R)-3-(5-amino-2,2-dimethylpentyl)[(4-methoxyphenyl)sulfonyl]amino-1-benzyl-2-hydroxypropyl)carbamate (Example (Compound 212)) in 1.5 mL of anhydrous DMF was treated with 10 μL (0.059 mmol) of N,N-diisopropylethylamine followed by 7.0 mg (0.059 mmol) of O-methyl-N-nitroisourea and the resulting solution was stirred at RT. After 20 hours the solution was concentrated in vacuo and the residue subjected to flash chromatography (SiO₂, 93:7 CH₂Cl₂/2M NH₃ in MeOH) to afford 19 mg (56%) of a white foam. H1-NMR (CDCl₃): 7.75 (2H), 7.37-7.13 (5H), 7.02 (2H), 5.75-5.23 (2H), 5.01 (1H), 4.20-3.48 (12H), 3.25-2.62 (9H), 2.10-1.75 (1H), 1.65-1.30 (5H), 0.98 (3H), 0.93 (3H).

EXAMPLE (COMPOUND 234)

Step 1:

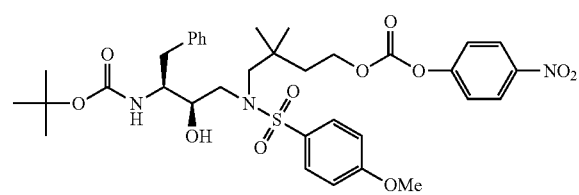

ter-Butyl N-((1S,2R)-1-benzyl-3-(2,2-dimethyl-4-
[(4-nitrophenyloxy)carbonyloxy]butyl)[(4-methox-
yphenyl)sulfonyl]amino-2-hydroxypropyl)carbamate To a solution of p-nitrophenyl chloroformate (320 mg, 1.6 mmol) in dichloromethane (8 mL) at 0° C. was added pyridine (2 mL) followed by a solution of the product from step 4, Example (Compound 221), (500 mg, 0.91 mmol) in dichloromethane (7 mL). The mixture was stirred at ambient temperature for 18 hours. The mixture was diluted with ethyl ether and washed with 0.5 N hydrochloric acid, saturated sodium bicarbonate, brine, dried (sodium sulfate), and evaporated. The residue was chromatographed (silica gel, hexanes/ethyl acetate, 7:3) to afford the title compound as a white foam (530 mg); ¹H NMR (DMSO-d₆): δ 0.97 (3H, s), 0.99 (3H, s), 1.2 (9H, s), 1.89 (2H, t), 2.40-2.46 (1H, m), 2.78 (1H, d), 2.88-3.00 (2H, m), 3.3-3.4 (3H, m), 3.75 (1H, br quartet), 3.8 (3H, s), 4.38 (2H, t), 5.05 (1H, d), 6.65 (1H, d), 7.06 (2H, d), 7.10-7.22 (5H, m), 7.55 (2H, d), 7.75 (2H, d), 8.3 (2H, d)

Step 2:

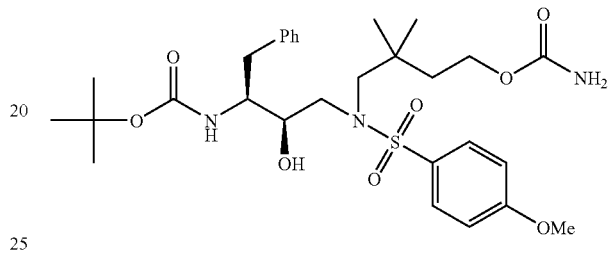

ter-Butyl N-((1S,2R)-1-benzyl-3-(4-carbamoyloxy-2,
2-dimethylbutyl)[(4-methoxyphenyl)sulfonyl]
amino-2-hydroxypropyl)carbamate To a solution of the product from step 1 (520 mg, 0.73 mmol) in tetrahydrofuran (10 mL) at 5° C. was added ammonium hydroxyde (30%, 2 mL) and the reaction was stirred at 5° C. for 40 minutes. The mixture was diluted with ethyl ether, washed with saturated sodium bicarbonate, dried (magnesium sulfate), and evaporated to provide the title compound (490 mg) containing p-nitrophenol (~10%). ¹H NMR (DMSO-d₆): δ 0.93 (3H, s), 0.96 (3H, s), 1.2 (9H, s), 1.6 (2H, t), 2.45 (1H, dd), 2.78 (1H, d), 2.85-2.95 (2H, m), 3.3-3.6 (3H, m), 3.7 (1H, quartet), 3.8 (3H, s), 3.96 (2H, t), 5.0 (1H, d), 6.4 (2H, br s), 6.6 (1H, d), 7.05 (2H, d), 7.10-7.25 (5H, m), 7.7 (2H, d).

EXAMPLE (COMPOUND 235)

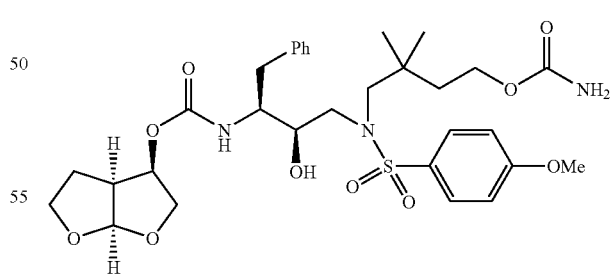

(3R,3aS,6aR)-Hexahydrofuro[2,3-b]furan-3-yl
N-((1S,2R)-1-benzyl-3-(4-carbamoyloxy-2,2-dim-
ethylbutyl)[(4-methoxyphenyl)sulfonyl]amino-2-
hydroxypropyl)carbamate The product from Example (Compound 234) was subjected to a procedure described in Example (Compound 216)

to afford the title compound as a foam; ¹H NMR (DMSO-d₆): δ 0.92 (3H, s), 0.96 (3H, s), 1.2 (1H, dd), 1.3-1.4 (1H, m), 1.6 (2H, t), 2.4 (1H, dd), 2.7-2.8 (2H, m), 2.9-3.0 (2H, m), 3.3-3.5 (3H, m), 3.55-3.65 (2H, m), 3.66-3.80 (2H, m), 3.8 (3H, s), 3.96 (2H, t), 4.8 (1H, quartet), 5.1 (1H, d), 5.5 (1H, d), 6.4 (2H, br s), 7.05 (2H, d), 7.1-7.3 (6H, m), 7.7 (2H, d); MS: 672 (M+23).

EXAMPLE (COMPOUND 236)

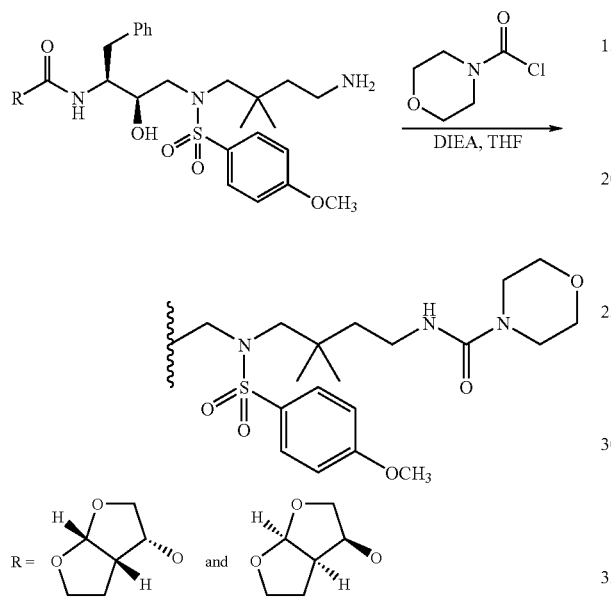

(3R,3aS,6aR)hexahydrofuro[2,3-b]furan-3-yl N-((1S,2R)-1-benzyl-3-2,2-dimethyl-4-[(morpholinocarbonyl)amino]butyl[(4-methoxyphenyl)sulfonyl]amino-2-hydroxypropyl)carbamate and (3S,3aR,6aS)hexahydrofuro[2,3-b]furan-3-yl N-((1S,2R)-1-benzyl-3-2,2-dimethyl-4-[(morpholinocarbonyl)amino]butyl[(4-methoxyphenyl)sulfonyl]amino-2-hydroxypropyl)carbamate A solution of 30 mg (0.050 mmol) of a 1:1 mixture of (3R,3aS,6aR)hexahydrofuro[2,3-b]furan-3-yl N-((1S,2R)-3-(4-amino-2,2-dimethylbutyl)[(4-methoxyphenyl)sulfonyl]amino-1-benzyl-2-hydroxypropyl)carbamate and (3S,3aR,6aS)hexahydrofuro[2,3-b]furan-3-yl N-((1S,2R)-3-(4-amino-2,2-dimethylbutyl)[(4-methoxyphenyl)sulfonyl]amino-1-benzyl-2-hydroxypropyl)carbamate in 1.5 mL of anhydrous THF was cooled to 0° C. and was treated with 9.6 µL (0.055 mmol) of N,N-diisopropylethylamine followed by 6.4 µL (0.055 mmol) of 4-morpholinecarbonyl chloride. The solution was allowed to warm to RT with stirring. After 2 hours the solution was concentrated in vacuo and the residue was subjected to flash chromatography (SiO₂, 95:5 CH₂Cl₂/2M NH₃ in MeOH) to afford 31 mg (86%) of the desired product as a white foam. H1-NMR (CDCl₃): 7.74 (2H), 7.37-7.13 (6H), 7.01 (2H), 5.68 (1H), 5.42 (1H), 5.00 (2H), 4.32 (1H), 4.11-3.50 (14H), 3.49-2.70 (11H), 2.10-1.22 (4H), 1.13-0.94 (6H). MS(ESI): 741(M+Na).

EXAMPLE (COMPOUND 237)

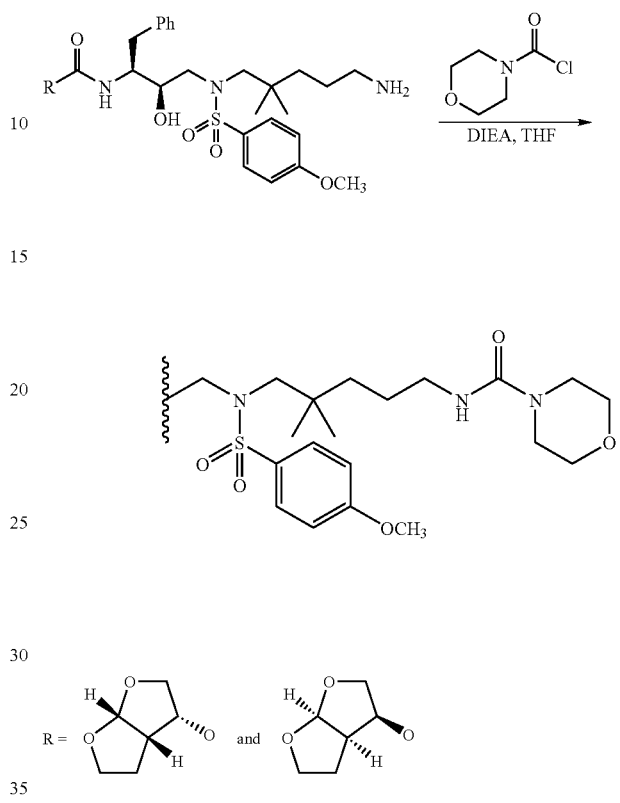

(3R,3aS,6aR)hexahydrofuro[2,3-b]furan-3-yl N-((1S,2R)-1-benzyl-3-2,2-dimethyl-5-[(morpholinocarbonyl)amino]pentyl[(4-methoxyphenyl)sulfonyl]amino-2-hydroxypropyl)carbamate and 3S,3aR,6aS)hexahydrofuro[2,3-b]furan-3-yl N-((1S,2R)-1-benzyl-3-2,2-dimethyl-5-[(morpholinocarbonyl)amino]pentyl[(4-methoxyphenyl)sulfonyl]amino-2-hydroxypropyl)carbamate A solution of 30 mg (0.048 mmol) of a 1:1 mixture of (3R,3aS,6aR)hexahydrofuro[2,3-b]furan-3-yl N-((1S,2R)-3-(5-amino-2,2-dimethylpentyl)[(4-methoxyphenyl)sulfonyl]amino-1-benzyl-2-hydroxypropyl)carbamate and (3S,3aR,6aS)hexahydrofuro[2,3-b]furan-3-yl N-((1S,2R)-3-(5-amino-2,2-dimethylpentyl)[(4-methoxyphenyl)sulfonyl]amino-1-benzyl-2-hydroxypropyl)carbamate in 1.5 mL of anhydrous THF at 0° C. was treated with 9.2 µL (0.053 mmol) of N,N-diisopropylethylamine followed by 6.2 µL (0.053 mmol) of 4-morpholinecarbonyl chloride. The resulting solution was allowed to warm to RT with stirring. After 2 hours the solution was concentrated in vacuo and the residue subjected to flash chromatography (SiO₂, 95:5 CH₂Cl₂/2M NH₃ in MeOH) to afford 31 mg (89%) of the desired product as a white foam. H1-NMR (CDCl₃): 7.74 (2H), 7.36-7.19 (6H), 7.02 (2H), 5.74-5.38 (2H), 4.98 (2H), 4.20 (1H), 4.12-3.46 (12H), 3.41-2.67 (13H), 2.04-1.22 (6H), 1.01-0.86 (6H). MS(ESI): 755(M+Na).

EXAMPLE (COMPOUND 238)

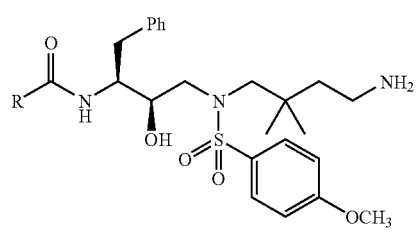

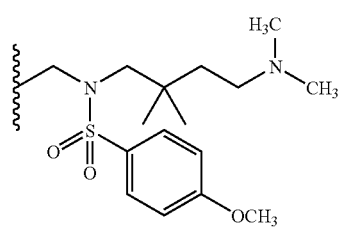

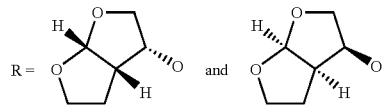

(3R,3aS,6aR)hexahydrofuro[2,3-b]furan-3-yl N-((1S,2R)-1-benzyl-3-[4-(dimethylamino)-2,2-dimethylbutyl][(4-methoxyphenyl)sulfonyl]amino-2-hydroxypropyl)carbamate and (3S,3aR,6aS)hexahydrofuro[2,3-b]furan-3-yl N-((1S,12R)-1-benzyl-3-[4-(dimethylamino)-2,2-dimethylbutyl][(4-methoxyphenyl)sulfonyl]amino-2-hydroxypropyl)carbamate A solution of 50 mg (0.083 mmol) of a 1:1 mixture of (3R,3aS,6aR)hexahydrofuro[2,3-b]furan-3-yl N-((1S,2R)-3-(4-amino-2,2-dimethylbutyl)[(4-methoxyphenyl)sulfonyl]amino-1-benzyl-2-hydroxypropyl)carbamate and (3S,3aR,6aS)hexahydrofuro[2,3-b]furan-3-yl N-((1S,2R)-3-(4-amino-2,2-dimethylbutyl) [(4-methoxyphenyl)sulfonyl]amino-1-benzyl-2-hydroxypropyl)carbamate and 0.034 mL (0.42 mmol) of 37% aqueous formaldehyde in 5 mL of THF was treated with 88 mg (0.42 mmol) of NaBH(OAc)$_3$ followed by 150 mg of powdered 4A molecular sieves. The resulting mixture was stirred at RT for 18 hours, filtered to remove solids, and the filtrate concentrated in vacuo. The residue was purified by flash chromatography (SiO$_2$, 95:5 to 9:1 CH$_2$Cl$_2$/2M NH$_3$ in MeOH) to afford 40 mg (75%) of the desired compound as a white foam. H1-NMR (CDCl$_3$): 7.70 (2H), 7.30-7.11 (6H), 6.98 (2H), 5.62 (1H), 5.42-5.22 (1H), 4.96 (1H), 4.09-3.44 (9H), 3.15-2.60 (7H), 2.38-1.30 (12H), 0.91 (6H). MS(ESI): 634(M+H).

EXAMPLE (COMPOUND 239)

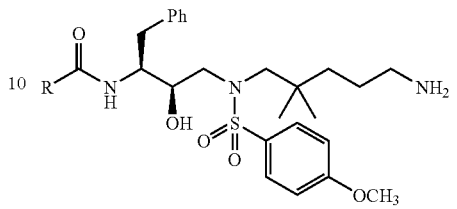

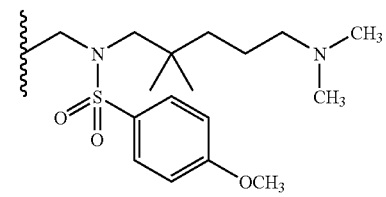

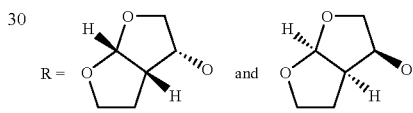

(3R,3aS,6aR)hexahydrofuro[2,3-b]furan-3-yl N-((1S,2R)-1-benzyl-3-[5-(dimethylamino)-2,2-dimethylpentyl][(4-methoxyphenyl)sulfonyl]amino-2-hydroxypropyl)carbamate and (3S,3aR,6aS)hexahydrofuro[2,3-b]furan-3-yl N-((1S,2R)-1-benzyl-3-[5-(dimethylamino)-2,2-dimethylpentyl][(4-methoxyphenyl)sulfonyl]amino-2-hydroxypropyl) carbamate A solution of 50 mg (0.081 mmol) of a 1:1 mixture of (3R,3aS,6aR)hexahydrofuro[2,3-b]furan-3-yl N-((1S,2R)-3-(5-amino-2,2-dimethylpentyl) [(4-methoxyphenyl)sulfonyl] amino-1-benzyl-2-hydroxypropyl)carbamate and (3S,3aR,6aS)hexahydrofuro[2,3-b]furan-3-yl N-((1S,2R)-3-(5-amino-2,2-dimethylpentyl)[(4-methoxyphenyl)sulfonyl] amino-1-benzyl-2-hydroxypropyl)carbamate and 0.033 mL (0.41 mmol) of 37% aqueous formaldehyde in 5 mL of THF was treated with 87 mg (0.41 mmol) of NaBH(OAc)$_3$ followed by 150 mg of powdered 4A molecular sieves. The resulting mixture was stirred at RT for 18 hours, filtered to remove solids, and the filtrate concentrated in vacuo. The residue was purified by flash chromatography (SiO$_2$, 9:1 CH$_2$Cl$_2$/2M NH$_3$ in MeOH) to afford 38 mg (73%) of the desired compound as a white foam. H1-NMR (CDCl$_3$): 7.72 (2H), 7.30-7.10 (6H), 7.00 (2H), 6.98-6.40 (1H), 5.60 (1H), 4.92 (1H), 4.00-3.07 (11H), 3.04-2.27 (5H), 2.18 (6H), 2.00-1.11 (8H), 1.03-0.81 (6H). MS(ESI): 648(M+H).

EXAMPLE (COMPOUND 240)

Step 1:

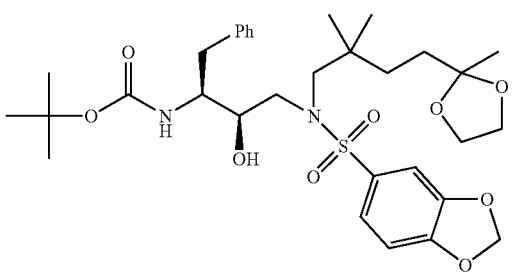

tert-Butyl N-((1S,2R)-1-benzyl-3-[2,2-dimethyl-4-(2-methyl-1,3-dioxolan-2-yl)butyl][(3,4-methylenedioxyphenyl)sulfonyl]amino-2-hydroxypropyl)carbamate The product form step 2 (Example (Compound 208)) was reacted with 3,4-methylenedioxyphenylsulfonyl chloride similar to procedure 3 (Example (Compound 208)) to provide the title compound as a foam; $^1$H NMR (DMSO-d$_6$): δ 0.85 (3H, s), 1.1-1.2 (1H, m), 1.22 (9H, s), 1.3 (2H, br dd), 1.5 (2H, br d), 2.2-2.4 (1H, m), 2.84 (1H, d), 2.9 (1H, dd), 2.97 (1H, dd), 3.30-3.45 (5H, m), 3.75 (1H, br quartet), 3.85 (4H, s), 5.0 (1H, d), 6.18 (2H, s), 6.6 (1H, d), 7.0 (1H, d), 7.1-7.3 (6H, m), 7.35 (1H, d); MS: 635 (MH$^+$); C$_{32}$H$_{46}$N$_2$O$_9$S.

Step 2:

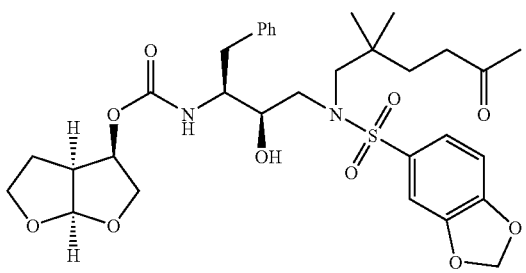

(3R,3aS,6aR)-Hexahydrofuro[2,3-b]furan-3-yl N-((1S,2R)-1-benzyl-3-(2,2-dimethyl-5-oxohexyl)[(3,4-methylenedioxyphenyl)sulfonyl]amino-2-hydroxypropyl)carbamate The product from step a was subjected to procedure similar to Example (Compound 205) to afford the title compound as a foam; $^1$H NMR (DMSO-d$_6$): δ 0.85 (3H, s), 0.90 (3H, s), 1.05 (1H, br dd), 1.2-1.4 (1H, m), 1.45 (2H, t), 2.1 (3H, s), 2.30-2.45 (3H, m), 2.73 (2H, br d), 2.9 (1H, dd), 2.95 (1H, d), 3.30-3.45 (3H, m), 3.5-3.6 (2H, m), 3.65-3.85 (3H, m), 4.8 (1H, quartet), 5.15 (1H, d), 5.5 (1H, d), 6.18 (2H, s), 7.03 (1H, d), 7.1-7.25 (7H, m), 7.35 (1H, d); MS: 669 (M+23); C$_{32}$H$_{42}$N$_2$O$_{10}$S.

EXAMPLE (COMPOUND 241)

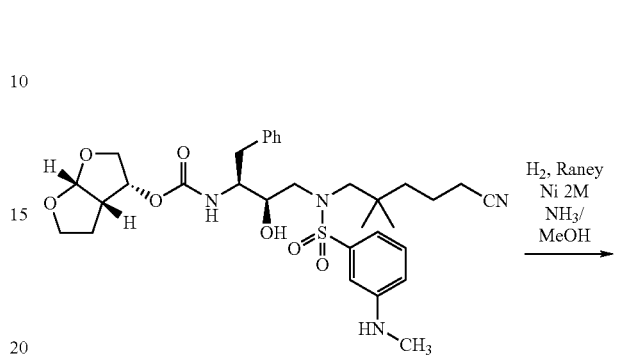

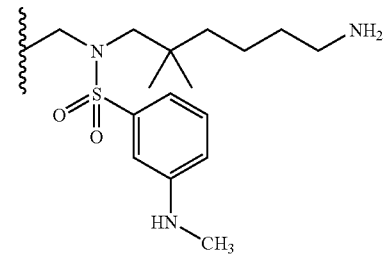

(3R,3aS,6aR)hexahydrofuro[2,3-b]furan-3-yl N-[(1S,2R)-3-((6-amino-2,2-dimethylhexyl)[3-(methylamino)phenyl]sulfonylamino)-1-benzyl-2-hydroxypropyl]carbamate A mixture of 0.18 g (0.29 mmol) of (3R,3aS,6aR)hexahydrofuro[2,3-b]furan-3-yl N-[(1S,2R)-1-benzyl-3-((5-cyano-2,2-dimethylpentyl)[3-(methylamino)phenyl]sulfonylamino)-2-hydroxypropyl]carbamate (obtained via a protocol directly analogous to Example (Compound 245)) and approximately 50 mg of Raney nickel (washed with water and then MeOH) in 40 mL of 2M NH$_3$/MeOH was subjected to hydrogenation at 40 psi. After 1.5 hours the vessel was purged with nitrogen, catalyst removed by filtration through celite and the filtrate concentrated to dryness in vacuo. The residue was subjected to flash chromatography (SiO2, 9:1 CH$_2$Cl$_2$, 2M NH$_3$ in MeOH) to afford 0.13 g (72%) of the desired amine as a white foam.

H1-NMR (CDCl$_3$): 7.31-7.12 (m, 6H), 7.01 (d, 1H), 6.92 (s, 1H), 6.75 (dd, 1H), 5.60 (d, 1H), 5.29 (d, 1H), 4.99 (q, 1H), 4.15 (br s, 1H), 4.00 (t, 1H), 3.89 (m, 1H), 3.80 (m, 2H), 3.67 (m, 2H), 3.21 (dd, 1H), 3.17-2.98 (m, 3H), 2.94-2.80 (m, 2H), 2.84 (s, 3H), 2.71 (m, 3H), 1.58 (m, 1H), 1.47-1.21 (m, 7H), 0.90 (s, 3H), 0.88 (s, 3H).

MS(ESI) 633(M+H)

EXAMPLE (COMPOUND 242)

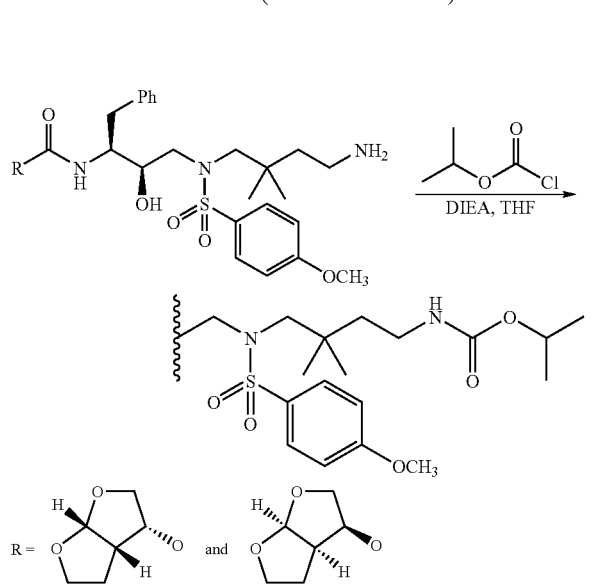

(3R,3aS,6aR)hexahydrofuro[2,3-b]furan-3-yl N-((1S,2R)-1-benzyl-2-hydroxy-3-4-[(isopropoxycarbonyl)amino]-2,2-dimethylbutyl[(4-methoxyphenyl)sulfonyl]aminopropyl)carbamate and (3S,3aR,6aS)hexahydrofuro[2,3-b]furan-3-yl N-((1S,2R)-1-benzyl-2-hydroxy-3-4-[(isopropoxycarbonyl)amino]-2,2-dimethylbutyl[(4-methoxyphenyl)sulfonyl]aminopropyl) carbamate A solution of 71 mg (0.12 mmol) of a 1:1 mixture of (3R,3aS,6aR)hexahydrofuro[2,3-b]furan-3-yl N-((1S,2R)-3-(4-amino-2,2-dimethylbutyl)[(4-methoxyphenyl)sulfonyl]amino-1-benzyl-2-hydroxypropyl)carbamate and (3S,3aR,6aS)hexahydrofuro[2,3-b]furan-3-yl N-((1S,2R)-3-(4-amino-2,2-dimethylbutyl)[(4-methoxyphenyl)sulfonyl]amino-1-benzyl-2-hydroxypropyl)carbamate in 5 mL of anhydrous THF at 0° C. was treated with 0.022 mL (0.13 mmol) of N,N-diisopropylethylamine followed by 0.13 mL (0.13 mmol) of 1M isopropyl chloroformate/toluene solution. The solution was allowed to warm to RT with stirring. After 18 hours the solution was concentrated in vacuo and the residue subjected to flash chromatography (SiO₂, 95:5 CH₂Cl₂/MeOH) to afford 48 mg (58%) of the desired compound as a white foam. H1-NMR (CDCl₃): 7.70 (2H), 7.30-7.14 (5H), 6.99 (2H), 5.62 (1H), 5.21 (1H), 5.01-4.81 (3H), 4.19-3.44 (10H), 3.27-2.68 (9H), 2.01-1.30 (4H), 1.21 (6H), 1.01-0.92 (6H). MS(ESI): 714(M+Na).

EXAMPLE (COMPOUND 243)

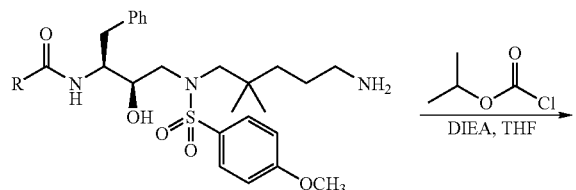

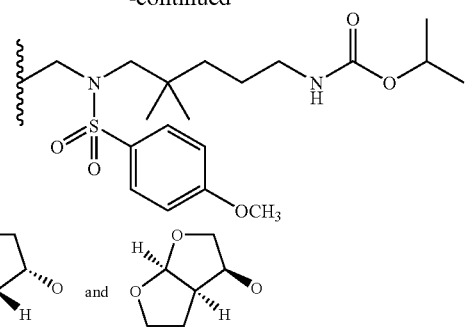

(3R,3aS,6aR)hexahydrofuro[2,3-b]furan-3-yl N-((1S,2R)-1-benzyl-2-hydroxy-3-5-[(isopropoxycarbonyl)amino]-2,2-dimethylpentyl[(4-methoxyphenyl)sulfonyl]aminopropyl)carbamate and (3S,3aR,6aS)hexahydrofuro[2,3-b]furan-3-yl N-((1S,2R)-1-benzyl-2-hydroxy-3-5-[(isopropoxycarbonyl)amino]-2,2-dimethylpentyl[(4-methoxyphenyl)sulfonyl]aminopropyl)carbamate.

A solution of 70 mg (0.11 mmol) of a 1:1 mixture of (3R,3aS,6aR)hexahydrofuro[2,3-b]furan-3-yl N-((1S,2R)-3-(5-amino-2,2-dimethylpentyl)[(4-methoxyphenyl)sulfonyl]amino-1-benzyl-2-hydroxypropyl)carbamate and (3S,3aR,6aS)hexahydrofuro[2,3-b]furan-3-yl N-((1S,2R)-3-(5-amino-2,2-dimethylpentyl)[(4-methoxyphenyl)sulfonyl]amino-1-benzyl-2-hydroxypropyl)carbamate in 5 mL of anhydrous THF at 0° C. was treated with 0.022 mL (0.13 mmol) of N,N-diisopropylethylamine followed by 0.12 mL (0.12 mmol) of 1M isopropyl chloroformate/toluene solution. The solution was allowed to warm to RT with stirring. After 18 hours the solution was concentrated in vacuo and the residue subjected to flash chromatography (SiO₂, 95:5 CH₂Cl₂/MeOH) to afford 75 mg (95%) of the desired compound as a white foam. H1-NMR (CDCl₃): 7.70 (2H), 7.30-7.11 (5H), 7.00 (2H), 5.65-5.26 (2H), 5.00-4.80 (3H), 4.18-3.42 (10H), 3.22-2.63 (9H), 2.00-1.18 (12H), 0.94-0.83 (6H). MS(ESI): 728(M+Na).

EXAMPLE (COMPOUND 244)

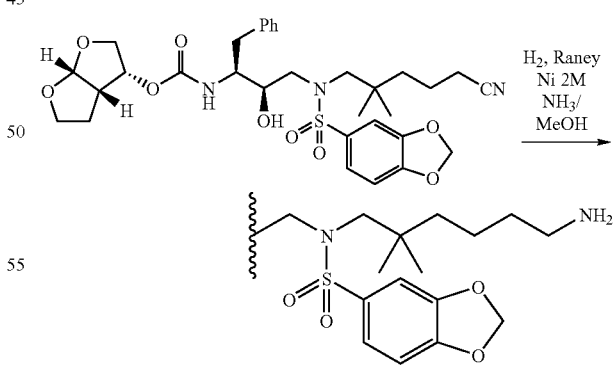

(3R,3aS,6aR) hexahydrofuro[2,3-b]furan-3-yl N-(1S,2R)-3-[(6-amino-2,2-dimethylhexyl)(1,3-benzodioxol-5-ylsulfonyl)amino]-1-benzyl-2-hydroxypropylcarbamate A mixture of 0.31 g (0.47 mmol) of (3R,3aS,6aR)hexahydrofuro[2,3-b]furan-3-yl N-(1S,2R)-3-[(1,3-benzodioxol-5- ylsulfonyl)(5-cyano-2,2-dimethylpentyl)amino]-1-benzyl-2-hydroxypropylcarbamate (obtained via a protocol directly analogous to Example (Compound 245)) and approximately 50 mg of Raney nickel (washed with water and then MeOH) in 40 mL of 2M $NH_3$/MeOH was subjected to hydrogenation at 45 psi. After 2.5 hours the vessel was purged with nitrogen, catalyst removed by filtration through celite and the filtrate concentrated to dryness in vacuo. The residue was subjected to flash chromatography ($SiO_2$, 9:1 $CH_2Cl_2$, 2M $NH_3$ in MeOH) to afford 0.27 g (90%) of the desired amine as a white foam. H1-NMR ($CDCl_3$): 7.33 (d, 1H), 7.28-7.13 (m, 6H), 6.87 (d, 1H), 6.08 (s, 2H), 5.60 (d, 1H), 5.31 (m, 1H), 5.00 (q, 1H), 4.00 (t, 1H), 3.91 (dd, 1H), 3.81 (m, 2H), 3.63 (m, 2H), 3.21-2.97 (m, 4H), 2.86 (m, 2H), 2.80-2.63 (m, 3H), 1.58 (m, 1H), 1.45-1.21 (m, 7H), 0.91 (d, 6H). MS(ESI): 648(M+H).

EXAMPLE (COMPOUND 245)

Step 1:

4-(1,3-Dioxolan-2-yl)-4-methylpentanenitrile 0.74 g (3.8 mmol) of 2-(4-chloro-1,1*dimethylbutyl)-1,3-dioxolane) and 0.50 g (7.7 mmol) of sodium cyanide in 5 mL of DMSO was heated to 100° C. with stirring. After 18 hours the solution was cooled to RT, diluted with water, and the mixture extracted with ether (3×). The combined ether extracts were washed with water. (3×), dried over $MgSO_{4}$, and concentrated in vacuo to afford 0.69 g (90%) of the desired compound as a light yellow liquid.

$^1$H NMR ($CDCl_3$): δ 0.92 (6H, s), 1.41-1.48 (2H, m), 1.65-1.75 (2H, m), 2.32 (2H, t), 3.82-3.97 (4H, m), 4.53 (1H, s).

Step 2:

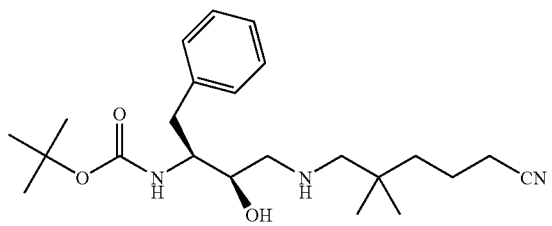

tert-Butyl N-(1S,2R)-1-benzyl-3-[(5-cyano-2,2-dimethylpentyl)amino]-2-hydroxypropylcarbamate The product from Step 1 (0.44 g (2.2 mmol) of 4-(1,3-dioxolan-2-yl)-4-methylpentyl azide) in 15 mL of THF was treated with 3 mL of 1M aqueous HCl and the solution stirred at reflux. After 4 hours the solution was cooled to RT and poured into 40 mL of rapidly stirred saturated aqueous $NaHCO_3$. The resulting mixture was extracted with ether (3×). The combined ether extracts were washed with water (2×), dried over $MgSO_4$ and concentrated to a volume of approximately 3 mL. This solution was added to a solution of 0.62 g (2.2 mmol) of tert-butyl N-(1S,2R)-3-amino-1-benzyl-2-hydroxypropylcarbamate in 20 mL of 1:1 THF/DMF. The solution was treated with 1 g of powdered 4A molecular sieves and the mixture heated at 50° C. After 2 hours the mixture was cooled in an ice water bath and treated with 0.47 g (2.2 mmol) of $NaBH(OAc)_3$. After stirring at RT for 18 hours the mixture was concentrated in vacuo. The residue was suspended in $CH_2Cl_2$ and stirred vigorously with 0.5M aqueous NaOH for 5 minutes. The layers were separated and the aqueous phase extracted with two additional portions of $CH_2Cl_2$. The combined $CH_2Cl_2$ solutions were washed with water (2×), dried over $MgSO_4$, and concentrated to give a clear viscous oil. This material was subjected to flash chromatography ($SiO_2$, 95:5 $CH_2Cl_2$/2M $NH_3$ in MeOH) to afford 0.45 g (49%) of the desired product as a white foam.

$^1$H NMR (DMSO-$d_6$): δ 0.82 (6H, s), 1.18-1.30 (1H, m), 1.40-1.53 (2H, m), 2.24 (2H, s), 2.38-2.62 (5H, m), 2.96 (1H, dd), 3.36-3.56 (2H, m), 4.75 (1H, br), 6.71 (1H, d), 7.08-7.26 (5H, m); MS 404 (MH+).

Step 3:

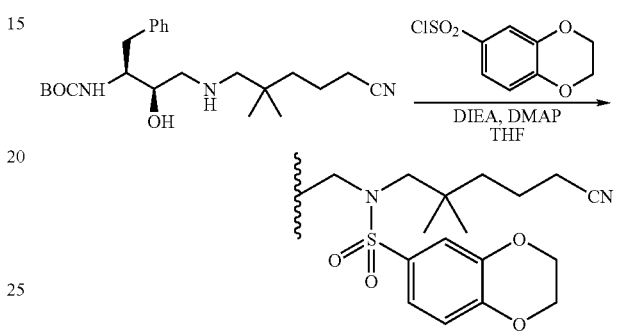

tert-butyl N-(1S,2R)-1-benzyl-3-[(5-cyano-2,2-dimethylpentyl)(2,3-dihydro-1,4-benzodioxin-6-ylsulfonyl)amino]-2-hydroxypropylcarbamate A solution of 0.35 g (0.87 mmol) of tert-butyl N-(1S,2R)-1-benzyl-3-[(5-cyano-2,2-dimethylpentyl)amino]-2-hydroxypropylcarbamate, 0.22 g (0.95 mmol) of 3,4-ethylenedioxy-benzenesulfonyl chloride, 0.18 mL (1.0 mmol) of N,N-diisopropylethylamine, and 10 mg of DMAP in 15 mL of anhydrous THF was stirred at RT. After 18 hours the solution was concentrated in vacuo and the residue subjected to flash chromatography ($SiO_2$, 6:4 hexane/EtOAc) to afford 0.39 g (75%) of the desired product as a white foam. H1-NMR ($CDCl_3$): 7.32-7.17 (m, 7H), 6.92 (d, 1H), 4.57 (d, 1H), 4.30 (m, 4H), 4.11 (m, 1H), 3.90 (m, 1H), 3.67 (m, 1H), 3.18-3.02 (m, 2H), 3.01-2.90 (m, 2H), 2.80 (m, 2H), 2.31 (t, 2H), 1.70-1.53 (m, 2H), 1.49-1.19 (m, 2H), 1.25 (s, 9H), 0.92 (s, 6H). MS(ESI): 624(M+Na).

Step 4:

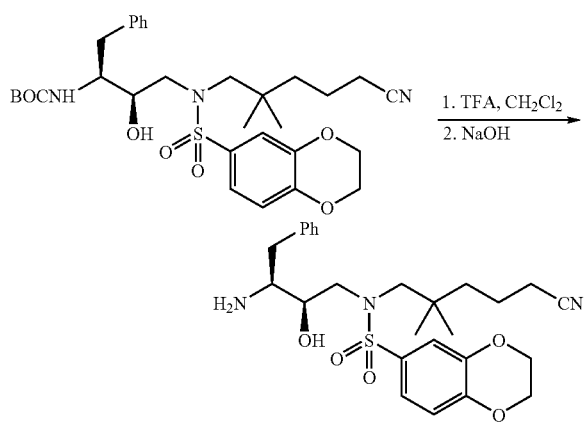

N-[(2R,3S)-3-amino-2-hydroxy-4-phenylbutyl]-N-(5-cyano-2,2-dimethylpentyl)-2,3-dihydro-1,4-benzodioxine-6-sulfonamide A solution of 0.39 g (0.65 mmol) of tert-butyl N-(1S,2R)-1-benzyl-3-[(5-cyano-2,2-dimethylpentyl)(2,3-dihydro-1,4-benzodioxin-6-ylsulfonyl)amino]-2-hydroxypropylcarbamate in 25 mL of 1:1 TFA/CH$_2$Cl$_2$ was stirred at RT for 2 hours and was then concentrated in vacuo. The residue was dissolved in CH$_2$Cl$_2$. The resulting solution was washed with 1M aqueous NaOH (1×), water (2×), dried over MgSO$_4$, and concentrated to give 0.31 g (95%) of the desired amine as a white foam. H1-NMR (CDCl$_3$): 7.34-7.15 (m, 7H), 6.94 (d, 1H), 4.29 (m, 4H), 3.89 (m, 1H), 3.32-3.19 (m, 2H), 3.02 (m, 3H), 2.87 (dd, 1H), 2.41 (dd, 1H), 2.32 (t, 2H), 1.80-1.30 (7H), 0.96 (s, 6H). MS(ESI): 502(M+H).

Step 5:

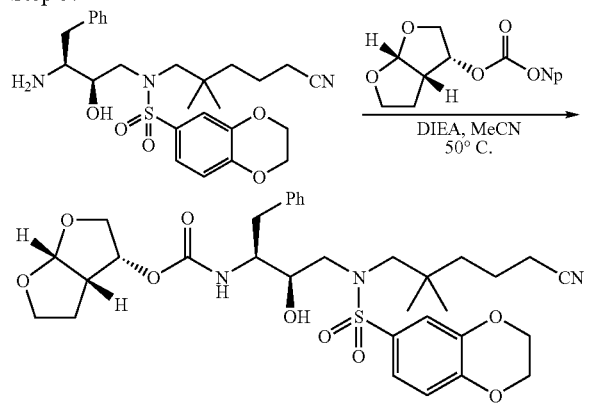

(3R,3aS,6aR)hexahydrofuro[2,3-b]furan-3-yl N-(1S,2R)-1-benzyl-3-[(5-cyano-2,2-dimethylpentyl)(2,3-dihydro-1,4-benzodioxin-6-ylsulfonyl)amino]-2-hydroxypropylcarbamate A solution of 0.31 g (0.62 mmol) of N-[(2R,3S)-3-amino-2-hydroxy-4-phenylbutyl]-N-(5-cyano-2,2-dimethylpentyl)-2,3-dihydro-1,4-benzodioxine-6-sulfonamide, 0.20 g (0.68 mmol) of (3R,3aS,6aR)hexahydrofuro[2,3-b]furan-3-yl (4-nitrophenyl)carbonate, and 0.22 mL (1.2 mmol) of N,N-diisopropylethylamine in 20 mL of MeCN was heated to 50° C. with stirring. After 18 hours the solution was cooled to RT and concentrated in vacuo. The residue was dissolved in CH$_2$Cl$_2$. The resulting solution was washed with 1M aqueous NaOH (1×), water (3×), dried over MgSO$_4$, and concentrated to dryness. The crude product was purified by flash chromatography (SiO$_2$, 95:5 CH$_2$Cl$_2$/MeOH) to afford 0.36 g (88%) of the desired compound as a white foam. H1-NMR (CDCl$_3$): 7.30-7.12 (m, 7H), 6.96 (d, 1H), 5.60 (d, 1H), 4.99 (m, 2H), 4.29 (m, 4H), 4.02 (m, 2H), 3.90 (dd, 1H), 3.80 (t, 2H), 3.63 (m, 2H), 3.21-3.01 (m, 3H), 2.94 (d, 1H), 2.84 (m, 1H), 2.80-2.63 (m, 2H), 2.35 (t, 2H), 1.70-1.30 (m, 6H), 0.94 (s, 3H), 0.90 (s, 3H). MS(ESI): 680(M+Na).

Step 6:

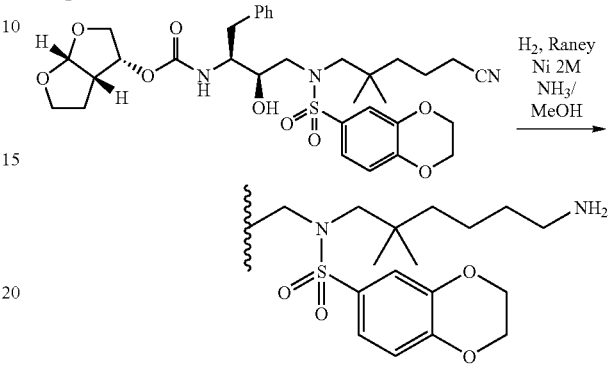

(3R,3aS,6aR)hexahydrofuro[2,3-b]furan-3-yl N-(1S,2R)-3-[(6-amino-2,2-dimethylhexyl)(2,3-dihydro-1,4-benzodioxin-6-ylsulfonyl)amino]-1-benzyl-2-hydroxypropylcarbamate A mixture of 0.35 g (0.53 mmol) of (3R,3aS,6aR)hexahydrofuro[2,3-b]furan-3-yl N-(1S,2R)-1-benzyl-3-[(5-cyano-2,2-dimethylpentyl)(2,3-dihydro-1,4-benzodioxin-6-ylsulfonyl)amino]-2-hydroxypropylcarbamate and approximately 50 mg of Raney nickel (washed with water and then MeOH) in 40 mL of 2M NH$_3$/MeOH was subjected to hydrogenation at 45 psi. After 3 hours the vessel was purged with nitrogen, catalyst removed by filtration through celite and the filtrate concentrated to dryness in vacuo. The residue was subjected to flash chromatography (SiO2, 9:1 CH$_2$Cl$_2$, 2M NH$_3$ in MeOH) to afford 0.31 g (89%) of the desired amine as a white foam.

H1-NMR (CDCl$_3$): 7.30-7.11 (m, 7H), 6.95 (d, 1H), 5.60 (d, 1H), 5.28 (m, 1H), 4.99 (q, 1H), 4.30 (m, 4H), 4.00 (t, 1H), 3.91 (dd, 1H), 3.81 (m, 2H), 3.66 (m, 2H), 3.17 (dd, 1H), 3.10-2.97 (m, 3H), 2.83 (m, 2H), 2.79-2.62 (m, 3H), 1.58 (m, 1H), 1.42-1.20 (m, 7H), 0.90 (d, 6H). MS(ESI): 662(M+H).

EXAMPLE (COMPOUND 246)

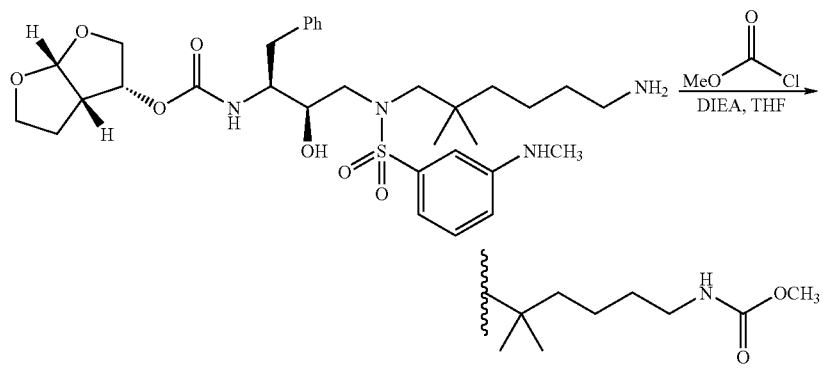

(3R,3aS,6aR)hexahydrofuro[2,3-b]furan-3-yl N-[(1S,2R)-1-benzyl-2-hydroxy-3-(6-[(methoxycarbonyl)amino]-2,2-dimethylhexyl[3-(methylamino)phenyl]sulfonylamino)propyl]carbamate A solution of 55 mg (0.087 mmol) of (3R,3aS,6aR)hexahydrofuro[2,3-b]furan-3-yl N-[(1S,2R)-3-((6-amino-2,2-dimethylhexyl)[3-(methylamino)phenyl]sulfonylamino)-1-benzyl-2-hydroxypropyl]carbamate and 17.0 μL (0.091 mmol) of N,N-diisopropylethylamine in 4 mL of anhydrous THF at 0° C. was treated with 7.0 μL (0.091 mmol) of methyl chloroformate. The solution was allowed to warm to RT with stirring.

After 18 hours the solution was concentrated in vacuo and the residue was subjected to flash chromatography (SiO$_2$, 95:5 CH$_2$Cl$_2$/2M NH$_3$ in MeOH) to afford 55 mg (92%) of the desired compound as a white foam. H1-NMR (CDCl$_3$): 7.34-7.12 (m, 6H), 7.02 (d, 1H), 6.94 (s, 1H), 6.78 (d, 1H), 5.60 (d, 1H), 5.17 (d, 1H), 5.02-4.70 (m, 2H), 4.14 (s, 1H), 4.02 (m, 1H), 3.89 (dd, 1H), 3.79 (m, 2H), 3.72-3.55 (m, 5H), 3.28-2.91 (m, 6H), 2.83 (s, 3H), 2.89-2.64 (m, 3H), 1.65-1.18 (m, 8H), 0.91 (s, 3H), 0.88 (s, 3H).

MS(ESI): 691(M+H)

EXAMPLE (COMPOUND 247)

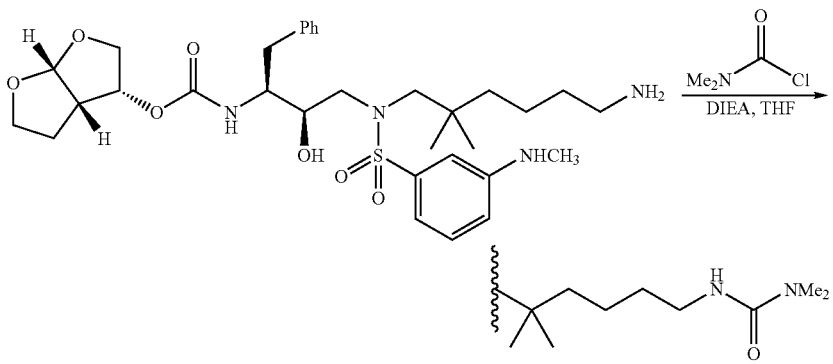

(3R,3aS,6aR)hexahydrofuro[2,3-b]furan-3-yl N-[(1S,2R)-1-benzyl-3-((6-[(dimethylamino)carbonyl]amino-2,2-dimethylhexyl) [3-(methylamino)phenyl]sulfonylamino)-2-hydroxypropyl]carbamate A solution of 55 mg (0.087 mmol) of (3R,3aS,6aR)hexahydrofuro[2,3-b]furan-3-yl N-[(1S,2R)-3-((6-amino-2,2-dimethylhexyl)[3-(methylamino)phenyl]sulfonylamino)-1-benzyl-2-hydroxypropyl]carbamate and 17 μL (0.091 mmol) of N,N-diisopropylethylamine in 4 mL of anhydrous THF at 0° C. was treated with 8.4 μL (0.091 mmol) of N,N-dimethylcarbamyl chloride. The solution was allowed to warm to RT with stirring. After 18 hours the solution was concentrated in vacuo and the residue was subjected to flash chromatography (SiO$_2$, 95:5 CH$_2$Cl$_2$/2M NH$_3$ in MeOH) to afford 49 mg (80%) of the desired compound as a white foam. H1-NMR (CDCl$_3$): 7.32-7.12 (m, 6H), 7.02 (d, 1H), 6.92 (s, 1H), 6.76 (d, 1H), 5.60 (m, 2H), 4.96 (q, 1H), 4.51 (m, 1H), 4.32 (s, 1H), 4.20 (br s, 1H), 4.01 (m, 1H), 3.88 (dd, 1H), 3.79 (m, 2H), 3.62 (m, 2H), 3.30-2.92 (m, 6H), 2.91-2.64 (m, 12H), 1.65-1.40 (m, 3H), 1.38-1.20 (m, 5H), 0.91 (s, 3H), 0.85 (s, 3H).

MS(ESI): 704(M+H).

EXAMPLE (COMPOUND 248)

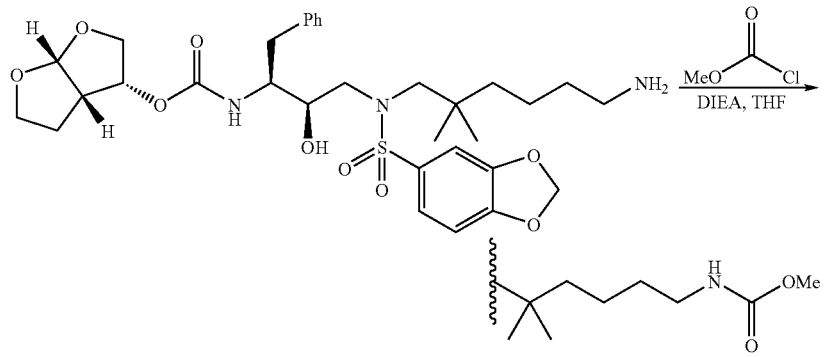

(3R,3aS,6aR)hexahydrofuro[2,3-b]furan-3-yl N-[(1S,2R)-3-((1,3-benzodioxol-5-ylsulfonyl)-6-[(methoxycarbonyl)amino]-2,2-dimethylhexylamino)-1-benzyl-2-hydroxypropyl]carbamate A solution of 60 mg (0.093 mmol) of (3R,3aS,6aR)hexahydrofuro[2,3-b]furan-3-yl N-(1S,2R)-3-[(6-amino-2,2-dimethylhexyl)(1,3-benzodioxol-5-ylsulfonyl)amino)]-1-benzyl-2-hydroxypropylcarbamate and 20 μL (0.11 mmol) of N,N-diisopropylethylamine in 5 mL of anhydrous THF at 0° C. was treated with 8.0 μL (0.10 mmol) of methyl chloroformate. The solution was allowed to warm to RT with stirring. After 18 hours the solution was concentrated in vacuo and the residue was subjected to flash chromatography (SiO$_2$, 95:5 CH$_2$Cl$_2$/2M NH$_3$ in MeOH) to afford 59 mg (89%) of the desired compound as a white foam. H1-NMR (CDCl$_3$): 7.40 (dd, 1H), 7.35-7.20 (m, 6H), 6.96 (d, 1H), 6.14 (s, 2H), 5.65 (d, 1H), 5.27 (d, 1H), 5.12-4.90 (m, 2H), 4.20 (br s, 1H), 4.08 (m, 1H), 3.98 (dd, 1H), 3.86 (m, 2H), 3.80-3.63 (m, 5H), 3.30-2.71 (m, 9H), 1.62-1.23 (m, 8H), 0.96 (s, 3H), 0.92 (s, 3H).

MS(ESI): 728(M+Na).

EXAMPLE (COMPOUND 249)

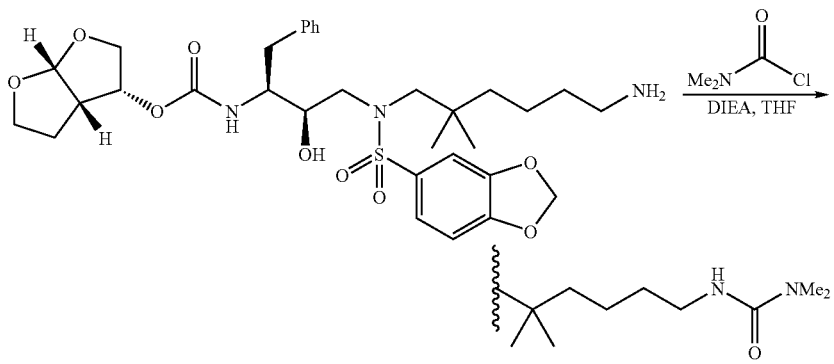

(3R,3aS,6aR)hexahydrofuro[2,3-b]furan-3-yl N-(1S,2R)-3-[(1,3-benzodioxol-5-ylsulfonyl)(6-[(dimethylamino)carbonyl]amino-2,2-dimethylhexyl)amino]-1-benzyl-2-hydroxypropylcarbamate.

A solution of 60 mg (0.093 mmol) of (3R,3aS,6aR)hexahydrofuro[2,3-b]furan-3-yl N-(1S,2R)-3-((6-amino-2,2-dimethylhexyl)(1,3-benzodioxol-5-ylsulfonyl)amino]-1-benzyl-2-hydroxypropylcarbamate and 20 μL (0.11 mmol) of N,N-diisopropylethylamine in 5 mL of anhydrous THF at 0° C. was treated with 9.4 μL (0.10 mmol) of N,N-dimethylcarbamyl chloride. The solution was allowed to warm to RT with stirring. After 18 hours the solution was concentrated in vacuo and the residue was subjected to flash chromatography (SiO$_2$, 95:5 CH$_2$Cl$_2$/2M NH$_3$ in MeOH) to afford 60 mg (90%) of the desired compound as a white foam. H1-NMR (CDCl$_3$): 7.39 (dd, 1H), 7.32-7.16 (m, 6H), 6.96 (d, 1H), 6.12 (s, 2H), 5.78 (d, 1H), 5.63 (d, 1H), 5.02 (q, 1H), 4.58 (t, 1H), 4.45 (br s, 1H), 4.07 (m, 1H), 3.95 (dd, 1H), 3.82 (m, 2H), 3.68 (m, 2H), 3.32-3.01 (m, 6H), 2.91 (s, 6H), 2.90-2.69 (m, 3H), 1.70-1.43 (m, 3H), 1.42-1.25 (m, 5H), 1.00 (s, 3H), 0.91 (s, 3H).

MS(ESI): 719(M+H).

EXAMPLE (COMPOUND 250)

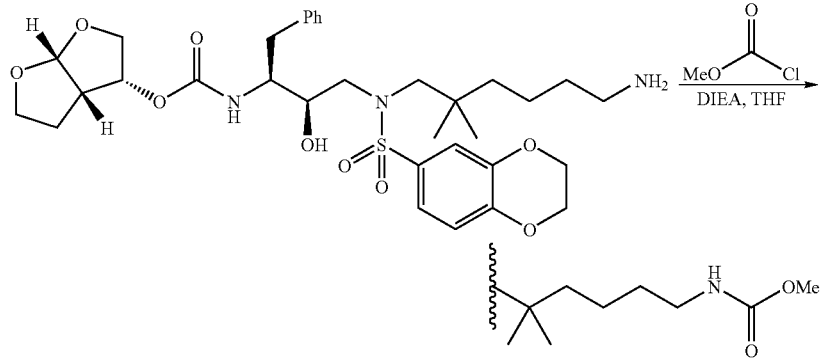

(3R,3aS,6aR)hexahydrofuro[2,3-b]furan-3-yl N-[(1S,2R)-1-benzyl-3-((2,3-dihydro-1,4-benzo-dioxin-6-ylsulfonyl) 6-[(methoxycarbonyl)amino]-2,2-dimethylhexylamino)-2-hydroxypropyl]carbamate.

A solution of 60 mg (0.091 mmol) of (3R,3aS,6aR)hexahydrofuro[2,3-b]furan-3-yl N-(1S,2R)-3-[(6-amino-2,2-dimethylhexyl) (2,3-dihydro-1,4-benzodioxin-6-ylsulfonyl)amino]-1-benzyl-2-hydroxypropylcarbamate and 20 µL (0.11 mmol) of N,N-diisopropylethylamine in 5 mL of anhydrous THF at 0° C. was treated with 7.7 µL (0.10 mmol) of methyl chloroformate. The solution was allowed to warm to RT with stirring. After 18 hours the solution was concentrated in vacuo and the residue was subjected to flash chromatography (SiO$_2$, 95:5 CH$_2$Cl$_2$/2M NH$_3$ in MeOH) to afford 65 mg (98%) of the desired compound as a white foam. H1-NMR (CDCl$_3$): 7.31-7.13 (m, 7H), 6.94 (d, 1H), 5.60 (d, 1H), 5.21 (d, 1H), 5.02-4.83 (m, 2H), 4.30 (m, 4H), 4.19 (br s, 1H), 4.01 (m, 1H), 3.89 (dd, 1H), 3.80 (m, 2H), 3.72-3.59 (m, 5H), 3.22-3.03 (m, 5H), 2.93 (d, 1H), 2.83 (m, 1H), 2.73 (m, 2H), 1.60-1.41 (m, 3H), 1.40-1.18 (m, 5H), 0.91 (s, 3H), 0.89 (s, 3H). MS(ESI): 742(M+Na).

EXAMPLE (COMPOUND 251)

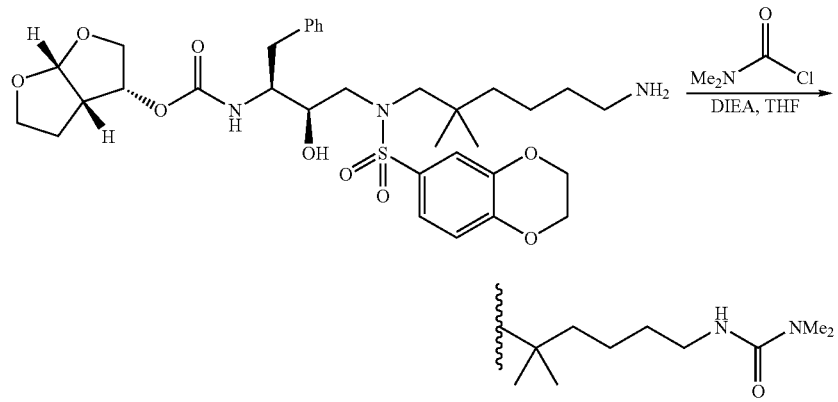

(3R,3aS,6aR)hexahydrofuro[2,3-b]furan-3-yl N-(1S,2R)-1-benzyl-3-[(2,3-dihydro-1,4-benzodioxin-6-ylsulfonyl)(6-[(dimethylamino)carbonyl]amino-2,2-dimethylhexyl)amino]-2-hydroxypropylcarbamate.

A solution of 60 mg (0.091 mmol) of (3R,3aS,6aR)hexahydrofuro[2,3-b]furan-3-yl N-(1S,2R)-3-[(6-amino-2,2-dimethylhexyl)(2,3-dihydro-1,4-benzodioxin-6-ylsulfonyl)amino]-1-benzyl-2-hydroxypropylcarbamate and 20 µL (0.11 mmol) of N,N-diisopropylethylamine in 5 mL of anhydrous THF at 0° C. was treated with 9.2 µL (0.10 mmol) of N,N-dimethylcarbamyl chloride. The solution was allowed to warm to RT with stirring. After 18 hours the solution was concentrated in vacuo and the residue was subjected to flash chromatography (SiO$_2$, 95:5 CH$_2$Cl$_2$/2M NH$_3$ in MeOH) to afford 54 mg (81%) of the desired compound as a white foam. H1-NMR (CDCl$_3$): 7.31-7.11 (m, 7H), 6.96 (d, 1H), 5.67 (d, 1H), 5.60 (d, 1H), 4.96 (q, 1H), 4.51 (m, 1H), 4.43 (br s, 1H), 4.30 (m, 4H), 4.01 (t, 1H), 3.90 (dd, 1H), 3.78 (m, 2H), 3.63 (m, 2H), 3.24-2.92 (m, 6H), 2.87 (s, 6H), 2.87-2.67 (m, 3H), 1.60-1.40 (m, 3H), 1.39-1.20 (m, 5H), 0.92 (s, 3H), 0.86 (s, 3H). MS(ESI): 733(M+H).

EXAMPLE (COMPOUND 252)

Step 1:

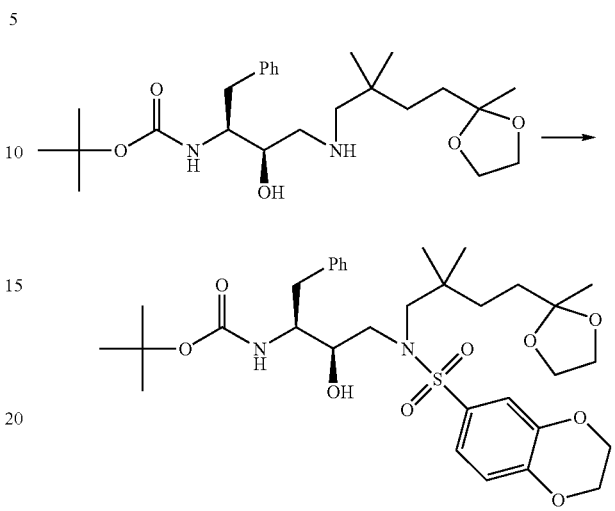

tert-Butyl N-((1S,2R)-3-(1,4-benzodioxan-6-sulfonyl)[2,2-dimethyl-4-(2-methyl-1,3-dioxolan-2-yl)butyl]amino-1-benzyl-2-hydroxypropyl)carbamate The product from step 2 (Example (Compound 208)) was reacted with 1,4-benzodioxan-6-sulfonyl chloride according to procedure 3 (Example (Compound 201)) to give the title compound as a foam; $^1$H NMR (DMSO-d$_6$): δ 0.9 (6H, s), 1.1 (1H, s), 1.2 (9H, s), 1.3 (2H, t), 1.5 (2H, t), 2.45-2.50 (1H, m), 2.8 (1H, d), 2.9 (1H, dd), 3.0 (1H, d), 3.2-3.4 (5H, m), 3.75 (1H, quartet), 3.80-3.85 (4H, m), 4.25-4.35 (4H, m), 5.0 (1H, d), 6.6 (1H, d), 7.0 (1H, d), 7.1-7.3 (7H, m); MS: 671.2 (MH$^+$); C$_{33}$H$_{48}$N$_2$O$_9$S.

Step 2:

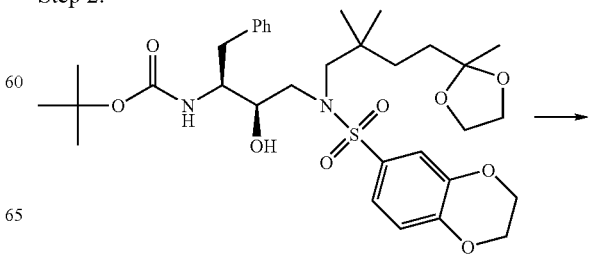

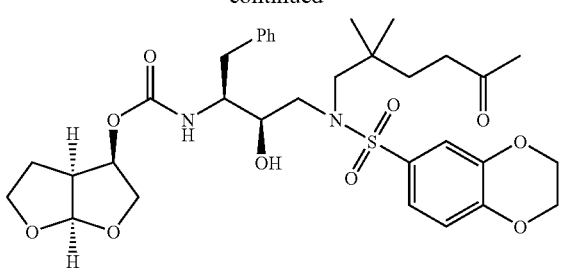

(3R,3aS,6aR)-Hexahydrofuro[2,3-b]furan-3-yl N-((1S,2R)-3-(1,4-benzodioxan-6-sulfonyl)(2,2-dimethyl-5-oxohexyl)amino-1-benzyl-2-hydroxypropyl)carbamate The product from step 1 was subjected to the procedure used in Example (Compound 205)) to afford the title compound as a foam; $^1$H NMR (DMSO-$d_6$): δ 0.86 (3H, s), 0.90 (3H, s), 1.1-1.2 (1H, m), 1.25-1.35 (1H, m), 1.45 (2H, t), 2.1 (3H, s), 2.35-2.45 (3H, m), 2.7-2.8 (2H, m), 2.82-3.00 (2H, m), 3.25-3.30 (2H, m), 3.4 (1H, br quartet), 3.5-3.6 (2H, m), 3.7 (1H, d), 3.75-3.85 (2H, m), 4.25-4.35 (4H, m), 4.8 (1H, dt), 5.18 (1H, d), 5.5 (1H, d), 7.0 (1H, d), 7.1-7.3 (8H, m); MS: 661.2 (MH$^+$); $C_{33}H_{44}N_2O_{10}S$.

EXAMPLE (COMPOUND 253)

Step 1:

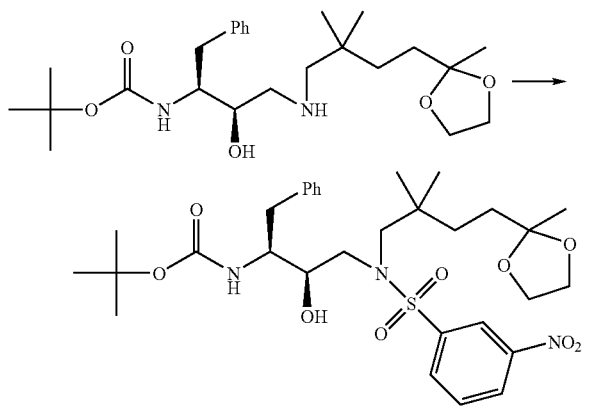

tert-Butyl N-((1S,2R)-1-benzyl-3-([2,2-dimethyl-4-(2-methyl-1,3-dioxolan-2-yl)butyl][(3-nitrophenyl)sulfonyl]amino-2-hydroxypropyl)carbamate The product from step 2 (Example (Compound 208)) was reacted with 3-nitrobenzenesulfonyl chloride according to procedure 3 (Example (Compound 201)) to give the title compound as a foam; $^1$H NMR (DMSO-$d_6$) δ 0.9 (3H, s), 0.93 (3H, s), 1.1 (1H, s), 1.15 (9H, s), 1.3-1.4 (2H, m), 1.5-1.6 (2H, m), 2.4 (1H, dd), 2.8 (1H, d), 3.0 (1H, d), 3.2-3.4 (4H, m), 3.4-3.5 (3H, m), 3.8 (4H, br s), 4.85 (1H, d), 6.6 (1H, d), 7.1-7.3 (5H, m), 7.85 (1H, t), 8.22 (1H, d), 8.45-8.55 (2H, m).

Step 2:

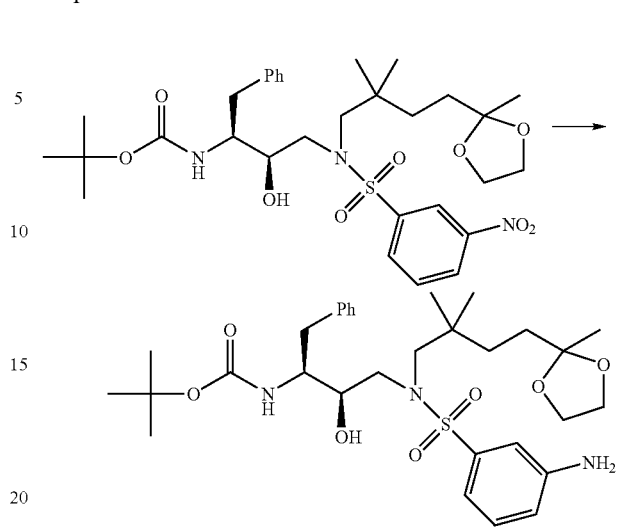

tert-Butyl N-((1S,2R)-3-([(3-aminophenyl)sulfonyl] [2,2-dimethyl-4-(2-methyl-1,3-dioxolan-2-yl)butyl] amino-1-benzyl-2-hydroxypropyl)carbamate A mixture of the product from step 1 (1.92 g, 3.0 mmol), 10% palladium/carbon (500 mg), and 2M ammonia/ethanol (40 mL) was hydrogenated at atmospheric pressure for 4.5 hours. The mixture was diluted with dichloromethane and filtered through celite. Solvent was evaporated and dried in vacuo to provide the title compound (1.6 g, 87%) as a white foam; $^1$H NMR (DMSO-$d_6$): δ 0.9 (6H, s), 1.1 (1H, s), 1.2 (9H, s), 1.3 (2H, t), 11.5 (2H, t), 2.4-2.5 (1H, m), 2.8 (1H, d), 2.9-3.0 (2H, m), 3.2-3.5 (5H, m), 3.75-3.80 (1H, m), 3.82 (4H, s), 4.95 (1H, d), 5.55 (2H, s), 6.58 (1H, d), 6.75 (1H, d), 6.85 (1H, d), 7.0 (1H, s), 7.1-7.3 (6H, m)

Step 3:

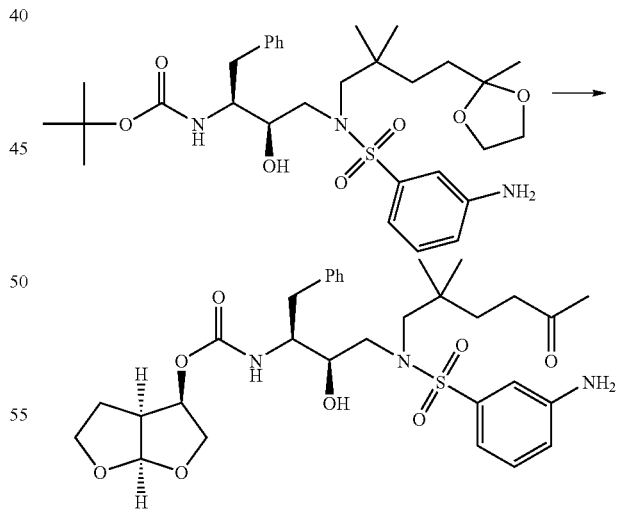

(3R,3aS,6aR)-Hexahydrofuro[2,3-b]furan-3-yl N-((1S,2R)-3-([(3-aminophenyl)sulfonyl](2,2-dimethyl-5-oxohexyl)amino-1-benzyl-2-hydroxypropyl) carbamate The product from step 2 was subjected to the procedure used in Example (Compound 205) to afford the title compound as a foam; ¹H NMR (DMSO-d₆): δ 0.85 (3H, s), 0.90 (3H, s), 1.1-1.2 (1H, m), 1.3-1.4 (1H, m), 1.45 (2H, t), 2.1 (3H, s), 2.25-2.35 (3H, m), 2.7-2.8 (2H, m), 2.85 (1H, dd), 2.90 (1H, dd), 3.30-3.35 (2H, m), 3.45 (1H, br quartet), 3.55 (1H, dd), 3.58-3.60 (1H, m), 3.7 (1H, td), 3.75-3.85 (2H, m), 4.8 (1H, dt), 5.1 (1H, d), 5.48 (1H, d), 5.55 (2H, br s), 6.77 (1H, dd), 6.85 (1H, br d), 6.97 (1H, s), 7.10-7.25 (7H, m); MS: 618.2 (MH⁺); $C_{31}H_{43}N_3O_8S$.

EXAMPLE (COMPOUND 254)

Step 1:

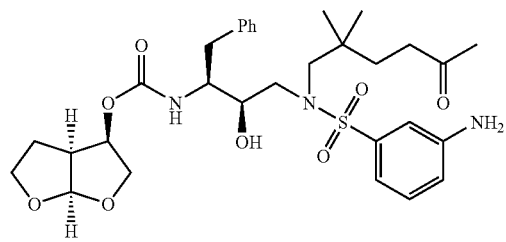

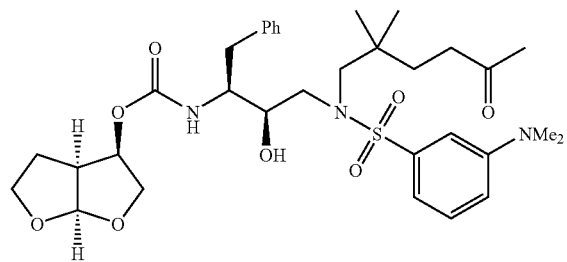

(3R,3aS,6aR)-Hexahydrofuro[2,3-b]furan-3-yl N-((1S,2R)-3-([(3-dimethylaminophenyl)sulfonyl](2,2-dimethyl-5-oxohexyl)amino-1-benzyl-2-hydroxypropyl)carbamate The product from step 1 (Example (Compound 253)) was dissolved (0.10 g) in ethanol (3 mL) and 37% HCOH/water (0.4 mL) was hydrogenated at atmospheric pressure with 10% Pd/C (25 mg) for 18 hours. The mixture was filtered through a bed celite, evaporated, and dissolved in dichloromethane. The solution was washed with water, dried (sodium sulfate), evaporated, and dried in vacuo to provide the title compound (90 mg) as a foam. 0.87 (3H, s), 0.88 (3H, s), 1.1-1.2 (1H, m), 1.25-1.40 (1H, m), 1.45 (2H, t), 2.05 (3H, s), 2.30-2.45 (3H, m), 2.7-2.8 (2H, m), 2.9 (8H, br s), 3.2-3.3 (2H, m), 3.4-3.6 (3H, m), 3.7 (1H, t), 3.8 (1H, d), 3.85 (1H, d), 4.8 (1H, dt), 5.1 (1H, d), 5.5 (1H, d), 6.97 (1H, d), 6.98 (1H, s), 7.0 (1H, d), 7.10-7.22 (6H, m), 7.35 (1H, t); MS: 646.2 (MH⁺); $C_{33}H_{47}N_3O_8S$.

EXAMPLE (COMPOUND 255)

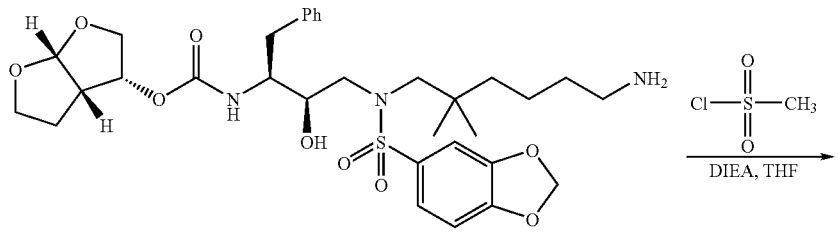

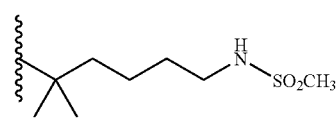

(3R,3aS,6aR)hexahydrofuro[2,3-b]furan-3-yl N-[(1S,2R)-3-((1,3-benzodioxol-5-ylsulfonyl)2,2-dimethyl-6-[(methylsulfonyl)amino]hexylamino)-1-benzyl-2-hydroxypropyl]carbamate A solution of 60 mg (0.093 mmol) of (3R,3aS,6aR)hexahydrofuro[2,3-b]furan-3-yl N-(1S,2R)-3-[(6-amino-2,2-dimethylhexyl)(1,3-benzodioxol-5-ylsulfonyl)amino]-1-benzyl-2-hydroxypropylcarbamate and 20 μL (0.11 mmol) of N,N-diisopropylethylamine in 5 mL of anhydrous THF at 0° C. was treated with 7.9 μL (0.10 mmol) of methanesulfonyl chloride. The solution was allowed to warm to RT with stirring. After 18 hours the solution was concentrated in vacuo and the residue was subjected to flash chromatography (SiO$_2$, 95:5 CH$_2$Cl$_2$/2M NH$_3$ in MeOH) to afford 58 mg (85%) of the desired compound as a white foam. H1-NMR (CDCl$_3$): 7.39 (dd, 1H), 7.34-7.20 (m, 6H), 6.96 (d, 1H), 6.15 (s, 2H), 5.66 (d, 1H), 5.03 (m, 1H), 4.82 (t, 1H), 4.16-3.81 (m, 5H), 3.72 (m, 2H), 3.26-2.72 (m, 9H), 2.99 (s, 3H), 1.60 (m, 3H), 1.49-1.30 (m, 5H), 0.99 (m, 6H). MS(ESI): 748(M+Na).

EXAMPLE (COMPOUND 256)

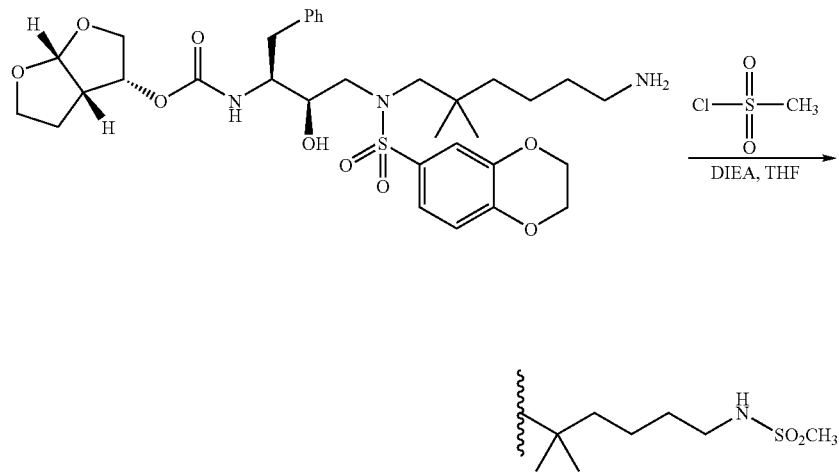

(3R,3aS,6aR)hexahydrofuro[2,3-b]furan-3-yl N-[(1S,2R)-1-benzyl-3-((2,3-dihydro-1,4-benzodioxin-6-ylsulfonyl)2,2-dimethyl-6-[(methylsulfonyl)amino]hexylamino)-2-hydroxypropyl]carbamate A solution of 60 mg (0.091 mmol) of (3R,3aS,6aR)hexahydrofuro[2,3-b]furan-3-yl N-(1S,2R)-3-[(6-amino-2,2-dimethylhexyl)(2,3-dihydro-1,4-benzodioxin-6-ylsulfonyl)amino]-1-benzyl-2-hydroxypropylcarbamate and 20 μL (0.11 mmol) of N,N-diisopropylethylamine in 5 mL of anhydrous THF at 0° C. was treated with 7.8 μL (0.10 mmol) of methanesulfonyl chloride. The solution was allowed to warm to RT with stirring. After 18 hours the solution was concentrated in vacuo and the residue was subjected to flash chromatography (SiO$_2$, 95:5 CH$_2$Cl$_2$/2M NH$_3$ in MeOH) to afford 58 mg (87%) of the desired compound as a white foam. H1-NMR (CDCl$_3$): 7.37-7.19 (m, 7H), 7.02 (d, 1H), 5.67 (d, 1H), 5.02 (m, 2H), 4.85 (t, 1H), 4.36 (m, 4H), 4.10 (m, 2H), 4.00-3.81 (m, 3H), 3.80-3.64 (m, 2H), 3.25-2.70 (m, 9H), 2.99 (s, 3H), 1.60 (m, 3H), 1.49-1.23 (m, 5H), 0.99. (m, 6H). MS(ESI): 762(M+Na).

EXAMPLE (COMPOUND 257)

Step 1:

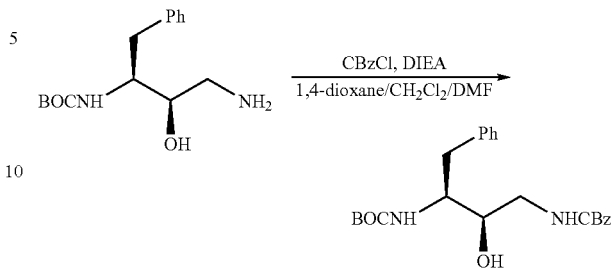

Benzyl N-(2R,3S)-3-[(tert-butoxycarbonyl)amino]-2-hydroxy-4-phenylbutylcarbamate A solution of 20.0 g (71.3 mmol) of tert-butyl N-[(1S,2R)-3-amino-1-benzyl-2-hydroxypropyl]carbamate in 1 L of 4:1:1 dioxane/CH$_2$Cl$_2$/DMF at 0° C. was treated with 13.7 mL (78.4 mmol) of N,N-diisopropylethylamine. A small amount of solid precipitated at this point. The mixture was treated with 10.2 mL (71.3 mmol) of benzyl chloroformate by slow addition over 5 minutes and then allowed to warm to RT. A clear solution resulted which was stirred at RT. After 18 hours the solution was concentrated in vacuo. The residue was suspended (would not dissolve) in CH$_2$Cl$_2$ and the mixture was shaken with 10% aqueous citric acid in a separatory funnel. The aqueous suspension was separated, filtered to remove solid and the aqueous filtrate discarded. The solid was combined with the CH$_2$Cl$_2$ suspension and the mixture concentrated to dryness at reduced pressure. The resulting residue was recrystallized from EtOH/water to afford 24.1 g (81%) of the desired compound at a white crystalline solid. NMR (DMSO-d$_6$): 7.43-7.03 (m, 11H), 6.63 (d, 1H), 5.04 (s, 2H), 4.99 (d, 1H), 3.61-3.40 (m, 2H), 3.30 (m, 1H), 3.06-2.84 (m, 2H), 252 (m, 1H), 1.27 (s, 9H). MS(ESI): 437(M+Na).

Step 2:

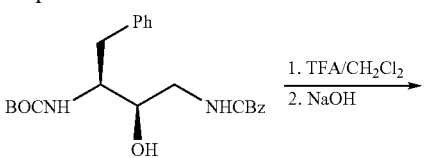

-continued

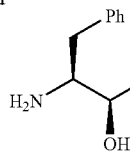

Benzyl N-[(2R,3S)-3-amino-2-hydroxy-4-phenylbutyl]carbamate

A solution of 7.0 g (16.9 mmol) of benzyl N-(2R,3S)-3-[(tert-butoxycarbonyl)amino]-2-hydroxy-4-phenylbutylcarbamate in 100 mL of 1:1 TFA/CH$_2$Cl$_2$ was stirred at RT. After 2.5 hours the solution was concentrated in vacuo. The residue was dissolved in 1:1 CH$_2$Cl$_2$/THF and the solution washed with 1M aqueous NaOH (1×) followed by water (2×). The solution was not exposed to drying agent as this induced crystallization but was instead directly concentrated to dryness at reduced pressure. The residual water was removed by storing in vacuo overnight. This afforded the desired amine as a white solid in quantitative yield. NMR (DMSO-d$_6$): 7.38-7.06 (m, 11H), 5.00 (s, 2H), 4.73 (d, 1H), 3.25 (m, 2H), 3.04 (m, 1H), 2.83 (dd, 1H), 2.71 (m, 1H), 2.29 (dd, 1H), 1.15 (br s, 2H). MS(ESI): 315(M+H).

Step 3:

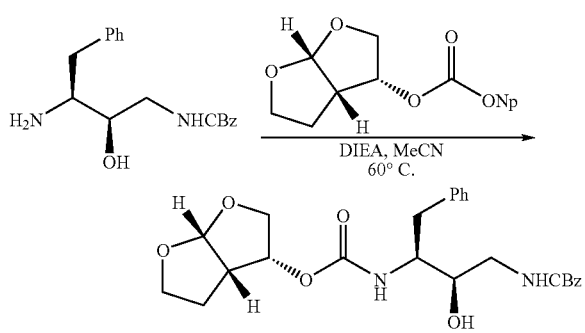

3R,3aS,6aR)hexahydrofuro[2,3-b]furan-3-yl N-((1S,2R)-1-benzyl-3-[(benzyloxy)carbonyl]amino-2-hydroxypropyl)carbamate A solution of 5.31 g (16.9 mmol) of benzyl N-[(2R,3S)-3-amino-2-hydroxy-4-phenylbutyl]carbamate, 4.99 g (16.9 mmol) of (3R,3aS,6aR)hexahydrofuro[2,3-b]furan-3-yl (4-nitrophenyl)carbonate and 5.9 mL (33 mmol) of N,N-diisopropylethylamine in 250 mL of MeCN was heated to 60° C. with stirring under nitrogen. After 24 hours product had precipitated from the solution giving a yellow suspension. The mixture was cooled to RT at which point additional product precipitated. The solid was collected by filtration and dried in vacuo to give 4.9 g of material. The filtrate was concentrated to dryness and the residue recrystallized from MeCN to afford an additional 0.85 g of product for a total yield of 5.8 g (73%). NMR (DMSO-d$_6$): 7.42-7.09 (m, 12H), 5.51 (d, 1H), 5.06 (m, 3H), 4.84 (q, 1H), 3.83 (dd, 1H), 3.72 (t, 1H), 3.67-3.41 (m, 4H), 3.28 (m, 1H), 3.10-2.72 (m, 4H), 2.41 (m, 1H), 1.26 (m, 1H). MS(ESI): 493(M+Na).

Step 4:

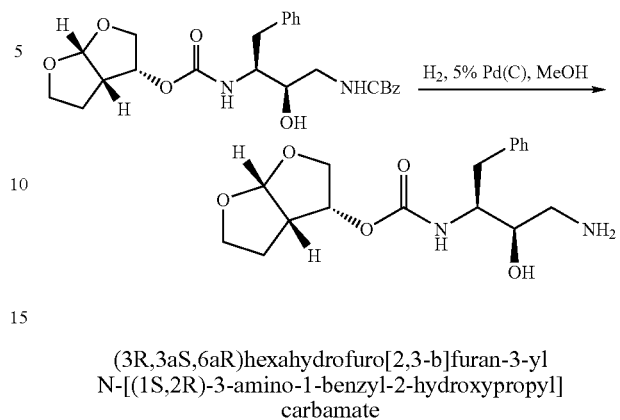

(3R,3aS,6aR)hexahydrofuro[2,3-b]furan-3-yl N-[(1S,2R)-3-amino-1-benzyl-2-hydroxypropyl]carbamate A suspension of 4.0 g (8.5 mmol) of 3R,3aS,6aR)hexahydrofuro[2,3-b]furan-3-yl N-((1S,2R)-1-benzyl-3-[(benzyloxy)carbonyl]amino-2-hydroxypropyl)carbamate and 0.5 g of 5% Pd(C) in 200 mL of MeOH was subjected to hydrogenation at 45 psi. After 3.5 hours the reaction vessel was purged with nitrogen, catalyst was removed by filtration through celite and the filtrate was concentrated in vacuo to afford 2.72 g (95%) of the desired product as a white solid. NMR (DMSO-d$_6$): 7.23-7.04 (m, 6H), 5.45 (d, 1H), 4.91-4.75 (m, 2H), 3.79 (dd, 1H), 3.68 (t, 1H), 3.53 (m, 3H), 3.21 (m, 2H), 3.01 (dd, 1H), 2.74 (q, 1H), 2.57 (dd, 1H), 2.41 (m, 1H), 1.60-1.28 (m, 3H), 1.22 (dd, 1H). MS(ESI): 337(M+H).

Step 5:

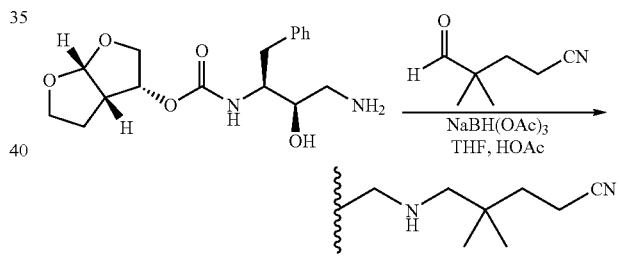

(3R,3aS,6aR)hexahydrofuro[2,3-b]furan-3-yl N-(1S,2R)-1-benzyl-3-[(4-cyano-2,2-dimethylbutyl)amino]-2-hydroxypropylcarbamate A solution of 3.22 g (9.57 mmol) of (3R,3aS,6aR)hexahydrofuro[2,3-b]furan-3-yl N-[(1S,2R)-3-amino-1-benzyl-2-hydroxypropyl]carbamate and 1.32 g (10.5 mmol) of 4-cyano-2,2-dimethylbutyraldehyde in 175 mL of 3:1 THF/glacial HOAc was treated with 2.23 g (10.5 mmol) of NaBH(OAc)$_3$ and the resulting solution was stirred at RT. After 18 hours the solution was concentrated in vacuo and the residue dissolved in CH$_2$Cl$_2$. The solution was washed with 1M aqueous NaOH (1×), brine (2×), dried over MgSO$_4$, and concentrated to give a viscous oil. The crude product was purified by flash chromatography (SiO$_2$, 95:5 CH$_2$Cl$_2$/2M NH$_3$ in MeOH) to afford 3.2 g (75%) of the desired compound as a white foam. NMR (CDCl$_3$): 7.38-7.20 (m, 5H), 5.67 (d, 1H), 5.08 (m, 2H), 4.04-3.81 (m, 3H), 3.72 (m, 2H), 3.59 (q, 1H), 3.13 (dd, 1H), 2.96 (m, 1H), 2.79 (m, 3H), 2.42 (s, 2H), 2.32 (t, 2H), 1.79-1.43 (m, 6H), 1.00 (m, 6H). MS(ESI): 446(M+H).

Step 6:

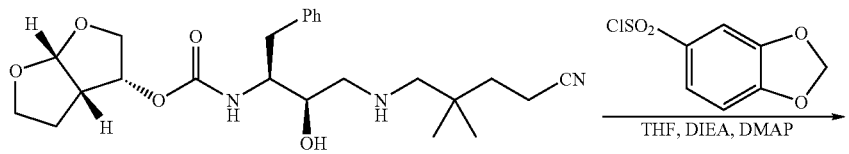

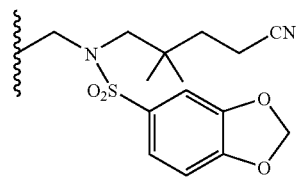

(3R,3aS,6aR)hexahydrofuro[2,3-b]furan-3-yl N-(1S,2R)-3-[(1,3-benzodioxol-5-ylsulfonyl)(4-cyano-2,2-dimethylbutyl)amino]-1-benzyl-2-hydroxypropylcarbamate A solution of 0.50 g (1.1 mmol) of (3R,3aS,6aR)hexahydrofuro[2,3-b]furan-3-yl N-(1S,2R)-1-benzyl-3-[(4-cyano-2,2-dimethylbutyl)amino]-2-hydroxypropylcarbamate, 0.27 g (1.2 mmol) of 3,4-methylenedioxybenzenesulfonyl chloride, 0.23 mL (1.3 mmol) of N,N-diisopropylethylamine, and 13 mg of DMAP in 15 mL of anhydrous THF was stirred at RT. After 18 hours the solution was concentrated in vacuo and the residue subjected to flash chromatography (SiO$_2$, 95:5 CH$_2$Cl$_2$/2M NH$_3$ in MeOH) to afford 0.63 g (91%) of the desired product as a white foam. NMR (CDCl$_3$): 7.32 (d, 1H), 7.30-7.14 (m, 6H), 6.90 (d, 1H), 6.09 (s, 2H), 5.61 (d, 1H), 4.99 (q, 1H), 4.82 (d, 1H), 4.02 (m, 11H), 3.92 (dd, 1H), 3.81 (m, 3H), 3.76-3.58 (m, 3H), 3.14 (dd, 1H), 3.04 (m, 2H), 2.86 (m, 2H), 2.71 (dd, 1H), 2.37 (t, 2H), 1.74 (t, 2H), 1.58 (m, 1H), 1.39 (m, 1H), 0.98 (s, 6H). MS(ESI): 652(M+Na).

Step 7:

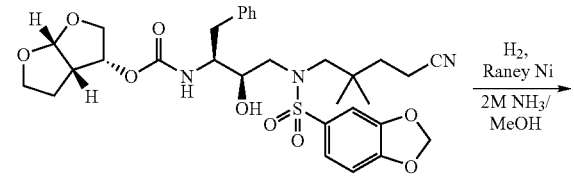

3R,3aS,6aR)hexahydrofuro[2,3-b]furan-3-yl N-(1S,2R)-3-[(5-amino-2,2-dimethylpentyl)(1,3-benzodioxol-5-ylsulfonyl)amino]-1-benzyl-2-hydroxypropylcarbamate A mixture of 0.63 g (0.99 mmol) of (3R,3aS,6aR)hexahydrofuro[2,3-b]furan-3-yl N-(1S,2R)-3-[(1,3-benzodioxol-5-ylsulfonyl)(4-cyano-2,2-dimethylbutyl)amino]-1-benzyl-2-hydroxypropylcarbamate and approximately 150 mg of Raney nickel (washed with water and MeOH) in 35 mL of 2M NH$_3$/MeOH was subjected to hydrogenation at 45 psi. After 3 hours the reaction vessel was purged with nitrogen, catalyst removed by filtration through celite and the filtrate concentrated in vacuo. The residue was subjected to flash chromatography (SiO$_2$, 9:1 CH$_2$Cl$_2$/2M NH$_3$ in MeOH) to afford 0.49 g (77%) of the desired amine as a white foam. NMR (CDCl$_3$): 7.40 (dd, 1H), 7.37-7.20 (m, 6H), 7.07 (d, 1H), 6.95 (d, 1H), 6.15 (s, 2H), 5.66 (d, 1H), 5.06 (q, 1H), 4.06-3.63 (7H), 3.37-2.58 (m, 9H), 1.73-1.05 (m, 6H), 1.03 (s, 3H), 0.92 (s, 3H). MS(ESI): 634(M+H).

EXAMPLE (COMPOUND 258)

Step 1:

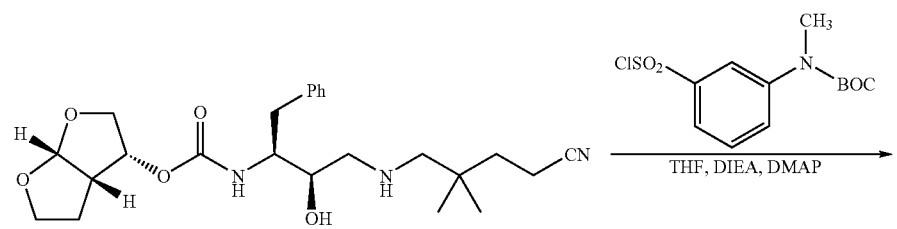

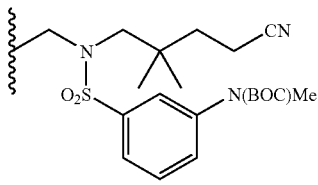

(3R,3aS,6aR)hexahydrofuro[2,3-b]furan-3-yl N-(1S, 2R)-1-benzyl-3-[(3-[(tert-butoxycarbonyl)(methyl) amino]phenylsulfonyl)(4-cyano-2,2-dimethylbutyl) amino]-2-hydroxypropylcarbamate A solution of 0.60 g (1.4 mmol) of (3R,3aS,6aR)hexahydrofuro[2,3-b]furan-3-yl N-(1S,2R)-1-benzyl-3-[(4-cyano-2,2-dimethylbutyl)amino]-2-hydroxypropylcarbamate (Example (Compound 257)), 0.83 g (2.7 mmol) of 3-[(tert-butoxycarbonyl)(methyl)amino]benzenesulfonyl chloride, 0.50 mL (2.8 mmol) of N,N-diisopropylethylamine, and 17 mg of DMAP in 15 mL of anhydrous THF was stirred at RT. After 18 hours the solution was concentrated in vacuo and the residue subjected to flash chromatography (SiO$_2$, 97:3 to 95:5 CH$_2$Cl$_2$/2M NH$_3$ in MeOH) to afford 0.36 g (36%) of the desired product as a light yellow foam. NMR (CDCl$_3$): 7.86 (s, 1H), 7.51 (m, 2H), 7.41 (d, 1H), 7.30-7.11 (m, 6H), 5.60 (d, 1H), 5.26 (m, 1H), 4.90 (q, 1H), 3.86 (m, 2H), 3.72 (m, 2H), 3.59 (m, 3H), 3.28 (s, 3H), 3.25 (d, 1H), 3.15 (m, 2H), 3.00 (d, 1H), 2.81 (m, 1H), 2.59 (dd, 1H), 2.39 (t, 2H), 1.78 (t, 2H), 1.54 (m, 1H), 1.52 (s, 9H), 1.26 (m, 1H), 1.00 (d, 6H). MS(ESI): 737(M+Na).

Step 2:

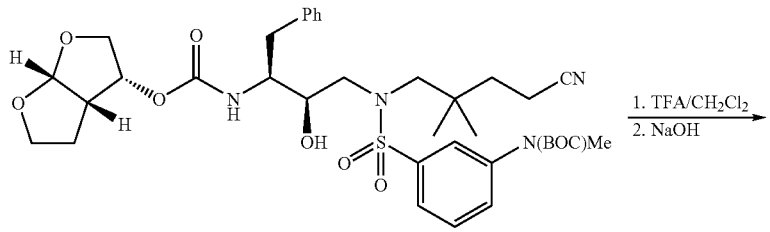

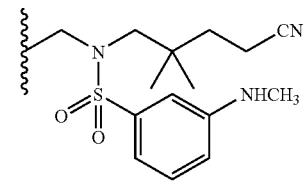

(3R,3aS,6aR)hexahydrofuro[2,3-b]furan-3-yl N-[(1S,2R)-1-benzyl-3-((4-cyano-2,2-dimethylbutyl) [3-(methylamino)phenyl]sulfonylamino)-2-hydroxypropyl]carbamate A solution of 0.35 g (0.49 mmol) of (3R,3aS,6aR)hexahydrofuro[2,3-b]furan-3-yl N-(1S,2R)-1-benzyl-3-[(3-[(tert-butoxycarbonyl)(methyl)amino]phenylsulfonyl)(4-cyano-2, 2-dimethylbutyl)amino]-2-hydroxypropylcarbamate in 20 mL of 1:1 TFA/CH$_2$Cl$_2$ was stirred at RT for 2 hours and then concentrated in vacuo. The residue was dissolved in CH$_2$Cl$_2$. The solution was washed with 1M aqueous NaOH (1×), aqueous brine (3×), dried over MgSO$_4$, and concentrated at reduced pressure to afford 0.29 g (95%) of the desired product as a colorless viscous oil. NMR (CDCl$_3$): 7.40-7.19 (m, 7H), 7.08 (d, 1H), 6.99 (s, 1H), 6.81 (dd, 1H), 5.68 (d, 1H), 5.02 (q, 1H), 4.88 (d, 1H), 4.23-3.62 (m, 7H), 3.34-2.84 (m, 8H), 2.79 (dd, 1H), 2.42 (t, 2H), 1.80 (t, 2H), 1.61 (m, 1H), 1.42 (m, 1H), 1.01 (s, 6H). MS(ESI): 615(M+H).

Step 3:

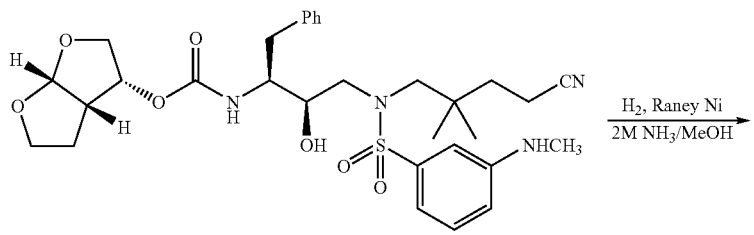

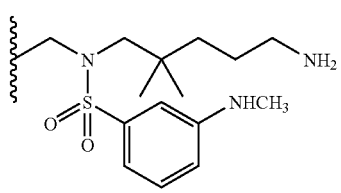

(3R,3aS,6aR)hexahydrofuro[2,3-b]furan-3-yl N-[(1S,2R)-3-((5-amino-2,2-dimethylpentyl) [3-(methylamino)phenyl]sulfonylamino)-1-benzyl-2-hydroxypropyl]carbamate A mixture of 0.29 g (0.46 mmol) of (3R,3aS,6aR)hexahydrofuro[2,3-b]furan-3-yl N-[(1S,2R)-1-benzyl-3-((4-cyano-2,2-dimethylbutyl) [3-(methylamino)phenyl]sulfonylamino)-2-hydroxypropyl]carbamate and approximately 50 mg of Raney nickel (washed with water and MeOH) in 60 mL of 2M $NH_3$/MeOH was subjected to hydrogenation at 45 psi. After 1.5 hours the reaction vessel was purged with nitrogen, catalyst-removed by filtration through celite and the filtrate concentrated in vacuo. The residue was subjected to flash chromatography ($SiO_2$, 9:1 $CH_2Cl_2$/2M $NH_3$ in MeOH) to afford 0.22 g (76%) of the desired amine as a white foam. NMR ($CDCl_3$): 7.39-7.19 (m, 6H), 7.10 (d, 1H), 7.04-6.92 (m, 2H), 6.81 (dd, 1H), 5.63 (d, 1H), 5.05 (q, 1H), 4.16 (br s, 1H), 4.09-3.80 (m, 4H), 3.70 (m, 2H), 3.31 (m, 2H), 3.21-3.00 (m, 3H), 2.99-2.58 (m, 5H), 2.90 (s, 3H), 2.57-2.10 (br, 2H), 1.82-1.07 (m, 6H), 1.04 (s, 3H), 0.92 (s, 3H). MS(ESI): 619 (M+H).

EXAMPLE (COMPOUND 259)

-continued

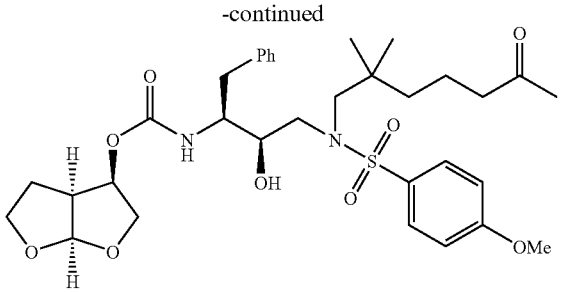

(3R,3aS,6aR)-Hexahydrofuro[2,3-b]furan-3-yl N-((1S,2R)-1-benzyl-3-(2,2-dimethyl-5-oxoheptyl) [(4-methoxyphenyl)sulfonyl]amino-2-hydroxypropyl)carbamate The product from step 3 (Example (Compound 209)) was subjected to procedures similar to those in Example (Compound 252) to give the title compound as a foam; $^1$H NMR (DMSO-$d_6$): δ 0.88 (6H, s), 1.10-1.25 (4H, m), 1.3-1.5 (2H, m), 2.03 (3H, s), 2.25-2.35 (3H, m), 2.73 (1H, d), 2.79 (1H, t), 2.85-3.00 (2H, m), 3.2-3.3 (3H, m), 3.35-3.40 (1H, m), 3.55 (1H, dd), 3.6 (1H, dd), 3.65-3.75 (2H, m), 3.8 (3H, s), 4.8 (1H, dt), 5.05 (1H, d), 5.5 (1H, d), 7.1 (2H, d), 7.15-7.25 (6H, m), 7.75 (2H, d); MS: 669.1 (M+23); $C_{33}H_{46}N_2O_9S$.

EXAMPLE (COMPOUND 260)

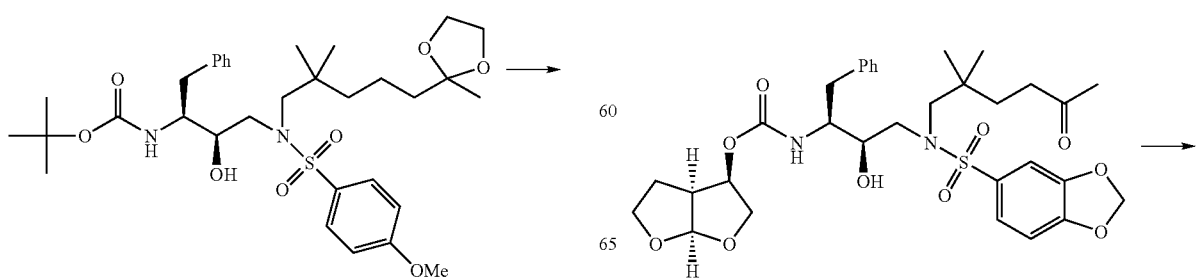

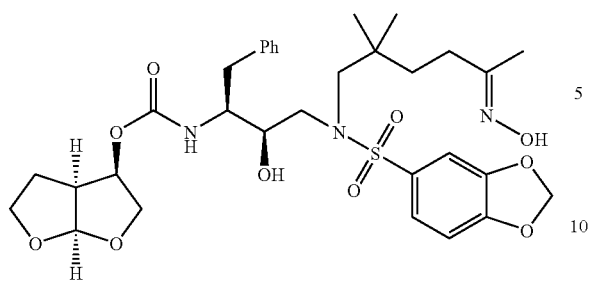

(3R,3aS,6aR)-Hexahydrofuro[2,3-b]furan-3-yl N-((1S,2R)-1-benzyl-3-(2,2-dimethyl-5-hydroxyimi- nohexyl)[(3,4-methylenedioxyphenyl)sulfonyl] amino-2-hydroxypropyl)carbamate The product from Example (Compound 240) was subjected to the procedure in Example (Compound 227) to afford the title compound as a foam; $^1$H NMR (DMSO-d$_6$): 0.90 (6H, s), 1.1 (1H, dd), 1.20-1.45 (3H, m), 1.75 (3H, s), 2.05-2.10 (2H, m), 2.2 (1H, d), 2.7-2.8 (2H, m), 2.9-3.0 (2H, m), 3.25-3.35 (2H, m), 3.37-3.42 (1H, m), 3.55 (1H, d), 3.60 (1H, d), 3.7 (1H, t), 3.72-3.75 (1H, m), 3.79 (1H, d), 3.80 (1H, d), 4.8 (1H, dt), 5.1 (1H, d), 5.5 (1H, d), 6.2 (2H, s), 7.05 (1H, d), 7.10-7.25 (7H, m), 7.35 (1H, d); MS: 662.1 (MH$^+$); C$_{32}$H$_{43}$N$_3$O$_{10}$S.

EXAMPLE (COMPOUND 261)

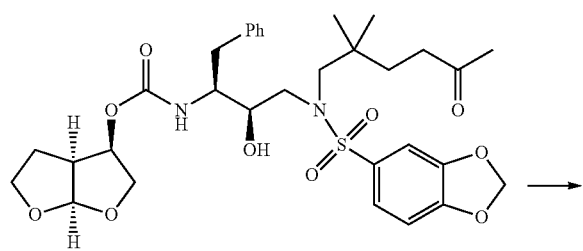

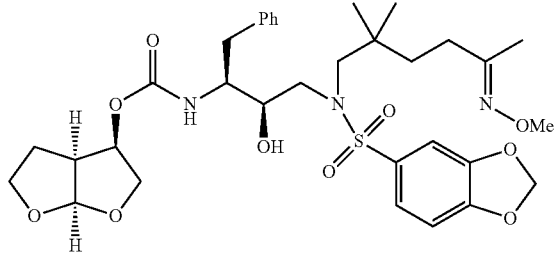

(3R,3aS,6aR)-Hexahydrofuro[2,3-b]furan-3-yl-N- ((1S,2R)-1-benzyl-3-(2,2-dimethyl-5-methoxyimino- hexyl)[(3,4-methylenedioxyphenyl)sulfonyl]amino- 2-hydroxypropyl)carbamate The product from Example (Compound 240) was subjected to a procedure similar to that of Example (Compound 227), using methoxylamine hydrochloride to provide the title compound as a foam; $^1$H NMR (DMSO-d$_6$): δ 0.90 (6H, s), 1.15 (1H, dd), 1.30-1.45 (3H, m), 1.75 (3H, s), 2.05-2.15 (2H, m), 2.2 (1H, d), 2.7-2.8 (2H, m), 2.95 (1H, d), 3.3-3.5 (3H, m), 3.52-3.60 (2H, m), 3.7 (3H, s), 3.75-3.83 (3H, m), 4.8 (1H, dt), 5.15 (1H, d), 5.5 (1H, d), 6.1 (2H, s), 7.05 (1H, d), 7.10-7.25 (7H, m), 7.35 (1H, d); MS: 676.2 (MH$^+$); C$_{33}$H$_{45}$N$_3$O$_{10}$S.

EXAMPLE (COMPOUND 262)

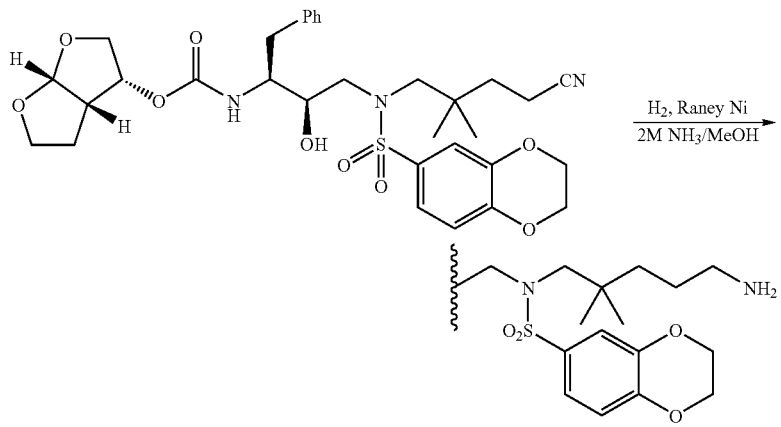

(3R,3aS,6aR)hexahydrofuro[2,3-b]furan-3-yl N-(1S, 2R)-3-[(5-amino-2,2-dimethylpentyl)(2,3-dihydro-1, 4-benzodioxin-6-ylsulfonyl)amino]-1-benzyl-2-hy- droxypropylcarbamate A mixture of 0.53 g (0.82 mmol) of (3R,3aS,6aR)hexahydrofuro[2,3-b]furan-3-yl N-(1S,2R)-1-benzyl-3-[(4-cyano-2,2-dimethylbutyl)(2,3-dihydro-1,4-benzodioxin-6-ylsulfonyl)amino]-2-hydroxypropylcarbamate (obtained in a directly analogous way to that outlined in Example (Compound 257)) and approximately 50 mg of Raney nickel (washed with water and MeOH) in 60 mL of 2M NH$_3$/MeOH was subjected to hydrogenation at 45 psi. After 2.0 hours the reaction vessel was purged with nitrogen, catalyst removed by filtration through celite and the filtrate concentrated in vacuo. The residue was subjected to flash chromatography (SiO$_2$, 9:1 CH$_2$Cl$_2$/2M NH$_3$ in MeOH) to afford 0.46 g (87%) of the desired amine as a white foam. NMR (CDCl$_3$): 7.37-7.19 (m, 8H), 7.01 (m, 2H), 5.64 (d, 1H), 5.05 (q, 1H), 4.36 (m, 4H), 4.06-3.79 (m, 4H), 3.70 (m, 2H), 3.36-2.58 (m, 11H), 2.58-2.00 (br, 2H), 1.71-1.27 (m, 4H), 1.02 (s, 3H), 0.91 (s, 3H). MS(ESI): 648(M+H).

EXAMPLE (COMPOUND 263)

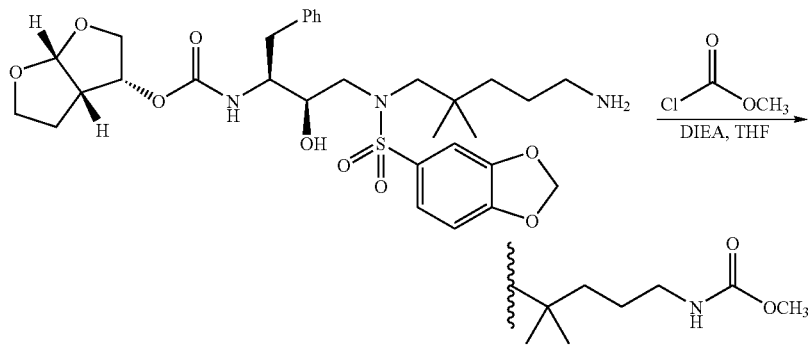

(3R,3aS,6aR)hexahydrofuro[2,3-b]furan-3-yl N-[(1S,2R)-3-((1,3-benzodioxol-5-ylsulfonyl)-5-[(methoxycarbonyl)amino]-2,2-dimethylpentylamino)-1-benzyl-2-hydroxypropyl]carbamate A solution of 60 mg (0.095 mmol) of 3R,3aS,6aR)hexahydrofuro[2,3-b]furan-3-yl N-(1S,2R)-3-[(5-amino-2,2-dimethylpentyl)(1,3-benzodioxol-5-ylsulfonyl)amino]-1-benzyl-2-hydroxypropylcarbamate and 20 µL (0.12 mmol) of N,N-diisopropylethylamine in 4 mL of anhydrous THF at 0° C. was treated with 8.1 µL (0.11 mmol) of methyl chloroformate. The solution was allowed to warm to RT with stirring. After 18 hours the solution was concentrated in vacuo and the residue was subjected to flash chromatography (SiO$_2$, 95:5 CH$_2$Cl$_2$/2M NH$_3$ in MeOH) to afford 65 mg (98%) of the desired compound as a white foam. H1-NMR (CDCl$_3$): 7.40 (dd, 1H), 7.32-7.20 (m, 6H), 6.95 (d, 1H), 6.13 (s, 2H), 5.65 (d, 1H), 5.45 (d, 1H), 5.04 (m, 2H), 4.20-3.80 (m, 5H), 3.71 (m, 5H), 3.30-2.68 (m, 9H), 1.70-1.20 (m, 6H), 0.98 (s, 3H), 0.92 (s, 3H).

MS(ESI): 714(M+Na).

EXAMPLE (COMPOUND 264)

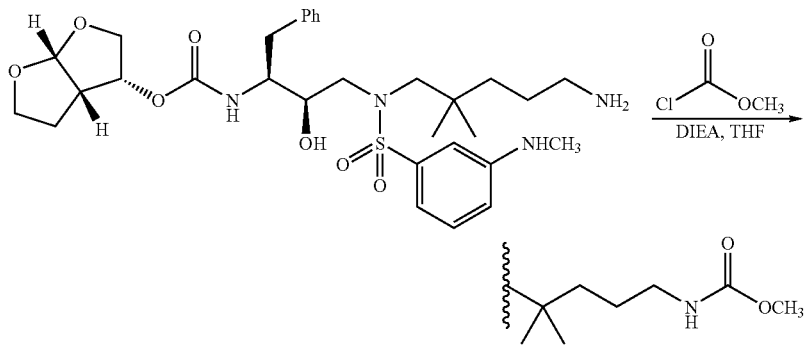

(3R,3aS,6aR)hexahydrofuro[2,3-b]furan-3-yl N-[(1S,2R)-1-benzyl-2-hydroxy-3-(5-[(methoxycarbonyl)amino]-2,2-dimethylpentyl[3-(methylamino)phenyl]sulfonylamino) propyl]carbamate A solution of 50 mg (0.081 mmol) of (3R,3aS,6aR)hexahydrofuro[2,3-b]furan-3-yl N-[(1S,2R)-3-((5-amino-2,2-dimethylpentyl)[3-(methylamino)phenyl]sulfonylamino)-1-benzyl-2-hydroxypropyl]carbamate and 17 µL (0.097 mmol) of N,N-diisopropylethylamine in 4 mL of anhydrous THF at 0° C. was treated with 6.9 µL (0.089 mmol) of methyl chloroformate. The solution was allowed to warm to RT with stirring. After 18 hours the solution was concentrated in vacuo and the residue was subjected to flash chromatography (SiO$_2$, 95:5 CH$_2$Cl$_2$/2M NH$_3$ in MeOH) to afford 54 mg (98%) of the desired compound as a white foam. H1-NMR (CDCl$_3$): 7.28 (m, 6H), 6.99 (d, 1H), 6.89 (s, 1H), 6.71 (dd, 1H), 5.54 (d, 1H), 5.30 (d, 1H), 4.93 (m, 2H), 4.17-3.50 (m, 11H), 3.25-2.60 (m, 12H), 1.60-1.12 (m, 6H), 0.89 (s, 3H), 0.81 (s, 3H). MS(ESI): 677(M+H)

EXAMPLE (COMPOUND 265)

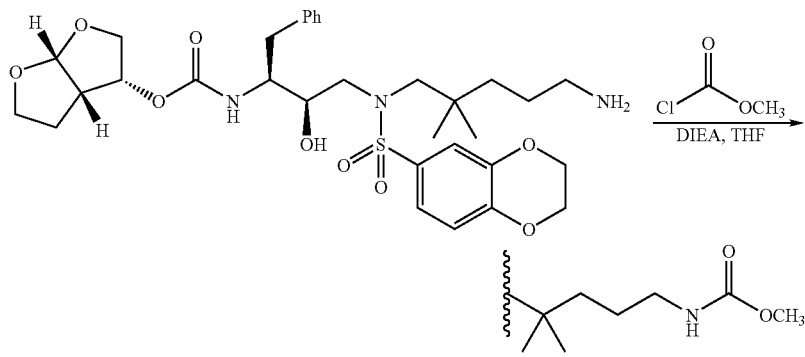

(3R,3aS,6aR)hexahydrofuro[2,3-b]furan-3-yl N-[1S,2R)-1-benzyl-3-((2,3-dihydro-1,4-benzodioxin-6-ylsulfonyl)-5-[(methoxycarbonyl)amino]-2,2-dimethylpentylamino)-2-hydroxypropyl]carbamate A solution of 60 mg (0.093 mmol) of (3R,3aS,6aR)hexahydrofuro[2,3-b]furan-3-yl N-(1S,2R)-3-[(5-amino-2,2-dimethylpentyl)(2,3-dihydro-1,4-benzodioxin-6-ylsulfonyl)amino]-1-benzyl-2-hydroxypropylcarbamate and 20 µL (0.11 mmol) of N,N-diisopropylethylamine in 4 mL of anhydrous THF at 0° C. was treated with 7.9 µL (0.10 mmol) of methyl chloroformate. The solution was allowed to warm to RT with stirring. After 18 hours the solution was concentrated in vacuo and the residue was subjected to flash chromatography (SiO₂, 95:5 CH$_2$Cl$_2$/2M NH$_3$ in MeOH) to afford 60 mg (91%) of the desired compound as a white foam. H1-NMR (CDCl$_3$): 7.38-7.19 (m, 7H), 7.01 (d, 1H), 5.64 (d, 1H), 5.42 (d, 1H), 5.02 (m/2H), 4.36 (m, 4H), 4.19 (s, 1H), 4.12-3.80 (m, 4H), 3.70 (m, 5H), 3.30-2.70 (m, 9H), 1.61-1.22 (m, 6H), 0.98 (s, 3H), 0.91 (s, 3H). MS(ESI): 728(M+Na).

EXAMPLE (COMPOUND 266)

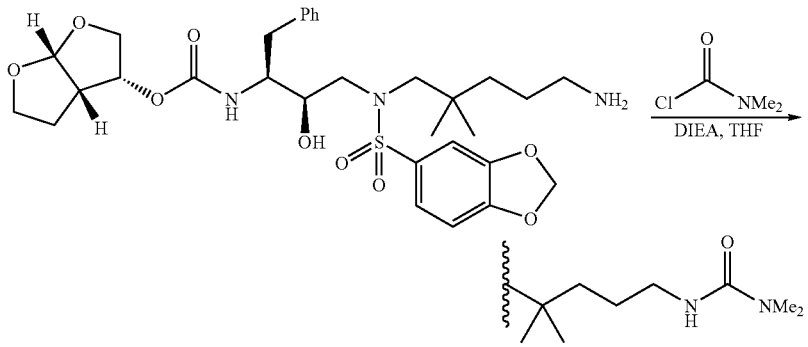

(3R,3aS,6aR)hexahydrofuro[2,3-b]furan-3-yl N-(1S,2R)-3-[(1,3-benzodioxol-5-ylsulfonyl)(5-[(dimethylamino)carbonyl]amino-2,2-dimethylpentyl)amino]-1-benzyl-2-hydroxypropylcarbamate A solution of 60 mg (0.095 mmol) of 3R,3aS,6aR)hexahydrofuro[2,3-b]furan-3-yl N-(1S,2R)-3-[(5-amino-2,2-dimethylpentyl)(1,3-benzodioxol-5-ylsulfonyl)amino]-1-benzyl-2-hydroxypropylcarbamate and 20 µL (0.11 mmol) of N,N-diisopropylethylamine in 5 mL of anhydrous THF at 0° C. was treated with 9.6 µL (0.11 mmol) of N,N-dimethylcarbamyl chloride. The solution was allowed to warm to RT with stirring. After 18 hours the solution was concentrated in vacuo and the residue was subjected to flash chromatography (SiO₂, 95:5 CH$_2$Cl$_2$/2M NH$_3$ in MeOH) to afford 55 mg (82%) of the desired compound as a white foam. H1-NMR (CDCl$_3$): 7.35 (d, 1H), 7.27-7.11 (m, 6H), 6.88 (d, 1H), 6.08 (s, 2H), 6.03 (d, 1H), 5.60 (d, 1H), 4.94 (q, 1H), 4.63 (br s, 1H), 3.89 (m, 2H), 3.80 (m, 2H), 3.62 (m, 2H), 3.32-3.01 (m, 6H), 2.88 (s, 6H), 2.81 (m, 3H), 2.69 (dd, 1H), 1.58-1.17 (m, 6H), 0.95 (s, 3H), 0.86 (s, 3H). MS(ESI): 705(M+H).

EXAMPLE (COMPOUND 267)

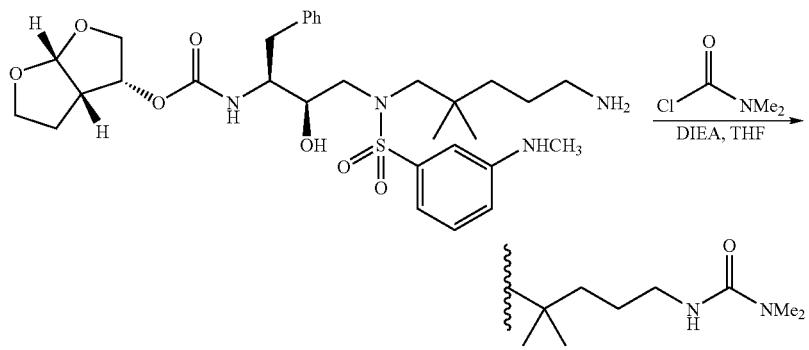

(3R,3aS,6aR)hexahydrofuro[2,3-b]furan-3-yl N-[(1S,2R)-1-benzyl-3-((5-[(dimethylamino)carbonyl]amino-2,2-dimethylpentyl)[3-(methylamino)phenyl]sulfonylamino)-2-hydroxypropyl]carbamate A solution of 50 mg (0.081 mmol) of (3R,3aS,6aR)hexahydrofuro[2,3-b]furan-3-yl N-[(1S,2R)-3-((5-amino-2,2-dimethylpentyl) [3-(methylamino)phenyl]sulfonylamino)-1-benzyl-2-hydroxypropyl]carbamate and 17 µL (0.097 mmol) of N,N-diisopropylethylamine in 5 mL of anhydrous THF at 0° C. was treated with 8.2 µL (0.089 mmol) of N,N-dimethylcarbamyl chloride. The solution was allowed to warm to RT with stirring. After 18 hours the solution was concentrated in vacuo and the residue was subjected to flash chromatography ($SiO_2$, 95:5 $CH_2Cl_2$/2M $NH_3$ in MeOH) to afford 44 mg (79%) of the desired compound as a white foam. H1-NMR ($CDCl_3$): 7.31-7.11 (m, 6H), 7.03 (d, 1H), 6.95 (s, 1H), 6.73 (d, 1H), 5.92 (d, 1H), 5.60 (d, 1H), 4.94 (q, 1H), 4.63 (t, 1H), 4.19 (m, 2H), 3.94-3.73 (m, 4H), 3.63 (m, 2H), 3.30-3.00 (m, 6H), 2.91-2.78 (m, 11H), 2.69 (dd, 1H), 1.59-1.19 (m, 6H), 0.94 (s, 3H), 0.86 (s, 3H). MS(ESI): 690(M+H).

EXAMPLE (COMPOUND 268)

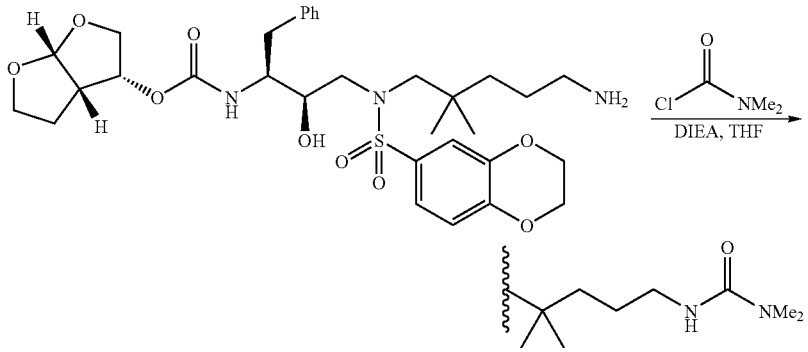

(3R,3aS,6aR)hexahydrofuro[2,3-b]furan-3-yl N-(1S,2R)-1-benzyl-3-[(2,3-dihydro-1,4-benzodioxin-6-ylsulfonyl)(5-[(dimethylamino)carbonyl]amino-2,2-dimethylpentyl)amino]-2-hydroxypropylcarbamate A solution of 60 mg (0.093 mmol) of (3R,3aS,6aR)hexahydrofuro[2,3-b]furan-3-yl N-(1S,2R)-3-[(5-amino-2,2-dimethylpentyl)(2,3-dihydro-1,4-benzodioxin-6-ylsulfonyl) amino]-1-benzyl-2-hydroxypropylcarbamate and 20 µL (0.11 mmol) of N,N-diisopropylethylamine in 5 mL of anhydrous THF at 0° C. was treated with 9.4 µL (0.10 mmol) of N,N-dimethylcarbamyl chloride. The solution was allowed to warm to RT with stirring. After 18 hours the solution was concentrated in vacuo and the residue was subjected to flash chromatography ($SiO_2$, 95:5 $CH_2Cl_2$/2M $NH_3$ in MeOH) to afford 54 mg (81%) of the desired compound as a white foam. H1-NMR ($CDCl_3$): 7.31-7.12 (m, 7H), 6.96 (d, 1H), 6.02 (d, 1H), 5.60 (d, 1H), 4.95 (q, 1H), 4.62 (t, 1H), 4.34-4.21 (m, 5H), 3.91 (m, 2H), 3.80 (m, 2H), 3.62 (m, 2H), 3.32-2.99 (m, 6H), 2.89 (s, 6H), 2.80 (m, 2H), 2.69 (dd, 1H), 1.58-1.18 (m, 6H), 0.93 (s, 3H), 0.86 (s, 3H). MS(ESI): 719(M+H).

EXAMPLE (COMPOUND 269)

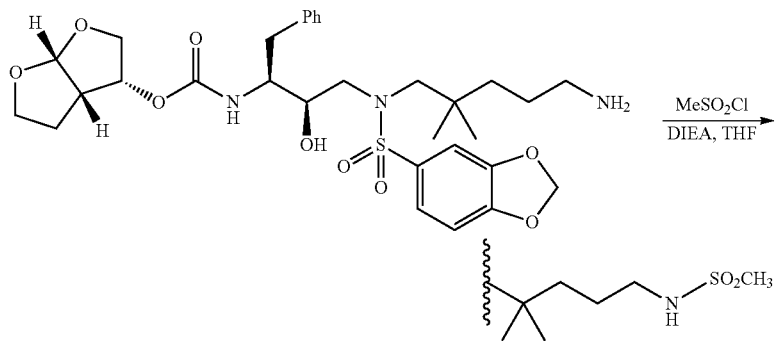

(3R,3aS,6aR)hexahydrofuro[2,3-b]furan-3-yl N-[(1S,2R)-3-((1,3-benzodioxol-5-ylsulfonyl)2,2-dimethyl-5-[(methylsulfonyl)amino]pentylamino)-1-benzyl-2-hydroxypropyl]carbamate A solution of 60 mg (0.095 mmol) of 3R,3aS,6aR)hexahydrofuro[2,3-b]furan-3-yl N-(1S,2R)-3-[(5-amino-2,2-dimethylpentyl)(1,3-benzodioxol-5-ylsulfonyl)amino]-1-benzyl-2-hydroxypropylcarbamate and 20 µL (0.11 mmol) of N,N-diisopropylethylamine in 5 mL of anhydrous THF at 0° C. was treated with 8.1 µL (0.11 mmol) of methanesulfonyl chloride. The solution was allowed to warm to RT with stirring. After 18 hours the solution was concentrated in vacuo and the residue was subjected to flash chromatography (SiO$_2$, 95:5 CH$_2$Cl$_2$/2M NH$_3$ in MeOH) to afford 66 mg (97%) of the desired compound as a white foam. H1-NMR (CDCl$_3$): 7.33 (d, 1H), 7.29-7.14 (m, 6H), 6.89 (d, 1H), 6.09 (s, 2H), 5.60 (d, 1H), 5.14 (d, 1H), 4.96 (m, 2H), 4.04 (m, 2H), 3.90 (dd, 1H), 3.81 (m, 2H), 3.68 (m, 2H), 3.21-3.02 (m, 5H), 2.96 (d, 1H), 2.91 (s, 3H), 2.89-2.66 (m, 3H), 1.55 (m, 3H), 1.47-1.28 (m, 3H), 0.95 (s, 3H), 0.90 (s, 3H). MS(ESI): 734(M+Na).

EXAMPLE (COMPOUND 270)

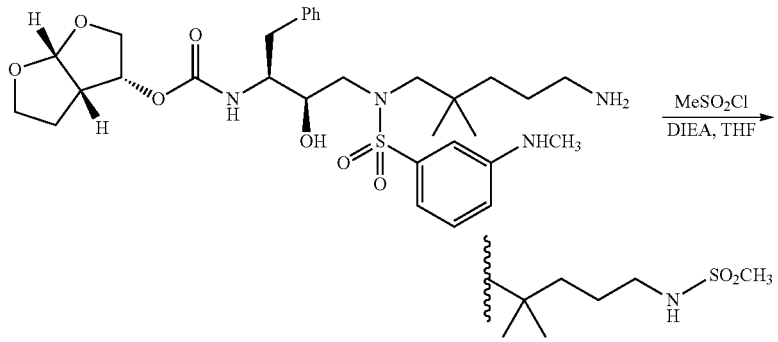

(3R,3aS,6aR)hexahydrofuro[2,3-b]furan-3-yl N-[(1S,2R)-1-benzyl-3-((5-[(methylsulfonyl]amino-2,2-dimethylpentyl)[3-(methylamino)phenyl]sulfonylamino)-2-hydroxypropyl]carbamate.

A solution of 50 mg (0.081 mmol) of (3R,3aS,6aR)hexahydrofuro[2,3-b]furan-3-yl N-[(1S,2R)-3-((5-amino-2,2-dimethylpentyl)[3-(methylamino)phenyl]sulfonylamino)-1-benzyl-2-hydroxypropyl]carbamate and 17 µL (0.097 mmol) of N,N-diisopropylethylamine in 5 mL of anhydrous THF at 0° C. was treated with 6.9 µL (0.089 mmol) of methanesulfonyl chloride. The solution was allowed to warm to RT with stirring. After 18 hours the solution was concentrated in vacuo and the residue was subjected to flash chromatography (SiO$_2$, 95:5 CH$_2$Cl$_2$/2M NH$_3$ in MeOH) to afford 55 mg (98%) of the desired compound as a white foam. H1-NMR (CDCl$_3$): 7.32-7.12 (m, 6H), 7.01 (d, 1H), 6.92 (s, 1H), 6.78 (dd, 1H), 5.60 (d, 1H), 5.11 (d, 1H), 5.01-4.88 (m, 2H), 4.12 (br s, 1H), 4.04 (m, 2H), 3.93-3.77 (m, 3H), 3.65 (m, 2H), 3.25 (dd, 1H), 3.20-2.90 (m, 5H), 2.91 (s, 3H), 2.90-2.81 (m, 5H), 2.71 (dd, 1H), 1.58 (m, 3H), 1.49-1.28 (m, 3H), 0.96 (s, 3H), 0.89 (s, 3H). MS(ESI): 719(M+Na).

EXAMPLE (COMPOUND 271)

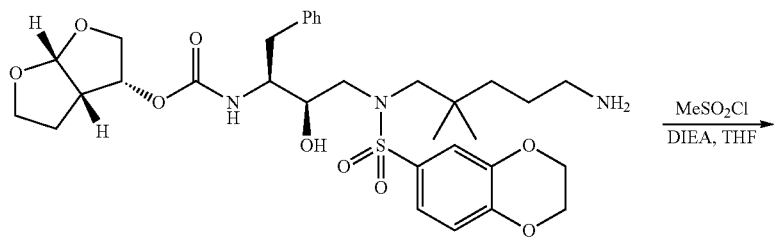

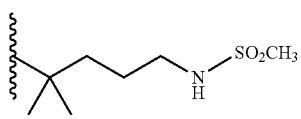

(3R,3aS,6aR)hexahydrofuro[2,3-b]furan-3-yl N-[(1S,2R)-3-((2,3-dihydro-1,4-benzodioxin-6-yl-sulfonyl)2,2-dimethyl-5-[(methylsulfonyl)amino]pentylamino)-1-benzyl-2-hydroxypropyl]carbamate A solution of 60 mg (0.093 mmol) of (3R,3aS,6aR)hexahydrofuro[2,3-b]furan-3-yl N-(1S,2R)-3-[(5-amino-2,2-dimethylpentyl)(2,3-dihydro-1,4-benzodioxin-6-ylsulfonyl)amino]-1-benzyl-2-hydroxypropylcarbamate and 20 μL (0.11 mmol) of N,N-diisopropylethylamine in 5 mL of anhydrous THF at 0° C. was treated with 7.9 μL (0.10 mmol) of methanesulfonyl chloride. The solution was allowed to warm to RT with stirring. After 18 hours the solution was concentrated in vacuo and the residue was subjected to flash chromatography (SiO$_2$, 95:5 CH$_2$Cl$_2$/2M NH$_3$ in MeOH) to afford 64 mg (94%) of the desired compound as a white foam. H1-NMR (CDCl$_3$): 7.30-7.13 (m, 7H), 6.97 (d, 1H), 5.60 (d, 1H), 5.12 (d, 1H), 5.01-4.89 (m, 2H), 4.32 (m, 4H), 4.10 (s, 1H), 4.04 (m, 1H), 3.89 (dd, 1H), 3.81 (m, 2H), 3.65 (m, 2H), 3.21-3.02 (m, 5H), 2.95 (d, 1H), 2.92 (s, 3H), 2.88-2.65 (m, 3H), 1.55 (m, 3H), 1.45-1.27 (m, 3H), 0.94 (s, 3H), 0.89 (s, 3H). MS(ESI): 748(M+Na).

EXAMPLE (COMPOUND 272)

Step 1:

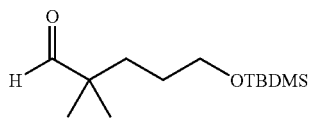

5-tert-Butyldimethylsilyloxy-2,2-dimethylpentanal

The title compound was prepared by procedure b (Example (Compound 24)) using 3-tert-butyldimethylsilyloxybromopropane as alkylating agent. $^1$H NMR (CDCl$_3$): δ −0.02 (6H, s), 0.84 (9H, s), 1.04 (6H, s), 1.38-1.42 (2H, m), 1.46-1.50 (2H, m), 3.55 (2H, t), 9.43 (1H, s); C$_{13}$H$_{28}$O$_2$Si.

Step 2

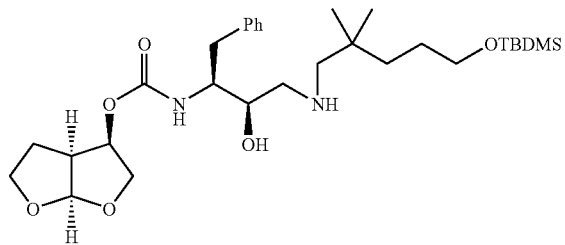

(3R,3aS,6aR)-Hexahydrofuro[2,3-b]furan-3-yl N-((1S,2R)-1-benzyl-3-[(5-tert-butyldimethylsilyloxy-2,2-dimethylpentyl)amino]-2-hydroxypropylcarbamate To a suspension of (3R,3aS,6aR)-hexahydrofuro[2,3-b]furan-3-yl N-((1S,2R)-3-amino-1-benzyl-2-hydroxypropylcarbamate (0.5 g, 1.5 mmol) in N,N-dimethylformamide (10 mL) and 1,2-dichloroethane (10 mL) was added a solution of the product from step a (0.33 g, 1.3 mmol) in tetrahydrofuran (10 mL). Acetic acid (0.3 mL) was added followed by sodium triacetoxyborohydride (0.32 g, 1.5 mmol) and the resulting mixture was stirred at ambient temperature under nitrogen atmosphere for 16 hours. The mixture was concentrated and 0.5 N sodium hydroxide/water (40 mL) was added. The mixture was extracted with ethyl acetate and the organic phase was washed with brine, dried (magnesium sulfate), and concentrated. The residue was chromatographed (silica gel, chloroform/methanol/ammonium hydroxide, 95:5:1) to provide the title compound as a white solid (0.61 g, 89%); $^1$H NMR (DMSO-d$_6$): δ −0.02 (6H, s), 0.80 (6H, s), 0.83 (9H, s), 1.15-1.20 (2H, m), 1.25-1.50 (4H, m), 2.25 (2H, dd), 2.45-2.52 (3H, m), 2.57 (1H, d), 2.76 (1H, quartet), 3.0 (1H, dd), 3.45 (1H, br s), 3.5-3.6 (5H, m), 3.7 (1H, t), 3.8 (1H, dd), 4.8-4.9 (2H, m), 5.5 (1H, d), 7.10-7.25 (6H, m); MS: 565.3 (MH$^+$); C$_{30}$H$_{52}$N$_2$O$_6$Si.

Step 3:

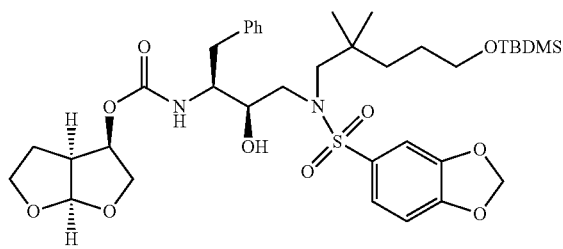

(3R,3aS,6aR)-Hexahydrofuro[2,3-b]furan-3-yl N-((1S,2R)-1-benzyl-3-(5-tert-butyldimethylsilyloxy-2,2-dimethylpentyl)[(3,4-methylenedioxyphenyl)sulfonyl]amino-2-hydroxypropyl)carbamate To a solution of the product from step b (0.2 g, 0.35 mmol) in dichloromethane (3 mL) at ~0° C. was added N-ethyldiisopropylamine (0.12 mL, 0.71 mmol) and 3,4-methylenedioxyphenylsulfonyl chloride (0.094 g, 0.42 mmol). The mixture was stirred at ambient temperature for 72 hours, concentrated and chromatographed (silica gel, hexane/ethyl acetate, 3:2) to afford the title compound (0.22 g, 83%) as a white foam; $^1$H NMR (DMSO-$d_6$): δ −0.02 (6H, s), 0.82 (9H, s), 0.88 (6H, s), 1.15 (1H, dd), 1.20-1.43 (4H, m), 2.4 (1H, dd), 2.5-2.6 (2H, m), 2.9-3.0 (2H, m), 3.30-3.38 (3H, m), 3.39-3.42 (1H, m), 3.5-3.6 (4H, m), 3.67 (1H, t), 3.75 (1H, quartet), 3.8 (1H, dd), 4.8 (1H, dt), 5.1 (1H, d), 5.45 (1H, d), 6.15 (2H, s), 7.02 (1H, d), 7.1-7.3 (7H, m), 7.34 (1H, d); $C_{37}H_{56}N_2O_{10}SSi$.

Step 4:

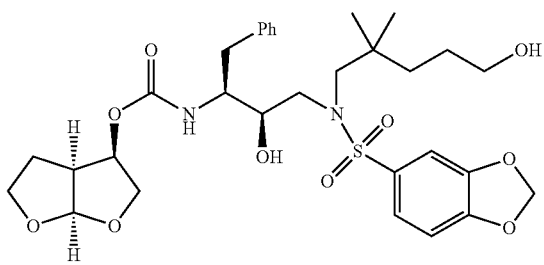

(3R,3aS,6aR)-Hexahydrofuro[2,3-b]furan-3-yl N-((1S,2R)-1-benzyl-3-(2,2-dimethyl-5-hydroxypentyl)[(3,4-methylenedioxyphenyl)sulfonyl]amino-2-hydroxypropyl)carbamate A solution of the product from step c (0.19 g, 0.26 mmol) in tetrahydrofuran (2 mL), acetic acid (2 mL), and water (0.65 mL) was stirred at ambient temperature for 16 hours. The mixture was poured into saturated sodium bicarbonate/water and extracted with diethyl ether (3×). The combined organic layers were washed with water, dried (magnesium sulfate), concentrated, and dried in vacuo to provide the title compound (~0.19 g) which was used in the next step without further purification.

Step 6:

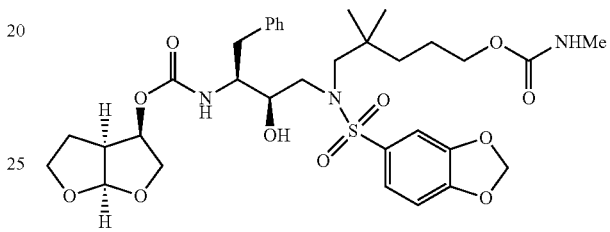

(3R,3aS,6aR)-Hexahydrofuro[2,3-b]furan-3-yl N-((1S,2R)-1-benzyl-3-[2,2-dimethyl-5-(N'-methylcarbamoyloxypentyl)][(3,4-methylenedioxyphenyl)sulfonyl]amino-2-hydroxypropyl)carbamate A solution of the product from step d (~0.19 g) and methyl isocyanate (0.36 mL, 6.1 mmol) in dichloromethane (2 mL) was stirred at ambient temperature for 64 hours. Solvent was evaporated and the residue was chromatographed (silica gel, chloroform/methanol, 98:2) to provide the title compound (0.11 g, 64%) as a white foam; $^1$H NMR (DMSO-$d_6$): δ 0.9 (3H, s), 0.92 (3H, s), 1.13 (1H, dd), 1.20-1.35 (2H, m), 1.45-1.55 (2H, m), 2.2 (1H, dd), 2.54 (3H, d), 2.7-2.8 (2H, m), 2.9 (1H, dd), 2.95 (1H, dd), 3.30-3.43 (5H, m), 3.5-3.6 (2H, m), 3.7 (1H, td), 3.75 (1H, br quartet), 3.85 (1H, dd), 3.88 (1H, t), 4.8 (1H, dt), 5.1 (1H, d), 5.5 (1H, d), 6.15 (2H, s), 6.9 (1H, quartet), 7.03 (1H, d), 7.1-7.25 (7H, m), 7.32 (1H, d); MS: 692.1 (MH$^+$); $C_{33}H_{45}N_3O_{11}S$.

EXAMPLE (COMPOUND 273)

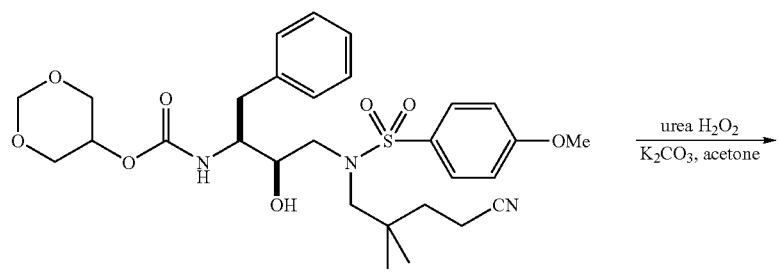

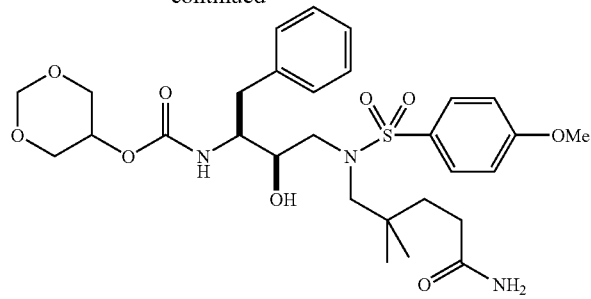

{(1S,2R)-1-Benzyl-3-[(4-carboxamide-2,2-dimethyl-butyl)-(4-methoxy-benzenesulfonyl)-amino]-2-hydroxy-propyl}-carbamic acid [1,3]dioxan-5-yl ester {(1S,2R)-1-Benzyl-3-[(4-cyano-2,2-dimethyl-butyl)-(4-methoxy-benzenesulfonyl)-amino]-2-hydroxy-propyl}-carbamic acid [1,3]dioxan-5-yl ester (0.042 g, 0.071 mmol) was dissolved in 2 mL of 1:1, acetone:water and treated with urea hydroperoxide (0.20 mg, 0.212 mmol) at ambient temperature under argon with stirring. After 15 h the reaction mixture was concentrated in vacuo, taken up in EtOAc, washed with sat. aq. NaHCO₃, and brine. The organic phase was dried over MgSO₄, filtered and solvent removed in vacuo. Purification by preparatory tlc (5% MeOH in CH₂Cl₂, SiO₂) gave 0.014 g of a white solid. MS (ES): 608 (M+1).

EXAMPLE (COMPOUND 274)

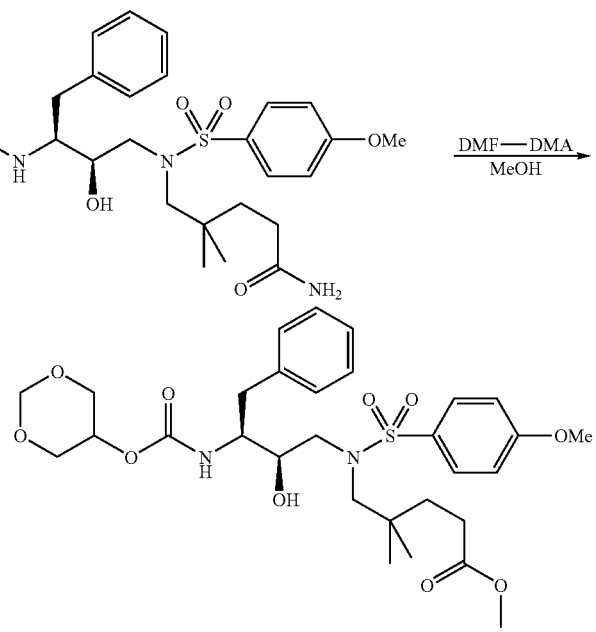

{(1S,2R)-1-Benzyl-3-[(4-carbomethoxy-2,2-dimethyl-butyl)-(4-methoxy-benzenesulfonyl)-amino]-2-hydroxy-propyl}-carbamic acid [1,3]dioxan-5-yl ester {(1S,2R)-1-Benzyl-3-[(4-carboxamide-2,2-dimethyl-butyl)-(4-methoxy-benzenesulfonyl)-amino]-2-hydroxy-propyl}-carbamic acid [1,3].dioxan-5-yl ester (0.0063 g, 0.01 mmol) was dissolved in 1 mL of methanol and treated with dimethyl formamide-dimethyl acetal (0.20 mL, 3 EQ.) at ambient temperature under argon with stirring. After 15 h the reaction mixture was concentrated in vacuo, taken up in EtOAc, washed with sat. aq. NaHCO₃, and brine. The organic phase was dried over MgSO₄, filtered and solvent removed in vacuo. Purification by preparatory tlc (5% MeOH in CH₂Cl₂) provided 2.5 mg of the derived methyl ester, MS(ES)=623 amu (M+1)

EXAMPLE (COMPOUND 275)

Step 1:

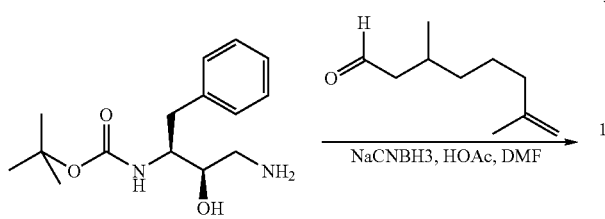

[(2R,3S)-3-tert-Butoxycarbonylamino-2-hydroxy-4-phenyl-(3,7-dimethylocte-7-nyl)butyl amine]

[(2R,3S)-3-tert-Butoxycarbonylamino-2-hydroxy-4-phenyl-(1-amino)butane] (0.94 g, 3.35 mmol) was added to a solution of racemic 3,7-dimethylocte-7-nyl carboxaldehyde in DMF (5 mL). This was followed by the addition of approximately one mL of glacial acetic acid and then NaCNBH3 (2.0 g, 9.6 mmol). The reaction was stirred under N2 for 15 hrs, followed by diluting with 100 mL of CH₂Cl₂. The reaction mixture was then washed with sat. NaHCO₃, and brine. The organic phase was dried with MgSO₄ and the solvent was removed in vacuo. Purification by SiO2 chromatography (5% MeOH/CH₂Cl₂). Isolated 0.055 g of the product as a colorless residue: Rf=0.50 (5% MeOH/CH₂Cl₂.

Step 2:

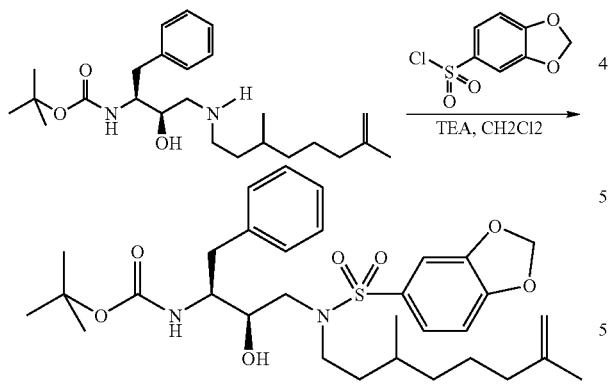

[(2R,3S)-3-tert-Butoxycarbonylamino-2-hydroxy-4-phenyl-(3,7-dimethyloct-7-enyl))[2-[(Benzo[1,3]dioxole-5-sulfonyl]butylamine

[(2R,3S)-3-tert-Butoxycarbonylamino-2-hydroxy-4-phenyl-(3,7-dimethylocte-7-nyl)butyl amine] (27.6 mg, 0.066 mmol) was dissolved in 1 mL of CH₂Cl₂ followed by [2-[(Benzo[1,3]dioxole-5-sulfonyl chloride (15 mg, 0.066 mmol). TEA (200 uL) was then added and the reaction was stirred for 14 hours at room temperature. The reaction was quenched by the addition of 3 mL of saturated NaHCO₃, followed by washing with sat. NaHCO₃, and then brine. The organic phase was dried with MgSO₄ and the solvent was removed in vacuo. Purification by SiO₂ chromatography (5% MeOH/CH₂Cl₂). Recovered 0.0038 g of the product as a colorless residue: Rf=0.50 (5% MeOH/CH₂Cl₂/SiO₂), MS(ES)=647 amu (M+1).

EXAMPLE (COMPOUND 276)

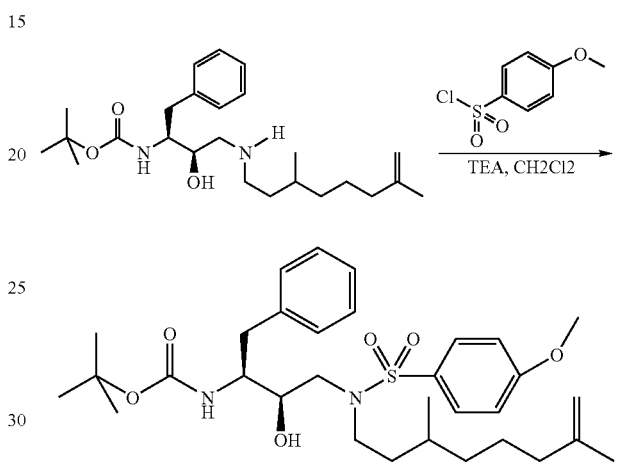

[(2R,3S)-3-tert-Butoxycarbonylamino-2-hydroxy-4-phenyl-(3,7-dimethyloct-7-enyl))[4-methoxyphenylsulfonyl]butylamine

[(2R,3S)-3-tert-Butoxycarbonylamino-2-hydroxy-4-phenyl-(3,7-dimethylocte-7-nyl)butyl amine] (27.6 mg, 0.066 mmol) was dissolved in 1 mL of CH₂Cl₂ followed by the addition of 4-methoxyphenylsulfonyl chloride (13.7 mg, 0.066 mmol). TEA (200 uL) was then added and the reaction was stirred for 14 hours at room temperature.

The reaction was quenched by the addition of 3 mL of saturated NaHCO₃, followed by washing with sat. NaHCO₃, and then brine. The organic phase was dried with MgSO₄ and the solvent was removed in vacuo. Purification by SiO₂ chromatography (5% MeOH/CH₂Cl₂). Recovered 0.0021 g of the product as a colorless residue: Rf=0.50 (5% MeOH/CH₂Cl₂/SiO₂), MS(ES)=633 amu (M+1).

EXAMPLE (COMPOUND 277)

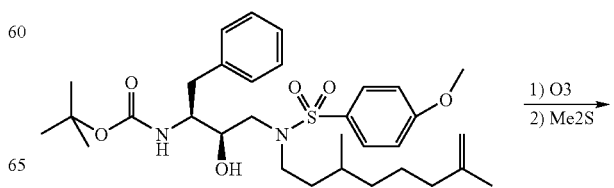

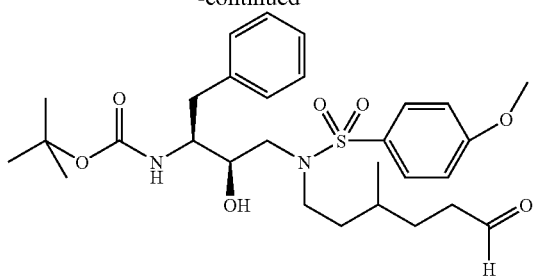

[(2R,3S)-3-tert-Butoxycarbonylamino-2-hydroxy-4-phenyl-(3,7-dimethylheptylcarboxaldehyde)][4-methoxyphenyl sulfonyl]butylamine

[(2R,3S)-3-tert-Butoxycarbonylamino-2-hydroxy-4-phenyl-(3,7-dimethyloct-7-enyl))[4-methoxyphenylsulfonyl]butylamine (0.9 mg) was dissolved in 1 mL of $CH_2Cl_2$ containing 100 uL of MeOH. The reaction mixture was cooled to −78° C. under a stream of $O_2$. A stream of ozone was then bubbled through the reaction mixture for five minutes, until a pale blue color was evident. The reaction was then purged of ozone by bubbling $O_2$ through for five minutes and then $N_2$ for an additional 5 minutes and the addition of 200 uL of dimethyl sulfide. After stirring for 30 minutes at −78° C. the reaction was warmed to room temperature and concentrated in vacuo. The reaction mixture was purified by prep. TLC ($SiO_2$) eluting with 5% MeOH/$CH_2Cl_2$, 0.5 mg of the desired aldehyde was isolated; MS(ES)=563 amu (M+1). Note that olefin migration occurred during the reaction conditions prior to exposure to.

EXAMPLE (COMPOUND 278)

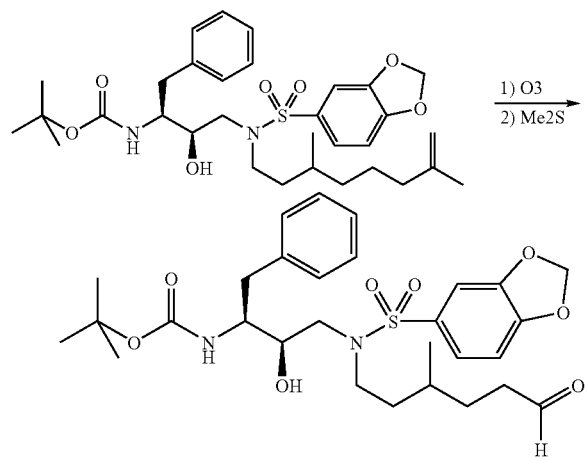

[(2R,3S)-3-tert-Butoxycarbonylamino-2-hydroxy-4-phenyl-(3,7-dimethylheptylcarboxaldehyde[(Benzo[1,3]dioxole-5-sulfonyl]butylamine

[(2R,3S)-3-tert-Butoxycarbonylamino-2-hydroxy-4-phenyl-(3,7-dimethyloct-7-enyl))[2-[(Benzo[1,3]dioxole-5-sulfonyl]butylamine (4.0 mg) was dissolved in 1 mL of $CH_2Cl_2$ containing 100 uL of MeOH and 1 mg $K_2CO_3$. The reaction mixture was cooled to −78° C. under a stream of $O_2$. A stream of ozone was then bubbled through the reaction mixture for five minutes, until a pale blue color was evident. The reaction was then purged of ozone by bubbling $O_2$ through for five minutes, followed by the addition of 200 uL of dimethyl sulfide. After stirring for 30 minutes at −78° C. the reaction was warmed to room temperature and concentrated in vacuo. The reaction mixture was purified by prep. TLC ($SiO_2$) eluting with 5% MeOH/$CH_2Cl_2$, 2.1 mg of the desired aldehyde was isolated; MS(ES) 577 amu (M+1), 621 amu for (M−1+TFA). Note that olefin migration occurred during the reaction conditions prior to exposure to ozone both with and without base present.

EXAMPLE (COMPOUND 279)

Step 1:

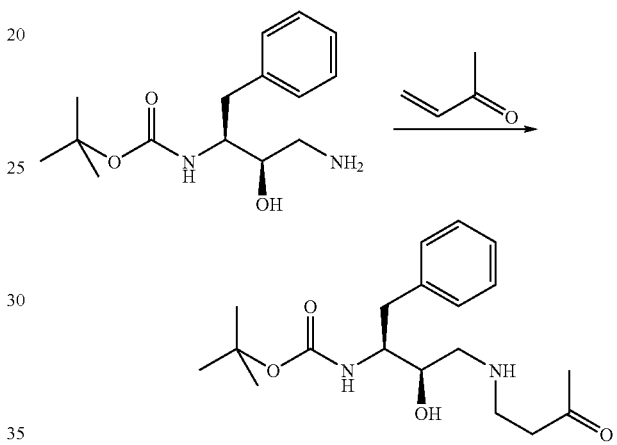

[(2R,3S)-3-tert-Butoxycarbonylamino-2-hydroxy-4-phenyl-(1-amino-3-butanone)butane]

[(2R,3S)-3-tert-Butoxycarbonylamino-2-hydroxy-4-phenyl-(1-amino)butane] (0.268 g, 1.0 mmol) was dissolved in EtOH (5 mL) and cooled to 0° C. This was followed by the addition methyl vinyl ketone (79.9 uL, 1.0 mmol). The reaction was stirred under N2 for 15 hrs and gradually warmed to room temperature as the ice bath melted. The reaction mixture was then concentrated in vacuo and purified by silica gel chromatography gradient from 2% MeOH/$CH_2Cl_2$ to 90% MeOH/$CH_2Cl_2$ to 85/10/5 MeOH/$CH_2Cl_2$/$NH_4OH$. Isolated both unreacted starting material, the mono (desired) and the bis addition product.

Step 2:

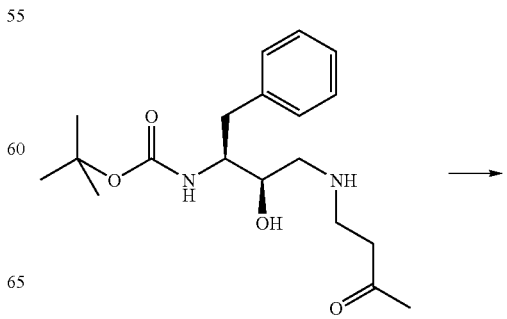

-continued

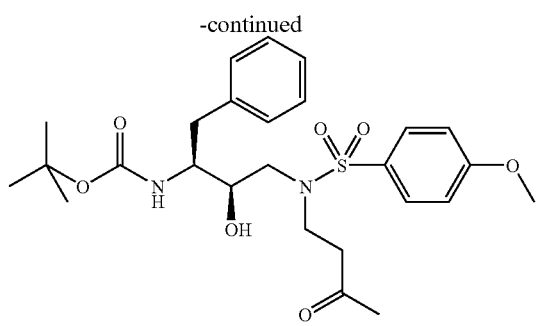

[(2R,3S)-3-tert-Butoxycarbonylamino-2-hydroxy-4-phenyl-(1-amino-(3-butanonyl(4-methoxyphenylsulfonyl))butane]

[(2R,3S)-3-tert-Butoxycarbonylamino-2-hydroxy-4-phenyl-(1-amino-3-butanone) butane] (124 mg, 0.4 mmol) was combined with 4-methoxyphenylsulfonyl chloride (146 mg, 0.7 mmol) in DMF and cooled to 0° C. This was followed by the addition of diisopropyl ethyl amine (186 uL, 1.1 mmol). The reaction was then warmed to room temperature and stirred for 15 hours. The reaction was quenched by the addition of 3 mLs of saturated NaHCO$_3$, followed by washing with sat. NaHCO$_3$, KHSO$_3$ and then brine. The organic phase was dried with MgSO$_4$ and the solvent was removed in vacuo. Purification by SiO$_2$ (1:3, EtOAc:Hex to 2:1 EtOAc:Hex). Isolated 0.038 g of the product as a colorless oil: 20.8% yield, Rf=0.27 (1:1 EtOAc:Hex,/SiO2), MS(ES)=521 amu (M+1).

EXAMPLE (COMPOUND 280)

{(1S,2R)-3-[(4-methoxybenzenesulfonyl)-(3-butanonyl)-amino]-1-benzyl-2-hydroxy-propyl}-carbamic acid (3R,3aS,6aR)hexahydro-furo[2,3-b]furan-3-yl ester Step 1:
[(2R,3S)-3-tert-Butoxycarbonylamino-2-hydroxy-4-phenyl-(1-amino-(3-butanonyl (4-methoxyphenylsulfonyl)) butane] (33.2 mg, 0.1 mmol) was dissolved in 1 mL of CH$_2$Cl$_2$ followed by the addition of 1 mL of TFA. The reaction was stirred at room temperature for 15 minutes followed by concentration in vacuo to provide the desired deprotected amine. This material was used without further purification.

Step 2:
25.2 mg (0.03 mmol) of the material provided in the above deprotection step was then dissolved into DMF (1 mL) followed by the 3R,3aS,6aR)hexahydro-furo[2,3-b]furan-3-yl derived mixed carbonate (18.8 mg, 0.03 mmol). After cooling to 0° C. diisopropylethyl amine (33.3 uL, 0.2 mmol) was added and the reaction was stirred for 15 hours (warmed to room temperature overnight). The reaction mixture was then diluted with EtOAc washed with sat. NaHCO$_3$, KHSO$_3$ and then brine. The organic phase was dried with MgSO$_4$ filtered and the solvent was removed in vacuo. Purification by Prep. TLC (SiO2 2:1, EtOAc:Hex). Isolated 0.0116 g of the product as a white foam: Rf=0.16 (2:1 EtOAc:Hex,/SiO2), MS(ES)= 577 amu (M+1).

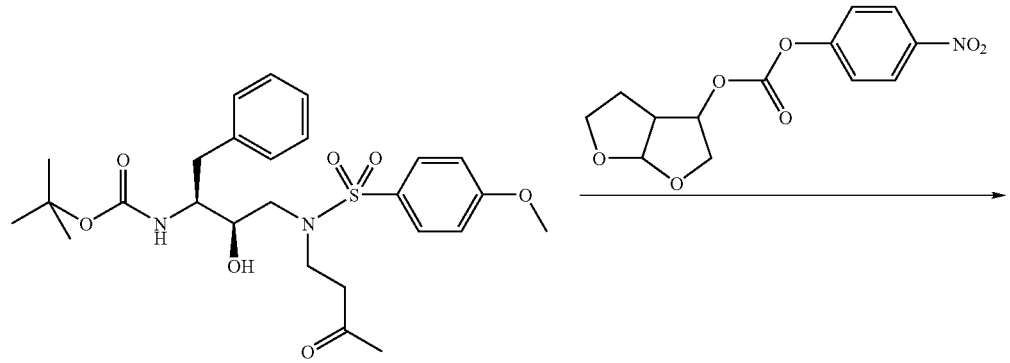

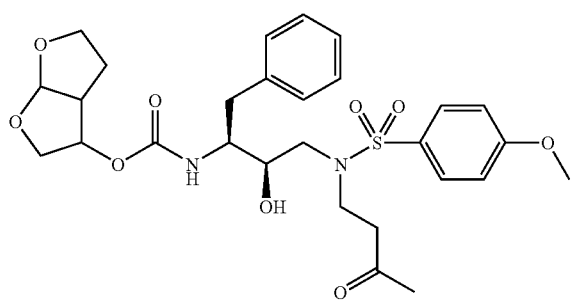

EXAMPLE (COMPOUND 281)

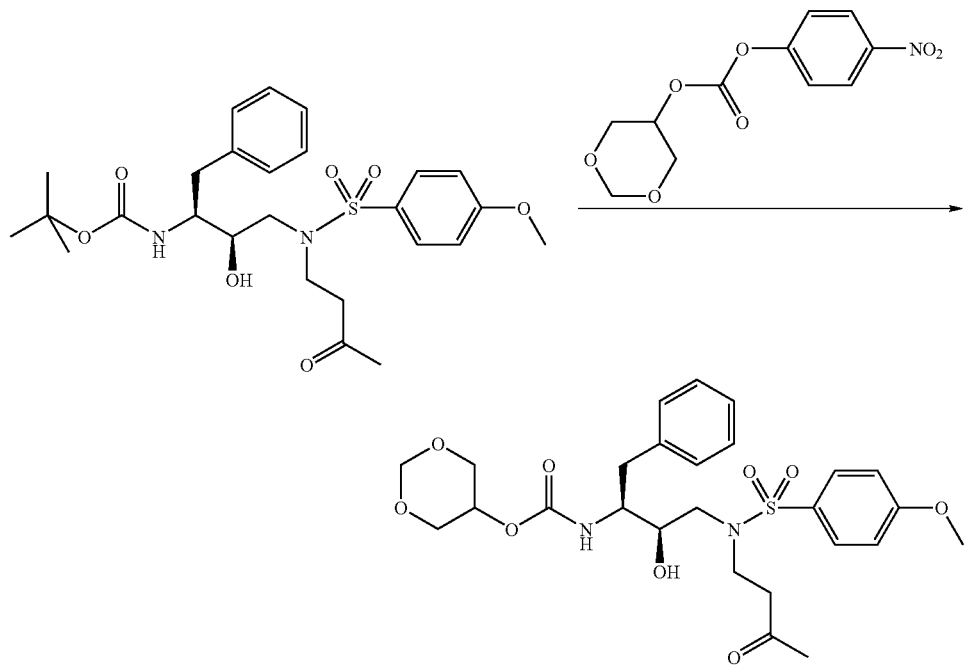

18.8 mg (0.03 mmol) of the material provided in the above deprotection step (step 1 example 279) was then dissolved into DMF (1 mL) followed by the 1,3-dioxan-5-yl derived mixed carbonate (17.2 mg, 0.1 mmol). After cooling to 0° C. diisopropylethyl amine (33.3 uL, 0.2 mmol) was added and the reaction was stirred for 15 hours warmed to room temperature overnight). The reaction mixture was then diluted with EtOAc washed with sat. NaHCO₃, KHSO₃ and then brine. The organic phase was dried with MgSO₄ and the solvent was removed in vacuo. Purification by Prep. TLC (SiO2 2:1, EtOAc:Hex). Isolated 0.0063 g of the product as a white foam: Rf=0.29 (2:1 EtOAc:Hex,/SiO2), MS(ES)=551 amu (M+1).

EXAMPLE (COMPOUND 282)

Step 1:

(3R,3aS,6aR)hexahydrofuro[2,3-b]furan-3-yl N-(1S,2R)-1-benzyl-3-[(4-[N,N-dibenzylamino]-2,2-dimethylbutyl)amino]-2-hydroxypropylcarbamate According to example 257, step 5, (3R,3aS,6aR)hexahydrofuro[2,3-b]furan-3-yl N-[(1S,2R)-3-amino-1-benzyl-2-hydroxypropyl]carbamate was subjected to reductive alkylation with of 4-(N,N-dibenzylamino)-2,2-dimethylbutyraldehyde to afford the desired compound as thick oil in 70% yield. MS(ESI): 616(M+H).

Step 2:

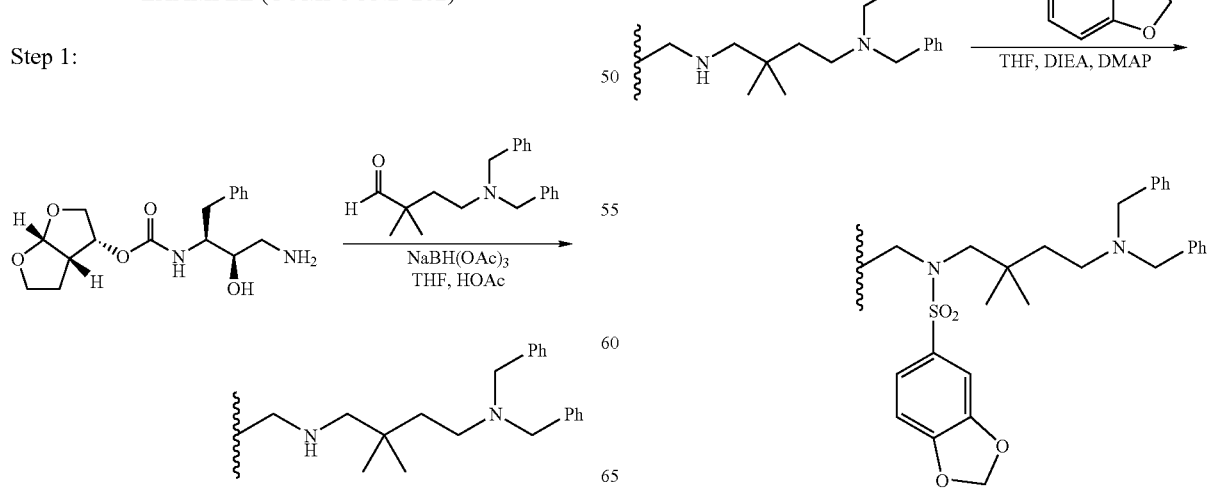

269

(3R,3aS,6aR)hexahydrofuro[2,3-b]furan-3-yl N-(1S,2R)-3-[(1,3-benzodioxol-5-ylsulfonyl)(4-[N,N-dibenzylamino]-2,2-dimethylbutyl)amino]-1-benzyl-2-ydroxypropylcarbamate According to example 257, step 6, (3R,3aS,6aR)hexahydrofuro[2,3-b]furan-3-yl N-(1S,2R)-1-benzyl-3-[(4-[N,N-dibenzylamino]-2,2-dimethylbutyl)amino]-2-hydroxypropylcarbamate was subjected to sulfonylation to afford the desired sulfonamide as a white foam in 89% yield. MS(ESI): 800(M+H).

Step 3:

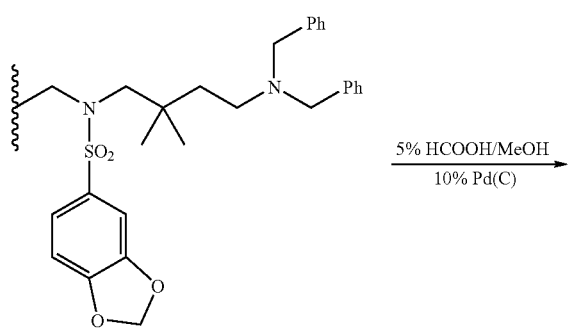

(3R,3aS,6aR)hexahydrofuro[2,3-b]furan-3-yl N-(1S,2R)-3-[(4-amino-2,2-dimethylbutyl)(1,3-benzodioxol-5-ylsulfonyl)amino]-1-benzyl-2-hydroxypropylcarbamate According to example 217, step 3, (3R,3aS,6aR)hexahydrofuro[2,3-b]furan-3-yl N-(1S,2R)-3-[(1,3-benzodioxol-5-ylsulfonyl)(4-[N,N-dibenzylamino]-2,2-dimethylbutyl)amino]-1-benzyl-2-ydroxypropylcarbamate was subjected to catalytic transfer hydrogenation to afford the desired amine as a white foam in 68% yield.

NMR (CDCl$_3$): 7.34 (dd, 1H), 7.27-7.13 (m, 7H), 6.95 (d, 1H), 6.15 (s, 2H), 5.81 (d, 1H), 5.61 (d, 1H), 5.01 (q, 1H), 4.02 (t, 1H), 3.92-3.79 (3H), 3.67 (m, 2H), 3.20-2.96 (m, 4H), 2.91-2.60 (m, 5H), 2.45-1.70 (br, 2H), 1.63-1.34 (m, 4H), 0.97 (s, 3H), 0.89 (s, 3H). MS(ESI): 620(M+H).

270

EXAMPLE (COMPOUND 283)

Step 1:

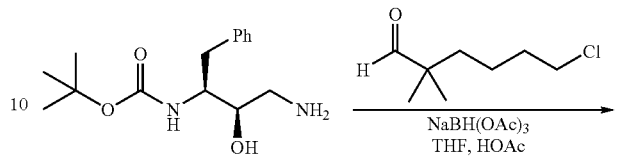

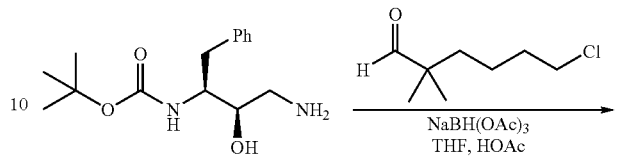

tert-butyl N-(1S,2R)-1-benzyl-3-[(6-chloro-2,2-dimethylhexyl)amino]-2-hydroxypropylcarbamate According to example 257, step 5, tert-butyl N-[(1S,2R)-3-amino-1-benzyl-2-hydroxypropyl]carbamate was subjected to reductive alkylation with 6-chloro-2,2-dimethylhexanal to afford the desired compound as a viscous oil in quantitative yield. MS(ESI): 428(M+H).

Step 2

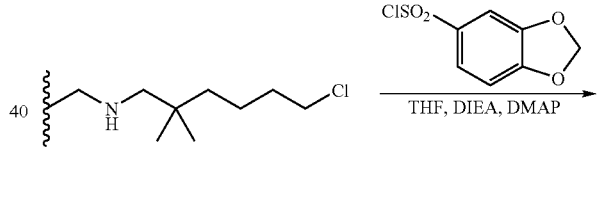

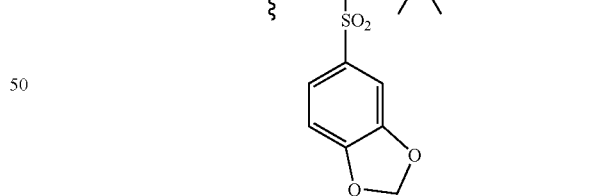

tert-butyl N-(1S,2R)-3-[(1,3-benzodioxol-5-ylsulfonyl)(6-chloro-2,2-dimethylhexyl)amino]-1-benzyl-2-hydroxypropylcarbamate According to example 257, step 6, tert-butyl N-(1S,2R)-1-benzyl-3-[(6-chloro-2,2-dimethylhexyl)amino]-2-hydroxypropylcarbamate was subjected to sulfonylation to afford the desired sulfonamide as a white foam in 70% yield. MS(ESI): 633(M+Na).

Step 3:

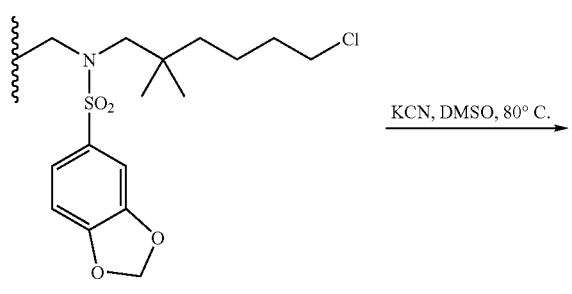

Step 4:

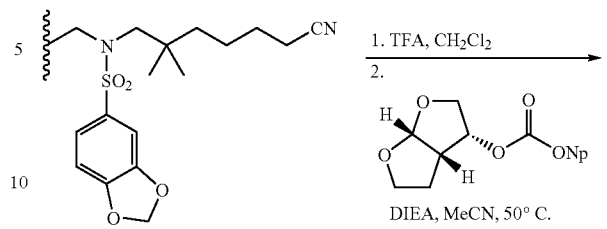

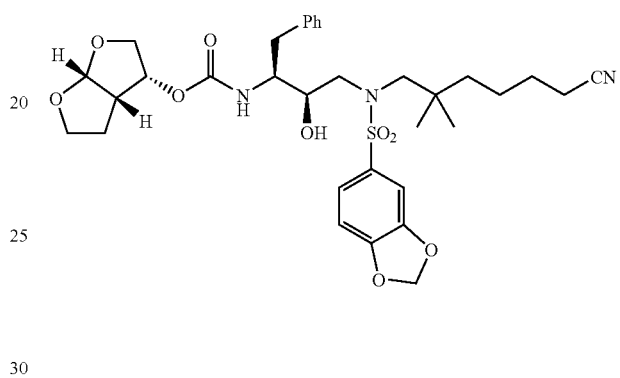

tert-butyl N-(1S,2R)-3-[(1,3-benzodioxol-5-ylsulfonyl)(6-cyano-2,2-dimethylhexyl)amino]-1-benzyl-2-hydroxypropylcarbamate A solution of 200 mg (0.327 mmol) of tert-butyl N-(1S,2R)-3-[(1,3-benzodioxol-5-ylsulfonyl)(6-chloro-2,2-dimethylhexyl)amino]-1-benzyl-2-hydroxypropylcarbamate and 43 mg (0.490 mmol) of KCN in 3 mL of DMSO was heated to 80° C. with stirring. After 2 hours the solution was cooled to RT, diluted with water and the mixture extracted with $CH_2Cl_2$ (3×). The combined extracts were washed with brine (3×), dried over $MgSO_4$, and concentrated in vacuo to afford 196 mg (99%) of the desired compound as a light yellow foam. MS(ESI): 602(M+H).

(3R,3aS,6aR)hexahydrofuro[2,3-b]furan-3-yl N-(1S,2R)-3-[(1,3-benzodioxol-5-ylsulfonyl)(6-cyano-2,2-dimethylhexyl)amino]-1-benzyl-2-hydroxypropylcarbamate According to example 245, steps 4 and 5, tert-butyl N-(1S,2R)-3-[(1,3-benzodioxol-5-ylsulfonyl)(6-cyano-2,2-dimethylhexyl)amino]-1-benzyl-2-hydroxypropylcarbamate was converted to the desired product in 66% overall yield. NMR ($CDCl_3$): 7.32 (dd, 1H), 7.30-7.12 (m, 6H), 6.89 (d, 1H), 6.07 (s, 2H), 5.61 (d, 1H), 4.97 (q, 1H), 4.88 (d, 1H), 4.02 (m, 1H), 3.92 (m, 2H), 3.81 (m, 2H), 3.65 (m, 2H), 3.17 (dd, 1H), 3.10-2.68 (m, 6H), 2.35 (t, 2H), 1.60 (m, 3H), 1.40 (m, 3H), 1.29 (m, 2H), 0.90 (d, 6H).

MS(ESI): 658(M+H).

Step 5:

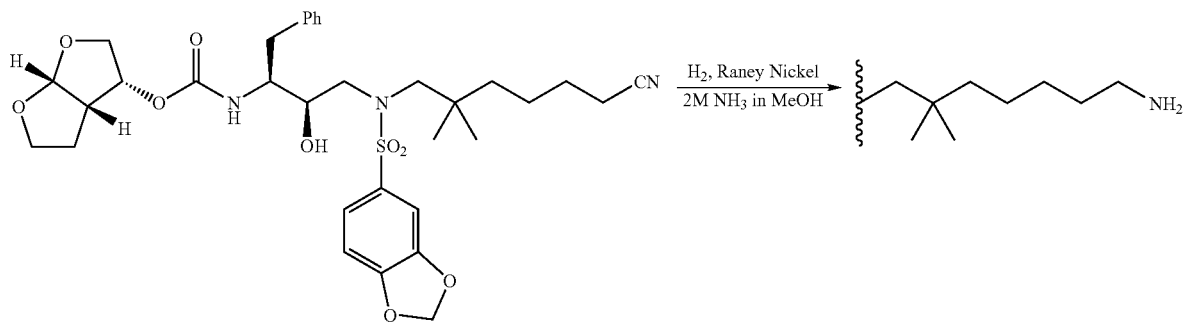

(3R,3aS,6aR)hexahydrofuro[2,3-b]furan-3-yl N-(1S,2R)-3-[(1,3-benzodioxol-5-ylsulfonyl)(7-amino-2,2-dimethylheptyl)amino]-1-benzyl-2-hydroxypropyl]carbamate According to example 245, step 6, (3R,3aS,6aR)hexahydrofuro[2,3-b]furan-3-yl N-(1S,2R)-3-[(1,3-benzodioxol-5-ylsulfonyl)(6-cyano-2,2-dimethylhexyl)amino]-1-benzyl-2-hydroxypropyl]carbamate was subjected to Raney nickel hydrogenation to afford the desired primary amine as a white foam in 89% yield. H1-NMR (CDCl₃): 7.40 (d, 1H), 7.28-7.16 (m, 6H), 6.86 (d, 1H), 6.12 (s, 2H), 5.75 (d, 1H), 5.62 (m, 1H), 5.03 (m, 1H), 4.60-3.70 (br, 2H), 4.21-3.61 (m, 6H), 3.25-2.71 (m, 10H), 1.85-1.24 (m, 10H), 0.95 (d, 6H).

EXAMPLE (COMPOUND 284)

Step 1:

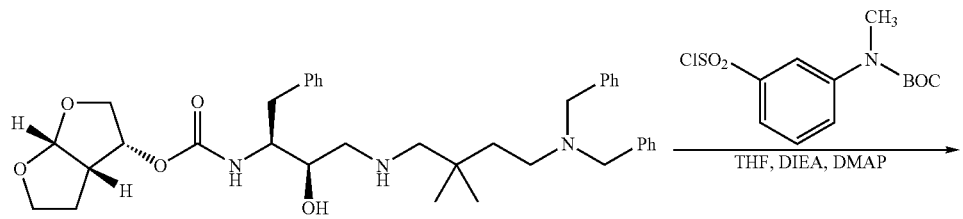

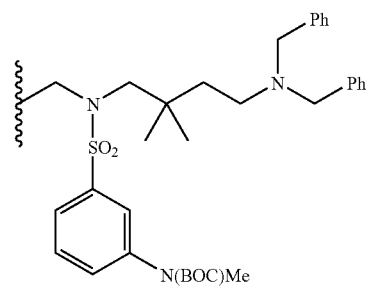

(3R,3aS,6aR)hexahydrofuro[2,3-b]furan-3-yl N-(1S,2R)-1-benzyl-3-[(3-[(tert-butoxycarbonyl)(methyl)amino]phenylsulfonyl)(4-[N,N-dibenzylamino]-2,2-dimethylbutyl)amino]-2-hydroxypropylcarbamate According to example 258, step 1, (3R,3aS,6aR)hexahydrofuro[2,3-b]furan-3-yl N-(1S,2R)-1-benzyl-3-[(4-[N,N-dibenzylamino]-2,2-dimethylbutyl)amino]-2-hydroxypropylcarbamate was subjected to sulfonylation to give the desired product as a light yellow foam in 54% yield. MS(ESI): 886(M+H).

Step 2:

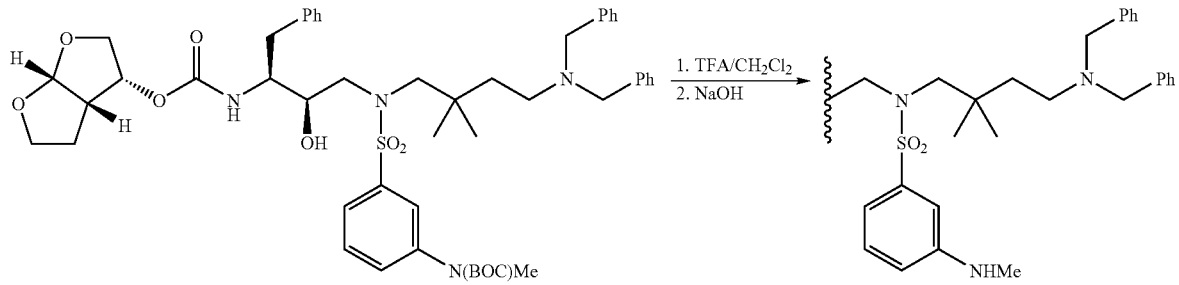

(3R,3aS,6aR)hexahydrofuro[2,3-b]furan-3-yl N-(1S, 2R)-1-benzyl-3-[(3-(methylamino)phenylsulfonyl) (4-[N,N-dibenzylamino]-2,2-dimethylbutyl)amino]- 2-hydroxypropylcarbamate According to example 258, step 2, (3R,3aS,6aR)hexahydrofuro[2,3-b]furan-3-yl N-(1S,2R)-1-benzyl-3-[(3-[(tert-butoxycarbonyl)(methyl)amino]phenylsulfonyl)(4-[N,N-dibenzylamino]-2,2-dimethylbutyl)amino]-2-hydroxypropylcarbamate was subjected to TFA deprotection to afford the desired product in 96% yield. MS(ESI): 786(M+H).

Step 3:

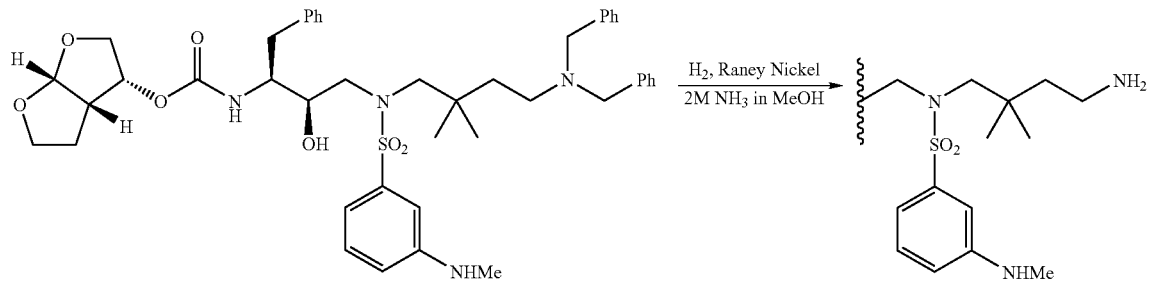

(3R,3aS,6aR)hexahydrofuro[2,3-b]furan-3-yl N-(1S, 2R)-1-benzyl-3-[(3-(methylamino)phenylsulfonyl) (4-amino-2,2-dimethylbutyl)amino]-2-hydroxypropylcarbamate According to example 245, step 6, (3R,3aS,6aR)hexahydrofuro[2,3-b]furan-3-yl N-(1S,2R)-1-benzyl-3-[(3-(methylamino)phenylsulfonyl)(4-[N,N-dibenzylamino]-2,2-dimethylbutyl)amino]-2-hydroxypropylcarbamate was subjected to Raney nickel reduction to afford the desired primary amine as a white foam in 45% yield. NMR (CDCl$_3$): 7.36-7.17 (m, 6H), 7.02 (d, 1H), 6.95 (s, 1H), 6.76 (dd, 1H), 5.78 (d, 1H), 5.60 (d, 1H), 4.99 (q, 1H), 4.11 (m, 1H), 4.02 (t, 1H), 3.91-3.78 (m, 3H), 3.73-3.59 (m, 2H), 3.25-2.99 (m, 5H), 2.83 (m, 5H), 2.78-2.59 (m, 3H), 2.60-1.90 (br, 2H), 1.63-1.33 (m, 4H), 0.98 (s, 3H), 0.89 (s, 3H). MS(ESI): 605 (M+H).

EXAMPLE (COMPOUND 285)

Step 1:

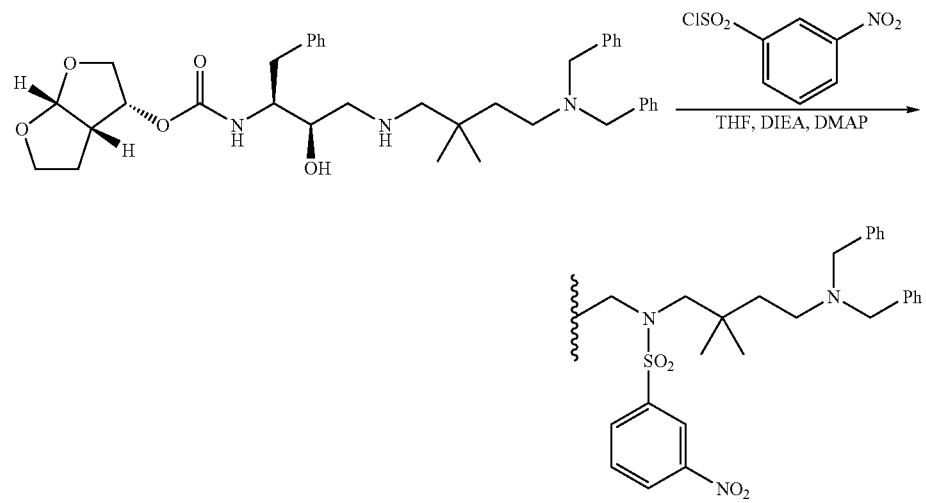

277

(3R,3aS,6aR)hexahydrofuro[2,3-b]furan-3-yl N-(1S, 2R)-1-benzyl-3-[(3-nitrophenylsulfonyl)(4-[N,N-dibenzylamino]-2,2-dimethylbutyl)amino]-2-hydroxypropylcarbamate According to example 257, step 6, (3R,3aS,6aR)hexahydrofuro[2,3-b]furan-3-yl N-(1S,2R)-1-benzyl-3-[(4-[N,N-dibenzylamino]-2,2-dimethylbutyl)amino]-2-hydroxypropylcarbamate was subjected to sulfonylation with 3-nitrobenzenesulfonyl chloride to afford the desired sulfonamide as a white foam in 90% yield.

MS(ESI): 801(M+H).

Step 2:

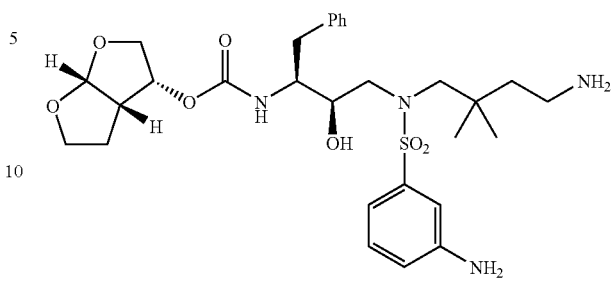

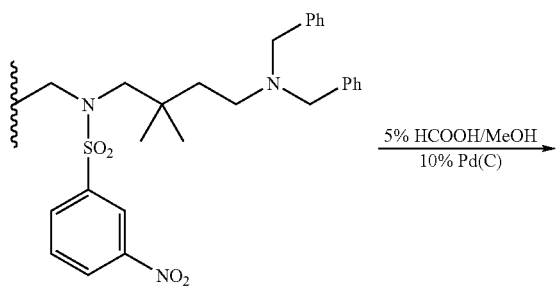

(3R,3aS,6aR)hexahydrofuro[2,3-b]furan-3-yl N-(1S, 2R)-1-benzyl-3-[((3-aminophenylsulfonyl)(4-amino-2,2-dimethylbutyl)amino]-2-hydroxypropylcarbamate According to example 217, step 3, (3R,3aS,6aR)hexahydrofuro[2,3-b]furan-3-yl N-(1S,2R)-1-benzyl-3-[(3-nitrophenylsulfonyl)(4-[N,N-dibenzylamino]-2,2-dimethylbutyl)amino]-2-hydroxypropylcarbamate was subjected to catalytic transfer hydrogenation to afford the desired primary amine as a white foam in 63% yield.

NMR (CDCl$_3$): 7.37-7.19 (m, 6H), 7.14 (m, 2H), 6.88 (dd, 1H), 5.84 (d, 1H), 5.65 (d, 1H), 5.04 (q, 1H), 4.10 (m, 3H), 3.99-3.81 (m, 3H), 3.80-3.64 (m, 2H), 3.32-3.01 (m, 5H), 2.91 (m, 2H), 2.82-2.65 (m, 3H), 2.60-2.00 (br, 2H), 1.70-1.39 (m, 4H), 1.04 (s, 3H), 0.95 (s, 3H). MS(ESI): 591(M+H).

EXAMPLE (COMPOUND 286)

Step 1:

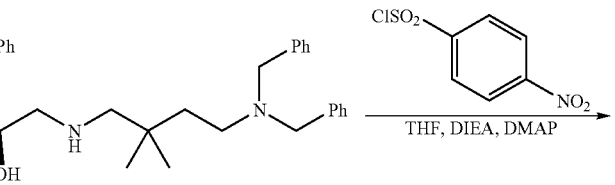

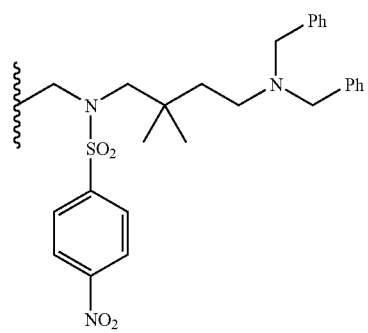

(3R,3aS,6aR)hexahydrofuro[2,3-b]furan-3-yl N-(1S,2R)-1-benzyl-3-[(4-nitrophenylsulfonyl)(4-[N,N-dibenzylamino]-2,2-dimethylbutyl)amino]-2-hydroxypropylcarbamate According to example 257, step 6, (3R,3aS,6aR)hexahydrofuro[2,3-b]furan-3-yl N-(1S,2R)-1-benzyl-3-[(4-[N,N-dibenzylamino]-2,2-dimethylbutyl)amino]-2-hydroxypropylcarbamate was subjected to sulfonylation with 4-nitrobenzenesulfonyl chloride to afford the desired sulfonamide as a light yellow foam in 86% yield.

MS(ESI): 801(M+H).

NMR (CDCl₃): 7.55 (d, 2H), 7.28-7.15 (m, 5H), 6.67 (d, 2H), 5.77 (d, 1H), 5.60 (d, 1H), 4.99 (q, 1H), 4.20 (s, 2H), 4.02 (t, 1H), 3.92-3.78 (m, 3H), 3.71-3.61 (m, 2H), 3.20-3.02 (m, 4H), 2.96 (d, 1H), 2.85 (q, 1H), 2.80-2.60 (m, 4H), 2.60-1.80 (br, 2H), 1.63-1.35 (m, 4H), 0.96 (s, 3H), 0.89 (s, 3H). MS(ESI): 591(M+H).

EXAMPLE (COMPOUND 287)

Step 1:

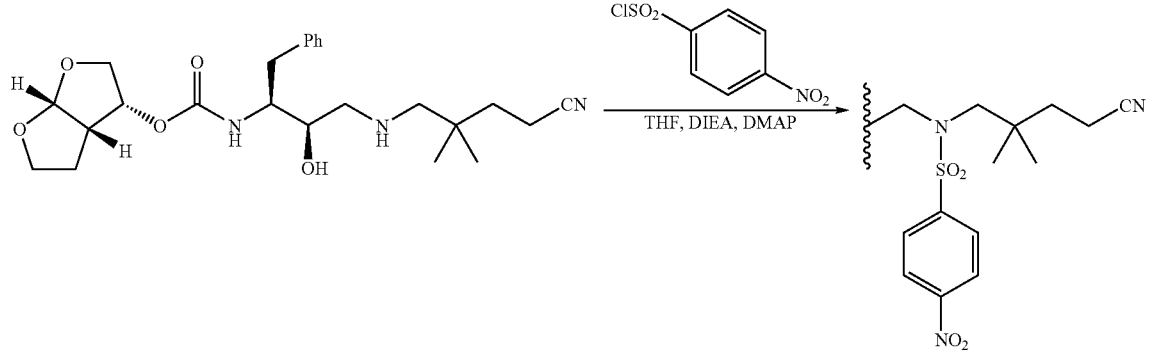

(3R,3aS,6aR)hexahydrofuro[2,3-b]furan-3-yl N-(1S,2R)-1-benzyl-3-[(4-nitrophenylsulfonyl)(4-cyano-2,2-dimethylbutyl)amino]-2-hydroxypropylcarbamate According to example 257, step 6, (3R,3aS,6aR)hexahydrofuro[2,3-b]furan-3-yl N-(1S,2R)-1-benzyl-3-[(4-cyano-2,2-dimethylbutyl)amino]-2-hydroxypropylcarbamate (example 257, step 5) was subjected to sulfonylation with 4-nitrobenzenesulfonyl chloride to afford the desired sulfonamide as a light yellow foam in 82% yield. MS(ESI): 653(M+Na).

Step 2:

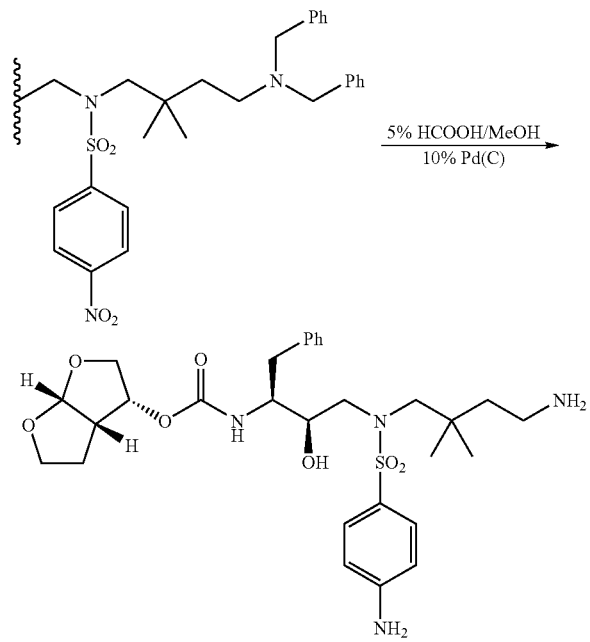

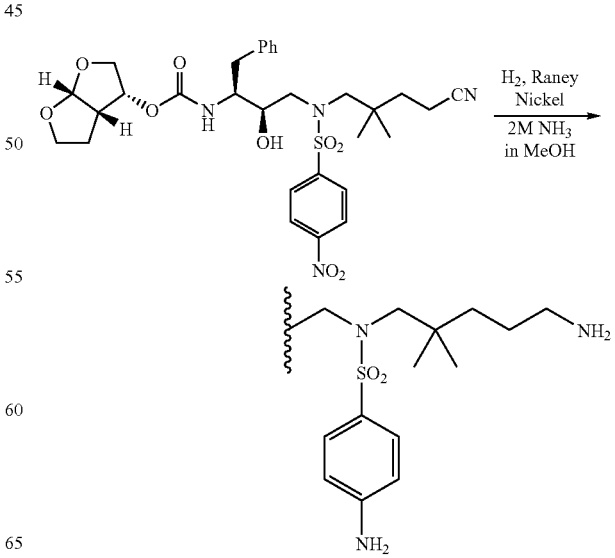

(3R,3aS,6aR)hexahydrofuro[2,3-b]furan-3-yl N-(1S,2R)-1-benzyl-3-[(4-aminophenylsulfonyl)(4-amino-2,2-dimethylbutyl)amino]-2-hydroxypropylcarbamate According to example 217, step 3, (3R,3aS,6aR)hexahydrofuro[2,3-b]furan-3-yl N-(1S,2R)-1-benzyl-3-[(4-nitrophenylsulfonyl)(4-[N,N-dibenzylamino]-2,2-dimethylbutyl)amino]-2-hydroxypropylcarbamate was subjected to catalytic transfer hydrogenation to afford the desired primary amine as a white foam in 63% yield.

281

(3R,3aS,6aR)hexahydrofuro[2,3-b]furan-3-yl N-(1S,2R)-1-benzyl-3-[(4-aminophenylsulfonyl)(5-amino-2,2-dimethylpentyl)amino]-2-hydroxypropylcarbamate According to example 245, step 6, (3R,3aS,6aR)hexahydrofuro[2,3-b].furan-3-yl N-(1S,2R)-1-benzyl-3-[(4-nitrophenylsulfonyl)(4-cyano-2,2-dimethylbutyl)amino]-2-hydroxypropylcarbamate was subjected to Raney nickel hydrogenation to afford the desired amine as a white foam in 79% yield. NMR (CDCl$_3$): 7.60 (d, 2H), 7.38-7.18 (m, 5H), 7.00 (d, 1H), 6.72 (d, 2H), 5.65 (d, 1H), 5.05 (q, 1H), 4.21 (s, 2H), 4.07-3.78 (m, 4H), 3.76-3.62 (m, 2H), 3.36-3.07 (m, 3H), 3.05-2.72 (m, 5H), 2.61 (m, 2H), 2.55-1.60 (br, 2H), 1.80-1.28 (m, 6H), 1.02 (s, 3H), 0.90 (s, 3H). MS(ESI): 605 (M+H).

EXAMPLE (COMPOUND 288)

Step 1:

282

-continued

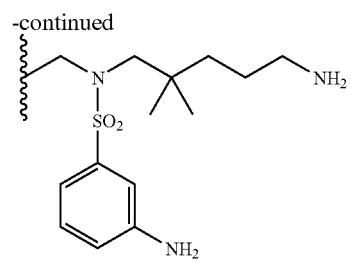

(3R,3aS,6aR)hexahydrofuro[2,3-b]furan-3-yl N-(1S,2R)-1-benzyl-3-[(3-aminophenylsulfonyl)(5-amino-2,2-dimethylpentyl)amino]-2-hydroxypropylcarbamate According to example 245, step 6, (3R,3aS,6aR)hexahydrofuro[2,3-b]furan-3-yl N-(1S,2R)-1-benzyl-3-[(3-nitrophenylsulfonyl)(4-cyano-2,2-dimethylbutyl)amino]-2-hydroxypropylcarbamate was subjected to Raney nickel hydrogenation to afford the desired amine as a white foam in 91% yield. NMR (CDCl$_3$): 7.37-7.08 (m, 8H), 7.00 (d, 1H), 6.89 (dd, 1H), 5.64 (d, 1H), 5.05 (q, 1H), 4.13-3.79 (m, 6H), 3.70 (m, 2H), 3.36-3.00 (m, 4H), 2.98-2.57 (m, 6H), 2.50-1.70 (br, 2H), 1.75-1.23 (m, 6H), 1.02 (s, 3H), 0.91 (s, 3H). MS(ESI): 605(M+H).

EXAMPLE (COMPOUND 289)

Step 1

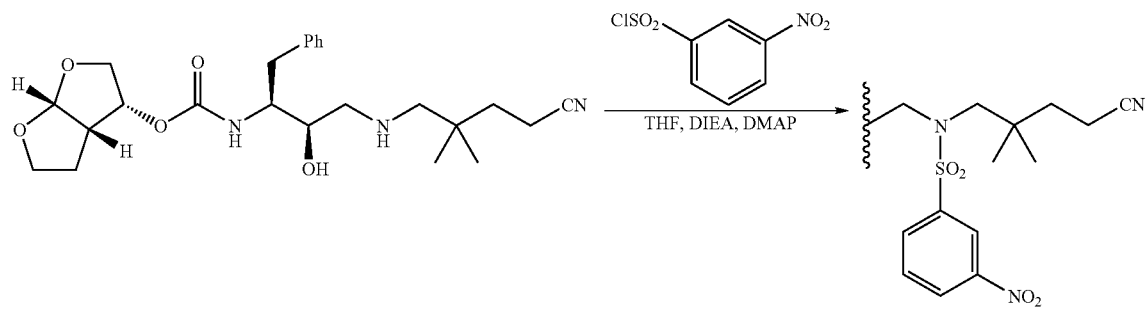

(3R,3aS,6aR)hexahydrofuro[2,3-b]furan-3-yl N-(1S,2R)-1-benzyl-3-[(3-nitrophenylsulfonyl)(4-cyano-2,2-dimethylbutyl)amino]-2-hydroxypropylcarbamate According to example 257, step 6, (3R,3aS,6aR)hexahydrofuro[2,3-b]furan-3-yl N-(1S,2R)-1-benzyl-3-[(4-cyano-2,2-dimethylbutyl)amino]-2-hydroxypropylcarbamate (example 257, step 5) was subjected to sulfonylation with 3-nitrobenzenesulfonyl chloride to afford the desired sulfonamide as a white foam in 80% yield. MS(ESI): 653(M+Na).

Step 2:

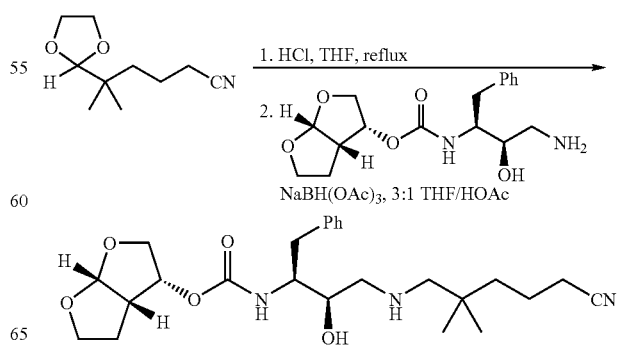

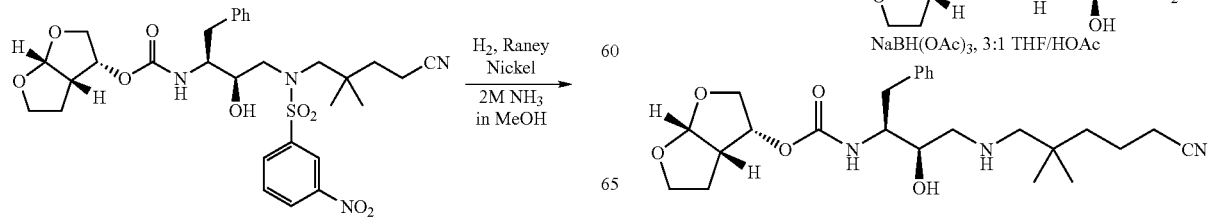

(3R,3aS,6aR)hexahydrofuro[2,3-b]furan-3-yl N-(1S, 2R)-1-benzyl-3-[(5-cyano-2,2-dimethylpentyl) amino]-2-hydroxypropylcarbamate According to example 18, steps 1 and 2,4-(1,3-dioxolan-2-yl)-4-methylpentanenitrile was subjected to acidic hydrolysis followed by reductive amination with (3R,3aS,6aR)hexahydrofuro[2,3-b]furan-3-yl N-[(1S,2R)-3-amino-1-benzyl-2-hydroxypropyl]carbamate (example 257, step 4) except that 3:1 THF/glacial acetic acid was used as the solvent in the second step. The crude product was purified by flash chromatography (SiO$_2$, 95:5 CH$_2$Cl$_2$/2M NH$_3$ in MeOH) to give the desired compound as a thick semi-solid in 58% yield.
MS(ESI): 460(M+H).

Step 2:

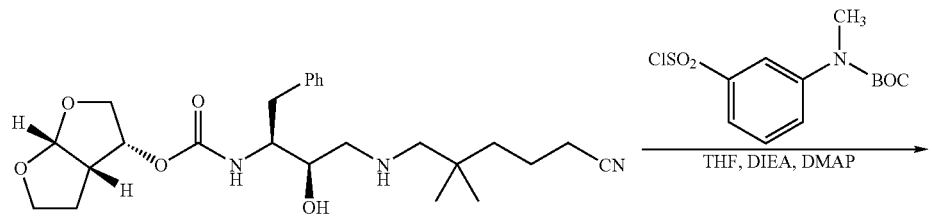

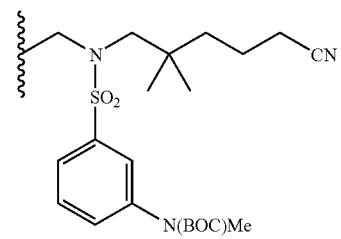

(3R,3aS,6aR)hexahydrofuro[2,3-b]furan-3-yl N-(1S, 2R)-1-benzyl-3-[(3-[(tert-butoxycarbonyl)(methyl) amino]phenylsulfonyl)(5-cyano-2,2-dimethylpentyl) amino]-2-hydroxypropylcarbamate According to example 258, step 1, (3R,3aS,6aR.)hexahydrofuro[2,3-b]furan-3-yl N-(1S,2R)-1-benzyl-3-[(5-cyano-2,2-dimethylpentyl)amino]-2-hydroxypropylcarbamate was subjected to sulfonylation to give the desired product as a white foam in 35% yield.
MS(ESI): 751(M+Na).

Step 3:

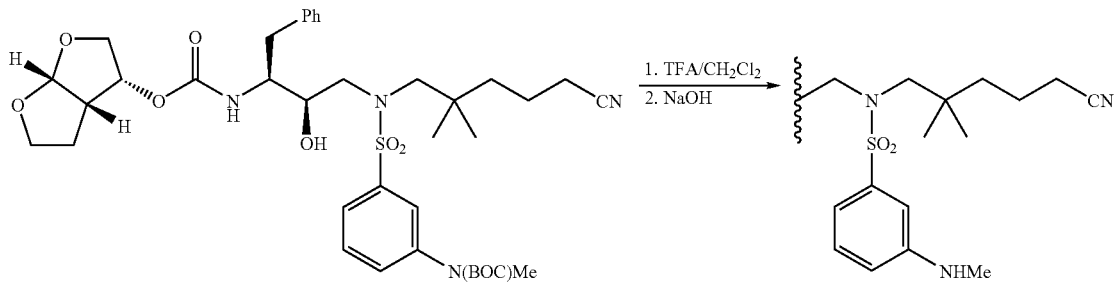

(3R,3aS,6aR)hexahydrofuro[2,3-b]furan-3-yl N-(1S,2R)-1-benzyl-3-[(3-(methylamino)phenylsulfonyl)(5-cyano-2,2-dimethylpentyl)amino]-2-hydroxypropylcarbamate According to example 258, step 2, (3R,3aS,6aR)hexahydrofuro[2,3-b]furan-3-yl N-(1S,2R)-1-benzyl-3-[(3-[(tert-butoxycarbonyl)(methyl)amino]phenylsulfonyl)(5-cyano-2,2-dimethylpentyl)amino]-2-hydroxypropylcarbamate was subjected to TFA deprotection to afford the desired product in 94% yield. MS(ESI): 629(M+H).

Step 4:

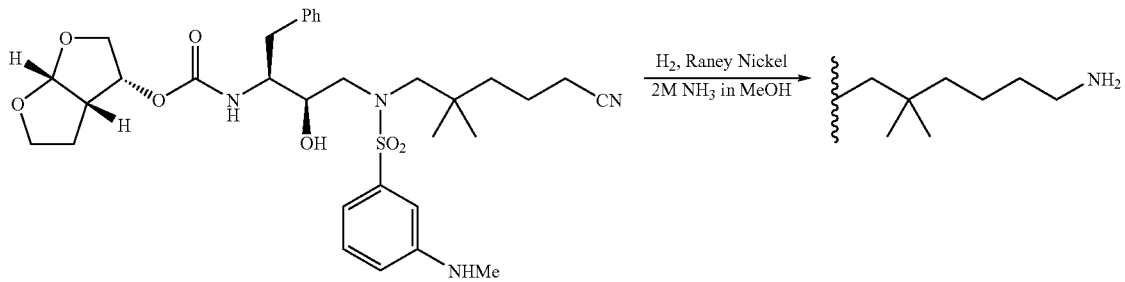

(3R,3aS,6aR)hexahydrofuro[2,3-b]furan-3-yl N-(1S,2R)-1-benzyl-3-[(3-(methylamino)phenylsulfonyl)(6-amino-2,2-dimethylhexyl)amino]-2-hydroxypropylcarbamate According to example 245, step 6, (3R,3aS,6aR)hexahydrofuro[2,3-b]furan-3-yl N-(1S,2R)-1-benzyl-3-[(3-(methylamino)phenylsulfonyl)(5-cyano-2,2-dimethylpentyl)amino]-2-hydroxypropylcarbamate was subjected to Raney nickel hydrogenation to afford the desired primary amine as a white foam in 79% yield. H1-NMR (CDCl$_3$): 7.37-7.17 (m, 6H), 7.09 (d, 1H), 7.01 (s, 1H), 6.80 (dd, 1H), 5.65 (d, 1H), 5.45 (d, 1H), 5.02 (q, 1H), 4.25 (br s, 1H), 4.06 (t, 1H), 4.01-3.63 (m, 5H), 3.33-2.40 (m, 15H), 1.72-1.27 (m, 8H), 0.96 (d, 6H).
MS(ESI): 633(M+H)

EXAMPLE (COMPOUND 290)

Step 1:

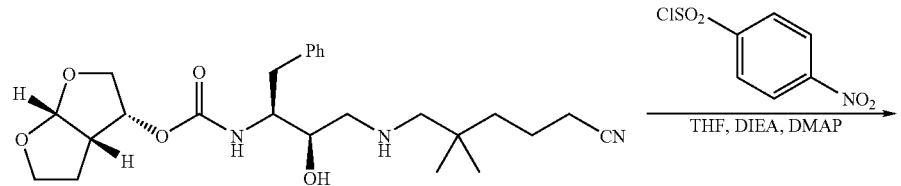

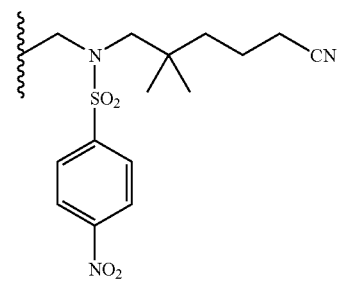

(3R,3aS,6aR)hexahydrofuro[2,3-b]furan-3-yl N-(1S,2R)-1-benzyl-3-[(4-nitrophenylsulfonyl)(5-cyano-2,2-dimethylpentyl)amino]-2-hydroxypropylcarbamate According to example 257, step 6, (3R,3aS,6aR)hexahydrofuro[2,3-b]furan-3-yl N-(1S,2R)-1-benzyl-3-[(5-cyano-2,2-dimethylpentyl)amino]-2-hydroxypropylcarbamate (example 289, step 1) was subjected to sulfonylation with 4-nitrobenzenesulfonyl chloride to afford the desired sulfonamide as a light yellow foam in 87% yield. MS(ESI): 667(M+Na).

Step 2:

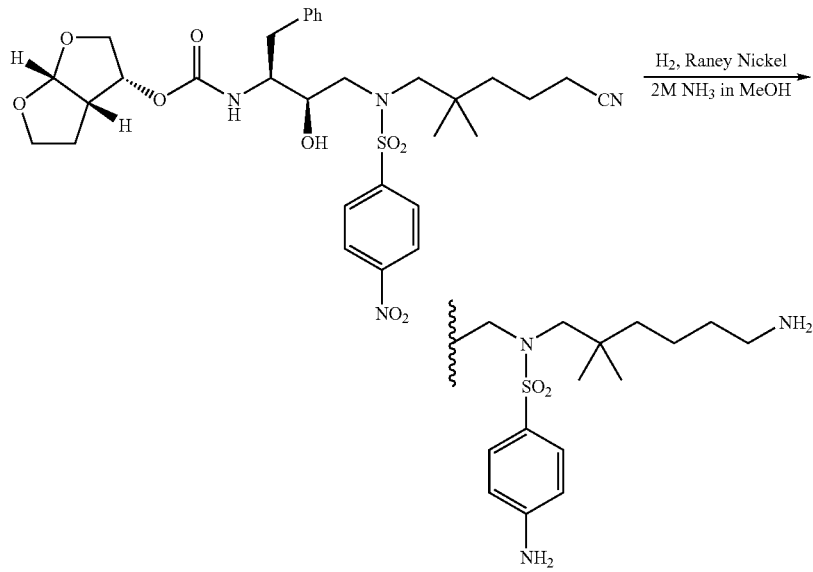

(3R,3aS,6aR)hexahydrofuro[2,3-b]furan-3-yl N-(1S,2R)-1-benzyl-3-[(4-aminophenylsulfonyl)(6-amino-2,2-dimethylhexyl)amino]-2-hydroxypropylcarbamate According to example 245, step 6, (3R,3aS,6aR)hexahydrofuro[2,3-b]furan-3-yl N-(1S,2R)-1-benzyl-3-[(4-nitrophenylsulfonyl)(5-cyano-2,2-dimethylpentyl)amino]-2-hydroxypropylcarbamate was subjected to Raney nickel hydrogenation to afford the desired primary amine as a white foam in 79% yield. H1-NMR (CDCl$_3$): 7.60 (d, 2H), 7.33-7.18 (m, 5H), 6.75 (d, 2H), 5.66 (s, 1H), 5.49 (d, 1H), 5.02 (q, 1H), 4.32 (s, 2H), 4.09 (t, 1H), 4.01-3.65 (m, 5H), 3.27-2.50 (m, 12H), 1.70-1.23 (m, 8H), 0.95 (d, 6H). MS(ESI): 619(M+H).

EXAMPLE (COMPOUND 291)

Step 1:

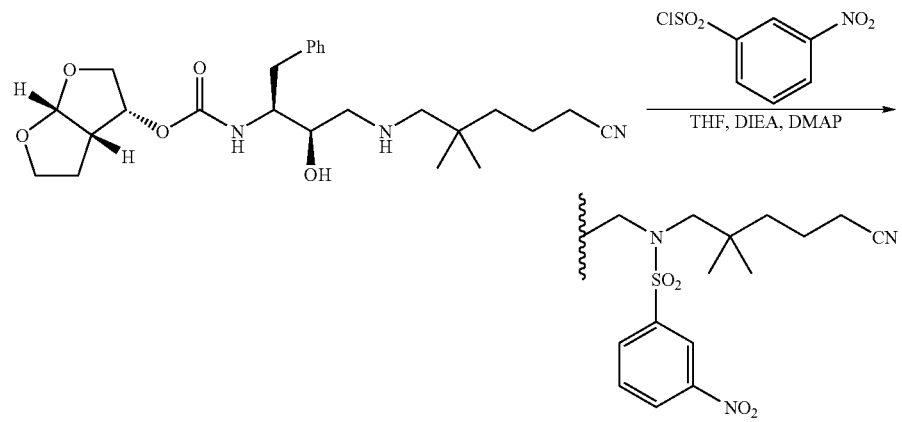

(3R,3aS,6aR)hexahydrofuro[2,3-b]furan-3-yl N-(1S,2R)-1-benzyl-3-[(3-nitrophenylsulfonyl)(5-cyano-2,2-dimethylpentyl)amino]-2-hydroxypropylcarbamate According to example 257, step 6, (3R,3aS,6aR)hexahydrofuro[2,3-b]furan-3-yl N-(1S,2R)-1-benzyl-3-[(5-cyano-2,2-dimethylpentyl)amino]-2-hydroxypropylcarbamate (example 289, step 1) was subjected to sulfonylation with 3-nitrobenzenesulfonyl chloride to afford the desired sulfonamide as a white foam in 90% yield. MS(ESI): 667(M+Na).

Step 2:

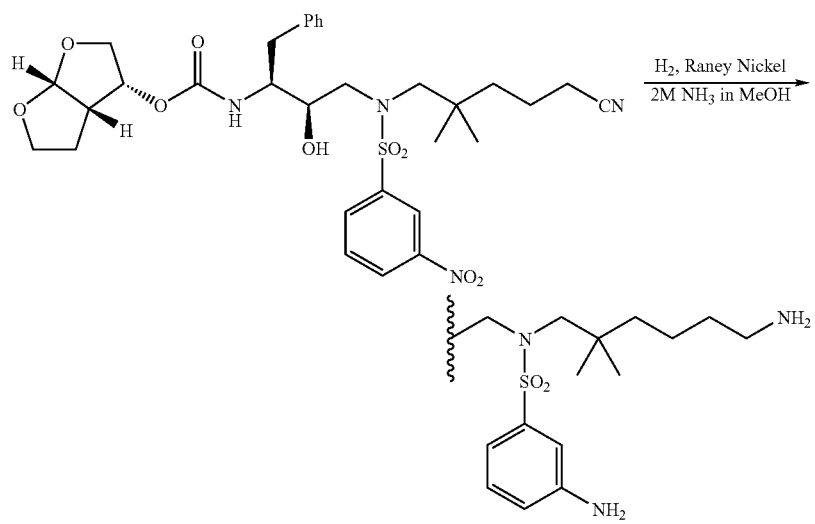

(3R,3aS,6aR)hexahydrofuro[2,3-b]furan-3-yl N-(1S,2R)-1-benzyl-3-[(3-aminophenylsulfonyl)(6-amino-2,2-dimethylhexyl)amino]-2-hydroxypropylcarbamate According to example 245, step 6, (3R,3aS,6aR)hexahydrofuro[2,3-b]furan-3-yl N-(1S,2R)-1-benzyl-3-[(3-nitrophenylsulfonyl)(5-cyano-2,2-dimethylpentyl)amino]-2-hydroxypropylcarbamate was subjected to Raney nickel hydrogenation to afford the desired primary amine as a white foam in 78% yield. H1-NMR (CDCl₃): 7.36-7.19 (m, 6H), 7.14 (m, 2H), 6.88 (dd, 1H), 5.66 (d, 1H), 5.46 (d, 1H), 5.04 (q, 1H), 4.30-4.01 (m, 3H), 4.00-3.65 (m, 5H), 3.33-2.40 (m, 12H), 1.72-1.25 (m, 8H), 0.95 (d, 6H). MS(ESI): 619(M+H).

EXAMPLE (COMPOUND 292)

Step 1:

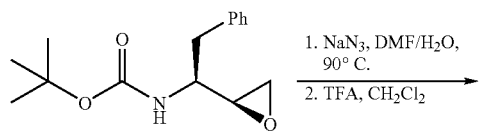

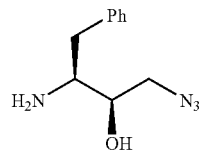

[(3S,2R)-3-amino-2-hydroxy-4-phenylbutyl]azide

A solution of 53 g (200 mMol) of tert-butyl N-(1S)-1-[(2S)oxiran-2-yl]-2-phenylethylcarbamate and 20 g of sodium azide (300 mMol) in 500 mL of DMF and 25 mL of water was heated to 90° C. for 3 hours. The mixture was cooled and the product was precipitated by the addition of 1 L of water. The solid was collected, re-dissolved in ethyl acetate and extracted with 1 N hydrochloric acid followed by saturated sodium bicarbonate. Drying over magnesium sulfate and evaporation of the volatiles afforded 31 g of the desired azide (m/e: 307 (M+H)) as a white solid which was dissolved in 200 mL of dichloromethane and treated with 200 mL of trifluoroacetic acid. The resulting solution was stirred at room temperature for 3 hours and the volatiles were removed in vacuo. The residue was partitioned between ethyl acetate and saturated sodium bicarbonate solution. The organic layer was dried and evaporated to give the free amine as a colorless syrup which solidified on standing. MS(ESI): 207(M+H).

Step 2:

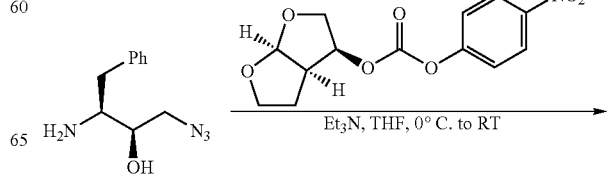

-continued

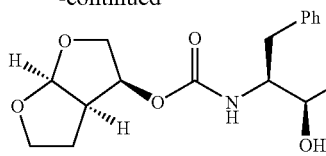

(3S,3aR,6aS)hexahydrofuro[2,3-b]furan-3-yl N-[(1S,2R)-3-azido-1-benzyl-2-hydroxypropyl]carbamate A solution of 1.91 g (9.26 mmol) of [(3S,2R)-3-amino-2-hydroxy-4-phenylbutyl]azide and 2.28 g (7.72 mmol) of (3S,3aR,6aS)hexahydrofuro[2,3-b]furan-3-yl (4-nitrophenyl) carbonate in 40 mL of THF was treated with 2.20 mL (15.5 mmol) of triethylamine. The resulting solution was stirred at RT. After 3 days the solution was concentrated in vacuo and the residue dissolved in CH$_2$Cl$_2$. The solution was washed with 5% aqueous citric acid (3×), 1M aqueous NaOH (3×) and then water (2×). The solution was dried over MgSO$_4$ and concentrated to afford 2.20 g (78%) of the desired carbamate as a light tan solid. MS(ESI): 385(M+H). The nitrophenyl-carbonate used in the above procedure was prepared by treating (3S,3aR,6aS)hexahydrofuro[2,3-b]furan-3-ol (Ghosh, Arun K.; Chen, Yan. Tetrahedron Lett. (1995), 36(4), 505-8) with 1.05 equiv. of 4-nitrophenyl chloroformate in CH$_2$Cl$_2$ in the presence of 1.05 equiv. of pyridine.

Step 3:

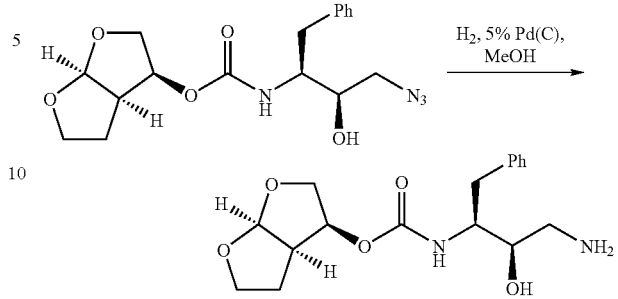

(3S,3aR,6aS)hexahydrofuro[2,3-b]furan-3-yl N-[(1S,2R)-3-amino-1-benzyl-2-hydroxypropyl]carbamate According to example 257, step 4, (3S,3aR,6aS)hexahydrofuro[2,3-b]furan-3-yl N-[(1S,2R)-3-azido-1-benzyl-2-hydroxypropyl]carbamate was subjected to catalytic hydrogenation. The crude product was purified by flash chromatography (SiO$_2$, CH$_2$Cl$_2$/2M NH$_3$ in MeOH) to afford the desired amine as a light yellow solid in 77% yield. MS(ESI): 337(M+H).

Step 4:

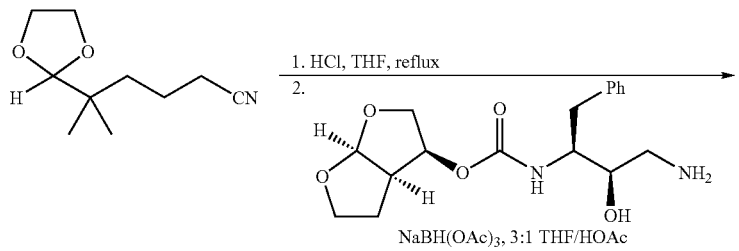

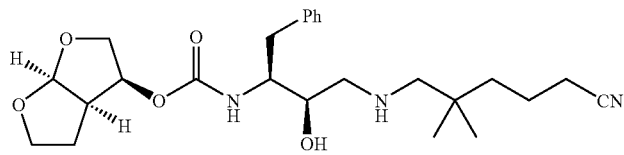

(3S,3aR,6aS)hexahydrofuro[2,3-b]furan-3-yl N-(1S,2R)-1-benzyl-3-[(5-cyano-2,2-dimethylpentyl)amino]-2-hydroxypropylcarbamate According to example 18, steps 1 and 2,4-(1,3-dioxolan-2-yl)-4-methylpentanenitrile was subjected to acidic hydrolysis followed by reductive amination with (3S,3aR,6aS)hexahydrofuro[2,3-b]furan-3-yl N-[(1S,2R)-3-amino-1-benzyl-2-hydroxypropyl]carbamate except that 3:1 THF/glacial acetic acid was used as the solvent in the second step. The crude product was purified by flash chromatography (SiO$_2$, 95:5 CH$_2$Cl$_2$/2M NH$_3$ in MeOH) to give the desired compound as a thick transparent oil in 52% yield. MS(ESI): 460(M+H).

Step 5:

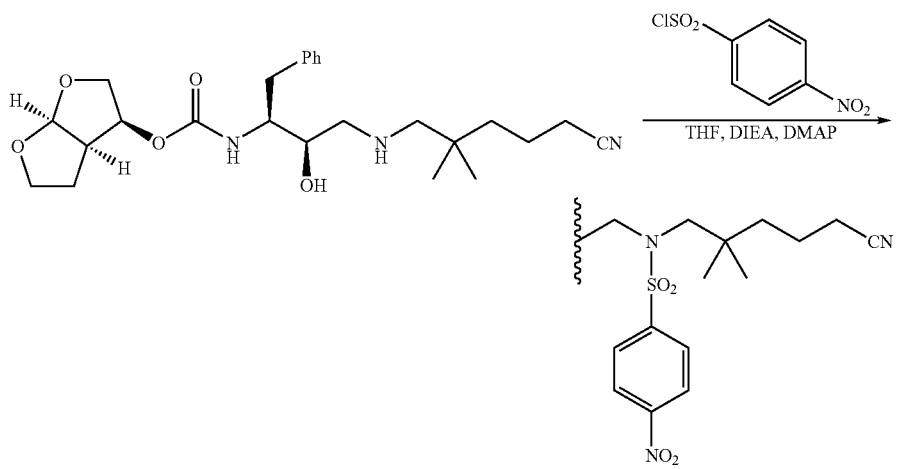

(3S,3aR,6aS)hexahydrofuro[2,3-b]furan-3-yl N-(1S, 2R)-1-benzyl-3-[(4-nitrophenylsulfonyl)(5-cyano-2, 2-dimethylpentyl)amino]-2-hydroxypropylcarbamate According to example 257, step 6, (3S,3aR,6aS)hexahydrofuro[2,3-b]furan-3-yl N-(1S,2R)-1-benzyl-3-[(5-cyano-2,2-dimethylpentyl)amino]-2-hydroxypropylcarbamate was subjected to sulfonylation with 4-nitrobenzenesulfonyl chloride to afford the desired sulfonamide as a white foam in 93% yield.

MS(ESI): 667(M+Na).

Step 6:

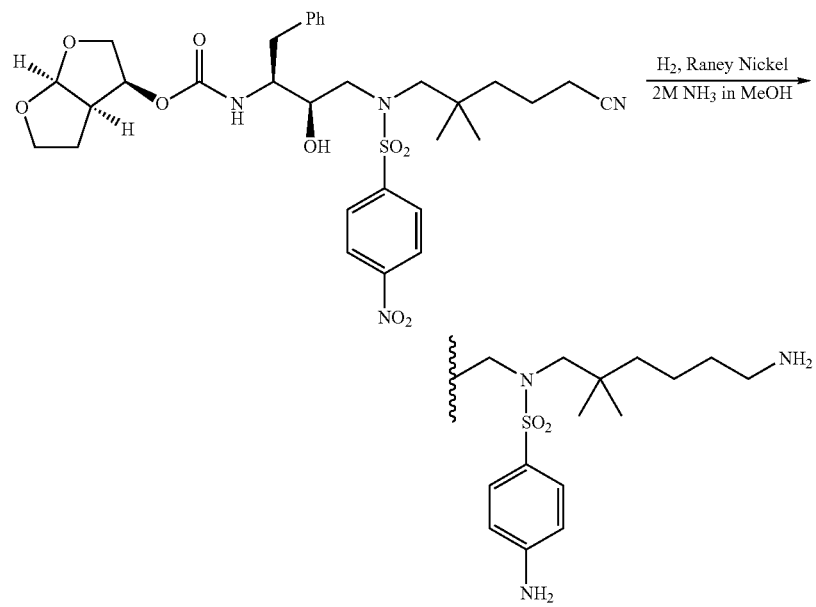

(3S,3aR,6aS)hexahydrofuro[2,3-b]furan-3-yl N-(1S, 2R)-1-benzyl-3-[(4-aminophenylsulfonyl)(6-amino-2,2-dimethylhexyl)amino]-2-hydroxypropylcarbamate According to example 245, step 6, (3S,3aR,6aS)hexahydrofuro[2,3-b]furan-3-yl N-(1S,2R)-1-benzyl-3-[(4-nitrophenylsulfonyl)(5-cyano-2,2-dimethylpentyl)amino]-2-hydroxypropylcarbamate was subjected to Raney nickel hydrogenation to afford the desired primary amine as a white foam in quantitative yield. H1-NMR (CDCl$_3$): 7.60 (d, 2H), 7.39-7.18 (m, 5H), 6.73 (d, 2H), 5.70 (d, 1H), 5.30 (d, 1H), 5.00 (q, 1H), 4.27 (s, 2H), 4.18-3.65 (m, 5H), 3.56 (dd, 1H), 3.28-2.20 (m, 12H), 2.00-1.20 (m, 6H), 0.89 (s, 6H). MS(ESI): 619(M+H).

EXAMPLE (COMPOUND 293)

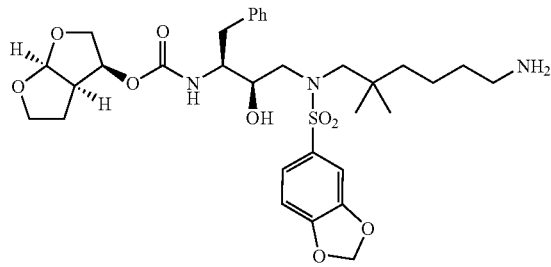

(3S,3aR,6aS)hexahydrofuro[2,3-b]furan-3-yl N-(1S, 2R)-3-[(6-amino-2,2-dimethylhexyl)(1,3-benzo-dioxol-5-ylsulfonyl)amino]-1-benzyl-2-hydroxypropylcarbamate According to example 292, steps 5 and 6, (3S,3aR,6aS) hexahydrofuro[2,3-b]furan-3-yl N-(1S,2R)-1-benzyl-3-[(5-cyano-2,2-dimethylpentyl)amino]-2-hydroxypropylcarbamate was subjected to sulfonylation (with 3,4-methylenedioxybenzenesulfonyl chloride instead of 4-nitrobenzenesulfonyl chloride) followed by Raney nickel reduction to afford the desired primary amine as a white foam. H1-NMR (DMSO-$d_6$): 7.41-7.12. (m, 8H), 7.08 (d, 1H), 6.20 (s, 2H), 5.56 (d, 1H), 4.81 (q, 1H), 3.89-3.66 (m, 4H), 3.65-2.39 (m, 14H), 1.90 (m, 1H), 1.71 (m, 1H), 1.50-1.12 (m, 6H), 0.93 (s, 6H). MS(ESI): 648(M+H).

EXAMPLE (COMPOUND 295)

Step 1:

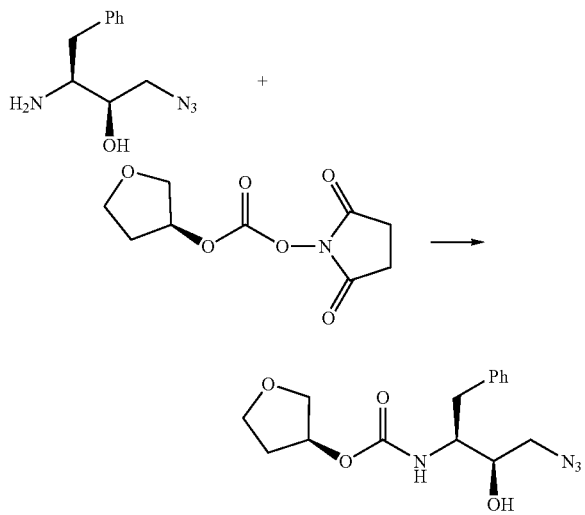

(3S)-tetrahydro-3-furanyl N-((1S,2R)-1-benzyl-3-azido-2-hydroxypropyl)carbamate

Obtained in a similar fashion to Example 292, step 2, using the corresponding activated carbonate (see U.S. Pat. No. 5,585,397). MS(ESI): 321(M+H)

Step 2:

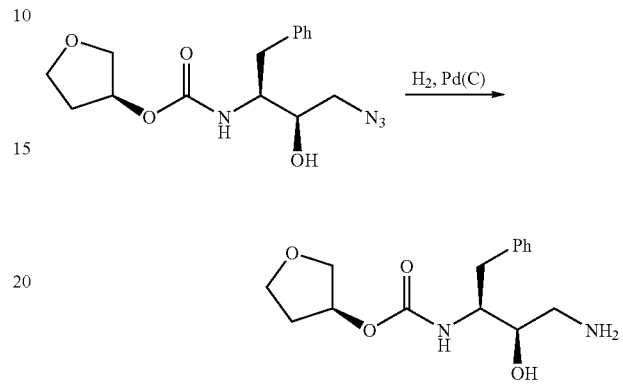

(3S)-tetrahydro-3-furanyl N-((1S,2R)-1-benzyl-3-amino-2-hydroxypropyl)carbamate

The reduction was carried out according to example 257, step 4, to afford the desired amine as a white crystalline solid. MS(ESI): 294(M+H).

Step 3:

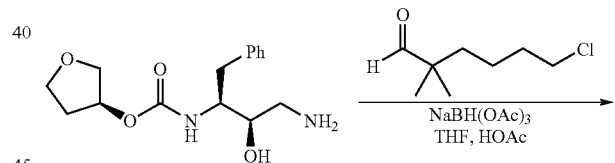

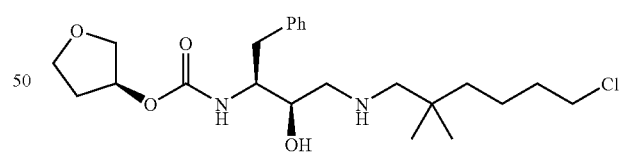

(3S)-tetrahydro-3-furanyl N-(1S,2R)-1-benzyl-3-[(6-chloro-2,2-dimethylhexyl)amino]-2-hydroxypropyl-carbamate According to example 257, step 5, (3S)-tetrahydro-3-furanyl N-((1S,2R)-1-benzyl-3-amino-2-hydroxypropyl)carbamate was subjected to reductive alkylation with 6-chloro-2,2-dimethylhexanal to afford the desired compound as a viscous oil in 93% yield. MS(ESI): 441(M+H).

Step 4:

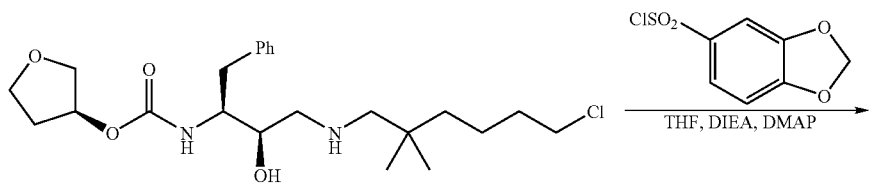

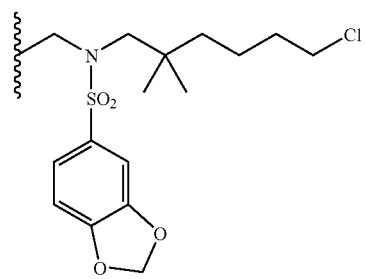

(3S)-tetrahydro-3-furanyl N-(1S,2R)-3-[(1,3-benzo-dioxol-5-ylsulfonyl)(6-chloro-2,2-dimethylhexyl)amino]-1-benzyl-2-hydroxypropylcarbamate According to example 257, step 6, (3S)-tetrahydro-3-furanyl N-(1S,2R)-1-benzyl-3-[(6-chloro-2,2-dimethylhexyl)amino]-2-hydroxypropylcarbamate was subjected to sulfonylation to afford the desired sulfonamide as a white foam in 65% yield. MS(ESI): 625(M+H).

Step 5:

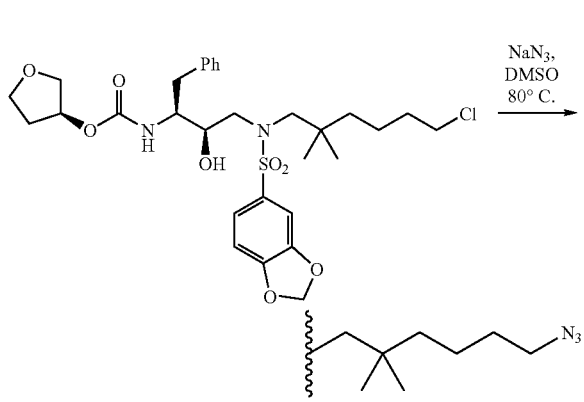

(3S)-tetrahydro-3-furanyl N-(1S,2R)-3-[(1,3-benzo-dioxol-5-ylsulfonyl)(6-azido-2,2-dimethylhexyl)amino]-1-benzyl-52-hydroxypropylcarbamate A solution of 0.320 g (0.512 mmol) of (3S)-tetrahydro-3-furanyl N-(1S,2R)-3-[(1,3-benzodioxol-5-ylsulfonyl)(6-chloro-2,2-dimethylhexyl)amino]-1-benzyl-2-hydroxypropylcarbamate and 66 mg (1.02 mmol) of sodium azide in 4 mL of DMSO was heated to 80° C. with stirring. After 2.5 hours the solution was cooled to RT and diluted with $CH_2Cl_2$, washed with water (3×), dried over $MgSO_4$, and concentrated in vacuo. The crude residue was purified by flash chromatography ($SiO_2$, $CH_2Cl_2$/MeOH) to afford 0.225 g (70%) of the desired azide as a clear viscous oil.

MS(ESI): 632(M+H)

Step 6:

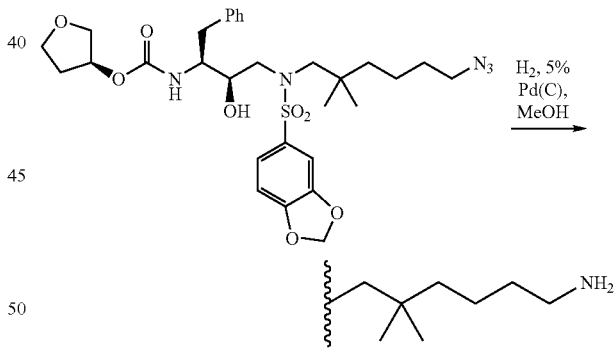

(3S)-tetrahydro-3-furanyl N-(1S,2R)-3-[(1,3-benzo-dioxol-5-ylsulfonyl)(6-amino-2,2-dimethylhexyl)amino]-1-benzyl-2-hydroxypropylcarbamate According to example 257, step 4, (3S)-tetrahydro-3-furanyl N-(1S,2R)-3-[(1,3-benzodioxol-5-ylsulfonyl)(6-azido-2,2-dimethylhexyl)amino]-1-benzyl-2-hydroxypropylcarbamate was subjected to catalytic hydrogenation followed by flash chromatography. ($SiO_2$, $CH_2Cl_2$/2M $NH_3$ in MeOH) to afford the desired amine as a white foam in 45% yield. H1-NMR ($CDCl_3$): 7.32 (dd, 1H), 7.28-7.15 (m, 6H), 6.87 (d, 1H), 6.07 (s, 2H), 5.18-5.03 (m, 2H), 3.95 (t, 1H), 3.85-3.67

(m, 4H), 3.54 (d, 1H), 3.20-2.30 (m, 11H), 2.08 (m, 1H), 1.88 (m, 1H), 1.48-1.21 (m, 6H), 0.89 (d, 6H). MS(ESI): 606(M+H).

EXAMPLE (COMPOUND 296)

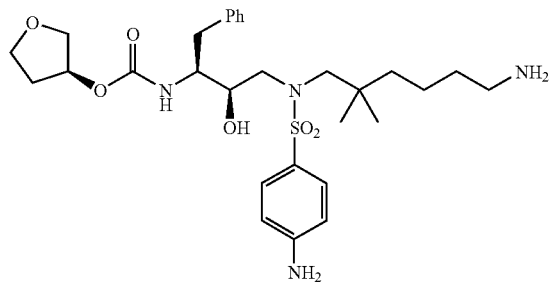

(3S)-tetrahydro-3-furanyl N-(1S,2R)-3-[(4-aminophenylsulfonyl)(6-amino-2,2-dimethylhexyl)amino]-1-benzyl-2-hydroxypropylcarbamate The title compound was prepared according to example 295 with the exception that 4-nitrobenzenesulfonyl chloride was used in step 4. H1-NMR (CDCl$_3$): 7.53 (d, 2H), 7.30-7.13 (m, 5H), 6.66 (d, 2H), 5.13 (d, 1H), 5.06 (br s, 1H), 4.21 (s, 2H), 3.97 (t, 1H), 3.89-3.65 (m, 4H), 3.52 (d, 1H), 3.20-2.30 (m, 11H), 2.04 (m, 1H), 1.88 (m, 1H), 1.48-1.15 (m, 6H), 0.87 (d, 6H). MS(ESI): 577(M+H).

EXAMPLE (COMPOUND 297)

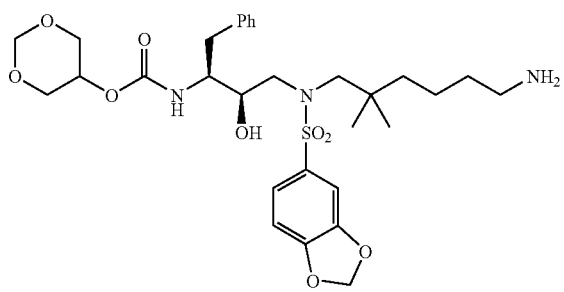

[1,3]-dioxan-5-yl N-(1S,2R)-3-[(1,3-benzodioxol-5-ylsulfonyl)(6-amino-2,2-dimethylhexyl)amino]-1-benzyl-2-hydroxypropylcarbamate The title compound was prepared according to example 295 with the exception that 1,3-dioxan-5-yl 4-nitrophenyl carbonate (see U.S. Pat. No. 5,585,397) was used as the acylating reagent in step 1. H1-NMR (CDCl$_3$): 7.32 (dd, 1H), 7.28-7.14 (m, 6H), 6.87 (d, 1H), 6.06 (s, 2H), 5.46 (d, 1H), 4.89 (d, 1H), 4.72 (d, 1H), 4.43 (br s, 1H), 3.98 (t, 1H), 3.94-3.72 (m, 4H), 3.68 (d, 1H), 3.21-2.50 (m, 1H), 1.49-1.38 (m, 2H), 1.33-1.21 (m, 4H), 0.89 (d, 6H). MS(ESI): 622(M+H).

EXAMPLE (COMPOUND 298)

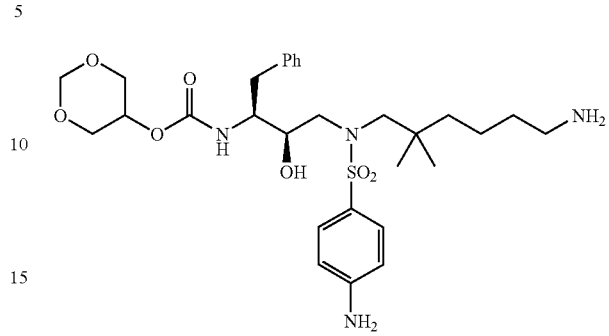

[1,3]-dioxan-5-yl N-(1S,2R)-3-[(4-aminophenylsulfonyl)(6-amino-2,2-dimethylhexyl)amino]-1-benzyl-2-hydroxypropylcarbamate The title compound was prepared according to example 295 with the exceptions that 1,3-dioxan-5-yl 4-nitrophenyl carbonate (see U.S. Pat. No. 5,585,397) was used as the acylating reagent in step 1 and 4-nitrobenzenesulfonyl chloride was used as the sulfonylating reagent in step 4. H1-NMR (CDCl$_3$): 7.52 (d, 2H), 7.30-7.13 (m, 5H), 6.67 (d, 2H), 5.40 (d, 1H), 4.89 (d, 1H), 4.70 (d, 1H), 4.43 (br s, 1H), 4.20 (s, 2H), 4.00 (t, 1H), 3.94-3.73 (m, 4H), 3.66 (d, 1H), 3.12 (dd, 1H), 3.07-2.40 (m, 10H), 1.45-1.33 (m, 2H), 1.30-1.19 (m, 6H), 0.88 (d, 6H). MS (ESI): 593 (M+H).

EXAMPLES (COMPOUNDS 299-372)

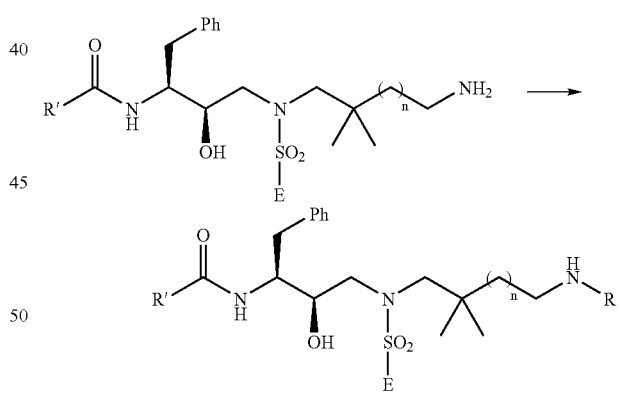

General Procedure for Reactions of Primary Amine Scaffolds with Various Electrophiles:

A solution of the primary amine (0.02 M) in anhydrous THF at 0° C. was treated with 1.05 equiv. of N,N-diisopropylethylamine (omitted for reactions with isocyanates, examples 301, 306, and 312) followed by 1.05 equiv. of the appropriate electrophile (chloroformate, sulfonyl chloride, carbamyl chloride, or isocyanate). The resulting solution was allowed to warm to RT with stirring. When analysis by TLC indicated the reaction to be complete the solution was concentrated in vacuo and the residue subjected to flash chromatography (SiO$_2$, CH$_2$Cl$_2$/MeOH or CH$_2$Cl$_2$/2M NH$_3$ in MeOH) to afford the purified product.

Mass Spectral Data for Compounds 299-372:

| Example | Amine Precursor | R' | E | n | R | MS (ESI) |
|---------|-----------------|----|----|---|---|----------|
| 299 | 244 | hexahydrofuro[3,2-b]furan-3-yloxy | benzo[1,3]dioxol-5-yl | 3 | C(O)OEt | 720 (M + H) |
| 300 | 244 | hexahydrofuro[3,2-b]furan-3-yloxy | benzo[1,3]dioxol-5-yl | 3 | C(O)OiPr | 734 (M + H) |
| 301 | 244 | hexahydrofuro[3,2-b]furan-3-yloxy | benzo[1,3]dioxol-5-yl | 3 | C(O)NHMe | 727 (M + Na) |
| 302 | 257 | hexahydrofuro[3,2-b]furan-3-yloxy | benzo[1,3]dioxol-5-yl | 2 | C(O)OEt | 706 (M + H) |
| 303 | 257 | hexahydrofuro[3,2-b]furan-3-yloxy | benzo[1,3]dioxol-5-yl | 2 | C(O)OiPr | 720 (M + H) |
| 304 | 257 | hexahydrofuro[3,2-b]furan-3-yloxy | benzo[1,3]dioxol-5-yl | 2 | C(O)SMe | 730 (M + Na) |
| 305 | 257 | hexahydrofuro[3,2-b]furan-3-yloxy | benzo[1,3]dioxol-5-yl | 2 | C(O)SEt | 744 (M + Na) |
| 306 | 257 | hexahydrofuro[3,2-b]furan-3-yloxy | benzo[1,3]dioxol-5-yl | 2 | C(O)NHMe | 713 (M + Na) |
| 307 | 282 | hexahydrofuro[3,2-b]furan-3-yloxy | benzo[1,3]dioxol-5-yl | 1 | C(O)OMe | 678 (M + H) |
| 308 | 282 | hexahydrofuro[3,2-b]furan-3-yloxy | benzo[1,3]dioxol-5-yl | 1 | C(O)OiPr | 706 (M + H) |

-continued

| Example | Amine Precursor | R' | E | n | R | MS (ESI) |
|---|---|---|---|---|---|---|
| 309 | 282 | hexahydrofuro[2,3-b]furan-O- | benzo[d][1,3]dioxol-5-yl | 1 | -C(O)OEt | 714 (M + Na) |
| 310 | 282 | hexahydrofuro[2,3-b]furan-O- | benzo[d][1,3]dioxol-5-yl | 1 | -SO₂Me | 720 (M + Na) |
| 311 | 282 | hexahydrofuro[2,3-b]furan-O- | benzo[d][1,3]dioxol-5-yl | 1 | -C(O)NMe₂ | 691 (M + H) |
| 312 | 282 | hexahydrofuro[2,3-b]furan-O- | benzo[d][1,3]dioxol-5-yl | 1 | -C(O)NHMe | 699 (M + Na) |
| 313 | 283 | hexahydrofuro[2,3-b]furan-O- | benzo[d][1,3]dioxol-5-yl | 4 | -C(O)OMe | 720 (M + H) |
| 314 | 283 | hexahydrofuro[2,3-b]furan-O- | benzo[d][1,3]dioxol-5-yl | 4 | -C(O)OEt | 734 (M + H) |
| 315 | 283 | hexahydrofuro[2,3-b]furan-O- | benzo[d][1,3]dioxol-5-yl | 4 | -C(O)OiPr | 748 (M + H) |
| 316 | 283 | hexahydrofuro[2,3-b]furan-O- | benzo[d][1,3]dioxol-5-yl | 4 | -SO₂Me | 762 (M + Na) |
| 317 | 284 | hexahydrofuro[2,3-b]furan-O- | 3-(NHMe)phenyl | 1 | -C(O)OMe | 663 (M + H) |
| 318 | 284 | hexahydrofuro[2,3-b]furan-O- | 3-(NHMe)phenyl | 1 | -SO₂Me | 705 (M + Na) |

-continued

| Example | Amine Precursor | R' | E | n | R | MS (ESI) |
|---------|-----------------|----|----|---|---|----------|
| 319 | 284 | hexahydrofuro[3,2-b]furan-3-yloxy | 3-NHMe-phenyl | 1 | C(O)NMe₂ | 676 (M + H) |
| 320 | 285 | hexahydrofuro[3,2-b]furan-3-yloxy | 3-NH₂-phenyl | 1 | C(O)OMe | 649 (M + H) |
| 321 | 285 | hexahydrofuro[3,2-b]furan-3-yloxy | 3-NH₂-phenyl | 1 | C(O)OEt | 663 (M + H) |
| 322 | 285 | hexahydrofuro[3,2-b]furan-3-yloxy | 3-NH₂-phenyl | 1 | C(O)OiPr | 677 (M + H) |
| 323 | 285 | hexahydrofuro[3,2-b]furan-3-yloxy | 3-NH₂-phenyl | 1 | C(O)NMe₂ | 662 (M + H) |
| 324 | 285 | hexahydrofuro[3,2-b]furan-3-yloxy | 3-NH₂-phenyl | 1 | SO₂Me | 669 (M + H) |
| 325 | 286 | hexahydrofuro[3,2-b]furan-3-yloxy | 4-NH₂-phenyl | 1 | C(O)OMe | 649 (M + H) |
| 326 | 286 | hexahydrofuro[3,2-b]furan-3-yloxy | 4-NH₂-phenyl | 1 | C(O)OEt | 663 (M + H) |
| 327 | 286 | hexahydrofuro[3,2-b]furan-3-yloxy | 4-NH₂-phenyl | 1 | SO₂Me | 691 (M + H) |
| 328 | 286 | hexahydrofuro[3,2-b]furan-3-yloxy | 4-NH₂-phenyl | 1 | C(O)NMe₂ | 662 (M + H) |

-continued

| Example | Amine Precursor | R' | E | n | R | MS (ESI) |
|---|---|---|---|---|---|---|
| 329 | 286 | hexahydrofuro[3,2-b]furan-O- | 4-aminophenyl | 1 | -C(O)O-iPr | 677 (M + H) |
| 330 | 287 | hexahydrofuro[3,2-b]furan-O- | 4-aminophenyl | 2 | -C(O)NMe₂ | 676 (M + H) |
| 331 | 287 | hexahydrofuro[3,2-b]furan-O- | 4-aminophenyl | 2 | -SO₂Me | 705 (M + Na) |
| 332 | 287 | hexahydrofuro[3,2-b]furan-O- | 4-aminophenyl | 2 | -C(O)OMe | 663 (M + H) |
| 333 | 287 | hexahydrofuro[3,2-b]furan-O- | 4-aminophenyl | 2 | -C(O)OEt | 699 (M + Na) |
| 334 | 287 | hexahydrofuro[3,2-b]furan-O- | 4-aminophenyl | 2 | -C(O)O-iPr | 691 (M + H) |
| 335 | 288 | hexahydrofuro[3,2-b]furan-O- | 3-aminophenyl | 2 | -C(O)OMe | 685 (M + Na) |
| 336 | 288 | hexahydrofuro[3,2-b]furan-O- | 3-aminophenyl | 2 | -C(O)NMe₂ | 698 (M + Na) |
| 337 | 288 | hexahydrofuro[3,2-b]furan-O- | 3-aminophenyl | 2 | -SO₂Me | 705 (M + Na) |
| 338 | 288 | hexahydrofuro[3,2-b]furan-O- | 3-aminophenyl | 2 | -C(O)OEt | 699 (M + Na) |

-continued

| Example | Amine Precursor | R' | E | n | R | MS (ESI) |
|---|---|---|---|---|---|---|
| 339 | 288 | hexahydrofuro[3,2-b]furan-3-yloxy | 3-aminophenyl | 2 | C(O)OiPr | 691 (M + H) |
| 340 | 289 | hexahydrofuro[3,2-b]furan-3-yloxy | 3-NHMe-phenyl | 2 | SO₂Me | 711 (M + H) |
| 341 | 289 | hexahydrofuro[3,2-b]furan-3-yloxy | 3-NHMe-phenyl | 3 | C(O)OEt | 705 (M + H) |
| 342 | 289 | hexahydrofuro[3,2-b]furan-3-yloxy | 3-NHMe-phenyl | 3 | C(O)OiPr | 719 (M + H) |
| 343 | 290 | hexahydrofuro[3,2-b]furan-3-yloxy | 4-aminophenyl | 3 | C(O)OMe | 677 (M + H) |
| 344 | 290 | hexahydrofuro[3,2-b]furan-3-yloxy | 4-aminophenyl | 3 | C(O)OEt | 691 (M + H) |
| 345 | 290 | hexahydrofuro[3,2-b]furan-3-yloxy | 4-aminophenyl | 3 | C(O)OiPr | 705 (M + H) |
| 346 | 290 | hexahydrofuro[3,2-b]furan-3-yloxy | 4-aminophenyl | 3 | C(O)NMe₂ | 690 (M + H) |
| 347 | 290 | hexahydrofuro[3,2-b]furan-3-yloxy | 4-aminophenyl | 3 | SO₂Me | 697 (M + H) |
| 348 | 291 | hexahydrofuro[3,2-b]furan-3-yloxy | 3-aminophenyl | 3 | C(O)OMe | 677 (M + H) |

-continued

| Example | Amine Precursor | R' | E | n | R | MS (ESI) |
|---|---|---|---|---|---|---|
| 349 | 291 | hexahydrofuro[3,2-b]furan-3-yl-O- | phenyl-NH₂ (meta) | 3 | C(=O)OEt | 691 (M + H) |
| 350 | 291 | hexahydrofuro[3,2-b]furan-3-yl-O- | phenyl-NH₂ (meta) | 3 | C(=O)OiPr | 705 (M + H) |
| 351 | 291 | hexahydrofuro[3,2-b]furan-3-yl-O- | phenyl-NH₂ (meta) | 3 | C(=O)NMe₂ | 690 (M + H) |
| 352 | 291 | hexahydrofuro[3,2-b]furan-3-yl-O- | phenyl-NH₂ (meta) | 3 | SO₂Me | 697 (M + H) |
| 353 | 291 | hexahydrofuro[3,2-b]furan-3-yl-O- | phenyl-NH₂ (meta) | 3 | C(=O)SMe | 693 (M + H) |
| 354 | 291 | hexahydrofuro[3,2-b]furan-3-yl-O- | phenyl-NH₂ (meta) | 3 | C(=O)SEt | 707 (M + H) |
| 355 | 292 | hexahydrofuro[3,2-b]furan-3-yl-O- | phenyl-NH₂ (para) | 3 | C(=O)OMe | 677 (M + H) |
| 356 | 292 | hexahydrofuro[3,2-b]furan-3-yl-O- | phenyl-NH₂ (para) | 3 | C(=O)OEt | 691 (M + H) |
| 357 | 292 | hexahydrofuro[3,2-b]furan-3-yl-O- | phenyl-NH₂ (para) | 3 | C(=O)OiPr | 705 (M + H) |
| 358 | 292 | hexahydrofuro[3,2-b]furan-3-yl-O- | phenyl-NH₂ (para) | 3 | SO₂Me | 697 (M + H) |

-continued

| Example | Amine Precursor | R' | E | n | R | MS (ESI) |
|---|---|---|---|---|---|---|
| 359 | 293 | (hexahydrofuro[3,2-b]furan-3-yloxy, H,H stereo) | benzo[1,3]dioxol-5-yl | 3 | C(=O)OMe | 728 (M + Na) |
| 360 | 293 | (hexahydrofuro[3,2-b]furan-3-yloxy) | benzo[1,3]dioxol-5-yl | 3 | C(=O)OEt | 720 (M + H) |
| 361 | 293 | (hexahydrofuro[3,2-b]furan-3-yloxy) | benzo[1,3]dioxol-5-yl | 3 | C(=O)OiPr | 734 (M + H) |
| 362 | 293 | (hexahydrofuro[3,2-b]furan-3-yloxy) | benzo[1,3]dioxol-5-yl | 3 | SO₂Me | 726 (M + H) |
| 363 | 294 | MeO-C(=O)-NH-CH(tBu)- | benzo[1,3]dioxol-5-yl | 3 | C(=O)OMe | 721 (M + H) |
| 364 | 294 | MeO-C(=O)-NH-CH(tBu)- | benzo[1,3]dioxol-5-yl | 3 | SO₂Me | 741 (M + H) |
| 365 | 295 | (tetrahydrofuran-3-yloxy) | benzo[1,3]dioxol-5-yl | 3 | C(=O)OMe | 664 (M + H) |
| 366 | 295 | (tetrahydrofuran-3-yloxy) | benzo[1,3]dioxol-5-yl | 3 | SO₂Me | 684 (M + H) |
| 367 | 296 | (tetrahydrofuran-3-yloxy) | 4-aminophenyl | 3 | C(=O)OMe | 635 (M + H) |

| Example | Amine Precursor | R' | E | n | R | MS (ESI) |
|---|---|---|---|---|---|---|
| 368 | 296 | (S)-tetrahydrofuran-3-yloxy | 4-aminophenyl | 3 | SO₂Me | 655 (M + H) |
| 369 | 297 | 1,3-dioxan-5-yloxy | benzo[1,3]dioxol-5-yl | 3 | C(O)OMe | 680 (M + H) |
| 370 | 297 | 1,3-dioxan-5-yloxy | benzo[1,3]dioxol-5-yl | 3 | SO₂Me | 722 (M + Na) |
| 371 | 298 | 1,3-dioxan-5-yloxy | 4-aminophenyl | 3 | C(O)OMe | 651 (M + H) |
| 372 | 298 | 1,3-dioxan-5-yloxy | 4-aminophenyl | 3 | SO₂Me | 671 (M + H) |

Proton NMR data for selected compounds from the above table:

Example (Compound 299) NMR (CDCl₃): 7.32 (dd, 1H), 7.29-7.14 (m, 6H), 6.89 (d, 1H), 6.07 (s, 2H), 5.60 (d, 1H), 5.24 (m, 1H), 4.98 (q, 1H), 4.81 (br s, 1H), 4.09 (q, 2H), 4.01 (m, 1H), 3.91 (dd, 1H), 3.80 (m, 2H), 3.63 (m, 2H), 3.21-3.01 (m, 5H), 2.96 (d, 1H), 2.90-2.65 (m, 3H), 1.70-1.17 (m, 11H), 0.89 (d, 6H).

Example (Compound 300) NMR (CDCl₃): 7.32 (dd, 1H), 7.28-7.11 (m, 6H), 6.89 (d, 1H), 6.08 (s, 2H), 5.60 (d, 1H), 5.29 (br s, 1H), 4.97 (q, 1H), 4.89 (m, 1H), 4.72 (br s, 1H), 4.01 (t, 1H), 3.91 (dd, 1H), 3.79 (m, 2H), 3.63 (m, 2H), 3.21-3.02 (m, 5H), 2.96 (d, 1H), 2.84 (m, 1H), 2.73 (m, 2H), 1.60-1.15 (m, 14H), 0.88 (d, 6H).

Example (Compound 307) NMR (CDCl₃): 7.32 (dd, 1H), 7.28-7.13 (m, 6H), 6.89 (d, 1H), 6.08 (s, 2H), 5.60 (d, 1H), 5.25 (m, 1H), 5.08 (br s, 1H), 4.96 (q, 1H), 4.20-3.95 (m, 2H), 3.91 (dd, 1H), 3.81 (m, 2H), 3.64 (m, 5H), 3.25-2.92 (m, 6H), 2.87 (m, 1H), 2.81-2.66 (m, 2H), 1.70-1.30 (m, 4H), 0.98 (s, 3H), 0.91 (s, 3H).

Example (Compound 309) NMR (CDCl₃): 7.32 (dd, 1H), 7.28-7.10 (m, 6H), 6.88 (d, 1H), 6.08 (s, 2H), 5.60 (d, 1H), 5.25 (m, 1H), 5.00 (m, 2H), 4.20-3.89 (m, 5H), 3.80 (m, 2H), 3.63 (m, 2H), 3.28-2.93 (m, 6H), 2.88 (m, 1H), 2.82-2.65 (m, 2H), 1.80-1.30 (m, 4H), 1.21 (t, 3H), 0.99 (s, 3H), 0.91 (s, 3H).

Example (Compound 313) NMR (CDCl₃): 7.32 (dd, 1H), 7.30-5 7.12 (m, 6H), 6.89 (d, 1H), 6.09 (s, 2H), 5.61 (d, 1H), 4.97 (m, 2H), 4.83 (br s, 1H), 4.03 (m, 1H), 3.92 (m, 1H), 3.82 (m, 2H), 3.64 (m, 5H), 3.21-2.67 (m, 9H), 1.70-1.33 (m, 4H), 1.23 (m, 6H), 0.87 (d, 6H).

Example (Compound 314) NMR (CDCl₃): 7.33 (dd, 1H), 7.29-7.13 (m, 6H), 6.89 (d, 1H), 6.09 (s, 2H), 5.60 (d, 1H), 4.98 (m, 2H), 4.76 (br s, 1H), 4.13-4.00 (m, 3H), 3.91 (dd, 1H), 3.82 (m, 2H), 3.66 (m, 2H), 3.21-2.68 (m, 9H), 1.66-1.33 (m, 5H), 1.23 (m, 8H), 0.89 (s, 6H).

Example (Compound 315) NMR (CDCl₃): 7.32 (dd, 1H), 7.28-7.13 (m, 6H), 6.90 (d, 1H), 6.08 (s, 2H), 5.61 (d, 1H), 4.98 (m, 2H), 4.88 (m, 1H), 4.67 (br s, 1H), 4.03 (m, 1H), 3.91 (dd, 1H), 3.82 (m, 2H), 3.66 (m, 2H), 3.21-2.66 (m, 9H), 1.70-1.31 (m, 6H), 1.24 (m, 10H), 0.89 (s, 6H).

Example (Compound 316) NMR (CDCl₃): 7.32 (dd, 1H), 7.30-7.12 (m, 6H), 6.90 (d, 1H), 6.09 (s, 2H), 5.61 (d, 1H), 4.98 (m, 2H), 4.62 (m, 1H), 4.04 (m, 2H), 4.95-3.76 (m, 3H), 3.68 (m, 2H), 3.21-3.05 (m, 4H), 3.04-2.82 (m, 6H), 2.73 (m, 2H), 1.56 (m, 3H), 1.43-1.20 (m, 7H), 0.90 (d, 6H).

Example (Compound 359) NMR (CDCl₃): 3.36-7.13 (m, 7H), 6.90 (d, 1H), 6.09 (s, 2H), 5.64 (d, 1H), 5.11 (d, 1H), 4.97 (q, 1H), 4.87 (br s, 1H), 4.07 (br s, 2H), 3.91 (m, 2H), 3.79 (m, 2H), 3.66 (s, 3H), 3.50 (m, 1H), 3.22-2.70 (m, 9H), 1.94 (m, 1H), 1.80 (m, 1H), 1.47 (br s, 2H), 1.24 (br s, 4H), 0.89 (d, 6H).

Example (Compound 360) NMR (CDCl₃): 7.36-7.12 (m, 7H), 6.88 (d, 1H), 6.09 (s, 2H), 5.64 (d, 1H), 5.14 (d, 1H), 4.96 (q, 1H), 4.80 (br s, 1H), 4.09 (br s, 4H), 3.91 (m, 2H), 3.76 (m, 2H), 3.49 (m, 1H), 3.21-2.68 (m, 9H), 1.95 (m, 1H), 1.80 (m, 1H), 1.47 (br s, 2H), 1.23 (m, 7H), 0.89 (d, 6H).

EXAMPLES (COMPOUNDS 373-519)

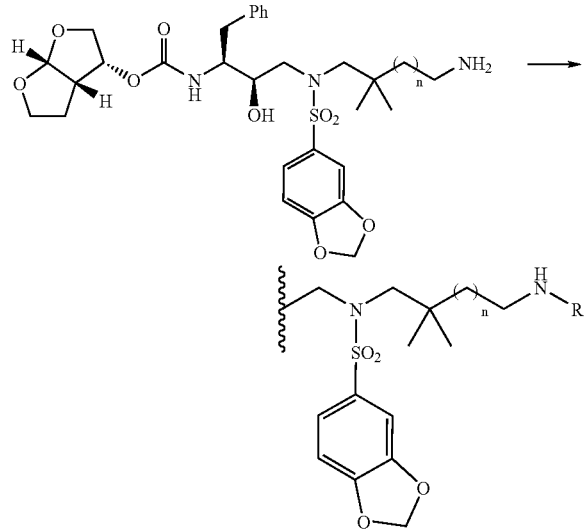

General Procedure for Reactions of Primary Amine Scaffolds with Various Electrophiles Using Scavenger Resins:

The following reactions were carried out in parallel, in sets ranging from 9 to 48, and were done in teflon-capped glass vials using a rotary shaker for agitation. To vials containing 5 to 10 equiv. of either Amberlyst A-21 resin (Aldrich, prepared by washing twice each with MeOH, CH$_2$Cl$_2$, THF, and then drying in vacuo at 60° C. overnight) or PS-DIEA resin (Argonaut Technologies, prepared as above) were added 2 mL of 16 mM solutions of the primary amine starting materials in anhydrous THF or anhydrous CH$_2$Cl$_2$. These resins were not employed when isocyanates or isothiocyanates were used as electrophiles. This was followed by addition of 3 to 5 equivalents of electrophile (acid chlorides, chloroformates, carbamyl chlorides, sulfonyl chlorides, isocyanates, isothiocyanates) either neat or as solutions in anhydrous CH$_2$Cl$_2$. The resulting mixtures were shaken at RT for 18 hours. The mixtures were then diluted two-fold with CH$_2$Cl$_2$ and treated with 5-10 equiv. of PS-Trisamine resin (Argonaut Technologies, prepared as above). This was followed by shaking at RT for an additional 18 hours. The resins were then removed by filtration and the filtrates concentrated to dryness under a stream of nitrogen to afford the desired compounds.

Mass Spectral Data for Compounds 373-519:

| Example | Amine Precursor | n | R | MS (ESI) |
|---|---|---|---|---|
| 373 | 282 | 1 | C(=O)CH$_3$ | 683 (M + Na) |
| 374 | 282 | 1 | C(=O)C(CH$_3$)$_3$ | 726 (M + Na) |
| 375 | 282 | 1 | C(=O)-cyclobutyl | 724 (M + Na) |
| 376 | 282 | 1 | C(=O)CH$_2$CH(CH$_3$)$_2$ | 726 (M + Na) |
| 377 | 282 | 1 | C(=O)Ph | 746 (M + Na) |
| 378 | 282 | 1 | C(=O)-2-furyl | 736 (M + Na) |
| 379 | 282 | 1 | C(=O)-2-thienyl | 752 (M + Na) |
| 380 | 282 | 1 | C(=O)O-n-propyl | 706 (M + H) |
| 381 | 282 | 1 | C(=O)O-n-butyl | 720 (M + H) |
| 382 | 282 | 1 | C(=O)OCH$_2$C≡CH | 702 (M + H) |
| 383 | 282 | 1 | C(=O)OC(CH$_3$)=CH$_2$ | 704 (M + H) |
| 384 | 282 | 1 | C(=O)OCH$_2$CH$_2$CH=CH$_2$ | 718 (M + H) |
| 385 | 282 | 1 | C(=O)O-(4-F-C$_6$H$_4$) | 758 (M + H) |

| Example | Amine Precursor | n | R | MS (ESI) |
|---|---|---|---|---|
| 386 | 282 | 1 | -C(O)NEt₂ | 719 (M + H) |
| 387 | 282 | 1 | -C(O)N(iPr)₂ | 747 (M + H) |
| 388 | 282 | 1 | -C(O)-morpholinyl | 732 (M + H) |
| 389 | 282 | 1 | -C(O)-pyrrolidinyl | 717 (M + H) |
| 390 | 282 | 1 | -SO₂Et | 712 (M + H) |
| 391 | 282 | 1 | -SO₂Pr | 726 (M + H) |
| 392 | 282 | 1 | -SO₂Bu | 740 (M + H) |
| 393 | 282 | 1 | -SO₂Ph | 760 (M + H) |
| 394 | 282 | 1 | -C(O)OCH₂CH₂OMe | 722 (M + H) |
| 395 | 282 | 1 | -C(O)-(4-F-cyclohexyl) | 742 (M + H) |
| 396 | 282 | 1 | -C(O)O-(4-OMe-C₆H₄) | 770 (M + H) |
| 397 | 282 | 1 | -C(O)CH₂OMe | 692 (M + H) |
| 398 | 282 | 1 | -C(O)CH(CH₃)₂ | 690 (M + H) |
| 399 | 282 | 1 | -C(O)CH₂C(CH₃)₃ | 718 (M + H) |
| 400 | 282 | 1 | -C(O)-cyclopropyl | 688 (M + H) |
| 401 | 282 | 1 | -C(O)-cyclopentyl | 716 (M + H) |
| 402 | 282 | 1 | -C(O)CH₂CH₂-cyclopentyl | 744 (M + H) |
| 403 | 282 | 1 | -C(O)CH₂CH₂C(O)OMe | 734 (M + H) |
| 404 | 282 | 1 | -C(O)-(3,5-diF-C₆H₃) | 760 (M + H) |
| 405 | 282 | 1 | -C(O)-(benzo[1,3]dioxol-5-yl) | 768 (M + H) |
| 406 | 282 | 1 | -SO₂-(4-F-C₆H₄) | 778 (M + H) |

-continued
| Example | Amine Precursor | n | R | MS (ESI) |
|---|---|---|---|---|
| 407 | 282 | 1 | 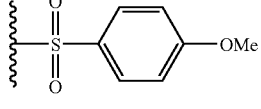 | 790 (M + H) |
| 408 | 282 | 1 | 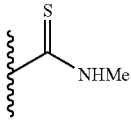 | 693 (M + H) |
| 409 | 282 | 1 | 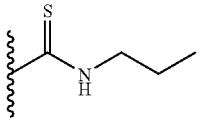 | 721 (M + H) |
| 410 | 282 | 1 | 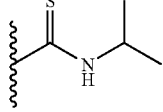 | 721 (M + H) |
| 411 | 282 | 1 | 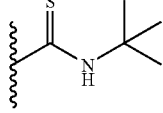 | 735 (M + H) |
| 412 | 282 | 1 | 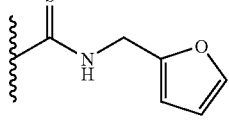 | 759 (M + H) |
| 413 | 282 | 1 | 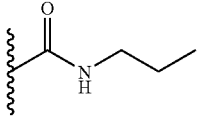 | 705 (M + H) |
| 414 | 282 | 1 | 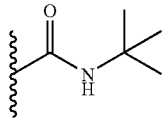 | 719 (M + H) |
| 415 | 282 | 1 | 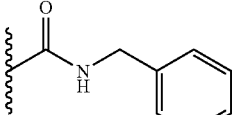 | 753 (M + H) |
| 416 | 257 | 2 | 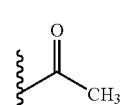 | 698 (M + Na) |
| 417 | 257 | 2 | 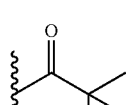 | 740 (M + Na) |
-continued
| Example | Amine Precursor | n | R | MS (ESI) |
|---|---|---|---|---|
| 418 | 257 | 2 | 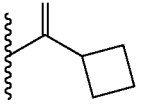 | 738 (M + Na) |
| 419 | 257 | 2 | 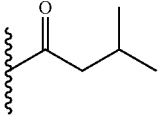 | 740 (M + Na) |
| 420 | 257 | 2 | 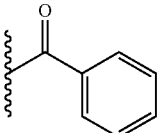 | 760 (M + Na) |
| 421 | 257 | 2 | 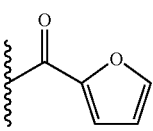 | 750 (M + Na) |
| 422 | 257 | 2 | 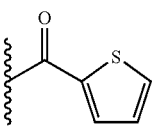 | 744 (M + H) |
| 423 | 257 | 2 | 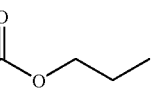 | 720 (M + H) |
| 424 | 257 | 2 | 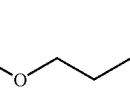 | 734 (M + H) |
| 425 | 257 | 2 | 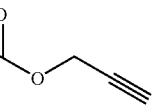 | 716 (M + H) |
| 426 | 257 | 2 | 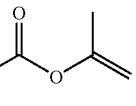 | 718 (M + H) |
| 427 | 257 | 2 | 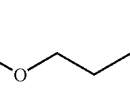 | 732 (M + H) |
| 428 | 257 | 2 | 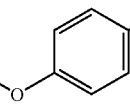 | 772 (M + H) |

323
-continued

| Example | Amine Precursor | n | R | MS (ESI) |
|---|---|---|---|---|
| 429 | 257 | 2 | 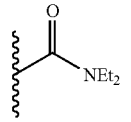 —C(O)NEt₂ | 733 (M + H) |
| 430 | 257 | 2 | 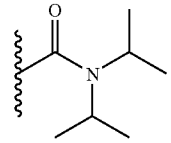 —C(O)N(iPr)₂ | 761 (M + H) |
| 431 | 257 | 2 | 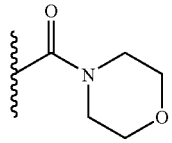 morpholine amide | 747 (M + H) |
| 432 | 257 | 2 | 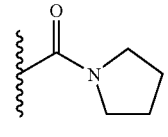 pyrrolidine amide | 731 (M + H) |
| 433 | 257 | 2 | 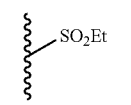 —SO₂Et | 726 (M + H) |
| 434 | 257 | 2 | 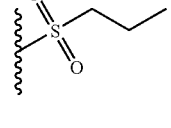 —SO₂Pr | 740 (M + H) |
| 435 | 257 | 2 | 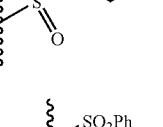 —SO₂Bu | 754 (M + H) |
| 436 | 257 | 2 | 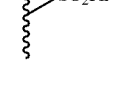 —SO₂Ph | 774 (M + H) |
| 437 | 257 | 2 | 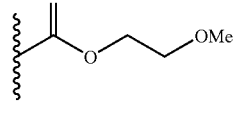 —C(O)OCH₂CH₂OMe | 736 (M + H) |
| 438 | 257 | 2 | 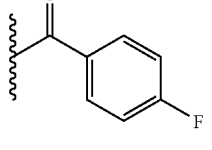 4-F-C₆H₄-C(O)- | 756 (M + H) |
| 439 | 257 | 2 | 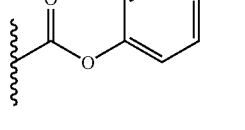 4-OMe-C₆H₄-O-C(O)- | 784 (M + H) |

324
-continued

| Example | Amine Precursor | n | R | MS (ESI) |
|---|---|---|---|---|
| 440 | 257 | 2 | 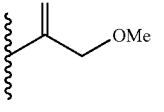 —C(O)CH₂OMe | 706 (M + H) |
| 441 | 257 | 2 | 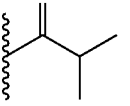 —C(O)iPr | 704 (M + H) |
| 442 | 257 | 2 | 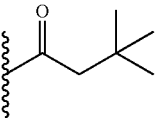 —C(O)CH₂tBu | 732 (M + H) |
| 443 | 257 | 2 | 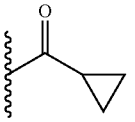 —C(O)-cyclopropyl | 702 (M + H) |
| 444 | 257 | 2 | 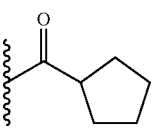 —C(O)-cyclopentyl | 730 (M + H) |
| 445 | 257 | 2 | 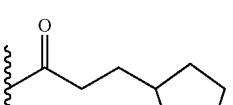 —C(O)CH₂CH₂-cyclopentyl | 758 (M + H) |
| 446 | 257 | 2 | 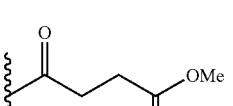 —C(O)CH₂CH₂C(O)OMe | 748 (M + H) |
| 447 | 257 | 2 | 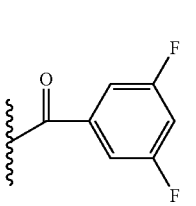 3,5-diF-C₆H₃-C(O)- | 774 (M + H) |
| 448 | 257 | 2 | 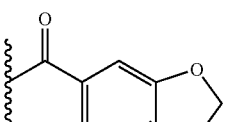 benzo[d][1,3]dioxol-5-yl-C(O)- | 782 (M + H) |
| 449 | 257 | 2 | 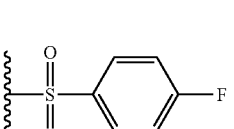 4-F-C₆H₄-SO₂- | 792 (M + H) |

325
-continued

| Example | Amine Precursor | n | R | MS (ESI) |
|---|---|---|---|---|
| 450 | 257 | 2 | -SO₂-C₆H₄-OMe (4-methoxyphenylsulfonyl) | 804 (M + H) |
| 451 | 257 | 2 | -C(=S)NHMe | 707 (M + H) |
| 452 | 257 | 2 | -C(=S)NH-propyl | 735 (M + H) |
| 453 | 257 | 2 | -C(=S)NH-isopropyl | 735 (M + H) |
| 454 | 257 | 2 | -C(=S)NH-tBu | 749 (M + H) |
| 455 | 257 | 2 | -C(=S)NH-CH₂-(2-furyl) | 773 (M + H) |
| 456 | 257 | 2 | -C(=O)NH-propyl | 719 (M + H) |
| 457 | 257 | 2 | -C(=O)NH-tBu | 733 (M + H) |
| 458 | 257 | 2 | -C(=O)NH-CH₂Ph | 767 (M + H) |
| 459 | 244 | 3 | -C(=O)CH₃ | 712 (M + Na) |
| 460 | 244 | 3 | -C(=O)C(CH₃)₃ | 754 (M + Na) |

326
-continued

| Example | Amine Precursor | n | R | MS (ESI) |
|---|---|---|---|---|
| 461 | 244 | 3 | -C(=O)-cyclobutyl | 752 (M + Na) |
| 462 | 244 | 3 | -C(=O)CH₂CH(CH₃)₂ | 754 (M + Na) |
| 463 | 244 | 3 | -C(=O)Ph | 774 (M + Na) |
| 464 | 244 | 3 | -C(=O)-(2-furyl) | 764 (M + Na) |
| 465 | 244 | 3 | -C(=O)-(2-thienyl) | 780 (M + Na) |
| 466 | 244 | 3 | -C(=O)O-propyl | 734 (M + H) |
| 467 | 244 | 3 | -C(=O)O-butyl | 748 (M + H) |
| 468 | 244 | 3 | -C(=O)O-CH₂C≡CH | 730 (M + H) |
| 469 | 244 | 3 | -C(=O)O-C(CH₃)=CH₂ | 732 (M + H) |
| 470 | 244 | 3 | -C(=O)O-CH₂CH₂CH=CH₂ | 746 (M + H) |
| 471 | 244 | 3 | -C(=O)O-C₆H₄-F (4-fluorophenyl) | 786 (M + H) |

| Example | Amine Precursor | n | R | MS (ESI) |
|---|---|---|---|---|
| 472 | 244 | 3 | 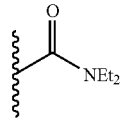 —C(O)NEt₂ | 747 (M + H) |
| 473 | 244 | 3 | 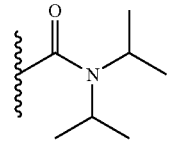 —C(O)N(iPr)₂ | 775 (M + H) |
| 474 | 244 | 3 | 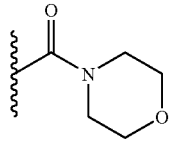 morpholine amide | 761 (M + H) |
| 475 | 244 | 3 | 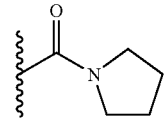 pyrrolidine amide | 745 (M + H) |
| 476 | 244 | 3 | 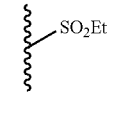 —SO₂Et | 740 (M + H) |
| 477 | 244 | 3 | 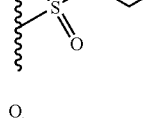 —SO₂Pr | 754 (M + H) |
| 478 | 244 | 3 | 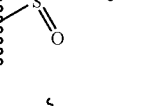 —SO₂Bu | 768 (M + H) |
| 479 | 244 | 3 |  —SO₂Ph | 788 (M + H) |
| 480 | 244 | 3 | 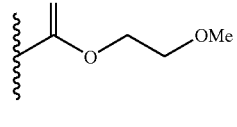 —C(O)OCH₂CH₂OMe | 750 (M + H) |
| 481 | 244 | 3 | 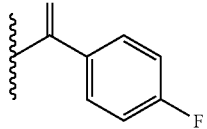 4-F-C₆H₄-C(O)— | 770 (M + H) |
| 482 | 244 | 3 | 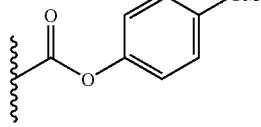 4-OMe-C₆H₄-OC(O)— | 798 (M + H) |

| Example | Amine Precursor | n | R | MS (ESI) |
|---|---|---|---|---|
| 483 | 244 | 3 | 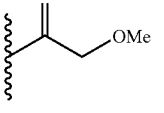 —C(O)CH₂OMe | 720 (M + H) |
| 484 | 244 | 3 | 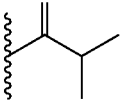 —C(O)iPr | 718 (M + H) |
| 485 | 244 | 3 | 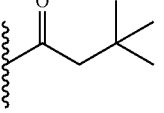 —C(O)CH₂tBu | 746 (M + H) |
| 486 | 244 | 3 | 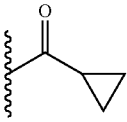 —C(O)-cyclopropyl | 716 (M + H) |
| 487 | 244 | 3 | 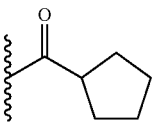 —C(O)-cyclopentyl | 744 (M + H) |
| 488 | 244 | 3 | 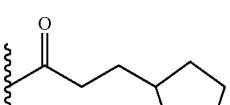 —C(O)CH₂CH₂-cyclopentyl | 772 (M + H) |
| 489 | 244 | 3 | 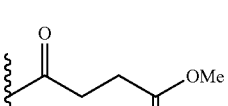 —C(O)CH₂CH₂C(O)OMe | 762 (M + H) |
| 490 | 244 | 3 | 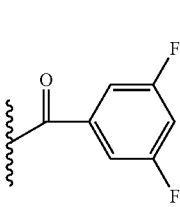 3,5-F₂-C₆H₃-C(O)— | 788 (M + H) |
| 491 | 244 | 3 | 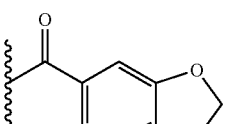 benzodioxole-C(O)— | 796 (M + H) |
| 492 | 244 | 3 | 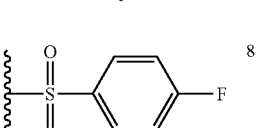 4-F-C₆H₄-SO₂— | 806 (M + H) |

329
-continued

| Example | Amine Precursor | n | R | MS (ESI) |
|---|---|---|---|---|
| 493 | 244 | 3 | 4-methoxyphenylsulfonyl | 718 (M + H) |
| 494 | 244 | 3 | C(=S)NHMe | 721 (M + H) |
| 495 | 244 | 3 | C(=S)NH-propyl | 749 (M + H) |
| 496 | 244 | 3 | C(=S)NH-iPr | 749 (M + H) |
| 497 | 244 | 3 | C(=S)NH-tBu | 763 (M + H) |
| 498 | 244 | 3 | C(=S)NHCH2-(2-furyl) | 787 (M + H) |
| 499 | 244 | 3 | C(=O)NH-propyl | 733 (M + H) |
| 500 | 244 | 3 | C(=O)NH-tBu | 747 (M + H) |
| 501 | 244 | 3 | C(=O)NHCH2Ph | 781 (M + H) |
| 502 | 283 | 4 | C(=O)CH3 | 704 (M + H) |
| 503 | 283 | 4 | C(=O)CH2CH(CH3)2 | 746 (M + H) |

330
-continued

| Example | Amine Precursor | n | R | MS (ESI) |
|---|---|---|---|---|
| 504 | 283 | 4 | C(=O)-cyclobutyl | 744 (M + H) |
| 505 | 283 | 4 | C(=O)-cyclopropyl | 730 (M + H) |
| 506 | 283 | 4 | C(=O)Ph | 766 (M + H) |
| 507 | 283 | 4 | C(=O)CH2OMe | 734 (M + H) |
| 508 | 283 | 4 | C(=O)-(2-furyl) | 756 (M + H) |
| 509 | 283 | 4 | C(=O)-(2-thienyl) | 772 (M + H) |
| 510 | 283 | 4 | C(=O)O-propyl | 748 (M + H) |
| 511 | 283 | 4 | C(=O)O-butyl | 762 (M + H) |
| 512 | 283 | 4 | C(=O)OC(=CH2)CH3 | 746 (M + H) |
| 513 | 283 | 4 | C(=O)OCH2CH2CH=CH2 | 760 (M + H) |
| 514 | 283 | 4 | C(=O)OCH2C≡CH | 744 (M + H) |

-continued

| Example | Amine Precursor | n | R | MS (ESI) |
|---|---|---|---|---|
| 515 | 283 | 4 | -C(O)O-CH2CH2-OMe | 764 (M + H) |
| 516 | 283 | 4 | -C(O)-NMe2 | 733 (M + H) |
| 517 | 283 | 4 | -C(O)-N(pyrrolidine) | 759 (M + H) |
| 518 | 283 | 4 | -C(O)-N(morpholine) | 775 (M + H) |
| 519 | 283 | 4 | -SO2Ph | 802 (M + H) |

Proton NMR data for selected compounds from the above table:

Example (Compound 375) NMR (CDCl₃): 7.39 (dd, 1H), 7.34-7.16 (m, 6H), 6.92 (d, 1H), 6.13 (s, 2H), 5.98 (br s, 1H), 5.66 (d, 1H), 5.50 (d, 1H), 5.01 (q, 1H), 4.29 (br S, 1H), 4.10-3.62 (m, 7H), 3.50-2.70 (m, 9H), 2.41-1.80 (m, 6H), 1.70-1.25 (m, 4H), 1.05 (s, 3H), 0.98 (s, 3H).

Example (Compound 378) NMR (CDCl₃): 7.46 (s, 1H), 7.39 (dd, 1H), 7.25 (m, 6H), 7.11 (m, 1H), 6.93 (d, 1H), 6.72 (t, 1H), 6.52 (m, 1H), 6.12 (s, 2H), 5.63 (d, 1H), 5.50 (d, 1H), 4.98 (q, 1H), 4.22 (br s, 1H), 4.04 (m, 1H), 3.97-2.68 (m, 14H), 1.85-1.20 (m, 4H), 1.11 (s, 3H), 1.03 (s, 3H).

Example (Compound 384) NMR (CDCl₃): 7.30 (dd, 1H), 7.26-7.07 (m, 6H), 6.86 (d, 1H), 6.04 (s, 2H), 5.73 (m, 1H), 5.58 (d, 1H), 5.24 (br s, 1H), 5.10-4.84 (m, 4H), 4.20-3.50 (m, 9H), 3.26-2.58 (m, 9H), 2.31 (m, 2H), 1.80-1.22 (m, 4H), 0.96 (s, 3H), 0.90 (s, 3H).

Example (Compound 421) NMR (CDCl₃): 7.47 (s, 1H), 0.39 (dd, 1H), 0.34-7.16 (m, 6H), 7.13 (m, 1H), 6.92 (d, 1H), 6.71 (t, 1H), 6.52 (m, 1H), 6.12 (s, 2H), 5.74 (d, 1H), 5.64 (d, 1H), 5.01 (q, 1H), 4.16 (br s, 1H), 4.10-3.60 (m, 6H), 3.59-2.68 (m, 9H), 1.80-1.23 (m, 6H), 0.99 (s, 3H), 0.91 (s, 3H).

Example (Compound 459) NMR (CDCl₃): 7.39 (dd, 1H), 7.33-7.16 (m, 6H), 6.93 (d, 1H), 6.12 (s, 2H), 5.87 (m, 1H), 5.64 (d, 1H), 5.36 (d, 1H), 5.02 (q, 1H), 4.28 (br s, 1H), 4.08 (m, 1H), 4.00-3.62 (m, 5H), 3.35-2.70 (m, 9H), 2.00 (s, 3H), 1.70-1.25 (m, 8H), 0.96 (s, 3H), 0.91 (s, 3H).

Example (Compound 464) NMR (CDCl₃): 7.45 (s, 1H), 7.39 (dd, 1H), 7.31-7.15 (m, 6H), 7.11 (1,1H), 6.93 (d, 1H), 6.65-6.47 (m, 2H), 6.12 (s, 2H), 5.64 (d, 1H), 5.52 (d, 1H), 5.01 (q, 1H), 4.30 (br s, 1H), 4.09 (m, 1H), 4.00-3.57 (m, 5H), 3.45 (m, 2H), 3.30-2.97 (m, 4H), 2.95-2.70 (m, 3H), 1.80-1.25 (m, 8H), 0.97 (s, 3H), 0.90 (s, 3H).

Example (Compound 483) NMR (CDCl₃): 7.30 (dd, 1H), 7.25-7.08 (m, 6H), 6.85 (d, 1H), 6.59 (m, 1H), 6.03 (s, 2H), 5.59 (d, 1H), 5.30 (d, 1H), 4.94 (q, 1H), 4.21 (br s, 1H), 4.10-3.50 (m, 7H), 3.47-2.63 (m, 13H), 1.60-1.05 (m, 8H), 0.92 (s, 3H), 0.88 (s, 3H).

Example (Compound 494) NMR (CDCl₃): 7.28 (dd, 1H), 7.23-7.07 (m, 6H), 6.84 (d, 1H), 6.17-5.89 (m, 4H), 5.54 (d, 1H), 5.02 (d, 1H), 4.92 (q, 1H), 4.10-3.90 (m, 2H), 3.89-3.27 (m, 7H), 3.18-2.57 (m, 10H), 1.50 (m, 3H), 1.25 (m, 5H), 0.83 (d, 6H).

Example (Compound 496) NMR (CDCl₃): 7.28 (dd, 1H), 7.22-7.05 (m, 6H), 6.85 (d, 1H), 6.02 (s, 2H), 5.57 (d, 1H), 4.95 (m, 2H), 4.18 (br s, 1H), 3.94 (t, 1H), 3.89-3.22 (m, 10H), 3.18-2.60 (m, 7H), 1.70-1.08 (m, 14H), 0.86 (d, 6H).

EXAMPLE (COMPOUND 520)

Step 1:

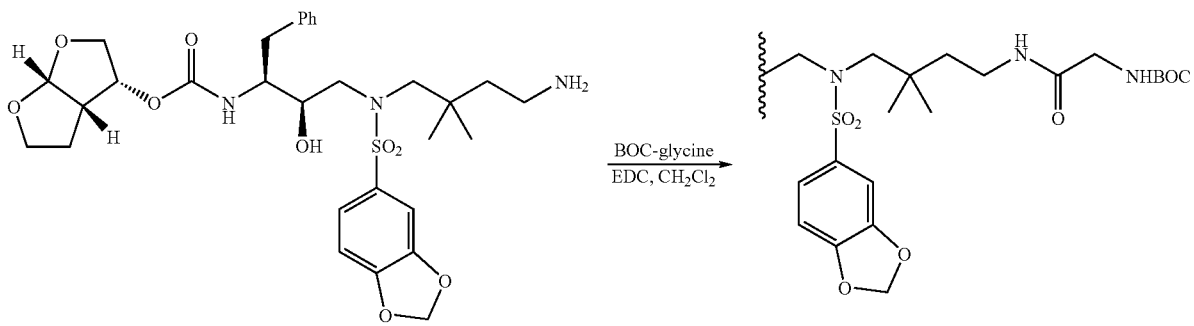

(3R,3aS,6aR)hexahydrofuro[2,3-b]furan-3-yl N-(1S,2R)-3-[(4-[(tert-butoxycarbonylamino)acetylamino]-2,2-dimethylbutyl)(1,3-benzodioxol-5-ylsulfonyl)amino]-1-benzyl-2-hydroxypropylcarbamate A solution of 0.300 g (0.484 mmol) of (3R,3aS,6aR) hexahydrofuro[2,3-b]furan-3-yl N-(1S,2R)-3-[(4-amino-2,2-dimethylbutyl)(1,3-benzodioxol-5-ylsulfonyl)amino]-1-benzyl-2-hydroxypropylcarbamate (example 282), and 0.127 g (0.726 mmol) of BOC-glycine in 8 mL of CH₂Cl₂ was treated with 0.139 g (0.726 mmol) of 1-ethyl-3-(dimethylaminopropyl)carbodiimide hydrochloride (EDC) and the resulting solution was stirred at RT. After 18 hours the solution was concentrated in vacuo and the crude material purified by flash chromatography (SiO₂, 95:5 CH₂Cl₂/2M NH₃ in MeOH) to afford 0.370 g (98%) of the desired compound as a white foam. MS(ESI): 799(M+Na).

Step 2:

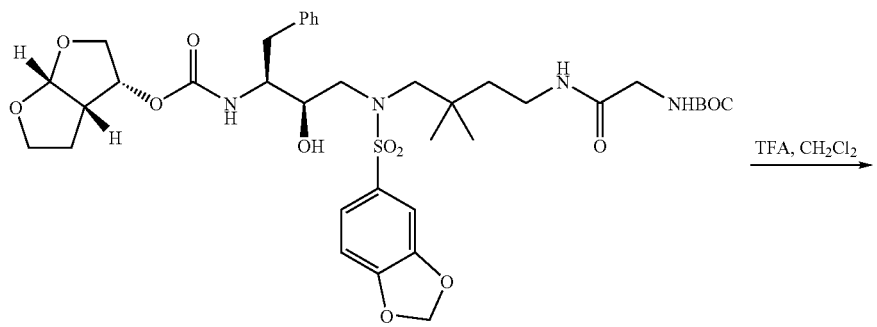

(3R,3aS,6aR)hexahydrofuro[2,3-b]furan-3-yl N-(1S,2R)-3-[(4-[(amino)acetylamino]-2,2-dimethylbutyl)(1,3-benzodioxol-5-ylsulfonyl)amino]-1-benzyl-2-hydroxypropylcarbamate A solution of 335 mg (0.431 mmol) of (3R,3aS,6aR) hexahydrofuro[2,3-b]furan-3-yl N-(1S,2R)-3-[(4-[(tert-butoxycarbonylamino)acetylamino]-2,2-dimethylbutyl)(1,3-benzodioxol-5-ylsulfonyl)amino]-1-benzyl-2-hydroxypropylcarbamate in 30 mL of 1:1 TFA/CH$_2$Cl$_2$ was stirred at RT. After 2.5 hours the solution was concentrated to dryness and the residue redissolved in CH$_2$Cl$_2$. The solution was washed with 0.5N aqueous NaOH (1×), brine (2×), dried over MgSO$_4$, and concentrated in vacuo to afford 0.247 g (85%) of the desired compound as a white foam. NMR (CDCl$_3$): 7.62 (t, 1H), 7.38 (dd, 1H), 7.36-7.17 (m, 6H), 6.92 (d, 1H), 6.13 (s, 2H), 5.62 (d, 1H), 5.65 (d, 1H), 5.01 (q, 1H), 4.08-3.58 (m, 7H), 3.50-3.03 (m, 8H), 2.96-2.80 (m, 2H), 2.72 (dd, 1H), 2.30-1.66 (m, 3H), 1.62-1.38 (m, 2H), 1.26 (dd, 1H), 1.05 (s, 3H), 0.93 (s, 3H). MS(ESI): 677(M+H).

EXAMPLE (COMPOUND 521)

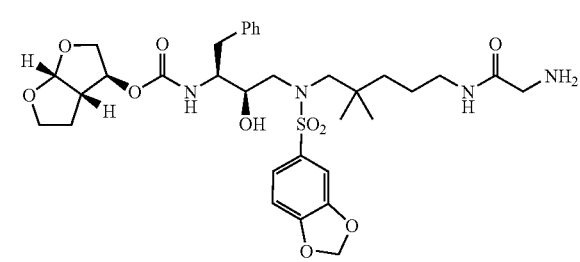

(3R,3aS,6aR)hexahydrofuro[2,3-b]furan-3-yl N-(1S,2R)-3-[(5-[(amino)acetylamino]-2,2-dimethylpentyl)(1,3-benzodioxol-5-ylsulfonyl)amino]-1-benzyl-2-hydroxypropylcarbamate According to example 520, (3R,3aS,6aR)hexahydrofuro[2,3-b]furan-3-yl N-(1S,2R)-3-(5-amino-2,2-dimethylpentyl)(1,3-benzodioxol-5-ylsulfonyl)amino)-1-benzyl-2-hydroxypropylcarbamate (example 257) was converted to the title compound which was obtained as a white foam. NMR (CDCl$_3$): 7.49 (t, 1H), 7.40 (dd, 1H), 7.33-7.14 (m, 6H), 6.92 (d, 1H), 6.12 (s, 2H), 5.82 (d, 1H), 5.64 (d, 1H), 5.02 (q, 1H), 4.08-3.63 (m, 7H), 3.42 (s, 2H), 3.40-3.02 (m, 6H), 2.89 (m, 2H), 2.72 (dd, 1H), 2.61-2.00 (br, 2H), 1.53 (m, 3H), 1.34 (m, 3H), 1.00 (s, 3H), 0.92 (s, 3H). MS(ESI): 691(M+H).

EXAMPLE (COMPOUND 522)

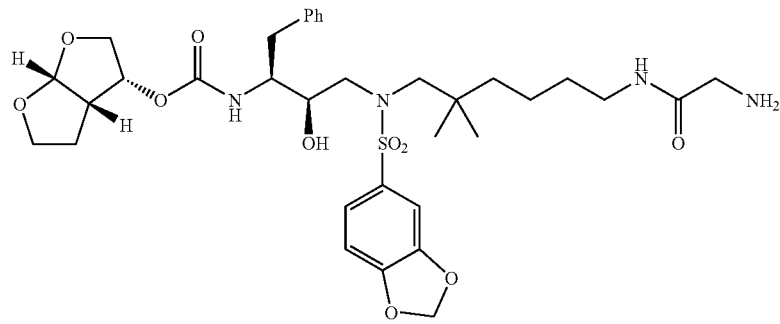

(3R,3aS,6aR)hexahydrofuro[2,3-b]furan-3-yl N-(1S, 2R)-3-[(6-[(amino)acetylamino]-2,2-dimethylhexyl) (1,3-benzodioxol-5-ylsulfonyl)amino]-1-benzyl-2-hydroxypropylcarbamate According to example 520, (3R,3aS,6aR)hexahydrofuro[2,3-b]furan-3-yl N-(1S,2R)-3-[(6-amino-2,2-dimethylhexyl)(1,3-benzodioxol-5-ylsulfonyl)amino]-1-benzyl-2-hydroxypropylcarbamate (example 244) was converted to the title compound which was obtained as a white foam. NMR (CDCl$_3$): 7.47-7.32 (m, 2H), 7.31-7.18 (m, 6H), 6.94 (d, 1H), 6.12 (s, 2H), 5.65 (d, 1H), 5.45 (d, 1H), 5.01 (q, 1H), 4.10 (t, 1H), 4.01-3.61 (m, 6H), 3.50-2.70 (m, 11H), 2.50-1.70 (br, 2H), 1.55 (m, 3H), 1.34 (m, 5H), 0.97 (s, 3H), 0.91 (s, 3H). MS(ESI): 705(M+H).

EXAMPLE (COMPOUNDS 523-543)

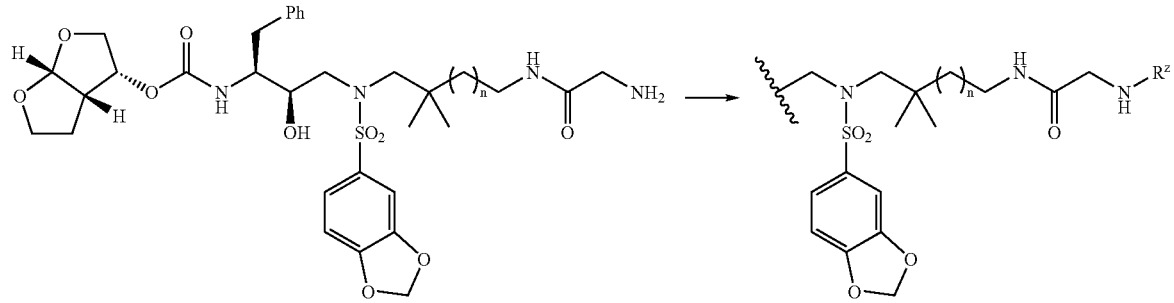

General Procedure for Reactions of Amines 520, 521, and 522 with Various Electrophiles Using Scavenger Resins:

The following reactions were carried out in parallel and were done in teflon-capped glass vials using a rotary shaker for agitation. To vials containing 130 mg of Amberlyst A-21 resin (Aldrich, prepared as in examples 373-519, not employed when methyl isocyanate was used as the electrophile) were added 1 mL of 30 mM solutions of the amine starting materials in anhydrous THF. This was followed by addition of 0.15 mL (5 equiv.) of 1M solutions of electrophiles (acid chlorides, alkyl chloroformates, N,N-dimethylcarbamyl chloride, methanesulfonyl chloride, methyl isocyanate) in anhydrous CH$_2$Cl$_2$. After the resulting mixtures were shaken at RT for 18 hours, they were diluted with CH$_2$Cl$_2$ (3×), treated with 125 mg of PS-Trisamine resin (3.75 mmol/g, Argonaut Technologies, prepared as in examples 373-519, not employed when methyl isocyanate was used as the electrophile) and shaken for an additional 18 hours. The resins were removed by filtration and the filtrates evaporated under a stream on nitrogen to afford the desired compounds.

Mass Spectral Data for Compounds 523-543:

| Example | Amine Precursor | n | R$^z$ | MS (ESI) |
|---|---|---|---|---|
| 523 | 520 | 1 | ⸺C(O)CH$_3$ | 719 (M + H) |
| 524 | 520 | 1 | ⸺C(O)OMe | 757 (M + Na) |

-continued

| Example | Amine Precursor | n | R$^z$ | MS (ESI) |
|---|---|---|---|---|
| 525 | 520 | 1 | ⸺C(O)OEt | 749 (M + H) |

| Example | Amine Precursor | n | R$^z$ | MS (ESI) |
|---|---|---|---|---|
| 526 | 520 | 1 | -C(O)NMe$_2$ | 770 (M + Na) |
| 527 | 520 | 1 | -C(O)CH$_2$OMe | 749 (M + H) |
| 528 | 520 | 1 | -SO$_2$Me | 777 (M + Na) |
| 529 | 520 | 1 | -C(O)NHMe | 756 (M + Na) |
| 530 | 521 | 2 | -C(O)CH$_3$ | 733 (M + H) |
| 531 | 521 | 2 | -C(O)OMe | 771 (M + Na) |
| 532 | 521 | 2 | -C(O)OEt | 785 (M + Na) |
| 533 | 521 | 2 | -C(O)NMe$_2$ | 784 (M + Na) |
| 534 | 521 | 2 | -C(O)CH$_2$OMe | 763 (M + H) |
| 535 | 521 | 2 | -SO$_2$Me | 791 (M + Na) |
| 536 | 521 | 2 | -C(O)NHMe | 770 (M + Na) |
| 537 | 522 | 3 | -C(O)CH$_3$ | 747 (M + H) |
| 538 | 522 | 3 | -C(O)OMe | 785 (M + Na) |
| 539 | 522 | 3 | -C(O)OEt | 777 (M + H) |
| 540 | 522 | 3 | -C(O)NMe$_2$ | 798 (M + Na) |
| 541 | 522 | 3 | -C(O)CH$_2$OMe | 777 (M + H) |
| 542 | 522 | 3 | -SO$_2$Me | 805 (M + Na) |
| 543 | 522 | 3 | -C(O)NHMe | 784 (M + Na) |

Proton NMR data for selected compounds from the above table:

Example (Compound 523) NMR (CDCl$_3$): 7.29 (dd, 1H), 7.23-7.04 (m, 6H), 6.81 (m, 3H), 6.02 (s, 2H), 5.72 (d, 1H), 5.55 (d, 1H), 4.96 (m, 1H), 4.03-3.47 (m, 8H), 3.29-2.54 (m, 10H), 2.10-1.40 (m, 5H), 1.32 (m, 1H), 1.10 (dd, 1H), 0.96 (s, 3H), 0.82 (s, 3H).

Example (Compound 524) NMR (CDCl$_3$): 7.29 (dd, 1H), 7.23-7.04 (m, 6H), 6.85 (d, 1H), 6.53 (m, 1H), 6.03 (s, 2H), 5.76 (m, 1H), 5.53 (m, 2H), 4.93 (q, 1H), 4.23 (br s, 1H), 3.98 (t, 1H), 3.87-3.44 (m, 10H), 3.38-3.02 (m, 4H), 3.01-2.71 (m, 3H), 2.62 (m, 2H), 1.80-1.25 (m, 3H), 1.16 (m, 1H), 0.99 (s, 3H), 0.84 (s, 3H).

Example (Compound 531) NMR (CDCl$_3$): 7.28 (dd, 1H), 7.23-7.04 (m, 6H), 6.84 (d, 1H), 6.45 (m, 1H), 6.03 (s, 2H), 5.60-5.40 (m, 3H), 4.92 (q, 1H), 4.11 (d, 1H), 3.98 (m, 1H), 3.89-3.51 (m, 10H), 3.29-2.88 (m, 6H), 2.79 (m, 2H), 2.62 (dd, 1H), 1.60-1.19 (m, 6H), 0.91 (s, 3H), 0.82 (s, 3H).

Example (Compound 542) NMR (CDCl$_3$): 7.41-7.20 (m, 7H), 6.96 (d, 1H), 6.62 (m, 1H), 6.14 (s, 2H), 5.73 (t, 1H), 5.67 (d, 1H), 5.31 (d, 1H), 5.05 (q, 1H), 4.43 (d, 1H), 4.11 (m, 1H), 3.98-3.61 (m, 6H), 3.52 (m, 1H), 3.34-2.85 (m, 11H), 2.76 (dd, 1H), 1.70-1.25 (m, 8H), 1.01 (s, 3H), 0.90 (s, 3H).

EXAMPLE (COMPOUND 544)

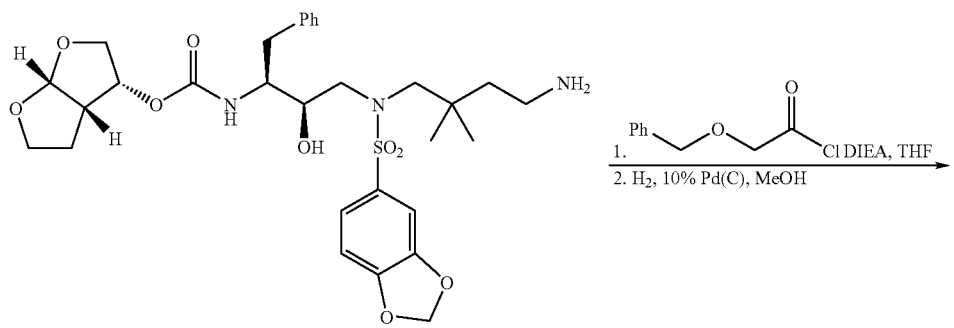

(3R,3aS,6aR)hexahydrofuro[2,3-b]furan-3-yl N-(1S,2R)-3-[(4-[(hydroxy)acetylamino]-2,2-dimethylbutyl)(1,3-benzodioxol-5-ylsulfonyl)amino]-1-benzyl-2-hydroxypropylcarbamate A solution of 50 mg (0.080 mmol) of (3R,3aS,6aR)hexahydrofuro[2,3-b]furan-3-yl N-(1S,2R)-3-[(4-amino-2,2-dimethylbutyl)(1,3-benzodioxol-5-ylsulfonyl)amino]-1-benzyl-2-hydroxypropylcarbamate (example 282) and 21 μL (0.12 mmol) of N,N-diisopropylethylamine in 4 mL of anhydrous THF at 0° C. was treated with 13.3 μL (0.084) of benzyloxyacetyl chloride. The resulting solution was allowed to warm to RT with stirring. After 2 hours the solution was concentrated in vacuo and the residue purified by flash chromatography (SiO2, 95:5 CH2Cl2/MeOH) to afford 52 mg (85%) of the desired intermediate as a white foam (m/e=768, M+H). This material (44 mg, 0.57 mmol) was then dissolved in 5 mL of MeOH and subjected to balloon hydrogenation in the presence of 25 mg of 10% Pd(C). After 2 hours the reaction vessel was purged with nitrogen, catalyst removed by filtration through celite, and the filtrate concentrated in vacuo to afford 31 mg (79%) of the desired product as a white foam. NMR (CDCl3): 7.31 (dd, 1H), 7.26-7.07 (m, 6H), 6.92 (br s, 1H), 6.87 (d, 1H), 6.04 (s, 2H), 5.69 (d, 1H), 5.56 (d, 1H), 4.95 (m, 1H), 4.12-3.90 (m, 3H), 3.86-3.62 (m, 4H), 3.54 (m, 1H), 3.36-3.15 (m, 5H), 3.02 (dd, 1H), 2.93 (d, 1H), 2.77 (q, 1H), 2.70-2.57 (m, 3H), 1.72 (m, 1H), 1.49 (m, 1H), 1.30 (m, 1H), 1.16-0.97 (m, 4H), 0.91 (s, 3H). MS(ESI): 678(M+H).

EXAMPLE (COMPOUND 545)

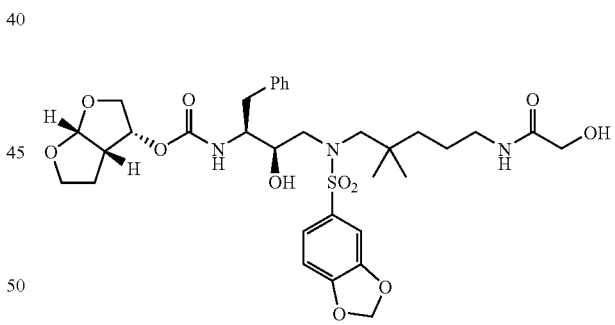

(3R,3aS,6aR)hexahydrofuro[2,3-b]furan-3-yl N-(1S,2R)-3-[((5-[(hydroxy)acetylamino]-2,2-dimethylpentyl)(1,3-benzodioxol-5-ylsulfonyl)amino]-1-benzyl-2-hydroxypropylcarbamate According to example 544, (3R,3aS,6aR)hexahydrofuro[2,3-b]furan-3-yl N-(1S,2R)-3-[(5-amino-2,2-dimethylpentyl)(1,3-benzodioxol-5-ylsulfonyl)amino]-1-benzyl-2-hydroxypropylcarbamate was converted to the title compound which was obtained as a white foam. NMR (CDCl3): 7.30 (dd, 1H), 7.27-7.10 (m, 6H), 6.88 (m, 2H), 6.05 (s, 2H), 5.55 (m, 2H), 4.96 (q, 1H), 4.14-3.91 (m, 3H), 3.89-3.71 (m, 3H), 3.70-3.54 (m, 2H), 3.36-2.90 (m, 8H), 2.81 (m, 2H), 2.63 (t, 1H), 1.50 (m, 3H), 1.41-1.17 (m, 3H), 0.91 (s, 3H), 0.85 (s, 3H). MS (ESI): 692 (M+H).

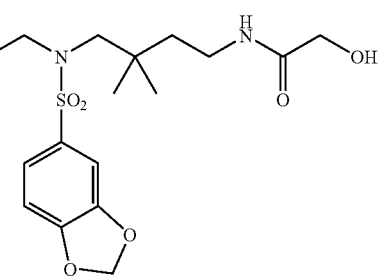

EXAMPLE (COMPOUND 546)

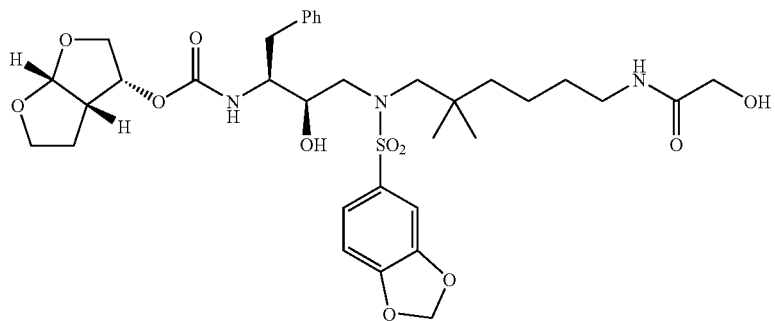

(3R,3aS,6aR)hexahydrofuro[2,3-b]furan-3-yl N-(1S,2R)-3-[(6-[(hydroxy)acetylamino]-2,2-dimethylhexyl)(1,3-benzodioxol-5-ylsulfonyl)amino]-1-benzyl-2-hydroxypropylcarbamate According to example 544, (3R,3aS,6aR)hexahydrofuro[2,3-b]furan-3-yl N-(1S,2R)-3-[(6-amino-2,2-dimethylhexyl)(1,3-benzodioxol-5-ylsulfonyl)amino]-1-benzyl-2-hydroxypropylcarbamate was converted to the title compound which was obtained as a white foam. NMR (CDCl3): 7.30 (dd, 1H), 7.27-7.11 (m, 6H), 6.88 (d, 1H), 6.74 (br s, 1H), 6.07 (s, 2H), 5.58 (d, 1H), 5.29 (d, 1H), 4.95 (q, 1H), 4.15-3.96 (m, 3H), 3.90-3.71 (m, 3H), 3.70-3.52 (m, 2H), 3.38 (m, 1H), 3.21 (m, 1H), 3.16-2.60 (m, 9H), 1.51 (m, 3H), 1.29 (m, 5H), 0.91 (s, 3H), 0.83 (s, 3H). MS(ESI): 706(M+H).

EXAMPLE (COMPOUND 547)

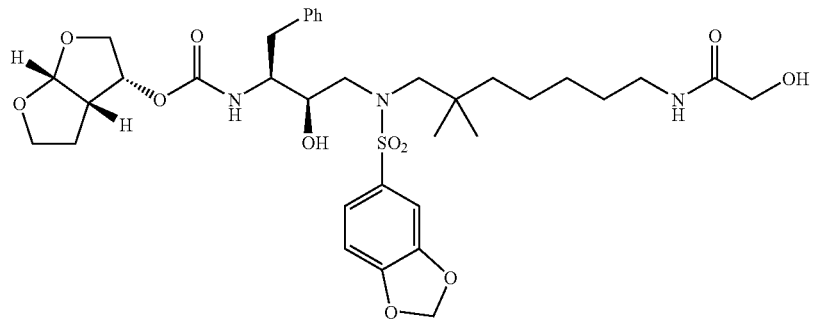

(3R,3aS,6aR)hexahydrofuro[2,3-b]furan-3-yl N-(1S,2R)-3-[(7-[(hydroxy)acetylamino]-2,2-dimethylheptyl)(1,3-benzodioxol-5-ylsulfonyl)amino]-1-benzyl-2-hydroxypropylcarbamate According to example 544, (3R,3aS,6aR)hexahydrofuro[2,3-b]furan-3-yl N-(1S,2R)-3-[(7-amino-2,2-dimethylheptyl)(1,3-benzodioxol-5-ylsulfonyl)amino]-1-benzyl-2-hydroxypropylcarbamate was converted to the title compound which was obtained as a white foam. NMR (CDCl3): 7.30 (dd, 1H), 7.26-7.08 (m, 6H), 6.88 (d, 1H), 6.74 (br s, 1H), 6.06 (s, 2H), 5.58 (d, 1H), 5.20 (d, 1H), 4.92 (q, 1H), 4.02 (br s, 3H), 3.92-3.71 (m, 3H), 3.70-3.55 (m, 2H), 3.37-2.60 (m, 11H), 1.51 (m, 3H), 1.40-1.11 (m, 7H), 0.89 (s, 3H), 0.85 (s, 3H). MS(ESI): 720(M+H).

EXAMPLE (COMPOUNDS 548-555)

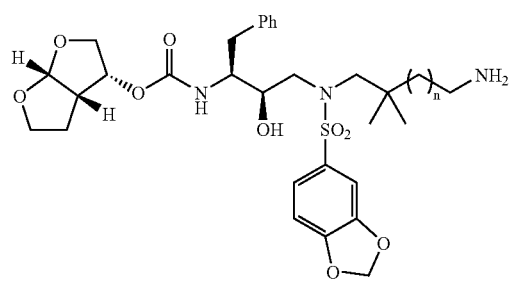

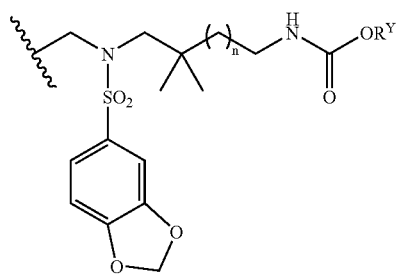

According to example 245, step 5 (with the exception that N-succinimidyl (3S)-tetrahydro-3-furanyl carbonate or 1,3-dioxan-5-yl 4-nitrophenyl carbonate was used as the acylating reagent), primary amines 282, 257, 244, and 283 were acylated to afford the desired products. See U.S. Pat. No. 5,585,397 for synthesis of the above active carbonates.

Mass Spectral Data for Compounds 548-555:

| Example | Amine Precursor | n | R$^y$ | MS (ESI) |
|---|---|---|---|---|
| 548 | 282 | 1 | (3S)-tetrahydrofuran-3-yl | 756 (M + Na) |
| 549 | 282 | 1 | 1,3-dioxan-5-yl | 750 (M + H) |
| 550 | 257 | 2 | (3S)-tetrahydrofuran-3-yl | 748 (M + H) |
| 551 | 257 | 2 | 1,3-dioxan-5-yl | 786 (M + Na) |
| 552 | 244 | 3 | (3S)-tetrahydrofuran-3-yl | 784 (M + Na) |
| 553 | 244 | 3 | 1,3-dioxan-5-yl | 778 (M + H) |
| 554 | 283 | 4 | (3S)-tetrahydrofuran-3-yl | 776 (M + H) |
| 555 | 283 | 4 | 1,3-dioxan-5-yl | 792 (M + H) |

Proton NMR data for selected compounds from the above table:

Example (Compound 548) NMR (CDCl3): 7.37 (dd, 1H), 7.35-7.16 (m, 6H), 6.95 (d, 1H), 6.14 (s, 2H), 5.67 (d, 1H), 5.32-5.10 (m, 3H), 5.03 (q, 1H), 4.20-3.60 (m, 11H), 3.34-2.70 (m, 9H), 2.28-1.96 (m, 2H), 1.80-1.35 (m, 4H), 1.06 (s, 3H), 1.00 (s, 3H).

Example (Compound 553) NMR (CDCl3): 7.31 (dd, 1H), 7.28-7.10 (m, 6H), 6.87 (d, 1H), 6.03 (s, 2H), 5.58 (d, 1H), 5.08 (m, 2H), 5.00-4.86 (m, 2H), 4.73 (d, 1H), 4.59 (m, 1H), 4.10-3.70 (m, 8H), 3.61 (m, 2H), 3.20-2.62 (m, 10H), 1.60-1.17 (m, 8H), 0.84 (d, 6H).

EXAMPLE (COMPOUND 556)

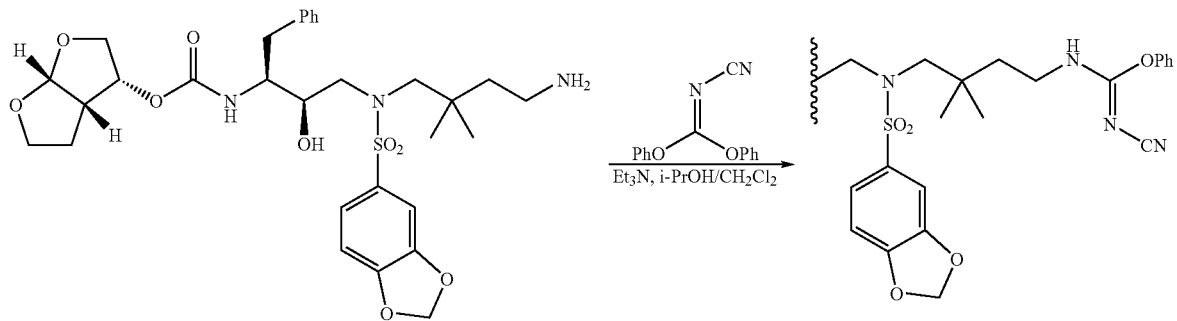

(3R,3aS,6aR)hexahydrofuro[2,3-b]furan-3-yl (1S, 2R)-3-[(1,3-benzodioxol-5-ylsulfonyl)(4-{[(cyanoimino)(phenoxy)methyl]amino}-2,2-dimethylbutyl)amino]-1-benzyl-2-hydroxypropylcarbamate A solution of 0.250 g (0.403 mmol) of (3R,3aS,6aR) hexahydrofuro[2,3-b]furan-3-yl N-(1S,2R)-3-[(4-amino-2,2-dimethylbutyl)(1,3-benzodioxol-5-ylsulfonyl)amino]-1-benzyl-2-hydroxypropylcarbamate in 15 mL of 3:1 i-PrOH/CH2Cl2 was treated with 84 μL (0.605 mmol) of Et₃N followed by 0.106 g (0.443 mmol) of diphenyl cyanocarbonimidate and the resulting solution was stirred at RT. After 3 hours the solution was concentrated in vacuo and the residue subjected to flash chromatography (SiO2, 97:3 CH2Cl₂/MeOH) to afford 0.269 g (87%) of the desired compound as a white foam. NMR (CDCl3): 7.40-7.10 (m, 9H), 7.06 (d, 2H), 6.91-6.69 (m, 2H), 6.04 (s, 2H), 5.81-4.73 (complex pattern, rotamers, 3H total), 4.06 (br s, 1H), 3.92-3.21 (m, 7H), 3.20-2.79 (m, 6H), 2.69 (dd, 1H), 2.40-1.43 (m, 5H), 1.37 (m, 1H), 0.95 (m, 6H). MS(ESI): 764(M+H).

EXAMPLE (COMPOUND 557)

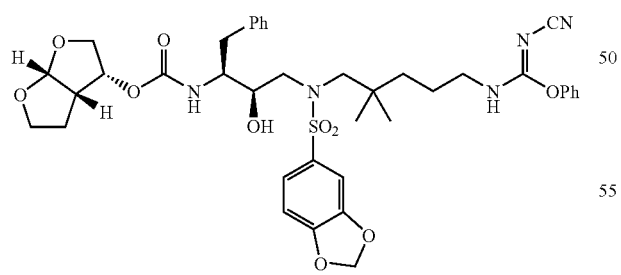

(3R,3aS,6aR)hexahydrofuro[2,3-b]furan-3-yl (1S, 2R)-3-[(1,3-benzodioxol-5-ylsulfonyl)(5-[(cyanoimino) (phenoxy)methyl]amino}-2,2-dimethylpentyl)amino]-1-benzyl-2-hydroxypropylcarbamate According to example 556, (3R,3aS,6aR)hexahydrofuro[2,3-b]furan-3-yl N-(1S,2R)-3-[(5-amino-2,2-dimethylpentyl)(1,3-benzodioxol-5-ylsulfonyl)amino]-1-benzyl-2-hydroxypropylcarbamate was converted to the title compound which was obtained as a white foam. NMR (CDCl3): 7.40-7.02 (m, 11H), 6.88 (d, 1H), 6.54 (br s, 1H), 6.07 (s, 2H), 5.80-4.80 (complex pattern, rotamers, 3H total), 4.13-3.92 (m, 1H), 3.90-3.72 (m, 3H), 3.70-3.54 (m, 2H), 3.50-3.25 (m, 2H), 3.17-2.76 (m, 6H), 2.70 (dd, 1H), 2.40-1.18 (m, 8H), 0.90 (m, 6H). MS(ESI): 778(M+H).

EXAMPLE (COMPOUND 558)

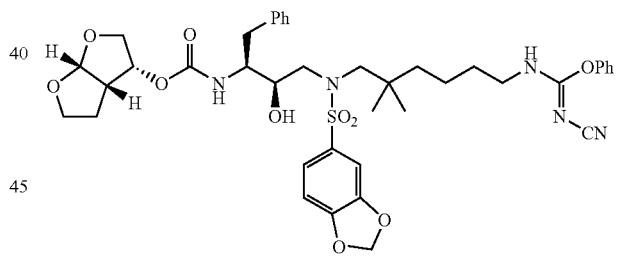

(3R,3aS,6aR)hexahydrofuro[2,3-b]furan-3-yl (1S, 2R)-3-[(1,3-benzodioxol-5-ylsulfonyl)(6-{[(cyanoimino)(phenoxy)methyl]amino}-2,2-dimethylhexyl)amino]-1-benzyl-2-hydroxypropylcarbamate According to example 556, (3R,3aS,6aR)hexahydrofuro[2,3-b]furan-3-yl N-(1S,2R)-3-[(6-amino-2,2-dimethylhexyl)(1,3-benzodioxol-5-ylsulfonyl)amino]-1-benzyl-2-hydroxypropylcarbamate was converted to the title compound which was obtained as a white foam. NMR (CDCl3): 7.40-7.01 (m, 11H), 6.87 (d, 1H), 6.52 (br s, 1H), 6.05 (s, 2H), 5.65-4.85 (complex pattern, rotamers, 3H total), 4.00 (m, 1H), 3.94-3.72 (m, 3H), 3.64 (m, 2H), 3.50-3.28 (m, 2H), 3.20-2.63 (m, 7H), 2.60-1.80 (br, 2H), 1.70-1.45 (m, 3H), 1.43-1.20 (m, 5H), 0.89 (m, 6H). MS(ESI): 792(M+H).

EXAMPLE (COMPOUND 559)

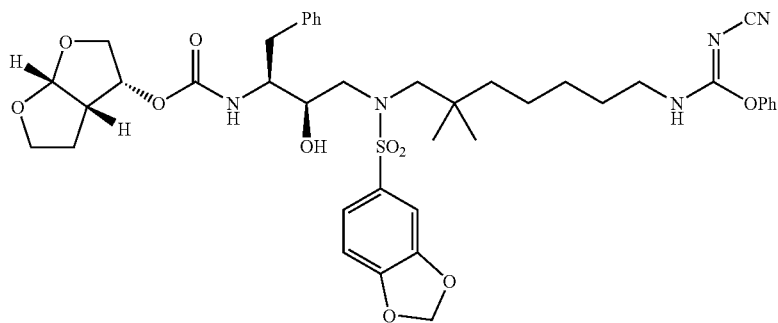

(3R,3aS,6aR)hexahydrofuro[2,3-b]furan-3-yl (1S,2R)-3-[(1,3-benzodioxol-5-ylsulfonyl)(7-{[(cyanoimino)(phenoxy)methyl]amino}-2,2-dimethylheptyl)amino]-1-benzyl-2-hydroxypropylcarbamate According to example 556, (3R,3aS,6aR)hexahydrofuro[2,3-b]furan-3-yl N-(1S,2R)-3-[(7-amino-2,2-dimethylheptyl)(1,3-benzodioxol-5-ylsulfonyl)amino]-1-benzyl-2-hydroxypropylcarbamate was converted to the title compound which was obtained as a white foam. NMR (CDCl3): 7.45-7.00 (m, 11H), 6.88 (d, 1H), 6.34 (br s, 1H), 6.06 (s, 2H), 5.65-4.70 (complex pattern, rotamers, 3H total), 4.01 (m, 1H), 3.94-3.72 (m, 3H), 3.62 (m, 2H), 3.48-2.25 (m, 2H), 3.20-2.62 (7H), 2.60-1.75 (br, 2H), 1.71-1.46 (m, 3H), 1.45-1.14 (m, 7H), 0.85 (m, 6H). MS(ESI) 806(M+H).

EXAMPLE (COMPOUNDS 560-575)

Procedure for Reactions of Compounds 556-559 with Various Amines Using P-TBD Resin to Remove Phenol By-product:

The following reactions were carried out in parallel and were done in teflon-capped sealed tubes equipped with magnetic stirrers. Solutions of 0.026 mmol of starting materials 556, 557, 558, and 559 in 3 mL of 1:1 THF/1-PrOH were treated with excess (40 equiv.) amine. Ammonia and MeNH$_2$ were added as 2 M solutions in MeOH and EtOH respectively; Me2NH was added as a 2M solution in THF; and n-PrNH2 was added neat. The vessels were capped and solutions heated to 80° C. with stirring. After 3 hours the vessels were cooled to RT and examined by tlc which indicated all reactions to be complete. The solutions were cooled to RT and evaporated under a stream of nitrogen. The resulting residues were dissolved in 3 mL of CH2Cl$_2$ and the solutions treated with 100 mg of polymer bound 1,3,4,6,7,8-hexahydro-2H-pyrimido[1,2-a]pyrimidine (P-TBD resin, 2.6 mmol/g, Aldrich). The mixtures were shaken on a rotary shaker for 3

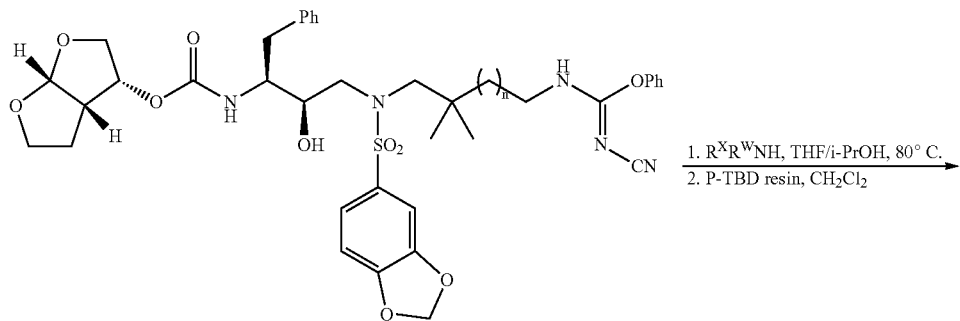

1. R$^X$R$^W$NH, THF/i-PrOH, 80° C.
2. P-TBD resin, CH$_2$Cl$_2$

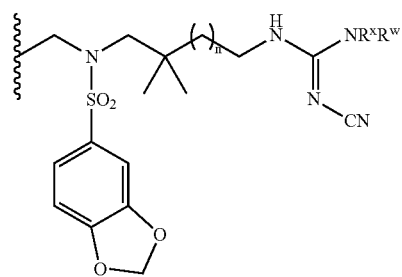

hours, filtered to remove the resin, and the filtrates evaporated under a stream of nitrogen to afford the desired products.

Mass Spectral Data for Compounds 560-575:

| Example | Starting Material | n | R$^x$ | R$^y$ | MS (ESI) |
|---------|-------------------|---|-------|-------|----------|
| 560 | 556 | 1 | H    | H  | 687 (M + H) |
| 561 | 556 | 1 | Me   | H  | 701 (M + H) |
| 562 | 556 | 1 | n-Pr | H  | 729 (M + H) |
| 563 | 556 | 1 | Me   | Me | 715 (M + H) |
| 564 | 557 | 2 | H    | H  | 701 (M + H) |
| 565 | 557 | 2 | Me   | H  | 715 (M + H) |
| 566 | 557 | 2 | n-Pr | H  | 743 (M + H) |
| 567 | 557 | 2 | Me   | Me | 729 (M + H) |
| 568 | 558 | 3 | H    | H  | 715 (M + H) |
| 569 | 558 | 3 | Me   | H  | 729 (M + H) |
| 570 | 558 | 3 | n-Pr | H  | 757 (M + H) |
| 571 | 558 | 3 | Me   | Me | 743 (M + H) |
| 572 | 559 | 4 | H    | H  | 729 (M + H) |
| 573 | 559 | 4 | Me   | H  | 743 (M + H) |
| 574 | 559 | 4 | n-Pr | H  | 771 (M + H) |
| 575 | 559 | 4 | Me   | Me | 757 (M + H) |

Proton NMR data for selected compounds from the above table:

Example (Compound 560) NMR (CDCl3): 7.31 (dd, 1H), 7.24-7.02 (m, 6H), 6.88 (d, 1H), 6.02 (s, 2H), 5.70-5.40 (m, 3H), 4.92 (m, 1H), 4.05 (br s, 1H), 3.96-3.42 (m, 8H), 3.36-2.50 (m, 9H), 1.80-1.07 (m, 4H), 0.98 (s, 3H), 0.82 (s, 3H).

Example (Compound 565) NMR (CDCl3): 7.40-7.04 (m, 7H), 6.88 (d, 1H), 6.07 (s, 2H), 5.58 (d, 1H), 5.45 (br s, 2H), 5.11 (d, 1H), 4.91 (m, 1H), 4.01 (m, 1H), 3.93-3.50 (m, 6H), 3.24-2.50 (m, 12H), 1.70-1.15 (m, 6H), 0.84 (d, 6H).

Example (Compound 571) NMR (CDCl3): 7.32 (dd, 1H), 7.30-7.08 (m, 6H), 6.90 (d, 1H), 6.07 (s, 2H), 5.61 (d, 1H), 5.31 (d, 1H), 5.00 (m, 2H), 4.01 (t, 1H), 3.96-3.61 (m, 5H), 3.50 (m, 2H), 3.20-2.65. (m, 14H), 1.70-1.20 (m, 8H), 0.90 (d, 6H).

EXAMPLE (COMPOUND 576)

Step 1:

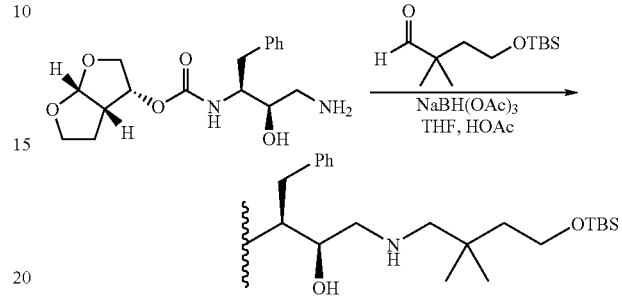

(3R,3aS,6aR)hexahydrofuro[2,3-b]furan-3-yl N-(1S, 2R)-1-benzyl-3-[(4-[tert-butyldimethylsiloxy]-2,2-dimethylbutyl)amino]-2-hydroxypropylcarbamate According to example 257, step 5, (3R,3aS,6aR)hexahydrofuro[2,3-b]furan-3-yl N-[(1S,2R)-3-amino-1-benzyl-2-hydroxypropyl]carbamate was subjected to reductive alkylation with of 4-(tert-butyldimethylsiloxy)-2,2-dimethylbutyraldehyde (example 221) to afford the desired compound as a white solid. MS (ESI): 551 (M+H).

Step 2:

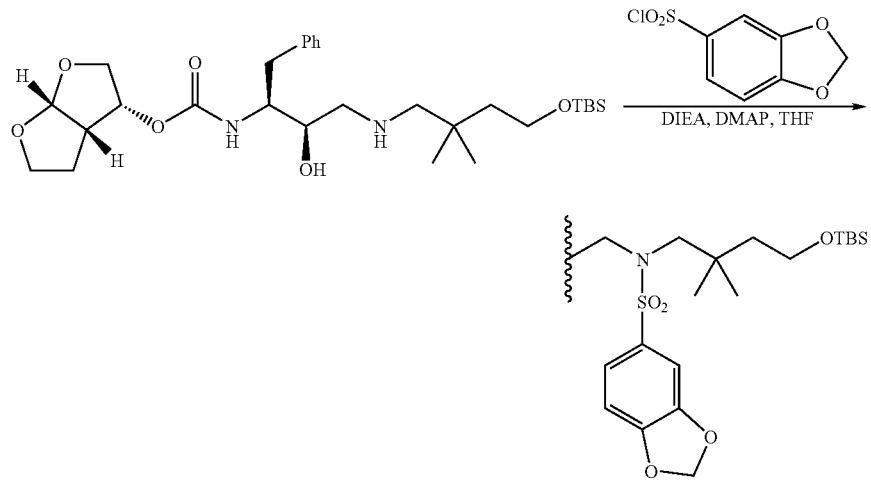

(3R,3aS,6aR)hexahydrofuro[2,3-b]furan-3-yl N-(1S, 2R)-3-[(1,3-benzodioxol-5-ylsulfonyl)(4-[tert-butyldimethylsiloxy]-2,2-dimethylbutyl)amino]-1-benzyl-2-hydroxypropylcarbamate According to example 257, step 6, (3R,3aS,6aR) hexahydrofuro[2,3-b]furan-3-yl N-(1S,2R)-1-benzyl-3-[(4-[(tert-butyldimethylsiloxy]-2,2-dimethylbutyl)amino]-2-hydroxypropylcarbamate was subjected to sulfonylation to afford the desired sulfonamide as a white foam. MS(ESI): 757(M+H).

Step 3:

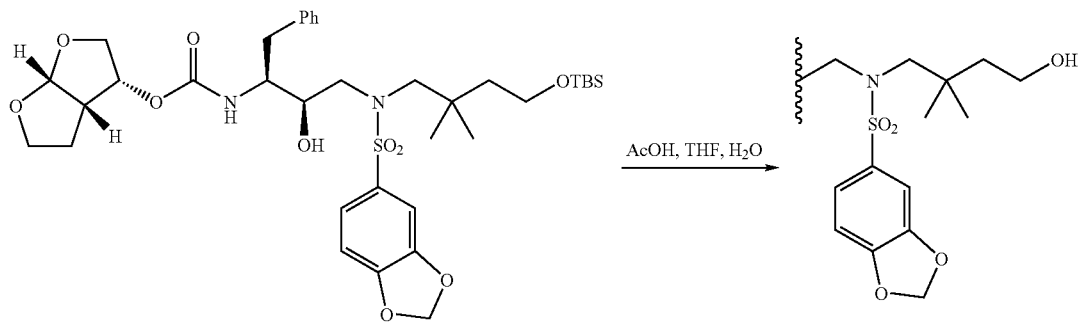

(3R,3aS,6aR)hexahydrofuro[2,3-b]furan-3-yl N-(1S,2R)-3-[(1,3-benzodioxol-5-ylsulfonyl)(2,2-dimethyl-4-hydroxybutyl)amino]-1-benzyl-2-hydroxypropylcarbamate A solution of 0.67 g (0.91 mmol) of (3R,3aS,6aR)hexahydrofuro[2,3-b]furan-3-yl N-(1S,2R)-3-[(1,3-benzodioxol-5-ylsulfonyl)(4-[tert-butyldimethylsiloxy]-2,2-dimethylbutyl)amino]-1-benzyl-2-hydroxypropylcarbamate in 25 mL of 3:1:1 AcOH/THF/H$_2$O was stirred at RT for 3 hours and then concentrated in vacuo. The crude product was purified by flash chromatography (SiO$_2$, hexane/EtOAc) to afford 0.50 g (89%) of the desired alcohol as a white foam. MS(ESI): 621(M+H).

Step 4:

(3R,3aS,6aR)hexahydrofuro[2,3-b]furan-3-yl N-(1S,2R)-3-[(1,3-benzodioxol-5-ylsulfonyl)(2,2-dimethyl-4-[(4-nitrophenyloxy)carbonyloxy]butyl)amino]-1-benzyl-2-hydroxypropylcarbamate According to example 234, step 1, (3R,3aS,6aR)hexahydrofuro[2,3-b]furan-3-yl N-(1S,2R)-3-[(1,3-benzodioxol-5-ylsulfonyl)(2,2-dimethyl-4-hydroxybutyl)amino]-1-benzyl-2-hydroxypropylcarbamate was converted to the desired compound which was obtained as a white foam. NMR (CDCl$_3$): 8.22 (d, 2H), 7.32 (m, 3H), 7.21 (m, 2H), 7.12 (m, 4H), 6.87 (d, 1H), 6.04 (s, 2H), 5.60 (d, 1H), 4.95 (q, 1H), 4.84 (d, 1H), 4.35 (t, 2H), 4.02 (m, 1H), 3.93-3.72 (m, 4H), 3.62 (m, 2H), 3.20-2.79 (m, 6H), 2.69 (dd, 1H), 1.80 (m, 2H), 1.55 (m, 1H), 1.31 (m, 1H), 1.01 (s, 6H). MS(ESI): 808(M+Na).

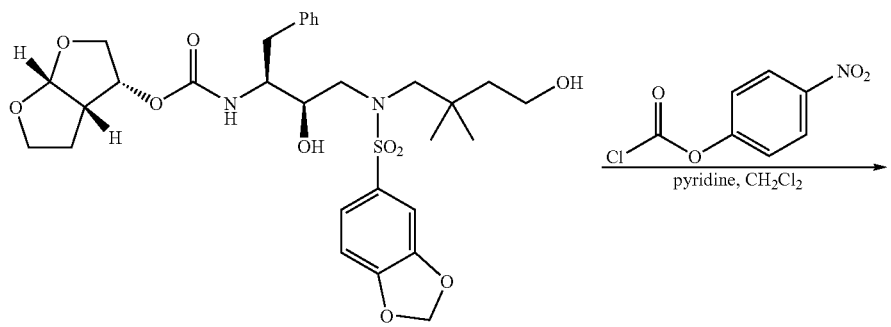

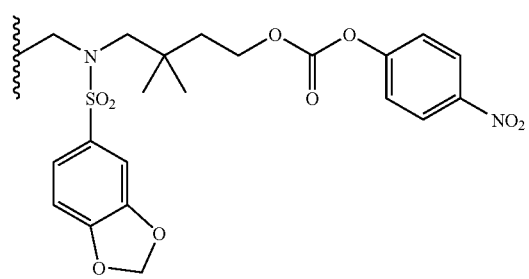

EXAMPLE (COMPOUND 577)

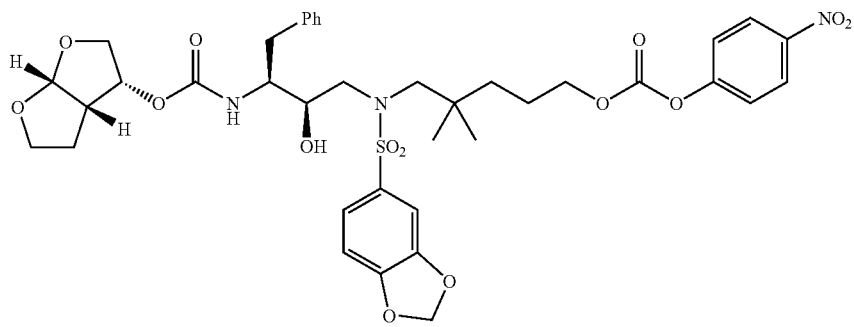

(3R,3aS,6aR)hexahydrofuro[2,3-b]furan-3-yl N-(1S,2R)-3-[(1,3-benzodioxol-5-ylsulfonyl)(2,2-dimethyl-5-[(4-nitrophenyloxy)carbonyloxy]pentyl)amino]-1-benzyl-2-hydroxypropylcarbamate The title compound was prepared according to example 576 with the exception that 5-(tert-butyldimethylsiloxy)-2,2-dimethylpentanal (see example 272) was used as the aldehyde component in step 1. NMR (CDCl₃): 8.23 (d, 2H), 7.33 (m, 3H), 7.26-7.09 (m, 6H), 6.88 (d, 1H), 6.06 (s, 2H), 5.59 (d, 1H), 4.95 (q, 1H), 4.85 (d, 1H), 4.26 (m, 2H), 4.01 (m, 1H), 3.97-3.72 (m, 4H), 3.62 (m, 2H), 3.20-2.74 (m, 6H), 2.68 (dd, 1H), 1.71 (m, 2H), 1.52 (m, 1H), 1.38 (m, 3H), 0.92 (s, 6H). MS(ESI): 822(M+Na).

EXAMPLE (COMPOUND 578)

Step 1:

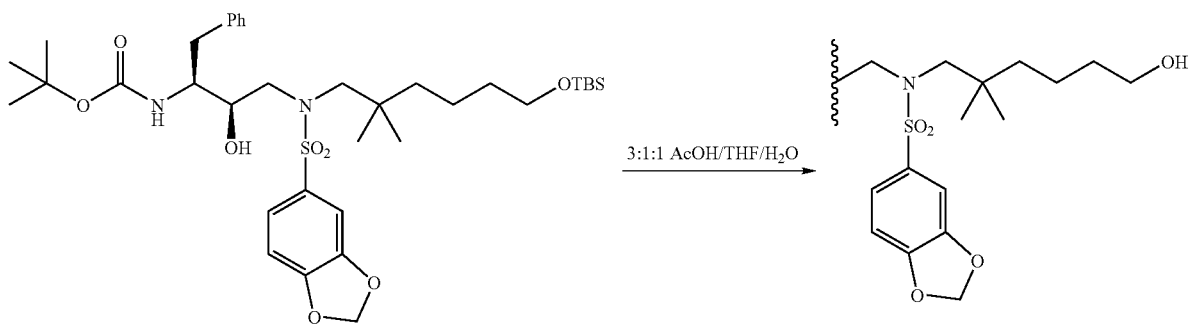

tert-Butyl N-(1S,2R)-3-[(1,3-benzodioxol-5-ylsulfonyl)(2,2-dimethyl-6-hydroxyhexyl)amino]-1-benzyl-2-hydroxypropylcarbamate According to example 576, step 3, tert-Butyl N-(1S,2R)-3-[(1,3-benzodioxol-5-ylsulfonyl)(2,2-dimethyl-6-[tert-butyldimethylsiloxy]hexyl)amino]-1-benzyl-2-hydroxypropylcarbamate (prepared in a manner similar to example 221) was desilylated to afford the desired compound as a white foam. MS(ESI): 593(M+H).

Step 2:

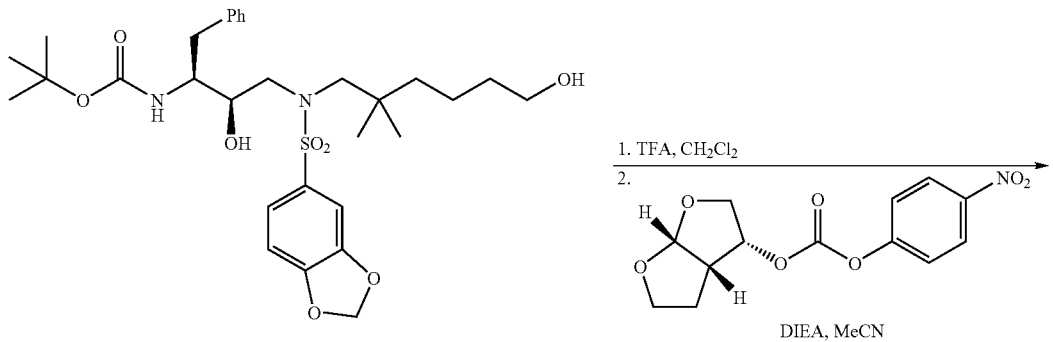

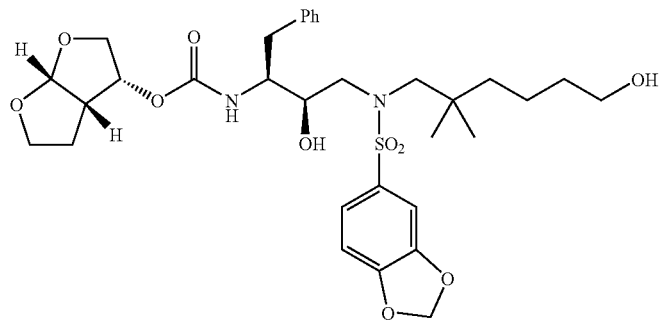
(3R,3aS,6aR)hexahydrofuro[2,3-b]furan-3-yl N-(1S,2R)-3-[(1,3-benzodioxol-5-ylsulfonyl)(2,2-dimethyl-6-hydroxyhexyl)amino]-1-benzyl-2-hydroxypropylcarbamate
According to example 245, steps 4 and 5, tert-butyl N-(1S,2R)-3-[(1,3-benzodioxol-5-ylsulfonyl)(2,2-dimethyl-6-hydroxyhexyl)amino]-1-benzyl-2-hydroxypropylcarbamate was converted to the desired product which was obtained as a white foam. MS(ESI): 671(M+Na).
Step 3:
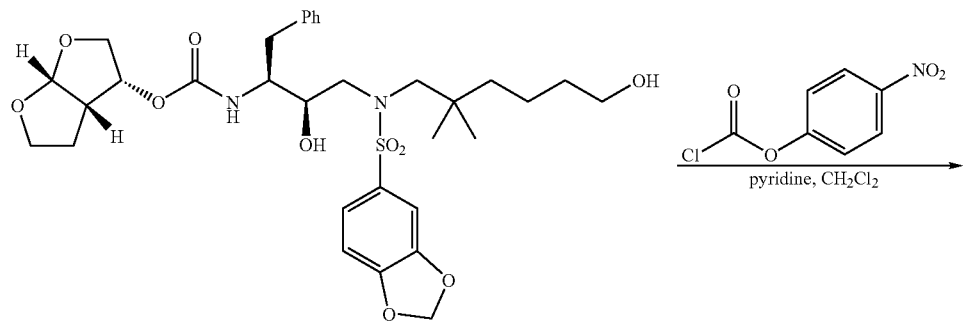
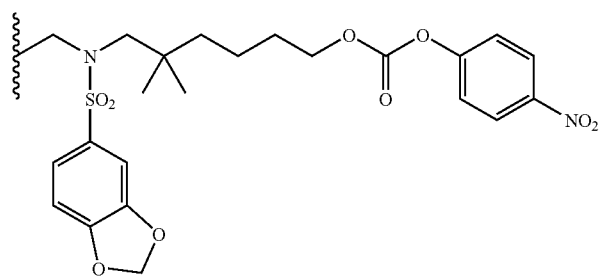

357

(3R,3aS,6aR)hexahydrofuro[2,3-b]furan-3-yl N-(1S, 2R)-3-[(1,3-benzodioxol-5-ylsulfonyl)(2,2-dimethyl-6-[(4-nitrophenyloxy)carbonyloxy]hexyl)amino]-1-benzyl-2-hydroxypropylcarbamate The title compound was prepared according to example 234, step 1. NMR (CDCl$_3$): 8.23 (d, 2H), 7.32 (m, 3H), 7.27-7.08 (m, 6H), 6.86 (d, 1H), 6.06 (s, 2H), 5.58 (d, 1H), 4.96 (q, 1H), 4.83 (d, 1H), 4.25 (t, 2H), 4.01 (m, 1H), 3.91 (m, 2H), 3.80 (m, 2H), 3.61 (m, 2H), 3.20-2.73 (m, 6H), 2.70 (dd, 1H), 1.70 (m, 2H), 1.55 (m, 1H), 1.32 (m, 5H), 0.89 (d, 6H). MS(ESI): 836(M+H).

EXAMPLE (COMPOUNDS 579-604)

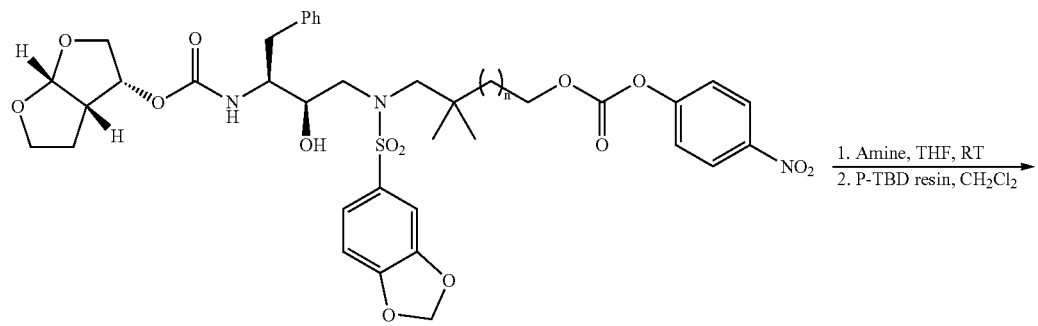

Procedure for Reactions of Compounds 576-578 with Various Amines Using P-TBD Resin to Remove 4-nitrophenol By-product:

The following reactions were carried out in parallel and were done in teflon-capped vials using a rotary shaker for agitation. Solutions of 0.025 mmol of starting materials 576, 577, and 578 in 1 mL of anhydrous THF were treated with 10 equiv. of amine. Ammonia was added as a 2M solution in MeOH; ethylamine and dimethylamine were added as 2M solutions in THF; and the remaining amines were added neat. The solutions were shaken briefly and then allowed to stand at RT. After 2 hours tlc indicated all reactions to be complete. The solutions were evaporated under a stream on nitrogen. The residues were dissolved in 4 mL of CH$_2$Cl$_2$ and the solutions treated with 100 mg of polymer bound 1,3,4,6,7,8-hexahydro-2H-pyrimido[1,2-a]pyrimidine (P-TBD resin, 2.6 mmol/g, Aldrich). The mixtures were shaken for 3 hours, filtered to remove the resin, and the filtrates evaporated under a stream of nitrogen to afford the desired products.

358

Mass Spectral Data for Compounds 579-604:

| Example | Starting Material | N | R$^v$ | MS (ESI) |
|---|---|---|---|---|
| 579 | 576 | 1 | —NMe$_2$ | 692 (M + H) |

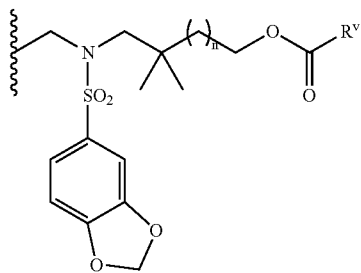

-continued

| Example | Starting Material | N | R$^v$ | MS (ESI) |
|---|---|---|---|---|
| 580 | 576 | 1 | —NH$_2$ | 664 (M + H) |
| 581 | 576 | 1 | —NHEt | 692 (M + H) |
| 582 | 576 | 1 | —NHn-Pr | 706 (M + H) |

359
-continued

| Example | Starting Material | N | R^v | MS (ESI) |
|---|---|---|---|---|
| 583 | 576 | 1 | —NHi-Pr | 706 (M + H) |
| 584 | 576 | 1 | —NHn-Bu | 720 (M + H) |
| 585 | 576 | 1 | 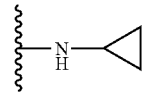 | 704 (M + H) |
| 586 | 576 | 1 | 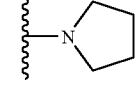 | 718 (M + H) |
| 587 | 576 | 1 | 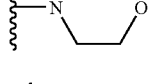 | 734 (M + H) |
| 588 | 576 | 1 | 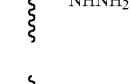—NHNH₂ | 679 (M + H) |
| 589 | 577 | 2 | —NHn-Pr | 742 (M + Na) |
| 590 | 577 | 2 | 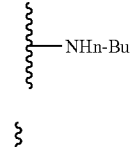—NHn-Bu | 756 (M + Na) |
| 591 | 577 | 2 |  | 740 (M + Na) |
| 592 | 577 | 2 | 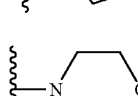 | 732 (M + H) |
| 593 | 577 | 2 | 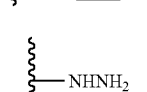 | 748 (M + H) |
| 594 | 577 | 2 | 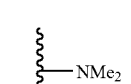—NHNH₂ | 693 (M + H) |
| 595 | 578 | 3 | 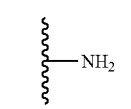—NMe₂ | 720 (M + H) |
| 596 | 578 | 3 | —NH₂ | 692 (M + H) |

360
-continued

| Example | Starting Material | N | R^v | MS (ESI) |
|---|---|---|---|---|
| 597 | 578 | 3 | 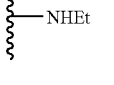—NHEt | 720 (M + H) |
| 598 | 578 | 3 | 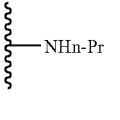—NHn-Pr | 734 (M + H) |
| 599 | 578 | 3 | 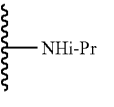—NHi-Pr | 734 (M + H) |
| 600 | 578 | 3 | 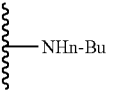—NHn-Bu | 748 (M + H) |
| 601 | 578 | 3 |  | 732 (M + H) |
| 602 | 578 | 3 | 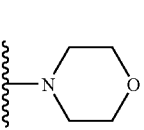 | 746 (M + H) |
| 603 | 578 | 3 | 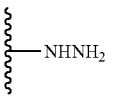 | 762 (M + H) |
| 604 | 578 | 3 | 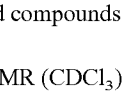—NHNH₂ | 707 (M + H) |

Proton NMR data for selected compounds from the above table:

Example (Compound 579) NMR (CDCl₃): 7.30 (dd, 1H), 7.25-7.09 (m, 6H), 6.84 (d, 1H), 6.06 (s, 2H), 5.58 (d, 1H), 5.32 (d, 1H), 4.92 (q, 1H), 4.09 (m, 3H), 3.94 (t, 1H), 3.88 (dd, 1H), 3.84-3.53 (m, 5H), 3.24-2.97 (m, 4H), 2.83 (m, 7H), 2.66 (dd, 1H), 1.80-1.22 (m, 4H), 0.97 (s, 3H), 0.93 (s, 3H).

Example (Compound 589) NMR (CDCl₃): 7.39 (dd, 1H), 7.33-7.12 (m, 6H), 6.93 (d, 1H), 6.13 (s, 2H), 5.66 (d, 1H), 5.32 (d, 1H), 5.01 (m, 2H), 4.25-3.64 (m, 9H), 3.32-2.66 (m, 9H), 1.80-1.23 (m, 9H), 0.97 (m, 9H).

Example (Compound 596) NMR (CDCl₃): 7.32 (dd, 1H), 7.26-7.08 (m, 6H), 6.85 (d, 1H), 6.06 (s, 2H), 5.59 (d, 1H), 5.06 (d, 1H), 4.96 (q, 1H), 4.69 (br s, 2H), 4.17-3.55 (m, 9H), 3.20-2.64 (m, 7H), 1.75-1.19 (m, 8H), 0.88 (s, 6H).

EXAMPLE (COMPOUNDS 605-616)

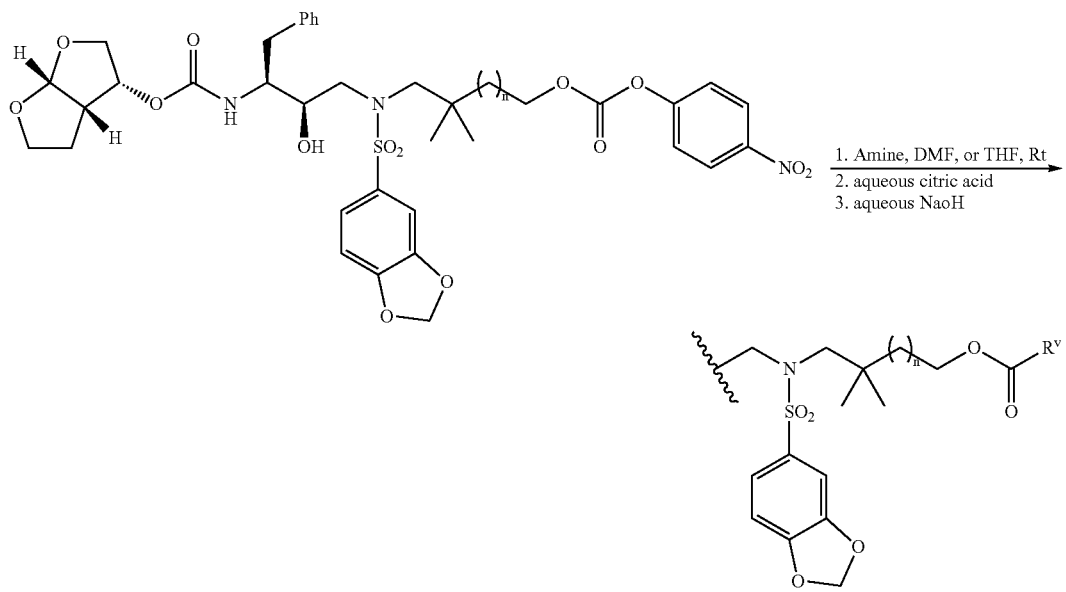

Procedure for Reactions of Compounds 576-578 with Various Amines Employing Aqueous Work-up:

The following reactions were carried out in parallel and were done in teflon-capped vials using a rotary shaker for agitation. Solutions of 0.038 mmol of starting materials 576, 577, and 578 in 1 mL of anhydrous DMF (THF was used for examples 608, 612, and 616) were treated with 0.13 mL of N,N-diisopropylethylamine fomitted for examples 608, 612, and 616) followed by 15 equiv. of amine (hydroxylamine hydrochloride, methoxylamine hydrochloride, N,O-dimethylhydroxylamine hydrochloride, or ethanolamine). The resulting solutions were shaken at RT. After 18 hours the solutions were diluted with 5 mL of $CH_2Cl_2$, washed with 10% aqueous citric acid (3×), 0.5N aqueous NaOH (2×), aqueous brine (1×), and then dried over $MgSO_4$. The drying agent was removed by filtration and the filtrates evaporated under a stream of nitrogen. Products 605, 607, 609, 611, 613, and 615 were purified by preparative tlc (2 mm silica gel plate, 98:2 $CH_2Cl_2$/MeOH). The remaining products were found to be sufficiently pure for biological evaluation.

Mass Spectral Data for Compounds 605-616:

| Example | Starting Material | N | $R^v$ | MS (ESI) |
|---|---|---|---|---|
| 605 | 576 | 1 | —N(H)OH | 680 (M + H) |
| 606 | 576 | 1 | —N(H)OMe | 694 (M + H) |
| 607 | 576 | 1 | —N(Me)OMe | 708 (M + H) |
| 608 | 576 | 1 | —N(H)CH₂CH₂OH | 708 (M + H) |
| 609 | 577 | 2 | —N(H)OH | 694 (M + H) |
| 610 | 577 | 2 | —N(H)OMe | 708 (M + H) |
| 611 | 577 | 2 | —N(Me)OMe | 722 (M + H) |
| 612 | 577 | 2 | —N(H)CH₂CH₂OH | 722 (M + H) |
| 613 | 578 | 3 | —N(H)OH | 708 (M + H) |

| Example | Starting Material | N | R^v | MS (ESI) |
|---|---|---|---|---|
| 614 | 578 | 3 | —N(H)(OMe) | 722 (M + H) |
| 615 | 578 | 3 | —N(Me)(OMe) | 736 (M + H) |
| 616 | 578 | 3 | —N(H)CH₂CH₂OH | 736 (M + H) |

Proton NMR data for selected compounds from the above table:

Example (Compound 606) NMR (CDCl₃): 8.01 (br s, 1H), 7.38 (dd, 1H), 7.33-7.17 (m, 6H), 6.93 (d, 1H), 6.14 (s, 2H), 5.64 (d, 1H), 5.18 (d, 1H), 5.02 (q, 1H), 4.36-4.12 (m, 2H), 4.05 (t, 1H), 3.98-3.62 (m, 8H), 3.30-2.61 (m, 8H), 1.85-1.22 (m, 4H), 1.04 (s, 3H), 1.00 (s, 3H).

Example (Compound 609) NMR (CDCl₃): 7.50-7.16 (m, 8H), 6.96 (d, 1H), 6.12 (s, 2H), 5.66 (d, 1H), 5.38 (d, 1H) 5.03 (m, 1H), 4.32-3.57 (m, 9H), 3.32-3.08 (m, 3H), 3.08-2.62 (m, 5H), 1.80-1.25 (m, 6H), 0.99 (s, 3H), 0.90 (s, 3H).

Example (Compound 616) NMR (CDCl₃): 7.44-7.13 (m, 7H), 6.94 (d, 1H), 6.12 (s, 2H), 5.66 (d, 1H), 5.50-5.12 (m, 2H), 5.01 (q, 1H), 4.24-3.54 (m, 13H), 3.40-2.63 (m, 8H), 1.61 (m, 3H), 1.46-1.20 (m, 5H), 0.93 (s, 6H).

EXAMPLE

Anti-Viral Activity

We measured the enzyme inhibition constants of the compounds listed in Table I against HIV-1 protease using the methods of: B. Maschera et al., "Human Immunodeficiency Virus Mutations in the Viral Protease that Confer Resistance to Saquinavir Increase the Dissociation Rate Constant for the Protease-Saquinavir Complex", *J. Biol. Chem.*, 271, pp. 33231-33235 (1996); and M. V. Toth et al., *Int. J. Peptide Protein Res.* 36, pp. 544-550. (1990)

Antiviral Activity Assay in MT4 Cells

Antiviral HIV activity and compound-induced cytotoxicity were measured in parallel by means of a propidium iodide based procedure in the human T-cell lymphotropic virus transformed cell line MT4. Aliquots of the test compounds were serially diluted in medium (RPMI 1640, 10% fetal-calf serum (FCS), and gentamycin) in 96-well plates (Costar 3598) using a Cetus Pro/Pette. Exponentially growing MT4 cells were harvested and centrifuged at 1000 rpm for 10 min in a Jouan centrifuge (model CR 4 12). Cell pellets were resuspended in fresh medium (RPMI 1640, 20% FCS, 20% IL-2, and gentamycin) to a density of $5 \times 10^5$ cells/ml. Cell aliquots were infected by the addition of HIV-1 (strain IIIB) diluted to give a viral multiplicity of infection of 100× $TCID_{50}$. A similar cell aliquot was diluted with medium to provide a mock-infected control. Cell infection was allowed to proceed for 1 hr at 370 in a tissue culture incubator with humidified 5% $CO_2$ atmosphere. After the 1 hr incubation the virus/cell suspensions were diluted 6-fold with fresh medium, and 125 μl of the cell suspension was added to each well of the plate containing pre-diluted compound. Plates were then placed in a tissue culture incubator with humidified 5% $CO_2$ for 5 days. At the end of the incubation period, 27 μl of 5% Nonidet-40 was added to each well of the incubation plate. After thorough mixing with a Costar multitip pipetter, 60 μl of the mixture was transferred to filter-bottomed 96-well plates. The plates were analyzed in an automated assay instrument (Screen Machine, Idexx Laboratories). The assay makes use of a propidium iodide dye to estimate the DNA content of each well.

REFERENCES

1. Averett, D. R. 1989. Anti-HIV compound assessment by two novel high capacity assays. *J. Virol. Methods* 23: 263-276.
2. Schwartz, O., et al. 1988. A rapid and simple calorimetric test for the study of anti-HIV agents. *AIDS Res. and Human Retroviruses*, 4(6):441-447.
3. Daluge, S. M., et al. 1994. 5-chloro-2'3'-deoxy-3'fluorouridine (935U83), a selective anti-human immuno-deficiency virus agent with an improved metabolic and toxicological profile. *Antimicro. Agents and Chemother.*, 38 (7):1590-1603.

The anti-viral potency in MT-4 cells of the compounds set forth in Tables 1 and 2 was determined using the above technique. The results are shown in Table 12.

TABLE 12

| Cmpd# | Ki | IC50 |
|---|---|---|
| 1 | A | G |
| 2 | A | H |
| 3 | A | H |
| 4 | B | F |
| 5 | A | H |
| 6 | A | NA |
| 7 | A | F |
| 8 | A | E |
| 9 | A | H |
| 10 | A | E |
| 11 | A | E |
| 12 | A | E |
| 13 | A | E |
| 14 | A | G |
| 15 | A | G |
| 16 | A | E |
| 17 | A | F |
| 18 | A | F |
| 19 | A | F |
| 20 | B | G |
| 21 | B | G |
| 22 | A | F |
| 23 | A | E |
| 24 | NA | NA |
| 25 | A | E |
| 26 | A | F |
| 28 | A | F |
| 29 | A | F |
| 30 | A | E |
| 31 | A | E |
| 32 | A | F |
| 33 | C | G |
| 35 | A | E |
| 36 | A | E |
| 37 | A | E |
| 38 | A | E |
| 39 | A | E |
| 40 | A | E |
| 41 | A | E |
| 42 | A | F |
| 43 | A | F |
| 44 | A | NA |
| 113 | C | G |

TABLE 12-continued

| Cmpd# | Ki | IC50 |
|---|---|---|
| 123 | C | NA |
| 124 | A | E |
| 125 | A | H |
| 127 | C | NA |
| 201 | B | H |
| 202 | B | H |
| 203 | A | G |
| 204 | B | G |
| 205 | A | G |
| 206 | A | E |
| 207 | A | E |
| 208 | A | F |
| 209 | A | F |
| 210 | A | E |
| 211 | A | E |
| 212 | A | E |
| 213 | A | E |
| 214 | A | E |
| 215 | A | E |
| 216 | A | E |
| 217 | A | F |
| 218 | A | E |
| 219 | A | E |
| 220 | A | E |
| 221 | A | E |
| 222 | A | G |
| 223 | A | E |
| 224 | A | E |
| 225 | A | H |
| 226 | A | E |
| 227 | A | E |
| 228 | A | F |
| 229 | A | E |
| 230 | A | E |
| 231 | A | E |
| 232 | A | H |
| 233 | A | F |
| 234 | A | NA |
| 235 | A | E |
| 236 | A | E |
| 237 | A | E |
| 238 | A | F |
| 239 | A | E |
| 240 | A | E |
| 241 | A | F |
| 242 | A | E |
| 243 | A | E |
| 244 | A | F |
| 245 | A | F |
| 246 | A | E |
| 247 | A | E |
| 248 | A | E |
| 249 | A | E |
| 250 | A | E |
| 251 | A | E |
| 252 | A | E |
| 253 | A | E |
| 254 | A | E |
| 255 | A | E |
| 256 | A | F |
| 257 | A | F |
| 258 | A | F |
| 259 | A | E |
| 260 | A | E |
| 261 | A | E |
| 262 | A | F |
| 263 | A | E |
| 264 | A | E |
| 265 | A | E |
| 266 | A | E |
| 267 | A | E |
| 268 | A | E |
| 269 | A | E |
| 270 | A | E |
| 271 | A | E |
| 272 | A | E |
| 273 | A | F |
| 274 | A | F |
| 277 | B | NA |
| 278 | B | NA |
| 279 | C | NA |
| 280 | A | F |
| 281 | B | F |

Biological Activity for Compounds 282-616

1. Compounds 295-616 all had Ki<1 nM (activity range "A") against the protease enzyme and IC50<100 nM (activity range "E") in the antiviral assay unless specified differently below.
2. Compounds 295-297, 402, 520, 523, 526, 527, 528, 540, 542, 563, 568, 605 had Ki in range "A" and IC50 in range "F".
3. Compounds 529, 536, 543 had Ki in range "A" but IC50 not available.
4. Compounds 506, 507, 508, 511, 560, 561, 564 had IC50 range >"E".
4. Compounds 506, 507, 508, 511, 560, 561, 564 had IC50 range >"E".

In Table 12 and Biological Activity for Compounds 282-616, the following classifications have been employed:

"I": $K_i$ of less than 0.005 pM;
"A": $K_i$ of less than 1 nM;
"B": $K_i$ between 1 and 10 nM;
"C": $K_i$ between 10 and 100 nM;
"D": $K_i$ greater than 100 nM;
"J": $IC_{50}$ between 1.0 and 10.0 nM;
"E": $IC_{50}$ of 0.1 μM or less;
"F": $IC_{50}$ between 0.1 and 0.5 μM;
"G": $IC_{50}$ between 0.5 and 1.0 μM;
"H": $IC_{50}$ greater than 1.0 μM.

The designation "NA" is used where a given compound was not tested.

EXAMPLE

A comparison of $K_1$ and $IC_{50}$ values for the nitriles and amides of the present invention versus the best compound, 4-amino-N-((2syn,3S)-2-hydroxy-4-phenyl-3-((S)-tetrahydrofuran-3-yloxycarbonylamino)-butyl)-N-isobutyl-benzenesulfonamide (Compound A) disclosed in International Publication WO94/05639 is set forth in Table 13.

4-Amino-N-((2 syn, 3S)-2-hydroxy-4-phenyl-3-((S)-tetrahydrofuran-3-yloxycarbonylamino)-butyl)-N-isobutyl-benzenesulfonamide (Compound A) has a Ki of 75 pM against the enzyme and an $IC_{50}$ of 80 nM in the MT-4 cell based assay.

TABLE 13

| Compound | Ki (pM) | IC50 (nM) |
|---|---|---|
| 12 | I | J |
| 39 | I | J |
| 374 | I | J |
| 375 | I | J |
| 376 | I | J |
| 377 | I | J |
| 378 | I | J |
| 379 | I | J |
| A | 75 | 80 |

We claim:
1. A compound of formula I:

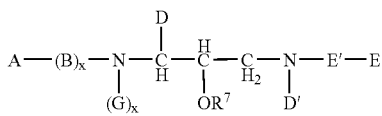

or a pharmaceutically acceptable salt thereof, wherein:
E' is —CO— or —SO$_2$—;
A is selected from R$^1$-Ht$_A$;
Ht$_A$ is 6 membered saturated or unsaturated heterocycle, containing two oxygen atoms; and wherein said Ht$_A$ is optionally substituted with one or more substituents independently selected from oxo, —OR$^2$, SR$^2$, —R$^2$, —N(R$^2$)(R$^2$), —R$^2$—OH, —CN, —CO$_2$R$^2$, —C(O)—N(R$^2$)$_2$, —S(O)$_2$—N(R$^2$)$_2$, —N(R$^2$)—C(O)—R$^2$, —N(R$^2$)—C(O)O—R$^2$, —C(O)—R$^2$, —S(O)$_n$—R$^2$, —OCF$_3$, —S(O)$_n$-Q, methylenedioxy, —N(R$^2$)—S(O)$_2$ (R$^2$), halo, —CF$_3$, —NO$_2$, Q, —OQ, —OR$^7$, —SR$^7$, —R$^7$, —N(R$^2$)(R$^7$) or —N(R$^7$)$_2$;
each R$^1$ is independently selected from —C(O)—, —S(O)$_2$—, —C(O)—C(O)—, —O—C(O)—, —O—S(O)$_2$, —NR$^2$—S(O)$_2$—, —NR$^2$—C(O)— or —NR$^2$—C(O)—C(O)—;
each Ht is independently selected from C$_3$-C$_7$ cycloalkyl; C$_5$-C$_7$ cycloalkenyl; C$_6$-C$_{14}$ aryl; or a 5-7 membered saturated or unsaturated heterocycle, containing one or more heteroatoms selected from N, O, or S; wherein said aryl or said heterocycle is optionally fused to Q; and wherein any member of said Ht is optionally substituted with one or more substituents independently selected from oxo, —OR$^2$, SR$^2$, —R$^2$, —N(R$^2$)(R$^2$), —R$^2$—OH, —CN, —CO$_2$R$^2$, —C(O)—N(R$^2$)$_2$, —S(O)$_2$—N(R$^2$)$_2$, —N(R$^2$)—C(O)—R$^2$, —N(R$^2$)—C(O)O—R$^2$, —C(O)—R$^2$, —S(O)$_n$—R$^2$, —OCF$_3$, —S(O)$_n$—Q, methylenedioxy, —N(R$^2$)—S(O)$_2$(R$^2$), halo, —CF$_3$, —NO$_2$, Q, —OQ, —OR$^7$, —SR$^7$, —R$^7$, —N(R$^2$)(R$^7$) or —N(R$^7$)$_2$;
each Q is independently selected from a 3-7 membered saturated, partially saturated or unsaturated carbocyclic ring system; or a 5-7 membered saturated, partially saturated or unsaturated heterocyclic ring containing one or more heteroatoms selected from O, N, or S;
wherein Q is optionally substituted with one or more groups selected from oxo, —OR$^2$, —R$^2$, —SO$_2$R$^2$, —SO$_2$—N(R$^2$)$_2$, —N(R$^2$)$_2$, —N(R$^2$)—C(O)—R$^2$, —R$^2$—OH, —CN, —CO$_2$R$^2$, —C(O)—N(R$^2$)$_2$, halo, —CF$_3$;
each R$^2$ is independently selected from H, or C$_1$-C$_4$ alkyl,; and wherein said alkyl, when not a substituent of Q, is optionally substituted with Q or —OR$^3$; wherein when said R$^2$ is an —OR$^3$ substituted moiety, said R$^3$ in —OR$^3$ may not be —OR$^2$ substituted;
B, when present, is —N(R$^2$)—C(R$^3$)$_2$—C(O)—;
each x is independently 0 or 1;
each R$^3$ is independently selected from H, Ht, C$_1$-C$_6$ alkyl, C$_2$-C$_6$ alkenyl, C$_2$-C$_6$ alkynyl, C$_3$-C$_6$ cycloalkyl or C$_5$-C$_6$ cycloalkenyl; wherein any member of said R$^3$, except H, is optionally substituted with one or more substituents selected from —OR$^2$, —C(O)—NH—R$^2$, —S(O)$_n$—N(R$^2$)(R$^2$), —N(R$^2$)$_2$, —N(R$^2$)—C(O)—O(R$^2$), —N(R$^2$)—C(O)—N(R$^2$), —N(R$^2$)—C(O)—(R$^2$), Ht, —CN, —SR$^2$, —CO$_2$R$^2$, or NR$^2$—C(O)—R$^2$;
each n is independently 1 or 2;

G, when present, is selected from H, R$^7$ or C$_1$-C$_4$ alkyl, or, when G is C$_1$-C$_4$ alkyl, G and R$^7$ are optionally bound to one another either directly or through a C$_1$-C$_3$ linker to form a heterocyclic ring; or
when G is not present, the nitrogen to which G is attached is bound directly to the R$^7$ group in —OR$^7$ with the concomitant displacement of one -ZM group from R$^7$;
D is selected from Q; C$_1$-C$_6$ alkyl optionally substituted with one or more groups selected from C$_3$-C$_6$ cycloalkyl, —OR$^2$, —S-Ht, —R$^3$, —O-Q or Q; C$_2$-C$_4$ alkenyl optionally substituted with one or more groups selected from —OR$^2$, —S-Ht, —R$^3$, —O-Q or Q; C$_3$-C$_6$ cycloalkyl optionally substituted with or fused to Q; or C$_5$-C$_6$ cycloalkenyl optionally substituted with or fused to Q;
D' is selected from C$_1$-C$_{15}$ alkyl, C$_2$-C$_{15}$ alkenyl or C$_2$-C$_{15}$ alkynyl, each of which contains one or more substituents selected from oxo, halo, —CF$_3$, —OCF$_3$, —NO$_2$, azido, —SH, —SR$^3$, —N(R$^3$)—N(R$^3$)$_2$, —O—N(R$^3$)$_2$, —(R$^3$)N—O—(R$^3$), —N(R$^3$)$_2$, —CN, —CO$_2$R$^3$, —C(O)—N(R$^3$)$_2$, —S(O)$_n$—N(R$^3$)$_2$, —N(R$^3$)—C(O)—R$^3$, —N(R$^3$)—C(O)—N(R$^3$)$_2$, —N(R$^3$)—C(O)—S(R$^3$), —C(O)—R$^3$, —S(O)$_n$—R$^3$, —N(R$^3$)—S(O)$_n$(R$^3$), —N(R$^3$)—S(O)$_n$—N(R$^3$)$_2$, —S—NR$^3$—C(O)R$^3$, —C(S)N(R$^3$)$_2$, —C(S)R$^3$, —NR$^3$—C(O)OR$^3$, —O—C(O)OR$^3$, —O—C(O)N(R$^3$)$_2$, —NR$^3$—C(S)R$^3$, =N—OH, =N—OR$^3$, =N—N(R$^3$)$_2$, =NR$^3$, =NNR$^3$C(O)N(R$^3$)$_2$, =NNR$^3$C(O)OR$^3$, =NNR$^3$S(O)$_n$, —N(R$^3$)$_2$, —NR$^3$—C(S)OR$^3$, —NR$^3$—C(S)N(R$^3$)$_2$, —NR$^3$—C[=N(R$^3$)]—N(R$^3$)$_2$, —N(R$^3$)—C[=N—NO$_2$]—N(R$^3$)$_2$, —N(R$^3$)—C[=N—NO$_2$]—OR$^3$, —N(R$^3$)—C[=N—CN]—OR$^3$, —N(R$^3$)—C[=N—CN]—(R$^3$)$_2$, —OC(O)R$^3$, —OC(S)R$^3$, —OC(O)N(R$^3$)$_2$, —C(O)N(R$^3$)—N(R$^3$)$_2$, —O—C(O)N(R$^3$)—N(R$^3$)$_2$, O—C(O)N(OR$^3$)(R$^3$), N(R$^3$)—N(R$^3$)C(O)R$^3$, N(R$^3$)—OC(O)R$^3$, N(R$^3$)—OC(O)R$^3$, N(R$^3$)—OC(O)R$^3$, —OC(S)N(R$^3$)$_2$, —OC(S)N(R$^3$)(R$^3$), or PO$_3$—R$^3$; with the proviso that when R$^7$ is H, E' is —SO$_2$, G is H or alkyl, and when B is present or when B is not present and R$^1$ is —C(O)—, D' may not be C$_1$-C$_{15}$ alkyl substituted with one substituent selected from —N(R$^3$)$_2$, —SR$^3$ or —S(O)$_n$—R$^3$, or substituted with two —N(R$^3$)$_2$ substituents;
E is selected from Ht; O-Ht; Ht-Ht; Ht fused with Ht; —O—R$^3$; —N(R$^2$)(R$^3$); C$_1$-C$_6$ alkyl optionally substituted with one or more groups selected from R$^4$ or Ht; C$_2$-C$_6$ alkenyl optionally substituted with one or more groups selected from R$^4$ or Ht; C$_3$-C$_6$ saturated carbocycle optionally substituted with one or more groups selected from R$^4$ or Ht; or C$_5$-C$_6$ unsaturated carbocycle optionally substituted with one or more groups selected from R$^4$ or Ht;
each R$^4$ is independently selected from —OR$^2$, —OR$^3$, —SR$^2$, —SOR$^2$, —SO$_2$R$^2$, —CO$_2$R$^2$, —C(O)—NHR$^2$, —C(O)—N(R$^2$)$_2$, —C(O)—NR$^2$(OR$^2$), —S(O)$_2$—NHR$^2$, halo, —NR$^2$—C(O)—R$^2$, —N(R$^2$)$_2$ or —CN;
each R$^7$ is independently selected from hydrogen,

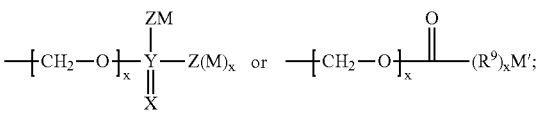

wherein each M is independently selected from H, Li, Na, K, Mg, Ca, Ba, —N(R$^2$)$_4$, C$_1$-C$_{12}$-alkyl, C$_2$-C$_{12}$-alkenyl, or —R⁶; wherein 1 to 4 —CH₂ radicals of the alkyl or alkenyl group, other than the —CH₂ that is bound to Z, is optionally replaced by a heteroatom group selected from O, S(O), S(O)₂, or N(R²); and wherein any hydrogen in said alkyl, alkenyl or R⁶ is optionally replaced with a substituent selected from oxo, —OR², —R², N(R²)₂, N(R²)₃, R²OH, —CN, —CO₂R², —C(O)—N(R²)₂, S(O)₂—N(R²)₂, N(R²)—C(O)—R², C(O)R², —S(O)ₙ—R², OCF₃, —S(O)ₙ—R⁶, N(R²)—S(O)₂(R²), halo, —CF₃, or —NO₂;

M' is H, C₁-C₁₂-alkyl, C₂-C₁₂-alkenyl, or —R⁶; wherein 1 to 4 —CH₂ radicals of the alkyl or alkenyl group is optionally replaced by a heteroatom group selected from O, S, S(O), S(O)₂, or N(R²); and wherein any hydrogen in said alkyl, alkenyl or R⁶ is optionally replaced with a substituent selected from oxo, OR², —R², —N(R²)₂, N(R²)₃, —R²OH, —CN, —CO₂R², —C(O)—N(R²)₂, —S(O)₂—N(R²)₂, —N(R²)—C(O)—R₂, —C(O)R², —S(O)ₙ—R², —OCF₃, —S(O)ₙ—R⁶, —N(R²)—S(O)₂(R²), halo, —CF₃, or —NO₂;

Z is O, S, N(R²)₂, or, when M is not present, H;

Y is P or S;

X is O or S;

R⁹ is C(R²)₂, O or N(R²); and wherein when Y is S, Z is not S;

R⁶ is a 5-6 membered saturated, partially saturated or unsaturated carbocyclic or heterocyclic ring system, or an 8-10 membered saturated, partially saturated or unsaturated bicyclic ring system; wherein any of said heterocyclic ring systems contains one or more heteroatoms selected from O, N, S, S(O)ₙ or N(R²); and wherein any of said ring systems optionally contains 1 to 4 substituents independently selected from OH, C₁-C₄ alkyl, —O—C₁-C₄ alkyl or —O—C(O)—C₁-C₄ alkyl.

2. The compound according to claim 1, having the formula IA:

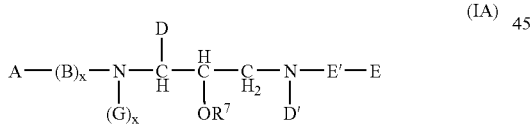

(IA)

wherein:

D' is selected from C₁₋₁₅ alkyl, C₂₋₁₅ alkenyl or C₂-C₁₅ alkynyl; each of which is substituted with one to two —CN groups and each of which is optionally substituted with C₃-C₈ cycloalkyl.

3. The compound according to claim 2 wherein:

D' is selected from C₁₋₁₅ alkyl or C₂₋₁₅ alkenyl; each of which is substituted with one to two —CN groups and each of which is optionally substituted with C₃-C₈ cycloalkyl.

4. The compound according to claim 2 wherein:

D' is C₂-C₁₅ alkynyl which is substituted with one to two —CN groups and each of which is optionally substituted with C₃-C₈ cycloalkyl.

5. The compound according to claim 1 having the formula IB:

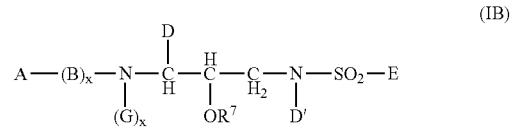

(IB)

wherein:

D' is selected from C₁-C₁₅ alkyl, C₂-C₁₅ alkenyl or C₂-C₁₅ alkynyl, each of which contains one or more substituents selected from oxo, halo, —CF₃, —OCF₃, —NO₂, azido, —SH, —SR³, —N(R³)—N(R³)₂, —O—N(R³)₂, —(R³)N—O—(R³), —N(R³)₂, —CO₂R³, —C(O)—N(R³)₂, —S(O)ₙ—N(R³)₂, —N(R³)—C(O)—R³, —N(R³)—C(O)—N(R³)₂, —N(R³)—C(O)—S(R³), —C(O)—R³, —S(O)ₙ—R³, —N(R³)—S(O)ₙ(R³), —N(R³)—S(O)ₙ—N(R³)₂, —S—NR³—C(O)R³, —C(S)N(R³)₂, —C(S)R³, —NR³—C(O)OR³, —O—C(O)OR³, —O—C(O)N(R³)₂, —NR³—C(S)R³, ═N—OH, ═N—OR³, ═N—N(R³)₂, ═NR³, ═NNR³C(O)N(R³)₂, ═NNR³C(O)OR³, ═NNR³S(O)ₙ—N(R³)₂, —NR³—C(S)OR³, —NR³—C(S)N(R³)₂, —NR³—C[═N(R³)]—N(R³)₂, —N(R³)—C[═N—NO₂]—N(R³)₂, —N(R³)—C[═N—NO₂]—OR³, —N(R³)—C[═N—CN]—OR³, —N(R³)—C[═N—CN]—(R³)₂, —OC(O)R³, —OC(S)R³, —OC(O)N(R³)₂, —C(O)N(R³)—N(R³)₂, —O—C(O)N(R³)—N(R³)₂, O—C(O)N(OR³)(R³), N(R³)—N(R³)C(O)R³, N(R³)—OC(O)R³, N(R³)—OC(O)R³, N(R³)—OC(O)R³, —OC(S)N(R³)₂, —OC(S)N(R³)(R³), or PO₃—R³; with the proviso that when R⁷ is H, E' is —SO₂—, G is H or alkyl, and when B is present or when B is not present and R¹ is —C(O)—, D' may not be C₁-C₁₅ alkyl substituted with one substituent selected from —N(R³)₂, —SR³ or —S(O)ₙ—R³, or substituted with two —N(R³)₂ substituents.

6. The compound according to claim 5 wherein:

D' is selected from C₁-C₁₅ alkyl or C₂-C₁₅ alkenyl, each of which contains one or more substituents selected from oxo, halo, —CF₃, —OCF₃, —NO₂, azido, —N(R³)—N(R³)₂, —O—N(R³)₂, —(R³)N—O—(R³), —N(R³)₂, —N(R³)—C(O)—N(R³)₂, —N(R³)—C(O)—S(R³), —C(O)—R³, —S(O)ₙ—R³, —N(R³)—S(O)ₙ(R³), —N(R³)—S(O)ₙ—N(R³)₂, —S—NR³—C(O)R³, —C(S)N(R³)₂, —C(S)R³, —NR³—C(O)OR³, —O—C(O)OR³, —O—C(O)N(R³)₂, —NR³—C(S)R³, ═N—OH, ═N—OR³, ═N—N(R³)₂, ═NR³, ═NNR³C(O)N(R³)₂, ═NNR³C(O)OR³, ═NNR³S(O)ₙ—N(R³)₂, —NR³—C(S)OR³, —NR³—C(S)N(R³)₂, —NR³—C[═N(R³)]—N(R³)₂, —N(R³)—C[═N—NO₂]—N(R³)₂, —N(R³)—C[═N—NO₂]—OR³, —N(R³)—C[═N—CN]—OR³, —N(R³)—C[═N—CN]—(R³)₂, —OC(O)R³, —OC(S)R³, —OC(O)N(R³)₂, —C(O)N(R³)—N(R³)₂, —O—C(O)N(R³)—N(R³)₂, O—C(O)N(OR³)(R³), N(R³)—N(R³)C(O)R³, N(R³)—OC(O)R³, N(R³)—OC(O)R³, N(R³)—OC(O)R³, —OC(S)N(R³)₂, —OC(S)N(R³)(R³), or PO₃—R³; C₂-C₁₅ alkynyl which contains one or more substituents selected from oxo, halo, —CF₃, —OCF₃, —NO₂, azido, —SH, —SR³, —N(R³)—N(R³)₂, —O—N(R³)₂, —(R³)N—O—(R³), —N(R³)₂, —CO₂R³, —C(O)—N(R³)₂, —S(O)ₙ—N(R³)₂, —N(R³)—C(O)—R³, —N(R³)—C(O)—N(R³)₂, —N(R³)—C(O)—S(R³), —C(O)—R³, —S(O)$_n$—R³, —N(R³)—S(O)$_n$(R³), —N(R³)—S(O)$_n$—N(R³)$_2$, —S—NR³—C(O)R³, —C(S)N(R³)$_2$, —C(S)R³, —NR³—C(O)OR³, —O—C(O)OR³, —O—C(O)N(R³)$_2$, —NR³—C(S)R³, =N—OH, =N—OR³, =N—N(R³)$_2$, =NR³, =NNR³C(O)N(R³)$_2$, =NNR³C(O)OR³, =NNR³S(O)$_n$—N(R³)$_2$, —NR³—C(S)OR³, —NR³—C(S)N(R³)$_2$, —NR³—C[=N(R³)]—N(R³)$_2$, —N(R³)—C[=N—NO$_2$]—N(R³)$_2$, —N(R³)—C[=N—NO$_2$]—OR³, —N(R³)—C[=N—CN]—OR³, —N(R³)—C[=N—CN]—(R³)$_2$, —OC(O)R³, —OC(S)R³, —OC(O)N(R³)$_2$, —C(O)N(R³)—N(R³)$_2$, —O—C(O)N(R³)—N(R³)$_2$, O—C(O)N(OR³)(R³), N(R³)—N(R³)C(O)R³, N(R³)—OC(O)R³, N(R³)—OC(O)R³, N(R³)—OC(O)R³, —OC(S)N(R³)$_2$, —OC(S)N(R³)(R³), or PO$_3$—R³; with the proviso that when R⁷ is H, E' is —SO$_2$—, G is H or alkyl, and when B is present or when B is not present and R¹ is —C(O)—, D' may not be C$_1$-C$_{15}$ alkyl substituted with one substituent selected from —N(R³)$_2$ or —S(O)$_n$—R³, or substituted with two —N(R³)$_2$ substituents.

7. The compound according to claim 5 wherein:

D' is selected from C$_1$-C$_{15}$ alkyl or C$_2$-C$_{15}$ alkenyl, each of which contains one or more substituents selected from —SH, —SR³, —CO$_2$R³, —C(O)—N(R³)$_2$, —S(O)$_n$—N(R³)$_2$ or —N(R³)—C(O)—R³; with the proviso that when R⁷ is H, E' is —SO$_2$—, G is H or alkyl, and when B is present or when B is not present and R¹ is —C(O)—, D' may not be C$_1$-C$_{15}$ alkyl substituted with one substituent selected from —SR³.

8. The compound according to claim 1, wherein E' is SO$_2$.

9. The compound according to claim 1, wherein at least one R⁷ is selected from:

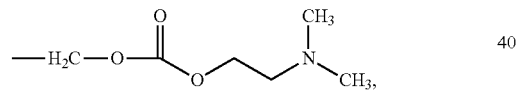

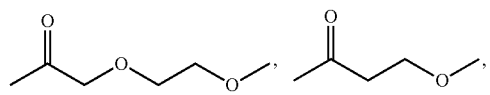

-(L)-lysine, —PO$_3$Na$_2$,

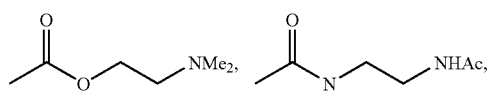

-(L)-tyrosine,

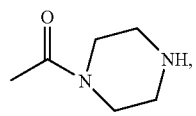

—PO$_3$Mg, —PO$_3$(NH$_4$)$_2$, —CH$_2$—OPO$_3$Na$_2$,

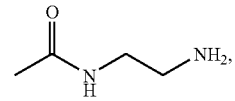

-(L)-serine, —SO$_3$Na$_2$,

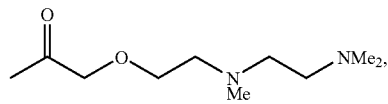

—SO$_3$Mg, —SO$_3$(NH$_4$)$_2$, —CH$_2$—OSO$_3$Na$_2$, —CH$_2$—OSO$_3$(NH$_4$)$_2$,

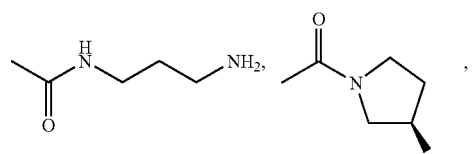

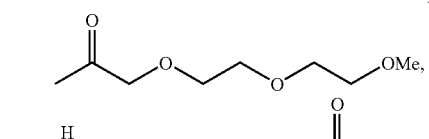

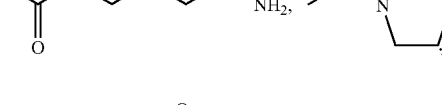

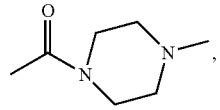

acetyl,

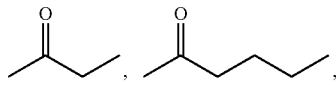

-(L)-valine, -(L)-glutamic acid, -(L)-aspartic acid, -(L)-γ-t-butyl-aspartic acid,

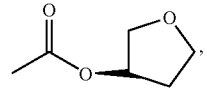

-(L)-(L)-3-pyridylalanine, -(L)-histidine, —CHO,

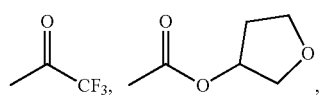

-continued

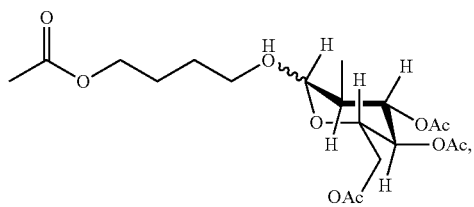

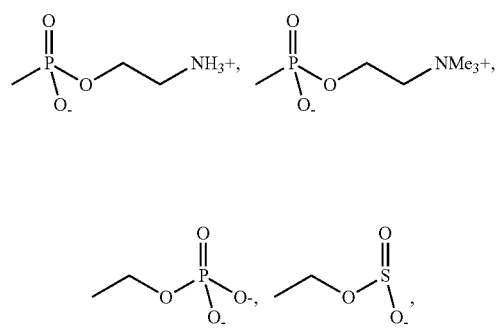

PO₃K₂, PO₃Ca, PO₃-spermine, PO₃-(spermidine)₂ or PO₃-(meglamine)₂.

10. The compound according to claim 8, having the formula II:

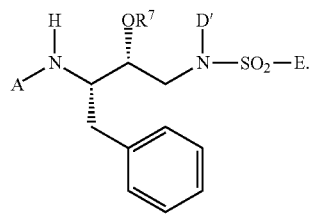

11. The compound according to claim 10, wherein:
A is R'—C(O)—; and
R' is

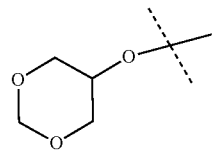

12. The compound according to claim 10, wherein:
D' is —CH₂—R"; and
R" is selected from

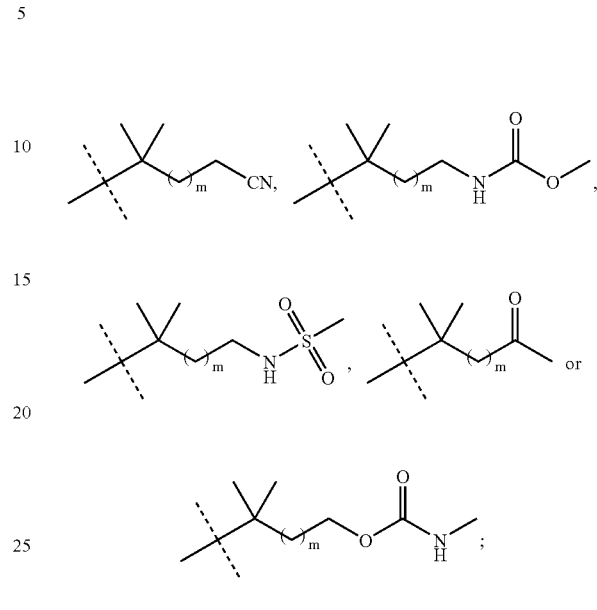

wherein m is 0 to 3.

13. The compound according to claim 10, wherein E is selected from

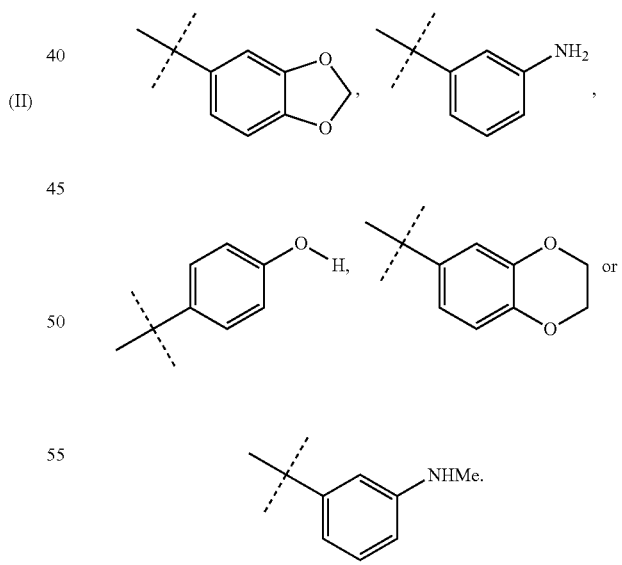

14. The compound according to claim 10, wherein R⁷ is —PO₃²⁻.

15. The compound according to claim 11, wherein said compound is selected from any one of compound numbers: 24, 33, 36, 125, 273, 274, 281, 297, 298, 369-372, having the structure

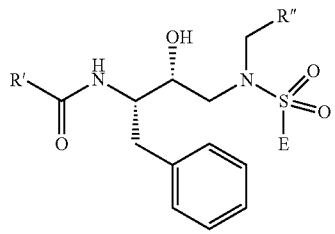

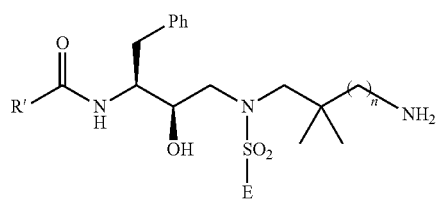

| Compound | R' | n | E |
|---|---|---|---|
| 297 | (1,3-dioxan-5-yloxy) | 4 | (benzo[d][1,3]dioxol-5-yl) |
| 298 | (1,3-dioxan-5-yloxy) | 4 | (4-aminophenyl) |

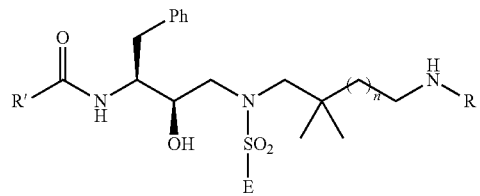

| Compound | R' | E | n | R |
|---|---|---|---|---|
| 370 | (1,3-dioxan-5-yloxy) | (benzo[d][1,3]dioxol-5-yl) | 3 | SO₂Me |
| 371 | (1,3-dioxan-5-yloxy) | (4-aminophenyl) | 3 | C(O)OMe |
| 372 | (1,3-dioxan-5-yloxy) | (4-aminophenyl) | 3 | SO₂Me. |

| Compound | R' | E | n | R |
|---|---|---|---|---|
| 369 | (1,3-dioxan-5-yloxy) | (benzo[d][1,3]dioxol-5-yl) | 3 | C(O)OMe |

16. A composition comprising a compound according to claim 1 or a pharmaceutically acceptable salt thereof in an amount sufficient to detectably inhibit aspartyl protease activity in a patient, and a pharmaceutically acceptable carrier.

17. The composition according to claim 16, further comprising an additional antiviral agent other than a compound of formula (I).

18. The composition according to claim 16, wherein said composition is formulated as a pharmaceutically acceptable, orally available tablet or capsule.

19. A method of treating an HIV virus infection in a human comprising the step of administering to said human a composition according to any one of claims 16 to 18.

20. The method according to claim 19, comprising the step of administering to said patient an additional antiviral agent other than a compound of formula I, wherein said additional antiviral agent is administered prior to, simultaneously with or following administration of said composition.

* * * * *